United States Patent
Gummadi et al.

(10) Patent No.: US 9,353,107 B2
(45) Date of Patent: May 31, 2016

(54) 3-(PYRAZOLYL)-1H-PYRROLO[2,3-B] PYRIDINE DERIVATIVES AS KINASE INHIBITORS

(71) Applicants: Aurigene Discovery Technologies Limited, Bangalore (IN); Um Pharmauji Sdn. Bhd., Kuala Lumpur (MY)

(72) Inventors: Venkateshwar Rao Gummadi, Bangalore (IN); Subramanya Hosahalli, Bangalore (IN); Srinivas Nanduri, Hyderabad (IN); Girish Aggunda Renukappa, Mysore (IN)

(73) Assignees: Aurigene Discovery Technologies Limited, Bangalore (IN); Um Pharmauji Sdn. Bhd., Kuala Lumpur (MY)

( * ) Notice: Subject to any disclaimer, the term of this patent is extended or adjusted under 35 U.S.C. 154(b) by 0 days.

(21) Appl. No.: 14/412,562

(22) PCT Filed: Jul. 1, 2013

(86) PCT No.: PCT/IB2013/055388
§ 371 (c)(1),
(2) Date: Jan. 2, 2015

(87) PCT Pub. No.: WO2014/006554
PCT Pub. Date: Jan. 9, 2014

(65) Prior Publication Data
US 2015/0336949 A1    Nov. 26, 2015

(30) Foreign Application Priority Data

Jul. 3, 2012  (IN) ............................ 2661/CHE/2012

(51) Int. Cl.
C07D 401/02    (2006.01)
C07D 401/10    (2006.01)
A61K 31/437    (2006.01)
A61K 31/4353   (2006.01)
C07D 471/04    (2006.01)

(52) U.S. Cl.
CPC .................................. *C07D 471/04* (2013.01)

(58) Field of Classification Search
CPC .. C07D 401/02; C07D 401/10; A61K 31/437; A61K 31/4353
USPC .......................................... 546/113; 514/300
See application file for complete search history.

(56) References Cited

FOREIGN PATENT DOCUMENTS

WO    2014/004863    *    1/2014

* cited by examiner

*Primary Examiner* — Niloofar Rahmani
(74) *Attorney, Agent, or Firm* — Benjamin Aaron Adler

(57) ABSTRACT

The present application relates to novel 3-(pyrazolyl)-1H-pyrrolo[2,3-b]pyridine derivatives of formula (I), as protein kinase inhibitors.

Formula (I)

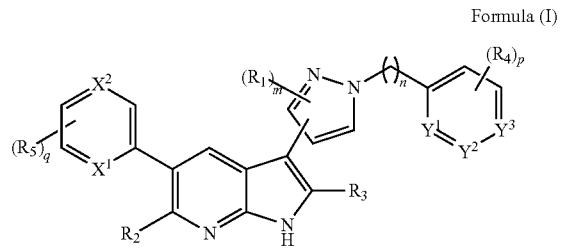

The invention particularly relates to compounds of formula (I), preparation of compounds and pharmaceutical compositions thereof. The invention further relates to pharmaceutically acceptable salts and compositions comprising the said novel 3-(pyrazolyl)-1H-pyrrolo[2,3-b]pyridine derivatives and their use in the treatment of various disorders.

17 Claims, No Drawings

3-(PYRAZOLYL)-1H-PYRROLO[2,3-B]PYRIDINE DERIVATIVES AS KINASE INHIBITORS

CROSS-REFERENCE TO RELATED APPLICATIONS

This application is a national stage application under 35 U.S.C. §371 of pending international application PCT/IB2013/055388 filed on Jul. 1, 2013 and claims the benefit under 35 U.S.C. §119(a) of Indian provisional application number 2661/CHE/2012 filed on Jul. 3, 2012, now abandoned, both of which are hereby incorporated by reference.

TECHNICAL FIELD

The invention relates to novel "3-(pyrazolyl)-1H-pyrrolo[2,3-b]pyridine derivatives of formula (I), as protein kinase inhibitors.

BACKGROUND

Protein Kinases are key regulators of cell function that constitute one of the largest and most functionally diverse gene families. Protein kinases participate in the signalling events that control the activation, growth and differentiation of cells in response to extracellular mediators and to changes in the environment. In general, these protein kinases fall into several groups; those which preferentially phosphorylate serine and/or threonine residues and those which preferentially phosphorylate tyrosine residues.

Protein kinases play crucial role in regulating the different cell processes which include, but are not limited to, proliferation, differentiation, apoptosis, motility, transcription, translation, signalling process and various regulatory mechanisms, by adding phosphate groups to the target protein residues. This phosphorylation event acts as molecular on/off switches that can modulate or regulate the target position biological function. Phosphorylation of targeted proteins occurs in response to a variety of extracellular signals. The appropriate protein kinase functions in signaling pathways to activate or deactivate. Uncontrolled signaling due to defective control of protein phosphorylation is known to contribute to various diseases. In the case of cancer, kinases are known to regulate many aspects of the cell growth, invasion that intrudes upon and destroys adjacent tissues and sometimes metastasis, or spreading to other locations in the body via lymph or blood.

The protein kinase family members include enzymes that control cell growth, migration, activation, proliferation, differentiation, signaling, survival and regulation of the cell cycle. Many diseases and/or disorders are associated with aberrant, abnormal or deregulated activity of one or more kinases. These diseases and/or disorders include, but are not limited to cancers, allergic diseases and/or disorders, autoimmune diseases and/or disorders, inflammatory diseases and/or disorder and/or conditions associated with inflammation and pain, proliferative diseases, hematopoietic disorders, hematological malignancies, bone disorders, fibrosis diseases and/or disorders, metabolic disorders, muscle diseases and/or disorders respiratory diseases and/or disorders, pulmonary disorders, genetic developmental diseases, neurological and neurodegenerative diseases/or disorders, chronic inflammatory demyelinating neuropathies, cardiovascular, vascular or heart diseases and/or disorders, ophthalmic/ocular diseases and/or disorders, wound repair, infection and viral diseases. Therefore, inhibition of one or more of kinases would have multiple therapeutic indications.

Anaplastic lymphoma kinase (ALK) is a member of the receptor tyrosine kinase superfamily. Anaplastic lymphoma kinase (ALK) also known as ALK tyrosine kinase receptor or CD246 (cluster of differentiation 246) is an enzyme that in humans is encoded by the ALK gene. The most abundant expression of ALK occurs in the neonatal brain, suggesting a possible role for ALK in brain development (Duyster, J. et al., Oncogene, 2001, 20, 5623-5637).

ALK is implicated in oncogenesis in hematopoietic and non-hematopoietic tumors. Approximately sixty percent of anaplastic large cell lymphomas (ALCL) are associated with a chromosome mutation that generates a fusion protein consisting of nucleophosmin (NPM) and the intracellular domain of ALK. This mutant protein, NPM-ALK, possesses a constitutively active tyrosine kinase domain that is responsible for its oncogenic property through activation of downstream effectors. In addition, the transforming EML4-ALK fusion gene has been identified in non-small-cell lung cancer (NSCLC) patients (Soda, M., et al., Nature, 2007, 448, 561-566) and represents another in a list of ALK fusion proteins that are promising targets for ALK inhibitor therapy. Experimental data have demonstrated that the aberrant expression of constitutively active ALK is directly implicated in the pathogenesis of ALCL and that inhibition of ALK can markedly impair the growth of ALK+ lymphoma cells. The constitutively activated chimeric ALK has also been demonstrated in about 60% of inflammatory myofibroblastic tumors (IMTs), a slow-growing sarcoma that mainly affects children and young adults.

Furthermore, the aberrant expression of full-length ALK receptor proteins has been reported in neuroblastomas and extremely virulent glioblastomas (brain cancer). ALK and its putative ligand, pleiotrophin, are overexpressed in human glioblastomas (Stoica, G. et al., J. Biol. Chem., 2001, 276, 16772-16779). In mouse studies, depletion of ALK reduced glioblastoma tumor growth and prolonged animal survival (Powers, C. et al., J. Biol. Chem., 2002, 277, 14153-14158).

More recently, a novel oncogenic ALK fusion, EML4-ALK, comprising portions of the echinoderm microtubule-associated protein-like 4 (EML4) gene and the anaplastic lymphoma kinase (ALK) gene, has been implicated in a subset of non-small cell lung cancer (NSCLC). Mouse 3T3 fibroblast cells forced to express this fusion tyrosine kinase generated transformed foci in culture and subcutaneous tumors in nude mice. The EML4-ALK fusion transcript was detected in 6.7% of the 75 NSCLC patients examined; these individuals were distinct from those harboring mutations in the epidermal growth factor receptor gene. These findings strongly suggest that EML4-ALK and TPM4-ALK fusions are promising candidates for a therapeutic target in a sizable subset of NSCLC and possibly in some esophageal carcinomas.

An ALK inhibitor would either permit durable cures when combined with current chemotherapy for ALCL, IMT, or glioblastoma, or be used as a single therapeutic agent in a maintenance role to prevent cancer recurrence in those patients. Various ALK inhibitors have been reported, including amino substituted pyrimidines (WO/2009/032703A1), triazine and pyrimidine compounds (WO/2009/126514), and pyrimidine compounds (WO/2011/143033A1).

Accordingly, a need exists for the identification of small-molecule compounds that specifically inhibit, regulate and/or modulate the signal transduction of kinases, particularly ALK, as a means to treat or prevent associated diseases.

SUMMARY OF THE INVENTION

The invention relates to novel 3-(pyrazolyl)-1H-pyrrolo[2,3-b]pyridine derivatives of formula (I), as protein kinase inhibitors.

In one aspect of the present invention, it relates to compound of formula (I):

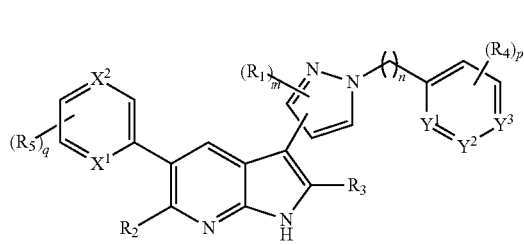

(I)

or a pharmaceutically acceptable salts or stereoisomers thereof;
wherein,
X$^1$ and X$^2$ are independently selected from CH or N;
—Y$^1$—Y$^2$—Y$^3$— is:
a) N=CH—CH=
b) CH=N—CH=
c) CH=CH—N= or
d) CH=CH—CH=
each R$_1$ represents alkyl;
R$_2$ and R$_3$ are independently selected from hydrogen, alkyl or cycloalkyl;
each R$_4$ is independently selected from alkyl, halo, haloalkyl, hydroxyl, alkoxy, haloalkoxy, —N(R$_a$)R$_b$, nitro, cyano or —NHC(O)alkyl;
each R$_5$ is independently selected from alkyl, —OR$_a$, —O(CH$_2$)$_q$N(R$_a$)R$_b$, —O(CH$_2$)$_q$OR$_a$, —N(H)SO$_2$R$_a$, —SO$_2$NHR$_a$, —N(R$_a$)R$_b$, halo, optionally substituted heterocyclylalkyl, optionally substituted heterocyclyl; wherein the optional substituent at each occurrence is independently selected from alkyl, cyanoalkyl, hydroxyl, hydroxyalkyl, —C(O)OR$_a$, —C(O)R$_a$, —(CH$_2$)$_n$N(R$_a$)R$_b$, —(CH$_2$)$_n$C(O)N(R$_a$)R$_b$, —C(O)N(R$_a$)R$_b$, —C(O)(CH$_2$)$_n$R$_a$, —SO$_2$R$_a$, —C(O)(CH$_2$)$_n$N(R$_a$)R$_b$, —C(O)(CH$_2$)$_n$OR$_a$, or —(CH$_2$)$_n$OR$_a$;
R$_a$ and R$_b$ are independently selected from hydrogen, alkyl, cycloalkyl or heterocyclyl;
'm' and 'p' are integers selected from 0 to 2, both inclusive;
'n' is an integer selected from 1 to 2, both inclusive;
'q' is an integer selected from 1 to 3 both inclusive.

In another aspect the present invention provides a pharmaceutical composition comprising the compound of formula (I), and at least one pharmaceutically acceptable excipient (such as a pharmaceutically acceptable carrier or diluent).

In yet another aspect the present invention relates to the preparation of the compounds of formula (I).

In further yet another aspect of the present invention, it provides 3-(pyrazolyl)-1H-pyrrolo[2,3-b]pyridine derivatives of formula (I), which are used for the treatment and prevention in diseases or disorder, in particular their use in diseases or disorder where there is an advantage in inhibiting protein kinases enzymes—particularly receptor tyrosine kinase, more particularly Anaplastic lymphoma kinase (ALK).

DETAILED DESCRIPTION OF THE INVENTION

Embodiments of the present application provides novel 3-(pyrazolyl)-1H-pyrrolo[2,3-b]pyridine derivatives of formula (I), as protein kinase inhibitors.

One of the embodiment of the present invention provides compound of formula (I):

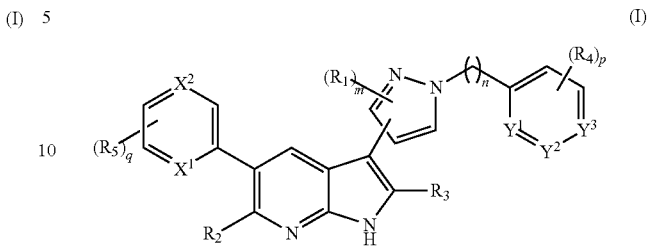

(I)

or a pharmaceutically acceptable salts or stereoisomers thereof;
wherein,
X$^1$ and X$^2$ are independently selected from CH or N;
—Y$^1$—Y$^2$—Y$^3$— is:
a) N=CH—CH=
b) CH=N—CH=
c) CH=CH—N= or
d) CH=CH—CH=
each R$_1$ represents alkyl;
R$_2$ and R$_3$ are independently selected from hydrogen, alkyl or cycloalkyl;
each R$_4$ is independently selected from alkyl, halo, haloalkyl, hydroxyl, alkoxy, haloalkoxy, —N(R$_a$)R$_b$, nitro, cyano or —NHC(O)alkyl;
each R$_5$ is independently selected from alkyl, —OR$_a$, —O(CH$_2$)$_q$N(R$_a$)R$_b$, —O(CH$_2$)$_q$OR$_a$, —N(H)SO$_2$R$_a$, —SO$_2$NHR$_a$, —N(R$_a$)R$_b$, halo, optionally substituted heterocyclylalkyl, optionally substituted heterocyclyl; wherein the optional substituent at each occurrence is independently selected from alkyl, cyanoalkyl, hydroxyl, hydroxyalkyl, —C(O)OR$_a$, —C(O)R$_a$, —(CH$_2$)$_n$N(R$_a$)R$_b$, —(CH$_2$)$_n$C(O)N(R$_a$)R$_b$, —C(O)N(R$_a$)R$_b$, —C(O)(CH$_2$)$_n$R$_a$, —SO$_2$R$_a$, —C(O)(CH$_2$)$_n$N(R$_a$)R$_b$, —C(O)(CH$_2$)$_n$OR$_a$, or —(CH$_2$)$_n$OR$_a$;
R$_a$ and R$_b$ are independently selected from hydrogen, alkyl, cycloalkyl or heterocyclyl;
'm' and 'p' are integers selected from 0 to 2, both inclusive;
'n' is an integer selected from 1 to 2, both inclusive;
'q' is an integer selected from 1 to 3 both inclusive.

The embodiment below are illustrative of the present invention and are not intended to limit the claims to the specific embodiments exemplified.

According to one embodiment, specifically provided are compounds of formula (I), in which R$_1$ is methyl.

According to yet another embodiment, specifically provided are compounds of formula (I), in which R$_2$ and R$_3$ are independently selected from hydrogen or cyclopropyl.

According to yet another embodiment, specifically provided are compounds of formula (I), in which each R$_4$ is independently selected from alkyl, halo, haloalkyl, hydroxyl, alkoxy, haloalkoxy, N(R$_a$)R$_b$, nitro, cyano or —NHC(O)alkyl; and p is 0, 1, or 2.

According to yet another embodiment, specifically provided are compounds of formula (I), in which R$_4$ is halogen; wherein halogen is fluoro or chloro.

According to yet another embodiment, specifically provided are compounds of formula (I), in which R$_4$ is independently selected from methyl, OH, methoxy, ethoxy, CF$_3$, OCF$_3$, —NO$_2$, NH$_2$, —CN or —NH(CO)CH$_3$.

According to yet another embodiment, specifically provided are compounds of formula (I), in which R$_5$ is independently selected from alkyl, —OR$_a$, —O(CH$_2$)$_q$N(R$_a$)R$_b$, —O(CH$_2$)$_q$OR$_a$, —N(H)SO$_2$R$_a$, —SO$_2$N(H)R$_a$, —N(R$_a$)R$_b$, halo, optionally substituted heterocyclylalkyl, optionally substituted heterocyclyl; wherein the optional substituent at each occurrence is independently selected from alkyl, cyanoalkyl, hydroxyl, hydroxyalkyl, —C(O)OR$_a$, —C(O)R$_a$, —(CH$_2$)$_n$N(R$_a$)R$_b$, —(CH$_2$)$_n$C(O)N(R$_a$)R$_b$, —C(O)N(R$_a$)R$_b$, —C(O)(CH$_2$)R$_a$, —SO$_2$R$_a$, —C(O)(CH$_2$)$_n$N(R$_a$)R$_b$, —C(O)(CH$_2$)$_n$OR$_a$, or —(CH$_2$)$_n$OR$_a$.

According to yet another embodiment, specifically provided are compounds of formula (I), in which R$_5$ is halo; wherein halo is fluoro.

According to yet another embodiment, specifically provided are compounds of formula (I), in which R$_5$ is —OR$_a$; wherein R$_a$ is methyl or piperidine.

According to yet another embodiment, specifically provided are compounds of formula (I), in which R$_5$ is —N(R$_a$)R$_b$; wherein R$_a$ is hydrogen and R$_b$ piperidine.

According to yet another embodiment, specifically provided are compounds of formula (I), in which R$_5$ is N(H)SO$_2$R$_a$, —SO$_2$NHR$_a$; wherein R$_a$ is methyl, ethyl or cyclopropyl.

According to yet another embodiment, specifically provided are compounds of formula (I), in which R$_5$ is alkyl; where alkyl is methyl.

According to yet another embodiment, specifically provided are compounds of formula (I), in which R$_5$ is heterocyclyl; wherein heterocyclyl is saturated heterocyclyl or unsaturated heterocyclyl.

According to yet another embodiment, specifically provided are compounds of formula (I), in which R$_5$ is saturated heterocyclyl; wherein saturated heterocyclyl is piperazine, piperidine, morpholine, and 1,4-diazepane.

According to yet another embodiment, specifically provided are compounds of formula (I), in which R$_5$ is unsaturated heterocyclyl; wherein unsaturated heterocyclyl is pyridine.

According to yet another embodiment, specifically provided are compounds of formula (I), in which R$_5$ is piperazine optionally substituted with alkyl, cyanoalkyl, hydroxyalkyl, —C(O)OR$_a$, —C(O)R$_a$, —(CH$_2$)$_n$N(R$_a$)R$_b$, —(CH$_2$)$_n$C(O)N(R$_a$)R$_b$, —C(O)N(R$_a$)R$_b$, —C(O)(CH$_2$)$_n$R$_a$.

According to yet another embodiment, specifically provided are compounds of formula (I), in which R$_5$ is piperazine optionally substituted with methyl and isopropyl.

According to yet another embodiment, specifically provided are compounds of formula (I), in which R$_5$ is piperazine optionally substituted hydroxyalkyl; wherein hydroxyalkyl is selected from CH$_2$—CH$_2$—OH, CH$_2$—CH(OH)—CH$_3$.

According to yet another embodiment, specifically provided are compounds of formula (I), in which R$_5$ is piperidine substituted with alkyl and hydroxyl group; wherein alkyl is methyl.

According to yet another embodiment, specifically provided are compounds of formula (I), in which R$_5$ is optionally substituted heterocyclylalkyl.

According to yet another embodiment, specifically provided are compounds of formula (I), in which R$_5$ is piperidin-4-ylmethyl.

In a particular embodiment of the compounds of formula (I), the invention comprises a particular series of compounds of formula (IA):

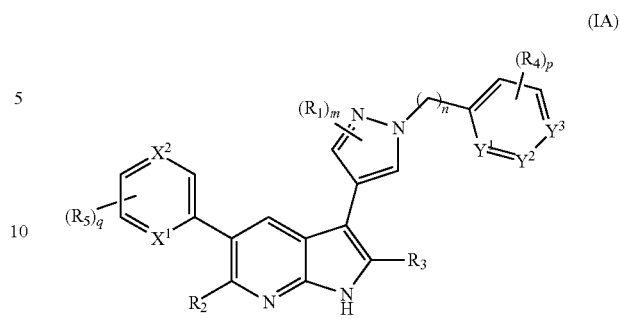

(IA)

wherein, R$_1$, R$_2$, R$_3$, R$_4$, R$_5$, X$^1$, X$^2$, Y$^1$, Y$^2$, Y$^3$, m, n, p and q are same as defined in formula (I); or pharmaceutically acceptable salts or stereoisomers thereof.

In another particular embodiment of the compounds of formula (I), the invention comprises another particular series of compounds of formula (IB):

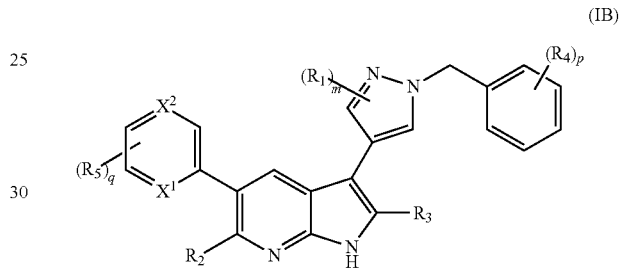

(IB)

wherein, R$_1$, R$_2$, R$_3$, R$_4$, R$_5$, X$^1$, X$^2$, m, p and q are same as defined in formula (I); or pharmaceutically acceptable salts or stereoisomers thereof.

According to yet another embodiment, specifically provided are compounds of formula (IB) in which X$^1$ is CH or N.

According to yet another embodiment, specifically provided are compounds of formula (IB) in which X$^2$ is CH.

According to yet another embodiment, specifically provided are compounds of formula (IB) in which X$^2$ is N.

According to yet another embodiment, specifically provided are compounds of formula (IB) in which R$_1$ is Alkyl; wherein the alkyl is methyl.

According to yet another embodiment, specifically provided are compounds of formula (IB) in which R$_4$ is halo; wherein the halo is fluorine.

According to yet another embodiment, specifically provided are compounds of formula (IB), in which R$_5$ is saturated heterocyclyl; wherein saturated heterocyclyl is selected from piperazine, piperidine and morpholine.

According to yet another embodiment, specifically provided are compounds of formula (IB), in which R$_5$ is piperazine optionally substituted with hydroxyalkyl; wherein hydroxylalkyl is —CH$_2$(CH)OHCH$_3$.

According to yet another embodiment, specifically provided are compounds of formula (IB), in which R$_5$ is piperidine optionally substituted with hydroxyl and alkyl; wherein alkyl is methyl.

According to yet another embodiment, specifically provided are compounds of formula (IB) in which m is 0.

According to yet another embodiment, specifically provided are compounds of formula (IB) in which m is 1.

According to yet another embodiment, specifically provided are compounds of formula (IB) in which m is 2.

According to yet another embodiment, specifically provided are compounds of formula (IB) R$_5$ is —OR$_a$; wherein R$_a$ is hydrogen or alkyl (methyl).

According to yet another embodiment, specifically provided are compounds of formula (IB) R$_5$ is N(R$_a$)R$_b$, —N(H)SO$_2$R$_a$, —C(O)(CH$_2$)$_n$N(R$_a$)R$_b$, —C(O)(CH$_2$)$_n$OR$_a$— or (CH$_2$)$_n$C(O)N(R$_a$)R$_b$; wherein each R$_a$ and R$_b$ are independently selected from hydrogen or alkyl.

In another particular embodiment of the compounds of formula (I), the invention comprises another particular series of compounds of formula (IC):

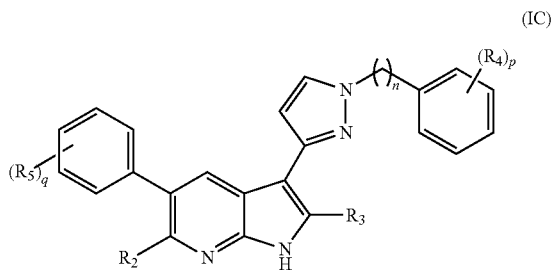

(IC)

wherein, R$_2$, R$_3$, R$_4$, R$_5$, n, p and q are same as defined in formula (I); or pharmaceutically acceptable salts or stereoisomers thereof.

In another particular embodiment of the compounds of formula (I), the invention comprises another particular series of compounds of formula (ID):

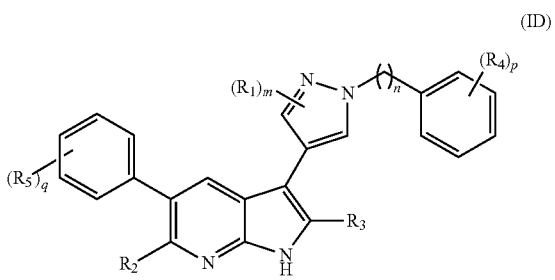

(ID)

wherein, R$_1$, R$_2$, R$_3$, R$_4$, R$_5$, m, n, p and q are same as defined in formula (I); or pharmaceutically acceptable salts or stereoisomers thereof.

Another embodiment of the present invention provided a pharmaceutical composition comprising the compound as disclosed, and a pharmaceutically acceptable carrier or diluent.

The compounds as disclosed in the present invention are formulated for pharmaceutical administration.

Yet another embodiment of the present invention provides use of the compounds as disclosed in the present invention for the preparation of a medicament for the treatment of cancer.

Yet another embodiment of the present invention provides a method of treatment of cancer, wherein the method comprises administration of an effective amount of the compound of the present invention to the subject in need thereof.

Yet another embodiment of the present invention provides a method for inhibiting growth of tumour cells and/or metastasis by administering an effective amount of the compound of the present invention to the subject in need thereof.

The compounds and pharmaceutically compositions of the present invention are used in the treatment and/or prevention of diseases and/or disorders in which aberrant, abnormal or deregulated activity of ALK; tyrosine kinases evolutionary and structurally related to ALK is Ret, Ros, Axl, and kinases that are members of Trk family (Trk A, B and C) kinase contribute to the pathology and/or symptomology of such diseases and/or disorders. Such diseases and/or disorders mediated by one or more of these kinases are provided herein.

The said tumour cells include cancer such as but not limited to melanoma, renal cancer, prostate cancer, breast cancer, colon cancer and lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumours of childhood, lymphocytic lymphoma, cancer of the bladder, cancer of the kidney or ureter, carcinoma of the renal pelvis, neoplasm of the central nervous system (CNS), primary CNS lymphoma, tumour angiogenesis, spinal axis tumour, brain stem glioma, pituitary adenoma, Kaposi's sarcoma, epidermoid cancer, squamous cell cancer, T-cell lymphoma, environmentally induced cancers including those induced by asbestos, and combinations of said cancers.

Still yet another embodiment of the present invention provides a method of treatment of cancer, by inhibiting ALK (Anaplastic lymphoma kinase), wherein the method comprises administration of an effective amount of the compound of the present invention to the subject in need thereof.

The compounds of the present invention may be used as single drugs or as a pharmaceutical composition in which the compound is mixed with various pharmacologically acceptable materials.

The pharmaceutical composition is usually administered by a parenteral administration route, but can be administered by oral or inhalation routes. Examples of the parenteral administration include administration by injection, and percutaneous, transmucosal, transnasal and trans pulmonary administrations.

The injectable materials include a solution, a suspension, and a solid injection that is dissolved or suspended in a solvent before use.

The injection is used after one or more active ingredients are dissolved, suspended or emulsified in a solvent. Examples of the solvent include water-soluble solvents (e.g., distilled water, physiological saline and Ringer's solution), oil solvents (e.g., vegetable oils such as olive oil, sesame oil, cotton oil and corn oil, and alcohols such as propylene glycol, polyethylene glycol and ethanol), and combinations thereof.

The dosage of the compounds of the present invention varies depending on age, weight, symptom, therapeutic efficacy, dosing regimen and/or treatment time. Generally, they may be administered by a parenteral route (preferably intravenous administration) in an amount of 1 mg to 100 mg per time, from once a couple of days, once 3 days, once 2 days, once a day to a couple of times a day, in the case of an adult, or continuously administered by intravenous administration from 1 to 24 hours a day. Since the dosage is affected by various conditions, an amount less than the above dosage may sometimes work well enough, or higher dosage may be required in some cases.

Parenteral administration by injection includes all forms of injections, and also includes intravenous fluids. For example, it includes intramuscular injections, subcutaneous injections, intradermal injections, intra-arterial injections, intravenous injections, intraperitoneal injections, injections to spinal cavity, and intravenous drops.

The compounds of the present invention may be administered in combination with other drugs for (1) complementation and/or enhancement of prevention and/or therapeutic efficacy of the preventive and/or therapeutic drug of the present invention, (2) dynamics, absorption improvement, dosage reduction of the preventive and/or therapeutic drug of the present invention, and/or (3) reduction of the side effects of the preventive and/or therapeutic drug of the present invention.

A concomitant medicine comprising the compounds of the present invention and other drug may be administered as a combination preparation in which both components are contained in a single formulation, or administered as separate formulations. The administration by separate formulations includes simultaneous administration and administration with some time intervals. In the case of the administration with some time intervals, the compound of the present invention can be administered first, followed by another drug or another drug can be administered first, followed by the compound of the present invention. The administration method of the respective drugs may be the same or different.

The dosage of the other drug can be properly selected, based on a dosage that has been clinically used. The compounding ratio of the compound of the present invention and the other drug can be properly selected according to age and weight of a subject to be administered, administration method, administration time, disorder to be treated, symptom and combination thereof. For example, the other drug may be used in an amount of 0.01 to 100 parts by mass, based on 1 part by mass of the compound of the present invention. The other drug may be a combination of two or more kind of arbitrary drugs in a proper proportion. The other drug that complements and/or enhances the preventive and/or therapeutic efficacy of the compound of the present invention includes not only those that have already been discovered, but those that will be discovered in future, based on the above mechanism.

Unless defined otherwise, all technical and scientific terms used herein have the same meaning as is commonly understood by one of skill in art to which the subject matter herein belongs.

As used in the specification and the appended claims, unless specified to the contrary, the following terms have the meaning indicated in order to facilitate the understanding of the present invention.

As used herein, the term 'compound(s)' comprises the compounds disclosed in the present invention.

As used herein, the term "comprise" or "comprising" is generally used in the sense of include, that is to say permitting the presence of one or more features or components.

As used herein, the term "or" means "and/or" unless stated otherwise.

As used herein, the term "including" as well as other forms, such as "include", "includes" and "included" is not limiting.

As used herein, the term "optionally substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

"Alkyl" refers to a hydrocarbon chain that may be a straight chain or branched chain, containing the indicated number of carbon atoms, for example, a $C_1$-$C_{10}$ alkyl group may have from 1 to 10 (inclusive) carbon atoms in it. Examples of $C_1$-$C_4$ and $C_1$-$C_6$ alkyl groups include, but are not limited to methyl, ethyl, propyl, butyl, pentyl, hexyl, isopropyl, isobutyl, sec-butyl, tert-butyl, isopentyl, neopentyl, and isohexyl.

As used herein the term "cycloalkyl" alone or in combination with other term(s) means —$C_3$-$C_{10}$ saturated cyclic hydrocarbyl ring. A cycloalkyl may be a single ring, which typically contains from 3 to 7 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

As used herein, the term "halo" or "halogen" alone or in combination with other term(s) means fluorine, chlorine, bromine and Iodine.

As used herein, the term "haloalkyl" means alkyl substituted with one or more halogen atoms, where alkyl groups are as defined above. The term "halo" is used herein interchangeably with the term "halogen" means F, Cl, Br or I. Examples of "haloalkyl" include but are not limited to trifluoromethyl, difluoromethyl, 2,2,2-trifluoroethyl and the like. A haloalkyl group can be unsubstituted or substituted with one or more suitable groups;

As used herein the term "hydroxyl" means OH group; "Cyano" refers to —CN group;

As used herein, the term "alkoxy" refers to a straight or branched, saturated aliphatic hydrocarbon radical bonded to an oxygen atom that is attached to a core structure. Examples of alkoxy groups include but are not limited to methoxy, ethoxy, propoxy, isopropoxy, butoxy, isobutoxy, tert-butoxy, pentoxy, 3-methyl butoxy and the like.

"Haloalkoxy" refers to an alkoxy group, as defined above, wherein one or more of the alkoxy group's hydrogen atoms has been replaced with —F, —Cl, —Br or —I. A haloalkoxy group can be unsubstituted or substituted with one or more suitable groups; As used herein, the term "nitro" alone or in combination with other term(s) means $NO_2$, In one embodiment $NO_2$ can be further modified to $NH_2$.

As used herein the terms "cyanoalkyl" means alkyl substituted with one CN group, where alkyl groups are as defined above. Examples of "cyanoalkyl" include but are not limited to cyanomethyl, cyanoethyl, cyanopropyl, cyanobutyl and the like.

"Hydroxylalkyl-" or "Hydroxyalkyl" refers to an alkyl group, as defined above, wherein one or more of the alkyl group's hydrogen atoms have been replaced with hydroxyl groups. Examples of hydroxylalkyl moieties include but are not limited to —$CH_2OH$, —$CH_2CH_2OH$, —$CH_2CH_2CH_2OH$, —$CH_2CH(OH)CH_2OH$, —$CH_2CH(OH)CH_3$, —$CH(CH_3)CH_2OH$.

As used herein, the term "heterocyclyl" alone or in combination with other term(s) means a saturated {i.e., "heterocycloalkyl"}, partially saturated {i.e., "heterocycloalkenyl"}, or completely unsaturated {i.e., "heteroaryl"} ring structure containing a total of 3 to 14 ring atoms. At least one of the ring atoms is a heteroatom {i.e., oxygen, nitrogen, or sulfur}, with the remaining ring atoms being independently selected from the group consisting of carbon, oxygen, nitrogen, and sulfur. A heterocyclyl may be a single-ring (monocyclic) or polycyclic ring structure. Heterocyclyl moieties include but are not limited to piperazine, piperidine morpholine, 1,4-diazepane and pyridine. A heterocyclyl group can be unsubstituted or substituted with one or more suitable groups.

"Heterocyclylalkyl" refers to an alkyl group, as defined above, wherein one or more of the alkyl group's hydrogen atoms have been replaced with a heterocyclyl as defined above. Heterocyclylalkyl moieties include but are not limited to piperidin-4-ylmethyl, pyrrolidin-1-ylmethyl. A hetreocyclylalkyl group can be unsubstituted or substituted with one or more suitable groups.

As used herein the term "substituted" refers to a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. It should be recognized that if there are more than one substitution on a substituent, each non-hydrogen radical may be identical or different, unless otherwise stated.

As used herein, the term "composition" is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

As used herein, the term "treat", "treating" and "treatment" refer to a method of alleviating or abrogating a disease and/or its attendant symptoms.

As used herein, the term "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

As used herein, the term "therapeutically effective amount" refers to that amount of the compound being administered sufficient to prevent development of or alleviate to some extent one or more of the symptoms of the condition or disorder being treated.

As used herein the term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

In a further aspect, the present invention relates to a process for preparing substituted pyridine derivatives of formula (I).

An embodiment of the present invention provides the ALK inhibitor compounds according to of formula (I) may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used but such conditions can be determined by the person skilled in the art, using routine optimisation procedures. Moreover, by utilizing the procedures described in detail, one of ordinary skill in the art can prepare additional compounds of the present invention claimed herein. All temperatures are in degrees Celsius (° C.) unless otherwise noted.

In a further aspect, the compounds of the present invention can also contain unnatural proportions of atomic isotopes at one or more of the atoms that constitute such compounds. For example the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention and their uses. Exemplary isotopes that can be incorporated in to compounds of the invention include isotopes of hydrogen, carbon, nitrogen, oxygen, phosphorous, sulfur, fluorine, chlorine and iodine, such as $^{2}H$ ("D"), $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically labeled compounds of the present inventions can generally be prepared by following procedures analogous to those disclosed in the Schemes and/or in the Examples herein below, by substituting an isotopically labeled reagent for a non-isotopically labeled reagent.

The abbreviations used in the entire specification may be summarized hereinbelow with their particular meaning.

° C. (degree Celsius); δ (delta); % (percentage); ACN (Acetonitrile); BnBr (Benzyl bromide); $(BoC)_2O$ (Di tert-butyl dicarbonate); $CDCl_3$ (Deuteriated chloroform); $CH_2Cl_2$/DCM (Dichloromethane); $CH_3SO_2CL$/$MeSO_2Cl$ (Methanesulfonyl chloride); $CuNO_2$ DMF (Dimethyl formamide); DMA (Dimethyl acetamide); DMSO (Dimethyl sulphoxide); DME (Dimethoxy ethane); DIPEA/DIEA (N, N-Diisopropyl ethylamine); DMAP (Dimethyl amino pyridine); DMSO-$d_6$ (Deuteriated DMSO); d (Doublet); dd (Doublet of doublet); dt (Doublet of triplet); EtOH (Ethanol); $Et_2O$ (Diethyl ether); EtOAc (Ethyl acetate); g or gr (gram); H or $H_2$ (Hydrogen); $H_2O$ (Water); HOBt (1-Hydroxy benzotriazole); HCl (Hydrochloric acid); h or hr (Hours); HATU (2-(1H-7-Azabenzotriazol-1-yl)-1,1,3,3-tetramethyl uranium hexafluoro phosphate methanaminium); Hz (Hertz); HPLC (High-performance liquid chromatography); $LiOH.H_2O$ (Lithium hydroxide mono hydrate); MeOH/$CH_3OH$ (Methanol); MP (Melting point); mmol (Millimol); M (Molar); µl (Micro liter); ml (Milliliter); mg (Milli gram); m (Multiplet); mm (Millimeter); MHz (Megahertz); MS (ES) (Mass spectroscopy-electro spray); min (Minutes); mM (milli molar); NaOH (Sodium hydroxide); $Na_2SO_4$ (Sodium sulphate); $N_2$ (Nitrogen); NMR (Nuclear magnetic resonance spectroscopy); $Na(OAc)_3BH$ (Sodium triacetoxy borohydride), $NH_4Cl$ (Ammonium chloride); $Na_2CO_3$ (Sodium carbonate); $NH_2OH.HCl$ (Hydroxylamine hydrochloride; 10% Pd/C (10% palladium activated carbon); $Pd(PPh_3)_2Cl_2$ (Bis(triphenylphosphino)palladium(II) dichloride); $Pd(dppf)_2Cl_2$(1,1'-Bis(diphenylphosphino)ferrocene) palladium(II) dichloride; $Pd_2(dba)_3$ (Trisdibenzylidene acetone) dipalladium; $Pd(pph_3)_4$ [Tetrakistriphenylphosphine palladium(0)]; P (o-tolyl)$_3$ (Tri-o-tolyl phosphine); RT (Room temperature), SiO$_2$ (Silicon Dioxide), S (Singlet); TEA (Triethyl amine); TFA (Trifluoroaceticacid); TLC (Thin Layer Chromatography); THF (Tetrahydrofuran); tert (Tertiary); TFA/CF$_3$COOH (Trifluoro acetic acid); t (Triplet); Xantphos (4,5-Bis(diphenylphosphino)-9,9-dimethylxanthene); Zn (Zinc), MHz (Mega Hertz), RM (Reaction mass), pH (Pouvoir hydrogen), TR-FRET (Time resolved fluorescence resonance energy transfer), IC (Inhibitory concentration), nM (Nano molar).

General Modes of Preparation:

Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

A general approach for the synthesis of compounds of general formula (I) is depicted in below schemes. As used herein the below schemes the terms R$_1$, R$_2$, R$_3$, R$_4$, R$_5$, X$^1$, X$^2$, Y$^1$, Y$^2$, Y$^3$, m, n, p and q represents all the possible substitutions as disclosed in formula (I). The term "PG" in below schemes means protecting groups, which include but are not limited to acetyl, benzoyl, benzyl (phenylmethyl), benzylidene, benzyloxycarbonyl (Cbz), tert-butoxycarbonyl (Boc), 3,4-dimethoxybenzyloxy carbonyl, diphenylmethyl, diphenylphosphoryl, formyl, methanesulfonyl, para-methoxy benzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Scheme-1A:

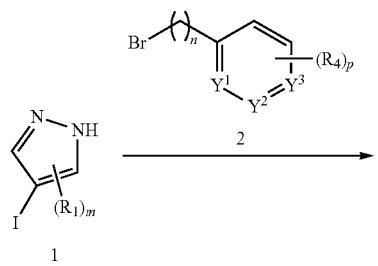

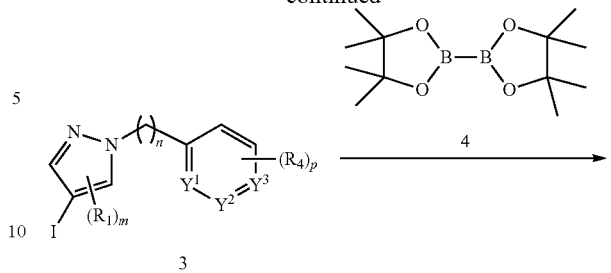

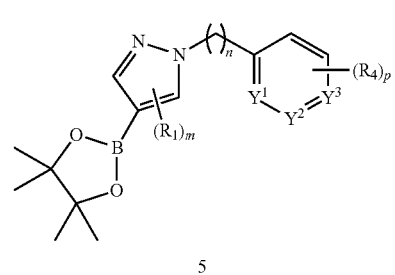

A general method for synthesis of compounds of formula 5 is depicted in scheme-1A; wherein the compounds of formula 1 was treated with compounds of formula 2 in presence of suitable base (K$_2$CO$_3$, Na$_2$CO$_3$ or NaH) and suitable solvent (DMF) to give compounds of formula 3, which on reacting with compound 4 in presence of suitable base (CH$_3$COO$^-$K$^+$) and catalyst (such as bis(triphenylphosphine)palladium(II) dichloride, 1,1'-bis(diphenylphosphino)ferrocene palladium (II) chloride) in presence of suitable solvent (DMSO) under inert conditions to affords boronate compounds of formula 5, which is e used for the preparation of compounds of formula (I).

A general approach for the synthesis of compounds of the present invention is depicted in scheme-1, scheme-2 and scheme-3.

Scheme-1:

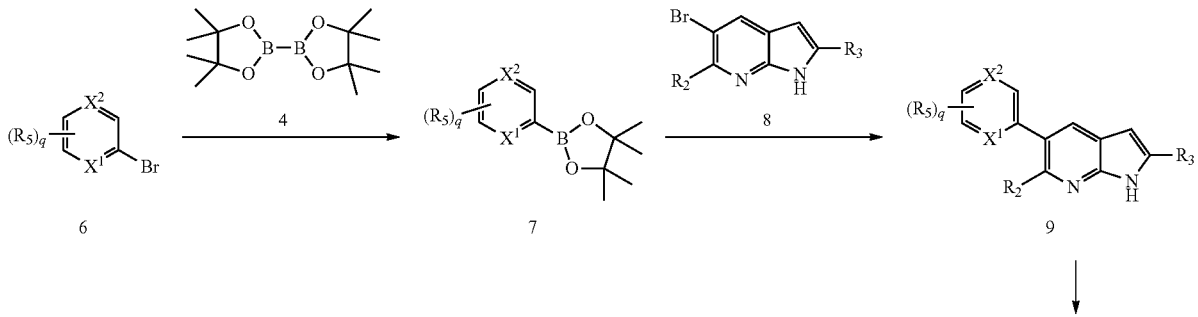

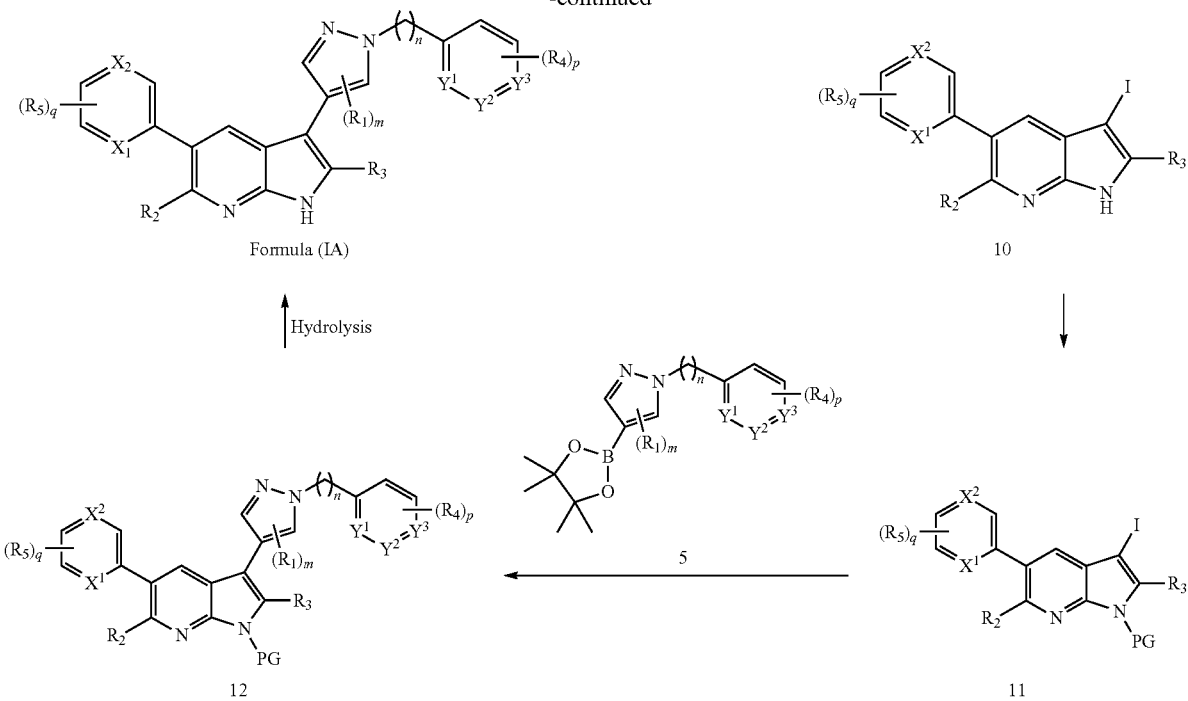

The first general approach for the synthesis of compounds of formula (IA) is depicted in scheme-1. The compound of formula 6 reacts with Bis(pinacolato)diboron of formula 4 in presence of suitable palladium catalyst to give boronic ester of formula 7. The compound of formula 7 couples with compound of formula 8 under standard coupling condition to give compound of formula 9 which on iodination with suitable reagent (for example N-iodo succinimide) and N-protection with suitable protecting group (for example t-BOC or p-toluene sulfonyl chloride) gives compound of formula 11. Coupling of compound of formula 11 with compound of formula 5 under standard coupling condition gives compound of formula 12 which on hydrolysis give compounds of formula (IA).

Scheme-2:

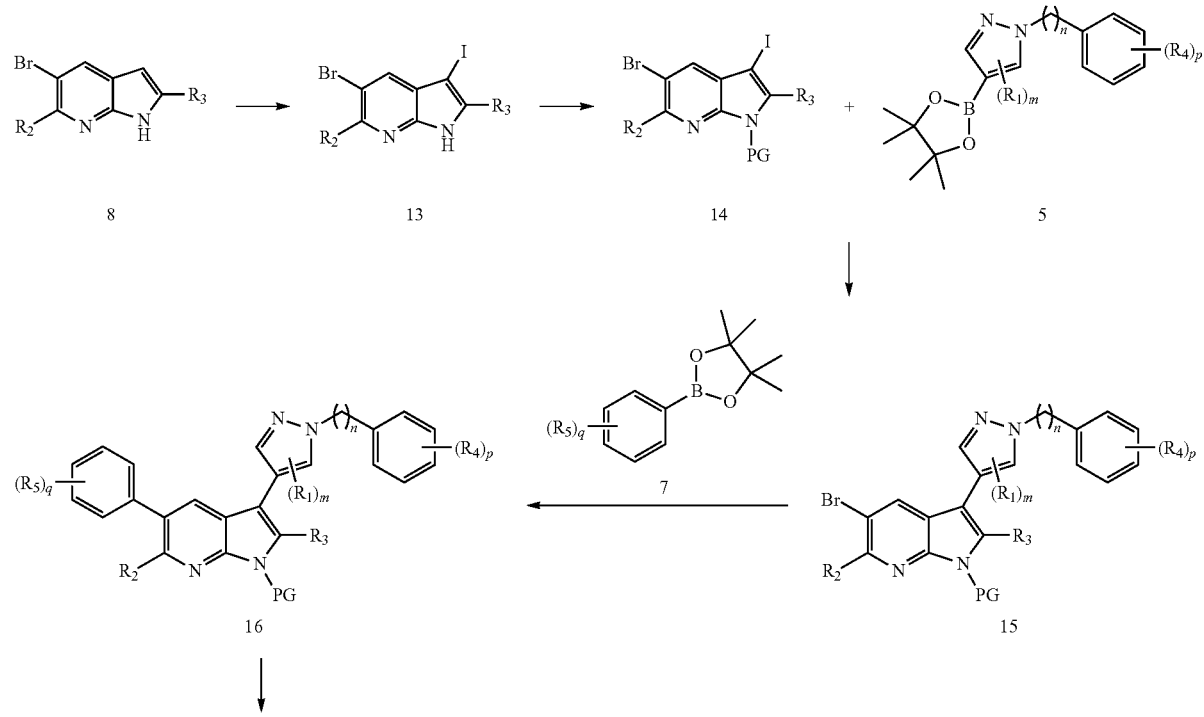

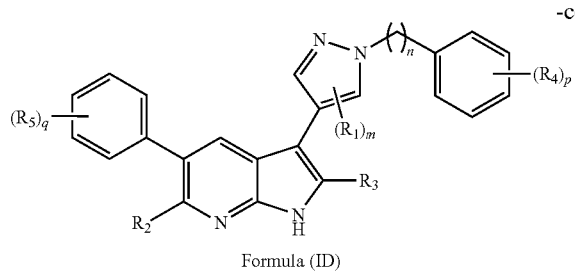

Formula (ID)

Alternatively compounds of formula (ID) can also be prepared by following general synthetic approach as depicted in scheme-2. Compound of formula 13 can be obtained by iodination of compound 8 followed by N-protection with appropriate protecting group. Coupling of compound 14 with compound 5 under standard coupling condition affords compound 15. Compound of formula 15 further couples with compound of formula 7 to give compound of formula 16 which on hydrolysis affords compounds of formula (ID).

Scheme-3:

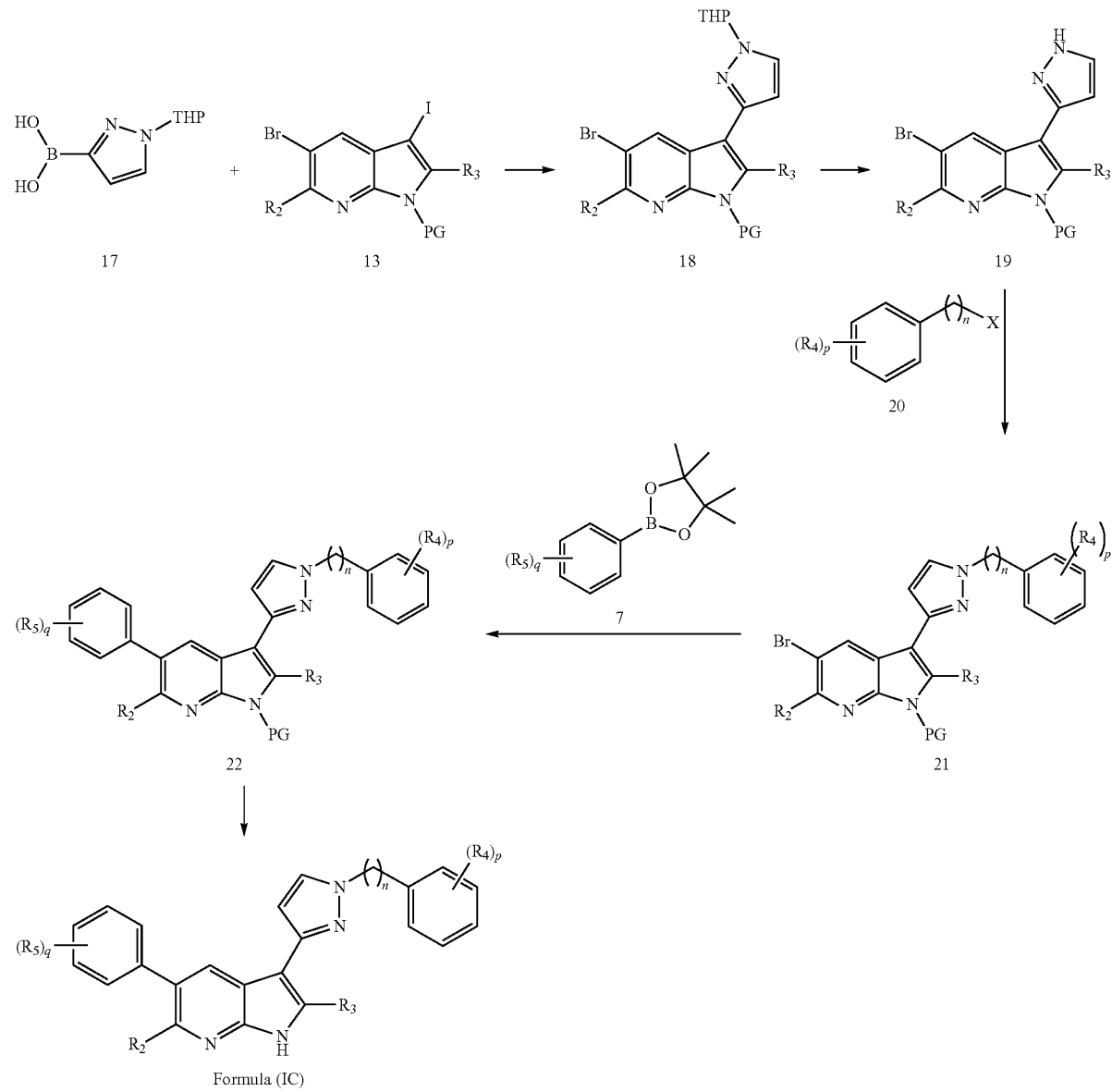

The first general approach for the synthesis of compounds of formula (IC) is depicted in scheme-3. The THP protected pyrazole boronic acid of formula 17 reacts with compound formula 13 in presence of suitable palladium catalyst to give compound of formula 18. THP deprotection of formula 18 with suitable deprotecting agent gives compound formula 19. The compound of formula 19 is alkylated with compound of formula 20 with suitable solvent like DMF and base gives compound of formula 21. The compound of formula 21 couples with formula 7 boronic ester to give compound of formula 22 which on hydrolysis give compounds of formula (IC).

The specifics of the process for preparing compounds of the present invention are detailed in the experimental section.

In the following, the present invention shall be illustrated by means of some examples, which are not construed to be viewed as limiting the scope of the invention.

The commercially available starting materials used in the following experimental description were purchased from Aldrich or Fluka unless otherwise reported.

EXPERIMENTAL

Unless otherwise stated, work-up includes distribution of the reaction mixture between the organic and aqueous phase indicated within parentheses, separation of layers and drying the organic layer over sodium sulphate, filtration and evaporation of the solvent. Purification, unless otherwise mentioned, includes purification by silica gel chromatographic techniques, generally using ethyl acetate/petroleum ether mixture of a suitable polarity as the mobile phase. Use of a different eluent system is indicated within parentheses.

Analysis for the compounds of the present invention unless mentioned, was conducted in the general methods well known to the person skilled in the art. Having described the invention with reference to certain preferred embodiments, other embodiments will become apparent to one skilled in the art from consideration of the specification. The invention is further defined by reference to the following examples, describing in detail the analysis of the compounds of the invention.

It will be apparent to those skilled in the art that many modifications, both to materials and methods, may be practiced without departing from the scope of the invention.

HPLC Methods for Measuring Chemical Purity of the compounds of the invention was conducted by the following methods. Unless otherwise mentioned the method of HPLC, the HPLC is conducted in method D.
Column: Agilent Eclipse XDB-C18 (150 mm×4.6 mm×5µ)
Method A: A=0.01% TFA in water, B=ACN:MeOH (1:1); gradient: 95:05
Method B: A=0.01% TFA in water, B=ACN:MeOH (1:1); gradient: 70:30
Method C: A=5 mM Ammonium acetate in water, B=ACN; gradient: 70:30
Method D: A=water, B=ACN; gradient: 95:05
If required some of the compounds of the present invention were purified by preparative HPLC by using the methods either method 1 or method 2.
COLUMN: WATERS XBRIDGE OBD C18 (19 mm×150 mm×5µ)
Or AGILENT ZORBAX XDB C18 (21.2 mm×150 mm×5µ)
FLOW: 15 to 20 ML/MIN
Method 1: Mobile phase A: 0.01% TFA IN WATER
 Mobile phase B: ACETONITRILE:METHANOL (1:1)
Method 2: Mobile phase A: 10 mM ammonium acetate
 Mobile phase B: ACETONITRILE

Intermediates

Intermediate 1: 5-Bromo-3-iodo-1-tosyl-1H-pyrrolo[2,3-b]pyridine

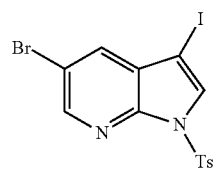 [SMILES: Cc1ccc(S(=O)(=O)n2cc(I)c3cc(Br)cnc32)cc1]

Step-i: 5-Bromo-3-iodo-1H-pyrrolo[2,3-b]pyridine

5-Bromo-1H-pyrrolo[2,3-b]pyridine (5 g, 25 mmol) was dissolved in anhydrous acetone (75 ml) and added N-iodo succinimide (6.18 g, 27.5 mmol) under nitrogen atmosphere and stirred at RT for 2 h. The reaction was monitored by TLC (10% Ethyl acetate in hexane). The reaction mixture was cooled to RT and filtered, washed with cold acetone (50 ml) and dried under vacuum to afford 7.05 g (87% yield) of 5-bromo-3-iodo-1H-pyrrolo[2,3-b]pyridine.
MS: m/z=324.6 (M+1); HPLC: 91.11% in method B.

Step-ii: 5-Bromo-3-iodo-1-tosyl-1H-pyrrolo[2,3-b]pyridine

5-Bromo-3-iodo-1H-pyrrolo[2,3-b]pyridine (7 g, 21.6 mmol) dissolved in dry DMF (50 ml) was added drop wise to a stirred slurry of sodium hydride (1.73 g, 43.2 mmol) in dry DMF (20 ml) at 0° C. and stirred for 30 min. Tosyl chloride (6.15 g, 32.4 mmol) dissolved in dry DMF (14 ml) and added slowly to the above reaction mixture and the reaction temperature was brought to RT and stirred for 30 min. The reaction was monitored by TLC (15% Ethyl acetate in hexane). The reaction mixture was quenched with ice water (500 ml) at 0° C. and filtered the solid precipitated and dried under vacuum to afford 9.92 g (96.3% yield) of 5-bromo-3-iodo-1-tosyl-1H-pyrrolo[2,3-b]pyridine MS: m/z=476.8 (M+1).

Intermediate 2: 1-(2-fluorobenzyl)-4-(4,4,5,5-tetramethyl-1,3,2-dioxaborolan-2-yl)-1H-pyrazole

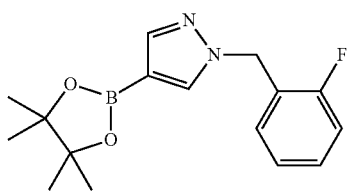 [SMILES: CC1(C)OB(c2cnn(Cc3ccccc3F)c2)OC1(C)C]

Step-i: 1-(2-fluorobenzyl)-4-iodo-1H-pyrazole

To a stirred solution 4-iodo-1H-pyrazole (1.5 g, 7.7 mmol) in DMF (15 ml) was added potassium carbonate (3.2 g, 23.2 mmol) followed by drop wise addition of 2-fluoro benzyl bromide (2.56 g, 8.5 mmol) and stirred the reaction at RT for 15 h. The reaction was monitored by TLC (50% ethyl acetate in hexane). The reaction mixture was diluted with ice water (150 ml) and extracted with ethyl acetate (2×50 ml). The organic layer was dried over $Na_2SO_4$, and concentrated under reduced pressure to afford 2.25 g (96.56% yield) of 1-(2-fluorobenzyl)-4-iodo-1H-pyrazole.

Step-ii: 1-(2-fluorobenzyl)-4-(4,4,5,5-tetramethyl-1,3,2-dioxaborolan-2-yl)-1H-pyrazole 1-(2-fluorobenzyl)-4-iodo-1H-pyrazole (2.25 g, 7.4 mmol) and bispinocalatodiboron (2.07 g, 8.2 mmol) were added to a solution of DMSO (20 ml) previously purged with argon (10 min). The reaction mixture was purged with argon for a further 15 mins, followed by the addition of potassium acetate (2.19 g, 22.3 mmol) and bis(triphenylphosphine)palladium (II)dichloride (261 mg, 0.3725 mmol). The resulting mixture was heated to reflux at 80° C. overnight. The reaction was monitored by TLC (40% ethyl acetate in hexane). The reaction mixture was cooled and diluted with ethyl acetate (100 ml) and filtered over celite bed and the filtrate was washed with cold water (2×100 ml). The organic layer was dried over $Na_2SO_4$, and concentrated under reduced pressure to afford 2.3 g of the crude product which was taken as such for next reaction. $^1$H NMR (DMSO-$d_6$, 300 MHz): δ 8.01 (s, 1H), 7.95 (s, 1H), 7.37 (m, 2H), 7.19-7.17 (m, 2H), 5.40 (s, 2H), 1.2 (m, 12H).

All the substituted 1-benzyl-1H-pyrazole boronic ester listed in Table 1 were prepared by using appropriate 4-halo-1H-pyrazole (reactant A) and substituted benzyl bromide (reactant B) by following similar procedure as depicted in intermediate-2. Most of these intermediates were used in the next step without further purification. Structure information and characterization data for some of the intermediates are given in Table-1.

TABLE 1

Intermediates prepared using similar procedure of Intermediate 2

| Intermediate | Reactant A | Reactant B | Product | MS (m/z) |
|---|---|---|---|---|
| 4. | 4-iodo-1H-pyrazole | 3-(trifluoromethyl)benzyl bromide | 1-(3-(trifluoromethyl)benzyl)-4-(pinacolboronate)-1H-pyrazole | — |
| 5. | 4-iodo-1H-pyrazole | 4-methoxybenzyl chloride | 1-(4-methoxybenzyl)-4-(pinacolboronate)-1H-pyrazole | — |
| 6. | 4-iodo-1H-pyrazole | 2,5-difluorobenzyl bromide | 1-(2,5-difluorobenzyl)-4-(pinacolboronate)-1H-pyrazole | 320.9 (M + 1) |
| 7. | 4-iodo-1H-pyrazole | 4-fluorobenzyl bromide | 1-(4-fluorobenzyl)-4-(pinacolboronate)-1H-pyrazole | — |
| 8. | 4-iodo-1H-pyrazole | 3,5-difluorobenzyl bromide | 1-(3,5-difluorobenzyl)-4-(pinacolboronate)-1H-pyrazole | — |

TABLE 1-continued

Intermediates prepared using similar procedure of Intermediate 2

| Intermediate | Reactant A | Reactant B | Product | MS (m/z) |
|---|---|---|---|---|
| 10. | 4-iodo-1H-pyrazole | 3-nitrobenzyl bromide | 1-(3-nitrobenzyl)-4-(4,4,5,5-tetramethyl-1,3,2-dioxaborolan-2-yl)-1H-pyrazole | 330.3 (M + 1) |
| 11. | 4-iodo-1H-pyrazole | 3-fluorobenzyl chloride | 1-(3-fluorobenzyl)-4-(4,4,5,5-tetramethyl-1,3,2-dioxaborolan-2-yl)-1H-pyrazole | 303.3 (M + 1) |
| 12. | 4-bromo-3-methyl-1H-pyrazole | 3-fluorobenzyl bromide | 1-(3-fluorobenzyl)-3-methyl-4-(4,4,5,5-tetramethyl-1,3,2-dioxaborolan-2-yl)-1H-pyrazole | — |
| 13. | 4-bromo-1H-pyrazole | 3-chlorobenzyl bromide | 1-(3-chlorobenzyl)-4-(4,4,5,5-tetramethyl-1,3,2-dioxaborolan-2-yl)-1H-pyrazole | — |
| 14. | 4-bromo-1H-pyrazole | 3-cyanobenzyl bromide | 3-((4-(4,4,5,5-tetramethyl-1,3,2-dioxaborolan-2-yl)-1H-pyrazol-1-yl)methyl)benzonitrile | 310.3 (M + 1) |
| 15. | 4-bromo-1H-pyrazole | benzyl bromide | 1-benzyl-4-(4,4,5,5-tetramethyl-1,3,2-dioxaborolan-2-yl)-1H-pyrazole | 285.3 (M + 1) |

TABLE 1-continued

Intermediates prepared using similar procedure of Intermediate 2

| Intermediate | Reactant A | Reactant B | Product | MS (m/z) |
|---|---|---|---|---|
| 64 | 4-iodo-1H-pyrazole | 3-(bromomethyl)pyridine | 3-((4-(4,4,5,5-tetramethyl-1,3,2-dioxaborolan-2-yl)-1H-pyrazol-1-yl)methyl)pyridine | — |
| 64A | 4-iodo-1H-pyrazole | 1-(2-chloroethyl)-2-fluorobenzene | 1-(2-(2-fluorophenyl)ethyl)-4-(4,4,5,5-tetramethyl-1,3,2-dioxaborolan-2-yl)-1H-pyrazole | — |
| 64B | 4-iodo-1H-pyrazole | 1-(2-bromoethyl)-3-fluorobenzene | 1-(2-(3-fluorophenyl)ethyl)-4-(4,4,5,5-tetramethyl-1,3,2-dioxaborolan-2-yl)-1H-pyrazole | — |
| 64C | 4-iodo-1H-pyrazole | 1-(2-bromoethyl)-4-fluorobenzene | 1-(2-(4-fluorophenyl)ethyl)-4-(4,4,5,5-tetramethyl-1,3,2-dioxaborolan-2-yl)-1H-pyrazole | — |
| 64D | 4-iodo-1H-pyrazole | 1-(bromomethyl)-3-methylbenzene | 1-(3-methylbenzyl)-4-(4,4,5,5-tetramethyl-1,3,2-dioxaborolan-2-yl)-1H-pyrazole | — |
| 64E | 4-iodo-1H-pyrazole | 1-(benzyloxy)-3-(bromomethyl)benzene | 1-(3-(benzyloxy)benzyl)-4-(4,4,5,5-tetramethyl-1,3,2-dioxaborolan-2-yl)-1H-pyrazole | — |

TABLE 1-continued

Intermediates prepared using similar procedure of Intermediate 2

| Inter-mediate | Reactant A | Reactant B | Product | MS (m/z) |
|---|---|---|---|---|
| 64F | | | | — |
| 64G | | | | — |
| 64H | | | | — |

Intermediate 3: N-(3-(4,4,5,5-tetramethyl-1,3,2-dioxaborolan-2-yl)phenyl)methane sulfonamide

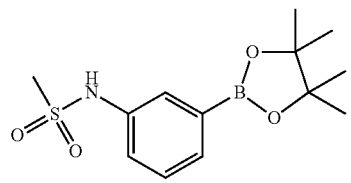 [SMILES: CC1(C)OB(c2cccc(NS(C)(=O)=O)c2)OC1(C)C]

Step-i: N-(3-Bromophenyl)methanesulfonamide

To a stirred solution of 3-bromo aniline (6 g, 34.87 mmol) in dry DCM (200 ml) at 10° C. was added pyridine (4.13 mg, 52.31 mmol) followed by methane sulfonyl chloride (5.194 g, 45.34 mmol) and stirred at RT for 15 h. The reaction was monitored by TLC (35% Ethyl acetate in hexane). The reaction mixture was diluted with DCM (50 ml) and washed with 1N HCl (25 ml). The organic layer was dried over $Na_2SO_4$, and concentrated under reduced pressure to afford 8.45 g (96.3% yield) of N-(3-bromophenyl) methanesulfonamide. $^1$H NMR (DMSO-$d_6$, 300 MHz): δ 10.01 (s, 1H), 7.368 (s, 1H), 7.365-7.19 (m, 3H), 3.03 (s, 1H). MS: m/z=251.8 (M+1).

Step-ii: N-(3-(4,4,5,5-tetramethyl-1,3,2-dioxaborolan-2-yl)phenyl)methanesulfonamide N-(3-bromophenyl) methane sulfonamide (8.3 g, 33 mmol) and bispinocalatodiboron (10.11 g, 39.8 mmol) were added to a solution of DME (80 ml) previously purged with argon (10 min). The reaction mixture was purged with argon for a further 15 mins, followed by the addition of potassium acetate (9.77 g, 94.6 mmol) and $PdCl_2$(dppf) (813 mg, 0.99 mmol). The resulting mixture was heated to reflux at 80° C. overnight. The reaction was monitored by TLC (15% ethyl acetate in hexane). The reaction mixture was cooled and diluted with ethyl acetate (100 ml) and filtered over celite bed and the filtrate was washed with water (2×100 ml). The organic layer was dried over $Na_2SO_4$, and concentrated under reduced pressure to afford the crude product. Purification by column chromatography on silica gel (15% ethyl acetate in hexane) afforded 9.3 g (94.8% yield) of N-(3-(4,4,5,5-tetramethyl-1,3,2-dioxaborolan-2-yl)phenyl) methane sulfonamide. MS: m/z=298.1 (M+1) All the substituted N-phenyl-methanesulfonamide boronic esters listed in Table 3 were prepared by using appropriate bromo anilines (Reactant A) and alkylsulfonylchloride (Reactant B) by following similar procedure as depicted in intermediate-3. Most of the intermediate were used in the next step of reaction without purification. Structure information and characterization data for selected intermediates are given in Table-2.

TABLE 2
Intermediates prepared using similar procedure of intermediate 3
| Intermediate | Reactant A | Reactant B | Product | MS (m/z) |
|---|---|---|---|---|
| 17. | 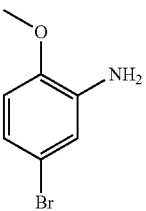 | Methane sulfonyl chloride | 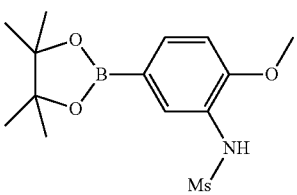 | — |
| 18. | 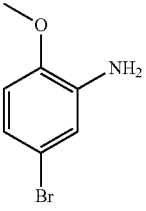 | Ethane sulfonyl chloride | 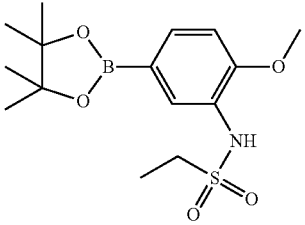 | — |
| 19. | 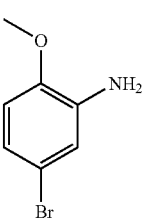 | Cyclopropyl sulfonyl chloride | 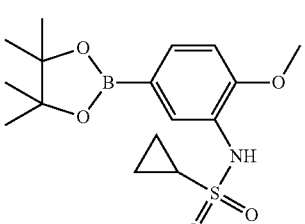 | — |
| 20. | 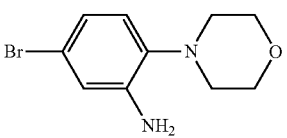 [SMILES: Nc1cc(Br)ccc1N1CCOCC1] | Methane sulfonyl chloride | 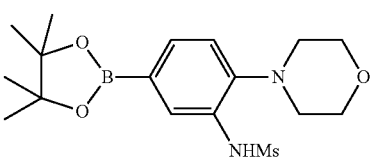 | 383.3 (M + 1) |
| 65 | 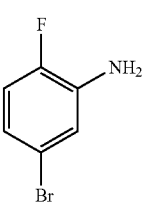 | Methane sulfonyl chloride | 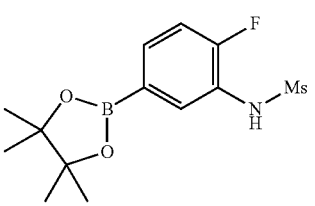 [SMILES: CC1(C)OB(c2ccc(F)c(NS(C)(=O)=O)c2)OC1(C)C] | — |
| 65A | 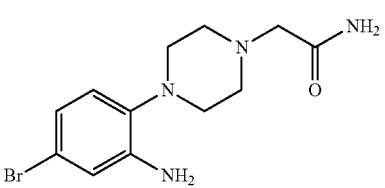 | Methane sulfonyl chloride | 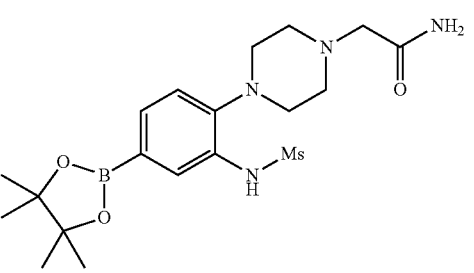 [SMILES: CC1(C)OB(c2ccc(N3CCN(CC(N)=O)CC3)c(NS(C)(=O)=O)c2)OC1(C)C] | — |

TABLE 2-continued

Intermediates prepared using similar procedure of intermediate 3

| Intermediate | Reactant A | Reactant B | Product | MS (m/z) |
|---|---|---|---|---|
| 65C | H₂N-, -OMe, -Br (aniline) | Methane sulfonyl chloride | Ms—HN-phenyl-OMe-Bpin | — |
| 65D | 5-bromo-2-methoxy-3-aminopyridine | Methane sulfonyl chloride | 2-methoxy-3-(NHMs)-5-Bpin-pyridine | — |
| 65E | 4-(N-Boc-tetrahydropyridinyl)-2-amino-bromobenzene | Methane sulfonyl chloride | 4-(N-Boc-tetrahydropyridinyl)-2-(NHMs)-Bpin-benzene | — |

Intermediate 9: N-(3-(3-iodo-1-tosyl-1H-pyrrolo[2, 3-b]pyridin-5-yl)phenyl)methane sulfonamide

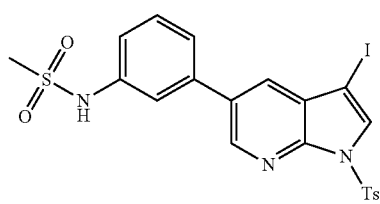 [SMILES: Cc1ccc(S(=O)(=O)n2cc(I)c3cc(-c4cccc(NS(C)(=O)=O)c4)cnc32)cc1]

Step-i: N-(3-(1H-pyrrolo[2,3-b]pyridin-5-yl)phenyl) methanesulfonamide 5-bromo-1H-pyrrolo[2,3-b]pyridine (1 g, 5 mmol) and N-(3-(4,4,5,5-tetramethyl-1,3,2-dioxaborolan-2-yl)phenyl) methanesulfonamide (intermediate 3) (1.6 g, 5 mmol) were added to a solution of toluene/ethanol/water (6/6/5 ml) previously purged with argon (10 min). The reaction mixture was purged with argon for a further 15 mins, followed by the addition of sodium carbonate (1.64 g, 15 mmol) and PdCl₂ (dppf) (181 mg, 0.2 mmol) and DME/water (10/5 ml). The resulting mixture was heated to reflux at 80° C. overnight. The reaction was monitored by TLC (50% ethylacetate in hexane). The reaction mixture was cooled and diluted with ethyl acetate (50 ml) and washed with water (2×50 ml). The organic layer was dried over Na₂SO₄, and concentrated under reduced pressure to afford crude product. Purification by column chromatography on silica gel (40% ethyl acetate in hexane) afforded 800 mg (57% yield) MS: m/z=287.9 (M+1).

Step-ii: N-(3-(3-iodo-1H-pyrrolo[2,3-b]pyridin-5-yl) phenyl)methanesulfonamide

Using similar reaction conditions as described in step i of intermediate 1, N-(3-(1H-pyrrolo[2,3-b]pyridin-5-yl)phenyl)methanesulfonamide (800 mg, 3 mmol) was iodinated with N-iodo succinimide (764 mg, 3 mmol) in acetone (5 ml) to afford 600 mg (50% yield) of the pure product. LCMS: m/z=413.4 (M+1).

Step-iii: N-(3-(3-iodo-1-tosyl-1H-pyrrolo[2,3-b]pyridin-5-yl)phenyl)methanesulfonamide Using similar reaction conditions as described in, step ii of Intermediate 1, N-(3-(3-iodo-1H-pyrrolo[2,3-b]pyridin-5-yl) phenyl)methanesulfonamide (800 mg, 1.93 mmol) was tosylated with p-toluene sulfonylchloride (100 mg, 2.09 mmol) and 60% suspension of sodium hydride in paraffin (193 mg, 4.82 mmol) in DMF (10 mL) to afford 800 mg of the titled compound.

All the substituted 5-phenyl pyrrolo[2,3-b]pyridine derivatives listed in table 5 were prepared by reacting Reactant A with Reactant B by following similar reaction procedure as described in intermediate-9. (Boc)₂O also used as a protecting group for some intermediates prepared using General procedure of intermediate 9. Most of the intermediate were used in the next step of reaction without purification. Structure information and characterization data for selected intermediates are given in Table-3.

TABLE 3
Intermediates Prepared Using General procedure of intermediate 9
| Intermediate | Reactant A | Reactant B |
|---|---|---|
| 22. | 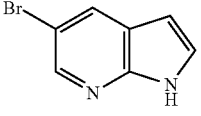 | 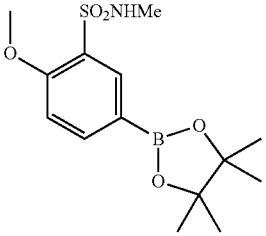 |
| 23. | 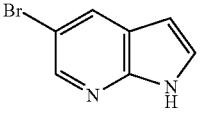 | 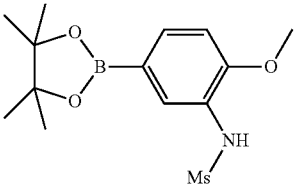 |
| 26. | 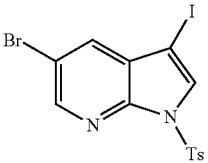 | 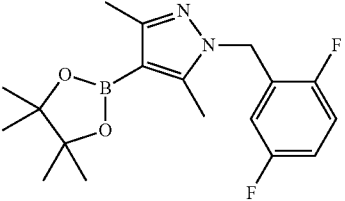 [SMILES: Cc1nn(Cc2cc(F)ccc2F)c(C)c1B1OC(C)(C)C(C)(C)O1] |
| 32 | 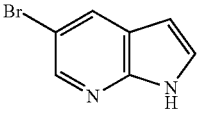 | 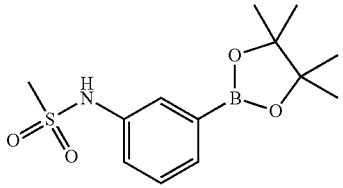 [SMILES: CC1(C)OB(c2cccc(NS(C)(=O)=O)c2)OC1(C)C] |
| 33. | 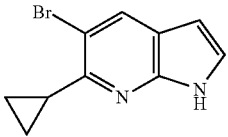 [SMILES: Brc1cc2cc[nH]c2nc1C1CC1] | 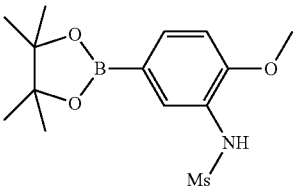 |
| 34. | 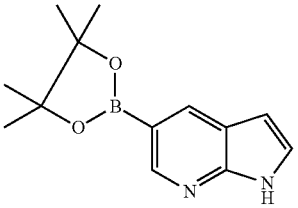 [SMILES: CC1(C)OB(c2cnc3[nH]ccc3c2)OC1(C)C] | 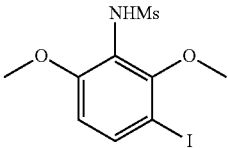 |
| 35. | 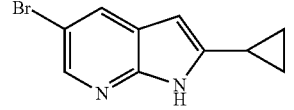 | 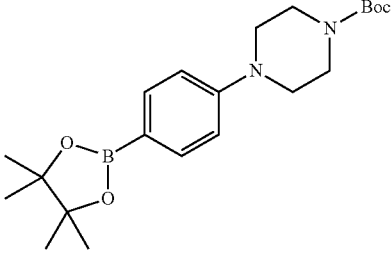 [SMILES: CC(C)(C)OC(=O)N1CCN(c2ccc(B3OC(C)(C)C(C)(C)O3)cc2)CC1] |

TABLE 3-continued
Intermediates Prepared Using General procedure of intermediate 9
| | | |
|---|---|---|
| 36. | 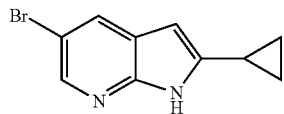 [SMILES: Brc1cnc2[nH]c(C3CC3)cc2c1] | 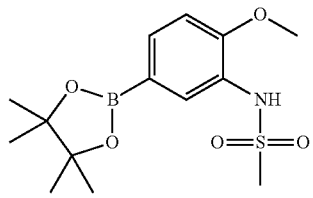 [SMILES: COc1ccc(B2OC(C)(C)C(C)(C)O2)cc1NS(C)(=O)=O] |
| 39. | 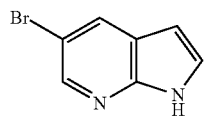 | 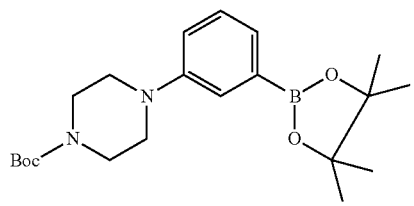 [SMILES: CC(C)(C)OC(=O)N1CCN(c2cccc(B3OC(C)(C)C(C)(C)O3)c2)CC1] |
| 41 | 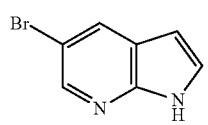 | 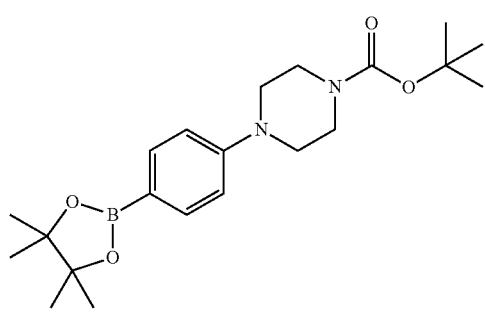 [SMILES: CC(C)(C)OC(=O)N1CCN(c2ccc(B3OC(C)(C)C(C)(C)O3)cc2)CC1] |
| 42. | 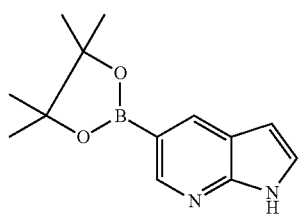 [SMILES: CC1(C)OB(c2cnc3[nH]ccc3c2)OC1(C)C] | 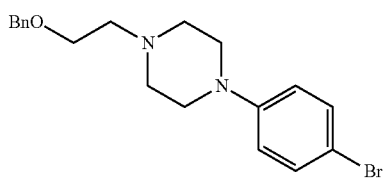 [SMILES: Brc1ccc(N2CCN(CCOCc3ccccc3)CC2)cc1] |
| 43. | 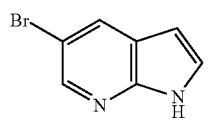 | 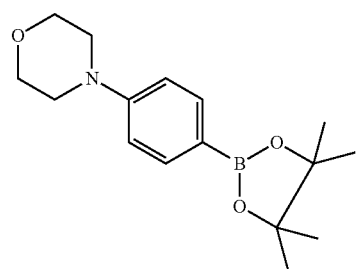 [SMILES: CC1(C)OB(c2ccc(N3CCOCC3)cc2)OC1(C)C] |
| 47. | 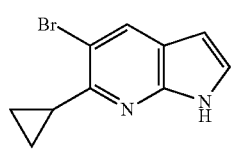 [SMILES: Brc1cc2cc[nH]c2nc1C1CC1] | 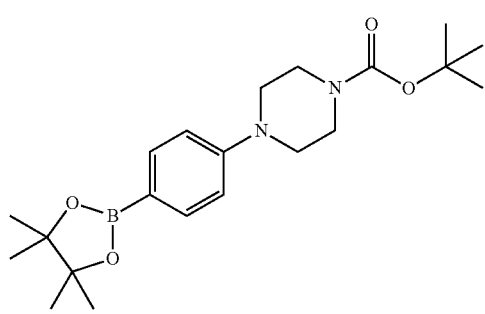 [SMILES: CC(C)(C)OC(=O)N1CCN(c2ccc(B3OC(C)(C)C(C)(C)O3)cc2)CC1] |

TABLE 3-continued
Intermediates Prepared Using General procedure of intermediate 9
48. 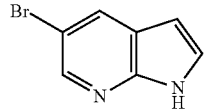 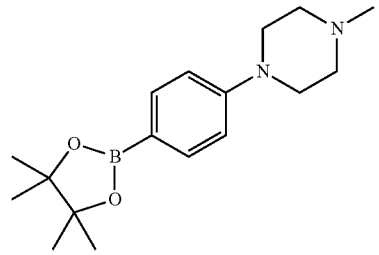
49. 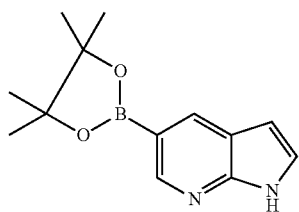 [SMILES: CC1(C)OB(c2cnc3[nH]ccc3c2)OC1(C)C] 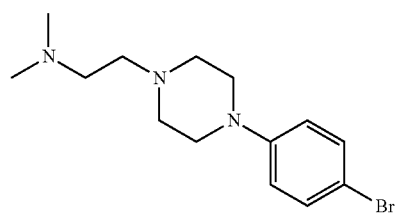 [SMILES: CN(C)CCN1CCN(c2ccc(Br)cc2)CC1]
50. 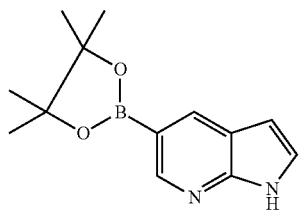 [SMILES: CC1(C)OB(c2cnc3[nH]ccc3c2)OC1(C)C] 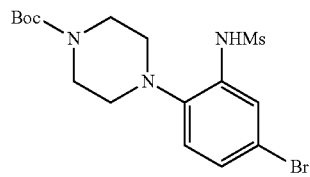
52. 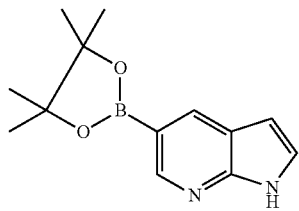 [SMILES: CC1(C)OB(c2cnc3[nH]ccc3c2)OC1(C)C] 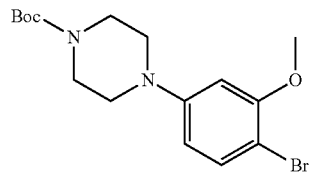
57. 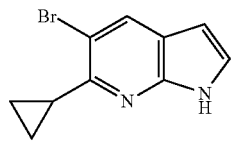 [SMILES: Brc1cc2cc[nH]c2nc1C1CC1] 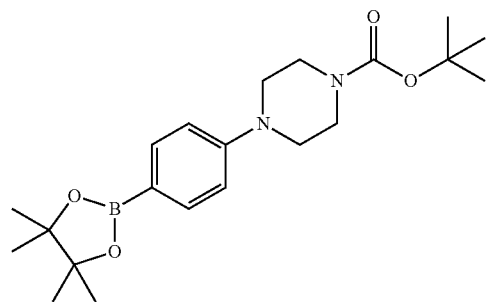 [SMILES: CC(C)(C)OC(=O)N1CCN(c2ccc(B3OC(C)(C)C(C)(C)O3)cc2)CC1]
58. 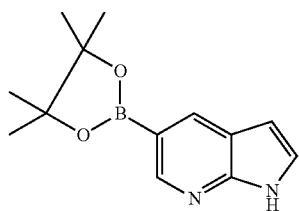 [SMILES: CC1(C)OB(c2cnc3[nH]ccc3c2)OC1(C)C] 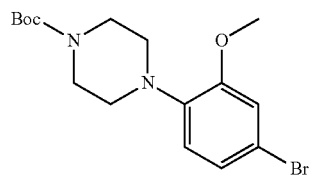 [SMILES: COc1cc(Br)ccc1N1CCN(C(=O)OC(C)(C)C)CC1]

TABLE 3-continued
Intermediates Prepared Using General procedure of intermediate 9
| | | |
|---|---|---|
| 66 | 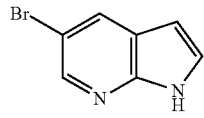 | 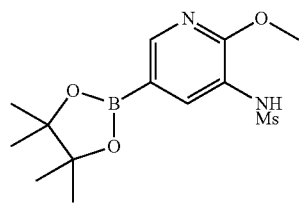 |
| 66A | 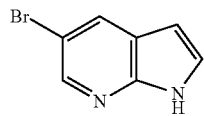 | 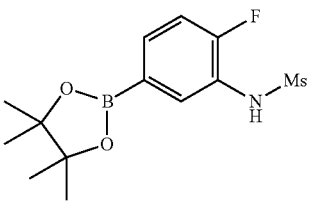 [SMILES: CC1(C)OB(c2ccc(F)c(NS(C)(=O)=O)c2)OC1(C)C] |
| 66B | 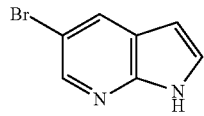 | 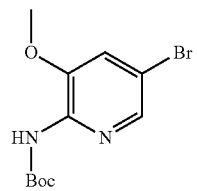 |
| 66C | 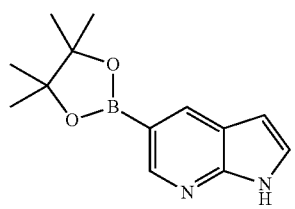 [SMILES: CC1(C)OB(c2cnc3[nH]ccc3c2)OC1(C)C] | 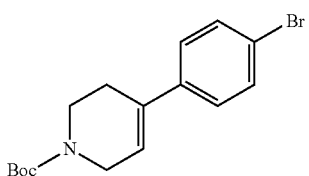 [SMILES: CC(C)(C)OC(=O)N1CC=C(c2ccc(Br)cc2)CC1] |
| 66D | 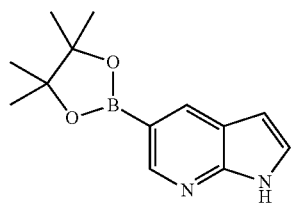 [SMILES: CC1(C)OB(c2cnc3[nH]ccc3c2)OC1(C)C] | 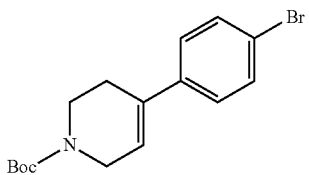 |
| 66E | 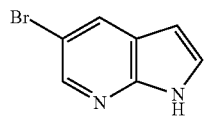 | 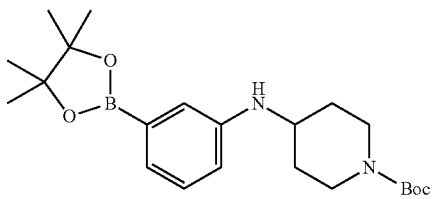 [SMILES: CC(C)(C)OC(=O)N1CCC(Nc2cccc(B3OC(C)(C)C(C)(C)O3)c2)CC1] |
| 66F | 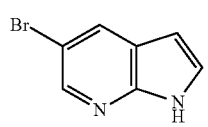 | 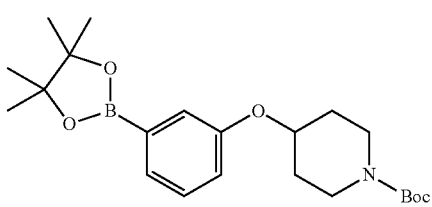 [SMILES: CC(C)(C)OC(=O)N1CCC(Oc2cccc(B3OC(C)(C)C(C)(C)O3)c2)CC1] |

TABLE 3-continued
Intermediates Prepared Using General procedure of intermediate 9
| | | |
|---|---|---|
| 66G | 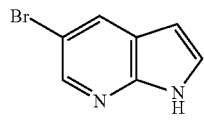 | 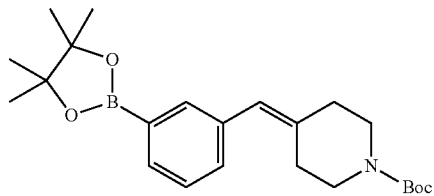 [SMILES: CC(C)(C)OC(=O)N1CCC(=Cc2cccc(B3OC(C)(C)C(C)(C)O3)c2)CC1] |
| 66H | 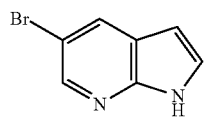 | 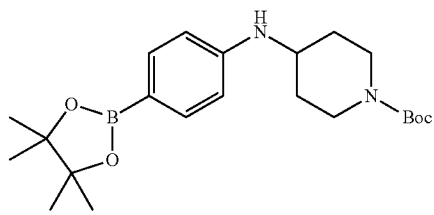 [SMILES: CC(C)(C)OC(=O)N1CCC(Nc2ccc(B3OC(C)(C)C(C)(C)O3)cc2)CC1] |
| 66I | 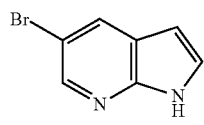 | 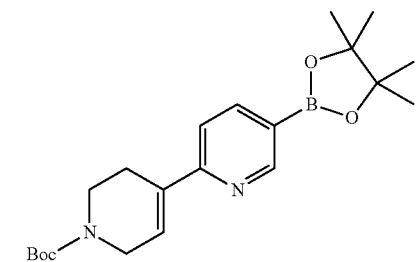 [SMILES: CC(C)(C)OC(=O)N1CC=C(c2ccc(B3OC(C)(C)C(C)(C)O3)cn2)CC1] |
| 66J | 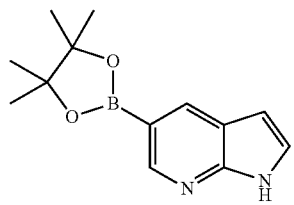 [SMILES: CC1(C)OB(c2cnc3[nH]ccc3c2)OC1(C)C] | 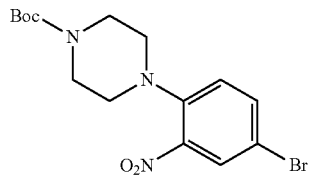 |
| 66K | 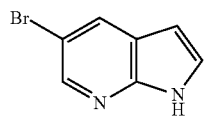 | 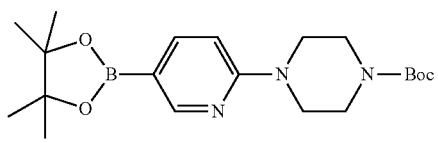 [SMILES: CC(C)(C)OC(=O)N1CCN(c2ccc(B3OC(C)(C)C(C)(C)O3)cn2)CC1] |
| 66L | 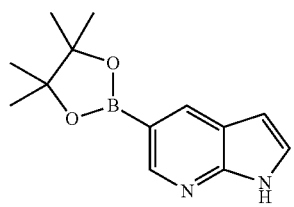 [SMILES: CC1(C)OB(c2cnc3[nH]ccc3c2)OC1(C)C] | 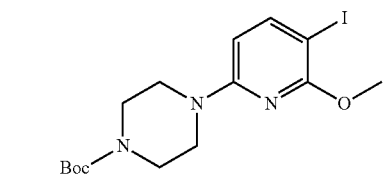 [SMILES: COc1nc(N2CCN(C(=O)OC(C)(C)C)CC2)ccc1I] |
| 66M | 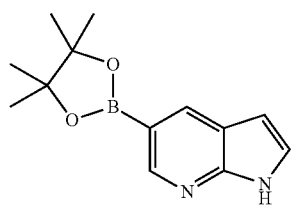 | 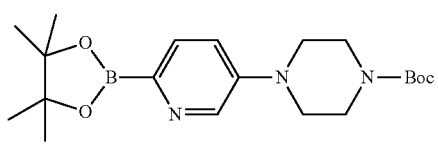 [SMILES: CC(C)(C)OC(=O)N1CCN(c2ccc(B3OC(C)(C)C(C)(C)O3)nc2)CC1] |

TABLE 3-continued
Intermediates Prepared Using General procedure of intermediate 9
| | | |
|---|---|---|
| 66N | 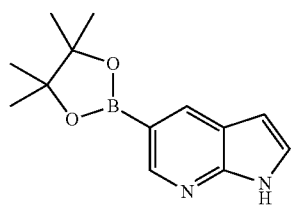 [SMILES: CC1(C)OB(c2cnc3[nH]ccc3c2)OC1(C)C] | 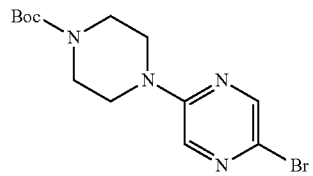 |
| 66P | 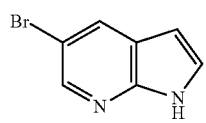 | 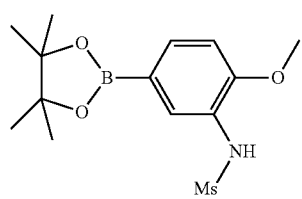 |
| 66Q | 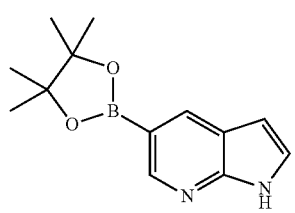 [SMILES: CC1(C)OB(c2cnc3[nH]ccc3c2)OC1(C)C] | 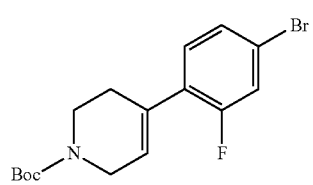 |
| 66R | 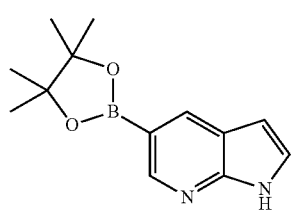 [SMILES: CC1(C)OB(c2cnc3[nH]ccc3c2)OC1(C)C] | 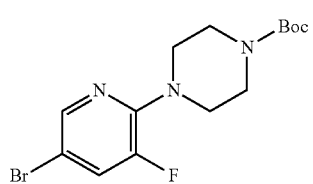 |
| 66S | 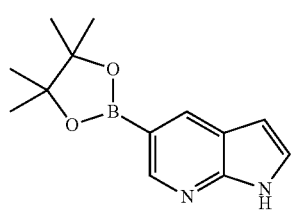 [SMILES: CC1(C)OB(c2cnc3[nH]ccc3c2)OC1(C)C] | 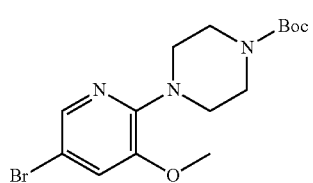 |
| 66T | 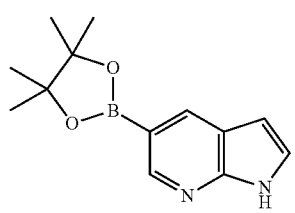 [SMILES: CC1(C)OB(c2cnc3[nH]ccc3c2)OC1(C)C] | 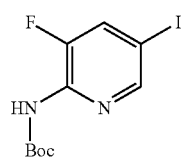 |
| Intermediate | Product | MS (m/z) |
|---|---|---|
| 22. | 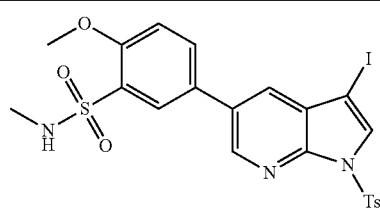 | 598.0 (M + 1) |

TABLE 3-continued
Intermediates Prepared Using General procedure of intermediate 9
| | | |
|---|---|---|
| 23. | 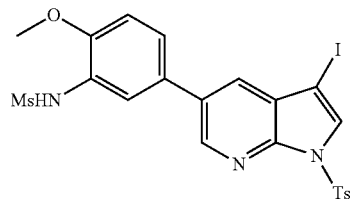 | — |
| 26. | 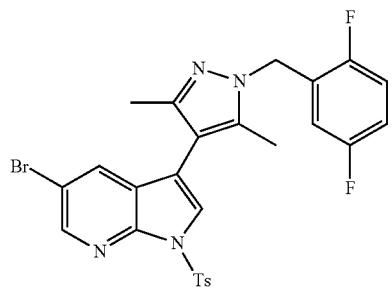 [SMILES: Cc1ccc(S(=O)(=O)n2cc(-c3c(C)nn(Cc4cc(F)ccc4F)c3C)c3cc(Br)cnc32)cc1] | — |
| 32 | 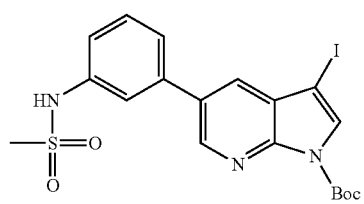 [SMILES: CC(C)(C)OC(=O)n1cc(I)c2cc(-c3cccc(NS(C)(=O)=O)c3)cnc21] | 514.1 (M + 1). |
| 33. | 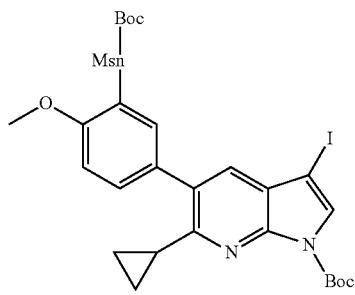 | — |
| 34. | 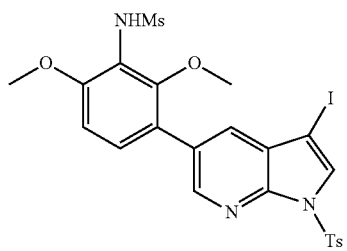 | 627.8 (M + 1) |
| 35. | 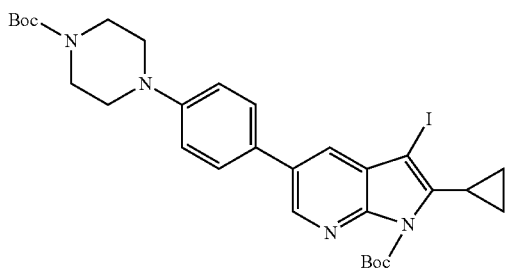 [SMILES: CC(C)(C)OC(=O)N1CCN(c2ccc(-c3cnc4c(c3)c(I)c(C3CC3)n4C(=O)OC(C)(C)C)cc2)CC1] | 645.1 (M + 1) |

TABLE 3-continued
Intermediates Prepared Using General procedure of intermediate 9
| 36. | 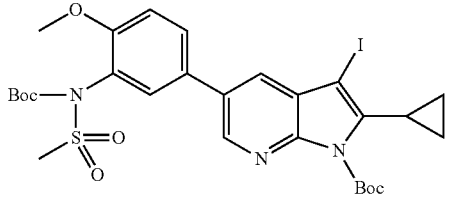 [SMILES: COc1ccc(-c2cnc3c(c2)c(I)c(C2CC2)n3C(=O)OC(C)(C)C)cc1N(C(=O)OC(C)(C)C)S(C)(=O)=O] | 683.8 (M + 1). |
| 39. | 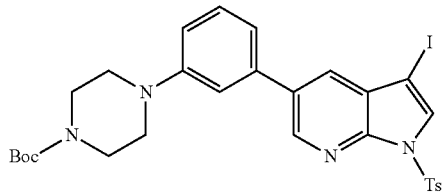 [SMILES: Cc1ccc(S(=O)(=O)n2cc(I)c3cc(-c4cccc(N5CCN(C(=O)OC(C)(C)C)CC5)c4)cnc32)cc1] | 659.0 (M + 1) |
| 41 | 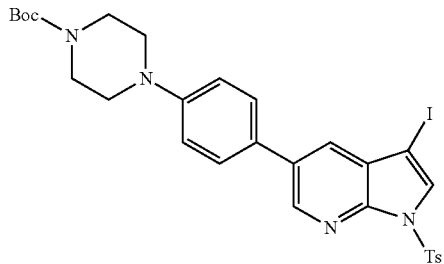 [SMILES: Cc1ccc(S(=O)(=O)n2cc(I)c3cc(-c4ccc(N5CCN(C(=O)OC(C)(C)C)CC5)cc4)cnc32)cc1] | 658.9 (M + 1) |
| 42. | 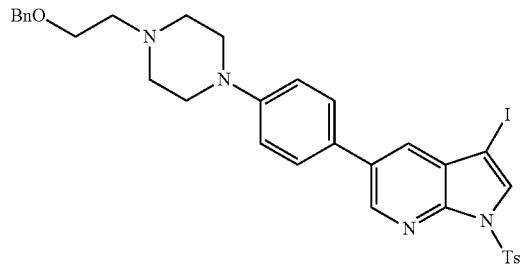 [SMILES: Cc1ccc(S(=O)(=O)n2cc(I)c3cc(-c4ccc(N5CCN(CCOCc6ccccc6)CC5)cc4)cnc32)cc1] | 693.0 (M + 1). |
| 43. | 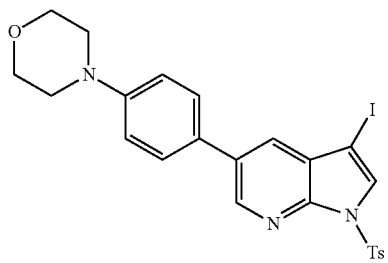 [SMILES: Cc1ccc(S(=O)(=O)n2cc(I)c3cc(-c4ccc(N5CCOCC5)cc4)cnc32)cc1] | 560.0 (M + 1) |
| 47. | 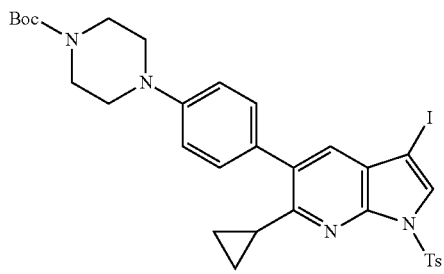 [SMILES: Cc1ccc(S(=O)(=O)n2cc(I)c3cc(-c4ccc(N5CCN(C(=O)OC(C)(C)C)CC5)cc4)c(C4CC4)nc32)cc1] | 699.0 (M + 1) |

TABLE 3-continued
Intermediates Prepared Using General procedure of intermediate 9
| | | |
|---|---|---|
| 48. | 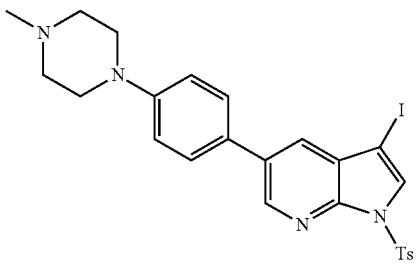 [SMILES: Cc1ccc(S(=O)(=O)n2cc(I)c3cc(-c4ccc(N5CCN(C)CC5)cc4)cnc32)cc1] | 573.0 (M + 1) |
| 49. | 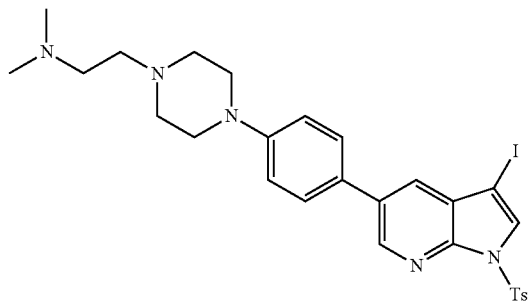 [SMILES: Cc1ccc(S(=O)(=O)n2cc(I)c3cc(-c4ccc(N5CCN(CCN(C)C)CC5)cc4)cnc32)cc1] | 630.1 (M + 1) |
| 50. | 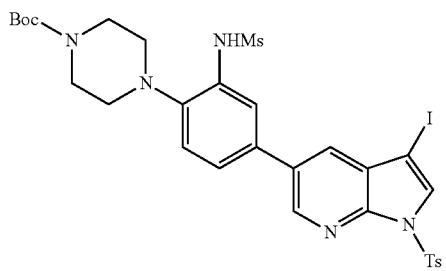 | — |
| 52 | 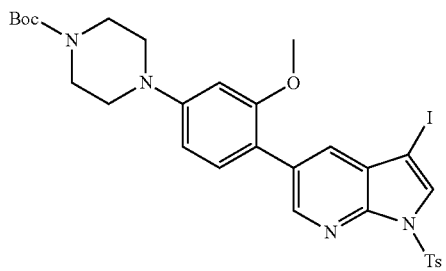 [SMILES: COc1cc(N2CCN(C(=O)OC(C)(C)C)CC2)ccc1-c1cnc2c(c1)c(I)cn2S(=O)(=O)c1ccc(C)cc1] | 689.1 (M + 1). |
| 57 | 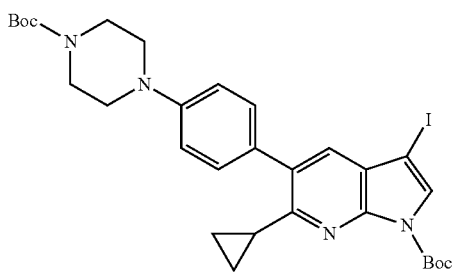 [SMILES: CC(C)(C)OC(=O)N1CCN(c2ccc(-c3cc4c(I)cn(C(=O)OC(C)(C)C)c4nc3C3CC3)cc2)CC1] | 588.8 (M + 1). |

TABLE 3-continued
Intermediates Prepared Using General procedure of intermediate 9
| | | |
|---|---|---|
| 58 | 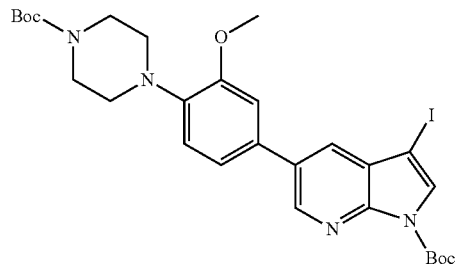 | 689.1 (M + 1). |
| 66 | 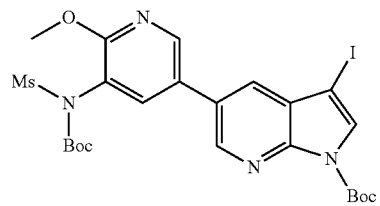 [SMILES: COc1ncc(-c2cnc3c(c2)c(I)cn3C(=O)OC(C)(C)C)cc1N(C(=O)OC(C)(C)C)S(C)(=O)=O] | — |
| 66A | 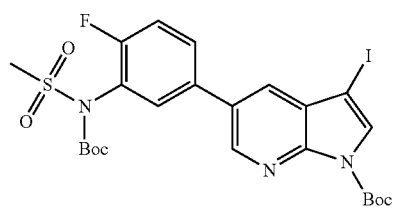 [SMILES: CC(C)(C)OC(=O)N(c1cc(-c2cnc3c(c2)c(I)cn3C(=O)OC(C)(C)C)ccc1F)S(C)(=O)=O] | — |
| 66B | 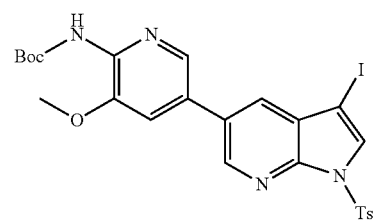 [SMILES: COc1cc(-c2cnc3c(c2)c(I)cn3S(=O)(=O)c2ccc(C)cc2)cnc1NC(=O)OC(C)(C)C] | — |
| 66C | 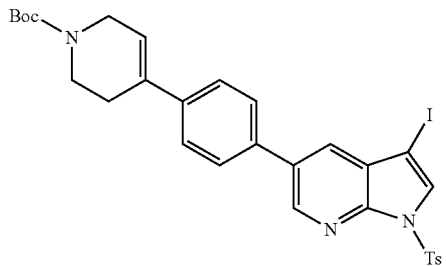 [SMILES: Cc1ccc(S(=O)(=O)n2cc(I)c3cc(-c4ccc(C5=CCN(C(=O)OC(C)(C)C)CC5)cc4)cnc32)cc1] | — |
| 66D | 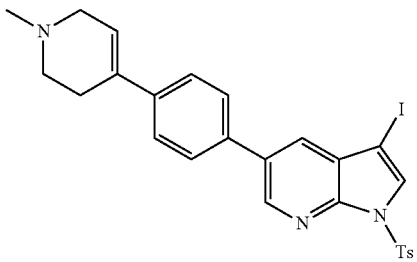 [SMILES: Cc1ccc(S(=O)(=O)n2cc(I)c3cc(-c4ccc(C5=CCN(C)CC5)cc4)cnc32)cc1] | — |

TABLE 3-continued
Intermediates Prepared Using General procedure of intermediate 9
| 66E | 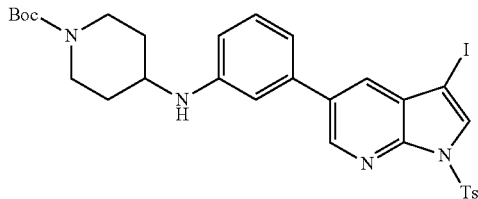 [SMILES: Cc1ccc(S(=O)(=O)n2cc(I)c3cc(-c4cccc(NC5CCN(C(=O)OC(C)(C)C)CC5)c4)cnc32)cc1] | — |
| 66F | 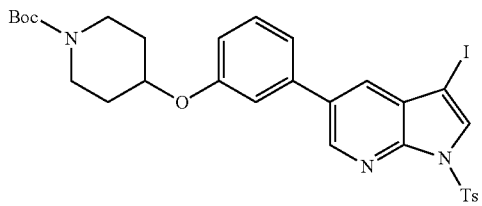 [SMILES: Cc1ccc(S(=O)(=O)n2cc(I)c3cc(-c4cccc(OC5CCN(C(=O)OC(C)(C)C)CC5)c4)cnc32)cc1] | — |
| 66G | 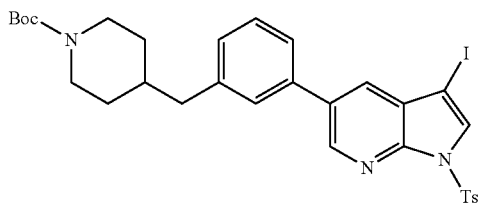 [SMILES: Cc1ccc(S(=O)(=O)n2cc(I)c3cc(-c4cccc(CC5CCN(C(=O)OC(C)(C)C)CC5)c4)cnc32)cc1] | — |
| 66H | 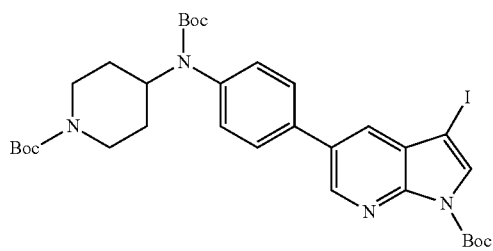 [SMILES: CC(C)(C)OC(=O)N1CCC(N(C(=O)OC(C)(C)C)c2ccc(-c3cnc4c(c3)c(I)cn4C(=O)OC(C)(C)C)cc2)CC1] | — |
| 66I | 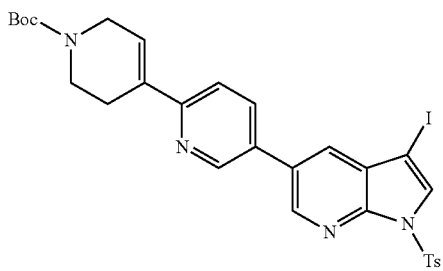 [SMILES: Cc1ccc(S(=O)(=O)n2cc(I)c3cc(-c4ccc(C5=CCN(C(=O)OC(C)(C)C)CC5)nc4)cnc32)cc1] | — |
| 66J | 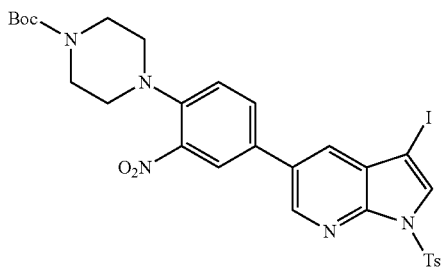 [SMILES: Cc1ccc(S(=O)(=O)n2cc(I)c3cc(-c4ccc(N5CCN(C(=O)OC(C)(C)C)CC5)c([N+](=O)[O-])c4)cnc32)cc1] | — |

TABLE 3-continued

Intermediates Prepared Using General procedure of intermediate 9

| | | |
|---|---|---|
| 66K | *[structure: Boc-piperazine-pyridine-iodo-pyrrolopyridine-Ts]* | — |
| 66L | *[structure: Boc-piperazine-(methoxy)pyridine-iodo-pyrrolopyridine-Ts]* | — |
| 66M | *[structure: Boc-piperazine-pyridine-iodo-pyrrolopyridine-Ts]* | — |
| 66N | *[structure: Boc-piperazine-pyrazine-iodo-pyrrolopyridine-Ts]* | — |
| 66P | *[structure: methoxy-phenyl with N(Ms)(Boc)-iodo-pyrrolopyridine-Boc]* | — |
| 66Q | *[structure: Boc-tetrahydropyridine-fluorophenyl-iodo-pyrrolopyridine-Ts]* | — |

TABLE 3-continued

Intermediates Prepared Using General procedure of intermediate 9

| 66R | 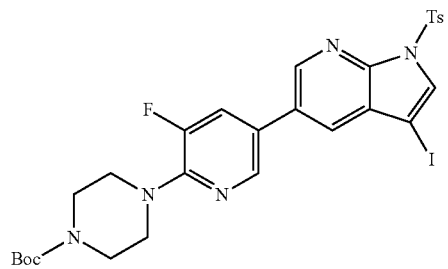 [SMILES: Cc1ccc(S(=O)(=O)n2cc(I)c3cc(-c4cnc(N5CCN(C(=O)OC(C)(C)C)CC5)c(F)c4)cnc32)cc1] | — |
| 66S | 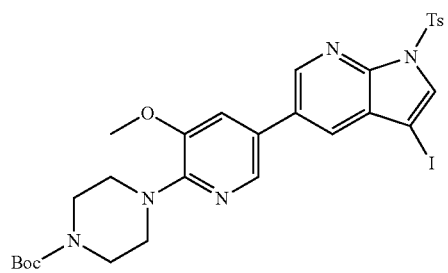 [SMILES: COc1cc(-c2cnc3c(c2)c(I)cn3S(=O)(=O)c2ccc(C)cc2)cnc1N1CCN(C(=O)OC(C)(C)C)CC1] | — |
| 66T | 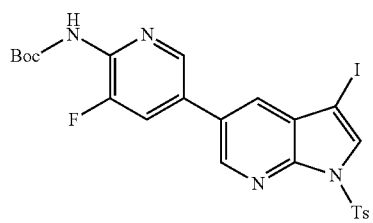 [SMILES: Cc1ccc(S(=O)(=O)n2cc(I)c3cc(-c4cnc(NC(=O)OC(C)(C)C)c(F)c4)cnc32)cc1] | — |

Intermediate 16: 1-(3-fluorobenzyl)-3,5-dimethyl-4-(4,4,5,5-tetramethyl-1,3,2-dioxaborolan-2-yl)-1H-pyrazole

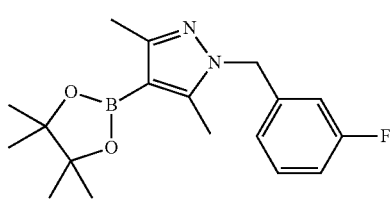 [SMILES: Cc1nn(Cc2cccc(F)c2)c(C)c1B1OC(C)(C)C(C)(C)O1]

Using similar reaction conditions as described in (step i of Intermediate-2), 3,5-dimethyl-4-(4,4,5,5-tetramethyl-1,3,2-dioxaborolan-2-yl)-1H-pyrazole (1 g, 4.5 mmol) was reacted with 3-fluoro benzyl bromide (1.02 g, 5.4 mmol) in DMF (10 ml) and potassium carbonate (1.86 g, 13.5 mmol) to afford 1.4 g (94.59% yield) of the pure product.

MS: m/z=331.2 (M+1).

All the substituted 1-(benzyl)-3,5-dimethyl-1H-pyrazole boronic ester listed in Table 2 were prepared by using appropriate 3,5-dimethyl-1H-pyrazole boronic ester (reactant A) and substituted benzyl bromide (Reactant B) by following similar procedure as depicted in intermediate-16. Most of the intermediate were used in the next step of reaction without purification. Structure information and characterization data for selected intermediates are given in Table-4.

TABLE 4

Intermediates prepared using similar procedure of Intermediate 16

| Intermediate | Reactant A | Reactant B | Product | MS (m/z) |
|---|---|---|---|---|
| 24. | | | | — |

TABLE 4-continued

Intermediates prepared using similar procedure of Intermediate 16

| Intermediate | Reactant A | Reactant B | Product | MS (m/z) |
|---|---|---|---|---|
| 25. | 3,5-dimethyl-1H-pyrazole-4-boronic acid pinacol ester | 2-bromomethyl-1,4-difluorobenzene | 1-(2,5-difluorobenzyl)-3,5-dimethyl-4-(4,4,5,5-tetramethyl-1,3,2-dioxaborolan-2-yl)-1H-pyrazole | — |
| 44. | 3,5-dimethyl-1H-pyrazole-4-boronic acid pinacol ester | 1-(bromomethyl)-3-(trifluoromethoxy)benzene | 3,5-dimethyl-4-(4,4,5,5-tetramethyl-1,3,2-dioxaborolan-2-yl)-1-(3-(trifluoromethoxy)benzyl)-1H-pyrazole | — |
| 46. | 3,5-dimethyl-1H-pyrazole-4-boronic acid pinacol ester | 1-(bromomethyl)-3-ethoxybenzene | 1-(3-ethoxybenzyl)-3,5-dimethyl-4-(4,4,5,5-tetramethyl-1,3,2-dioxaborolan-2-yl)-1H-pyrazole | 357.2 (M + 1) |
| 53. | 3,5-dimethyl-1H-pyrazole-4-boronic acid pinacol ester | 1-(bromomethyl)-3-methoxybenzene | 1-(3-methoxybenzyl)-3,5-dimethyl-4-(4,4,5,5-tetramethyl-1,3,2-dioxaborolan-2-yl)-1H-pyrazole | 492.3 (M + 1) |
| 54. | 3,5-dimethyl-1H-pyrazole-4-boronic acid pinacol ester | 1-(bromomethyl)-3-chlorobenzene | 1-(3-chlorobenzyl)-3,5-dimethyl-4-(4,4,5,5-tetramethyl-1,3,2-dioxaborolan-2-yl)-1H-pyrazole | 347.1 (M + 1) |
| 55. | 3,5-dimethyl-1H-pyrazole-4-boronic acid pinacol ester | 3-(bromomethyl)benzonitrile | 3-((3,5-dimethyl-4-(4,4,5,5-tetramethyl-1,3,2-dioxaborolan-2-yl)-1H-pyrazol-1-yl)methyl)benzonitrile | — |

TABLE 4-continued

Intermediates prepared using similar procedure of Intermediate 16

| Intermediate | Reactant A | Reactant B | Product | MS (m/z) |
|---|---|---|---|---|
| 56. | (pyrazole-Bpin structure) | 3-nitrobenzyl bromide | (N-benzylated pyrazole-Bpin product) | — |
| 56A. | (N-methyl pyrazole-Bpin structure) | 3-methylbenzyl bromide | (N-benzylated pyrazole-Bpin product) | — |

Intermediate 21: 2-methoxy-N-methyl-5-(4,4,5,5-tetramethyl-1,3,2-dioxaborolan-2-yl)benzene sulfonamide

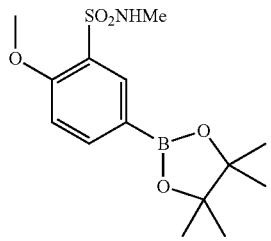

Step-i: 5-bromo-2-methoxy-N-methylbenzenesulfonamide

To a stirred ice cold mixture of methylamine hydrochloride (231.1 mg, 3.5 mmol), triethylamine (1.26 mL, 8.755 mmol) in DCM was added a solution of 5-bromo-2-methoxybenzene-1-sulfonyl chloride (500 mg, 1.751 mmol) in DCM at 0° C. This was stirred at RT for three hours. This mixture was then poured on to ice cold water and extracted with DCM, dried over sodium sulfate and concentrated to get 400 mg (81.63% yield) of titled compound.

Step-ii: 2-methoxy-N-methyl-5-(4,4,5,5-tetramethyl-1,3,2-dioxaborolan-2-yl)benzene sulfonamide Using similar reaction conditions as described in step ii of intermediate-3,5-bromo-2-methoxy-N-methylbenzenesulfonamide (400 mg, 0.716 mmol) was coupled with 4,4,4',4',5,5,5',5'-octamethyl-2,2'-bi(1,3,2-dioxaborolane) (466 mg, 0.917 mmol) in potassium acetate (420 mg, 2.14 mmol), PdCl$_2$(dppf).DCM complex (52.2 mg, 0.0358 mmol), 1,4-Dioxane (10 mL) to give 250 mg (53.53% yield) of the pure product after purification by chromatographic column (Silicagel-60/120) using 20% ethyl acetate as eluent. $^1$H NMR (CDCl$_3$, 300 MHz): δ 8.35 (s, 1H), 7.98-7.95 (dd, 1H), 7.03-7.00 (d, 1H), 4.77-4.75 (d, 1H), 4.00 (s, 3H), 2.59-2.58 (d, 3H) 1.33 (s, 12H). MS: m/z=328.0 (M+1).

Intermediate 27: N-(2-(2-(dimethylamino)ethoxy)-5-(4,4,5,5-tetramethyl-1,3,2-dioxaborolan-2-yl)phenyl)methanesulfonamide

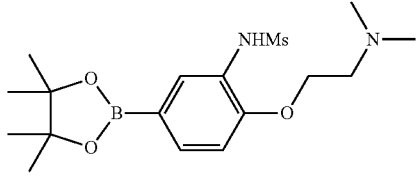

Step-i: 2-(4-bromo-2-nitrophenoxy)-N,N-dimethylethanamine

A solution of 2-(dimethylamino)ethanol (2.2 g, 24.9 mmol), DMF was added slowly to a stirred suspension of sodium hydride (2.17 g, 56.7 mmol), DMF at 0° C. This was then added a solution of 4-bromo-2-fluoro-1-nitrobenzene (5 g, 22.7 mmol) in DMF dropwise at the same temperature. The reaction completed in half an hour. Reaction mass was quenched by ice and this was extracted into ethyl acetate (150 ml). Organic portion was dried and concentrated to afford 4.1 g (62.5% yield) of the title compound. $^1$H NMR (CDCl3, 300 MHz): δ7.958-7.95 (d, 1H), 7.63-7.59 (dd, 1H), 7.00-6.97 (d, 1H), 4.19-4.16 (t, 2H), 2.79-2.76 (t, 2H), 2.33 (s, 6H). LCMS: m/z=288.9 (M+1).

Step-ii: 5-bromo-2-(2-(dimethylamino)ethoxy)aniline

Zinc dust (4.52 g, 69.2 mmol) was added to a stirred solution of 2-(4-bromo-2-nitrophenoxy)-N,N-dimethylethanamine (4 g, 13.8 mmol), ammonium chloride (3.7 g, 69.2 mmol), THF/Water (40/40 mL) at RT. Reaction completed in 4 hours. The RM was filtered and the filtrate was concentrated. The residue was dissolved in ethyl acetate and washed with water, dried over sodium sulfate, concentrated to get the crude mass which was washed with hexanes to afford titled compound 1.85 g (51.67% yield) as solid. $^1$H NMR (DMSO-d$_6$, 300 MHz): δ 6.74-6.70 (m, 2H), 6.59-6.56 (m, 1H), 4.99 (s, 2H), 3.97-3.93 (t, 2H), 2.59-2.56 (t, 2H), 2.18 (s, 6H). LCMS: m/z=260.8 (M+2).

Step-iii: N-(5-bromo-2-(2-(dimethylamino) ethoxy) phenyl)methanesulfonamide

Using similar reaction conditions as described in step i of intermediate 17, 5-bromo-2-(2-(dimethylamino)ethoxy) aniline (1.8 g, 6.94 mmol) was mesylated with methanesulfonyl chloride (875 mg, 7.63 mol), pyridine (822 mg, 10.4 mmol), DCM (20 mL) to afford 1.97 g (83.12% yield) of the titled compound. $^1$H NMR (CDCl$_3$, 300 MHz): δ 7.71-7.0 (d, 1H), 7.2-7.16 (dd, 1H), 6.92-6.89 (d, 1H), 4.07-4.04 (t, 2H), 2.92 (s, 3H), 2.56-2.53 (t, 2H), 2.35 (s, 6H).

Step-iv: N-(2-(2-(dimethylamino)ethoxy)-5-(4,4,5,5-tetramethyl-1,3,2-dioxaborolan-2-yl)phenyl) methanesulfonamide Using similar reaction conditions as described in step ii of intermediate 2, N-(5-bromo-2-(2-(dimethylamino)ethoxy) phenyl)methanesulfonamide (1.9 g, 5.6 mmol) was coupled with 4,4,4',4',5,5,5',5'-octamethyl-2,2'-bi(1,3,2-dioxaborolane) (2.13 g, 8.45 mmol) in potassium acetate (1.65 g, 16.8 mmol), PdCl2 (dppf) (204.68 mg, 0.28 mmol), DMSO (40 mL) to give 250 mg (11.57% yield) of the title compound. LCMS: m/z=385.1 (M+1)

All the substituted N-(alkoxyphenyl)methanesulfonamide boronic esters listed in Table 4 were prepared by reacting Reactant A with Reactant B by following similar procedure as depicted in intermediate-27. Most of the intermediate were used in the next step of reaction without purification. Structure information and characterization data for selected intermediates are given in Table 5.

TABLE 5

Intermediates Prepared Using General procedure of intermediate 27

| Intermediate | Reactant A | Reactant B | Product | MS (m/z) |
|---|---|---|---|---|
| 28 | BnO-CH$_2$CH$_2$-OH | O$_2$N, Br, F-substituted benzene | BnO/MsHN-substituted phenyl boronic ester | 448.3 (M + 1) |
| 29. | 4-methoxybenzyl-O-CH$_2$CH$_2$CH$_2$-OH | Br, F, NO$_2$-substituted benzene | 4-methoxybenzyl ether linked phenyl boronic ester with NHMs | 492.3 (M + 1) |
| 30 | Me$_2$N-CH$_2$CH$_2$CH$_2$-OH | Br, F, NO$_2$-substituted benzene | MsHN-substituted phenyl boronic ester with dimethylaminopropoxy | — |
| 37 | Cl-CH$_2$CH$_2$CH$_2$-NH-CH$_2$CH$_2$CH$_2$-Cl | H$_2$N, Br-substituted benzene | phenyl boronic ester with N-Boc piperazine | — |

TABLE 5-continued

Intermediates Prepared Using General procedure of intermediate 27

| Intermediate | Reactant A | Reactant B | Product | MS (m/z) |
|---|---|---|---|---|
| 38. | (3-bromopropanenitrile) | 1-(3-bromophenyl)piperazine | 3-(4-(3-(4,4,5,5-tetramethyl-1,3,2-dioxaborolan-2-yl)phenyl)piperazin-1-yl)propanenitrile | 342.5 (M + 1) |
| 40. | bis(3-chloropropyl)amine | 4-bromoaniline | tert-butyl 4-(4-(4,4,5,5-tetramethyl-1,3,2-dioxaborolan-2-yl)phenyl)piperazine-1-carboxylate | 243 (M + 2) |
| 51. | morpholine | 4-bromo-1-fluoro-2-nitrobenzene | N-(2-morpholino-5-(4,4,5,5-tetramethyl-1,3,2-dioxaborolan-2-yl)phenyl)methanesulfonamide | 383.1 (M + 1) |
| 69 | bis(3-chloropropyl)amine | 4-bromo-2-fluoroaniline | tert-butyl 4-(2-fluoro-4-(4,4,5,5-tetramethyl-1,3,2-dioxaborolan-2-yl)phenyl)piperazine-1-carboxylate | — |
| 69A | bis(3-chloropropyl)amine | 4-bromo-2-methylaniline | tert-butyl 4-(2-methyl-4-(4,4,5,5-tetramethyl-1,3,2-dioxaborolan-2-yl)phenyl)piperazine-1-carboxylate | — |
| 69B | bis(3-chloropropyl)amine | 4-bromo-3-fluoroaniline | tert-butyl 4-(3-fluoro-4-(4,4,5,5-tetramethyl-1,3,2-dioxaborolan-2-yl)phenyl)piperazine-1-carboxylate | — |
| 69C | tert-butyl piperazine-1-carboxylate | 2,5-dibromopyridine | tert-butyl 4-(5-(4,4,5,5-tetramethyl-1,3,2-dioxaborolan-2-yl)pyridin-2-yl)piperazine-1-carboxylate | — |
| 69D | tert-butyl piperazine-1-carboxylate | 5-bromo-2-chloropyridine | tert-butyl 4-(6-(4,4,5,5-tetramethyl-1,3,2-dioxaborolan-2-yl)pyridin-3-yl)piperazine-1-carboxylate | — |

TABLE 5-continued

Intermediates Prepared Using General procedure of intermediate 27

| Intermediate | Reactant A | Reactant B | Product | MS (m/z) |
|---|---|---|---|---|
| 69E | 4-hydroxypiperidine | 2,5-dibromopyridine | 1-(5-(4,4,5,5-tetramethyl-1,3,2-dioxaborolan-2-yl)pyridin-2-yl)piperidin-4-ol | — |
| 69F | 1-Boc-homopiperazine | 1,4-dibromobenzene | tert-butyl 4-(4-(4,4,5,5-tetramethyl-1,3,2-dioxaborolan-2-yl)phenyl)-1,4-diazepane-1-carboxylate | — |
| 69G | 1-Boc-piperazine | 4-bromo-1-fluoro-2-nitrobenzene | Boc-piperazinyl aryl pinacol boronate with NHMs | — |

Intermediate 31: 5-bromo-6-cyclopropyl-1H-pyrrolo[2,3-b]pyridine

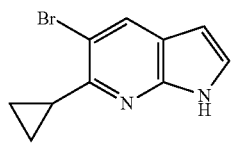 [SMILES: Brc1cc2cc[nH]c2nc1C1CC1]

Step-i: N-(6-bromopyridin-2-yl)pivalamide

To an ice cold solution of 6-bromopyridine-2-amine (7 g, 40.5 mmol) in DCM was added pivaloyl chloride (5.23 mL, 42.48 mmol), N-ethyl-N-isopropylpropan-2-amine (13.6 mL, 82.9 mmol) sequentially. The solution was stirred for an hour then diluted with 50 mL of ether. The mixture was washed with saturated sodium bicarbonate. The organic layer was dried over sodium sulfate, filtered concentrated. The residue was slowly solidified after scratching in ethyl acetate-hexane mixture to afford 7.2 gm (69.2% yield) of the titled compound. LCMS: m/z=257.0 (M+1).

Step-ii: N-(6-cyclopropylpyridin-2-yl)pivalamide

A mixture of N-(6-bromopyridin-2-yl)pivalamide (2 g, 7.77 mmol), cyclopropylboronic acid (935 mg, 10.88 mmol), potassium phosphate (toluene/water (10/3 mL) taken in screw cap tube was purged with argon for 15 minutes and then added palladium(II)acetate (174 mg, 0.77 mmol), tricyclohexylphosphine (435.7 mg, 1.55 mmol) sequentially, purged argon for another 5 min. The resultant mixture was stirred at 100° C. under closed argon atmosphere. Reaction completed in 14 h, reaction mass was cooled to room temperature, extracted into ethyl acetate, (100 ml) organic portion was washed with water, dried over sodium sulfate and concentrated to afford 4 g of the titled compound. LCMS: m/z=219.0 (M+1).

Step-iii: 6-cyclopropylpyridin-2-amine

To a solution of N-(6-cyclopropylpyridin-2-yl)pivalamide (4.25 gm, 19.49 mmol) in dioxane (34 ml) was added 9N HCl (34 ml). The mixture was stirred for 18 hours at 90° C. After cooling to 25° C., the pH of the reaction was adjusted with to achieve pH-9. The solution was diluted with ethyl acetate (200 ml) quantity and washed with saturated sodium bicarbonate. Next, the organic portion was dried over sodium sulfate and concentrated to get 2 gm (77.5% yield) clear oil.

Step-iv: 5-bromo-6-cyclopropylpyridin-2-amine

A solution of 6-cyclopropylpyridin-2-amine (2 g, 14.93 mmol), methanol (25 mL) was added N-bromosuccinimide (2.64 g, 14.93 mmol) portionwise. After stirring at room temperature for 30 minutes, mixture was evaporated and the residue obtained was purified on column (SiO$_2$) using 10% ethyl acetate in hexanes as eluent. This afforded 2.1 gm (68.5% yield) of title compound. $^1$H NMR (CDCl$_3$, 300 MHz): δ 7.45-7.43 (d, 1H), 6.16-6.13 (d, 1H), 4.30-4.20 (bs, 2H), 2.40-2.30 (m, 1H), 1.00-0.90 (m, 2H), 0.85-0.80 (m, 2H). MS: m/z=215.0 (M+1).

Step-v: 5-bromo-6-cyclopropyl-3-iodopyridin-2-amine

A solution of 5-bromo-6-cyclopropylpyridin-2-amine (2.1 g, 9.81 mmol), trifluoroaceticacid (170 mg, 1.47 mmol), N-iodosuccinimide (2.2 g, 9.81 mmol) stirred at room temperature for 30 minutes. Reaction mass was quenched with water, basified with ammonium hydroxide solution. Solid separated was filtered and dried to get 3.3 g (100% yield) of titled compound. 1H NMR (CDCl₃, 300 MHz): δ 7.85 (s, 1H), 4.80-4.65 (bs, 2H), 2.39-2.25 (m, 1H), 1.0-0.90 (m, 4H). MS: m/z=338.9 (M+1).

Step-vi: 5-bromo-6-cyclopropyl-3-((trimethylsilyl)ethynyl)pyridin-2-amine

Cuprous iodide (11.23 mg, 0.059 mmol) was added to a mixture of 5-bromo-6-cyclopropyl-3-iodopyridin-2-amine (1 g, 2.95 mmol), triethylamine (13.4 g, 132.75 mmol) and THF (4 mL) and the resultant mixture was purged with nitrogen gas. Ethynyltrimethylsilane (347.7 mg, 3.54 mmol) and Pd(PPh₃)₂Cl₂ (41.36 mg, 0.059 mmol) were added and purged with argon. The resultant mixture was stirred under argon atmosphere for 5 hours. The mixture was concentrated to residue. Residue was dissolved in ethyl acetate, washed with water, brine and dried over sodium sulfate and concentrated to get solid which was further purified on column (SiO₂) using 15% ethyl acetate in hexane as eluent. This afforded 1.2 g (crude) of the pure compound.

Step-vii: 5-bromo-6-cyclopropyl-2-(trimethylsilyl)-1H-pyrrolo[2,3-b]pyridine

A stirred solution of 5-bromo-6-cyclopropyl-3-((trimethylsilyl)ethynyl)pyridin-2-amine (1 g, 3.2 mmol), tert-butanol (10 mL) was added potassium tert-butoxide (1.45 g, 12.9 mmol) and stirred at ambient temperature for 15 min. RM was quenched with water and extracted with ethyl acetate, organic portion was dried over sodium sulfate and concentrated to give 1.2 g of the titled compound. ¹H NMR (CDCl₃, 300 MHz): δ 7.86-7.85 (m, 1H), 6.45-6.42 (m, 1H), 4.98-4.96 (m, 1H), 4.88-4.7 (m, 1H), 4.55 (s, 2H), 2.35-2.31 (m, 1H), 2.0 (s, 9H), 1.04-0.86 (m, 4H). LCMS: m/z=311.1 (M+1).

Step-viii: 5-bromo-6-cyclopropyl-1H-pyrrolo[2,3-b]pyridine

A stirred solution of 5-bromo-6-cyclopropyl-2-(trimethylsilyl)-1H-pyrrolo[2,3-b]pyridine (1.5 g, 4.84 mmol), tert-butanol (15 mL), 9N-hydrochloric acid (15 mL) was heated to reflux for 8 hours. Reaction mixture was cooled and basified with 50% sodium hydroxide to pH 8, extracted with ethyl acetate. Organic portion was in turn washed with brine, dried over sodium sulfate and concentrated to give 910 mg (79.13% yield) of the title compound. ¹H NMR (CDCl₃, 300 MHz) δ 9.43 (bs, 1H), 8.06 (s, 1H), 6.39-6.38 (m, 1H), 2.647-2.603 (m, 1H), 1.09-1 (m, 4H). LCMS: m/z=237.0 (M+1).

Intermediate 45: 4-(4-(4,4,5,5-tetramethyl-1,3,2-dioxaborolan-2-yl)phenyl)pyridine

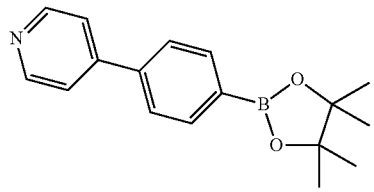 [SMILES: CC1(C)OB(c2ccc(-c3ccncc3)cc2)OC1(C)C]

Step-i: 4-(4-bromophenyl)pyridine

Using similar reaction conditions as described in step i of intermediate 9, 4-bromo pyridine (2 g, 8.44 mmol) was coupled with (4-bromophenyl) boronic acid (1 g, 9.2 mmol) in sodium carbonate (3.57 g, 33.7 mmol), Pd(PPh₃)₄ (487 mg, 0.422 mmol) and toluene/ethanol/water (50/50/20 ml) to afford 2.2 g of the crude product which was taken as such for next reaction. LCMS: 235.9 m/z=(M+2).

Step-ii: 4-(4-(4,4,5,5-tetramethyl-1,3,2-dioxaborolan-2-yl)phenyl)pyridine

Using similar reaction conditions as described in step ii of intermediate 2, 4-(4-bromophenyl)pyridine (1 g, 4.27 mmol) was reacted with bispinocalatodiboron (1.3 g, 5.12 mmol) in potassium acetate (2 g, 20.62 mmol), bis(triphenylphosphine)palladium(II)dichloride (156 mg, 0.21 mmol) and 1,4-dioxane (30 ml) to afford 720 mg (60% yield) of the crude product which was taken as such for next reaction. ¹H NMR (DMSO-d₆, 300 MHz): δ 8.66-8.64 (m, 1H), 7.94-7.91 (m, 1H), 7.71 (m, 1H), 7.67-7.63 (m, 2H), 7.59-7.54 (m, 2H), 7.45-7.3 (m, 1H), 1.38-1.22 (m, 12H).

Intermediate 59: 1-phenethyl-4-(4,4,5,5-tetramethyl-1,3,2-dioxaborolan-2-yl)-1H-pyrazole

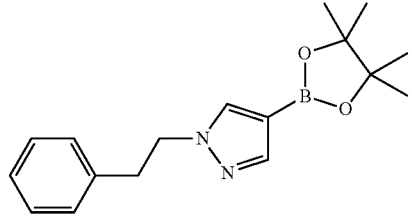 [SMILES: CC1(C)OB(c2cnn(CCc3ccccc3)c2)OC1(C)C]

To a stirred solution 4-(4,4,5,5-tetramethyl-1,3,2-dioxaborolan-2-yl)-1H-pyrazole (300 mg, 1.5463 mmol) in DMF (2 ml) cooled at 0° C. was added sodium hydride (124 mg, 3.0927 mmol) and stirred at 0° C. for further 20 min. Phenethyl bromide (344 mg, 1.8556 mmol) was then added drop wise and stirred the reaction at RT for 3 hrs. The reaction mixture was diluted with ice water (150 ml) and extracted with dichloromethane (2×50 ml). The organic layer was dried over Na₂SO₄ and concentrated under reduced pressure to afford 300 mg (43.47% yield) of the titled compound. MS: m/z=299.4 (M+1). ¹H NMR (CDCl₃, 300 MHz): δ 7.81 (s, 1H), 7.54 (s, 1H), 7.29-7.21 (m, 2H), 7.10-7.08 (d, 1H), 4.35-4.30 (t, 2H), 3.19-3.14 (t, 2H), 1.28 (s, 12H).

Intermediate 60: 2-methoxy-5-(4,4,5,5-tetramethyl-1,3,2-dioxaborolan-2-yl)pyridin-3-amine

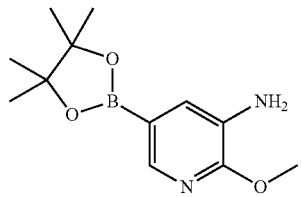

Using similar reaction conditions as described in step ii of intermediate-3,5-bromo-2-methoxypyridin-3-amine (891 mg, 4.39 mmol) was coupled with 4,4,4',4',5,5,5',5'-octamethyl-2,2'-bi(1,3,2-dioxaborolane) (1.86 g, 5.27 mmol) using potassium acetate (1.46 g, 14.92 mmol) and PdCl$_2$(dppf) (160 mg, 0.21 mmol) in 1,4-dioxane (30 mL) to give 1 g (91.1% yield) of the pure product after purification by chromatographic column (Silicagel-60/120) using 20% ethyl acetate as eluent.

Intermediate 61: tert-butyl 4-(3-(4,4,5,5-tetramethyl-1,3,2-dioxaborolan-2-yl)phenoxy) piperidine-1-carboxylate

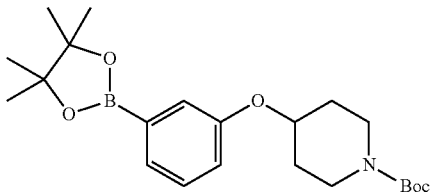 [SMILES: CC(C)(C)OC(=O)N1CCC(Oc2cccc(B3OC(C)(C)C(C)(C)O3)c2)CC1]

Step-i tert-butyl 4-(3-bromophenoxyl)piperidine-1-carboxylate

The mixture of 3-bromophenol (2.0 g, 11.56 mmol), tert-butyl 4-((methylsulfonyl)oxy)piperidine-1-carboxylate (3.87 g, 13.872 mmol) and caesium carbonate (11.27 g, 34.68 mmol) in DMF (25 ml) was heated at 65° C. for 14 hours. Cooled to RT and diluted with ether. Ether layer was washed with water and brine, dried over sodium sulphate and distilled off the solvent to afford 3.5 g (85.3% yield) of the titled product after purification with (60/120 silica gel) column chromatography using 5% ethyl acetate in hexane as eluent. MS: m/z=356.0 (M+1).

Step-ii: tert-butyl 4-(3-(4,4,5,5-tetramethyl-1,3,2-dioxaborolan-2-yl)phenoxy)piperidine-1-carboxylate Using similar reaction conditions as described in step ii of intermediate-3, tert-butyl 4-(3-bromophenoxyl)piperidine-1-carboxylate (2.0 g, 5.71 mmol) was coupled with 4,4,4',4',5,5,5',5'-octamethyl-2,2'-bi(1,3,2-dioxaborolane) (1.73 g, 6.85 mmol) using potassium acetate (1.67 g, 17.13 mmol) and PdCl$_2$(dppf) (208 mg, 0.285 mmol) in dioxane (20 mL) to give 2.1 g (91.3% yield) of the titled product after purification by chromatographic column (Silicagel-60/120) using 5% ethyl acetate as eluent. MS: m/z=304.0 (M-Boc+1).

Intermediate 62: tert-butyl 4-(5-bromopyrazin-2-yl)piperazine-1-carboxylate

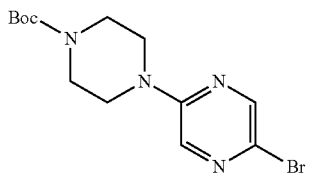 [SMILES: CC(C)(C)OC(=O)N1CCN(c2cnc(Br)cn2)CC1]

Step-i tert-butyl 4-(pyrazin-2-yl)piperazine-1-carboxylate

A mixture of 2-chloropyrazine (2.13 g, 18.7 mmol), tert-butyl piperazine-1-carboxylate (3.16 g, 17 mmol) and caesium carbonate (7.7 g, 23.7 mmol) in DMF (35 ml) was heated at 100° C. for 16 hours. Cooled to RT and diluted with ether. Ether layer was washed with water and brine, dried over sodium sulphate and distilled off the solvent to afford 2 g (40.7% yield) of the titled product after purification with (60/120 silica gel) column chromatography using 40% ethyl acetate in hexane as eluent.

Step-ii tert-butyl 4-(5-bromopyrazin-2-yl)piperazine-1-carboxylate

Using similar reaction conditions as described in step i of intermediate 1, tert-butyl 4-(pyrazin-2-yl)piperazine-1-carboxylate (2 g, 7.5 mmol) was brominated with N-bromosuccinimide (1.46 g, 8.25 mmol) in chloroform (20 ml) to afford 1.4 g (54% yield) of the pure product. MS: m/z=343.1 (M+1).

Intermediate 63: 5-bromo-3-(1-(2,5-difluorobenzyl)-1H-pyrazol-3-yl)-1-tosyl-1H-pyrrolo[2,3-b]pyridine

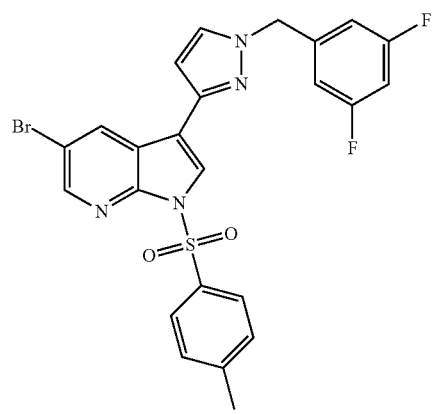 [SMILES: Cc1ccc(S(=O)(=O)n2cc(-c3ccn(Cc4cc(F)cc(F)c4)n3)c3cc(Br)cnc32)cc1]

Step-i: 5-bromo-3-(1-(tetrahydro-2H-pyran-2-yl)-1H-pyrazol-3-yl)-1-tosyl-1H-pyrrolo[2,3-b]pyridine Using the same reaction conditions as described in step-i of example 1,5-bromo-3-iodo-1-tosyl-1H-pyrrolo[2,3-b]pyridine (Intermediate 1) (100 mg, 0.209 mmol) was coupled with (1-(tetrahydro-2H-pyran-2-yl)-1H-pyrazol-3-yl)boronic acid (103 mg, 0.524 mmol) using sodium carbonate (66 mg, 0.627 mmol) and Pd(PPh$_3$)$_2$Cl$_2$ (7 mg, 0.0104 mmol) in DME/water (3/0.7 ml) to afford 60 mg (crude) product. MS: m/z=501.1 (M+1).

Step-ii: 5-bromo-3-(1H-pyrazol-3-yl)-1-tosyl-1H-pyrrolo[2,3-b]pyridine hydrochloride Using the same reaction conditions as described in Step-ii of example-7, (1-(tetrahydro-2H-pyran-2-yl)-1H-pyrazol-3-yl)boronic acid (100 mg, 0.198 mmol) was deprotected in chloroform/HCl in ether (1/1 ml) to afford 60 mg (66.8%) of the titled compound.

Step-iii: 5-bromo-3-(1-(3,5-difluorobenzyl)-1H-pyrazol-3-yl)-1-tosyl-1H-pyrrolo[2,3-b]pyridine Using similar reaction conditions as described in, step ii of Intermediate 1,5-bromo-3-(1H-pyrazol-3-yl)-1-tosyl-1H-pyrrolo[2,3-b]pyridine hydrochloride (100 mg, 0.239 mmol) was alkylated with 1-(bromomethyl)-3,5-difluorobenzene (45 mg, 0.239 mmol) and 60% suspension of sodium hydride in paraffin (28 mg, 0.717 mmol) in DMF (5 mL) to afford 100 mg (crude) of the titled compound.

ethyl-1,3,2-dioxaborolan-2-yl)-5,6-dihydropyridine-1(2H)-carboxylate (1 g, 3.322 mmol) using sodium carbonate (1.056 g, 9.966 mmol) and PdCl$_2$(dppf) (122 mg, 0.166 mmol) in THF/water (10/2 ml) at 75° C. for 2 hours to afford 450 mg (44.64%) of the crude product after purification with (60/120 silica gel) column chromatography using 10% ethyl acetate in hexane as eluent. MS: m/z=212.0 (M-Boc+1). $^1$H NMR (CDCl$_3$, 300 MHz): δ 7.16-7.04 (m, 3H), 5.92 (s, 1H), 4.06-4.05 (d, 2H), 3.62-3.58 (t, 2H), 2.46 (s, 2H), 1.488 (s, 9H).

TABLE 6

Intermediates prepared using similar procedure of Intermediate 63

| Intermediate | Reactant A | Reactant B | Product |
|---|---|---|---|
| 63A | | | |
| 63B | | | |

Intermediate 67: tert-butyl 4-(2-fluoro-4-(3-iodo-1-tosyl-1H-pyrrolo[2,3-b]pyridin-5-yl)phenyl) piperidine-1-carboxylate

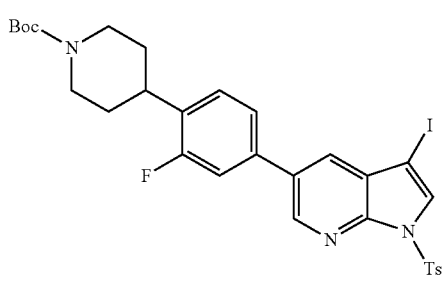 [SMILES: Cc1ccc(S(=O)(=O)n2cc(I)c3cc(-c4ccc(C5CCN(C(=O)OC(C)(C)C)CC5)c(F)c4)cnc32)cc1]

Step-i tert-butyl 4-(4-chloro-2-fluorophenyl)-5,6-dihydropyridine-1(2H)-carboxylate Using similar reaction conditions as described in step i of intermediate 9,4-chloro-2-fluoro-1-iodobenzene (681 mg, 2.657 mmol) was coupled with tert-butyl 4-(4,4,5,5-tetram-

Step-ii tert-butyl 4-(2-fluoro-4-(1H-pyrrolo[2,3-b]pyridin-5-yl)phenyl)-5,6-dihydropyridine-1(2H)-carboxylate Using similar reaction conditions as described in step i of intermediate 9, tert-butyl 4-(4-chloro-2-fluorophenyl)-5,6-dihydropyridine-1(2H)-carboxylate (320 mg, 1.025 mmol) was coupled with 5-(4,4,5,5-tetramethyl-1,3,2-dioxaborolan-2-yl)-1H-pyrrolo[2,3-b]pyridine (375 mg, 1.538 mmol) using potassium carbonate (653 mg, 3.076 mmol), Pd(PPh$_3$)$_2$Cl$_2$ (94 mg, 0.102 mmol) and tricyclohexylphosphine (43 mg, 0.153 mmol) in dioxane/water (10/2 ml) to afford 320 mg of the product after purification with (60/120 silica gel) column chromatography using 2% methanol in DCM as eluent.

Step-iii: tert-butyl 4-(2-fluoro-4-(1H-pyrrolo[2,3-b]pyridin-5-yl)phenyl)piperidine-1-carboxylate To a solution of tert-butyl 4-(2-fluoro-4-(1H-pyrrolo[2,3-b]pyridin-5-yl)phenyl)-5,6-dihydropyridine-1(2H)-carboxylate (320 mg, 0.814 mmol) in ethyl acetate/methanol 20/20 mL was added palladium hydroxide (160 mg) and stirred under hydrogen atmosphere for 7 days. The catalyst was filtered through celite and the solvent was distilled off to get 320 mg (99.37% yield) of the titled compound. MS: m/z=396.3 (M+1).

Step-iv: tert-butyl 4-(2-fluoro-4-(3-iodo-1H-pyrrolo[2,3-b]pyridin-5-yl)phenyl)piperidine-1-carboxylate Using similar reaction conditions as described in step i of intermediate 1, tert-butyl 4-(2-fluoro-4-(1H-pyrrolo[2,3-b]pyridin-5-yl)phenyl)piperidine-1-carboxylate (320 mg, 0.810 mmol) was iodinated with N-iodosuccinimide (219 mg, 0.972 mmol) in DCM (20 ml) to afford 400 mg (94.7% yield) of the pure product. MS: m/z=522.1 (M+1).

Step v: tert-butyl 4-(2-fluoro-4-(3-iodo-1-tosyl-1H-pyrrolo[2,3-b]pyridin-5-yl)phenyl)piperidine-1-carboxylate Using similar reaction conditions as described in, step ii of Intermediate 1, tert-butyl 4-(2-fluoro-4-(3-iodo-1H-pyrrolo[2,3-b]pyridin-5-yl)phenyl)piperidine-1-carboxylate (400 mg, 0.767 mmol) was tosylated with p-toluene sulfonylchloride (220 mg, 1.151 mmol) and DMAP (282 mg, 2.303 mmol) in DCM (20 mL) to afford 250 mg (48.26% yield) of the titled compound after purification with (60/120 silica gel) column chromatography using 1% methanol in DCM as eluent. MS: m/z=676.3 (M+1). $^1$H NMR (CDCl$_3$, 300 MHz): δ 8.619-8.611 (d, 1H), 8.12-8.09 (d, 2H), 7.89 (s, 1H), 7.767-7.760 (d, 1H), 7.31-7.23 (m, 5H), 4.26 (s, 2H), 3.08-3.00 (m, 1H), 2.95-2.75 (m, 2H), 2.38 (s, 3H), 1.86-1.64 (m, 4H), 1.489 (s, 9H).

Step-i: tert-butyl 4-((4-bromophenyl)amino)piperidine-1-carboxylate

Using similar reaction conditions as described in step-iii of example-133, tert-butyl 4-oxopiperidine-1-carboxylate (3 gm, 15.0 mmol) and 4-bromoaniline (2.59 gm, 15.0 mmol) were reacted using Na(OAc)$_3$BH (105 mg, 0.494 mmol) and 3 drops of acetic acid in dichloroethane (80 mL) to afford 6.7 gm (crude) of the titled compound. MS: m/z=256.8 (M-Boc+1).

Step-ii: tert-butyl 4-((4-(4,4,5,5-tetramethyl-1,3,2-dioxaborolan-2-yl)phenyl)amino)piperidine-1-carboxylate Using similar reaction conditions as described in step ii of intermediate-3, tert-butyl 4-((4-bromophenyl)amino)piperidine-1-carboxylate (6.7 g, 18.8 mmol) was coupled with 4,4,4',4',5,5,5',5'-octamethyl-2,2'-bi(1,3,2-dioxaborolane) (7.19 g, 28.3 mmol) using potassium acetate (6.45 g, 65.8 mmol) and Pd(dppf)Cl$_2$.DCM (410 mg, 0.5 mmol) in 1,4-Dioxane (150 mL) to give 5.0 g (65.8% yield) of the pure product after purification by chromatographic column (Silicagel-60/120) using 75% ethyl acetate as eluent. MS: m/z=402.9 (M+1).

TABLE 7

Intermediates Prepared Using General procedure of intermediate 67

| Intermediate | Reactant A | Reactant B | Reactant C | Product |
|---|---|---|---|---|
| 67A | | | | |
| 67B | | | | |

Intermediate 68: tert-butyl 4-((4-(4,4,5,5-tetramethyl-1,3,2-dioxaborolan-2-yl)phenyl)amino) piperidine-1-carboxylate

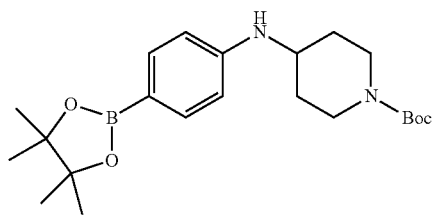 [SMILES: CC(C)(C)OC(=O)N1CCC(Nc2ccc(B3OC(C)(C)C(C)(C)O3)cc2)CC1]

Intermediate 70: tert-butyl 4-(2-fluoro-4-(4,4,5,5-tetramethyl-1,3,2-dioxaborolan-2-yl)phenyl)-5,6-dihydropyridine-1(2H)-carboxylate

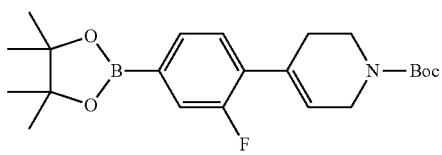

Step-i: tert-butyl 4-(4-bromo-2-fluorophenyl)-5,6-dihydropyridine-1(2H)-carboxylate Using similar reaction conditions as described in step i of intermediate 9,4-bromo-2-fluoro-1-iodobenzene (500 mg, 1.95 mmol) was coupled with tert-butyl 4-(4,4,5,5-tetramethyl-1,3,2-dioxaborolan-2-yl)-5,6-dihydropyridine-1(2H)-carboxylate (660 mg, 2.14 mmol) using sodium carbonate (620 mg, 5.85 mmol) and PdCl$_2$(PPh$_3$)$_2$ (69 mg, 0.097 mmol) in DME/water (10/2 ml) at 85° C. for 2 hours to afford 300 mg (50.5%) of the crude product after purification with (60/120 silica gel) column chromatography using 20% ethyl acetate in hexane as eluent. MS: m/z=300.0 (M+1) (t-butyl cleaved mass was observed).

Step-ii: tert-butyl 4-(2-fluoro-4-(4,4,5,5-tetramethyl-1,3,2-dioxaborolan-2-yl)phenyl)-5,6-dihydropyridine-1(2H)-carboxylate Using similar reaction conditions as described in step ii of intermediate-3, tert-butyl 4-(4-bromo-2-fluorophenyl)-5,6-dihydropyridine-1(2H)-carboxylate (250 mg, 0.698 mmol) was coupled with 4,4,4',4',5,5,5',5'-octamethyl-2,2'-bi(1,3,2-dioxaborolane) (265 mg, 1.047 mmol) using potassium acetate (205 mg, 2.09 mmol) and Pd(dppf)Cl$_2$ (26 mg, 0.035 mmol) in 1,4-dioxane (10 mL) to give 270 mg (96.42% yield) of the pure product after purification by chromatographic column (silicagel-60/120) using 15% ethyl acetate as eluent. MS: m/z=404.4 (M+1).

Intermediate 71: 2-(4-(2-amino-4-bromophenyl)piperazin-1-yl)acetamide

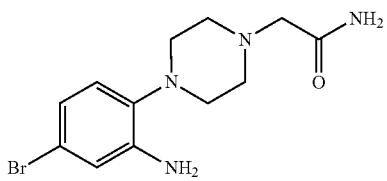 [SMILES: NC(=O)CN1CCN(c2ccc(Br)cc2N)CC1]

Step-i: 1-(4-bromo-2-nitrophenyl)piperazine hydrochloride

Using similar reaction conditions as described in (step i of Intermediate-2), tert-butyl piperazine-1-carboxylate (1.5 g, 6.81 mmol) was reacted with 4-bromo-1-fluoro-2-nitrobenzene (1.28 g, 6.81 mmol) in DMF (25 ml) and potassium carbonate (2.35 g, 17.02 mmol) to afford crude product. Using similar reaction conditions as described in Step-ii of example-7, above crude was deprotected in HCl in ether/methanol (10/10 ml). This afforded 2.0 g (99% yield).

Step-ii: 2-(4-(4-bromo-2-nitrophenyl)piperazin-1-yl)acetamide

Using the same reaction conditions as described in step-i of example-82A, 1-(4-bromo-2-nitrophenyl)piperazine hydrochloride (1.2 g 3.69 mmol) was alkylated using 2-chloroacetamide (517 mg, 5.53 mmol) and sodium carbonate (930 mg, 11.07 mmol) in toluene/ethanol (15/15 mL) to get 510 mg (40.3% yield) of the titled compound. MS: m/z=343.0 (M+1).

Step-iii: 2-(4-(2-amino-4-bromophenyl)piperazin-1-yl)acetamide

Using similar reaction conditions as described in step ii of Intermediate-27, 2-(4-(4-bromo-2-nitrophenyl)piperazin-1-yl)acetamide (600 mg, 1.74 mmol) was reduced using zinc dust (568 mg, 8.74 mmol) and ammonium chloride (461 mg, 8.74 mmol) in THF/water 10/10 ml to afford 508 mg (93% yield) of the titled product.

Intermediate 72: tert-butyl 4-(2-amino-4-bromophenyl)-5,6-dihydropyridine-1(2H)-carboxylate

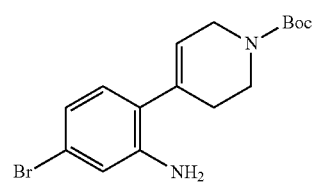 [SMILES: CC(C)(C)OC(=O)N1CC=C(c2ccc(Br)cc2N)CC1]

Step-i: tert-butyl 4-(4-bromo-2-nitrophenyl)-5,6-dihydropyridine-1(2H)-carboxylate Using similar reaction conditions as described in step i of intermediate 9,4-bromo-1-iodo-2-nitrobenzene (500 mg, 1.53 mmol) was coupled with tert-butyl 4-(4,4,5,5-tetramethyl-1,3,2-dioxaborolan-2-yl)-5,6-dihydropyridine-1(2H)-carboxylate (475 mg, 1.53 mmol) using sodium carbonate (486 mg, 4.59 mmol) and Pd(PPh$_3$)$_2$Cl$_2$ (53 mg, 0.07 mmol) in DME/water (10/2 ml) at 80° C. for 3 hours to afford 400 mg (68.9%) of the product after purification with (60/120 silica gel) column chromatography using 30% ethyl acetate in hexane as eluent.

Step-ii: tert-butyl 4-(2-amino-4-bromophenyl)-5,6-dihydropyridine-1(2H)-carboxylate Using similar reaction conditions as described in step ii of Intermediate-27, tert-butyl 4-(4-bromo-2-nitrophenyl)-5,6-dihydropyridine-1(2H)-carboxylate (450 mg, 1.17 mmol) was reduced using zinc dust (610 mg, 9.39 mmol) and ammonium chloride (1.0 g, 18.72 mmol) in THF/water 10/5 ml to afford 300 mg (72.4% yield) of the titled product after purification with (60/120 silica gel) column chromatography using 30% ethyl acetate in hexane as eluent. MS: m/z=295.1 (M-Boc+1).

Intermediate 73: tert-butyl 4-(3-(4,4,5,5-tetramethyl-1,3,2-dioxaborolan-2-yl)benzylidene) piperidine-1-carboxylate

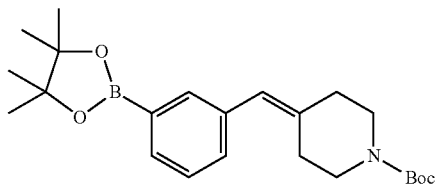 [SMILES: CC(C)(C)OC(=O)N1CCC(=Cc2cccc(B3OC(C)(C)C(C)(C)O3)c2)CC1]

Step-i: tert-butyl 4-(3-bromobenzylidene)piperidine-1-carboxylate

The mixture of 1-bromo-3-(bromomethyl)benzene (6.2 g, 24.8 mmol) and triethyl phosphite (4.53 g, 27.28 mmol) was heated at 90° C. for 12 hours, cooled to 0° C., added DME (40 ml) and tert-butyl 4-oxopiperidine-1-carboxylate (5.73 g, 28.8 mmol) and sodium hydride (1.19 g, 49.6 mmol) and stirred at RT for 2-3 hours. Diluted with water and extracted with ether to afford 4.5 g (51.5% yield) of the titled product after purification with (60/120 silica gel) column chromatography using 10% ethyl acetate in hexane as eluent. MS: m/z=353.2 (M+1).

Step-ii: tert-butyl 4-(3-(4,4,5,5-tetramethyl-1,3,2-dioxaborolan-2-yl)benzylidene)piperidine-1-carboxylate Using similar reaction conditions as described in step ii of intermediate-3, tert-butyl 4-(3-bromobenzylidene)piperidine-1-carboxylate (4.5 g, 12.7 mmol) was coupled with 4,4,4',4',5,5,5',5'-octamethyl-2,2'-bi(1,3,2-dioxaborolane) (3.87 g, 15.2 mmol) using potassium acetate (3.73 g, 38.1 mmol) and $PdCl_2$(dppf) (460 mg, 0.63 mmol) in DME (100 mL) to give 6 g (crude) of the titled product after purification by chromatographic column (Silicagel-60/120) using 15% ethyl acetate as eluent. MS: m/z=344.1 (M-Boc+1).

EXAMPLES

The present invention is further exemplified, but not limited, by the following examples that illustrate the preparation of compounds according to the invention.

Example 1

N-(3-(3-(1-(2-fluorobenzyl)-1H-pyrazol-4-yl)-1H-pyrrolo[2,3-b]pyridin-5-yl)phenyl)methanesulfonamide

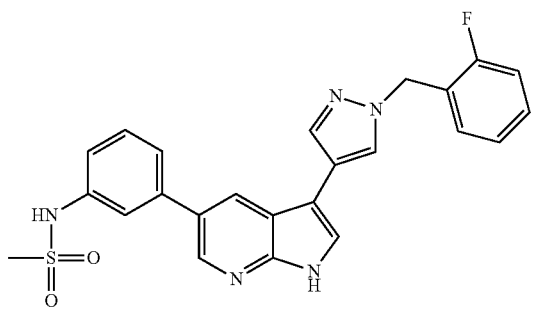 [SMILES: CS(=O)(=O)Nc1cccc(-c2cnc3[nH]cc(-c4cnn(Cc5ccccc5F)c4)c3c2)c1]

Step-i: 5-Bromo-3-(1-(2-fluorobenzyl)-1H-pyrazol-4-yl)-1-tosyl-1H-pyrrolo[2,3-b]pyridine 5-Bromo-3-iodo-1-tosyl-1H-pyrrolo[2,3-b]pyridine (Intermediate-1) (350 mg, 0.83 mmol) and 1-(2-fluorobenzyl)-4-(4,4,5,5-tetramethyl-1,3,2-dioxaborolan-2-yl)-1H-pyrazole (Intermediate-2) (301 mg, 0.99 mmol) were added to a solution of toluene/ethanol/water (5/5/2.5 ml) previously purged with argon (10 min). The reaction mixture was purged with argon for a further 15 mins, followed by the addition of potassium carbonate (230 mg, 1.6 mmol) and Pd(PPh$_3$)$_4$ (48 mg, 0.0415 mmol). The resulting mixture was heated to reflux at 80° C. overnight. The reaction was monitored by TLC (50% ethylacetate in hexane). The reaction mixture was cooled and diluted with ethyl acetate (50 ml) and washed with water (2×50 ml). The organic layer was dried over $Na_2SO_4$, and concentrated under reduced pressure to afford crude product. Purification by column chromatography on silica gel (20% ethyl acetate in hexane) afforded 285 mg (43.64% yield) of titled compound. MS: m/z=527.0 (M+1).

Step-ii: N-(3-(3-(1-(2-fluorobenzyl)-1H-pyrazol-4-yl)-1-tosyl-1H-pyrrolo[2,3-b]pyridin-5-yl)phenyl)methanesulfonamide 5-Bromo-3-(1-(2-fluorobenzyl)-1H-pyrazol-4-yl)-1-tosyl-1H-pyrrolo[2,3-b]pyridine (140 mg, 0.267 mmol) and N-(3-(4,4,5,5-tetramethyl-1,3,2-dioxaborolan-2-yl)phenyl) methane sulfonamide (Intermediate 3) (95 mg, 0.32 mmol) were added to a solution of toluene/ethanol/water (5/5/2.5 ml) previously purged with argon (10 min). The reaction mixture was purged with argon for a further 15 mins, followed by the addition of potassium carbonate (74 mg, 0.534 mmol) and Pd(PPh$_3$)$_4$ (15 mg, 0.0133 mmol). The resulting mixture was heated to reflux at 80° C. for 2 h. The reaction was monitored by TLC (50% ethyl acetate in hexane). The reaction mixture was cooled and diluted with ethyl acetate (50 ml) and washed with water (2×50 ml). The organic layer was dried over $Na_2SO_4$, and concentrated under reduced pressure to afford 205 mg of crude product which was taken as such for next reaction. MS: m/z=616.1 (M+1).

Step-iii: N-(3-(3-(1-(2-fluorobenzyl)-1H-pyrazol-4-yl)-1H-pyrrolo[2,3-b]pyridin-5-yl)phenyl) methanesulfonamide N-(3-(3-(1-(2-fluorobenzyl)-1H-pyrazol-4-yl)-1-tosyl-1H-pyrrolo[2,3-b]pyridin-5-yl)phenyl) methanesulfonamide (200 mg) dissolved in 12.5 ml of THF-water-methanol (1:1:0.5) mixture and added lithium hydroxide (40.8 mg, 0.97 mmol) at 0° C. and stirred at room temperature for 15 h. The reaction was monitored by TLC (100% ethyl acetate in hexane) until TLC indicated that reaction was complete. The reaction mixture was diluted with ethyl acetate (25 ml) and washed with water (2×25 ml). The organic layer was dried over $Na_2SO_4$, and concentrated under reduced pressure to afford crude product. Purification by preparative TLC (5% methanol in DCM) afforded 17 mg (14.99% yield) of tilted compound. $^1$H NMR (DMSO-d$_6$, 300 MHz): δ 9.83 (s, 1H), 8.479-8.472 (d, 1H), 8.38 (s, 1H), 8.33-8.32 (d, 1H), 7.95-7.78 (m, 2H), 7.53-7.43 (m, 4H), 7.27-7.18 (m, 3H), 5.44 (s, 2H), 3.05 (s, 1H). MS: m/z=462.1 (M+1), HPLC: 95.83% in method A.

Example 2

N-(3-(3-(1-(3-(trifluoromethyl)benzyl)-1H-pyrazol-4-yl)-1H-pyrrolo[2,3-b]pyridin-5-yl)phenyl) methanesulfonamide

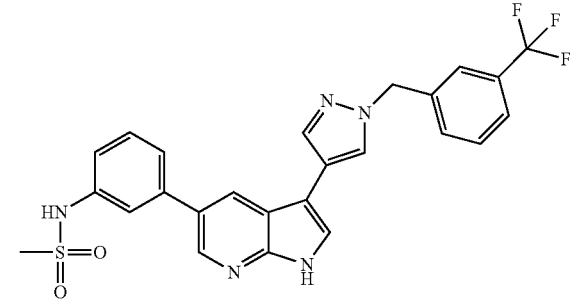 [SMILES: CS(=O)(=O)Nc1cccc(-c2cnc3[nH]cc(-c4cnn(Cc5cccc(C(F)(F)F)c5)c4)c3c2)c1]

Step-i: 5-bromo-1-tosyl-3-(1-(3-(trifluoromethyl) benzyl)-1H-pyrazol-4-yl)-1H-pyrrolo[2,3-b]pyridine Using similar reaction conditions as described in step-i of example-1,5-bromo-3-iodo-1-tosyl-1H-pyrrolo[2,3-b]pyridine (Intermediate 1) (300 mg, 0.629 mmol) was coupled with 4-(4,4,5,5-tetramethyl-1,3,2-dioxaborolan-2-yl)-1-(3-(trifluoromethyl)benzyl)-1H-pyrazole (Intermediate 4) (310 mg, 0.88 mmol) in sodium carbonate (200 mg, 1.88 mmol), bis(triphenyl phosphine)palladium(ii) dichloride (22 mg, 0.0314 mmol) and toluene/ethanol/water (30/10/2.5 ml) to afford 167 mg (46.2% yield) of the pure product after column purification using 30% ethyl acetate in hexane as eluent. MS: m/z=577.00 (M+2).

Step-ii: N-(3-(1-tosyl-3-(1-(3-(trifluoromethyl)benzyl)-1H-pyrazol-4-yl)-1H-pyrrolo[2,3-b]pyridin-5-yl)phenyl)methanesulfonamide Using similar reaction conditions as described in step 2 of example 1, 5-bromo-1-tosyl-3-(1-(3-(trifluoromethyl)benzyl)-1H-pyrazol-4-yl)-1H-pyrrolo[2,3-b]pyridine (165 mg, 0.28 mmol) was coupled with N-(3-(4,4,5,5-tetramethyl-1,3,2-dioxaborolan-2-yl)phenyl) methane sulfonamide (Intermediate 3) (119 mg, 0.401 mmol) in sodium carbonate (91 mg, 0.86 mmol), bis(triphenyl phosphine)palladium(ii) dichloride (10 mg, 0.014 mmol) and toluene/ethanol/water (15/6/2 ml) to afford 188 mg (98.4% yield) of the pure product after column purification using 60% ethyl acetate in hexane as eluent. MS: m/z=666.10 (M+1).

Step-iii: N-(3-(3-(1-(3-(trifluoromethyl)benzyl)-1H-pyrazol-4-yl)-1H-pyrrolo[2,3-b]pyridin-5-yl)phenyl)methanesulfonamide Using similar reaction conditions as described in step-iii in example 1,5-N-(3-(1-tosyl-3-(1-(3-(trifluoromethyl)benzyl)-1H-pyrazol-4-yl)-1H-pyrrolo[2,3-b]pyridin-5-yl)phenyl)methane sulfon amide (188 mg, 0.28 mmol) was hydrolyzed with lithium hydroxide (35.5 mg, 0.847 mmol) in THF/water/methanol (12/6/3 ml) mixture to afford 20 mg (14% yield) of the pure product. 1H NMR (CDCl$_3$, 300 MHz): δ 11.07 (s, 1H), 10.27 (s, 1H), 8.79 (s, 1H), 8.31 (s, 1H), 7.89 (s, 1H), 7.72 (s, 1H), 7.7-7.649 (m, 1H), 7.6-7.447 (m, 7H), 5.46 (s, 2H), 3.12 (s, 3H). MS: m/z=512.1 (M+1), HPLC: 98.88% in method A.

Example 3

N-(3-(3-(1-(4-methoxybenzyl)-1H-pyrazol-4-yl)-1H-pyrrolo[2,3-b]pyridin-5-yl)phenyl)n methane sulfonamide

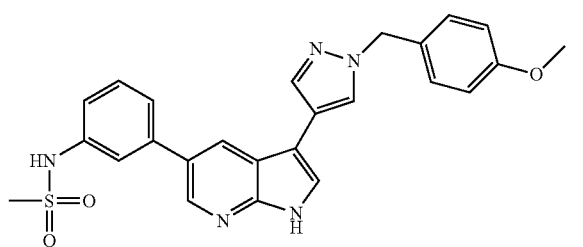

Step-i: 5-bromo-3-(1-(4-methoxybenzyl)-1H-pyrazol-4-yl)-1-tosyl-1H-pyrrolo[2,3-b]pyridine Using similar reaction conditions as described in step-i of example-1,5-bromo-3-iodo-1-tosyl-1H-pyrrolo[2,3-b]pyridine (Intermediate 1) (750 mg, 1.78 mmol) was coupled with 1-(4-methoxybenzyl)-4-(4,4,5,5-tetramethyl-1,3,2-dioxaborolan-2-yl)-1H-pyrazole (Intermediate 5) (671 mg, 2.13 mmol) in sodium carbonate (614 mg, 4.4 mol), bis(triphenyl phosphine)palladium(ii) dichloride (62 mg, 2.13 mmol) and toluene/ethanol/water (10/10/5 ml) to afford 550.0 mg (57.95% yield) of the pure product after column purification using 30% ethyl acetate in hexane as eluent. $^1$H NMR (DMSO-d$_6$, 300 MHz): δ 8.56-8.50 (m, 3H), 8.25 (s, 1H), 8.08 (s, 1H), 7.97-7.94 (d, 2H), 7.41-7.39 (d, 2H), 7.27-7.24 (d, 2H), 6.91-6.89 (d, 2H), 5.27 (s, 2H), 3.72 (s, 3H), 2.32 (s, 3H). MS: m/z=539.0 (M+2).

Step-ii: N-(3-(3-(1-(4-methoxybenzyl)-1H-pyrazol-4-yl)-1-tosyl-1H-pyrrolo[2,3-b]pyridin-5-yl)phenyl) methanesulfonamide Using similar reaction conditions as described in step-ii of example-1, 5-bromo-3-(1-(4-methoxybenzyl)-1H-pyrazol-4-yl)-1-tosyl-1H-pyrrolo[2,3-b]pyridine (240 mg, 0.44 mmol) was coupled with N-(3-(4,4,5,5-tetramethyl-1,3,2-dioxaborolan-2-yl)phenyl) methane sulfonamide (intermediate 3) (160 mg, 0.53 mmol) in sodium carbonate (142 mg, 1.34 mmol), bis(triphenyl phosphine)palladium(ii) dichloride (16 mg, 0.022 mmol) and toluene/ethanol/water (7/7/4 ml) to afford 250 mg (89.28% yield) of the pure product after column purification using 35% ethyl acetate in hexane as eluent. MS: m/z=628.3 (M+1).

Step-iii: N-(3-(3-(1-(4-methoxybenzyl)-1H-pyrazol-4-yl)-1H-pyrrolo[2,3-b]pyridin-5-yl)phenyl) methanesulfonamide Using similar reaction conditions as described in step-iii of example-1, N-(3-(3-(1-(4-methoxybenzyl)-1H-pyrazol-4-yl)-1-tosyl-1H-pyrrolo[2,3-b]pyridin-5-yl)phenyl)methane sulfon amide (250 mg, 0.39 mmol) was hydrolyzed with lithium hydroxide (66 mg, 1.6 mmol) in THF/water/methanol (4/3/1 ml) mixture to afford 15 mg (9.57% yield) of the pure product after purification by prep TLC using 2% methanol in DCM as eluent. $^1$H NMR (DMSO-d$_6$, 300 MHz): δ 11.79 (s, 1H), 9.83 (s, 1H), 8.469 (s, 1H), 8.33-8.31 (d, 2H), 7.91 (s, 1H), 7.75 (s, 1H), 7.52-7.43 (m, 3H), 7.27-7.22 (t, 3H), 6.91-6.89 (d, 2H), 5.28 (s, 2H), 3.72 (s, 3H), 3.05 (s, 3H). MS: m/z=474.2 (M+1), HPLC: 94.18% in Method-C.

Example 4

N-(3-(3-(1-(2,5-difluorobenzyl)-1H-pyrazol-4-yl)-1H-pyrrolo[2,3-b]pyridin-5-yl)phenyl)methane sulfonamide

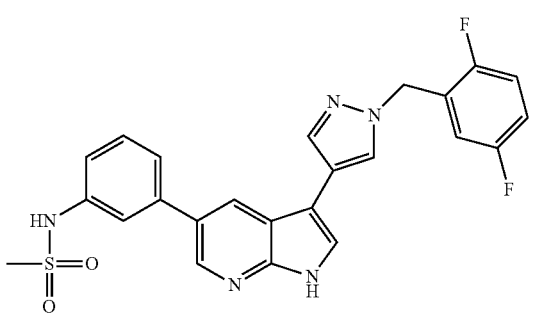 [SMILES: CS(=O)(=O)Nc1cccc(-c2cnc3[nH]cc(-c4cnn(Cc5cc(F)ccc5F)c4)c3c2)c1]

Step-i: 5-bromo-3-(1-(2,5-difluorobenzyl)-1H-pyrazol-4-yl)-1-tosyl-1H-pyrrolo[2,3-b]pyridine Using similar reaction conditions as described in step-i of example 1,5-bromo-3-iodo-1-tosyl-1H-pyrrolo[2,3-b]pyridine (Intermediate 1) (1 g, 2.37 mmol) was coupled with 1-(2,5-difluorobenzyl)-4-(4,4,5,5-tetramethyl-1,3,2-dioxaborolan-2-yl)-1H-pyrazole (Intermediate 6) (688 mg, 3.3 mmol) in sodium carbonate (749 mg, 7.07 mmol), bis(triphenyl phosphine)palladium(ii) dichloride (83 mg, 0.11 mmol) and toluene/ethanol/water (10/10/5 ml) to afford 550 mg (42.63% yield) of the pure product after column purification using 30% ethyl acetate in hexane as eluent. $^1$H NMR (DMSO-$d_6$, 300 MHz): δ 8.59-8.51 (m, 3H), 8.29 (s, 1H), 8.13 (s, 1H), 7.98-7.95 (d, 2H), 7.42-7.40 (d, 2H), 7.35-7.10 (m, 4H), 5.52 (s, 2H), 2.33 (s, 3H). MS: m/z=542.6 (M−1).

Step-ii: N-(3-(3-(1-(2,5-difluorobenzyl)-1H-pyrazol-4-yl)-1-tosyl-1H-pyrrolo[2,3-b]pyridin-5-yl)phenyl) methanesulfonamide Using similar reaction conditions as described in step-ii of example-1, 5-bromo-3-(1-(2,5-difluorobenzyl)-1H-pyrazol-4-yl)-1-tosyl-1H-pyrrolo[2,3-b]pyridine (250 mg, 0.46 mmol) was coupled with N-(3-(4,4,5,5-tetramethyl-1,3,2-dioxaborolan-2-yl)phenyl) methane sulfonamide (intermediate 3) (150 mg, 0.506 mol) in sodium carbonate (146 mg, 1.38 mol), bis(triphenyl phosphine)palladium(ii) dichloride (16 mg, 0.023 mmol) and toluene/ethanol/water (7/7/4 ml) to afford 250.0 mg (85.91% yield) of the pure product after column purification using 40% ethyl acetate in hexane as eluent.

Step-iii: N-(3-(3-(1-(2,5-difluorobenzyl)-1H-pyrazol-4-yl)-1H-pyrrolo[2,3-b]pyridin-5-yl)phenyl) methanesulfonamide Using similar reaction conditions as described in step-iii of example-1, N-(3-(3-(1-(2,5-difluorobenzyl)-1H-pyrazol-4-yl)-1-tosyl-1H-pyrrolo[2,3-b]pyridin-5-yl)phenyl) methanesulfonamide (250 mg, 0.39 mmol) was hydrolyzed with lithium hydroxide (66 mg, 1.57 mmol) in THF/water/methanol (5/4/3 ml) mixture to afford 170 mg (89.94% yield) of the pure product. $^1$H NMR (DMSO-$d_6$, 300 MHz): δ 11.83 (s, 1H), 8.47-8.32 (m, 3H), 7.97 (s, 1H), 7.799-7.794 (d, 1H), 7.64-7.55 (m, 3H), 7.49-7.44 (m, 3H), 7.32-7.21 (m, 2H), 5.44 (s, 2H), 3.03 (s, 3H) MS: m/z=479.8 (M+1), HPLC: 73.14% in method A.

Example 5

N-(3-(3-(1-(4-fluorobenzyl)-1H-pyrazol-4-yl)-1H-pyrrolo[2,3-b]pyridin-5-yl)phenyl) methanesulfonamide

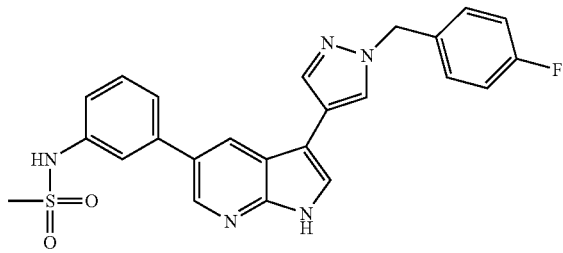 [SMILES: CS(=O)(=O)Nc1cccc(-c2cnc3[nH]cc(-c4cnn(Cc5ccc(F)cc5)c4)c3c2)c1]

Step-i: 5-bromo-3-(1-(4-fluorobenzyl)-1H-pyrazol-4-yl)-1-tosyl-1H-pyrrolo[2,3-b]pyridine Using similar reaction conditions as described in step-i of example-1,5-bromo-3-iodo-1-tosyl-1H-pyrrolo[2,3-b]pyridine (Intermediate 1) (700 mg, 1.46 mmol) was coupled with 1-(4-fluorobenzyl)-4-(4,4,5,5-tetramethyl-1,3,2-dioxaborolan-2-yl)-1H-pyrazole (intermediate 7) (554 mg, 1.83 mmol) in sodium carbonate (466 mg, 4.4 mmol), bis(triphenylphosphine) palladium(ii)dichloride (51 mg, 0.073 mmol) and toluene/ethanol/water (20/8/2 ml) to afford 300 mg (38.9% yield) of the pure product after column purification using 20% ethyl acetate in hexane as eluent. MS: m/z=526.7 (M+1).

Step-ii: N-(3-(3-(1-(4-fluorobenzyl)-1H-pyrazol-4-yl)-1-tosyl-1H-pyrrolo[2,3-b]pyridin-5-yl)phenyl) methanesulfonamide Using similar reaction conditions as described in step-ii of example-1, 5-bromo-3-(1-(4-fluorobenzyl)-1H-pyrazol-4-yl)-1-tosyl-1H-pyrrolo[2,3-b]pyridine (150 mg, 0.285 mmol) was coupled with N-(3-(4,4,5,5-tetramethyl-1,3,2-dioxaborolan-2-yl)phenyl) methane sulfonamide (intermediate 3) (127 mg, 0.427 mmol) in sodium carbonate (90.6 mg, 0.855 mmol), bis(triphenyl phosphine)palladium(ii) dichloride (39.8 mg, 0.057 mmol) and toluene/ethanol/water (20/8/2 ml) to afford 138 mg (79% yield) of the pure product after column purification using 40% ethyl acetate in hexane as eluent. MS: m/z=616.3 (M+1).

Step-iii: N-(3-(3-(1-(4-fluorobenzyl)-1H-pyrazol-4-yl)-1H-pyrrolo[2,3-b]pyridin-5-yl)phenyl) methane sulfonamide Using similar reaction conditions as described in step-iii of example-1, N-(3-(3-(1-(4-fluorobenzyl)-1H-pyrazol-4-yl)-1-tosyl-1H-pyrrolo[2,3-b]pyridin-5-yl)phenyl)methane sulfonamide (137 mg, 0.222 mmol) was hydrolyzed with lithium hydroxide (47 mg, 1.111 mmol) in THF/water/methanol (12/6/3 ml) mixture to afford 1 mg (1% yield) of the title compound. $^1$H NMR (CD$_3$OD, 600 MHz): δ 8.48 (br, 1H), 8.365-8.361 (d, 1H), 8.183 (s, 1H), 7.922 (s, 1H), 7.64 (s, 1H), 7.568 (m, 1H), 7.52-7.50 (m, 2H), 7.48-7.44 (m, 1H), 7.37-7.34 (m, 2H), 7.31-7.29 (m, 1H), 7.127-7.083 (m, 2H), 5.411 (s, 2H), 3.025 (s, 3H). MS: m/z=462.4 (M+1), HPLC: 90.99% in method B.

Example 6

N-(3-(3-(1-(3,5-difluorobenzyl)-1H-pyrazol-4-yl)-1H-pyrrolo[2,3-b]pyridin-5-yl)phenyl) methane sulfonamide

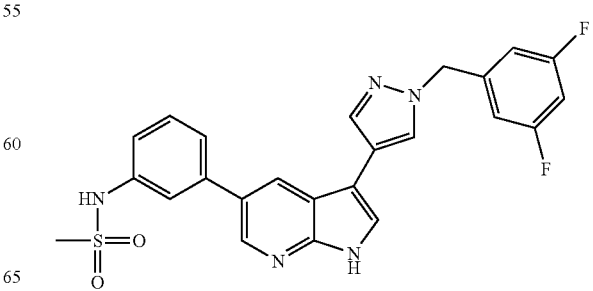

Step-i: N-(3-(3-(1-(3,5-difluorobenzyl)-1H-pyrazol-4-yl)-1-tosyl-1H-pyrrolo[2,3-b]pyridin-5-yl)phenyl) methanesulfonamide Using similar reaction conditions as described in step-i of example-1, N-(3-(3-iodo-1-tosyl-1H-pyrrolo[2,3-b]pyridin-5-yl)phenyl)methanesulfonamide (intermediate 9) (200 mg, 0.352 mmol) was coupled with 1-(3,5-difluorobenzyl)-4-(4,4,5,5-tetramethyl-1,3,2-dioxaborolan-2-yl)-1H-pyrazole (Intermediate 8) (159 mg, 0.528 mmol) in sodium carbonate (112 mg, 1.05 mmol), PdCl$_2$(dppf) (13 mg, 0.017 mmol) and toluene/ethanol/water (18/12/8 ml) to afford 300 mg of the crude product.

Step-ii: N-(3-(3-(1-(3,5-difluorobenzyl)-1H-pyrazol-4-yl)-1H-pyrrolo[2,3-b]pyridin-5-yl)phenyl) methane sulfonamide Using similar reaction conditions as described in step-iii of example-1, N-(3-(3-(1-(3,5-difluorobenzyl)-1H-pyrazol-4-yl)-1-tosyl-1H-pyrrolo[2,3-b]pyridin-5-yl)phenyl)methane sulfonamide (300 mg, 0.473 mmol) was hydrolyzed with lithium hydroxide (40 mg, 0.946 mmol) in THF/water/methanol (15/10/5 ml) mixture to afford 20 mg (8.8% yield) of the desired compound. $^1$H NMR (DMSO-d$_6$, 400 MHz): δ 11.82 (s, 1H), 9.82 (s, 1H), 8.48-8.47 (d, 1H), 8.43 (s, 1H), 8.355-8.350 (d, 1H), 8.00 (s, 1H), 7.71-7.80 (d, 1H), 7.53-7.46 (m, 3H), 7.25-7.23 (m, 2H), 6.98-6.97 (d, 2H), 5.42 (s, 2H), 3.05 (s, 3H). MS: m/z=479.8 (M+1), HPLC: 94.78% (Method-B).

Example 7

N-(3-(3-(1-(3-nitrobenzyl)-1H-pyrazol-4-yl)-1H-pyrrolo[2,3-b]pyridin-5-yl)phenyl)methane sulfonamide

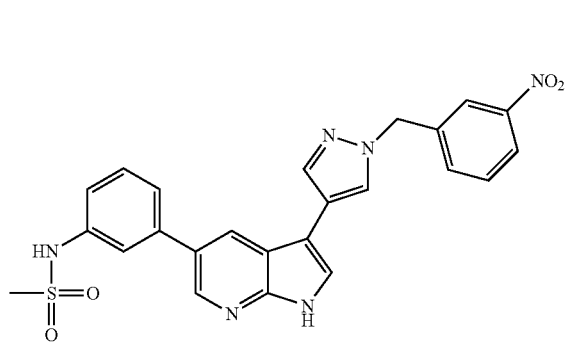 [SMILES: CS(=O)(=O)Nc1cccc(-c2cnc3[nH]cc(-c4cnn(Cc5cccc([N+](=O)[O-])c5)c4)c3c2)c1]

Step-i: tert-butyl 5-(3-(methylsulfonamido)phenyl)-3-(1-(3-nitrobenzyl)-1H-pyrazol-4-yl)-1H-pyrrolo[2,3-b]pyridine-1-carboxylate Using similar reaction conditions as described in step-i of example 1, tert-butyl 3-iodo-5-(3-(methylsulfonamido)phenyl)-1H-pyrrolo[2,3-b]pyridine-1-carboxylate (intermediate-32) (300 mg, 0.5 mmol) was coupled with 1-(3-nitrobenzyl)-4-(4,4,5,5-tetramethyl-1,3,2-dioxaborolan-2-yl)-1H-pyrazole (intermediate 10) (211 mg, 0.6 mmol) in sodium carbonate (189 mg, 1.7 mmol), PdCl$_2$(dppf) (20 mg, 0.02 mmol) and DME/water (3/3 ml) to afford 200 mg (59% yield) of the pure product after column purification using 30% ethyl acetate in hexane as eluent.

Step-ii: N-(3-(3-(1-(3-nitrobenzyl)-1H-pyrazol-4-yl)-1H-pyrrolo[2,3-b]pyridin-5-yl)phenyl) methane sulfonamide tert-butyl 5-(3-(methylsulfonamido)phenyl)-3-(1-(3-nitrobenzyl)-1H-pyrazol-4-yl)-1H-pyrrolo[2,3-b]pyridine-1-carboxylate (200 mg, 0.409 mmol) dissolved in 10 ml of methanol and added 1,4-dioxane/HCl (2 ml) at 0° C. and stirred at room temperature for 15 h. The reaction was monitored by TLC (30% ethyl acetate in hexane). The reaction mixture was concentrated under reduced pressure to afford crude product. The residue was basified with saturated sodium bicarbonate solution and extracted with ethyl acetate (2×25 ml). The organic layer was dried over Na$_2$SO$_4$, and concentrated under reduced pressure to afford 100 mg (62% yield) of the pure required product. $^1$H NMR (DMSO-d$_6$, 400 MHz): δ11.82 (s, 1H), 9.85 (s, 1H), 8.47 (s, 2H), 8.33 (s, 1H), 8.18-8.15 (d, 2H), 8.00 (s, 1H), 7.806-7.7.800 (d, 1H), 7.75-7.34 (d, 1H), 7.69-7.65 (t, 1H), 7.52-7.44 (m, 3H), 7.24-7.22 (d, 1H), 5.55 (s, 2H), 3.05 (s, 3H). MS: m/z=489.3 (M+1), HPLC: 93.67% (method B).

Example 8

N-(3-(3-(1-(3-aminobenzyl)-1H-pyrazol-4-yl)-1H-pyrrolo[2,3-b]pyridin-5-yl)phenyl) methane sulfonamide

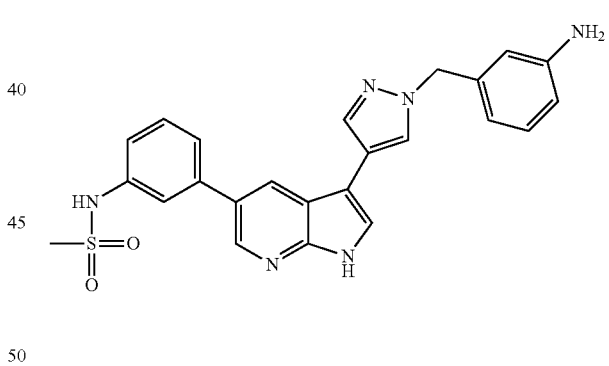

N-(3-(3-(1-(3-nitrobenzyl)-1H-pyrazol-4-yl)-1H-pyrrolo[2,3-b]pyridin-5-yl)phenyl)methane sulfonamide (Example-7) (80 mg, 0.163 mmol), was reduced by palladium on carbon (8 mg, 10% W/W) in THF/MeOH (2/2 mL) under positive pressure of hydrogen using a bladder. The catalyst filtered off and concentrated to get crude compound. This was then purified by preparative TLC using 10% ethyl acetate in hexanes as eluent yielded 12 mg (16% yield) of pure titled compound. $^1$H NMR (DMSO-d$_6$, 400 MHz): δ11.85 (s, 1H), 9.83 (s, 1H), 8.47-8.46 (d, 1H), 8.33-8.32 (m, 2H), 7.92 (s, 1H), 7.775-7.770 (d, 1H), 7.53-7.44 (m, 3H), 7.24-7.22 (d, 1H), 6.96-6.94 (t, 1H), 6.46-6.42 (m, 2H), 5.20 (s, 2H), 5.10 (b, 2H), 3.05 (s, 3H). MS: m/z=459.3 (M+1), HPLC: 92.06% (method B).

Example 9

N-(3-(3-(1-(3-fluorobenzyl)-1H-pyrazol-4-yl)-1H-pyrrolo[2,3-b]pyridin-5-yl)phenyl)methanesulfonamide

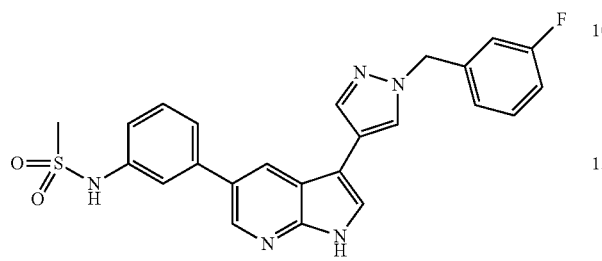

Step-i: 5-bromo-3-(1-(3-fluorobenzyl)-1H-pyrazol-4-yl)-1-tosyl-1H-pyrrolo[2,3-b]pyridine Using similar reaction conditions as described in step-i of example-1, 5-bromo-3-iodo-1-tosyl-1H-pyrrolo[2,3-b]pyridine (intermediate 1) (700 mg, 1.46 mmol) was coupled with 1-(3-fluorobenzyl)-4-(4,4,5,5-tetramethyl-1,3,2-dioxaborolan-2-yl)-1H-pyrazole (intermediate 11) (554 mg, 1.83 mmol) in sodium carbonate (466 mg, 4.4 mmol), bis(triphenyl phosphine)palladium(ii) dichloride (51 mg, 0.073 mmol) and toluene/ethanol/water (30/10/4 ml) to afford 422 mg (54.8% yield) of the pure product after column purification using 20% ethyl acetate in hexane as eluent.

Step-ii: N-(3-(3-(1-(3-fluorobenzyl)-1H-pyrazol-4-yl)-1-tosyl-1H-pyrrolo[2,3-b]pyridin-5-yl)phenyl)methanesulfonamide Using similar reaction conditions as described in step-ii of example-1, 5-bromo-3-(1-(3-fluorobenzyl)-1H-pyrazol-4-yl)-1-tosyl-1H-pyrrolo[2,3-b]pyridine (100 mg, 0.19 mmol) was coupled with N-(3-(4,4,5,5-tetramethyl-1,3,2-dioxaborolan-2-yl)phenyl) methane sulfonamide (intermediate 3) (84.8 mg, 0.285 mmol) in sodium carbonate (60.5 mg, 0.57 mmol), bis(triphenyl phosphine)palladium(ii) dichloride (13.3 mg, 0.019 mmol) and toluene/ethanol/water (12/6/2 ml) to afford 106 mg of the crude product which was taken as such for next step. MS: m/z=615.7 (M+1).

Step-iii: N-(3-(3-(1-(3-fluorobenzyl)-1H-pyrazol-4-yl)-1H-pyrrolo[2,3-b]pyridin-5-yl)phenyl) methanesulfonamide Using similar reaction conditions as described in step-iii of example-1, N-(3-(3-(1-(3-fluorobenzyl)-1H-pyrazol-4-yl)-1-tosyl-1H-pyrrolo[2,3-b]pyridin-5-yl)phenyl)methane sulfonamide (106 mg, 0.17 mmol) was hydrolyzed with lithium hydroxide (36 mg, 0.861 mmol) in THF/water/methanol (12/6/2 ml) mixture to afford 10 mg (12.6% yield) of the pure product. $^1$H NMR (CD$_3$OD, 300 MHz): δ 8.464-8.458 (d, 1H), 8.352-8.347 (d, 1H), 8.185 (s, 1H), 7.923 (s, 1H), 7.64 (s, 1H), 7.544-7.538 (m, 1H), 7.514-7.431 (m, 2H), 7.37-7.26 (m, 2H), 7.115-6.997 (m, 2H), 5.426 (s, 2H), 3.002 (s, 3H). MS: m/z=461.8 (M+1), HPLC: 96.947% in method A.

Example 10

N-(3-(3-(1-(3-chlorobenzyl)-1H-pyrazol-4-yl)-1H-pyrrolo[2,3-b]pyridin-5-yl)phenyl)methane sulfonamide

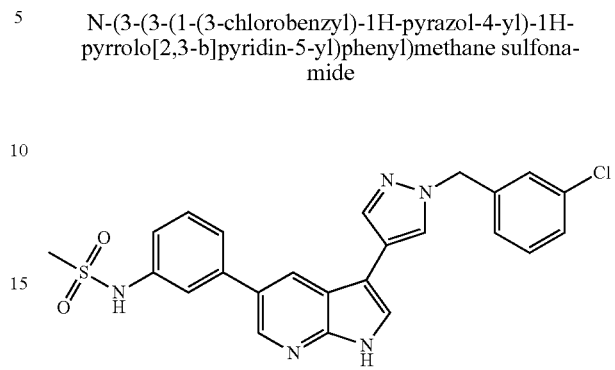

Step-i: N-(3-(3-(1-(3-chlorobenzyl)-1H-pyrazol-4-yl)-1-tosyl-1H-pyrrolo[2,3-b]pyridin-5-yl)phenyl) methanesulfonamide Using similar reaction conditions as described in step-i of example-1, N-(3-(3-iodo-1-tosyl-1H-pyrrolo[2,3-b]pyridin-5-yl)phenyl)methanesulfonamide (intermediate 9) (200 mg, 0.35 mmol), was coupled with 1-(3-chlorobenzyl)-4-(4,4,5,5-tetramethyl-1,3,2-dioxaborolan-2-yl)-1H-pyrazole (intermediate 13) (123 mg, 0.385 mmol), in sodium carbonate (111 mg, 1.05 mmol), PdCl$_2$(dppf) (12.8 mg, 0.017 mmol) and DME/water (2/1 ml) to afford 90 mg (41% yield) of the pure product after column purification using 40% ethyl acetate in hexane as eluent.

Step-ii: N-(3-(3-(1-(3-chlorobenzyl)-1H-pyrazol-4-yl)-1H-pyrrolo[2,3-b]pyridin-5-yl)phenyl) methanesulfonamide Using similar reaction conditions as described in step-iii of example-1, N-(3-(3-(1-(3-chlorobenzyl)-1H-pyrazol-4-yl)-1-tosyl-1H-pyrrolo[2,3-b]pyridin-5-yl)phenyl)methane sulfonamide (90 mg, 0.14 mmol) was hydrolyzed with lithium hydroxide (18 mg, 0.42 mmol) in THF/water/methanol (1/0.5/1 ml) mixture to afford 12 mg (18% yield) of the pure product after purification by preparative TLC (Silicagel-1000 micron) using 10% ethyl acetate in hexane as eluent. $^1$H NMR (DMSO-d$_6$, 400 MHz): δ 11.83 (s, 1H), 9.85 (s, 1H), 8.48-8.47 (d, 1H), 8.43 (s, 1H), 8.346-8.342 (d, 1H), 7.90 (s, 1H), 7.80-7.79 (d, 1H), 7.51-7.25 (m, 8H), 5.40 (s, 2H), 3.06 (s, 3H). MS: m/z=478.2 (M+1), HPLC: 92.01% (method B).

Example 11

N-(3-(3-(1-(3-cyanobenzyl)-1H-pyrazol-4-yl)-1H-pyrrolo[2,3-b]pyridin-5-yl)phenyl)methane sulfonamide

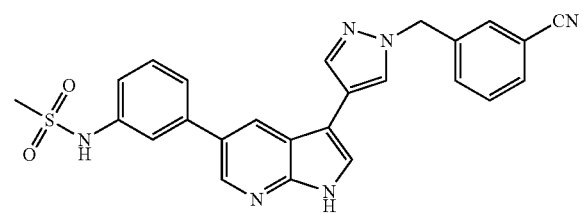 [SMILES: CS(=O)(=O)Nc1cccc(-c2cnc3[nH]cc(-c4cnn(Cc5cccc(C#N)c5)c4)c3c2)c1]

Step-i: N-(3-(3-(1-(3-cyanobenzyl)-1H-pyrazol-4-yl)-1-tosyl-1H-pyrrolo[2,3-b]pyridin-5-yl)phenyl) methanesulfonamide Using similar reaction conditions as described in step-ii of example-1, N-(3-(3-iodo-1-tosyl-1H-pyrrolo[2,3-b]pyridin-5-yl)phenyl)methanesulfonamide (Intermediate 9) (200 mg, 0.35 mmol) was coupled with 3-((4-(4,4,5,5-tetramethyl-1,3,2-dioxaborolan-2-yl)-1H-pyrazol-1-yl)methyl)benzonitrile (Intermediate 14) (119.8 mg, 0.38 mmol) in sodium carbonate (111 mg, 1.05 mmol), $PdCl_2$(dppf) (12.8 mg, 0.017 mmol) and DME/water (2/1 ml) to afford 90 mg (30% yield) of the pure product after column purification using 50% ethyl acetate in hexane as eluent.

Step-ii: N-(3-(3-(1-(3-cyanobenzyl)-1H-pyrazol-4-yl)-1H-pyrrolo[2,3-b]pyridin-5-yl)phenyl) methanesulfonamide Using similar reaction conditions as described in step-iii of example-1, N-(3-(3-(1-(3-cyanobenzyl)-1H-pyrazol-4-yl)-1-tosyl-1H-pyrrolo[2,3-b]pyridin-5-yl)phenyl) methane sulfonamide (90 mg, 0.14 mmol) was hydrolyzed with lithium hydroxide (18 mg, 0.43 mmol) in THF/water/methanol (1/0.5/1 ml) mixture to afford 10 mg (15% yield) of the pure product after purification by preparative TLC (Silicagel-1000 micron) using 10% ethyl acetate in hexane as eluent. $^1H$ NMR (DMSO-$d_6$, 400 MHz): δ11.88 (s, 1H), 9.85 (b, 1H), 8.478-8.475 (d, 1H), 8.43 (s, 1H), 8.34 (s, 1H), 7.986 (s, 1H), 7.80-7.75 (m, 3H), 7.60-7.45 (m, 5H), 7.26-7.24 (d, 1H) 5.46 (s, 2H), 3.05 (s, 3H) MS: m/z=469.4 (M+1), HPLC 93.92%, (method A).

Example 12

N-(3-(3-(1-benzyl-1H-pyrazol-4-yl)-1H-pyrrolo[2,3-b]pyridin-5-yl)phenyl) methanesulfonamide

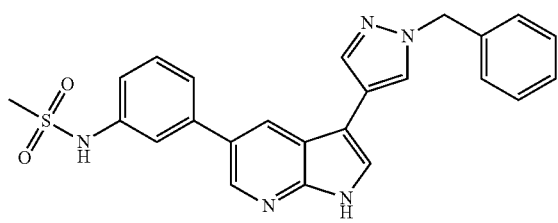 [SMILES: CS(=O)(=O)Nc1cccc(-c2cnc3[nH]cc(-c4cnn(Cc5ccccc5)c4)c3c2)c1]

Step-i: 3-(1-benzyl-1H-pyrazol-4-yl)-5-bromo-1-tosyl-1H-pyrrolo[2,3-b]pyridine Using similar reaction conditions as described in step-i of example-1, 5-Bromo-3-iodo-1-tosyl-1H-pyrrolo[2,3-b]pyridine (intermediate 1) (400 mg, 0.83 mmol), 1-benzyl-4-(4,4,5,5-tetramethyl-1,3,2-dioxaborolan-2-yl)-1H-pyrazole (intermediate 15) (262.05 mg, 0.92 mmol) in sodium carbonate (263.9 mg, 105.99 mmol), bis(triphenylphosphine) palladium (ii) dichloride (29 mg, 0.04 mmol) and toluene/ethanol/water (6/6/2 ml) to afford 220 mg (51.7% yield) of the pure product after column purification using 30% ethyl acetate in hexane as eluent.

Step-ii: N-(3-(3-(1-benzyl-1H-pyrazol-4-yl)-1-tosyl-1H-pyrrolo[2,3-b]pyridin-5-yl)phenyl) methane sulfonamide Using similar reaction conditions as described in step-ii of example-1, 3-(1-benzyl-1H-pyrazol-4-yl)-5-bromo-1-tosyl-1H-pyrrolo[2,3-b]pyridine (220 mg, 0.433 mmol) was coupled with N-(3-(4,4,5,5-tetramethyl-1,3,2-dioxaborolan-2-yl)phenyl)methanesulfonamide (intermediate 3) in Sodium carbonate (137.68 mg, 1.29 mmol), $PdCl_2$(dppf) (15.8 mg, 0.02 mmol), toluene/ethanol/water (5/5/2 ml). This on purification by preparative TLC using methanol/chloroform as eluent afforded 120 mg (46.3% yield) of the pure compound.

Step-iii: N-(3-(3-(1-benzyl-1H-pyrazol-4-yl)-1H-pyrrolo[2,3-b]pyridin-5-yl)phenyl) methane sulfonamide Using similar reaction conditions as described in step-iii of example-1, N-(3-(3-(1-benzyl-1H-pyrazol-4-yl)-1-tosyl-1H-pyrrolo[2,3-b]pyridin-5-yl)phenyl)methanesulfonamide (60 mg, 0.1 mmol) was hydrolyzed by lithium hydroxide (9 mg, 0.2 mmol) in methanol/water/THF (1/1/1 ml) which afforded 4 mg (9% yield) after purification by preparative TLC (silicagel-1000 micron) using 5% methanol in chloroform as eluent. $^1H$ NMR (DMSO-$d_6$, 300 MHz): δ 8.46-8.45 (d, 1H), 8.34-8.33 (d, 1H), 8.14 (s, 1H), 7.9 (s, 1H), 7.62 (s, 1H), 7.54 (m, 1H), 7.5-7.43 (m, 2H), 7.37-7.33 (m, 2H), 7.3-7.27 (m, 3H), 5.4 (s, 2H), 3.0 (s, 3H). MS: m/z=443.6 (M+1), HPLC: 88.2%, Method A.

Example 13

N-(5-(3-(1-(3-fluorobenzyl)-1H-pyrazol-4-yl)-1H-pyrrolo[2,3-b]pyridin-5-yl)-2-methoxyphenyl) methane sulfonamide

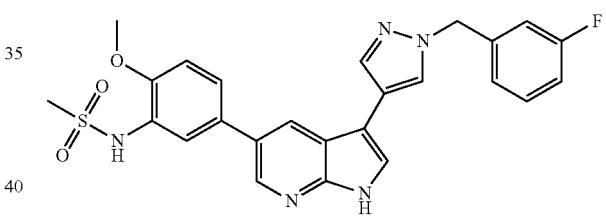

Step-i: N-(5-(3-(1-(3-fluorobenzyl)-1H-pyrazol-4-yl)-1-tosyl-1H-pyrrolo[2,3-b]pyridin-5-yl)-2-methoxyphenyl) methanesulfonamide Using similar reaction conditions as described in step-ii of example-1, 5-bromo-3-(1-(3-fluorobenzyl)-1H-pyrazol-4-yl)-1-tosyl-1H-pyrrolo[2,3-b]pyridine (compound of step-i of example 9) (200 mg, 0.380 mmol) was coupled with N-(2-methoxy-5-(4,4,5,5-tetramethyl-1,3,2-dioxaborolan-2-yl)phenyl)methanesulfonamide (Intermediate 17) (185 mg, 0.58 mmol) in sodium carbonate (121 mg, 1.14 mmol), $Pd(PPh_3)_2Cl_2$ (26.6 mg, 0.038 mmol), toluene/ethanol/water (20/7/3 mL). This afforded 153 mg (62.4% yield) after purification by column (Silica gel 6/120) using 3% methanol in chloroform as eluent. MS: m/z=645.7 (M+1).

Step-ii: N-(5-(3-(1-(3-fluorobenzyl)-1H-pyrazol-4-yl)-1H-pyrrolo[2,3-b]pyridin-5-yl)-2-methoxy phenyl) methanesulfonamide Using similar reaction conditions as described in step-iii of example-1, N-(5-(3-(1-(3-fluorobenzyl)-1H-pyrazol-4-yl)-1-tosyl-1H-pyrrolo[2,3-b]pyridin-5-yl)-2-methoxyphenyl) methane sulfonamide (150 mg, 0.232 mmol) was hydrolyzed with lithium hydroxide (49 mg, 1.162 mmol) in THF/Methanol/Water (15/6/4 mL) to yield 17 mg (15% yield) after purification by preparative TLC (Silicagel-1000 micron) using 2% methanol in chloroform as eluent. $^1$H NMR (CD$_3$OD, 400 MHz): δ 8.446-8.441 (d, 1H), 8.327-8.322 (d, 1H), 8.215 (s, 1H), 7.936 (s, 1H), 7.746-7.741 (d, 1H), 7.643 (s, 1H). 7.577-7.551 (m, 1H), 7.398-7.364 (m, 1H), 7.21-7.188 (d, 1H), 7.210-7.188 (d, 1H), 7.137-7.118 (d, 1H), 7.067-7.026 (m, 2H), 5.426 (s, 2H), 3.98 (s, 3H), 3.002 (s, 3H). MS: m/z=491.8 (M+1), HPLC: 97.01% in method A.

Example 14

N-(5-(3-(1-(3-fluorobenzyl)-3,5-dimethyl-1H-pyrazol-4-yl)-1H-pyrrolo[2,3-b]pyridin-5-yl)-2-methoxy phenyl)methanesulfonamide

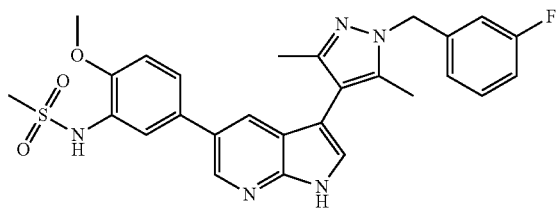 [SMILES: COc1ccc(-c2cnc3[nH]cc(-c4c(C)nn(Cc5cccc(F)c5)c4C)c3c2)cc1NS(C)(=O)=O]

Step-i: 5-bromo-3-(1-(3-fluorobenzyl)-3,5-dimethyl-1H-pyrazol-4-yl)-1-tosyl-1H-pyrrolo[2,3-b]pyridine Using similar reaction conditions as described in step-i of example-1, 5-bromo-3-iodo-1-tosyl-1H-pyrrolo[2,3-b]pyridine (intermediate 1) (711 mg, 1.46 mmol) was coupled with 1-(3-fluoro benzyl)-3,5-dimethyl-4-(4,4,5,5-tetramethyl-1,3,2-dioxaborolan-2-yl)-1H-pyrazole (intermediate 16) (581 mg, 1.76 mmol) in 2 molar sodium carbonate (5 mL), Pd(PPh$_3$)$_2$Cl$_2$ (51 mg, 0.073 mmol), acetonitrile (25 mL). This afforded 300 mg yield 48.5% of titled compound after purification by column using 25% ethyl acetate in hexane.

Step-ii: N-(5-(3-(1-(3-fluorobenzyl)-3,5-dimethyl-1H-pyrazol-4-yl)-1-tosyl-1H-pyrrolo[2,3-b]pyridin-5-yl)-2-methoxyphenyl)methanesulfonamide Using similar reaction conditions as described in step-ii of example-1, 5-bromo-3-(1-(3-fluorobenzyl)-3,5-dimethyl-1H-pyrazol-4-yl)-1-tosyl-1H-pyrrolo[2,3-b]pyridine (300 mg, 0.542 mmol) was coupled with N-(2-methoxy-5-(4,4,5,5-tetramethyl-1,3,2-dioxaborolan-2-yl)phenyl)methane sulfonamide (intermediate-17) (212 mg, 0.650 mmol) in sodium carbonate (172 mg, 1.62 mmol), 1,2-methoxyethane (15 mL). This afforded 350 mg of the crude titled compound.

Step-iii: N-(5-(3-(1-(3-fluorobenzyl)-3,5-dimethyl-1H-pyrazol-4-yl)-1H-pyrrolo[2,3-b]pyridin-5-yl)-2-methoxyphenyl)methanesulfonamide Using similar reaction conditions as described in step-iii of example-1, N-(5-(3-(1-(3-fluorobenzyl)-3,5-dimethyl-1H-pyrazol-4-yl)-1-tosyl-1H-pyrrolo[2,3-b]pyridin-5-yl)-2-methoxy phenyl)methanesulfonamide was hydrolyzed with lithium hydroxide (65 mg, 1.56 mmol) in THF/Methanol/water (10/3/2 mL). This yielded 22 mg (8.4% yield) of pure compound after purification by flash chromatography. $^1$H NMR (DMSO-d$_6$, 300 MHz): δ 11.9 (s, 1H), 9.07 (s, 1H), 8.519-8.515 (d, 2H), 7.827-8.23 (d, 2H), 7.56-7.43 (m, 3H), 7.21-7.04 (m, 4H), 5.36 (s, 2H), 3.90 (s, 3H), 3.03 (s, 3H), 2.21-2.17 (d, 6H). MS: m/z=520.1 (M+1), HPLC: 95.74% (Method-B).

Example 15

N-(5-(3-(1-(3-fluorobenzyl)-3,5-dimethyl-1H-pyrazol-4-yl)-1H-pyrrolo[2,3-b]pyridin-5-yl)-2-methoxy phenyl)ethanesulfonamide

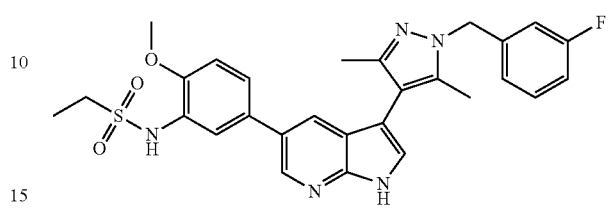

Step-i: N-(5-(3-(1-(3-fluorobenzyl)-3,5-dimethyl-1H-pyrazol-4-yl)-1-tosyl-1H-pyrrolo[2,3-b]pyridin-5-yl)-2-methoxyphenyl)ethanesulfonamide Using similar reaction conditions as described in step-i of example-1, 5-bromo-3-(1-(3-fluorobenzyl)-3,5-dimethyl-1H-pyrazol-4-yl)-1-tosyl-1H-pyrrolo[2,3-b]pyridine (compound of step-i of example 14) (170 mg, 0.307 mmol) was coupled with N-(2-methoxy-5-(4,4,5,5-tetramethyl-1,3,2-dioxaborolan-2-yl)phenyl)ethanesulfonamide (intermediate 18) (125 mg, 0.368 mmol) using PdCl$_2$(dppf) (50 mg, 0.0614 mmol) in sodium carbonate (97 mg, 0.920 mmol), DME/water (10/2 mL) to afford 200 mg of the crude titled compound.

Step-ii: N-(5-(3-(1-(3-fluorobenzyl)-3,5-dimethyl-1H-pyrazol-4-yl)-1H-pyrrolo[2,3-b]pyridin-5-yl)-2-methoxyphenyl)ethanesulfonamide Using similar reaction conditions as described in step-iii of example-1, N-(5-(3-(1-(3-fluorobenzyl)-3,5-dimethyl-1H-pyrazol-4-yl)-1-tosyl-1H-pyrrolo[2,3-b]pyridin-5-yl)-2-methoxy phenyl)ethane sulfonamide (200 mg, 0.291 mmol) was hydrolyzed by lithium hydroxide (36 mg, 0.87 mmol) in THF/Methanol/Water (10/3/2 ml) to give 25 mg (16.5% yield) after purification by flash chromatography. $^1$H NMR (DMSO-d$_6$, 300 MHz): δ 11.9 (s, 1H), 9.02 (s, 1H), 8.45 (s, 1H), 7.79 (s, 1H), 7.54-7.49 (m, 3H), 7.19-7.0 (m, 4H), 5.33 (s, 2H), 3.86 (s, 3H), 3.06-3.04 (m, 2H0, 2.17-2.13 (d, 6H), 1.27-1.23 (t, 3H). MS: m/z=534.8 (M+1), HPLC: 90.27% (Method-B).

Example 16

N-(5-(3-(1-(3-fluorobenzyl)-1H-pyrazol-4-yl)-1H-pyrrolo[2,3-b]pyridin-5-yl)-2-methoxyphenyl)cyclopropanesulfonamide

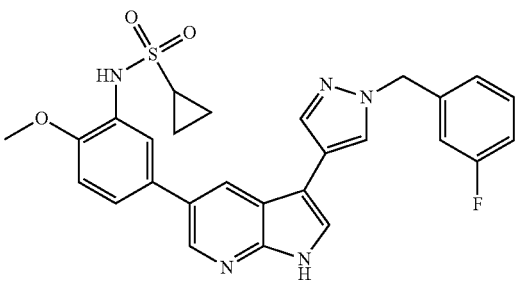 [SMILES: COc1ccc(-c2cnc3[nH]cc(-c4cnn(Cc5cccc(F)c5)c4)c3c2)cc1NS(=O)(=O)C1CC1]

Step-i: N-(5-(3-(1-(3-fluorobenzyl)-1H-pyrazol-4-yl)-1-tosyl-1H-pyrrolo[2,3-b]pyridin-5-yl)-2-methoxyphenyl)cyclopropanesulfonamide Using similar reaction conditions as described in step-ii of example-1, 5-bromo-3-(1-(3-fluorobenzyl)-1H-pyrazol-4-yl)-1-tosyl-1H-pyrrolo[2,3-b]pyridine (Compound of step-i of –9) (150 mg, 2.85 mmol) was coupled with N-(2-methoxy-5-(4,4,5,5-tetramethyl-1,3,2-dioxaborolan-2-yl)phenyl)cyclopropanesulfonamide (intermediate 19) (131 mg, 0.371 mmol), Pd(PPh$_3$)$_2$Cl$_2$ (10 mg, 0.0142 mmol), Toluene/ethanol/water (15/10/5 ml) to afford 120 mg (62.82% yield) of the titled compound. MS: m/z=672.2 (M+1).

Step-ii: N-(5-(3-(1-(3-fluorobenzyl)-1H-pyrazol-4-yl)-1H-pyrrolo[2,3-b]pyridin-5-yl)-2-methoxy phenyl)cyclopropanesulfonamide Using similar reaction conditions as described in step-iii of example-1, N-(5-(3-(1-(3-fluorobenzyl)-1H-pyrazol-4-yl)-1-tosyl-1H-pyrrolo[2,3-b]pyridin-5-yl)-2-methoxyphenyl)cyclo propanesulfonamide (80 mg, 0.119 mmol) was hydrolyzed by lithium hydroxide (0.0109 g, 0.238 mmol), THF/Methanol/water (12/8/4 mL) to afford 5 mg (8.19% yield) of the titled compound. $^1$H NMR (DMSO-d$_6$, 300 MHz): δ 11.8 (s, 1H), 9.04 (s, 1H), 8.44-8.42 (d, 2H), 8.29 (s, 1H), 7.96 (s, 1H), 7.77 (s, 1H), 7.61-7.58 (m, 2H0, 7.20-7.10 (m, 4H), 5.41 (s, 2H), 3.88 (s, 3H), 0.92-0.88 (m, 4H). MS: m/z=517.8 (M+1), HPLC: 84.12% Method B.

Example 17

N-(5-(3-(1-(3-fluorobenzyl)-1H-pyrazol-4-yl)-1H-pyrrolo[2,3-b]pyridin-5-yl)-2-morpholino phenyl)methanesulfonamide

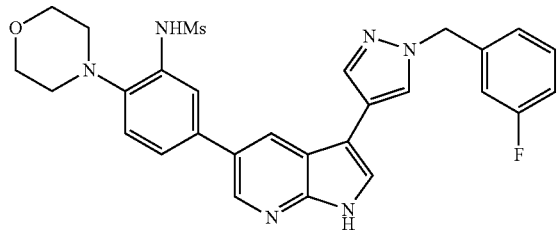

Step-i: N-(5-(3-(1-(3-fluorobenzyl)-1H-pyrazol-4-yl)-1-tosyl-1H-pyrrolo[2,3-b]pyridin-5-yl)-2-morpholinophenyl)methanesulfonamide Using similar reaction conditions as described in step-ii of example-1, 5-bromo-3-(1-(3-fluorobenzyl)-1H-pyrazol-4-yl)-1-tosyl-1H-pyrrolo[2,3-b]pyridine Compound of step-I in Example 9) (200 mg, 0.3809 mmol) was coupled with N-(2-morpholino-5-(4,4,5,5-tetramethyl-1,3,2-dioxaborolan-2-yl)phenyl)methane sulfonamide (Intermediate 20) (220 mg, 0.5714 mmol), Pd(PPh$_3$)$_2$Cl$_2$ (13.5 mg, 0.01904 mmol), Toluene/ethanol/water (20/10/4 ml) to afford 240 mg (90.2% yield) of the titled compound.

Step-ii: N-(5-(3-(1-(3-fluorobenzyl)-1H-pyrazol-4-yl)-1H-pyrrolo[2,3-b]pyridin-5-yl)-2-morpholinophenyl)methanesulfonamide Using similar reaction conditions as described in step-iii of example-1, N-(5-(3-(1-(3-fluorobenzyl)-1H-pyrazol-4-yl)-1-tosyl-1H-pyrrolo[2,3-b]pyridin-5-yl)-2-morpholinophenyl) methanesulfonamide (240 mg, 0.342 mmol) was hydrolyzed by lithium hydroxide (143 mg, 3.42 mmol), THF/Methanol/water (20/8/8 mL) to yield 34 mg (18%) of the titled compound. $^1$H NMR (DMSO-D$_6$, 400 MHz): δ 11.8 (s, 1H), 8.618 (s, 1H), 8.469-8.464 (m, 1H), 8.421 (s, 1H), 8.317-8.313 (d, 1H), 7.963 (s, 1H), 7.782-7.777 (d, 1H), 7.649-7.645 (d, 1H), 7.58-7.52 (m, 1H), 7.44-7.366 (m, 2H), 7.16-7.08 (m, 3H), 5.402 (s, 2H), 3.80.3-3.791 (m, 4H), 3.197 (s, 3H), 2.898-2.887 (m, 4H). MS: m/z=546.8 (M+1); HPLC: 96.04% in method B.

Example 18

5-(3-(1-(3-fluorobenzyl)-3,5-dimethyl-1H-pyrazol-4-yl)-1H-pyrrolo[2,3-b]pyridin-5-yl)-2-methoxy-N-methylbenzenesulfonamide

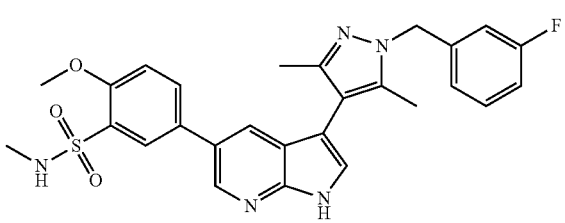 [SMILES: CNS(=O)(=O)c1cc(-c2cnc3[nH]cc(-c4c(C)nn(Cc5cccc(F)c5)c4C)c3c2)ccc1OC]

Step-i: 5-(3-(1-(3-fluorobenzyl)-3,5-dimethyl-1H-pyrazol-4-yl)-1-tosyl-1H-pyrrolo[2,3-b]pyridin-5-yl)-2-methoxy-N-methylbenzenesulfonamide Using similar reaction conditions as described in step-i of example-1, 5-(3-iodo-1-tosyl-1H-pyrrolo[2,3-b]pyridin-5-yl)-2-methoxy-N-methylbenzenesulfonamide (intermediate 22) (140 mg, 0.234 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (154 mg, 0.469 mmol), Pd(PPh$_3$)$_2$Cl$_2$ (3.22 mg, 0.011 mmol), sodium carbonate (75 mg, 0.702 mmol), Toluene/ethanol (3/5 ml) to afford 80 mg (51% yield) of the titled compound. $^1$H NMR (CDCl$_3$, 300 MHz): δ 8.63 (s, 1H), 8.14-8.12 (d, 2H), 8.04 (s, 1H), 7.73-7.64 (m, 3H), 7.49-7.46 (m, 1H), 7.33-7.30 (m, 3H), 7.15-7.12 (d, 1H), 7.01-6.95 (m, 2H), 6.86-6.83 (d, 1H), 5.31 (s, 2H), 4.84-4.83 (m, 1H), 4.03 (s, 3H), 2.63-2.61 (d, 3H), 2.39 (s, 3H), 2.20 (s, 3H), 2.13 (s, 3H). MS: m/z=674.2 (M+1).

Step-ii: 5-(3-(1-(3-fluorobenzyl)-3,5-dimethyl-1H-pyrazol-4-yl)-1H-pyrrolo[2,3-b]pyridin-5-yl)-2-methoxy-N-methylbenzenesulfonamide Using similar reaction conditions as described in step-iii of example-1, 5-(3-(1-(3-fluorobenzyl)-3,5-dimethyl-1H-pyrazol-4-yl)-1-tosyl-1H-pyrrolo[2,3-b]pyridin-5-yl)-2-methoxy-N-methylbenzenesulfonamide (80 mg, 0.118 mmol) was hydrolyzed by lithium hydroxide (143 mg, 0.593 mmol), THF/Methanol/water (1/1/0.5 mL) to afford 22 mg (36.06% yield) of the titled compound. $^1$H NMR (CD$_3$OD, 400 MHz): δ 8.47-8.46 (d, 1H), 8.029-8.024 (d, 1H), 7.89-7.86 (m, 2H), 7.41 (s, 1H), 7.38-7.30 (m, 2H), 7.05-6.96 (m, 2H), 6.90-6.85 (m, 1H), 5.36 (s, 2H), 4.00 (s, 3H), 2.53 (s, 3H), 2.21 (s, 3H), 2.18 (s, 3H). MS: m/z=520.1 (M+1), HPLC Purity: 93.81% (Method B).

Example 19

N-(5-(3-(1-(3,5-difluorobenzyl)-1H-pyrazol-4-yl)-1H-pyrrolo[2,3-b]pyridin-5-yl)-2-methoxyphenyl)methanesulfonamide

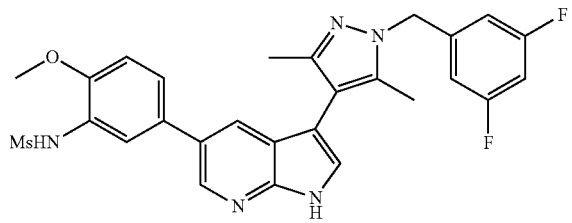

Step-i: N-(5-(3-(1-(3,5-difluorobenzyl)-3,5-dimethyl-1H-pyrazol-4-yl)-1-tosyl-1H-pyrrolo[2,3-b]pyridin-5-yl)-2-methoxyphenyl)methanesulfonamide Using similar reaction conditions as described in step-ii of example-1, N-(5-(3-iodo-1-tosyl-1H-pyrrolo[2,3-b]pyridin-5-yl)-2-methoxyphenyl)methanesulfonamide (Intermediate 23) (160 mg, 0.267 mmol) was coupled with 1-(3,5-difluorobenzyl)-3,5-dimethyl-4-(4,4,5,5-tetramethyl-1,3,2-dioxaborolan-2-yl)-1H-pyrazole (intermediate 24) (111.89 mg, 0.321 mmol) in sodium carbonate (84.89 mg, 0.801 mmol) Pd(PPh$_3$)$_2$Cl$_2$ (9.7 mg, 0.013), Toluene/ethanol/water (7/7/2 mL) to afford 210 mg of the crude compound. MS: m/z=692.1 (M+1).

Step-ii: N-(5-(3-(1-(3,5-difluorobenzyl)-1H-pyrazol-4-yl)-1H-pyrrolo[2,3-b]pyridin-5-yl)-2-methoxyphenyl)methanesulfonamide Using similar reaction conditions as described in step-iii of example-1, N-(5-(3-(1-(3,5-difluorobenzyl)-3,5-dimethyl-1H-pyrazol-4-yl)-1-tosyl-1H-pyrrolo[2,3-b]pyridin-5-yl)-2-methoxy phenyl) methanesulfonamide (210 mg, 0.3 mmol) was hydrolyzed by lithium hydroxide (34.2 mg, 0.91 mmol), THF/Methanol/water (4/6/1 mL) to afford 1.6 mg of the titled compound after purification by preparative TLC (SiO$_2$-1000 micron) eluted by 3% MeOH in CHCl$_3$). $^1$H NMR (CDCl$_3$, 300 MHz): δ 8.9 (b, 1H), 8.5 (s, 1H), 7.84 (m, 1H), 7.78 (m, 1H), 7.0 (m, 1H), 6.85 (m, 1H), 6.78-6.7 (m, 3H), 5.29 (s, 2H), 3.93 (s, 3H), 2.98 (s, 3H), 2.51 (s, 3H), 2.17 (s, 3H). MS: m/z=538.1 (M+1), HPLC: 86.27% in method B.

Example 20

5-(3-(1-(2,5-difluorobenzyl)-3,5-dimethyl-1H-pyrazol-4-yl)-1H-pyrrolo[2,3-b]pyridin-5-yl)-2-methoxy-N-methylbenzenesulfonamide

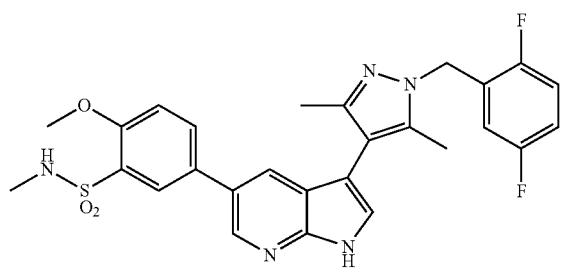 [SMILES: CNS(=O)(=O)c1cc(-c2cnc3[nH]cc(-c4c(C)nn(Cc5cc(F)ccc5F)c4C)c3c2)ccc1OC]

Step-i: 5-(3-(1-(2,5-difluorobenzyl)-3,5-dimethyl-1H-pyrazol-4-yl)-1-tosyl-1H-pyrrolo[2,3-b]pyridin-5-yl)-2-methoxy-N-methylbenzenesulfonamide Using similar reaction conditions as described in step-ii of example 15-(3-iodo-1-tosyl-1H-pyrrolo[2,3-b]pyridin-5-yl)-2-methoxy-N-methylbenzenesulfonamide (intermediate 22) (200 mg, 0.335 mmol) was coupled with 1-(2,5-difluorobenzyl)-3,5-dimethyl-4-(4,4,5,5-tetramethyl-1,3,2-dioxaborolan-2-yl)-1H-pyrazole (Intermediate 25) (146 mg, 0.418 mmol) in sodium carbonate (106 mg, 1.0 mmol), Pd(PPh$_3$)$_2$Cl$_2$ (11.7 mg, 0.011 mmol), Toluene/ethanol/water (20/10/2 ml) to afford 142 mg (61.4% yield) of the titled compound after purification by column (SiO$_2$-eluted by 0.4 to 1.2% MeOH in CHCl$_3$). MS: m/z=692.1 (M+1).

Step-ii: 5-(3-(1-(2,5-difluorobenzyl)-3,5-dimethyl-1H-pyrazol-4-yl)-1-tosyl-1H-pyrrolo[2,3-b]pyridin-5-yl)-2-methoxy-N-methylbenzenesulfonamide Using similar reaction conditions as described in Step-iii of example 1, 15-(3-iodo-1-tosyl-1H-pyrrolo[2,3-b]pyridin-5-yl)-2-methoxy-N-methylbenzenesulfonamide (140 mg, 0.202 mmol) was hydrolyzed by lithium hydroxide (81 mg, 2.02 mmol), THF/Methanol/water (24/12/6 ml) to yield 9 mg (8.3% yield) of the titled compound after purification by preparative TLC (SiO$_2$-1000 micron eluted by 3% MeOH in CHCl$_3$). $^1$H NMR (CD$_3$OD, 300 MHz): δ 8.382 (b, 1H), 7.942-7.935 (d, 1H), 7.815-7.808 (m, 2H), 7.334 (s, 1H), 7.241-7.213 (d, 1H), 7.08-6.96 (m, 1H), 6.66-6.56 (m, 1H), 5.289 (s, 2H), 3.914 (s, 3H), 2.444 (s, 3H), 2.138-2.110 (d, 6H). MS: m/z=538.2 (M+1); HPLC: 95.57% in method B.

Example 21

(3-(1-(3,5-difluorobenzyl)-3,5-dimethyl-1H-pyrazol-4-yl)-1H-pyrrolo[2,3-b]pyridin-5-yl)-2-methoxy-N-methylbenzenesulfonamide

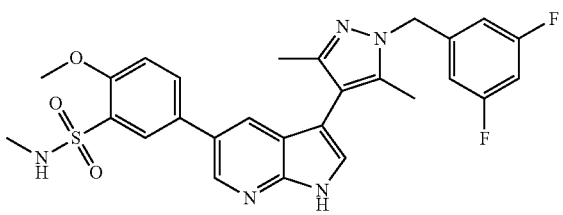 [SMILES: CNS(=O)(=O)c1cc(-c2cnc3[nH]cc(-c4c(C)nn(Cc5cc(F)cc(F)c5)c4C)c3c2)ccc1OC]

Step-i: 5-(3-(1-(3,5-difluorobenzyl)-3,5-dimethyl-1H-pyrazol-4-yl)-1-tosyl-1H-pyrrolo[2,3-b]pyridin-5-yl)-2-methoxy-N-methylbenzenesulfonamide Using similar reaction conditions as described in step-ii of example 1, 5-(3-iodo-1-tosyl-1H-pyrrolo[2,3-b]pyridin-5-yl)-2-methoxy-N-methylbenzenesulfonamide (intermediate 22) (200 mg, 0.335 mmol) was coupled with 1-(3,5-difluorobenzyl)-3,5-dimethyl-4-(4,4,5,5-tetramethyl-1,3,2-dioxaborolan-2-yl)-1H-pyrazole (intermediate 24) (146 mg, 0.418 mmol) in sodium carbonate (100 mg, 1.0 mmol) Pd(PPh$_3$)$_2$Cl$_2$ (11.7 mg, 0.011 mmol), Toluene/ethanol/water (20/10/2 ml) to afford 180 mg (77.9% yield) of the titled compound after purification by column (SiO$_2$-eluted by 0.4 to 1.2% MeOH in CHCl$_3$). MS: m/z=692.0 (M+1).

Step-ii: 5-(3-(1-(3,5-difluorobenzyl)-3,5-dimethyl-1H-pyrazol-4-yl)-1H-pyrrolo[2,3-b]pyridin-5-yl)-2-methoxy-N-methylbenzenesulfonamide Using similar reaction conditions as described in step-iii of example 1, 5-(3-(1-(2,5-difluorobenzyl)-3,5-dimethyl-1H-pyrazol-4-yl)-1-tosyl-1H-pyrrolo[2,3-b]pyridin-5-yl)-2-methoxy-N-methylbenzenesulfonamide (180 mg, 0.2604 mmol) was hydrolyzed by lithium hydroxide (109 mg, 2.604 mmol), THF/Methanol/water (24/12/6 ml) to yield 16 mg (11.4% yield) of the titled compound after purification by preparative TLC (SiO2-1000 micron eluted by 3% MeOH in CHCl₃). ¹H NMR (CD₃OD, 300 MHz): δ 8.382 (m, 1H), 7.940-7.935 (d, 1H), 7.816-7.779 (m, 2H), 7.342 (s, 1H), 7.241-7.213 (d, 1H), 6.68-6.64 (m, 1H), 5.275 (s, 2H), 3.914 (s, 3H), 2.441 (s, 3H), 2.128-2.101 (d, 6H). MS: m/z=538.1 (M+1); HPLC: 95.69% in method B.

Example 22

N-(5-(3-(1-(2,5-difluorobenzyl)-3,5-dimethyl-1H-pyrazol-4-yl)-1H-pyrrolo[2,3-b]pyridin-5-yl)-2-methoxyphenyl)methanesulfonamide

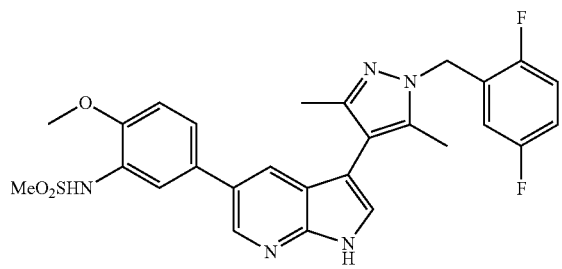

Step-i: N-(5-(3-(1-(3,5-difluorobenzyl)-3,5-dimethyl-1H-pyrazol-4-yl)-1-tosyl-1H-pyrrolo[2,3-b]pyridin-5-yl)-2-methoxyphenyl)methanesulfonamide Using similar reaction conditions as described in step-ii of example-1, 5-bromo-3-(1-(2,5-difluorobenzyl)-3,5-dimethyl-1H-pyrazol-4-yl)-1-tosyl-1H-pyrrolo[2,3-b]pyridine (Intermediate 26) (125 mg, 0.218 mmol) was coupled with N-(2-methoxy-5-(4,4,5,5-tetramethyl-1,3,2-dioxaborolan-2-yl)phenyl)methanesulfonamide (intermediate 17) (107.2 mg, 0.327 mmol) in sodium carbonate (69.3 mg, 0.654 mmol) Pd(PPh₃)₂Cl₂ (7.65 mg, 0.01 mmol), Toluene/ethanol/water (5/3/2 ml) to afford 100 mg (66.6% yield) of the titled compound after purification by column (SiO₂-eluted by 80% EtOAc in hexanes). MS: m/z=692.1 (M+1).

Step-ii: N-(5-(3-(1-(2,5-difluorobenzyl)-3,5-dimethyl-1H-pyrazol-4-yl)-1H-pyrrolo[2,3-b]pyridin-5-yl)-2-methoxyphenyl)methanesulfonamide Using similar reaction conditions as described in step-iii of example-1, N-(5-(3-(1-(2,5-difluorobenzyl)-3,5-dimethyl-1H-pyrazol-4-yl)-1-tosyl-1H-pyrrolo[2,3-b]pyridin-5-yl)-2-methoxy phenyl)methanesulfonamide (100 mg, 0.14 mmol) was hydrolyzed by lithium hydroxide (30.3 mg, 0.722 mmol), THF/Methanol/water (3/3/1 ml) to afford 13 mg (28.2% yield) of the titled compound after purification by column (SiO₂-eluted by 2% MeOH in CHCl3). ¹H NMR (CDCl₃, 300 MHz): δ 9.37 (s, 1H), 8.54 (s, 1H), 7.84-7.78 (m, 2H), 7.37-7.35 (m, 1H), 7.02-6.99 (m, 1H), 6.95-6.85 (m, 1H), 6.80-6.60 (m, 2H), 5.29 (s, 2H), 3.94 (s, 3H), 2.99 (s, 3H), 2.25 (s, 3H), 2.17 (s, 3H). MS: m/z=538.1 (M+1), HPLC Purity: 91.44%, (Method: B).

Example 23

N-(2-(2-(dimethylamino)ethoxy)-5-(3-(1-(3-fluorobenzyl)-3,5-dimethyl-1H-pyrazol-4-yl)-1H-pyrrolo[2,3-b]pyridin-5-yl)phenyl)methanesulfonamide

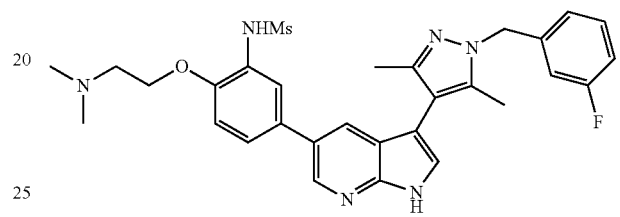

Step-i: 2-(4-(3-(1-(3-fluorobenzyl)-3,5-dimethyl-1H-pyrazol-4-yl)-1-tosyl-1H-pyrrolo[2,3-b]pyridin-5-yl)phenoxy)-N,N-dimethylethanamine Using similar reaction conditions as described in step-ii of example-1, 5-bromo-3-(1-(3-fluorobenzyl)-3,5-dimethyl-1H-pyrazol-4-yl)-1-tosyl-1H-pyrrolo[2,3-b]pyridine (compound of step 1 of Example 14) (100 mg, 0.18 mmol) was coupled with N-(2-(2-(dimethylamino)ethoxy)-5-(4,4,5,5-tetramethyl-1,3,2-dioxaborolan-2-yl)phenyl)methane sulfonamide (Intermediate 27) (229 mg, 0.596 mmol) in sodium carbonate (57 mg, 0.54 mmol) Pd(PPh₃)₂Cl₂ (6 mg, 0.009 mmol), Toluene/ethanol/water (5/2.5/1 ml) to afford 52 mg (39.39% yield) of the titled compound after purification by preparative TLC (SiO2-eluted by 5% methanolic ammonia in DCM). MS: m/z=731.4 (M+1).

Step-ii: N-(2-(2-(dimethylamino)ethoxy)-5-(3-(1-(3-fluorobenzyl)-3,5-dimethyl-1H-pyrazol-4-yl)-1H-pyrrolo[2,3-b]pyridin-5-yl)phenyl)methanesulfonamide Using similar reaction conditions as described in step-iii of example-1, N-(5-(3-(1-(2,6-dichloro-3-fluorobenzyl)-3,5-dimethyl-1H-pyrazol-4-yl)-1-tosyl-1H-pyrrolo[2,3-b]pyridin-5-yl)-2-methoxyphenyl) methanesulfonamide (200 mg, 0.264 mmol) was hydrolyzed by lithium hydroxide (55.5 mg, 1.32 mmol), THF/Methanol/water (4/3/1 ml) to afford 6 mg (15.2% yield) of the titled compound after purification by recrystallization in 7:3 ether-Chloroform. ¹H NMR (CDCl3, 300 MHz): δ 9.36 (s, 1H), 8.56-8.55 (d, 1H), 7.87-7.79 (m, 2H), 7.35-7.31 (m, 2H), 7.14-7.11 (d, 1H), 6.99-6.96 (d, 1H), 6.72 s, 1H), 5.31 (s, 2H), 4.17-4.13 (t, 2H), 2.94 (s, 3H), 2.61-2.57 (t, 3H), 2.39 (s, 6H), 2.25 (s, 3H), 2.17 (s, 4H). MS: m/z=577.2 (M+1), HPLC: 92.87% in Method B.

Example 24

N-(5-(3-(1-(3-fluorobenzyl)-3,5-dimethyl-1H-pyrazol-4-yl)-1H-pyrrolo[2,3-b]pyridin-5-yl)-2-(2-hydroxyethoxyl)phenyl)methanesulfonamide

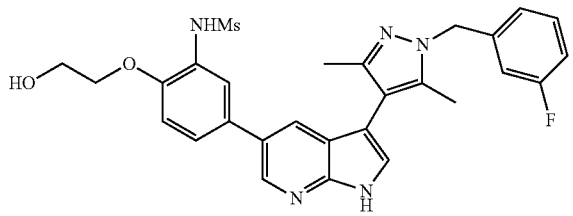

Step-i: N-(2-(2-(benzyloxy)ethoxy)-5-(3-(1-(3-fluorobenzyl)-3,5-dimethyl-1H-pyrazol-4-yl)-1-tosyl-1H-pyrrolo[2,3-b]pyridin-5-yl)phenyl)methanesulfonamide Using similar reaction conditions as described in step-ii of example-1, 5-bromo-3-(1-(3-fluorobenzyl)-3,5-dimethyl-1H-pyrazol-4-yl)-1-tosyl-1H-pyrrolo[2,3-b]pyridine (compound of step-i of example-14) (150 mg, 0.271 mmol) was coupled with N-(2-(2-(benzyloxy)ethoxy)-5-(4,4,5,5-tetramethyl-1,3,2-dioxaborolan-2-yl)phenyl)methanesulfonamide (intermediate 28) (242 mg, 0.542 mmol) in sodium carbonate (86 mg, 0.813 mmol) Pd(PPh$_3$)$_2$Cl$_2$ (10 mg, 0.0135 mmol), Toluene/ethanol/water (5/2.5/1 ml) to afford 120 mg (55.8% yield) of the titled compound after purification by column (SiO$_2$-eluted by 30% EA in hexanes). MS: m/z=794.1 (M+1).

Step-ii: N-(5-(3-(1-(3-fluorobenzyl)-3,5-dimethyl-1H-pyrazol-4-yl)-1-tosyl-1H-pyrrolo[2,3-b]pyridin-5-yl)-2-(2-hydroxyethoxyl)phenyl)methanesulfonamide A stirred solution of N-(2-(2-(benzyloxy)ethoxy)-5-(3-(1-(3-fluorobenzyl)-3,5-dimethyl-1H-pyrazol-4-yl)-1-tosyl-1H-pyrrolo[2,3-b]pyridin-5-yl)phenyl)methane sulfonamide (120 mg, 0.151 mmol), toluene/TFA (5/5 ml) was heated to 70° C. for overnight. TLC showed reaction completion. Reaction mass was cooled to RT and solvents evaporated under reduced pressure. This afforded 152 mg of the crude titled compound. MS: m/z=704.2 (M+1).

Step-iii: N-(5-(3-(1-(3-fluorobenzyl)-3,5-dimethyl-1H-pyrazol-4-yl)-1H-pyrrolo[2,3-b]pyridin-5-yl)-2-(2-hydroxyethoxy)phenyl)methanesulfonamide Using similar reaction conditions as described in step-iii of example-1, N-(5-(3-(1-(3-fluorobenzyl)-3,5-dimethyl-1H-pyrazol-4-yl)-1-tosyl-1H-pyrrolo[2,3-b]pyridin-5-yl)-2-(2-hydroxyethoxyl)phenyl) methanesulfonamide (150 mg, 0.208 mmol) was hydrolyzed by lithium hydroxide (88 mg, 2.08 mmol), THF/Methanol/water (3/3/1.5 ml) to afford 15 mg (15.38% yield) of the title compound. $^1$H NMR (DMSO-d$_6$, 300 MHz): δ11.9 (s, 1H), 9.00 (s, 1H), 8.49 (s, 1H), 7.81 (s, 1H), 7.59 (s, 1H), 7.51-7.41 (m, 3H), 7.15-7.12 (d, 1H), 7.05-7.03 (m, 1H), 6.87 (s, 1H), 4.06 (m, 2H), 3.78 (m, 2H), 3.00 (s, 3H), 2.18-2.14 (d, 6H), MS: m/z=550.1 (M+1), HPLC: 87.11% in Method B.

Example 25

N-(5-(3-(1-(3-fluorobenzyl)-3,5-dimethyl-1H-pyrazol-4-yl)-1H-pyrrolo[2,3-b]pyridin-5-yl)-2-(3-hydroxypropoxyl)phenyl)methanesulfonamide

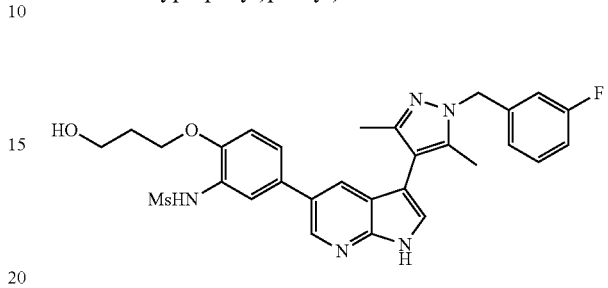

Step-i: N-(5-(3-(1-(3-fluorobenzyl)-3,5-dimethyl-1H-pyrazol-4-yl)-1-tosyl-1H-pyrrolo[2,3-b]pyridin-5-yl)-2-(3-((4-methoxybenzyl)oxy)prop oxy)phenyl)methanesulfonamide Using similar reaction conditions as described in step-ii of example-1, 5-bromo-3-(1-(3-fluorobenzyl)-3,5-dimethyl-1H-pyrazol-4-yl)-1-tosyl-1H-pyrrolo[2,3-b]pyridine (step-i of example-14) (200 mg, 0.3 mmol) was coupled with N-(2-(3-(4-methoxyphenoxyl)propoxy)-5-(4,4,5,5-tetramethyl-1,3,2-dioxaborolan-2-yl)phenyl)methanesulfonamide (intermediate 29) (160 mg, 0.3 mmol) in sodium carbonate (120 mg, 1 mmol) PdCl2 (dppf) (14 mg, 0.001 mmol), 1,2-dimethoxy ethane/water (2/2 mL) to afford 120 mg (41% yield) of the titled compound after purification by column (SiO$_2$-eluted by 30% EA in hexanes).

Step-ii: N-(5-(3-(1-(3-fluorobenzyl)-3,5-dimethyl-1H-pyrazol-4-yl)-1-tosyl-1H-pyrrolo[2,3-b]pyridin-5-yl)-2-(3-hydroxyprop oxy)phenyl)methanesulfonamide A stirred solution of N-(5-(3-(1-(3-fluorobenzyl)-3,5-dimethyl-1H-pyrazol-4-yl)-1-tosyl-1H-pyrrolo[2,3-b]pyridin-5-yl)-2-(3-((4-methoxybenzyl)oxy)prop oxy)phenyl)methanesulfonamide (120 mg, 0.1 mmol), TFA/toluene (169 mg/3 mL) was heated to 80° C. for overnight. TLC showed reaction completion. Reaction mass was cooled to RT and solvents evaporated under reduced pressure. This afforded 60 mg of the crude titled compound. MS: m/z=718.2 (M+1).

Step-iii: N-(5-(3-(1-(3-fluorobenzyl)-3,5-dimethyl-1H-pyrazol-4-yl)-1H-pyrrolo[2,3-b]pyridin-5-yl)-2-(3-hydroxypropoxy)phenyl)methanesulfonamide Using similar reaction conditions as described in step-iii of example-1, N-(5-(3-(1-(3-fluorobenzyl)-3,5-dimethyl-1H-pyrazol-4-yl)-1-tosyl-1H-pyrrolo[2,3-b]pyridin-5-yl)-2-(3-hydroxypropoxyl)phenyl) methanesulfonamide (60 mg, 0.08 mmol) was hydrolyzed by lithium hydroxide (6 mg, 0.25 mmol), THF/methanol/water (1/1/0.5 ml) to afford 5 mg (1.1% yield) of the titled compound. $^1$H NMR (DMSO-d$_6$, 400 MHz): δ 11.85 (s, 1H), 8.90 (s, 1H), 8.47 (s, 1H), 7.77 (s, 1H), 7.52-7.41 (m, 4H), 7.15-7.00 (m, 4H), 5.32 (s, 2H), 4.60

(b, 1H), 4.13 (t, 2H), 3.63-3.61 (t, 2H), 2.97 (s, 3H), 2.17-2.13 (d, 6H), 1.93 (m, 2H). MS: m/z=564.1 (M+1), HPLC: 98.85% (method-B).

Example 26

N-(2-(3-(dimethylamino)propoxy)-5-(3-(1-(3-fluorobenzyl)-3,5-dimethyl-1H-pyrazol-4-yl)-1H-pyrrolo[2,3-b]pyridin-5-yl)phenyl)methanesulfonamide

Step-i: N-(2-(3-(dimethylamino)propoxy)-5-(3-(1-(3-fluorobenzyl)-3,5-dimethyl-1H-pyrazol-4-yl)-1-tosyl-1H-pyrrolo[2,3-b]pyridin-5-yl)phenyl)methanesulfonamide Using similar reaction conditions as described in step-ii of example 1, 5-bromo-3-(1-(3-fluorobenzyl)-3,5-dimethyl-1H-pyrazol-4-yl)-1-tosyl-1H-pyrrolo[2,3-b]pyridine (step-i of example-14) (250 mg, 0.4 mmol) was coupled with N-(2-(3-(dimethylamino)propoxy)-5-(4,4,5,5-tetramethyl-1,3,2-dioxaborolan-2-yl)phenyl)methanesulfonamide (intermediate-30) (200 mg, 0.5 mmol) in sodium carbonate (154 mg, 1.4 mmol) PdCl$_2$(dppf) (18 mg, 0.05 mmol), 1,2-dimethoxyethane/water (2/2 mL) to afford 40 mg (12% yield) of the titled compound after purification by preparative TLC (SiO$_2$)-eluted by 30% ethyl acetate in hexane.

Step-ii: N-(2-(3-(dimethylamino)propoxy)-5-(3-(1-(3-fluorobenzyl)-3,5-dimethyl-1H-pyrazol-4-yl)-1H-pyrrolo[2,3-b]pyridin-5-yl)phenyl)methanesulfonamide Using similar reaction conditions as described in step-iii of example-1, N-(2-(3-(dimethylamino)propoxy)-5-(3-(1-(3-fluorobenzyl)-3,5-dimethyl-1H-pyrazol-4-yl)-1-tosyl-1H-pyrrolo[2,3-b]pyridin-5-yl)phenyl)methanesulfonamide (40 mg, 0.05 mmol) was hydrolyzed by lithium hydroxide (4 mg, 0.16 mmol), THF/methanol/water (1/1/0.5 ml) to afford 5 mg (16% yield) of the titled compound after purification by preparative TLC (SiO$_2$)-eluted by 5% methanol in DCM. $^1$H NMR (CDCl$_3$, 400 MHz): δ 8.88 (s, 1H), 8.54-8.53 (d, 1H), 7.84 (s, 1H), 7.808-7.803 (d, 1H), 7.33-7.23 (m, 3H), 7.05-7.03 (d, 1H), 6.99-6.90 (m, 2H), 6.87-6.852 (d, 1H), 5.31 (s, 2H), 4.16-4.13 (t, 2H), 2.96 (s, 3H), 2.52-2.49 (t, 2H), 2.31 (s, 6H), 2.25 (s, 3H), 2.17 (s, 3H), 2.00-1.97 (m, 2H). MS: m/z=591.4 (M+1), HPLC: 91.28% in method B.

Example 27

N-(5-(6-cyclopropyl-3-(1-(3,5-difluorobenzyl)-3,5-dimethyl-1H-pyrazol-4-yl)-1H-pyrrolo[2,3-b]pyridin-5-yl)-2-methoxyphenyl)methanesulfonamide

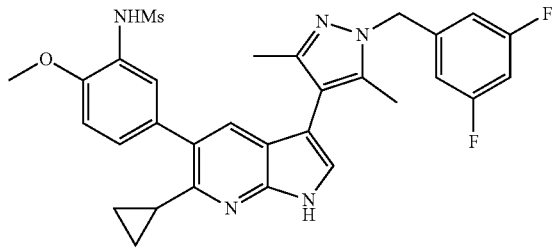

Step-i: tert-butyl 5-(3-(N-(tert-butoxycarbonyl)methylsulfonamido)-4-methoxyphenyl)-6-cyclopropyl-3-(1-(3,5-difluorobenzyl)-3,5-dimethyl-1H-pyrazol-4-yl)-1H-pyrrolo[2,3-b]pyridine-1-carboxylate Using similar reaction conditions as described in step-ii of example-1, tert-butyl 5-(3-(N-(tert-butoxycarbonyl)methylsulfonamido)-4-methoxyphenyl)-6-cyclopropyl-3-iodo-1H-pyrrolo[2,3-b]pyridine-1-carboxylate (intermediate 33) (150 mg, 0.21 mmol) was coupled with 1-(3,5-difluorobenzyl)-3,5-dimethyl-4-(4,4,5,5-tetramethyl-1,3,2-dioxaborolan-2-yl)-1H-pyrazole (intermediate 24) (91.69 mg, 0.24 mmol) in sodium carbonate (66.77 mg, 0.483 mmol), Pd(PPh$_3$)$_2$Cl$_2$ (7.36 mg, 0.01 mmol), 1,2-dimethoxyethane/water (10/2 ml) to give 70 mg (41% yield) of titled compound. MS: m/z=778.0 (M+1).

Step-ii: N-(5-(6-cyclopropyl-3-(1-(3,5-difluorobenzyl)-3,5-dimethyl-1H-pyrazol-4-yl)-1H-pyrrolo[2,3-b]pyridin-5-yl)-2-methoxyphenyl)methanesulfonamide Using similar reaction conditions as described in step-ii of example-7, tert-butyl 6-cyclopropyl-3-(1-(3,5-difluorobenzyl)-3,5-dimethyl-1H-pyrazol-4-yl)-5-(4-methoxy-3-(methylsulfonamido)phenyl)-1H-pyrrolo[2,3-b]pyridine-1-carboxylate (70 mg, 0.103 mmol) was deprotected in HCl in 1,4-dioxane (2 ml). This afforded 5 mg (9.1% yield) of the titled compound. $^1$H NMR (CD3OD, 300 MHz): δ 8.24 (s, 1H), 7.66 (s, 1H), 7.59-7.58 (m, 1H), 7.38-7.34 (dd, 1H), 7.22-7.19 (m, 1H), 6.93-6.90 (m, 1H), 6.82-6.76 (m, 1H), 5.45-5.39 (t, 2H), 3.96 (s, 3H), 2.94 (s, 3H), 2.5-2.4 (m, 1H), 2.25 (s, 3H), 1.4-1.0 (m, 4H). MS: m/z=538.1 (M+1), HPLC: 81% method B.

Example 28

N-(5-(6-cyclopropyl-3-(1-(3-fluorobenzyl)-3,5-dimethyl-1H-pyrazol-4-yl)-1H-pyrrolo[2,3-b]pyridin-5-yl)-2-methoxyphenyl)methanesulfonamide

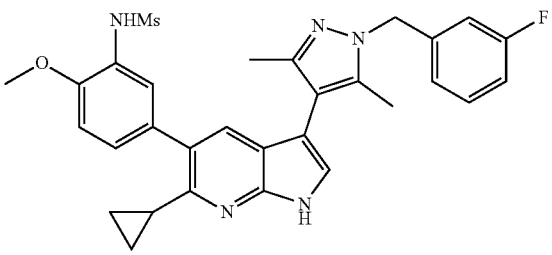

Step-i: tert-butyl 5-(3-(N-(tert-butoxycarbonyl)methylsulfonamido)-4-methoxyphenyl)-6-cyclopropyl-3-(1-(3-fluorobenzyl)-3,5-dimethyl-1H-pyrazol-4-yl)-1H-pyrrolo[2,3-b]pyridine-1-carboxylate Using similar reaction conditions as described in step-ii of example-1, tert-butyl 5-(3-(N-(tert-butoxycarbonyl)methylsulfonamido)-4-methoxyphenyl)-6-cyclopropyl-3-iodo-1H-pyrrolo[2,3-b]pyridine-1-carboxylate (intermediate 33) (200 mg, 0.31 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (123.15 mg, 0.37 mmol) in sodiumcarbonate (98.57 mg, 0.93 mmol), Pd(PPh$_3$)$_2$Cl$_2$ (10.8 mg, 0.01 mmol), 1,2-dimethoxyethane/water (10/2 ml) to give 60 mg (25.4% yield) of titled compound. MS: m/z=760.1 (M+1).

Step-ii: N-(5-(6-cyclopropyl-3-(1-(3-fluorobenzyl)-3,5-dimethyl-1H-pyrazol-4-yl)-1H-pyrrolo[2,3-b]pyridin-5-yl)-2-methoxyphenyl)methanesulfonamide Using similar reaction conditions as described in step-ii of example-7, tert-butyl 5-(3-(N-(tert-butoxycarbonyl)methylsulfonamido)-4-methoxyphenyl)-6-cyclopropyl-3-(1-(3-fluorobenzyl)-3,5-dimethyl-1H-pyrazol-4-yl)-1H-pyrrolo[2,3-b]pyridine-1-carboxylate (60 mg, 0.078 mmol) was deprotected in HCl in 1,4-dioxane (2 ml). This afforded 8 mg (18.1% yield) of the titled compound. $^1$H NMR (CDCl3, 300 MHz): δ 9.1-9.0 (b, 1H), 7.679-7.673 (d, 1H), 7.52 (s, 1H), 7.14-7.13 (d, 1H), 6.99-6.96 (m, 3H), 6.85 (m, 2H), 5.28 (s, 3H), 3.93 (s, 3H), 2.99 (s, 3H), 2.23 (s, 3H), 2.14 (s, 3H), 0.89-0.85 (m, 4H). MS: m/z=559.9 (M+1), HPLC: 85.5% in method B.

Example 29

N-(3-(3-(1-(3-fluorobenzyl)-3,5-dimethyl-1H-pyrazol-4-yl)-1H-pyrrolo[2,3-b]pyridin-5-yl)-2,6-dimethoxy phenyl)methanesulfonamide

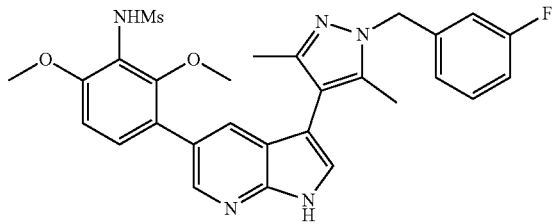

Step-i: N-(3-(3-(1-(3-fluorobenzyl)-3,5-dimethyl-1H-pyrazol-4-yl)-1-tosyl-1H-pyrrolo[2,3-b]pyridin-5-yl)-2,6-dimethoxyphenyl)methanesulfonamide Using similar reaction conditions as described in step-ii of example-1, N-(3-(3-iodo-1-tosyl-1H-pyrrolo[2,3-b]pyridin-5-yl)-2,6-dimethoxyphenyl) methane sulfonamide (intermediate 34) (55 mg, 0.485 mmol) was coupled with 1-(3-fluorobenzyl)-3,5-dimethyl-4-(4,4,5,5-tetramethyl-1,3,2-dioxaborolan-2-yl)-1H-pyrazole (intermediate-16) (57.8 mg, 0.175 mmol) in sodium carbonate (28 mg, 0.263 mmol), Pd(PPh$_3$)$_2$Cl$_2$ (3.0 mg, 0.0043 mmol), Toluene/ethanol/water (10/5/2 ml) to give 40 mg (64.5% yield) of titled compound. MS: m/z=704.2 (M+1).

Step-ii: N-(3-(3-(1-(3-fluorobenzyl)-3,5-dimethyl-1H-pyrazol-4-yl)-1H-pyrrolo[2,3-b]pyridin-5-yl)-2,6-dimethoxyphenyl)methanesulfonamide Using similar reaction conditions as described in step-iii of example-1, N-(3-(3-(1-(3-fluorobenzyl)-3,5-dimethyl-1H-pyrazol-4-yl)-1-tosyl-1H-pyrrolo[2,3-b]pyridin-5-yl)-2,6-dimethoxy phenyl)methanesulfonamide (40 mg, 0.05 mmol) was hydrolyzed by lithium hydroxide (23.8 mg, 0.5 mmol), THF/Methanol/water (12/4/4 ml) to afford 7 mg (25.9% yield) of the titled compound. $^1$H NMR (CD$_3$OD, 400 MHz): δ 8.5 (b, 1H), 8.181-8.177 (d, 1H), 7.525 (s, 1H), 7.356-7.334 (m, 2H), 6.991-6.957 (m, 3H), 6.9-6.85 (m, 1H), 5.363 (s, 2H), 3.930 (s, 3H), 3.499 (s, 3H), 3.184 (s, 1H), 2.231-2.204 (d, 6H). MS: m/z=550.0 (M+1); HPLC: 94.463% in method A.

Example 30

N-(5-(2-cyclopropyl-3-(1-(3-fluorobenzyl)-3,5-dimethyl-1H-pyrazol-4-yl)-1H-pyrrolo[2,3-b]pyridin-5-yl)-2-methoxyphenyl)methanesulfonamide

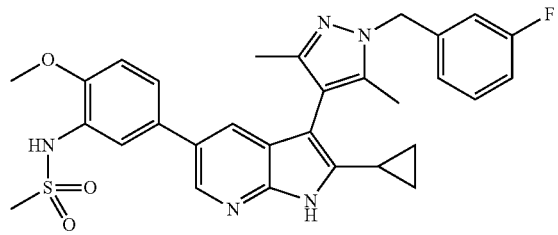 [SMILES: COc1ccc(-c2cnc3[nH]c(C4CC4)c(-c4c(C)nn(Cc5cccc(F)c5)c4C)c3c2)cc1NS(C)(=O)=O]

Step-i: tert-butyl 5-(3-(N-(tert-butoxycarbonyl)methylsulfonamido)-4-methoxyphenyl)-2-cyclopropyl-3-(1-(3-fluorobenzyl)-3,5-dimethyl-1H-pyrazol-4-yl)-1H-pyrrolo[2,3-b]pyridine-1-carboxylate Using similar reaction conditions as described in step-ii of example-1, tert-butyl 5-(3-(N-(tert-butoxycarbonyl)methylsulfonamido)-4-methoxyphenyl)-2-cyclopropyl-3-iodo-1H-pyrrolo[2,3-b]pyridine-1-carboxylate (intermediate 36) (110 mg, 0.1610 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (61 mg, 0.1771 mmol) in sodium carbonate (51 mg, 0.4831 mmol), Pd(PPh$_3$)$_4$ (10 mg, 0.0080 mmol) and DME/water (3/1 ml) to afford 150 mg of the crude product which was taken as such for next reaction.

Step-ii: N-(5-(2-cyclopropyl-3-(1-(3-fluorobenzyl)-3,5-dimethyl-1H-pyrazol-4-yl)-1H-pyrrolo[2,3-b]pyridin-5-yl)-2-methoxyphenyl)methanesulfonamide tert-butyl5-(3-(N-(tert-butoxycarbonyl)methylsulfonamido)-4-methoxyphenyl)-2-cyclopropyl-3-(1-(3-fluorobenzyl)-3,5-dimethyl-1H-pyrazol-4-yl)-1H-pyrrolo[2,3-b]pyridine-1-carboxylate (150 mg) was hydrolyzed with methanol/HCl (5 ml) at 0° C. and purified by prep HPLC to afford 9 mg (8.18% yield) of the pure required product. $^1$H NMR (CD$_3$OD, 400 MHz): δ 8.32-8.31 (s, 1H), 7.65-7.64 (d, 1H), 7.54-7.7.53 (d, 1H), 7.42-7.37 (q, 1H), 7.06-6.94 (m, 3H), 6.88-6.86 (d, 1H), 5.39 (s, 2H), 3.85 (s, 3H), 3.82 (s, 3H), 2.14 (s, 3H), 2.04 (s, 3H), 1.94-1.93 (m, 1H), 1.04-0.90 (m, 4H). MS: m/z=560.0 (M+1), HPLC Purity: 78.69% Method: B.

Example 31 tert-butyl 4-(3-(3-(1-(2,5-difluorobenzyl)-1 h-pyrazol-4-yl)-1 h-pyrrolo[2,3-b]pyridin-5-yl)phenyl)piperazine-1-carboxylate

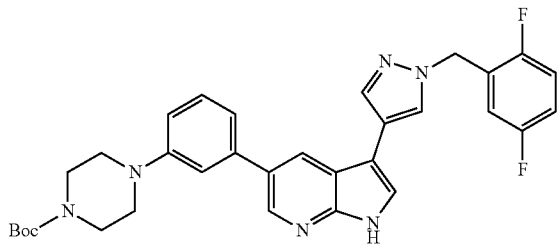 [SMILES: CC(C)(C)OC(=O)N1CCN(c2cccc(-c3cnc4[nH]cc(-c5cnn(Cc6cc(F)ccc6F)c5)c4c3)c2)CC1]

Step-i: tert-butyl 4-(3-(3-(1-(2,5-difluorobenzyl)-1H-pyrazol-4-yl)-1-tosyl-1H-pyrrolo[2,3-b]pyridin-5-yl)phenyl) piperazine-1-carboxylate Using similar reaction conditions as described in step-ii of example-1, 5-bromo-3-(1-(2,5-difluorobenzyl)-1H-pyrazol-4-yl)-1-tosyl-1H-pyrrolo[2,3-b]pyridine (step-i of example-4) (380 mg, 0.552 mmol) was coupled with tert-butyl 4-(3-(4,4,5,5-tetramethyl-1,3,2-dioxaborolan-2-yl)phenyl) piperazine-1-carboxylate (intermediate 37) (428 mg, 1.104 mmol) in sodium carbonate (176 mg, 1.657 mmol), Pd(PPh$_3$)$_2$Cl$_2$ (38.7 mg, 0.0552 mmol), toluene/ethanol/water (30/15/6 ml). This afforded 454 mg (89.7% yield) after purification by column (Silica gel 60/120) using 35% ethyl acetate in hexane as eluent. MS: m/z=725.6 (M+2).

Step-ii tert-butyl 4-(3-(3-(1-(2,5-difluorobenzyl)-1 h-pyrazol-4-yl)-1 h-pyrrolo[2,3-b]pyridin-5-yl)phenyl) piperazine-1-carboxylate Using similar reaction conditions as described in step-iii of example-1, tert-butyl 4-(3-(3-(1-(2,5-difluorobenzyl)-1H-pyrazol-4-yl)-1-tosyl-1H-pyrrolo[2,3-b]pyridin-5-yl)phenyl)piperazine-1-carboxylate (450 mg, 0.621 mmol) was hydrolyzed by lithium hydroxide (130 mg, 3.107 mmol), THF/Methanol/water (20/10/4 ml) to yield 300.0 mg yield 84% of the titled compound after purification by preparative TLC (SiO2-using 2% methanol in chloroform as eluent). $^1$H NMR (CD$_3$OD, 300 MHz): δ 9.05 (b, 1H), 8.559-8.552 (d, 1H), 8.187-8.180 (m, 1H), 7.866 (s, 1H), 7.760 (s, 1H), 7.449-7.370 (m, 1H), 7.164-7.150 (m, 1H), 7.1-6.85 (m, 3H), 5.423 (s, 2H), 3.645-3.611 (m, 4H), 3.241-3.224 (m, 4H), 1.496 (s, 9H). MS: m/z=571.1 (M+1); HPLC: 90.45% in method B.

Example 32

3-(1-(2,5-difluorobenzyl)-1H-pyrazol-4-yl)-5-(3-(piperazin-1-yl)phenyl)-1H-pyrrolo[2,3-b]pyridine

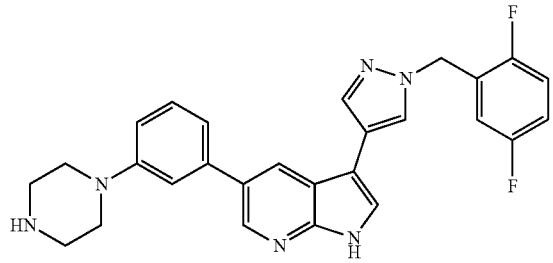 [SMILES: Fc1ccc(F)c(Cn2cc(-c3c[nH]c4ncc(-c5cccc(N6CCNCC6)c5)cc34)cn2)c1]

To a stirred solution of tert-butyl 4-(3-(3-(1-(2,5-difluorobenzyl)-1H-pyrazol-4-yl)-1H- pyrrolo[2,3-b]pyridin-5-yl) phenyl)piperazine-1-carboxylate (Example-31) (200 mg, 0.351 mmol) in methanol (5 ml) added saturated HCl in methanol at 0° C. This gradually brought to RT and stirred for four hours. Reaction mass was cooled and added ether to get solids. Solvents decanted and solids washed by ethyl acetate and dried. This residue was made free base using saturated sodium carbonate. This afforded 16.0 mg (9.75% yield) of titled compound after purification by preparative TLC (SiO2 using 3% methanol in chloroform as eluent). $^1$H NMR (CD$_3$OD, 300 MHz): δ 8.557-8.550 (d, 1H), 8.192-8.184 (d, 1H), 7.866 (s, 1H), 7.762 (s, 1H), 7.446-7.360 (m, 2H), 7.160-7.10 (m, 2H), 7.05-6.85 (m, 3H), 5.420 (s, 2H), 3.276-3.242 (m, 4H), 3.119-3.086 (m, 4H). MS: m/z=470.9 (M+1); HPLC: 97.41% in method A.

Example 33

3-(1-(3-fluorobenzyl)-1H-pyrazol-4-yl)-5-(3-(piperazin-1-yl)phenyl)-1H-pyrrolo[2,3-b]pyridine hydrochloride

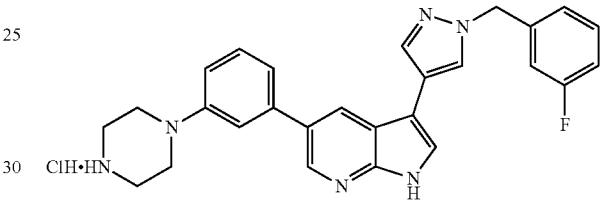

Step-i: tert-butyl 4-(3-(3-(1-(3-fluorobenzyl)-1H-pyrazol-4-yl)-1-tosyl-1H-pyrrolo[2,3-b]pyridin-5-yl) phenyl) piperazine-1-carboxylate Using similar reaction conditions as described in step-ii of example-1, 5-bromo-3-(1-(3-fluorobenzyl)-1H-pyrazol-4-yl)-1-tosyl-1H-pyrrolo[2,3-b]pyridine (compound of step-i of example-9) (225 mg, 0.428 mmol) was coupled with tert-butyl 4-(3-(4,4,5,5-tetramethyl-1,3,2-dioxaborolan-2-yl) phenyl) piperazine-1-carboxylate (intermediate 37) (332 mg, 0.857 mmol) in sodium carbonate (182 mg, 1.714 mmol), Pd(PPh$_3$)$_2$Cl$_2$ (34 mg, 0.0285 mmol), toluene/ethanol/water (22/11/5.5 ml). This afforded 147 mg (48.6% yield) after purification by column (Silica gel 60/120) using 35% ethyl acetate in hexane as eluent. MS: m/z=706.8 (M+1).

Step-ii: tert-butyl 4-(3-(3-(1-(3-fluorobenzyl)-1H-pyrazol-4-yl)-1H-pyrrolo[2,3-b]pyridin-5-yl)phenyl) piperazine-1-carboxylate Using similar reaction conditions as described in step-iii of example-1, tert-butyl 4-(3-(3-(1-(3-fluorobenzyl)-1H-pyrazol-4-yl)-1-tosyl-1H-pyrrolo[2,3-b]pyridin-5-yl)phenyl) piperazine-1-carboxylate (142 mg, 0.2 mmol) was hydrolyzed by lithium hydroxide (84 mg, 2 mmol), THF/Methanol/water (20/8/5 ml) to yield 77 mg (70% yield) of the titled compound.

Step-iii: 3-(1-(3-fluorobenzyl)-1H-pyrazol-4-yl)-5-(3-(piperazin-1-yl)phenyl)-1H-pyrrolo[2,3-b]pyridine hydrochloride To a stirred solution of tert-butyl 4-(3-(3-(1-(2,5-difluorobenzyl)-1H-pyrazol-4-yl)-1H- pyrrolo[2,3-b]pyridin-5-yl)

phenyl)piperazine-1-carboxylate (76 mg, 0.137 mmol) in methanol (5 ml) added saturated HCl in dioxane at 0° C. This gradually brought to RT and stirred for four hours. Reaction mass was cooled and added ether to get solids. Solvents decanted and solids washed by ethyl acetate and dried. This afforded 20 mg (29.8% yield) titled compound. $^1$H NMR (CD$_3$OD, 400 MHz): δ 9.071-9.067 (d, 1H), 8.778-8.774 (d, 1H), 8.605 (s, 1H), 8.215 (s, 1H), 8.009 (s, 1H), 7.618-7.614 (m, 1H), 7.535-7.496 (t, 1H), 7.460-7.441 (m, 1H), 7.405-7.351 (m, 1H), 7.272-7.248 (m, 1H), 7.174-7.155 (m, 1H), 7.086-7.030 (m, 2H), 5.530 (s, 2H), 3.682-3.656 (m, 4H), 3.497-3.471 (m, 4H), 3.339 (s, 3H). MS: m/z=453.4 (M+1); HPLC: 89.28% in method A.

Example 34

3-(4-(3-(3-(1-(3-fluorobenzyl)-1H-pyrazol-4-yl)-1H-pyrrolo[2,3-b]pyridin-5-yl)phenyl)piperazin-1-yl) propanenitrile

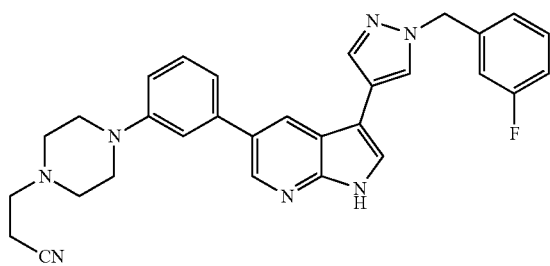 [SMILES: N#CCCN1CCN(c2cccc(-c3cnc4[nH]cc(-c5cnn(Cc6cccc(F)c6)c5)c4c3)c2)CC1]

Step-i: 3-(4-(3-(3-(1-(3-fluorobenzyl)-1H-pyrazol-4-yl)-1-tosyl-1H-pyrrolo[2,3-b]pyridin-5-yl)phenyl piperazin-1-yl)propanenitrile Using similar reaction conditions as described in step-ii of example-1, 5-bromo-3-(1-(3-fluorobenzyl)-1H-pyrazol-4-yl)-1-tosyl-1H-pyrrolo[2,3-b]pyridine (compound of step-i of example-9) (165 mg, 0.314 mmol) was coupled with 3-(4-(3-(4,4,5,5-tetramethyl-1,3,2-dioxaborolan-2-yl)phenyl)piperazin-1-yl)propanenitrile (intermediate 38) (160 mg, 0.471 mmol) in sodium carbonate (100 mg, 0.942 mmol), Pd(PPh$_3$)$_2$Cl$_2$ (22 mg, 0.0314 mmol), toluene/ethanol/water (20/10/5 ml). This afforded 88 mg (42.5% yield) after purification by column (Silica gel 60/120) using 1.5% methanol in chloroform as eluent. MS: m/z=660.4 (M+1).

Step-ii: 3-(4-(3-(3-(1-(3-fluorobenzyl)-1H-pyrazol-4-yl)-1H-pyrrolo[2,3-b]pyridin-5-yl)phenyl) piperazin-1-yl)propanenitrile Using similar reaction conditions as described in step-iii of example-1, 3-(4-(3-(3-(1-(3-fluorobenzyl)-1H-pyrazol-4-yl)-1-tosyl-1H-pyrrolo[2,3-b]pyridin-5-yl)phenyl)piperazin-1-yl) propanenitrile (86 mg, 0.13 mmol) was hydrolyzed by lithium hydroxide (27 mg, 6.525 mmol), THF/Methanol/water (15/4/4 ml) to yield 5 mg (5.6% yield) of the titled compound. $^1$H NMR (CD$_3$OD, 400 MHz): δ 8.481 (s, 1H), 8.407-8.402 (d, 1H), 8.198 (s, 1H), 7.955 (s, 1H), 7.674 (s, 1H), 7.48-7.292 (m, 4H), 7.123-6.98 (m, 4H), 5.439 (s, 2H), 3.8-3.4 (m, 4H), 3.2-3.0 (t, 2H). MS: m/z=506.4 (M+1); HPLC: 98.91% in method A.

Example 35

3-(1-(3-fluorobenzyl)-1H-pyrazol-4-yl)-5-(3-(4-isopropylpiperazin-1-yl)phenyl)-1H-pyrrolo[2,3-b]pyridine

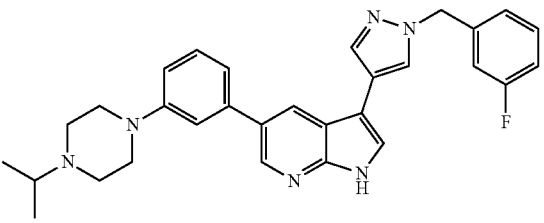 [SMILES: CC(C)N1CCN(c2cccc(-c3cnc4[nH]cc(-c5cnn(Cc6cccc(F)c6)c5)c4c3)c2)CC1]

Step-i: 3-(1-(3-fluorobenzyl)-1H-pyrazol-4-yl)-5-(3-(piperazin-1-yl)phenyl)-1-tosyl-1H-pyrrolo[2,3-b] pyridine hydrochloride Using similar reaction conditions as described in step-iii of example-33, tert-butyl 4-(3-(3-(1-(3-fluorobenzyl)-1H-pyrazol-4-yl)-1-tosyl-1H-pyrrolo[2,3-b]pyridin-5-yl)phenyl)piperazine-1-carboxylate (compound of step-i of example-33) (130 mg, 0.184 mmol) was deprotected using methanol/HCl in dioxane (5/5 mL) to give 86 mg, (72.8%) of the titled compound.

Step-ii: 3-(1-(3-fluorobenzyl)-1H-pyrazol-4-yl)-5-(3-(piperazin-1-yl)phenyl)-1-tosyl-1H-pyrrolo[2,3-b] pyridine hydrochloride To a stirred solution of 3-(1-(3-fluorobenzyl)-1H-pyrazol-4-yl)-5-(3-(piperazin-1-yl)phenyl)-1-tosyl-1H-pyrrolo[2,3-b]pyridine hydrochloride (85 mg, 1.132 mmol), potassium carbonate (54.7 mg, 0.396 mmol), DMF (5 ml) added 2-bromopropane (18 mg, 0.145 mmol) and the mixture was heated to 50° C. for overnight. Then reaction mass was cooled to room temperature and water was added, this was then extracted into ethyl acetate, organic portion was dried over sodium sulfate and concentrated to give 80 mg (93% yield) of the titled compound. MS: m/z=649.4 (M+1).

Step-iii: 3-(1-(3-fluorobenzyl)-1H-pyrazol-4-yl)-5-(3-(4-isopropylpiperazin-1-yl)phenyl)-1H-pyrrolo[2, 3-b]pyridine Using similar reaction conditions as described in step-iii of example-1, 3-(1-(3-fluorobenzyl)-1H-pyrazol-4-yl)-5-(3-(4-isopropylpiperazin-1-yl)phenyl)-1-tosyl-1H-pyrrolo[2,3-b] pyridine (79 mg, 0.121 mmol) was hydrolyzed by lithium hydroxide (55 mg, 1.21 mmol), THF/Methanol/water (15/5/5 ml) to yield 8 mg (13.3% yield) of the titled compound. $^1$H NMR (CDCl$_3$, 300 MHz): δ 9.0 (b, 1H), 8.55 (s, 1H), 8.15 (s, 1H), 7.88 (s, 1H), 7.7 (s, 1H), 7.46-7.3 (m, 3H), 7.2-6.9 (m, 3H), 5.389 (s, 2H), 3.4 (m, 4H), 2.7 (m, 4H), 1.4-1.0 (m, 7H). MS: m/z=495.4 (M+1); HPLC: 89.22% in method B.

Example 36

3-(1-(3-fluorobenzyl)-1H-pyrazol-4-yl)-5-(3-(4-methylpiperazin-1-yl)phenyl)-1H-pyrrolo[2,3-b]pyridine

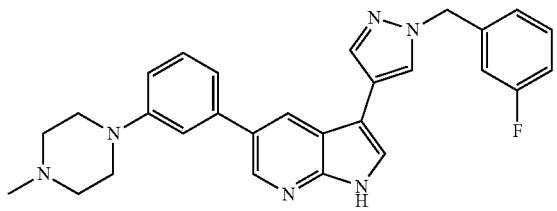 [SMILES: CN1CCN(c2cccc(-c3cnc4[nH]cc(-c5cnn(Cc6cccc(F)c6)c5)c4c3)c2)CC1]

Step-i: 3-(1-(3-fluorobenzyl)-1H-pyrazol-4-yl)-5-(3-(4-methylpiperazin-1-yl)phenyl)-1-tosyl-1H-pyrrolo[2,3-b]pyridine A mixture of 3-(1-(3-fluorobenzyl)-1H-pyrazol-4-yl)-5-(3-(piperazin-1-yl)phenyl)-1-tosyl-1H-pyrrolo[2,3-b]pyridine (step-i of example-35) (87 mg, 0.143 mmol), HCHO (13 mg, 0.43 mmol), 1,2-dichloroethane (2 ml) was stirred at RT under nitrogen for 30 minutes. Sodium triacetoxy borohydride (91 mg, 0.43 mmol) was then added and stirred at the same temperature for overnight. Reaction mass quenched water, basified by saturated sodium bicarbonate and extracted into ethyl acetate. Organic layer dried over sodium sulfate and concentrated to give 74 mg (84% yield) of the titled compound. MS: m/z=621.0 (M+1).

Step-ii: 3-(1-(3-fluorobenzyl)-1H-pyrazol-4-yl)-5-(3-(4-methylpiperazin-1-yl)phenyl)-1H-pyrrolo[2,3-b]pyridine Using similar reaction conditions as described in step-iii of example-1, 3-(1-(3-fluorobenzyl)-1H-pyrazol-4-yl)-5-(3-(4-methylpiperazin-1-yl)phenyl)-1-tosyl-1H-pyrrolo[2,3-b]pyridine (74 mg, 0.119 mmol) was hydrolyzed by lithium hydroxide (50 mg, 1.19 mmol), THF/Methanol/water (12/6/3 ml) to yield 8 mg (30 mg 53.9% yield) of the titled compound. $^1$H NMR (CDCl$_3$, 300 MHz): δ 9.4 (b, 1H), 8.566-8.559 (d, 1H), 8.185-8.178 (d, 1H), 7.874 (s, 1H), 7.706 (s, 1H), 7.451-7.443 (d, 1H), 7.413-7.3 (m, 2H), 7.2-6.956 (m, 5H), 5.392 (s, 2H), 3.340-3.307 (m, 4H), 2.669-2.636 (m, 4H), 2.401 (s, 3H). MS: m/z=467.4 (M+1); HPLC: 98.239% in method B.

Example 37

3-(1-(3-fluorobenzyl)-3-methyl-1H-pyrazol-4-yl)-5-(3-(piperazin-1-yl)phenyl)-1H-pyrrolo[2,3-b]pyridine

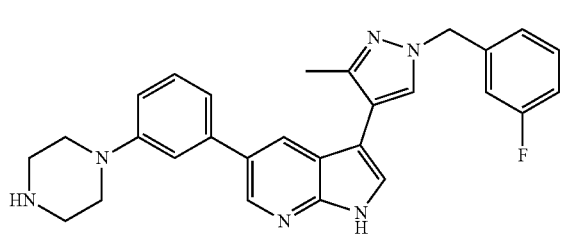 [SMILES: Cc1nn(Cc2cccc(F)c2)cc1-c1c[nH]c2ncc(-c3cccc(N4CCNCC4)c3)cc12]

Step-i: tert-butyl 4-(3-(3-(1-(3-fluorobenzyl)-3-methyl-1H-pyrazol-4-yl)-1-tosyl-1H-pyrrolo[2,3-b]pyridin-5-yl)phenyl)piperazine-1-carboxylate Using similar reaction conditions as described in step-ii of example-1, tert-butyl 4-(3-(3-iodo-1-tosyl-1H-pyrrolo[2,3-b]pyridin-5-yl)phenyl)piperazine-1-carboxylate (intermediate 39) (200 mg, 0.308 mmol) was coupled with 1-(3-fluorobenzyl)-3-methyl-4-(4,4,5,5-tetramethyl-1,3-dioxolan-2-yl)-1H-pyrazole (intermediate 12) (244 mg, 0.772 mmol) in sodium carbonate (98 mg, 0.926 mmol), Pd(PPh$_3$)$_2$Cl$_2$ (11 mg, 0.015 mmol), toluene/ethanol/water (3/3/3 ml). This afforded 130 g (59.6% yield) after purification by column (Silica gel 60/120) using 1.5% of methanol in chloroform as eluent. MS: m/z=710.3 (M+1).

Step-ii: tert-butyl 4-(3-(3-(1-(3-fluorobenzyl)-3-methyl-1H-pyrazol-4-yl)-1H-pyrrolo[2,3-b]pyridin-5-yl)phenyl)piperazine-1-carboxylate Using similar reaction conditions as described in step-iii of example-1, tert-butyl 4-(3-(3-(1-(3-fluorobenzyl)-3-methyl-1H-pyrazol-4-yl)-1-tosyl-1H-pyrrolo[2,3-b]pyridin-5-yl)phenyl) piperazine-1-carboxylate (130 mg, 0.183 mmol) was hydrolyzed by lithium hydroxide (77 mg, 1.83 mmol), THF/Methanol/water (12/6/3 ml) to yield 8 mg (102 mg 96% yield) of the titled compound. MS: m/z=557.3 (M+2).

Step-iii: 3-(1-(3-fluorobenzyl)-3-methyl-1H-pyrazol-4-yl)-5-(3-(piperazin-1-yl)phenyl)-1H-pyrrolo[2,3-b]pyridine Using similar reaction conditions as described in step-ii of example-7, tert-butyl 4-(3-(3-(1-(3-fluorobenzyl)-3-methyl-1H-pyrazol-4-yl)-1H-pyrrolo[2,3-b]pyridin-5-yl)phenyl)piperazine-1-carboxylate (83 mg, 0.146 mmol) was deprotected in methanol (5 ml), HCl in dioaxane (5 ml). This afforded 20 mg (27.1% yield) of the titled compound. $^1$H NMR (CD$_3$OD, 400 MHz): δ 8.852-8.818 (m, 1H), 8.726-8.723 (d, 1H), 8.272 (s, 1H), 7.951 (s, 1H), 7.832-7.798 (d, 1H), 7.499-7.459 (t, 1H), 7.407-7.317 (m, 3H), 7.160-7.129 (m, 2H), 7.070-7.048 (m, 2H), 5.404 (s, 2H), 3.549-3.523 (m, 4H), 3.418-3.393 (m, 4H), 2.392 (s, 3H). MS: m/z=467.2 (M+1); HPLC: 94.845% in method A.

Example 38

3-(1-(3-fluorobenzyl)-3,5-dimethyl-1H-pyrazol-4-yl)-5-(3-(piperazin-1-yl)phenyl)-1H-pyrrolo[2,3-b]pyridine

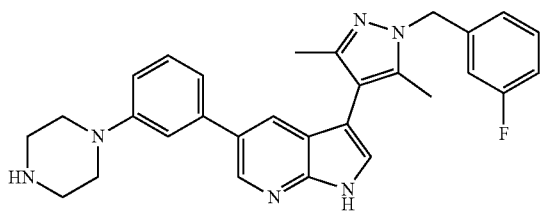

Step-i: tert-butyl 4-(3-(3-(1-(3-fluorobenzyl)-3,5-dimethyl-1H-pyrazol-4-yl)-1-tosyl-1H-pyrrolo[2,3-b]pyridin-5-yl)phenyl)piperazine-1-carboxylate Using similar reaction conditions as described in step-ii of example-1, tert-butyl 4-(3-(3-iodo-1-tosyl-1H-pyrrolo[2,3- b]pyridin-5-yl)phenyl)piperazine-1-carboxylate (intermediate 39) (250 mg, 0.379 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (220 mg, 0.666 mmol) in sodium carbonate (121 mg, 1.139 mmol), Pd(PPh$_3$)$_2$Cl$_2$ (13.3 mg, 0.0189 mmol), toluene/ethanol/water (25/12.5/6 ml). This afforded 267 g (60% yield) after purification by column (Silica gel 60/120) using 1.5% of methanol in chloroform as eluent. MS: m/z=735.3 (M+1).

Step-ii: tert-butyl 4-(3-(3-(1-(3-fluorobenzyl)-3,5-dimethyl-1H-pyrazol-4-yl)-1H-pyrrolo[2,3-b]pyridin-5-yl)phenyl)piperazine-1-carboxylate Using similar reaction conditions as described in step-iii of example-1, tert-butyl 4-(3-(3-(1-(3-fluorobenzyl)-3,5-dimethyl-1H-pyrazol-4-yl)-1-tosyl-1H-pyrrolo[2,3-b]pyridin-5-yl)phenyl) piperazine-1-carboxylate (160 mg, 0.363 mmol) was hydrolyzed by lithium hydroxide (152 mg, 3.633 mmol), THF/Methanol/water (20/10/5 ml) to yield 8 mg (96.7 mg 79.5% yield) of the titled compound. MS: m/z=581.2 (M+2).

Step-iii: 3-(1-(3-fluorobenzyl)-3,5-dimethyl-1H-pyrazol-4-yl)-5-(3-(piperazin-1-yl)phenyl)-1H-pyrrolo[2,3-b]pyridine Using similar reaction conditions as described in step-ii of example-7, tert-butyl 4-(3-(3-(1-(3-fluorobenzyl)-3,5-dimethyl-1H-pyrazol-4-yl)-1H-pyrrolo[2,3-b]pyridin-5-yl)phenyl)piperazine-1-carboxylate (96 mg, 0.165 mmol) was deprotected in methanol (5 ml), HCl in dioaxane (5 ml). This afforded 20 mg (23.5% yield) of the titled compound. $^1$H NMR (CD$_3$OD, 400 MHz): δ 8.759-8.755 (d, 1H), 8.639-8.635 (d, 1H), 7.818 (s, 1H), 7.482-7.370 (m, 3H), 7.284-7.265 (d, 1H), 7.154-7.087 (m, 3H), 6.995-6.971 (m, 1H), 5.489 (s, 2H), 3.530-3.516 (m, 4H), 3.413-3.387 (m, 4H), 2.288 (s, 6H). MS: m/z=481.1 (M+1); HPLC: 85.59% in method A.

Example 39

3-(1-(3-fluorobenzyl)-1H-pyrazol-4-yl)-5-(4-(piperazin-1-yl)phenyl)-1H-pyrrolo[2,3-b]pyridine hydrochloride

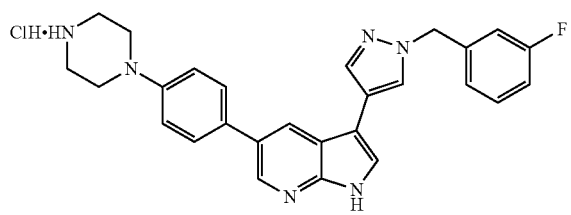

Step-i: tert-butyl 4-(4-(3-(1-(3-fluorobenzyl)-1H-pyrazol-4-yl)-1-tosyl-1H-pyrrolo[2,3-b]pyridin-5-yl)phenyl)piperazine-1-carboxylate Using similar reaction conditions as described in step-ii of example-1, 5-bromo-3-(1-(3-fluorobenzyl)-1H-pyrazol-4-yl)-1-tosyl-1H-pyrrolo[2,3-b]pyridine (compound of step-i of example-9) (200 mg, 0.53 mmol) was coupled with tert-butyl 4-(4-(4,4,5,5-tetramethyl-1,3,2-dioxaborolan-2-yl)phenyl)piperazine-1-carboxylate (intermediate 40) (251 mg, 0.64 mmol) in sodium carbonate (168 mg, 1.59 mmol) PdCl2 (dppf) (19 mg, 0.0265 mmol), 1,2-Dimethoxyethane/water (25/3 ml) to afford 160 mg (59.47% yield) of the titled compound. MS: m/z=707.1 (M+1).

Step-ii: tert-butyl 4-(4-(3-(1-(3-fluorobenzyl)-1H-pyrazol-4-yl)-1H-pyrrolo[2,3-b]pyridin-5-yl)phenyl)piperazine-1-carboxylate Using similar reaction conditions as described in step-iii of example-1, tert-butyl 4-(4-(3-(1-(3-fluorobenzyl)-1H-pyrazol-4-yl)-1-tosyl-1H-pyrrolo[2,3-b]pyridin-5-yl)phenyl)piperazine-1-carboxylate (160 mg, 0.22 mmol) was hydrolyzed by lithium hydroxide (28.5 mg, 0.67 mmol), THF/Methanol/water (3/2/1 ml) to afford 90 mg (72% yield) of the titled compound. MS: 553.2 m/z=(M+1).

Step-iii: 3-(1-(3-fluorobenzyl)-1H-pyrazol-4-yl)-5-(4-(piperazin-1-yl)phenyl)-1H-pyrrolo[2,3-b]pyridine hydrochloride Using similar reaction conditions as described in step-ii of example-7, tert-butyl 4-(3-(3-(1-(3-fluorobenzyl)-3,5-dimethyl-1H-pyrazol-4-yl)-1H-pyrrolo[2,3-b]pyridin-5-yl)phenyl) piperazine-1-carboxylate (96 mg, 0.165 mmol) was deprotected in dioxane (1 ml), HCl in dioxane (3 ml). This afforded 20 mg (23.7% yield) of the titled compound. $^1$H NMR (DMSO-d$_6$, 300 MHz): δ 9.1-9.0 (b, 1H), 8.54-8.53 (d, 1H), 8.46 (s, 1H), 8.42 (m, 1H), 8.0 (s, 1H), 7.81 (d, 1H), 7.73-7.70 (m 2H), 7.4 (m, 1H), 7.14-7.11 (m, 4H), 5.41 (s, 2H), 3.43-3.41 (m, 6H), 3.3-3.2 (b, 4H). MS: 453.2 m/z=(M+1), HPLC: 96.3% in method B.

Example 40

3-(1-(3-fluorobenzyl)-3,5-dimethyl-1H-pyrazol-4-yl)-5-(4-(piperazin-1-yl)phenyl)-1H-pyrrolo[2,3-b]pyridine hydrochloride

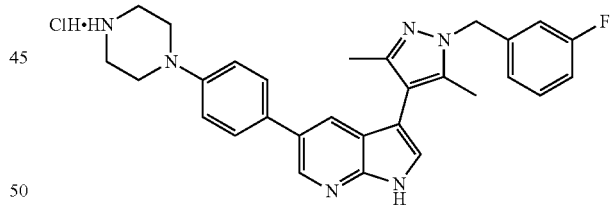

Step-i: tert-butyl 4-(4-(3-(1-(3-fluorobenzyl)-3,5-dimethyl-1H-pyrazol-4-yl)-1-tosyl-1H-pyrrolo[2,3-b]pyridin-5-yl)phenyl)piperazine-1-carboxylate Using similar reaction conditions as described in step-ii of example-1, tert-butyl 4-(4-(3-iodo-1-tosyl-1H-pyrrolo[2,3-b]pyridin-5-yl)phenyl)piperazine-1-carboxylate (intermediate 41) (130 mg, 0.19 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (71 mg, 0.21 mmol) in sodium carbonate (40 mg, 0.38 mmol), PdCl$_2$ (dppf) (6.94 mg, 0.0095 mmol), 1,2-Dimethoxyethane/water (15/1.5 ml) to give titled compound quantity and yield as off white solid. MS: m/z=735.2 (M+1).

Step-ii: tert-butyl 4-(4-(3-(1-(3-fluorobenzyl)-3,5-dimethyl-1H-pyrazol-4-yl)-1H-pyrrolo[2,3-b]pyridin-5-yl)phenyl)piperazine-1-carboxylate Using similar reaction conditions as described in step-iii of example-1, tert-butyl 4-(4-(3-(1-(3-fluorobenzyl)-3,5-dimethyl-1H-pyrazol-4-yl)-1-tosyl-1H-pyrrolo[2,3-b]pyridin-5-yl)phenyl) piperazine-1-carboxylate (200 mg, 0.270 mmol) was hydrolyzed by lithium hydroxide (34.2 mg, 081 mmol), THF/Methanol/water (10/5/1 ml) to yield 80 mg (50.6% yield) of the titled compound.

Step-iii: 3-(1-(3-fluorobenzyl)-3,5-dimethyl-1H-pyrazol-4-yl)-5-(4-(piperazin-1-yl)phenyl)-1H-pyrrolo[2,3-b]pyridine hydrochloride Using similar reaction conditions as described in step-ii of example-7, tert-butyl 4-(4-(3-(1-(3-fluorobenzyl)-3,5-dimethyl-1H-pyrazol-4-yl)-1H-pyrrolo[2,3-b]pyridin-5-yl)phenyl)piperazine-1-carboxylate (80 mg, 0.137 mmol) was deprotected in dioxane (1 ml), HCl in dioxane (3 ml). This afforded 5 mg (23.5% yield) of the titled compound. $^1$H NMR (DMSO-$d_6$, 300 MHz): δ 9.14-9.0 (b, 1H), 8.54 (d, 1H), 7.92 (s, 1H), 7.63-7.60 (s 2H), 7.54-7.53 (s, 1H), 7.5 (m, 1H), 7.10-7.04 (m, 5H), 5.34 (s, 2H), 3.41 (m, 4H), 3.25 (m, 4H), 2.17-2.14 (d, 4H). MS: m/z=481.2 (M+1), HPLC: 90.3% in Method B.

Example 41

2-(4-(4-(3-(1-(3-fluorobenzyl)-3,5-dimethyl-1H-pyrazol-4-yl)-1H-pyrrolo[2,3-b]pyridin-5-yl)phenyl)piperazin-1-yl)ethanol

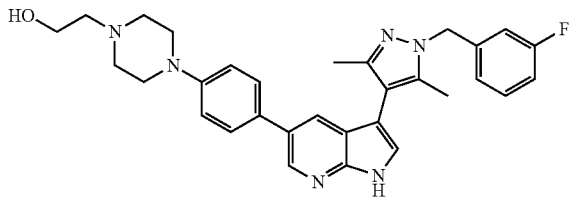 [SMILES: Cc1nn(Cc2cccc(F)c2)c(C)c1-c1c[nH]c2ncc(-c3ccc(N4CCN(CCO)CC4)cc3)cc12]

Step-i: 5-(4-(4-(2-(benzyloxy)ethyl)piperazin-1-yl)phenyl)-3-(1-(3-fluorobenzyl)-3,5-dimethyl-1H-pyrazol-4-yl)-1-tosyl-1H-pyrrolo[2,3-b]pyridine Using similar reaction conditions as described in step-ii of example-1, 5-(4-(4-(2-(benzyloxy)ethyl)piperazin-1-yl)phenyl)-3-iodo-1-tosyl-1H-pyrrolo[2,3-b]pyridine (intermediate 42) (130 mg, 0.203 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (101 mg, 0.305 mmol) in sodium carbonate (65 mg, 0.602 mmol), Pd(PPh$_3$)$_2$Cl$_2$ (7 mg, 0.0101 mmol), Toluene/ethanol/water (5/2.5/1 ml) to give 155 mg of the crude titled compound. MS: m/z=769.3 (M+1).

Step-ii: 2-(4-(4-(3-(1-(3-fluorobenzyl)-3,5-dimethyl-1H-pyrazol-4-yl)-1-tosyl-1H-pyrrolo[2,3-b]pyridin-5-yl)phenyl)piperazin-1-yl)ethanol 5-(4-(4-(2-(benzyloxy)ethyl)piperazin-1-yl)phenyl)-3-(1-(3-fluorobenzyl)-3,5-dimethyl-1H-pyrazol-4-yl)-1-tosyl-1H-pyrrolo[2,3-b]pyridine (150 mg, 0.195 mmol) was dissolved in trifluoroacetic acid/toluene (5/5 ml) and heated to 70° C. for overnight. Solvents evaporated off to yield 208 mg of the crude titled compound.

Step-iii: 2-(4-(4-(3-(1-(3-fluorobenzyl)-3,5-dimethyl-1H-pyrazol-4-yl)-1H-pyrrolo[2,3-b]pyridin-5-yl)phenyl)piperazin-1-yl)ethanol Using similar reaction conditions as described in step-iii of example-1, 2-(4-(4-(3-(1-(3-fluorobenzyl)-3,5-dimethyl-1H-pyrazol-4-yl)-1-tosyl-1H-pyrrolo[2,3-b]pyridin-5-yl)phenyl)piperazin-1-yl)ethanol (200 mg, 0.259 mmol) was hydrolyzed by lithium hydroxide (108 mg, 2.59 mmol), THF/Methanol/water (5/5/2.5 ml) to yield 3 mg (2.2% yield) of the titled compound. $^1$H NMR (CD$_3$OD, 300 MHz): δ 8.34 (s, 1H), 7.75-7.74 (d, 1H), 7.44-7.41 (m, 2H), 7.28-7.27 (m, 2H), 7.00-6.7 (m, 4H), 6.52-6.51 (d, 1H), 5.26 (s, 2H), 3.73-3.69 (t, 2H), 3.26 (m, 4H), 2.91 (m, 4H), 2.79-2.77 (t, 2H), 2.12-2.08 (m, 6H). MS: m/z=525.2 (M+1), HPLC: 80.69% in method A.

Example 42

3-(1-(2,5-difluorobenzyl)-3,5-dimethyl-1H-pyrazol-4-yl)-5-(4-(piperazin-1-yl)phenyl)-1H-pyrrolo[2,3-b]pyridine hydrochloride

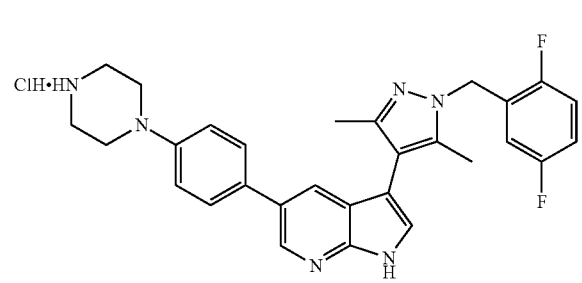

Step-i: tert-butyl 4-(4-(3-(1-(2,5-difluorobenzyl)-3,5-dimethyl-1H-pyrazol-4-yl)-1-tosyl-1H-pyrrolo[2,3-b]pyridin-5-yl)phenyl)piperazine-1-carboxylate Using similar reaction conditions as described in step-ii of example-1, tert-butyl 4-(4-(3-iodo-1-tosyl-1H-pyrrolo[2,3-b]pyridin-5-yl)phenyl)piperazine-1-carboxylate (intermediate 41) (160 mg, 0.243 mmol) was coupled with 1-(2,5-difluorobenzyl)-3,5-dimethyl-4-(4,4,5,5-tetramethyl-1,3,2-dioxaborolan-2-yl)-1H-pyrazole (intermediate 25) (85 mg, 0.243 mmol) in sodium carbonate (77 mg, 0.729 mmol), Pd(PPh$_3$)$_2$Cl$_2$ (17 mg, 0.0243 mmol), Toluene/ethanol/water (15/7.5/1 ml) to give 230 mg of titled compound. MS: m/z=753.1 (M+1).

Step-ii: tert-butyl 4-(4-(3-(1-(2,5-difluorobenzyl)-3,5-dimethyl-1H-pyrazol-4-yl)-1H-pyrrolo[2,3-b]pyridin-5-yl)phenyl)piperazine-1-carboxylate Using similar reaction conditions as described in step-iii of example-1, tert-butyl 4-(4-(3-(1-(2,5-difluorobenzyl)-3,5-dimethyl-1H-pyrazol-4-yl)-1-tosyl-1H-pyrrolo[2,3-b]pyridin-5-yl)phenyl)piperazine-1-carboxylate (230 mg, 0.305 mmol) was hydrolyzed by lithium hydroxide (129 mg, 3.05 mmol), THF/Methanol/water (12/4/4 ml) to afford 46 mg (25.2% yield) of the titled compound. MS: m/z=599.3 (M+1).

Step-iii: 3-(1-(2,5-difluorobenzyl)-3,5-dimethyl-1H-pyrazol-4-yl)-5-(4-(piperazin-1-yl)phenyl)-1H-pyrrolo[2,3-b]pyridine hydrochloride Using similar reaction conditions as described in step-ii of example-7, tert-butyl 4-(4-(3-(1-(2,5-difluorobenzyl)-3,5-dimethyl-1H-pyrazol-4-yl)-1H-pyrrolo[2,3-b]pyridin-5-yl)phenyl) piperazine-1-carboxylate (45 mg, 0.07 mmol) was deprotected in methanol (5 ml), HCl in 1,4-dioaxane (5 ml). This afforded 5 mg (14.7% yield) of the titled compound. $^1$H NMR (CD$_3$OD, 300 MHz): δ 8.351-8.345 (d, 1H), 7.763-7.756 (d, 1H), 7.440-7.412 (m, 2H), 7.293 (s, 1H), 7.095-7.081 (m, 1H), 6.996-6.967 (m, 3H), 6.584 (m, 1H), 5.287 (s, 2H), 3.146-3.114 (m, 4H), 2.972-2.940 (m, 4H), 2.132-2.109 (d, 6H). MS: m/z=499.2 (M+1); HPLC: 85.79% in method B.

Example 43

3-(1-(3,5-difluorobenzyl)-3,5-dimethyl-1H-pyrazol-4-yl)-5-(4-(piperazin-1-yl)phenyl)-1H-pyrrolo[2,3-b]pyridine hydrochloride

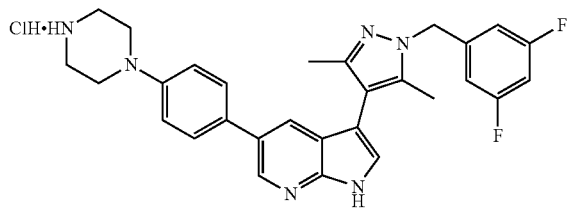

Step-i: tert-butyl 4-(4-(3-(1-(3,5-difluorobenzyl)-3,5-dimethyl-1H-pyrazol-4-yl)-1-tosyl-1H-pyrrolo[2,3-b]pyridin-5-yl)phenyl)piperazine-1-carboxylate Using similar reaction conditions as described in step-ii of example-1, tert-butyl 4-(4-(3-iodo-1-tosyl-1H-pyrrolo[2,3-b]pyridin-5-yl)phenyl)piperazine-1-carboxylate (intermediate 41) (200 mg, 0.303 mmol) was coupled with 1-(3,5-difluorobenzyl)-3,5-dimethyl-4-(4,4,5,5-tetramethyl-1,3,2-dioxaborolan-2-yl)-1H-pyrazole (intermediate 24)(126 mg, 0.364 mmol) in sodium carbonate (96.3 mg, 0.909 mmol), Pd(PPh$_3$)$_2$Cl$_2$ (10.63 mg, 0.015 mmol), toluene/ethanol/water (3/5/1 ml) to give 160 mg (72.7% yield) of titled compound. MS: m/z=753.1 (M+1).

Step-ii: tert-butyl 4-(4-(3-(1-(3,5-difluorobenzyl)-3,5-dimethyl-1H-pyrazol-4-yl)-1H-pyrrolo[2,3-b]pyridin-5-yl)phenyl)piperazine-1-carboxylate Using similar reaction conditions as described in step-iii of example-1, tert-butyl 4-(4-(3-(1-(3,5-difluorobenzyl)-3,5-dimethyl-1H-pyrazol-4-yl)-1-tosyl-1H-pyrrolo[2,3-b]pyridin-5-yl)phenyl) piperazine-1-carboxylate (160 mg, 0.212 mmol) was hydrolyzed by lithium hydroxide (44.6 mg, 1.063 mmol), THF/Methanol/water (2/3/1 ml) to yield 100 mg (63.3% yield) of the titled compound.

Step-iii: 3-(1-(3,5-difluorobenzyl)-3,5-dimethyl-1H-pyrazol-4-yl)-5-(4-(piperazin-1-yl)phenyl)-1H-pyrrolo[2,3-b]pyridine hydrochloride Using similar reaction conditions as described in step-ii of example-7, tert-butyl 4-(4-(3-(1-(3,5-difluorobenzyl)-3,5-dimethyl-1H-pyrazol-4-yl)-1H-pyrrolo[2,3-b]pyridin-5-yl)phenyl)piperazine-1-carboxylate (100 mg, 0.167 mmol) was deprotected in methanol (5 ml), HCl in 1,4-dioaxane (5 ml). This afforded 100 mg (63.3% yield) of the titled compound. $^1$H NMR (CDCl$_3$, 300 MHz): δ 8.56 (s, 1H), 7.858-7.853 (d, 1H), 7.54-7.51 (d, 2H), 7.03-7.01 (d, 2H), 6.69-6.67 (m, 2H), 5.29 (s, 2H), 3.65-3.59 (t, 4H), 3.21-3.19 (t, 4H), 2.26 (s, 3H), 2.15 (s, 3H), 1.49 (s, 9H). MS: m/z=599.2 (M+1).

Example 44

3-(1-(3-fluorobenzyl)-5-methyl-1H-pyrazol-4-yl)-5-(4-(piperazin-1-yl)phenyl)-1H-pyrrolo[2,3-b]pyridine hydrochloride

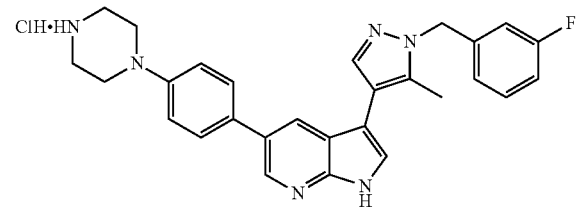

Step-i: tert-butyl 4-(4-(3-(1-(3-fluorobenzyl)-5-methyl-1H-pyrazol-4-yl)-1-tosyl-1H-pyrrolo[2,3-b]pyridin-5-yl)phenyl)piperazine-1-carboxylate Using similar reaction conditions as described in step-ii of example-1, tert-butyl 4-(4-(3-iodo-1-tosyl-1H-pyrrolo[2,3-b]pyridin-5-yl)phenyl)piperazine-1-carboxylate (intermediate 41) (300 mg, 0.455 mmol) was coupled with 1-(3-fluorobenzyl)-5-methyl-4-(4,4,5,5-tetramethyl-1,3,2-dioxaborolan-2-yl)-1H-pyrazole (intermediate 12) (187 mg, 0.592 mmol) in sodium carbonate (145 mg, 1.365 mmol), Pd(PPh$_3$)$_2$Cl$_2$ (16 mg, 0.0227 mmol), Toluene/ethanol/water (5/10/1 ml) to give 250 mg (76.2% yield) of titled compound after purification by column (SiO2) using 20% ethyl acetate in hexane as eluent. $^1$H NMR (CDCl$_3$, 300 MHz): δ 8.64 (s, 1H), 8.12-8.09 (d, 2H), 7.87 (s, 1H), 7.70 (s, 1H), 7.56 (s, 1H), 7.49-7.44 (m, 2H), 7.34-7.25 (m, 2H), 7.01-6.99 (m, 3H), 5.31 (s, 2H), 3.62-3.60 (t, 4H), 3.25-3.19 (t, 4H), 2.39 (s, 3H), 2.37 (s, 3H), 1.49 (s, 9H). MS: m/z=721.1 (M+1).

Step-ii: tert-butyl 4-(4-(3-(1-(3-fluorobenzyl)-5-methyl-1H-pyrazol-4-yl)-1H-pyrrolo[2,3-b]pyridin-5-yl)phenyl)piperazine-1-carboxylate Using similar reaction conditions as described in step-iii of example-1, tert-butyl 4-(4-(3-(1-(3-fluorobenzyl)-5-methyl-1H-pyrazol-4-yl)-1-tosyl-1H-pyrrolo[2,3-b]pyridin-5-yl)phenyl)piperazine-1-carboxylate (250 mg, 0.346 mmol) was hydrolyzed by lithium hydroxide (72.8 mg, 1.734 mmol), THF/Methanol/water (2/3/1 ml) to yield 100 mg (52% yield) of the titled compound. $^1$H NMR (CDCl$_3$, 400 MHz): δ 9.28 (S, 1H), 8.54 (s, 1H), 8.01 (s, 1H), 7.59-7.52 (m, 3H), 7.34-7.27 (m, 2H), 7.05-6.94 (m, 4H), 5.32 (s, 2H), 3.61-3.60 (m, 4H), 3.19 (s, 4H), 2.40 (s, 3H), 1.49 (s, 9H). MS: m/z=657.2 (M+1).

Step-iii: 3-(1-(3-fluorobenzyl)-5-methyl-1H-pyrazol-4-yl)-5-(4-(piperazin-1-yl)phenyl)-1H-pyrrolo[2,3-b]pyridine hydrochloride Using similar reaction conditions as described in step-ii of example-7, tert-butyl 4-(4-(3-(1-(3-fluorobenzyl)-5-methyl- 1H-pyrazol-4-yl)-1H-pyrrolo[2,3-b]pyridin-5-yl)phenyl) piperazine-1-carboxylate (100 mg, 0.176 mmol) was deprotected with HCl in 1,4-dioaxane (5 ml). This afforded 50 mg (60.9% yield) of the titled compound. ¹H NMR (CDCl₃, 300 MHz): δ 9.08 (s, 1H), 8.55-8.54 (d, 1H), 8.02-8.01 (d, 1H), 7.60 (s, 1H), 7.54-7.51 (d, 2H), 7.34-7.31 (m, 2H), 7.10-6.95 (m, 4H), 5.32 (s, 2H), 3.23-3.19 (m, 4H), 3.09-3.05 (m, 4H), 2.41 (s, 3H). MS: m/z=467.4 (M+1), HPLC Purity: 96.37% Method: A.

Example 45

4-(4-(3-(1-(3-fluorobenzyl)-3,5-dimethyl-1H-pyrazol-4-yl)-1H-pyrrolo[2,3-b]pyridin-5-yl)phenyl) morpholine

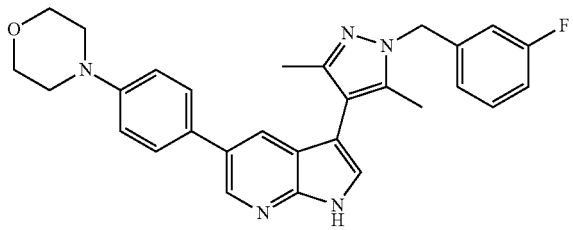 [SMILES: Cc1nn(Cc2cccc(F)c2)c(C)c1-c1c[nH]c2ncc(-c3ccc(N4CCOCC4)cc3)cc12]

Step-i: 4-(4-(3-(1-(3-fluorobenzyl)-3,5-dimethyl-1H-pyrazol-4-yl)-1-tosyl-1H-pyrrolo[2,3-b]pyridin-5-yl) phenyl) morpholine Using similar reaction conditions as described in step-ii of example-1, 4-(4-(3-iodo-1-tosyl-1H-pyrrolo[2,3-b]pyridin-5-yl)phenyl)morpholine (intermediate 43) (150 mg, 0.268 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (133 mg, 0.402 mmol) in sodium carbonate (86 mg, 0.805 mmol), Pd(PPh₃)₂Cl₂ (10 mg, 0.0134 mmol), Toluene/ethanol/water (5/5/5 ml) to afford 100 mg (58.82% yield) of titled compound. MS: m/z=636.1 (M+1).

Step-ii: 4-(4-(3-(1-(3-fluorobenzyl)-3,5-dimethyl-1H-pyrazol-4-yl)-1H-pyrrolo[2,3-b]pyridin-5-yl) phenyl)morpholine Using similar reaction conditions as described in step-iii of example-1, 4-(4-(3-(1-(3-fluorobenzyl)-3,5-dimethyl-1H-pyrazol-4-yl)-1-tosyl-1H-pyrrolo[2,3-b]pyridin-5-yl)phenyl) morpholine (100 mg, 0.157 mmol) was hydrolyzed by lithium hydroxide (33 mg, 0.786 mmol), THF/Methanol/water (5/5/3 ml) to afford 24 mg (32% yield) of the titled compound. ¹H NMR (CDCl₃, 300 MHz): δ 9.36 (s, 1H), 8.56 (s, 1H), 7.87 (s, 1H), 7.75-7.52 (d, 2H), 7.40-7.30 (m, 1H), 7.10-6.95 (m, 3H), 6.90-6.80 (d, 1H), 5.32 (s, 2H), 3.91-3.88 (m, 4H), 3.23-3.20 (m, 4H), 2.26 (s, 3H), 2.15 (s, 3H). MS: m/z=482.3 (M+1), HPLC Purity: 99.13% Method: B.

Example 46

3-(1-(3-methoxybenzyl)-3,5-dimethyl-1H-pyrazol-4-yl)-5-(4-(piperazin-1-yl)phenyl)-1H-pyrrolo[2,3-b] pyridine hydrochloride

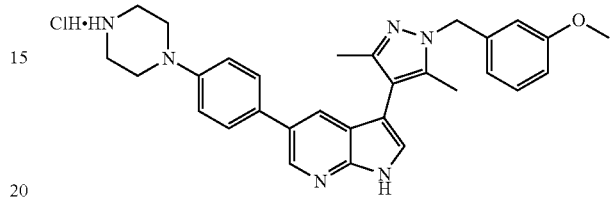

Step-i: tert-butyl 4-(4-(3-(1-(3-methoxybenzyl)-3,5-dimethyl-1H-pyrazol-4-yl)-1-tosyl-1H-pyrrolo[2,3-b]pyridin-5-yl)phenyl)piperazine-1-carboxylate Using similar reaction conditions as described in step-ii of example-1, tert-butyl 4-(4-(3-iodo-1-tosyl-1H-pyrrolo[2,3-b]pyridin-5-yl)phenyl)piperazine-1-carboxylate (intermediate 41) (250 mg, 0.3 mmol) was coupled with 1-(3-methoxybenzyl)-3,5-dimethyl-4-(4,4,5,5-tetramethyl-1,3,2-dioxaborolan-2-yl)-1H-pyrazole (intermediate 53) (131 mg, 0.4 mmol) in sodium carbonate (123 mg, 1 mmol), PdCl₂(dppf) (140 mg, 0.18 mmol), Toluene/ethanol/water (2/2/1 ml) to give 40 mg (14% yield) of titled compound. MS: m/z=747.3 (M+1).

Step-ii: tert-butyl 4-(4-(3-(1-(3-methoxybenzyl)-3,5-dimethyl-1H-pyrazol-4-yl)-1H-pyrrolo[2,3-b]pyridin-5-yl)phenyl)piperazine-1-carboxylate Using similar reaction conditions as described in step-iii of example-1, tert-butyl 4-(4-(3-(1-(3-methoxybenzyl)-3,5-dimethyl-1H-pyrazol-4-yl)-1-tosyl-1H-pyrrolo[2,3-b]pyridin-5-yl)phenyl) piperazine-1-carboxylate (70 mg, 0.9 mmol) was hydrolyzed by lithium hydroxide (7 mg, 0.22 mmol), THF/Methanol/water (2/2/1 ml) to afford 17 mg (31% yield) of the titled compound after purification by column (SiO2) using 70% ethyl acetate in hexane as eluent. MS: m/z=593.3 (M+1).

Step-iii: 3-(1-(3-methoxybenzyl)-3,5-dimethyl-1H-pyrazol-4-yl)-5-(4-(piperazin-1-yl)phenyl)-1H-pyrrolo[2,3-b]pyridine hydrochloride Using similar reaction conditions as described in step-ii of example-7, tert-butyl 4-(4-(3-(1-(3-methoxybenzyl)-3,5-dimethyl-1H-pyrazol-4-yl)-1H-pyrrolo[2,3-b]pyridin-5-yl) phenyl)piperazine-1-carboxylate (17 mg, 0.023 mmol) was deprotected in methanol/1,4-dioxane in (0.5/2 ml). This afforded 5 mg (36% yield) of the titled compound. ¹H NMR (CD₃OD, 400 MHz): δ 8.75 (s, 2H), 7.90 (s, 1H), 7.72 (m, 2H), 7.35-7.34 (d, 1H), 7.20 (m, 2H), 6.97-6.86 (m, 3H), 5.57

(s, 2H), 3.81 (s, 3H), 3.53 (m, 4H), 3.40 (m, 4H), 2.39-2.38 (d, 6H). MS: m/z=493.1 (M+1), HPLC—91.06% (method A).

Example 47

3-(1-(3-chlorobenzyl)-3,5-dimethyl-1H-pyrazol-4-yl)-5-(4-(piperazin-1-yl)phenyl)-1H-pyrrolo[2,3-b]pyridine hydrochloride

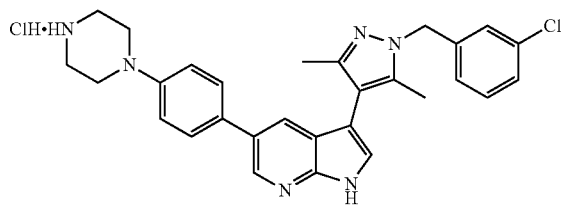

Step-i: tert-butyl 4-(4-(3-(1-(3-chlorobenzyl)-3,5-dimethyl-1H-pyrazol-4-yl)-1-tosyl-1H-pyrrolo[2,3-b]pyridin-5-yl)phenyl)piperazine-1-carboxylate Using similar reaction conditions as described in step-ii of example-1, tert-butyl 4-(4-(3-iodo-1-tosyl-1H-pyrrolo[2,3-b]pyridin-5-yl)phenyl)piperazine-1-carboxylate (intermediate 41) (200 mg, 0.3 mmol) was coupled with 1-(3-chlorobenzyl)-3,5-dimethyl-4-(4,4,5,5-tetramethyl-1,3,2-dioxaborolan-2-yl)-1H-pyrazole (intermediate 54) (107 mg, 0.33 mmol) in sodium carbonate (99 mg, 0.9 mmol), Pd(dppf)Cl$_2$ (12 mg, 0.01 mmol), toluene/ethanol/water (2/2/1 ml) to give 70 mg (31% yield) of titled compound.

Step-ii: tert-butyl 4-(4-(3-(1-(3-chlorobenzyl)-3,5-dimethyl-1H-pyrazol-4-yl)-1H-pyrrolo[2,3-b]pyridin-5-yl)phenyl)piperazine-1-carboxylate Using similar reaction conditions as described in step-iii of example-1, tert-butyl 4-(4-(3-(1-(3-chlorobenzyl)-3,5-dimethyl-1H-pyrazol-4-yl)-1-tosyl-1H-pyrrolo[2,3-b]pyridin-5-yl)phenyl) piperazine-1-carboxylate (70 mg, 0.9 mmol) was hydrolyzed by lithium hydroxide (7 mg, 0.27 mmol), THF/Methanol/water (1/1/0.5 ml) to afford 12 mg (22% yield) of the titled compound after purification by column (SiO$_2$) using 70% ethyl acetate in hexane as eluent.

Step-iii: 3-(1-(3-chlorobenzyl)-3,5-dimethyl-1H-pyrazol-4-yl)-5-(4-(piperazin-1-yl)phenyl)-1H-pyrrolo[2,3-b]pyridine hydrochloride Using similar reaction conditions as described in step-ii of example-7, tert-butyl 4-(4-(3-(1-(3-chlorobenzyl)-3,5-dimethyl-1H-pyrazol-4-yl)-1H-pyrrolo[2,3-b]pyridin-5-yl)phenyl)piperazine-1-carboxylate (12 mg, 0.02 mmol) was deprotected in methanol/1,4-dioxane in (0.3/2 ml). This afforded 5 mg (55% yield) of the titled compound. $^1$H NMR (CD$_3$OD, 400 MHz): δ 8.72 (s, 1H), 8.669 (s, 1H), 7.85 (s, 1H), 7.71-7.69 (d, 2H), 7.42-7.39 (m, 2H), 7.32 (s, 1H), 7.24-7.18 (m, 3H), 5.52 (s, 2H), 3.53-3.50 (m, 4H), 3.41-3.38 (m, 4H), 2.33-2.32 (d, 6H). MS: m/z=497.2 (M+1), HPLC—95.77% (method-B).

Example 48

3-((3,5-dimethyl-4-(5-(4-(piperazin-1-yl)phenyl)-1H-pyrrolo[2,3-b]pyridin-3-yl)-1H-pyrazol-1-yl)methyl)benzonitrile hydrochloride

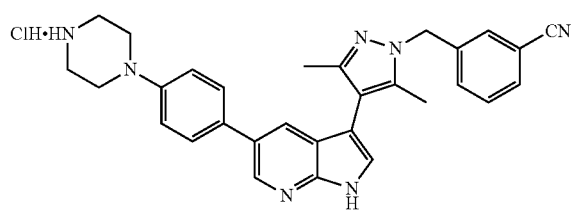

Step-i: tert-butyl 4-(4-(3-(1-(3-cyanobenzyl)-3,5-dimethyl-1H-pyrazol-4-yl)-1-tosyl-1H-pyrrolo[2,3-b]pyridin-5-yl)phenyl)piperazine-1-carboxylate Using similar reaction conditions as described in step-ii of example-1, tert-butyl 4-(4-(3-iodo-1-tosyl-1H-pyrrolo[2,3-b]pyridin-5-yl)phenyl)piperazine-1-carboxylate (intermediate 41) (200 mg, 0.3 mmol) was coupled with 3-((3,5-dimethyl-4-(4,4,5,5-tetramethyl-1,3,2-dioxaborolan-2-yl)-1H-pyrazol-1-yl)methyl)benzonitrile (intermediate 55) (103 mg, 0.3 mmol) in sodium carbonate (98 mg, 0.9 mmol), PdCl$_2$(dppf) (11 mg, 0.01 mmol), toluene/ethanol/water (2/2/1 ml) to give 80 mg (36% yield) of titled compound. $^1$H NMR (CD$_3$OD, 400 MHz): δ8.44-8.43 (d, 1H), 7.85-7.84 (d, 1H), 7.55-7.49 (m, 5H), 7.38 (s, 1H), 7.09-7.07 (d, 2H), 6.60 (s, 1H), 5.41 (s, 2H), 3.27-3.24 (m, 4H), 3.11-3.09 (m, 4H), 2.21-2.17 (m, 6H). MS: m/z=488.1 (M+1), HPLC—92.75% (method-B).

Step-ii: 3-((3,5-dimethyl-4-(5-(4-(piperazin-1-yl)phenyl)-1H-pyrrolo[2,3-b]pyridin-3-yl)-1H-pyrazol-1-yl)methyl)benzonitrile hydrochloride Using similar reaction conditions as described in step-iii of example-1, tert-butyl 4-(4-(3-(1-(3-cyanobenzyl)-3,5-dimethyl-1H-pyrazol-4-yl)-1-tosyl-1H-pyrrolo[2,3-b]pyridin-5-yl)phenyl) piperazine-1-carboxylate (80 mg, 0.1 mmol) was hydrolyzed by lithium hydroxide (6 mg, 0.2 mmol), THF/Methanol/water (1/1/0.5 ml) to give tert-butyl 4-(4-(3-(1-(3-cyanobenzyl)-3,5-dimethyl-1H-pyrazol-4-yl)-1H-pyrrolo[2,3-b]pyridin-5-yl)phenyl)piperazine-1-carboxylate, which was then deprotected Using similar reaction conditions as described in Step-ii example 7, in methanol/1,4-dioxane (0.3/2 ml). This afforded 3 mg (5% yield) of the titled compound. $^1$H NMR (CD$_3$OD, 400 MHz): δ8.44-8.43 (d, 1H), 7.85-7.84 (d, 1H), 7.55-7.49 (m, 5H), 7.38 (s, 1H), 7.09-7.07

(d, 2H), 6.60 (s, 1H), 5.41 (s, 2H), 3.27-3.24 (m, 4H), 3.11-3.09 (m, 4H), 2.21-2.17 (m, 6H). MS: m/z=488.1 (M+1), HPLC—92.75% (method B).

Example 49

1-(4-(4-(3-(1-(3-fluorobenzyl)-3,5-dimethyl-1H-pyrazol-4-yl)-1H-pyrrolo[2,3-b]pyridin-5-yl)phenyl)piperazin-1-yl)ethanone

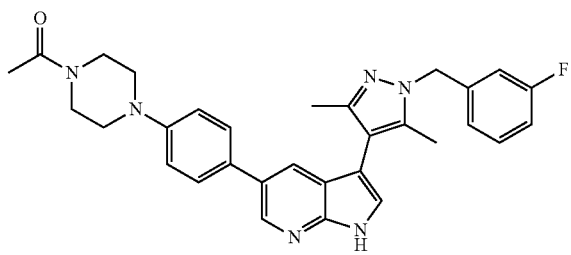 [SMILES: CC(=O)N1CCN(c2ccc(-c3cnc4[nH]cc(-c5c(C)nn(Cc6cccc(F)c6)c5C)c4c3)cc2)CC1]

Step-i: 3-(1-(3-fluorobenzyl)-3,5-dimethyl-1H-pyrazol-4-yl)-5-(4-(piperazin-1-yl)phenyl)-1-tosyl-1H-pyrrolo[2,3-b]pyridine Using similar reaction conditions as described in step-iii of example-38, tert-butyl 4-(3-(3-(1-(3-fluorobenzyl)-3,5-dimethyl-1H-pyrazol-4-yl)-1-tosyl-1H-pyrrolo[2,3-b]pyridin-5-yl)phenyl) piperazine-1-carboxylate (compound of step-i of example-40) (190 mg, 0.258 mmol) was deprotected using methanol/HCl in dioxane (7/7 mL) to give 110 mg, (64.2%) of the titled compound.

Step-ii: 1-(4-(4-(3-(1-(3-fluorobenzyl)-3,5-dimethyl-1H-pyrazol-4-yl)-1-tosyl-1H-pyrrolo[2,3-b]pyridin-5-yl)phenyl)piperazin-1-yl) ethanone A stirred solution of 3-(1-(3-fluorobenzyl)-3,5-dimethyl-1H-pyrazol-4-yl)-5-(4-(piperazin-1-yl)phenyl)-1-tosyl-1H-pyrrolo[2,3-b]pyridine (100 mg, 0.157 mmol), triethylamine (47.8 mg, 0.473 mmol), DCM (3 ml) was added acetyl chloride (18.5 mg, 0.236 mmol) drop wise at 0° C. Reaction mass was gradually warmed to room temperature, reaction completed in an hour. Reaction mass was diluted with DCM and washed with water, dried over sodium sulfate and concentrated to give 98 mg (92.4% yield) of the titled compound. MS: m/z=677.2 (M+1).

Step-iii: 1-(4-(4-(3-(1-(3-fluorobenzyl)-3,5-dimethyl-1H-pyrazol-4-yl)-1H-pyrrolo[2,3-b]pyridin-5-yl)phenyl) piperazin-1-yl)ethanone Using similar reaction conditions as described in step-iii of example-1, 1-(4-(4-(4-(3-(1-(3-fluorobenzyl)-3,5-dimethyl-1H-pyrazol-4-yl)-1-tosyl-1H-pyrrolo[2,3-b]pyridin-5-yl)phenyl)piperazin-1-yl)ethanone (98 mg, 0.144 mmol) was hydrolyzed by lithium hydroxide (61 mg, 1.44 mmol), THF/Methanol/water (12/6/3 ml) to afford 16 mg (21.3% yield) of the titled compound. $^1$H NMR (CD$_3$OD, 400 MHz): δ 8.545 (b, 1H), 8.270-8.264 (m, 1H), 7.577-7.549 (m, 3H), 7.379-7.306 (m, 1H), 7.115-7.086 (d, 2H), 7.022-6.966 (m, 1H), 6.875-6.843 (m, 1H), 5.344 (s, 2H), 3.735-3.663 (m, 4H), 3.231-3.196 (m, 4H), 2.185-2.165 (d, 2H), 2.115 (s, 3H). MS: m/z=523.1 (M+1); HPLC: 97.70% in method B.

Example 50

N-(3-((3,5-dimethyl-4-(5-(4-(piperazin-1-yl)phenyl)-1H-pyrrolo[2,3-b]pyridin-3-yl)-1H-pyrazol-1-yl)methyl)phenyl)acetamide

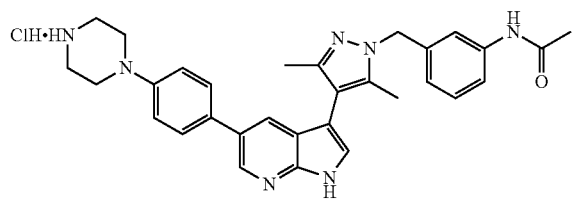

Step-i: tert-butyl 4-(4-(3-(3,5-dimethyl-1-(3-nitrobenzyl)-1H-pyrazol-4-yl)-1-tosyl-1H-pyrrolo[2,3-b]pyridin-5-yl)phenyl)piperazine-1-carboxylate Using similar reaction conditions as described in step-ii of intermediate 1, tert-butyl 4-(4-(3-iodo-1-tosyl-1H-pyrrolo[2,3-b]pyridin-5-yl)phenyl)piperazine-1-carboxylate (intermediate 41) (400 mg, 0.6 mmol) was coupled with 3,5-dimethyl-1-(3-nitrobenzyl)-4-(4,4,5,5-tetramethyl-1,3,2-dioxaborolan-2-yl)-1H-pyrazole (intermediate 56) (240 mg, 0.66 mmol) in sodium carbonate (196 mg, 1 mmol), PdCl$_2$(dppf) (22 mg, 0.03 mmol), toluene/ethanol/water (2/2/2 ml) to give 200 mg (43% yield) of titled compound after purification by column (SiO$_2$) using 30% ethyl acetate in hexane as eluent. MS: m/z=762.3 (M+1).

Step-ii: tert-butyl 4-(4-(3-(1-(3-aminobenzyl)-3,5-dimethyl-1H-pyrazol-4-yl)-1-tosyl-1H-pyrrolo[2,3-b]pyridin-5-yl)phenyl)piperazine-1-carboxylate Using similar reaction conditions as described in example-8, tert-butyl 4-(4-(3-(3,5-dimethyl-1-(3-nitrobenzyl)-1H-pyrazol-4-yl)-1-tosyl-1H-pyrrolo[2,3-b]pyridin-5-yl)phenyl)piperazine-1-carboxylate (200 mg, 0.262 mmol) was reduced by 10% palladium on carbon (20 mg, 10% W/W), ethanol (3 mL) to yield 150 mg (yield 78.08%) of the titled compound. MS: m/z=7 32.3 (M+1).

Step-iii: tert-butyl 4-(4-(3-(1-(3-acetamidobenzyl)-3,5-dimethyl-1H-pyrazol-4-yl)-1-tosyl-1H-pyrrolo[2,3-b]pyridin-5-yl)phenyl)piperazine-1-carboxylate Using similar reaction conditions as described in step-i of example-49, tert-butyl 4-(4-(3-(1-(3-aminobenzyl)-3,5-dimethyl-1H-pyrazol-4-yl)-1-tosyl-1H-pyrrolo[2,3-b]pyridin-5-yl)phenyl) piperazine-1-carboxylate (150 mg, 2 mmol) was acylated with acetyl chloride (21 mg, 0.26 mmol) in triethylamine (0.088 ml, 6 mmol) and DCM (3 ml) to afford 70 mg (44% yield) of the titled compound. MS: m/z=774.1 (M+1).

Step-iv: tert-butyl 4-(4-(3-(1-(3-acetamidobenzyl)-3,5-dimethyl-1H-pyrazol-4-yl)-1H-pyrrolo[2,3-b]pyridin-5-yl)phenyl)piperazine-1-carboxylate Using similar reaction conditions as described in step-iii of example-1, tert-butyl 4-(4-(3-(1-(3-acetamidobenzyl)-3,5- dimethyl-1H-pyrazol-4-yl)-1-tosyl-1H-pyrrolo[2,3-b]pyridin-5-yl)phenyl) piperazine-1-carboxylate (90 mg, 0.1 mmol) was hydrolyzed by lithium hydroxide (9 mg, 0.3 mmol), THF/Methanol/water (1/1/0.5 ml) to yield 20 mg (29% yield) of the titled compound.

Step-v: N-(3-((3,5-dimethyl-4-(5-(4-(piperazin-1-yl)phenyl)-1H-pyrrolo[2,3-b]pyridin-3-yl)-1H-pyrazol-1-yl)methyl)phenyl)acetamide Using similar reaction conditions as described in step-ii of example-7, tert-butyl 4-(4-(3-(1-(3-acetamidobenzyl)-3,5-dimethyl-1H-pyrazol-4-yl)-1H-pyrrolo[2,3-b]pyridin-5-yl)phenyl) piperazine-1-carboxylate (20 mg, mmol) was deprotected in methanol/1,4-dioxane HCl in (0.2/2 ml) to afford 6 mg (38% yield) of the titled compound. ¹H NMR (CD₃OD, 400 MHz): δ 8.78-8.72 (d, 2H), 7.93 (s, 1H), 7.73-7.69 (m, 3H), 7.39-7.36 (m, 2H), 7.21-7.19 (d, 2H), 7.11-7.10 (d, 1H), 5.61 (s, 2H), 3.54-3.51 (m, 4H), 3.41-3.40 (m, 4H), 2.40-2.38 (d, 6H) 2.05 (s, 3H). MS: m/z=520.2 (M+1), HPLC—88.65% (method-A).

Example 51

3-(3,5-dimethyl-1-(3-methylbenzyl)-1H-pyrazol-4-yl)-5-(4-(piperazin-1-yl)phenyl)-1H-pyrrolo[2,3-b]pyridine hydrochloride

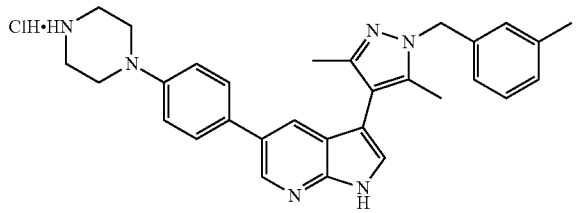

Step-i: tert-butyl 4-(4-(3-(3,5-dimethyl-1-(3-methylbenzyl)-1H-pyrazol-4-yl)-1-tosyl-1H-pyrrolo[2,3-b]pyridin-5-yl)phenyl)piperazine-1-carboxylate Using similar reaction conditions as described in step-ii of example-1, tert-butyl 4-(4-(3-iodo-1-tosyl-1H-pyrrolo[2,3-b]pyridin-5-yl)phenyl)piperazine-1-carboxylate (intermediate 41) (300 mg, 0.4 mmol) was coupled with (Intermediate 56A) 3,5-dimethyl-1-(3-methylbenzyl)-4-(4,4,5,5-tetramethyl-1,3,2-dioxaborolan-2-yl)-1H-pyrazole (163 mg, 0.5 mmol) in sodium carbonate (147 mg, 1.0 mmol), PdCl₂(dppf) (17 mg, 0.02 mmol), toluene/ethanol/water (2/2/3 ml) to give 90 mg (28% yield) of titled compound.

Step-ii: tert-butyl 4-(4-(3-(3,5-dimethyl-1-(3-methylbenzyl)-1H-pyrazol-4-yl)-1H-pyrrolo[2,3-b]pyridin-5-yl)phenyl)piperazine-1-carboxylate Using similar reaction conditions as described in step-iii of example-1, tert-butyl 4-(4-(3-(3,5-dimethyl-1-(3-methylbenzyl)-1H-pyrazol-4-yl)-1-tosyl-1H-pyrrolo[2,3-b]pyridin-5-yl)phenyl)piperazine-1-carboxylate (90 mg, 0.1 mmol) was hydrolyzed by lithium hydroxide (9 mg, 0.3 mmol), THF/Methanol/water (1/1/0.5 ml) to afford 20 mg (29% yield) of the titled compound. MS: m/z=577.2 (M+1).

Step-iii: 3-(3,5-dimethyl-1-(3-methylbenzyl)-1H-pyrazol-4-yl)-5-(4-(piperazin-1-yl)phenyl)-1H-pyrrolo[2,3-b]pyridine hydrochloride Using similar reaction conditions as described in step-ii of example-7, tert-butyl 4-(4-(3-(3,5-dimethyl-1-(3-methylbenzyl)-1H-pyrazol-4-yl)-1H-pyrrolo[2,3-b]pyridin-5-yl)phenyl)piperazine-1-carboxylate (20 mg, 0.034 mmol) was deprotected in methanol/1,4-dioxane HCl in (0.3/1 ml). This afforded 10 mg (63% yield) of the titled compound. ¹H NMR (CD₃OD, 400 MHz): δ 8.74 (s, 1H), 8.65 (s, 1H), 7.86 (s, 1H), 7.71-7.69 (d, 2H), 7.32-7.29 (t, 1H), 7.20-7.15 (m, 4H), 7.09-7.07 (d, 1H), 5.51 (s, 2H), 3.53-3.50 (m, 4H), 3.41-3.38 (m, 4H), 2.36-2.34 (m, 9H). MS: m/z=477.2 (M+1) HPLC 98.14% (method B).

Example 52

3-(3,5-dimethyl-1-(3-(trifluoromethoxy)benzyl)-1H-pyrazol-4-yl)-5-(4-(piperazin-1-yl)phenyl)-1H-pyrrolo[2,3-b]pyridine hydrochloride

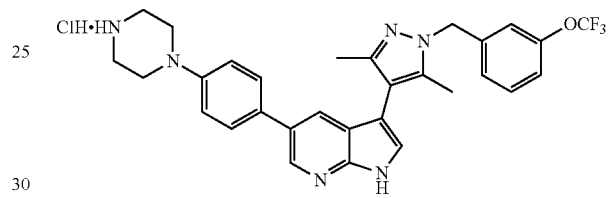

Step-i: tert-butyl 4-(4-(3-(3,5-dimethyl-1-(3-(trifluoromethoxy)benzyl)-1H-pyrazol-4-yl)-1-tosyl-1H-pyrrolo[2,3-b]pyridin-5-yl)phenyl)piperazine-1-carboxylate Using similar reaction conditions as described in step-ii of example-1, tert-butyl 4-(4-(3-iodo-1-tosyl-1H-pyrrolo[2,3-b]pyridin-5-yl)phenyl)piperazine-1-carboxylate (intermediate 41) (150 mg, 0.227 mmol) was coupled with 3,5-dimethyl-4-(4,4,5,5-tetramethyl-1,3,2-dioxaborolan-2-yl)-1-(3-(trifluoromethoxy)benzyl)-1H-pyrazole (Intermediate 44) (135.6 mg, 0.34 mmol) in sodium carbonate (72.4 mg, 0.68 mmol), PdCl₂(dppf)Cl₂ (8 mg, 0.011 mmol), toluene/ethanol/water (3/5/1 ml) to give 140 mg (76.9% yield) of titled compound. MS: m/z=801.3 (M+1).

Step-ii: tert-butyl 4-(4-(3-(3,5-dimethyl-1-(3-(trifluoromethoxy)benzyl)-1H-pyrazol-4-yl)-1H-pyrrolo[2,3-b]pyridin-5-yl)phenyl)piperazine-1-carboxylate Using similar reaction conditions as described in step-iii of example-1, tert-butyl 4-(4-(3-(3,5-dimethyl-1-(3-(trifluoromethoxy)benzyl)-1H-pyrazol-4-yl)-1-tosyl-1H-pyrrolo[2,3-b]pyridin-5-yl)phenyl)piperazine-1-carboxylate (140 mg, 0.174 mmol) was hydrolyzed by lithium hydroxide (36.7 mg, 0.27 mmol), THF/Methanol/water (2/3/1 ml) to afford 90 mg (80.3% yield) of the titled compound. LCMS: m/z=647.2 (M+1).

Step-iii: 3-(3,5-dimethyl-1-(3-(trifluoromethoxy)benzyl)-1H-pyrazol-4-yl)-5-(4-(piperazin-1-yl)phenyl)-1H-pyrrolo[2,3-b]pyridine hydrochloride Using similar reaction conditions as described in step-ii of example-7, tert-butyl 4-(4-(3-(3,5-dimethyl-1-(3-(trifluororomethoxy)benzyl)-1H-pyrazol-4-yl)-1H-pyrrolo[2,3-b]pyridin-5-yl)phenyl) piperazine-1-carboxylate (90 mg, 0.139 mmol) was deprotected with HCl in methanol (5 ml). This afforded 18 mg (23.6% yield) of the titled compound. $^1$H NMR (CDCl$_3$, 400 MHz): δ 9.12 (s, 1H), 8.56-8.55 (d, 1H), 7.846-7.841 (d, 1H), 7.52-7.50 (d, 2H), 7.40-7.36 (t, 1H), 7.22 (s, 1H), 7.13-7.09 (m, 2H), 7.03-7.00 (m, 3H), 5.33 (s, 2H), 4.40-4.25 (bs, 1H), 3.22-3.19 (m, 4H), 3.08-3.05 (m, 4H), 2.25 (s, 3H), 2.14 (s, 3H). MS: m/z=547.2 (M+1), HPLC Purity: 87.04% Method: B.

Example 53

3-(1-(3-fluorobenzyl)-3,5-dimethyl-1H-pyrazol-4-yl)-5-(4-(pyridin-4-yl)phenyl)-1H-pyrrolo[2,3-b]pyridine

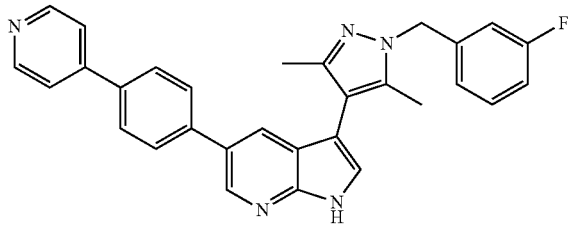 [SMILES: Cc1nn(Cc2cccc(F)c2)c(C)c1-c1c[nH]c2ncc(-c3ccc(-c4ccncc4)cc3)cc12]

Step-i: 3-(1-(3-fluorobenzyl)-3,5-dimethyl-1H-pyrazol-4-yl)-5-(4-(pyridin-4-yl)phenyl)-1-tosyl-1H-pyrrolo[2,3-b]pyridine Using similar reaction conditions as described in step-ii of example-1, 5-bromo-3-(1-(3-fluorobenzyl)-3,5-dimethyl-1H-pyrazol-4-yl)-1-tosyl-1H-pyrrolo[2,3-b]pyridine (step-i of example-14) (150 mg, 0.27 mmol) was coupled with 4-(4-(4,4,5,5-tetramethyl-1,3,2-dioxaborolan-2-yl)phenyl)pyridine (intermediate 45) (91.44 mh, 0.32 mmol) in sodium carbonate (85.86, 0.81 mmol), toluene/ethanol/water (5/5/2 ml). This afforded 120 mg (70.5% yield) of the titled compound.

Step-ii: 3-(1-(3-fluorobenzyl)-3,5-dimethyl-1H-pyrazol-4-yl)-5-(4-(pyridin-4-yl)phenyl)-1H-pyrrolo[2,3-b]pyridine Using similar reaction conditions as described in step-iii of example-1, 3-(1-(3-fluorobenzyl)-3,5-dimethyl-1H-pyrazol-4-yl)-5-(4-(pyridin-4-yl)phenyl)-1-tosyl-1H-pyrrolo[2,3-b]pyridine (120 mg, 0.19 mmol) was hydrolyzed by lithium hydroxide (36.7 mg, 0.27 mmol), in THF/Methanol/water (2/2/1 ml) to afford 22 mg 24.3% yield of pure compound after purification by preparative TLC (SiO$_2$) using 5% methanol in chloroform as eluent. $^1$H NMR (DMSO-d$_6$, 300 MHz): δ 8.44-8.3 (b, 1H), 7.899-7.877 (d, 1H), 7.767-7.743 (s, 1H), 7.44 (m, 1H), 7.34-7.30 (m, 1H), 7.02-6.99 (m, 1H), 6.87-6.84 (m, 1H), 5.32 (s, 1H), 2.16 (s, 6H). MS: 453.2 m/z=(M+1), HPLC: 93.5% in method A.

Example 54

3-(1-(3-ethoxybenzyl)-3,5-dimethyl-1H-pyrazol-4-yl)-5-(4-(piperazin-1-yl)phenyl)-1H-pyrrolo[2,3-b]pyridine hydrochloride

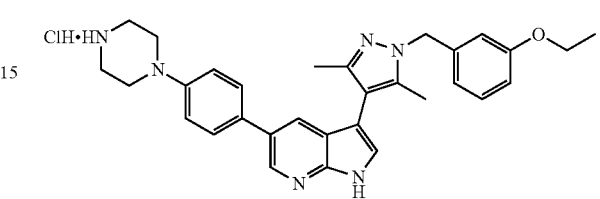

Step-i: tert-butyl 4-(4-(3-(1-(3-ethoxybenzyl)-3,5-dimethyl-1H-pyrazol-4-yl)-1-tosyl-1H-pyrrolo[2,3-b]pyridin-5-yl)phenyl)piperazine-1-carboxylate Using similar reaction conditions as described in step-ii of example-1, tert-butyl 4-(4-(3-iodo-1-tosyl-1H-pyrrolo[2,3-b]pyridin-5-yl)phenyl)piperazine-1-carboxylate (intermediate 41) (125 mg, 0.189 mmol) was coupled with 1-(3-ethoxybenzyl)-3,5-dimethyl-4-(4,4,5,5-tetramethyl-1,3,2-dioxaborolan-2-yl)-1H-pyrazole (intermediate 46) (81.13 mg, 0.227 mmol) in sodium carbonate (60.1 mg, 0.567 mmol), Pd(PPh$_3$)$_2$Cl$_2$ (6.6 mg, 0.0095 mmol), toluene/ethanol/water (3/5/1 ml) to give 140 mg of titled compound. MS: m/z=761.0 (M+1).

Step-ii: tert-butyl 4-(4-(3-(1-(3-ethoxybenzyl)-3,5-dimethyl-1H-pyrazol-4-yl)-1H-pyrrolo[2,3-b]pyridin-5-yl)phenyl)piperazine-1-carboxylate Using similar reaction conditions as described in step-iii of example-1, tert-butyl 4-(4-(3-(1-(3-ethoxybenzyl)-3,5-dimethyl-1H-pyrazol-4-yl)-1-tosyl-1H-pyrrolo[2,3-b]pyridin-5-yl)phenyl) piperazine-1-carboxylate (140 mg, 0.183 mmol) was hydrolyzed by lithium hydroxide (38.6 mg, 0.919 mmol), THF/Methanol/water (2/3/1 mL) to afford 100 mg (90% yield) of the titled compound. MS: m/z=607.3 (M+1).

Step-iii: 3-(1-(3-ethoxybenzyl)-3,5-dimethyl-1H-pyrazol-4-yl)-5-(4-(piperazin-1-yl)phenyl)-1H-pyrrolo[2,3-b]pyridine hydrochloride Using similar reaction conditions as described in step-ii of example-7, tert-butyl 4-(4-(3-(1-(3-ethoxybenzyl)-3,5-dimethyl-1H-pyrazol-4-yl)-1H-pyrrolo[2,3-b]pyridin-5-yl)phenyl)piperazine-1-carboxylate (100 mg, 0.139 mmol) was deprotected with HCl in methanol (5 ml) to afford 4 mg (4.8% yield) of the titled compound. $^1$H NMR (CD$_3$OD, 300 MHz): δ 8.39-8.38 (d, 1H), 7.79-7.78 (d, 1H), 7.48-7.45 (m, 2H), 7.32 (s, 1H), 7.22-7.17 (t, 1H), 7.05-7.02 (d, 2H), 6.78-6.76 (dd, 1H), 6.69-6.67 (d, 1H), 6.59 (s, 1H), 5.27 (s, 2H), 3.95-3.93 (q, 2H), 3.95-3.57 (d, 2H), 3.26-3.19 (m, 4H), 3.05-3.02

(m, 2H), 2.16 (s, 3H), 2.12 (s, 3H), 1.30-1.26 (t, 3H). MS: m/z=507.3 (M+1), HPLC Purity: 92.87% Method: B.

Example 55

6-cyclopropyl-3-(1-(3-fluorobenzyl)-3,5-dimethyl-1H-pyrazol-4-yl)-5-(4-(piperazin-1-yl)phenyl)-1H-pyrrolo[2,3-b]pyridine hydrochloride

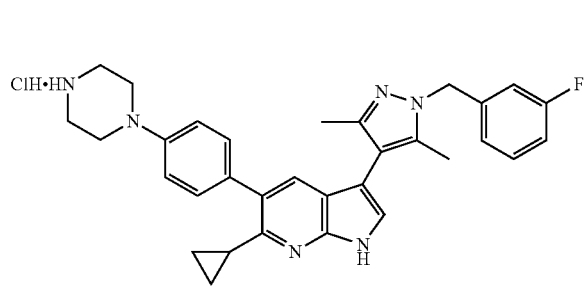

Step-i: tert-butyl 4-(4-(6-cyclopropyl-3-(1-(3-fluorobenzyl)-3,5-dimethyl-1H-pyrazol-4-yl)-1-tosyl-1H-pyrrolo[2,3-b]pyridin-5-yl)phenyl)piperazine-1-carboxylate Using similar reaction conditions as described in step-ii of example-1, tert-butyl 4-(4-(6-cyclopropyl-3-iodo-1-tosyl-1H-pyrrolo[2,3-b]pyridin-5-yl)phenyl)piperazine-1-carboxylate (intermediate 47) (115 mg, 0.161 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (81.53 mg, 0.24 mmol) in sodium carbonate (51.9 mg, 0.483 mmol), Pd(PPh$_3$)$_2$Cl$_2$ (5.6 mg, 0.008 mmol), 1,2-dimethoxyethane/water (10/2 ml) to afford 113 mg (89% yield) of titled compound.

Step-ii: tert-butyl 4-(4-(6-cyclopropyl-3-(1-(3-fluorobenzyl)-3,5-dimethyl-1H-pyrazol-4-yl)-1H-pyrrolo[2,3-b]pyridin-5-yl)phenyl)piperazine-1-carboxylate Using similar reaction conditions as described in step-iii of example-1, tert-butyl 4-(4-(6-cyclopropyl-3-(1-(3-fluorobenzyl)-3,5-dimethyl-1H-pyrazol-4-yl)-1-tosyl-1H-pyrrolo[2,3-b]pyridin-5-yl)phenyl)piperazine-1-carboxylate (111 mg, 0.14 mmol) was hydrolyzed by lithium hydroxide (17.6 mg, 0.42 mmol), in methanol/water (3/2 ml) to afford 14 mg of the titled compound. $^1$H NMR (CDCl3, 300 MHz): δ 8.7 (b, 1H), 7.52 (s, 1H), 7.40-7.37 (m, 2H), 7.107-7.099 (d, 1H), 7.002-6.9 (m, 3H), 6.9-6.8 (m, 1H), 5.26 (s, 2H), 3.62-3.59 (t, 3H), 3.209-3.117 (t, 3H), 2.22 (s, 1H), 3.12 (s, 3H), 1.496 (s, 9H), 1.16-1.15 (m, 2H), 0.91-0.87 (m, 2H). MS: m/z=621.3 (M+1).

Step-iii: 6-cyclopropyl-3-(1-(3-fluorobenzyl)-3,5-dimethyl-1H-pyrazol-4-yl)-5-(4-(piperazin-1-yl) phenyl)-1H-pyrrolo[2,3-b]pyridine hydrochloride Using similar reaction conditions as described in step-ii of example-7, tert-butyl 4-(4-(6-cyclopropyl-3-(1-(3-fluorobenzyl)-3,5-dimethyl-1H-pyrazol-4-yl)-1H-pyrrolo[2,3-b]pyridin-5-yl)phenyl) piperazine-1-carboxylate (14 mg, 0.022 mmol) was deprotected in HCl in 1,4-dioxane (2 ml) to afford 8 mg (64% yield) of the titled compound. $^1$H NMR (CDCl3, 300 MHz): δ 8.21 (s, 1H), 7.69 (s, 1H), 7.48-7.38 (m, 3H), 7.19-7.7.16 (d, 2H), 7.08-7.05 (d, 1H), 7.001-6.96 (m, 1H), 5.49 (s, 2H), 3.53-3.49 (t, 3H), 3.41-3.38 (t, 3H), 2.5-2.4 (m, 1H), 2.29-2.28 (d, 6H), 1.4-1.25 (m, 2H), 1.21-1.12 (m, 4H). MS: 521.2 m/z=(M+1), HPLC: 93.079% in Method A.

Example 56

3-(1-(3-fluorobenzyl)-3,5-dimethyl-1H-pyrazol-4-yl)-5-(4-(4-methylpiperazin-1-yl)phenyl)-1H pyrrolo[2,3-b]pyridine

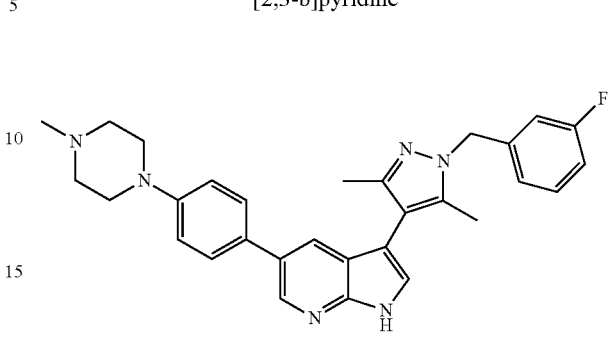

Step-i: 3-(1-(3-fluorobenzyl)-3,5-dimethyl-1H-pyrazol-4-yl)-5-(4-(4-methylpiperazin-1-yl)phenyl)-1-tosyl-1H-pyrrolo[2,3-b]pyridine Using similar reaction conditions as described in step-ii of example-1, 3-iodo-5-(4-(4-methylpiperazin-1-yl)phenyl)-1-tosyl-1H-pyrrolo[2,3-b]pyridine (intermediate 48) (200 mg, 0.349 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (231 mg, 0.699 mmol) in sodium carbonate (111 mg, 1.048 mmol), PdCl$_2$(dppf) (12.7 mg, 0.017 mmol), Toluene/ethanol/water (20/10/2 ml) to afford 262 mg of the crude titled compound. MS: m/z=649 (M+1).

Step-ii: 3-(1-(3-fluorobenzyl)-3,5-dimethyl-1H-pyrazol-4-yl)-5-(4-(4-methylpiperazin-1-yl)phenyl)-1H-pyrrolo[2,3-b]pyridine Using similar reaction conditions as described in step-iii of example-1, 4-(4-(3-(1-(3-fluorobenzyl)-3,5-dimethyl-1H-pyrazol-4-yl)-1-tosyl-1H-pyrrolo[2,3-b]pyridin-5-yl)phenyl)morpholine (260 mg, 0.4 mmol) was hydrolyzed by lithium hydroxide (160 mg, 4 mmol), THF/Methanol/water (12/6/3 ml) to afford 16 mg (8.1% yield) of the titled compound. $^1$H NMR (CD$_3$OD, 300 MHz): δ 8.535 (s, 1H), 8.135-8.130 (d, 1H), 7.623-7.595 (d, 1H), 7.535 (s, 1H), 7.390-7.340 (m, 1H), 7.167-7.138 (d, 3H), 7.028-7.001 (m, 2H), 6.899-6.85 (m, 1H), 5.378 (s, 2H), 3.964-3.919 (m, 2H), 3.649-3.610 (m, 2H), 3.15-3.02 (m, 2H), 2.983 (s, 3H), 2.218-2.196 (d, 6H). MS: m/z=495.1 (M+1); HPLC: 82.46% in method B.

Example 57

2-(4-(4-(3-(1-(3-fluorobenzyl)-3,5-dimethyl-1H-pyrazol-4-yl)-1H-pyrrolo[2,3-b]pyridin-5-yl)phenyl) piperazin-1-yl)-N,N-dimethylethanamine

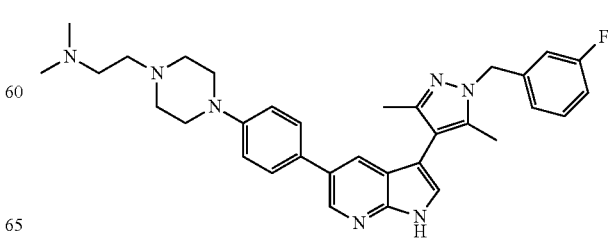

Step-i: 2-(4-(4-(3-(1-(3-fluorobenzyl)-3,5-dimethyl-1H-pyrazol-4-yl)-1-tosyl-1H-pyrrolo[2,3-b]pyridin-5-yl)phenyl)piperazin-1-yl)-N,N-dimethylethanamine Using similar reaction conditions as described in step-ii of intermediate 1, 2-(4-(4-(3-iodo-1-tosyl-1H-pyrrolo[2,3-b]pyridin-5-yl)phenyl)piperazin-1-yl)-N,N-dimethylethanamine (intermediate 49) (150 mg, 0.485 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (157 mg, 0.477 mmol) in sodium carbonate (76 mg, 0.716 mmol), PdCl$_2$(dppf) (8.7 mg, 0.011 mmol), Toluene/ethanol/water (15/7.5/1.5 ml) to afford 192 mg yield % of the crude titled compound. MS: m/z=706.0 (M+1).

Step-ii: 2-(4-(4-(3-(1-(3-fluorobenzyl)-3,5-dimethyl-1H-pyrazol-4-yl)-1H-pyrrolo[2,3-b]pyridin-5-yl)phenyl)piperazin-1-yl)-N,N-dimethylethanamine Using similar reaction conditions as described in step-iii of intermediate 1, 2-(4-(4-(3-(1-(3-fluorobenzyl)-3,5-dimethyl-1H-pyrazol-4-yl)-1-tosyl-1H-pyrrolo[2,3-b]pyridin-5-yl)phenyl) piperazin-1-yl)-N,N-dimethylethanamine (190 mg, 0.269 mmol) was hydrolyzed by lithium hydroxide (113 mg, 2.69 mmol), THF/Methanol/water (12/6/3 ml) to afford 34 mg (23% yield) of the titled compound. $^1$H NMR (CD$_3$OD, 300 MHz): δ 8.432-8.426 (d, 1H), 7.835-7.829 (d, 1H), 7.512-7.475 (m, 2H), 7.367-7.324 (m, 1H), 7.069-6.968 (m, 3H), 6.878-6.845 (m, 1H), 5.349 (s, 2H), 3.68-3.48 (m, 2H), 3.162-3.12 (t, 2H), 2.967 (t, 1H), 2.82-2.715 (m, 8H), 2.206-2.166 (d, 6H), 1.923 (s, 1H). MS: m/z=552.2 (M+1); HPLC: 94.87% in method B.

Example 58

N-(5-(3-(1-(3-fluorobenzyl)-3,5-dimethyl-1H-pyrazol-4-yl)-1H-pyrrolo[2,3-b]pyridin-5-yl)-2-(piperazin-1-yl)phenyl)methanesulfonamide hydrochloride

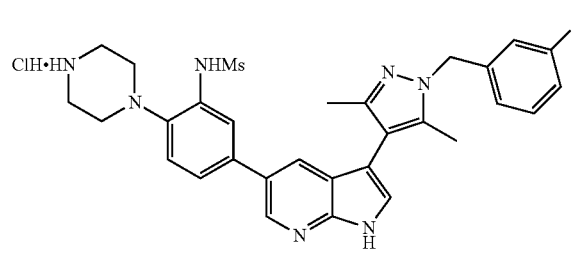

Step-i: tert-butyl 5-(4-(4-(tert-butoxycarbonyl)piperazin-1-yl)-3-(methylsulfonamido)phenyl)-3-(1-(3-fluorobenzyl)-3,5-dimethyl-1H-pyrazol-4-yl)-1H-pyrrolo[2,3-b]pyridine-1-carboxylate Using similar reaction conditions as described in step-ii of example-1, tert-butyl 5-(4-(4-(tert-butoxycarbonyl)piperazin-1-yl)-3-(methylsulfonamido)phenyl)-3-iodo-1H-pyrrolo[2,3-b]pyridine-1-carboxylate (intermediate 50) (200 mg, 0.286 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (123 mg, 0.373 mmol) in sodium carbonate (90 mg, 0.858 mmol), Pd(PPh$_3$)$_2$Cl$_2$ (10 mg, 0.0143 mmol), Toluene/ethanol/water (5/5/2.5 ml) to afford 6 mg (2.7% yield) of titled compound. MS: m/z=774.2 (M+1).

Step-ii: N-(5-(3-(1-(3-fluorobenzyl)-3,5-dimethyl-1H-pyrazol-4-yl)-1H-pyrrolo[2,3-b]pyridin-5-yl)-2-(piperazin-1-yl)phenyl)methanesulfonamide hydrochloride Using similar reaction conditions as described in step-ii of example-7, tert-butyl 4-(4-(3-(1-(3,5-difluorobenzyl)-1H-pyrazol-4-yl)-1H-pyrrolo[2,3-b]pyridin-5-yl)-1H-pyrazol-1-yl) piperidine-1-carboxylate (187 mg, 0.334 mmol) was deprotected in methanol/HCl in diethyl ether (0.5/2 ml) to afford 3 mg (63.42% yield) of the titled compound. $^1$H NMR (CD3OD), 300 MHz): δ8.77-8.71 (d, 2H), 7.92-7.83 (m, 2H), 7.59-7.44 (m, 3H), 7.15-7.06 (m, 2H), 5.59 (s 2H), 3.49-3.45 (m, 4H), 3.23-3.20 (m, 7H), 2.39-2.37 (d, 6H). MS: m/z=574.1 (M+1), HPLC: 95.99% Method A.

Example 59

N-(5-(3-(1-(3-fluorobenzyl)-3,5-dimethyl-1H-pyrazol-4-yl)-1H-pyrrolo[2,3-b]pyridin-5-yl)-2-morpholinophenyl)methanesulfonamide

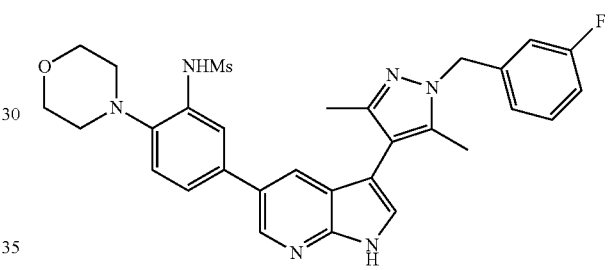

Step-i: N-(5-(3-(1-(3-fluorobenzyl)-3,5-dimethyl-1H-pyrazol-4-yl)-1-tosyl-1H-pyrrolo[2,3-b]pyridin-5-yl)-2-morpholinophenyl)methanesulfonamide Using similar reaction conditions as described in step-ii of example-1, 5-bromo-3-(1-(3-fluorobenzyl)-3,5-dimethyl-1H-pyrazol-4-yl)-1-tosyl-1H-pyrrolo[2,3-b]pyridine (compound of step-i of example-14) (250 mg, 0.451 mmol) was coupled with N-(2-morpholino-5-(4,4,5,5-tetramethyl-1,3,2-dioxaborolan-2-yl)phenyl)methane sulfonamide (intermediate 51) (259 mg, 0.677 mmol) in sodium carbonate (143.4 mg, 1.353 mmol), Toluene/ethanol/water (3/8/1 ml). This afforded 150 mg (45.59% yield) of the titled compound. MS: m/z=728.9 (M+1).

Step-ii: N-(5-(3-(1-(3-fluorobenzyl)-3,5-dimethyl-1H-pyrazol-4-yl)-1H-pyrrolo[2,3-b]pyridin-5-yl)-2-morpholinophenyl)methanesulfonamide Using similar reaction conditions as described in step-iii of example-1, N-(5-(3-(1-(3-fluorobenzyl)-3,5-dimethyl-1H-pyrazol-4-yl)-1-tosyl-1H-pyrrolo[2,3-b]pyridin-5-yl)-2-morpholino phenyl)methanesulfonamide (150 mg, 0.205 mmol) was hydrolyzed with lithium hydroxide (43.2 mg, 1.02 mmol) in THF/Methanol/water (2/3/1 ml). This yielded 23 mg (19.49% yield) of pure compound. $^1$H NMR (CDCl$_3$, 300 MHz): δ 9.17 (s, 1H), 8.55 (s, 1H), 7.86 (s, 2H), 7.75 (s, 1H), 7.32 (s, 3H), 6.99-6.97 (m, 2H), 6.90-6.80 (d, 1H), 5.31 (s, 2H), 3.91-3.88 (m, 4H), 3.10 (s, 3H), 2.92-2.89 (m, 4H), 2.26 (s, 3H), 2.17 (s, 3H). MS: m/z=575.1 (M+1), HPLC Purity: 98.92% Method: B.

Example 60

6-cyclopropyl-3-(1-(3,5-difluorobenzyl)-3,5-dimethyl-1H-pyrazol-4-yl)-5-(4-(piperazin-1-yl)phenyl)-1H-pyrrolo[2,3-b]pyridine hydrochloride

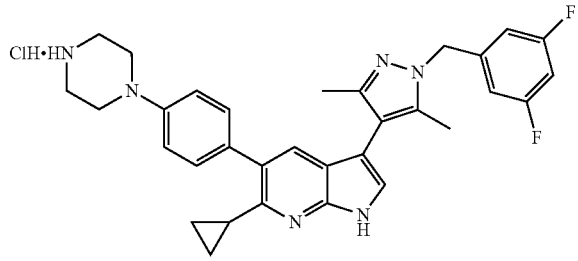

Step-i: tert-butyl 5-(4-(4-(tert-butoxycarbonyl)piperazin-1-yl)phenyl)-6-cyclopropyl-3-(1-(3,5-difluorobenzyl)-3,5-dimethyl-1H-pyrazol-4-yl)-1H-pyrrolo[2,3-b]pyridine-1-carboxylate Using similar reaction conditions as described in step-ii of example-1, tert-butyl 5-(4-(4-(tert-butoxycarbonyl)piperazin-1-yl)phenyl)-6-cyclopropyl-3-iodo-1H-pyrrolo[2,3-b]pyridine-1-carboxylate (intermediate 57) (120 mg, 0.186 mmol) was coupled with 1-(3,5-difluorobenzyl)-3,5-dimethyl-4-(4,4,5,5-tetramethyl-1,3,2-dioxaborolan-2-yl)-1H-pyrazole (intermediate 24) (97.24 mg, 0.27 mmol) in sodium carbonate (59.1 mg, 0.483 mmol), Pd(PPh$_3$)$_2$Cl$_2$ (6.5 mg, 0.009 mmol), 1,2-dimethoxyethane/water (15/2 ml) to afford 62 mg (45% yield) of titled compound. MS: m/z=739.2 (M+1).

Step-ii: 6-cyclopropyl-3-(1-(3,5-difluorobenzyl)-3,5-dimethyl-1H-pyrazol-4-yl)-5-(4-(piperazin-1-yl)phenyl)-1H-pyrrolo[2,3-b]pyridine hydrochloride Using similar reaction conditions as described in Step-ii of example-7, tert-butyl 5-(4-(4-(tert-butoxycarbonyl)piperazin-1-yl)phenyl)-6-cyclopropyl-3-(1-(3,5-difluorobenzyl)-3,5-dimethyl-1H-pyrazol-4-yl)-1H-pyrrolo[2,3-b]pyridine-1-carboxylate (62 mg, 0.022 mmol) was deprotected in HCl in methanol (2 ml). This afforded 4 mg (5% yield) of the titled compound. $^1$H NMR (CDCl3, 300 MHz): δ 8.44 (b, 1H), 7.68 (s, 1H), 7.42-7.39 (d, 2H), 7.02-7.00 (d, 2H), 6.661-6.641 (m, 1H), 6.311-6.305 (d, 1H), 5.26 (s, 2H), 3.25-3.21 (m, 3H), 3.10-3.07 (t, 3H), 2.41 (s, 3H), 2.32 (s, 3H), 1.13-1.10 (m, 2H), 0.88-0.85 (m, 4H). MS: m/z=539.2 (M+1).

Example 61

3-(1-(3-fluorobenzyl)-3,5-dimethyl-1H-pyrazol-4-yl)-5-(2-methoxy-4-(piperazin-1-yl)phenyl)-1H-pyrrolo[2,3-b]pyridine hydrochloride

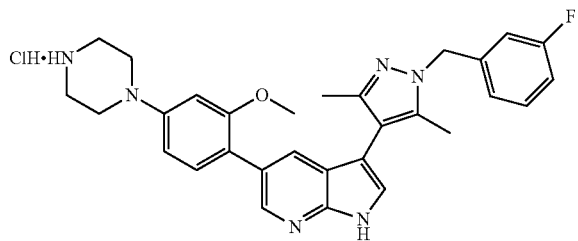

Step-i: tert-butyl 4-(4-(3-(1-(3-fluorobenzyl)-3,5-dimethyl-1H-pyrazol-4-yl)-1-tosyl-1H-pyrrolo[2,3-b]pyridin-5-yl)-3-methoxyphenyl)piperazine-1-carboxylate Using similar reaction conditions as described in step-ii of example-1, tert-butyl 4-(4-(3-iodo-1-tosyl-1H-pyrrolo[2,3-b]pyridin-5-yl)-3-methoxyphenyl)piperazine-1-carboxylate (intermediate 52) (30 mg, 0.043 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (17 mg, 0.052 mmol) in sodium carbonate (14 mg, 0.13 mmol), Pd(PPh$_3$)$_2$Cl$_2$ (1.5 mg, 0.00218 mmol), Toluene/ethanol/water (2/1/0.5 ml) to afford 156.0 mg (crude) of titled compound. MS: m/z=766.3 (M+1).

Step-ii: tert-butyl 4-(4-(3-(1-(3-fluorobenzyl)-3,5-dimethyl-1H-pyrazol-4-yl)-1H-pyrrolo[2,3-b]pyridin-5-yl)-3-methoxyphenyl)piperazine-1-carboxylate Using similar reaction conditions as described in step-iii of example-1, tert-butyl 4-(4-(3-(1-(3-fluorobenzyl)-3,5-dimethyl-1H-pyrazol-4-yl)-1-tosyl-1H-pyrrolo[2,3-b]pyridin-5-yl)-3-methoxy phenyl) piperazine-1-carboxylate (150 mg, 0.196 mmol) was hydrolyzed by lithium hydroxide (25 mg, 0.588 mmol), THF/Methanol/water (2/2/1 ml) to yield 16 mg of the titled compound after purification by preparative TLC (SiO2) using 50% ethyl acetate in hexane as eluent. MS: m/z=611.3 (M+1).

Step-iii: 3-(1-(3-fluorobenzyl)-3,5-dimethyl-1H-pyrazol-4-yl)-5-(2-methoxy-4-(piperazin-1-yl)phenyl)-1H-pyrrolo[2,3-b]pyridine hydrochloride Using similar reaction conditions as described in step-iii of example-7, tert-butyl 4-(4-(3-(1-(3-fluorobenzyl)-3,5-dimethyl-1H-pyrazol-4-yl)-1H-pyrrolo[2,3-b]pyridin-5-yl)-3-methoxyphenyl) piperazine-1-carboxylate (16 mg, 0.026 mmol) was deprotected in HCl in ether/methanol (2/0.5 ml). This afforded 13.0 mg (97.23% yield) of the titled compound. $^1$H NMR (CD3OD, 300 MHz): δ 8.60 (s, 2H), 7.85 (s, 1H), 7.41-7.38 (m, 2H), 7.12 (m, 3H), 6.79-6.78 (m, 2H), 5.55 (s, 2H), 3.85 (s, 3H), 3.56-3.53 (m, 4H), 3.41-3.38 (m, 4H), 2.35 (s, 6H). MS: m/z=511.3 (M+1), HPLC: 99.2% in method B.

Example 62

3-(1-(3-fluorobenzyl)-3,5-dimethyl-1H-pyrazol-4-yl)-5-(3-methoxy-4-(piperazin-1-yl)phenyl)-1H-pyrrolo[2,3-b]pyridine hydrochloride

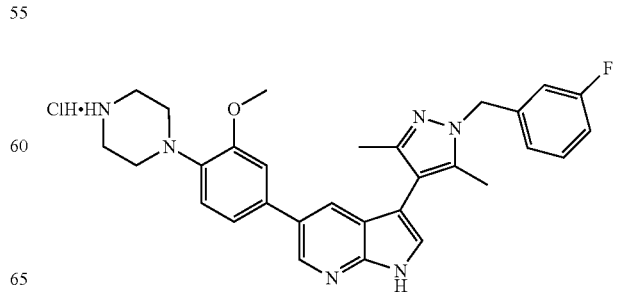

Step-i: tert-butyl 4-(4-(3-(1-(3-fluorobenzyl)-3,5-dimethyl-1H-pyrazol-4-yl)-1-tosyl-1H-pyrrolo[2,3-b]pyridin-5-yl)-2-methoxyphenyl)piperazine-1-carboxylate Using similar reaction conditions as described in step-ii of example-1, tert-butyl 4-(4-(3-iodo-1-tosyl-1H-pyrrolo[2,3-b]pyridin-5-yl)-2-methoxyphenyl)piperazine-1-carboxylate (intermediate 58) (200 mg, 0.3 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (130 mg, 0.13 mmol) in sodium carbonate (95 mg, 0.9 mmol), Pd(PPh3)2Cl2 (15 mg, 0.015 mmol), Toluene/ethanol/water (10/2/2.5 ml) to give 150 mg (64.65% yield) of titled compound. MS: m/z=765.3 (M+1).

Step-ii: tert-butyl 4-(4-(3-(1-(3-fluorobenzyl)-3,5-dimethyl-1H-pyrazol-4-yl)-1H-pyrrolo[2,3-b]pyridin-5-yl)-2-methoxyphenyl)piperazine-1-carboxylate Using similar reaction conditions as described in step-iii of example-1, tert-butyl 4-(4-(3-(1-(3-fluorobenzyl)-3,5-dimethyl-1H-pyrazol-4-yl)-1-tosyl-1H-pyrrolo[2,3-b]pyridin-5-yl)-2-methoxy phenyl)piperazine-1-carboxylate (140 mg, 0.18 mmol) was hydrolyzed by lithium hydroxide (23 mg, 0.554 mmol), THF/Methanol/water (5/5/2 ml) to afford 70 mg of the titled compound. MS: m/z=610.9 (M+1).

Step-iii: 3-(1-(3-fluorobenzyl)-3,5-dimethyl-1H-pyrazol-4-yl)-5-(3-methoxy-4-(piperazin-1-yl)phenyl)-1H-pyrrolo[2,3-b]pyridine hydrochloride Using similar reaction conditions as described in step-ii of example-7, tert-butyl 4-(4-(3-(1-(3-fluorobenzyl)-3,5-dimethyl-1H-pyrazol-4-yl)-1H-pyrrolo[2,3-b]pyridin-5-yl)-2-methoxyphenyl) piperazine-1-carboxylate (70 mg, 0.114 mmol) was deprotected in HCl in 1,4-dioxane/1,4-dioxane (5/5 m). This afforded 3 mg (4.54% yield) of the titled compound. $^1$H NMR (DMSO-$d_6$, 400 MHz): δ 11.82 (s, 1H), 8.55 (s, 1H), 7.84 (s, 1H), 7.50-7.43 (m, 2H), 7.19-6.94 (m, 6H), 5.35 (s, 1H), 3.88 (s, 3H), 2.93-2.86 (d, 8H), 2.19-2.16 (d, 6H). MS: m/z=511 (M+1), HPLC: 94.29% in Method-B.

Example 63

2-cyclopropyl-3-(1-(3-fluorobenzyl)-3,5-dimethyl-1H-pyrazol-4-yl)-5-(4-(piperazin-1-yl)phenyl)-1H-pyrrolo[2,3-b]pyridine

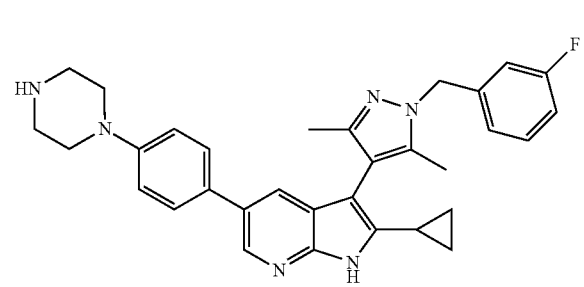 [SMILES: Cc1nn(Cc2cccc(F)c2)c(C)c1-c1c(C2CC2)[nH]c2ncc(-c3ccc(N4CCNCC4)cc3)cc12]

Step-i: tert-butyl 5-(4-(4-(tert-butoxycarbonyl)piperazin-1-yl)phenyl)-2-cyclopropyl-3-(1-(3-fluorobenzyl)-3,5-dimethyl-1H-pyrazol-4-yl)-1H-pyrrolo[2,3-b]pyridine-1-carboxylate Using similar reaction conditions as described in step-ii of example-1, tert-butyl 5-(4-(4-(tert-butoxycarbonyl)piperazin-1-yl)phenyl)-2-cyclopropyl-3-iodo-1H-pyrrolo[2,3-b]pyridine-1-carboxylate (Intermediate 35) (50 mg, 0.07763 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (30 mg, 0.08540 mmol) in sodium carbonate (25 mg, 0.2329 mmol), Pd(PPh$_3$)$_4$ (5 mg, 0.00388 mmol) and DME/water (5/1 ml) to afford 100 mg of the crude product which was taken as such for next reaction. MS: m/z=721.0 (M+1).

Step-ii: 2-cyclopropyl-3-(1-(3-fluorobenzyl)-3,5-dimethyl-1H-pyrazol-4-yl)-5-(4-(piperazin-1-yl)phenyl)-1H-pyrrolo[2,3-b]pyridine tert-butyl 5-(4-(4-(tert-butoxycarbonyl)piperazin-1-yl)phenyl)-2-cyclopropyl-3-(1-(3-fluorobenzyl)-3,5-dimethyl-1H-pyrazol-4-yl)-1H-pyrrolo[2,3-b]pyridine-1-carboxylate (100 mg) dissolved in 2 ml of methanol and added methanol/HCl (3 ml) at 0° C. and stirred at room temperature for 30 min. The reaction was monitored by TLC (10% methanol in chloroform). The reaction mixture was concentrated under reduced pressure to afford crude product. The residue was basified with saturated sodium bicarbonate solution and extracted with DCM (2×25 ml). The organic layer was dried over Na$_2$SO$_4$, and concentrated under reduced pressure to afford 7 mg (9.72% yield) of the pure required product. $^1$H NMR (DMSO-$d_6$, 400 MHz): δ 11.30 (s, 1H), 8.34 (s, 1H), 7.64-7.39 (m, 5H), 7.15-7.11 (t, 1H), 7.01-6.95 (m, 4H), 5.34 (s, 2H), 4.20-4.00 (m, 4H), 3.10-3.00 (m, 4H), 2.09 (s, 3H), 2.08 (s, 3H), 1.82-1.79 (m, 1H), 0.96-0.95 (m, 4H). MS: m/z=521.4 (M+1), HPLC Purity: 80.32% Method: A.

Example 64

N-(2-methoxy-5-(3-(1-phenethyl-1H-pyrazol-4-yl)-1H-pyrrolo[2,3-b]pyridin-5-yl)phenyl) methanesulfonamide

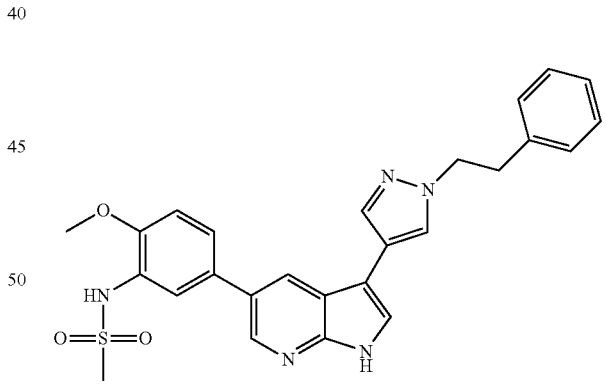

Step-i: N-(2-methoxy-5-(3-(1-phenethyl-1H-pyrazol-4-yl)-1-tosyl-1H-pyrrolo[2,3-b]pyridin-5-yl)phenyl) methanesulfonamide Using similar reaction conditions as described in step-ii of example-1, N-(5-(3-iodo-1-tosyl-1H-pyrrolo[2,3-b]pyridin-5-yl)-2-methoxyphenyl)methanesulfonamide (Intermediate 23) (90 mg, 0.1506 mmol) was coupled with 1-phenethyl-4-(4,4,5,5-tetramethyl-1,3,2-dioxaborolan-2-yl)-1H-pyrazole (intermediate 59) (67 mg, 0.225 mmol) using Pd(PPh$_3$)$_2$Cl$_2$ (6 mg, 0.05 mmol) and sodium carbonate (40 mg, 0.376 mmol) in toluene/ethanol/water (3/2/1 ml) to afford 100 mg of the crude compound. MS: m/z=642.7 (M+1).

Step-ii: N-(2-methoxy-5-(3-(1-phenethyl-1H-pyrazol-4-yl)-1H-pyrrolo[2,3-b]pyridin-5-yl)phenyl) methanesulfonamide Using similar reaction conditions as described in step-iii of example-1, N-(2-methoxy-5-(3-(1-phenethyl-1H-pyrazol-4-yl)-1-tosyl-1H-pyrrolo[2,3-b]pyridin-5-yl)phenyl)methanesulfonamide (100 mg, 0.155 mmol) was hydrolyzed by lithium hydroxide (13 mg, 0.311 mmol) in THF/methanol/water (5/1/2 mL) to afford 13 mg of the titled compound. $^1$H NMR (DMSO-d$_6$, 400 MHz): δ 9.07 (s, 1H), 8.45-8.44 (d, 1H), 8.186-8.182 (d, 1H), 8.13, s 1H), 7.89 (s, 1H), 7.716-7.710 (d, 1H), 7.60-7.59 (m, 2H), 7.31-7.28 (m, 2H), 7.24-7.19 (m, 4H), 4.43-4.39 (t, 2H), 3.91 (s, 3H), 3.20-3.16 (t, 2H), 3.02 (s, 3H). MS: m/z=487.8 (M+1), HPLC: 95.48% in method A.

Example 65

5-(3-(1-(3-fluorobenzyl)-1H-pyrazol-4-yl)-1H-pyrrolo[2,3-b]pyridin-5-yl)-2-methoxypyridin-3-amine

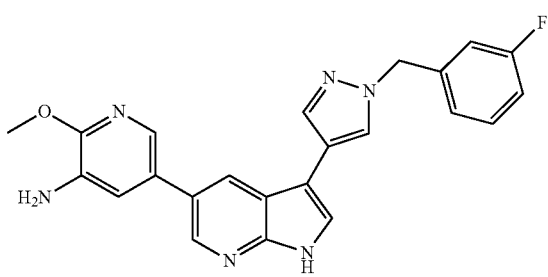 [SMILES: COc1ncc(-c2cnc3[nH]cc(-c4cnn(Cc5cccc(F)c5)c4)c3c2)cc1N]

Step-i: 5-(3-(1-(3-fluorobenzyl)-1H-pyrazol-4-yl)-1-tosyl-1H-pyrrolo[2,3-b]pyridin-5-yl)-2-methoxy pyridin-3-amine Using similar reaction conditions as described in step-ii of example-1, 5-bromo-3-(1-(3-fluorobenzyl)-1H-pyrazol-4-yl)-1-tosyl-1H-pyrrolo[2,3-b]pyridine (compound of Step-i of example 9) (150 mg, 0.280 mmol) was coupled with 2-methoxy-5-(4,4,5,5-tetramethyl-1,3,2-dioxaborolan-2-yl) pyridin-3-amine (Intermediate 60) (86 mg, 0.34 mmol) using sodium carbonate (89 mg, 0.84 mmol) and Pd(PPh$_3$)$_2$Cl$_2$ (10 mg, 0.014 mmol) in DME/water (10/1 mL) to afford 80 mg (49.2% yield) after purification by column (Silica gel 6/120) using 4/1/5 EtOAc/methanol/hexane as eluent.

Step-ii: 5-(3-(1-(3-fluorobenzyl)-1H-pyrazol-4-yl)-1H-pyrrolo[2,3-b]pyridin-5-yl)-2-methoxypyridin-3-amine Using similar reaction conditions as described in step-iii of example-1, 5-(3-(1-(3-fluorobenzyl)-1H-pyrazol-4-yl)-1-tosyl-1H-pyrrolo[2,3-b]pyridin-5-yl)-2-methoxypyridin-3-amine (80 mg, 0.14 mmol) was hydrolyzed with lithium hydroxide (12 mg, 0.28 mmol) in THF/methanol/water (2/2/1 mL) to yield 10 mg (17.1% yield) after purification by preparative TLC(Silicagel-1000 micron) using 5% methanol in chloroform as eluent. $^1$H NMR (CD$_3$OD, 300 MHz): δ 8.37 (s, 1H), 8.27 (s, 1H), 8.17 (s, 1H), 7.91 (s, 1H), 7.717-7.712 (d, 1H), 7.61 (s, 1H), 7.36-7.29 (m, 2H), 7.10-6.98 (m, 3H), 5.41 (s, 2H), 4.00 (s, 3H). MS: m/z=415.2 (M+1), HPLC: 88.73% in method B.

Example 66

N-(5-(3-(1-(3-fluorobenzyl)-3,5-dimethyl-1H-pyrazol-4-yl)-1H-pyrrolo[2,3-b]pyridin-5-yl)-2-hydroxypyridin-3-yl)methanesulfonamide

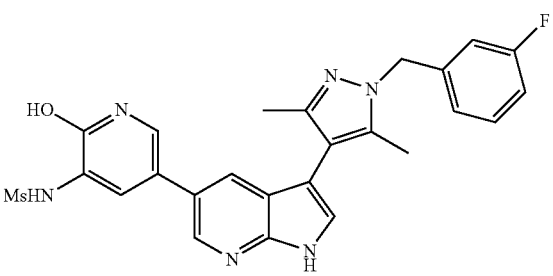

Step-i: tert-butyl 3-(1-(3-fluorobenzyl)-3,5-dimethyl-1H-pyrazol-4-yl)-5-(6-methoxy-5-(methyl sulfonamido)pyridin-3-yl)-1H-pyrrolo[2,3-b]pyridine-1-carboxylate Using similar reaction conditions as described in step-i of example-1, tert-butyl 5-(5-(N-(tert-butoxycarbonyl)methylsulfonamido)-6-methoxypyridin-3-yl)-3-iodo-1H-pyrrolo[2,3-b]pyridine-1-carboxylate (intermediate 66) (100 mg, 0.155 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (61 mg, 0.186 mmol) using Pd(PPh$_3$)$_2$Cl$_2$ (5 mg, 0.0077 mol) and sodium carbonate (49 mg, 0.465 mmol) in DME/water (10/1 ml) to afford 61 mg (54.5% yield) of the titled compound. MS: m/z=621.2 (M+1).

Step-ii: N-(5-(3-(1-(3-fluorobenzyl)-3,5-dimethyl-1H-pyrazol-4-yl)-1H-pyrrolo[2,3-b]pyridin-5-yl)-2-hydroxypyridin-3-yl)methanesulfonamide Using similar reaction conditions as described in step-ii of example-7, tert-butyl 3-(1-(3-fluorobenzyl)-3,5-dimethyl-1H-pyrazol-4-yl)-5-(6-methoxy-5-(methylsulfonamido)pyridin-3-yl)-1H-pyrrolo[2,3-b]pyridine-1-carboxylate (61 mg, 0.098 mmol) was deprotected in HCl in MeOH (3 ml) to afford 5 mg (11.3% yield) of the titled compound. $^1$H NMR (CD$_3$OD, 300 MHz): δ 8.71-8.62 (d, 2H), 7.91-7.88 (d, 2H), 7.68 (s, 1H), 7.47-7.42 (m, 1H), 7.15-7.02 (m, 3H), 6.60 (s, 1H), 5.57 (s, 2H), 3.09 (s, 3H), 2.36 (s, 3H), 2.35 (s, 3H). MS: m/z=506.8 (M+1), HPLC: 90.22% in method B.

Example 67

N-(5-(3-(1-(3-fluorobenzyl)-1H-pyrazol-4-yl)-1H-pyrrolo[2,3-b]pyridin-5-yl)-2-methoxypyridin-3-yl) methanesulfonamide

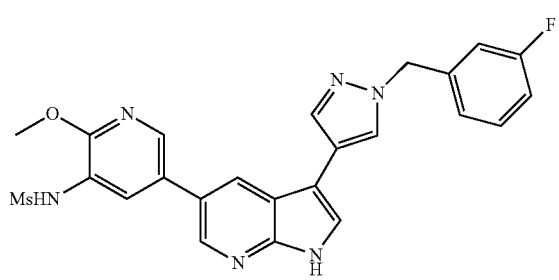

Step-i: N-(5-(3-(1-(3-fluorobenzyl)-1H-pyrazol-4-yl)-1-tosyl-1H-pyrrolo[2,3-b]pyridin-5-yl)-2-methoxypyridin-3-yl)methanesulfonamide Using similar reaction conditions as described in step-ii of example-1, 5-bromo-3-(1-(3-fluorobenzyl)-1H-pyrazol-4-yl)-1-tosyl-1H-pyrrolo[2,3-b]pyridine (compound of step-i of example 9) (100 mg, 0.19 mmol) was coupled with N-(2-methoxy-5-(4,4,5,5-tetramethyl-1,3,2-dioxaborolan-2-yl)pyridin-3-yl)methanesulfonamide (Intermediate 65D) (69 mg, 0.20 mmol) using sodium carbonate (61 mg, 0.57 mmol) and Pd(PPh$_3$)$_2$Cl$_2$ (7 mg, 0.009 mmol) in DME/water (5/0.5 mL). This afforded 72 mg (58.5% yield) of the titled compound.

Step-ii: N-(5-(3-(1-(3-fluorobenzyl)-1H-pyrazol-4-yl)-1H-pyrrolo[2,3-b]pyridin-5-yl)-2-methoxypyridin-3-yl)methanesulfonamide Using similar reaction conditions as described in step-iii of example-1, N-(5-(3-(1-(3-fluorobenzyl)-1H-pyrazol-4-yl)-1-tosyl-1H-pyrrolo[2,3-b]pyridin-5-yl)-2-methoxypyridin-3-yl) methanesulfonamide (70 mg, 0.108 mmol) was hydrolyzed with lithium hydroxide (14 mg, 0.324 mmol) in THF/methanol/water (3.5/3.5/0.5 mL) to yield 17 mg (31.8% yield) after purification by preparative TLC (Silicagel-1000 micron) using 5% methanol in chloroform as eluent. $^1$H NMR (CD$_3$OD, 300 MHz): δ 8.42 (s, 1H), 8.34-8.33 (s, 1H), 8.288-8.280 (d, 1H), 8.22 (s, 1H), 8.04-8.03 (d, 1H), 7.934-7.931 (d, 1H), 8.04-8.03 (d, 1H), 7.934-7.931 (d, 1H), 7.65 (s, 1H), 7.38-7.35 (q, 1H), 7.12-7.09 (d, 1H), 7.03-6.99 (m, 2H), 5.42 (s, 2H), 4.06 (s, 3H), 3.03 (s, 3H). MS: m/z=492.8 (M+1), HPLC: 96.33% in method B.

Example 68

N-(4-(3-(1-(3-fluorobenzyl)-1H-pyrazol-4-yl)-1H-pyrrolo[2,3-b]pyridin-5-yl)-2-methoxyphenyl) methanesulfonamide

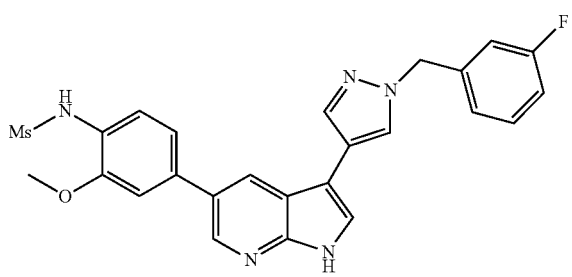 [SMILES: COc1cc(-c2cnc3[nH]cc(-c4cnn(Cc5cccc(F)c5)c4)c3c2)ccc1NS(C)(=O)=O]

Step-i: N-(5-(3-(1-(3-fluorobenzyl)-1H-pyrazol-4-yl)-1-tosyl-1H-pyrrolo[2,3-b]pyridin-5-yl)-2-methoxyphenyl) methanesulfonamide Using similar reaction conditions as described in step-ii of example-1, 5-bromo-3-(1-(3-fluorobenzyl)-1H-pyrazol-4-yl)-1-tosyl-1H-pyrrolo[2,3-b]pyridine (compound of step-i of example 9) (100 mg, 0.19 mmol) was coupled with N-(2-methoxy-4-(4,4,5,5-tetramethyl-1,3,2-dioxaborolan-2-yl)phenyl)methanesulfonamide (Intermediate 65C) (62 mg, 0.19 mmol) using potassium carbonate (60 mg, 0.57 mmol) and Pd(PPh$_3$)$_4$ (11 mg, 0.0095 mmol) in toluene/ethanol/water (2/2/1 mL). This afforded 63 mg (51.4% yield) after purification by preparative TLC (silicagel-1000 micron) using 40% ethyl acetate in hexane as eluent. MS: m/z=646.2 (M+1).

Step-ii: N-(4-(3-(1-(3-fluorobenzyl)-1H-pyrazol-4-yl)-1H-pyrrolo[2,3-b]pyridin-5-yl)-2-methoxyphenyl)methanesulfonamide Using similar reaction conditions as described in step-iii of example-1, N-(5-(3-(1-(3-fluorobenzyl)-1H-pyrazol-4-yl)-1-tosyl-1H-pyrrolo[2,3-b]pyridin-5-yl)-2-methoxyphenyl) methane sulfonamide (60 mg, 0.093 mmol) was hydrolyzed with lithium hydroxide (12 mg, 0.279 mmol) in THF/methanol/water (2/2/1 mL) to yield 20 mg (43.8% yield) of title compound. $^1$H NMR (DMSO-d$_6$, 300 MHz): δ 11.8 (s, 1H), 8.99 (s, 1H), 8.578-8.571 (d, 1H), 8.43 (s, 1H), 8.386-8.380 (d, 2H), 7.99 (s, 1H), 7.78-7.77 (d, 1H), 7.41-7.34 (m, 4H), 7.15-7.08 (m, 3H), 5.40 (s, 2H), 3.95 (s, 3H), 2.97 (s, 3H). MS: m/z=492.2 (M+1), HPLC: 91.15% in method B.

Example 69

N-(5-(3-(1-(3,5-difluorobenzyl)-1H-pyrazol-3-yl)-1H-pyrrolo[2,3-b]pyridin-5-yl)-2-methoxy phenyl) methanesulfonamide

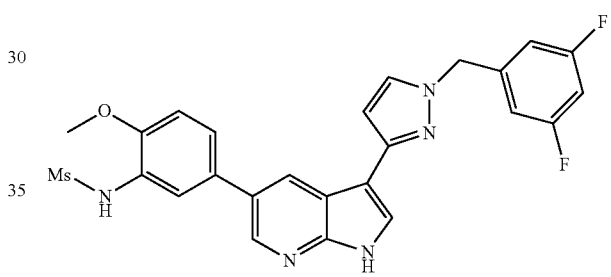

Step-i: N-(5-(3-(1-(3,5-difluorobenzyl)-1H-pyrazol-3-yl)-1-tosyl-1H-pyrrolo[2,3-b]pyridin-5-yl)-2-methoxyphenyl)methanesulfonamide Using similar reaction conditions as described in step-ii of example-1, 5-bromo-3-(1-(3,5-difluorobenzyl)-1H-pyrazol-3-yl)-1-tosyl-1H-pyrrolo[2,3-b]pyridine (Intermediate 63) (100 mg, 0.184 mmol) was coupled with N-(2-methoxy-5-(4,4,5,5-tetramethyl-1,3,2-dioxaborolan-2-yl)phenyl)methanesulfonamide (Intermediate 17) (65 mg, 0.22 mmol) using sodium carbonate (58 mg, 0.552 mmol) and Pd(PPh$_3$)$_4$ (10 mg, 0.0092 mmol) in toluene/ethanol/water (2/2/1 ml) to afford 46 mg (37.7% yield) after purification by preparative TLC (silicagel-1000 micron) using 40% ethyl acetate in hexane as eluent. MS: m/z=664.1 (M+1).

Step-ii: N-(5-(3-(1-(3,5-difluorobenzyl)-1H-pyrazol-3-yl)-1H-pyrrolo[2,3-b]pyridin-5-yl)-2-methoxy phenyl)methanesulfonamide Using similar reaction conditions as described in step-iii of example-1, N-(5-(3-(1-(3,5-difluorobenzyl)-1H-pyrazol-3-yl)-1-tosyl-1H-pyrrolo[2,3-b]pyridin-5-yl)-2-methoxyphenyl) methane sulfonamide (53 mg, 0.0799 mmol) was hydrolyzed by lithium hydroxide (17 mg, 0.399 mmol) in THF/methanol/water (2/2/1 ml) to yield 20 mg of the titled compound. $^1$H NMR (DMSO-d$_6$, 300 MHz): δ 11.8 (s, 1H), 9.00 (s, 1H), 8.538-8.530 (d, 1H), 8.45-8.44 (d, 1H), 7.89-7.88 (d, 2H), 7.55-7.54 (d, 1H), 7.50-7.46 (dd, 1H), 7.19-7.15 (m, 2H), 7.00-6.98 (m, 2H), 6.699-6.692 (d, 1H), 5.40 (s, 2H), 3.86 (s, 3H), 2.97 (s, 3H). MS: m/z=510.1 (M+1), HPLC: 96.47% in method B.

Example 70

N-(5-(3-(1-(2,5-difluorobenzyl)-1H-pyrazol-4-yl)-1H-pyrrolo[2,3-b]pyridin-5-yl)-2-methoxy phenyl)methanesulfonamide

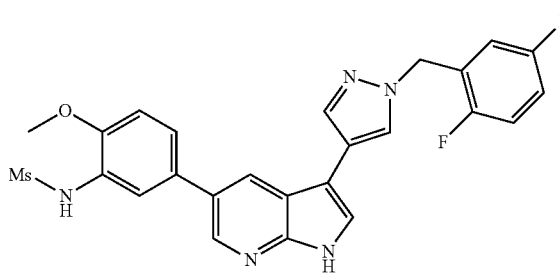

Step-i: N-(5-(3-(1-(2,5-difluorobenzyl)-1H-pyrazol-4-yl)-1-tosyl-1H-pyrrolo[2,3-b]pyridin-5-yl)-2-methoxyphenyl)methanesulfonamide Using similar reaction conditions as described in step-ii of example-1, 5-bromo-3-(1-(2,5-difluorobenzyl)-1H-pyrazol-4-yl)-1-tosyl-1H-pyrrolo[2,3-b]pyridine (step-i of example-4) (200 mg, 0.368 mmol) was coupled with N-(2-methoxy-5-(4,4,5,5-tetramethyl-1,3,2-dioxaborolan-2-yl)phenyl)methanesulfonamide (Intermediate 17) (120 mg, 0.368 mmol) using sodium carbonate (117 mg, 1.1049 mmol) and Pd(PPh$_3$)$_2$Cl$_2$ (14 mg, 0.018 mmol) in DME/water (15/2 ml) to afford 121 mg (49.5% yield) after purification by column chromatography (Silica gel 230/400) using 50% ethyl acetate in hexane as eluent. MS: m/z=664.2 (M+1).

Step-ii: N-(5-(3-(1-(2,5-difluorobenzyl)-1H-pyrazol-4-yl)-1H-pyrrolo[2,3-b]pyridin-5-yl)-2-methoxyphenyl)methanesulfonamide Using similar reaction conditions as described in step-iii of example-1, N-(5-(3-(1-(2,5-difluorobenzyl)-1H-pyrazol-4-yl)-1-tosyl-1H-pyrrolo[2,3-b]pyridin-5-yl)-2-methoxyphenyl)methanesulfonamide (120 mg, 0.180 mmol) was hydrolyzed by lithium hydroxide 38 mg, 0.904 mmol) in THF/methanol/water (15/7.5/4 ml) to yield 21 mg of the titled compound. $^1$H NMR (CDCl$_3$, 400 MHz): δ 10.3 (s, 1H), 8.49-8.48 (d, 1H), 8.256-8.252 (d, 1H), 7.85 (s, 1H), 7.81-7.80 (d, 1H), 7.77 (s, 1H), 7.48-7.47 (d, 1H), 7.39-7.37 (dd, 1H), 7.26-6.91 (m, 5H), 5.42 (s, 2H), 3.96 (s, 3H), 3.01 (s, 3H). MS: m/z=510.1 (M+1), HPLC: 96.37% in method B.

Example 71

N-(5-(3-(1-(3,5-difluorobenzyl)-1H-pyrazol-4-yl)-1H-pyrrolo[2,3-b]pyridin-5-yl)-2-methoxy phenyl)methanesulfonamide

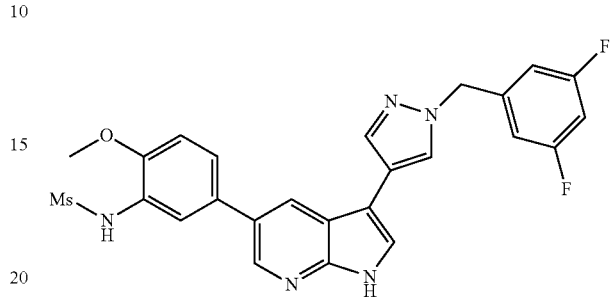

Step-i: 5-bromo-1-tosyl-3-(1-(3-(trifluoromethyl)benzyl)-1H-pyrazol-4-yl)-1H-pyrrolo[2,3-b]pyridine Using similar reaction conditions as described in step-i of example-1,5-bromo-3-iodo-1-tosyl-1H-pyrrolo[2,3-b]pyridine (Intermediate 1) (1 g, 2.09 mmol) was coupled with 1-(3,5-difluorobenzyl)-4-(4,4,5,5-tetramethyl-1,3,2-dioxaborolan-2-yl)-1H-pyrazole (Intermediate 8) (805 mg, 2.51 mmol) using sodium carbonate (645 mg, 6.27 mmol) and Pd(PPh$_3$)$_2$Cl$_2$ (77 mg, 0.1047 mmol) in toluene/ethanol/water (10/10/2 ml) to afford 680 mg (60.1% yield) of the pure product after column purification using 30% ethyl acetate in hexane as eluent.

Step-ii: N-(5-(3-(1-(3,5-difluorobenzyl)-1H-pyrazol-4-yl)-1-tosyl-1H-pyrrolo[2,3-b]pyridin-5-yl)-2-methoxyphenyl)methanesulfonamide Using similar reaction conditions as described in step-ii of example-1, 5-bromo-3-(1-(3,5-difluorobenzyl)-1H-pyrazol-4-yl)-1-tosyl-1H-pyrrolo[2,3-b]pyridine (200 mg, 0.3683 mmol) was coupled with N-(2-methoxy-5-(4,4,5,5-tetramethyl-1,3,2-dioxaborolan-2-yl)phenyl methane sulfonamide (Intermediate 17) (120 mg, 0.368 mmol) using sodium carbonate (117 mg, 1.1049 mmol) and Pd(PPh$_3$)$_2$Cl$_2$ (14 mg, 0.0184 mmol) in DME/water (15/2 ml). This afforded 107 mg (43.8% yield) after purification by column (Silica gel 230/400) using 65% ethyl acetate in hexane as eluent. MS: m/z=664.1 (M+1).

Step-iii: N-(5-(3-(1-(3,5-difluorobenzyl)-1H-pyrazol-4-yl)-1H-pyrrolo[2,3-b]pyridin-5-yl)-2-methoxyphenyl)methanesulfonamide Using similar reaction conditions as described in step-iii of example-1, N-(5-(3-(1-(3,5-difluorobenzyl)-1H-pyrazol-4-yl)-1-tosyl-1H-pyrrolo[2,3-b]pyridin-5-yl)-2-methoxyphenyl)methane sulfonamide (105 mg, 0.1582 mmol) was hydrolyzed by lithium hydroxide (34 mg, 0.791 mmol) in THF/methanol/water (15/7.5/4 ml) to yield 13 mg of the titled compound. $^1$H NMR (CD$_3$OD, 300 MHz): δ 8.556-8.551 (d, 2H), 8.51-8.50 (d, 1H), 8.28 (s, 1H), 7.98 (s, 1H), 7.76-7.75 (m, 2H), 7.64-7.76 (dd, 1H), 7.22-7.20 (d, 1H), 6.94-6.84 (m, 2H), 5.44 (s, 2H), 3.99 (s, 3H), 2.99 (s, 3H). MS: m/z=510.1 (M+1), HPLC: 98.06% in method B.

Example 72

N-(2-methoxy-5-(3-(1-(pyridin-3-ylmethyl)-1H-pyrazol-4-yl)-1H-pyrrolo[2,3-b]pyridin-5-yl)phenyl)methanesulfonamide

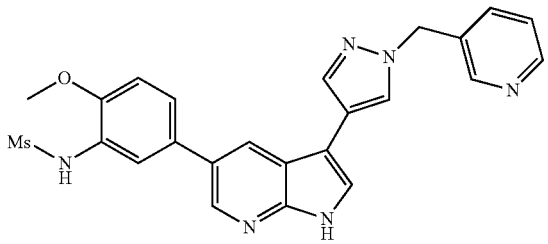 [SMILES: COc1ccc(-c2cnc3[nH]cc(-c4cnn(Cc5cccnc5)c4)c3c2)cc1NS(C)(=O)=O]

Step-i: tert-butyl 5-(3-(N-(tert-butoxycarbonyl)methylsulfonamido)-4-methoxyphenyl)-3-(1-(pyridin-3-ylmethyl)-1H-pyrazol-4-yl)-1H-pyrrolo[2,3-b]pyridine-1-carboxylate Using similar reaction conditions as described in step-i of example-1, tert-butyl 5-(5-(N-(tert-butoxycarbonyl)methylsulfonamido)-6-methoxypyridin-3-yl)-3-iodo-1H-pyrrolo[2,3-b]pyridine-1-carboxylate (intermediate 66P) (150 mg, 0.233 mmol) was coupled with 3-((4-(4,4,5,5-tetramethyl-1,3,2-dioxaborolan-2-yl)-1H-pyrazol-1-yl)methyl)pyridine (intermediate 64) (73 mg, 0.256 mmol) using Pd(PPh$_3$)$_2$Cl$_2$ (9 mg, 0.0116 mol) and sodium carbonate (74 mg, 0.699 mmol) in toluene/ethanol/water (3/3/2 ml) to afford 60 mg (38% yield) of the titled compound after purification by column (Silica gel 60/120) using 30% ethyl acetate in hexane as eluent. MS: m/z=675.1 (M+1).

Step-ii: N-(2-methoxy-5-(3-(1-(pyridin-3-ylmethyl)-1H-pyrazol-4-yl)-1H-pyrrolo[2,3-b]pyridin-5-yl)phenyl)methanesulfonamide Using similar reaction conditions as described in step-ii of example-7, tert-butyl 5-(3-(N-(tert-butoxycarbonyl)methylsulfonamido)-4-methoxyphenyl)-3-(1-(pyridin-3-ylmethyl)-1H-pyrazol-4-yl)-1H-pyrrolo[2,3-b]pyridine-1-carboxylate (60 mg, 0.219 mmol) was deprotected in HCl in ether/MeOH (1/3 ml) to afford 13 mg (29% yield) of the titled compound. $^1$H NMR (CD$_3$OD, 400 MHz): δ 8.78 (s, 2H), 8.53 (s, 2H), 8.42-8.37 (m, 2H), 8.02 (s, 1H), 8.00-7.94 (m, 1H), 7.77-7.76 (m, 2H), 7.62-7.59 (dd, 1H), 7.24-7.21 (d, 1H), 5.66 (s, 2H), 3.98 (s, 3H), 2.99 (s, 3H). MS: m/z=475.1 (M+1), HPLC: 97.36% in method A.

Example 73

N-(4-(3-(1-(3,5-difluorobenzyl)-1H-pyrazol-4-yl)-1H-pyrrolo[2,3-b]pyridin-5-yl)-2-methoxy phenyl)methanesulfonamide

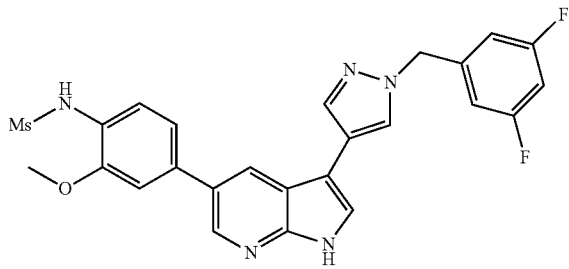 [SMILES: COc1cc(-c2cnc3[nH]cc(-c4cnn(Cc5cc(F)cc(F)c5)c4)c3c2)ccc1NS(C)(=O)=O]

Step-i: N-(4-(3-(1-(3,5-difluorobenzyl)-1H-pyrazol-4-yl)-1-tosyl-1H-pyrrolo[2,3-b]pyridin-5-yl)-2-methoxyphenyl)methanesulfonamide Using similar reaction conditions as described in step-ii of example-1, 5-bromo-3-(1-(3,5-difluorobenzyl)-1H-pyrazol-4-yl)-1-tosyl-1H-pyrrolo[2,3-b]pyridine (step 1 example 71) (150 mg, 0.38 mmol) was coupled with N-(2-methoxy-4-(4,4,5,5-tetramethyl-1,3,2-dioxaborolan-2-yl)phenyl)methanesulfonamide (Intermediate 65C) (149 mg, 0.45 mmol) using sodium carbonate (121 mg, 1.14 mmol) and Pd(PPh$_3$)$_2$Cl$_2$ (2 mg, 0.001 mmol) in DME/water (10/1 ml) to afford 98 mg (26.2% yield) after purification by column (Silica gel 60/120) using 65% ethyl acetate in hexane as eluent.

Step-ii: N-(4-(3-(1-(3,5-difluorobenzyl)-1H-pyrazol-4-yl)-1H-pyrrolo[2,3-b]pyridin-5-yl)-2-methoxy phenyl)methanesulfonamide Using similar reaction conditions as described in step-iii of example-1, N-(4-(3-(1-(3,5-difluorobenzyl)-1H-pyrazol-4-yl)-1-tosyl-1H-pyrrolo[2,3-b]pyridin-5-yl)-2-methoxyphenyl)methane sulfonamide (95 mg, 0.14 mmol) was hydrolyzed by lithium hydroxide (18 mg, 0.42 mmol) in THF/methanol/water (2/2/1 ml) to yield 38 mg (52.1% yield) of the titled compound after purification by preparative TLC (Silicagel-1000 micron) using 5% methanol in chloroform as eluent. $^1$H NMR (DMSO-d$_6$, 300 MHz): δ 11.8 (s, 1H), 8.95 (s, 1H), 8.559-8.552 (d, 1H), 8.42 (s, 1H), 8.367-8.361 (d, 1H), 7.99 (s, 1H), 7.77-7.76 (d, 1H), 7.38 (s, 1H), 7.35-7.32 (m, 2H), 7.20-7.10 (m, 1H), 6.97-6.95 (d, 2H), 5.39 (s, 2H), 3.94 (s, 3H), 2.96 (s, 3H). MS: m/z=510.1 (M+1), HPLC: 87.42% in method B.

Example 74

N-(5-(3-(1-(2-fluorophenethyl)-1H-pyrazol-4-yl)-1H-pyrrolo[2,3-b]pyridin-5-yl)-2-methoxy phenyl)methanesulfonamide

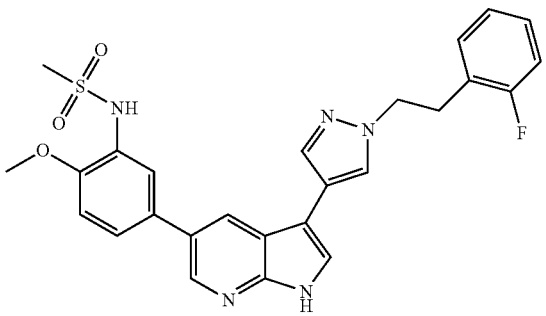 [SMILES: COc1ccc(-c2cnc3[nH]cc(-c4cnn(CCc5ccccc5F)c4)c3c2)cc1NS(C)(=O)=O]

Step-i: tert-butyl 5-(3-(N-(tert-butoxycarbonyl)methylsulfonamido)-4-methoxyphenyl)-3-(1-(pyridin-3-ylmethyl)-1H-pyrazol-4-yl)-1H-pyrrolo[2,3-b]pyridine-1-carboxylate Using similar reaction conditions as described in step-i of example-1, tert-butyl 5-(5-(N-(tert-butoxycarbonyl)methylsulfonamido)-6-methoxypyridin-3-yl)-3-iodo-1H-pyrrolo[2,3-b]pyridine-1-carboxylate (intermediate 66P) (150 mg, 0.233 mmol) was coupled with 1-(2-fluorophenethyl)-4-(4,4,5,5-tetramethyl-1,3,2-dioxaborolan-2-yl)-1H-pyrazole (intermediate 64A) (81 mg, 0.256 mmol) using Pd(PPh$_3$)$_2$Cl$_2$ (9 mg, 0.0116 mol) and sodium carbonate (74 mg, 0.699 mmol) in toluene/ethanol/water (3/3/2 ml) to afford 40 mg (24% yield) of the titled compound after purification by column (Silica gel 60/120) using 30% ethyl acetate in hexane as eluent.

Step-ii: N-(5-(3-(1-(2-fluorophenethyl)-1H-pyrazol-4-yl)-1H-pyrrolo[2,3-b]pyridin-5-yl)-2-methoxyphenyl)methanesulfonamide Using similar reaction conditions as described in step-ii of example-7, tert-butyl 5-(3-(N-(tert-butoxycarbonyl)methylsulfonamido)-4-methoxyphenyl)-3-(1-(pyridin-3-ylmethyl)-1H-pyrazol-4-yl)-1H-pyrrolo[2,3-b]pyridine-1-carboxylate (40 mg, mmol) was deprotected in HCl in ether/MeOH (1/3 ml). This afforded 5 mg (17% yield) of the titled compound. $^1$H NMR (CD$_3$OD, 400 MHz): δ 8.49 (s, 1H), 8.30 (s, 1H), 7.87-7.86 (d, 2H), 7.747-7.742 (d, 1H), 7.65 (s, 1H), 7.59-7.57 (dd, 1H), 7.26-7.02 (m, 5H), 4.51-4.48 (t, 2H), 4.00 (s, 3H), 3.32-3.25 (t, 2H), 3.00 (s, 3H). MS: m/z=506.2 (M+1), HPLC: 97.44% in method B.

Example 75

N-(5-(3-(1-(3-fluorophenethyl)-1H-pyrazol-4-yl)-1H-pyrrolo[2,3-b]pyridin-5-yl)-2-methoxy phenyl)methanesulfonamide

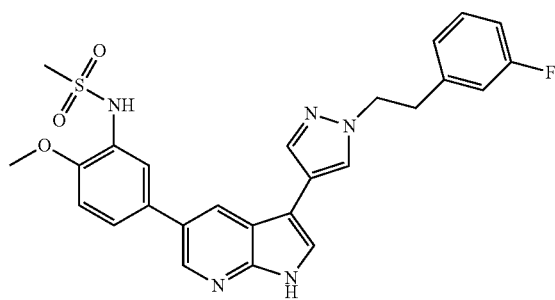 [SMILES: COc1ccc(-c2cnc3[nH]cc(-c4cnn(CCc5cccc(F)c5)c4)c3c2)cc1NS(C)(=O)=O]

Step-i: 5-bromo-3-(1-(3-fluorophenethyl)-1H-pyrazol-4-yl)-1-tosyl-1H-pyrrolo[2,3-b]pyridine Using similar reaction conditions as described in step-i of example-1,5-bromo-3-iodo-1-tosyl-1H-pyrrolo[2,3-b]pyridine (Intermediate 1) (200 mg, 0.41 mmol) was coupled with 1-(3-fluorophenethyl)-4-(4,4,5,5-tetramethyl-1,3,2-dioxaborolan-2-yl)-1H-pyrazole (Intermediate 64B) (172 mg, 0.54 mmol) using sodium carbonate (130 mg, 1.23 mmol) and Pd(PPh$_3$)$_2$Cl$_2$ (14 mg, 0.020 mmol) in toluene/ethanol/water (20/10/5 ml) to afford 80 mg (35.39% yield) of the pure product after column purification using 30% ethyl acetate in hexane as eluent. MS: m/z=539.1 (M+1).

Step-ii: N-(5-(3-(1-(3-fluorophenethyl)-1H-pyrazol-4-yl)-1-tosyl-1H-pyrrolo[2,3-b]pyridin-5-yl)-2-methoxyphenyl)methanesulfonamide Using similar reaction conditions as described in step-ii of example-1, 5-bromo-3-(1-(3-fluorophenethyl)-1H-pyrazol-4-yl)-1-tosyl-1H-pyrrolo[2,3-b]pyridine (80 mg, 0.148 mmol) was coupled with N-(2-methoxy-5-(4,4,5,5-tetramethyl-1,3,2-dioxaborolan-2-yl)phenyl)methane sulfon amide (Intermediate 17) (58 mg, 0.178 mmol) using sodium carbonate (47 mg, 0.444 mmol) and Pd(PPh$_3$)$_2$Cl$_2$ (5 mg, 0.0074 mmol) in DME/water (10/1 ml). This afforded 27 mg (43.8% yield) after purification by column (Silica gel 60/120) using 30% ethyl acetate in hexane as eluent.

Step-iii: N-(5-(3-(1-(3-fluorophenethyl)-1H-pyrazol-4-yl)-1H-pyrrolo[2,3-b]pyridin-5-yl)-2-methoxyphenyl)methanesulfonamide Using similar reaction conditions as described in step-iii of example-1, N-(5-(3-(1-(3-fluorophenethyl)-1H-pyrazol-4-yl)-1-tosyl-1H-pyrrolo[2,3-b]pyridin-5-yl)-2-methoxyphenyl)methane sulfonamide (27 mg, 0.0409 mmol) was hydrolyzed by lithium hydroxide (34 mg, 0.818 mmol) in THF/methanol/water (2/2/1 ml) to yield 8 mg (40.0% yield) of the titled compound. $^1$H NMR (DMSO-d$_6$, 300 MHz): δ 11.7 (s, 1H), 9.04 (s, 1H), 8.43-8.42 (d, 1H), 8.176-8.170 (d, 1H), 8.13 (s, 1H), 7.87 (s, 1H), 7.69-7.68 (d, 1H), 7.58-7.57 (m, 2H), 7.32-7.19 (m, 2H), 7.06-7.01 (m, 2H), 4.33-4.38 (t, 2H), 3.89 (s, 3H), 3.21-3.16 (t, 2H), 3.00 (s, 3H). MS: m/z=506.1 (M+1), HPLC: 91.31% in method B.

Example 76

N-(5-(3-(1-(4-fluorophenethyl)-1H-pyrazol-4-yl)-1H-pyrrolo[2,3-b]pyridin-5-yl)-2-methoxy phenyl)methanesulfonamide

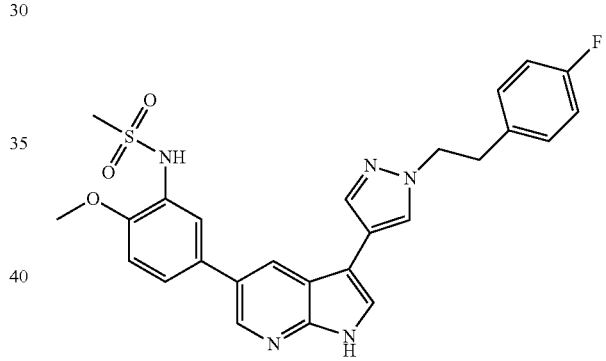

Step-i: 5-bromo-3-(1-(4-fluorophenethyl)-1H-pyrazol-4-yl)-1-tosyl-1H-pyrrolo[2,3-b]pyridine Using similar reaction conditions as described in step-i of example-1,5-bromo-3-iodo-1-tosyl-1H-pyrrolo[2,3-b]pyridine (Intermediate 1) (200 mg, 0.41 mmol) was coupled with 1-(4-fluorophenethyl)-4-(4,4,5,5-tetramethyl-1,3,2-dioxaborolan-2-yl)-1H-pyrazole (Intermediate 64C) (172 mg, 0.54 mmol) using sodium carbonate (130 mg, 1.23 mmol) and Pd(PPh$_3$)$_2$Cl$_2$ (14 mg, 0.020 mmol) in toluene/ethanol/water (20/10/5 ml) to afford 70 mg (30.97% yield) of the pure product after column purification using 30% ethyl acetate in hexane as eluent. MS: m/z=540.9 (M+1).

Step-ii: N-(5-(3-(1-(4-fluorophenethyl)-1H-pyrazol-4-yl)-1-tosyl-1H-pyrrolo[2,3-b]pyridin-5-yl)-2-methoxyphenyl)methanesulfonamide Using similar reaction conditions as described in step-ii of example-1, 5-bromo-3-(1-(4-fluorophenethyl)-1H-pyrazol-4-yl)-1-tosyl-1H-pyrrolo[2,3-b]pyridine (70 mg, 0.129 mmol) was coupled with N-(2-methoxy-5-(4,4,5,5-tetramethyl-1,3,2-dioxaborolan-2-yl)phenyl)methane sulfonamide (Intermediate 17) (50 mg, 0.155 mmol) using sodium carbonate (41 mg, 0.387 mmol) and Pd(PPh$_3$)$_2$Cl$_2$ (4 mg, 0.0064 mmol) in DME/water (10/1 ml). This afforded 25 mg (29.41% yield) after purification by column (Silica gel 60/120) using 30% ethyl acetate in hexane as eluent. MS: m/z=660.1 (M+1).

Step-iii: N-(5-(3-(1-(4-fluorophenethyl)-1H-pyrazol-4-yl)-1H-pyrrolo[2,3-b]pyridin-5-yl)-2-methoxyphenyl)methanesulfonamide Using similar reaction conditions as described in step-iii of example-1, N-(5-(3-(1-(4-fluorophenethyl)-1H-pyrazol-4-yl)-1-tosyl-1H-pyrrolo[2,3-b]pyridin-5-yl)-2-methoxyphenyl) methanesulfonamide (25 mg, 0.0379 mmol) was hydrolyzed by lithium hydroxide (15 mg, 0.379 mmol) in THF/methanol/water (2/2/1 ml) to yield 8 mg (40.0% yield) of the titled compound. $^1$H NMR (DMSO-d$_6$, 300 MHz): δ 11.7 (s, 1H), 9.034-9.035 (d, 1H), 8.43-8.42 (d, 1H), 8.20 (s, 1H), 8.14 (s, 1H), 7.87 (s, 1H), 7.69-7.68 (d, 2H), 7.58-7.56 (m, 2H), 7.26-7.18 (m, 3H), 7.11-7.05 (m, 2H), 4.39-4.35 (t, 2H), 3.89 (s, 3H), 3.18-3.13 (t, 2H), 3.00 (s, 3H). MS: m/z=506.5 (M+1), HPLC: 96.65% in method B.

Example 77

N-(2-fluoro-5-(3-(1-phenethyl-1H-pyrazol-4-yl)-1H-pyrrolo[2,3-b]pyridin-5-yl)phenyl)methane sulfonamide

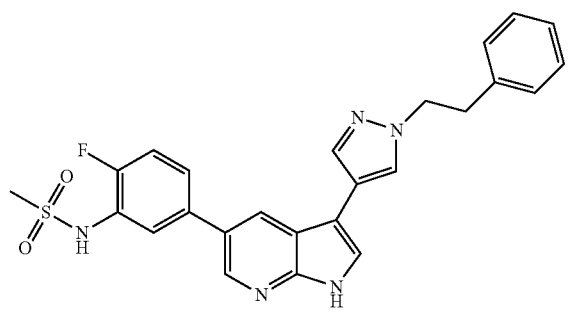 [SMILES: CS(=O)(=O)Nc1cc(-c2cnc3[nH]cc(-c4cnn(CCc5ccccc5)c4)c3c2)ccc1F]

Step-i: 5-bromo-3-(1-phenethyl-1H-pyrazol-4-yl)-1-tosyl-1H-pyrrolo[2,3-b]pyridine Using similar reaction conditions as described in step-i of example-1,5-bromo-3-iodo-1-tosyl-1H-pyrrolo[2,3-b]pyridine (Intermediate 1) (400 mg, 0.838 mmol) was coupled with 1-phenethyl-4-(4,4,5,5-tetramethyl-1,3,2-dioxaborolan-2-yl)-1H-pyrazole (Intermediate 59) (250 mg, 0.838 mmol) using sodium carbonate (266 mg, 2.515 mmol) and Pd(PPh$_3$)$_2$Cl$_2$ (30 mg, 0.041 mmol) in toluene/ethanol/water (20/10/5 ml) to afford 191 mg (44% yield) of the pure product after column purification using 20% ethyl acetate in hexane as eluent. MS: m/z=521.1 (M+1).

Step-ii: N-(2-fluoro-5-(3-(1-phenethyl-1H-pyrazol-4-yl)-1-tosyl-1H-pyrrolo[2,3-b]pyridin-5-yl)phenyl) methanesulfonamide Using similar reaction conditions as described in step-ii of example-1, 5-bromo-3-(1-phenethyl-1H-pyrazol-4-yl)-1-tosyl-1H-pyrrolo[2,3-b]pyridine (190 mg, 0.364 mmol) was coupled with N-(2-fluoro-5-(4,4,5,5-tetramethyl-1,3,2-dioxaborolan-2-yl)phenyl)methanesulfonamide (Intermediate 65) (115 mg, 0.364 mmol) using sodium carbonate (115 mg, 1.093 mmol) and Pd(PPh$_3$)$_2$Cl$_2$ (14 mg, 0.0182 mmol) in DME/water (15/2 ml). This afforded 147 mg (64.1% yield) after purification by column (Silica gel 60/120) using 25% ethyl acetate in chloroform as eluent. MS: m/z=630.3 (M+1).

Step-iii: N-(2-fluoro-5-(3-(1-phenethyl-1H-pyrazol-4-yl)-1H-pyrrolo[2,3-b]pyridin-5-yl)phenyl) methanesulfonamide Using similar reaction conditions as described in step-iii of example-1, N-(2-fluoro-5-(3-(1-phenethyl-1H-pyrazol-4-yl)-1-tosyl-1H-pyrrolo[2,3-b]pyridin-5-yl)phenyl)methanesulfonamide (145 mg, 0.230 mmol) was hydrolyzed by lithium hydroxide (48 mg, 1.15 mmol) in THF/methanol/water (15/5/5 ml) to yield 41 mg (37.6% yield) of the titled compound after purification by preparative TLC(Silicagel-1000 micron) using 50% ethyl acetate in hexane as eluent. $^1$H NMR (CD$_3$OD, 300 MHz): δ 8.44-8.40 (d, 1H), 8.108-8.101 (d, 1H), 7.83-7.74 (m, 2H), 7.58-7.50 (m, 2H), 7.40-7.10 (m, 5H), 4.46-4.42 (t, 2H), 3.20-3.16 (t, 2H), 3.06 (s, 3H). MS: m/z=476.5 (M+1), HPLC: 93.52% in method A.

Example 78

N-(2-fluoro-5-(3-(1-(3-fluorobenzyl)-1H-pyrazol-4-yl)-1H-pyrrolo[2,3-b]pyridin-5-yl)phenyl) methanesulfonamide

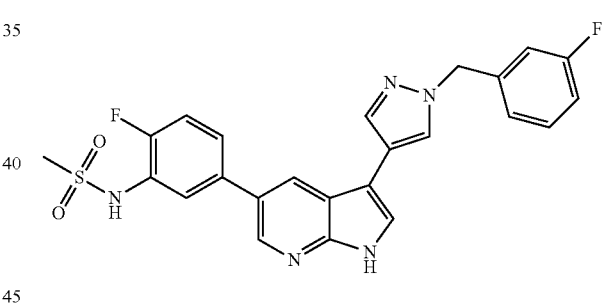

Step-i: N-(2-fluoro-5-(3-(1-(3-fluorobenzyl)-1H-pyrazol-4-yl)-1-tosyl-1H-pyrrolo[2,3-b]pyridin-5-yl) phenyl)methanesulfonamide Using similar reaction conditions as described in step-ii of example-1, 5-bromo-3-(1-(3-fluorobenzyl)-1H-pyrazol-4-yl)-1-tosyl-1H-pyrrolo[2,3-b]pyridine (compound of Step-i of example 9) (166 mg, 0.317 mmol) was coupled with N-(2-fluoro-5-(4,4,5,5-tetramethyl-1,3,2-dioxaborolan-2-yl)phenyl)methanesulfonamide (Intermediate 65) (100 mg, 0.317 mmol) using sodium carbonate (101 mg, 0.952 mmol) and Pd(PPh$_3$)$_2$Cl$_2$ (12 mg, 0.015 mmol) in DME/water (15/2 mL). This afforded 190 mg (94.5% yield) of the titled compound. MS: m/z=634.0 (M+1).

Step-ii: N-(2-fluoro-5-(3-(1-(3-fluorobenzyl)-1H-pyrazol-4-yl)-1H-pyrrolo[2,3-b]pyridin-5-yl)phenyl) methanesulfonamide Using similar reaction conditions as described in step-iii of example-1, N-(2-fluoro-5-(3-(1-(3-fluorobenzyl)-1H-pyrazol-4-yl)-1-tosyl-1H-pyrrolo[2,3-b]pyridin-5-yl)phenyl)
methanesulfonamide (60 mg, 0.094 mmol) was hydrolyzed
with lithium hydroxide (20 mg, 0.474 mmol) in THF/methanol/water (15/5/5 mL) to yield 22 mg (48.8% yield). $^1$H NMR
(CD$_3$OD, 400 MHz): δ 8.467-8.462 (d, 1H), 8.36-8.35 (d,
1H), 8.22 (s, 1H), 7.95 (s, 1H), 7.84-7.80 (dd, 1H), 7.63-7.57
(m, 1H), 7.44-7.32 (m, 2H), 7.16-7.12 (d, 1H), 7.10-7.02 (m,
2H). MS: m/z=480.3 (M+1), HPLC: 92.50% in method B.

Example 79

N-(5-(3-(1-(3,5-difluorobenzyl)-1H-pyrazol-4-yl)-
1H-pyrrolo[2,3-b]pyridin-5-yl)-2-fluorophenyl)
methanesulfonamide

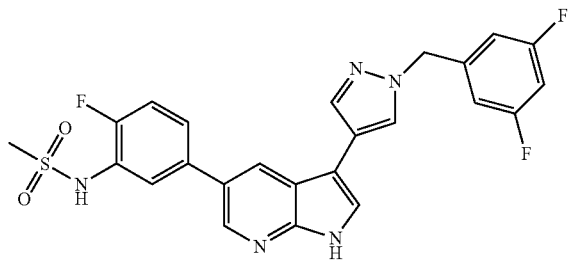 [SMILES: CS(=O)(=O)Nc1cc(-c2cnc3[nH]cc(-c4cnn(Cc5cc(F)cc(F)c5)c4)c3c2)ccc1F]

Step-i: N-(5-(3-(1-(3,5-difluorobenzyl)-1H-pyrazol-
4-yl)-1-tosyl-1H-pyrrolo[2,3-b]pyridin-5-yl)-2-fluorophenyl)methanesulfonamide Using similar reaction conditions as described in step-ii of
example-1, 5-bromo-3-(1-(3,5-difluorobenzyl)-1H-pyrazol-
4-yl)-1-tosyl-1H-pyrrolo[2,3-b]pyridine (Step 1 example 71)
(172 mg, 0.317 mmol) was coupled with N-(2-fluoro-5-(4,4,
5,5-tetramethyl-1,3,2-dioxaborolan-2-yl)phenyl) methanesulfonamide (Intermediate 65) (100 mg, 0.317 mmol) using
sodium carbonate (101 mg, 0.952 mmol) and Pd(PPh$_3$)$_2$Cl$_2$
(12 mg, 0.015 mmol) in DME/water (15/2 ml). This afforded
54 mg (26.2% yield). MS: m/z=652.0 (M+1).

Step-ii: N-(5-(3-(1-(3,5-difluorobenzyl)-1H-pyrazol-
4-yl)-1H-pyrrolo[2,3-b]pyridin-5-yl)-2-fluoro phenyl)methanesulfonamide Using similar reaction conditions as described in step-iii of
example-1, N-(5-(3-(1-(3,5-difluorobenzyl)-1H-pyrazol-4-
yl)-1-tosyl-1H-pyrrolo[2,3-b]pyridin-5-yl)-2-fluorophenyl)
methane sulfonamide (53 mg, 0.184 mmol) was hydrolyzed
by lithium hydroxide (18 mg, 0.407 mmol) in THF/methanol/
water (15/5/5 ml) to yield 34 mg (85% yield) of the titled
compound. $^1$H NMR (CD$_3$OD, 400 MHz): δ 8.44-8.43 (d,
1H), 8.35-8.34 (d, 1H), 8.23 (s, 1H), 7.953-7.951 (d, 1H),
7.80-7.77 (dd, 1H), 7.66 (s, 1H), 7.59-7.55 (m, 1H), 7.34-7.29
(m, 1H), 6.90-6.86 (m, 2H), 5.43 (s, 2H), 305 (s, 3H). MS:
m/z=498.1 (M+1), HPLC: 93.19% in method B.

Example 80

N-(5-(3-(1-(3,5-difluorobenzyl)-3,5-dimethyl-1H-
pyrazol-4-yl)-1H-pyrrolo[2,3-b]pyridin-5-yl)-2-fluorophenyl)methanesulfonamide

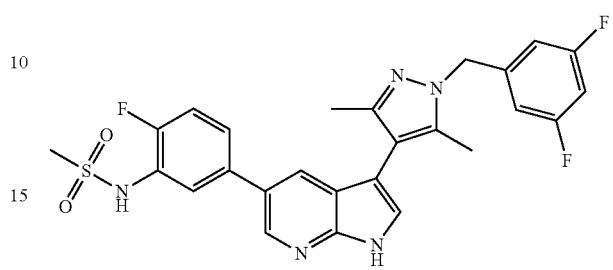

Step-i: tert-butyl 5-(3-(N-(tert-butoxycarbonyl)methylsulfonamido)-4-fluorophenyl)-3-(1-(3,5-difluorobenzyl)-3,5-dimethyl-1H-pyrazol-4-yl)-1H-pyrrolo
[2,3-b]pyridine-1-carboxylate Using similar reaction conditions as described in step-ii of
example-1, tert-butyl 5-(3-(N-(tert-butoxycarbonyl)methylsulfonamido)-4-fluorophenyl)-3-iodo-1H-pyrrolo[2,3-b]pyridine-1-carboxylate (Intermediate 66A)(85 mg, 0.134
mmol) was coupled with 1-(3,5-difluorobenzyl)-3,5-dimethyl-4-(4,4,5,5-tetramethyl-1,3,2-dioxaborolan-2-yl)-1H-
pyrazole (intermediate 24) (93 mg, 0.269 mmol) using
sodium carbonate (43 mg, 0.404 mmol) and Pd(PPh$_3$)$_2$Cl$_2$ (5
mg, 0.006) in DME/water (20/4 mL) to afford 89 mg of the
crude compound. MS: m/z=670.2 (M+1) (de boc mass
observed).

Step-ii: N-(5-(3-(1-(3,5-difluorobenzyl)-3,5-dimethyl-1H-pyrazol-4-yl)-1H-pyrrolo[2,3-b]pyridin-5-
yl)-2-fluorophenyl)methanesulfonamide Using similar reaction conditions as described in step-ii of
example-7, tert-butyl 5-(3-(N-(tert-butoxycarbonyl)methylsulfonamido)-4-fluorophenyl)-3-(1-(3,5-difluorobenzyl)-3,
5-dimethyl-1H-pyrazol-4-yl)-1H-pyrrolo[2,3-b]pyridine-1-
carboxylate (88 mg, 0.121 mmol) was deprotected in HCl in
dioxane/MeOH (5/2 ml). This afforded 27 mg (35% yield) of
the titled compound. $^1$H NMR (CDCl$_3$, 300 MHz): δ 13.6 (s,
1H), 8.42 (s, 1H), 8.26 (s, 1H), 7.80-7.77 (d, 1H), 7.50 (s, 1H),
7.33-7.32 (m, 2H), 6.79-6.69 (m, 4H), 5.33 (s, 2H), 3.09 (s,
3H), 2.24 (s, 3H), 2.18 (s, 3H). MS: m/z=526.2 (M+1),
HPLC: 94.82% in method B.

Example 81

5-(3-(1-(3-fluorobenzyl)-1H-pyrazol-4-yl)-1H-pyrrolo[2,3-b]pyridin-5-yl)-3-methoxypyridin-2-amine

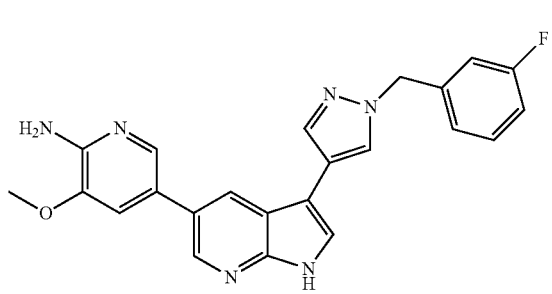 [SMILES: COc1cc(-c2cnc3[nH]cc(-c4cnn(Cc5cccc(F)c5)c4)c3c2)cnc1N]

Step-i: tert-butyl (5-(3-(1-(3-fluorobenzyl)-1H-pyrazol-4-yl)-1-tosyl-1H-pyrrolo[2,3-b]pyridin-5-yl)-3-methoxypyridin-2-yl)carbamate Using similar reaction conditions as described in step-i of example-1, tert-butyl (5-(3-iodo-1-tosyl-1H-pyrrolo[2,3-b]pyridin-5-yl)-3-methoxypyridin-2-yl)carbamate (intermediate 66B) (200 mg, 0.322 mmol) was coupled with 1-(3-fluorobenzyl)-4-(4,4,5,5-tetramethyl-1,3,2-dioxaborolan-2-yl)-1H-pyrazole (intermediate 11) (147 mg, 0.483 mmol) using Pd(PPh$_3$)$_2$Cl$_2$ (12 mg, 0.016 mol) and sodium carbonate (86 mg, 0.806 mmol) in toluene/ethanol/water (10/2/2 ml) to afford 200 mg (93.2% yield) of the titled compound after column purification using 40% ethyl acetate in hexane as eluent. MS: m/z=669.1 (M+1).

Step-ii: tert-butyl (5-(3-(1-(3-fluorobenzyl)-1H-pyrazol-4-yl)-1H-pyrrolo[2,3-b]pyridin-5-yl)-3-methoxypyridin-2-yl)carbamate Using similar reaction conditions as described in step-iii of example-1, tert-butyl (5-(3-(1-(3-fluorobenzyl)-1H-pyrazol-4-yl)-1-tosyl-1H-pyrrolo[2,3-b]pyridin-5-yl)-3-methoxypyridin-2-yl) carbamate (200 mg, 0.299 mmol) was hydrolyzed by lithium hydroxide (25 mg, 0.598 mmol) in THF/methanol/water (5/1/1 ml) to yield 120 mg (78.4% yield) of the titled compound. MS: m/z=515.1 (M+1).

Step-iii: 5-(3-(1-(3-fluorobenzyl)-1H-pyrazol-4-yl)-1H-pyrrolo[2,3-b]pyridin-5-yl)-3-methoxy pyridin-2-amine Using similar reaction conditions as described in step-ii of example-7, tert-butyl (5-(3-(1-(3-fluorobenzyl)-1H-pyrazol-4-yl)-1H-pyrrolo[2,3-b]pyridin-5-yl)-3-methoxypyridin-2-yl)carbamate (120 mg, 0.233 mmol) was deprotected in TFA/DCM (1/5 ml). This afforded 27 mg (21.9% yield) of the titled compound. $^1$H NMR (DMSO-d$_6$, 400 MHz): δ 8.577-8.572 (d, 1H), 8.417-8.413 (d, 1H), 8.37 (s, 1H), 8.03 (s, 2H), 7.956-7.953 (d, 1H), 7.86-7.79 (s, 1H), 7.799-7.793 (d, 1H), 7.40-7.39 (q, 1H), 7.12-7.07 (m, 3H), 5.40 (s, 2H), 4.06 (s, 3H). MS: m/z=415.6 (M+1), HPLC: 93.86% in method A.

Example 82

3-(1-(3-fluorobenzyl)-1H-pyrazol-4-yl)-5-(4-(piperidin-4-yl)phenyl)-1H-pyrrolo[2,3-b]pyridine

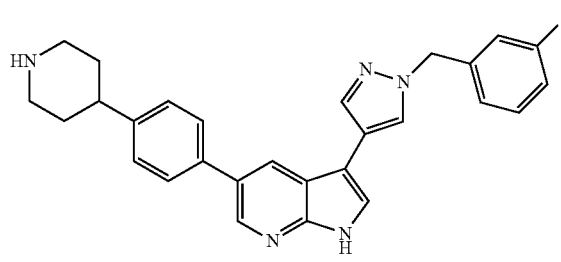

Step-i: tert-butyl 4-(4-(3-(1-(3-fluorobenzyl)-1H-pyrazol-4-yl)-1-tosyl-1H-pyrrolo[2,3-b]pyridin-5-yl)phenyl)-5,6-dihydropyridine-1(2H)-carboxylate Using similar reaction conditions as described in step-i of example-1, tert-butyl 4-(4-(3-iodo-1-tosyl-1H-pyrrolo[2,3-b]pyridin-5-yl)phenyl)-5,6-dihydropyridine-1(2H)-carboxylate (intermediate 66C) (250 mg, 0.381 mmol) was coupled with 1-(3-fluorobenzyl)-4-(4,4,5,5-tetramethyl-1,3,2-dioxaborolan-2-yl)-1H-pyrazole (intermediate 11) (172 mg, 0.571 mmol) using Pd(PPh$_3$)$_2$Cl$_2$ (14 mg, 0.019 mol) and sodium carbonate (121 mg, 1.143 mmol) in toluene/ethanol/water (20/10/4 ml) to afford 237 mg (88% yield) of the titled. MS: m/z=704.3 (M+1).

Step-ii: tert-butyl 4-(4-(3-(1-(3-fluorobenzyl)-1H-pyrazol-4-yl)-1-tosyl-1H-pyrrolo[2,3-b]pyridin-5-yl)phenyl)piperidine-1-carboxylate To a solution of tert-butyl 4-(4-(3-(1-(3-fluorobenzyl)-1H-pyrazol-4-yl)-1-tosyl-1H-pyrrolo[2,3-b]pyridin-5-yl)phenyl)-5,6-dihydropyridine-1(2H)-carboxylate (235 mg, 0.334 mmol) in ethyl acetate/ethanol 15/15 mL was added palladium hydroxide (60 mg) and stirred under hydrogen atmosphere for 18 hours. The catalyst was filtered through celite and the solvent was distilled off to get 191 mg (81.0% yield) of the titled compound. MS: m/z=706.3 (M+1).

Step-iii: 3-(1-(3-fluorobenzyl)-1H-pyrazol-4-yl)-5-(4-(piperidin-4-yl)phenyl)-1-tosyl-1H-pyrrolo[2,3-b]pyridine hydrochloride Using similar reaction conditions as described in step-ii of example-7, tert-butyl 4-(4-(3-(1-(3-fluorobenzyl)-1H-pyrazol-4-yl)-1-tosyl-1H-pyrrolo[2,3-b]pyridin-5-yl)phenyl)piperidine-1-carboxylate (191 mg, 0.270 mmol) was deprotected in HCl in dioxane/MeOH (5/5 ml). This afforded 173 mg (99% yield) of the titled. MS: m/z=606.8 (M+1).

Step-iv: 3-(1-(3-fluorobenzyl)-1H-pyrazol-4-yl)-5-(4-(piperidin-4-yl)phenyl)-1H-pyrrolo[2,3-b]pyridine Using similar reaction conditions as described in step-iii of example-1, 3-(1-(3-fluorobenzyl)-1H-pyrazol-4-yl)-5-(4-(piperidin-4-yl)phenyl)-1-tosyl-1H-pyrrolo[2,3-b]pyridine hydrochloride (170 mg, 0.026 mmol) was hydrolyzed by lithium hydroxide (12 mg, 0.264 mmol) in THF/methanol/water (10/5/2.5 ml) to yield 60 mg (40% yield) of the titled compound. $^1$H NMR (CD$_3$OD, 300 MHz): δ 8.54 (s, 2H), 8.229-8.227 (d, 1H), 7.959-7.957 (d, 1H), 7.73-7.70 (m, 3H), 7.44-7.41 (d, 2H), 7.38-7.23 (m, 1H), 7.12-7.09 (d, 1H), 7.08-7.00 (m, 2H), 5.43 (s, 2H), 3.55-3.50 (d, 2H), 3.21-3.13 (m, 2H), 3.05-2.93 (m, 1H), 2.16-2.11 (d, 2H), 2.02-1.89 (m, 2H). MS: m/z=452.5 (M+1), HPLC: 96.75% in method A.

Example 82A

(S)-1-(4-(4-(3-(1-(3-fluorobenzyl)-1H-pyrazol-4-yl)-1H-pyrrolo[2,3-b]pyridin-5-yl)phenyl)piperidin-1-yl)propan-2-ol

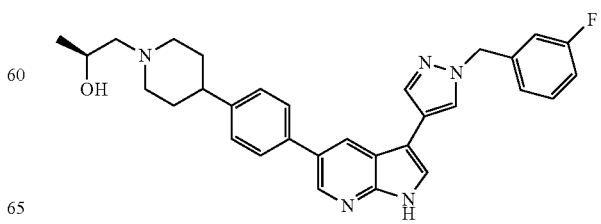

Step 1 (S)-1-(4-(4-(3-(1-(3-fluorobenzyl)-1H-pyrazol-4-yl)-1-tosyl-1H-pyrrolo[2,3-b]pyridin-5-yl)phenyl)piperidin-1-yl)propan-2-ol Seal tube containing 3-(1-(3-fluorobenzyl)-1H-pyrazol-4-yl)-5-(4-(piperidin-4-yl)phenyl)-1-tosyl-1H-pyrrolo[2,3-b]pyridine hydrochloride (product of step-iii of example 82) (125 mg, 0.194 mmol), (S)-2-methyloxirane (23 mg, 0.389 mmol), DIPEA (100 mg, 0.778 mmol) and ethanol were heated at 85° C. for 3 hours and distilled the solvent on rotavapor to get 128 mg (99% yield) of the titled compound. MS: m/z=664.4 (M+1).

Step-ii: 3-(1-(3-fluorobenzyl)-1H-pyrazol-4-yl)-5-(4-(piperidin-4-yl)phenyl)-1H-pyrrolo[2,3-b]pyridine Using similar reaction conditions as described in step-iii of example-1, (S)-1-(4-(4-(3-(1-(3-fluorobenzyl)-1H-pyrazol-4-yl)-1-tosyl-1H-pyrrolo[2,3-b]pyridin-5-yl)phenyl)piperidin-1-yl)propan-2-ol (127 mg, 0.191 mmol) was hydrolyzed by lithium hydroxide (80 mg, 1.913 mmol) in THF/methanol/water (20/10/5 ml) to yield 15 mg (5% yield) of the titled. $^1$H NMR (CD$_3$OD, 400 MHz): δ 7.46-8.45 (d, 1H), 8.33-8.32 (d, 1H), 8.19 (s, 1H), 7.93 (s, 1H), 7.63-7.61 (m, 3H), 7.39-7.34 (m, 3H), 7.11-7.09 (d, 1H), 7.06-7.01 (m, 2H), 5.43 (s, 2H), 4.05-4.00 (m, 1H), 3.25-3.19 (t, 2H), 2.64-2.33 (m, 4H), 1.93-1.85 (m, 4H), 1.30-1.26 (m, 1H), 1.20-1.18 (d, 3H). MS: m/z=510.2 (M+1), HPLC: 96.39% in method A.

Example 83

3-(1-(3-fluorobenzyl)-1H-pyrazol-4-yl)-5-(4-(1-methylpiperidin-4-yl)phenyl)-1H-pyrrolo[2,3-b]pyridine

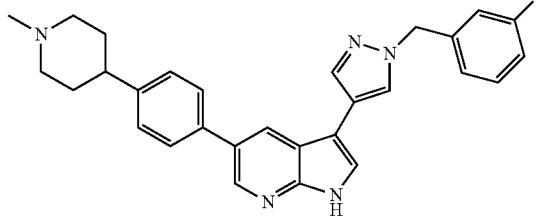

Step-i: 3-(1-(3-fluorobenzyl)-1H-pyrazol-4-yl)-5-(4-(1-methyl-1,2,3,6-tetrahydropyridin-4-yl)phenyl)-1-tosyl-1H-pyrrolo[2,3-b]pyridine Using similar reaction conditions as described in step-i of example-1, 3-iodo-5-(4-(1-methyl-1,2,3,6-tetrahydropyridin-4-yl)phenyl)-1-tosyl-1H-pyrrolo[2,3-b]pyridine (intermediate 66D) (200 mg, 0.351 mmol) was coupled with 1-(3-fluorobenzyl)-4-(4,4,5,5-tetramethyl-1,3,2-dioxaborolan-2-yl)-1H-pyrazole (intermediate 11) (117 mg, 0.386 mmol) using Pd(PPh$_3$)$_2$Cl$_2$ (13 mg, 0.017 mol) and sodium carbonate (112 mg, 1.053 mmol) in toluene/ethanol/water (3/3/2 ml) to afford 180 mg (83% yield) of the titled compound after column purification using 10% methanol in DCM as eluent. MS: m/z=617.9 (M+1).

Step-ii: 3-(1-(3-fluorobenzyl)-1H-pyrazol-4-yl)-5-(4-(1-methyl-1,2,3,6-tetrahydropyridin-4-yl)phenyl)-1H-pyrrolo[2,3-b]pyridine Using similar reaction conditions as described in step-iii of example-1, 3-(1-(3-fluorobenzyl)-1H-pyrazol-4-yl)-5-(4-(1-methyl-1,2,3,6-tetrahydropyridin-4-yl)phenyl)-1-tosyl-1H-pyrrolo[2,3-b]pyridine (180 mg, 0.291 mmol) was hydrolyzed by lithium hydroxide (37 mg, 0.874 mmol) in THF/methanol/water (2/2/2 ml) to yield crude 230 mg of the titled compound.

Step-iii: 3-(1-(3-fluorobenzyl)-1H-pyrazol-4-yl)-5-(4-(1-methylpiperidin-4-yl)phenyl)-1H-pyrrolo[2,3-b]pyridine Using similar reaction conditions as described in step-ii of example-82, 3-(1-(3-fluorobenzyl)-1H-pyrazol-4-yl)-5-(4-(1-methyl-1,2,3,6-tetrahydropyridin-4-yl)phenyl)-1H-pyrrolo[2,3-b]pyridine (130 mg, 0.280 mmol) was reduced with palladium hydroxide (50 mg) in ethyl acetate/ethanol 5/5 mL to afford 10 mg (6.0% yield) of the titled compound. $^1$H NMR (CD$_3$OD, 300 MHz): δ 8.627-8.621 (d, 1H), 8.56 (s, 1H), 8.26 (s, 1H), 7.97 (s, 1H), 7.77-7.73 (m, 3H), 7.45-7.42 (d, 2H), 7.38-7.33 (m, 1H), 7.13-7.00 (m, 3H), 5.44 (s, 2H), 3.67-3.63 (d, 2H), 3.22-3.15 (t, 2H), 3.03-2.94 (m, 4H), 2.20-2.00 (m, 4H). MS: m/z=466.7 (M+1), HPLC: 95.92% in method B.

Example 84

5-(3-fluoro-4-(piperidin-4-yl)phenyl)-3-(1-(3-fluorobenzyl)-1H-pyrazol-4-yl)-1H-pyrrolo[2,3-b]pyridine

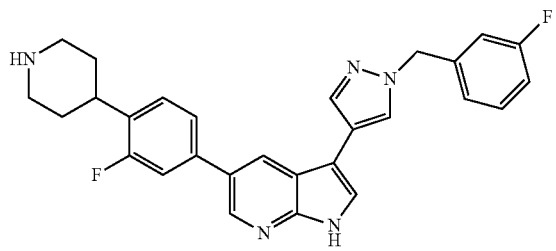 [SMILES: Fc1cccc(Cn2cc(-c3c[nH]c4ncc(-c5ccc(C6CCNCC6)c(F)c5)cc34)cn2)c1]

Step-i: tert-butyl 4-(2-fluoro-4-(3-(1-(3-fluorobenzyl)-1H-pyrazol-4-yl)-1-tosyl-1H-pyrrolo[2,3-b]pyridin-5-yl)phenyl)piperidine-1-carboxylate Using similar reaction conditions as described in step-i of example-1, tert-butyl 4-(2-fluoro-4-(3-iodo-1-tosyl-1H-pyrrolo[2,3-b]pyridin-5-yl)phenyl)piperidine-1-carboxylate (intermediate 67) (250 mg, 0.370 mmol) was coupled with 1-(3-fluorobenzyl)-4-(4,4,5,5-tetramethyl-1,3,2-dioxaborolan-2-yl)-1H-pyrazole (intermediate 11) (168 mg, 0.555 mmol) using Pd(DPPF)Cl$_2$ (14 mg, 0.018 mol) and sodium carbonate (118 mg, 1.110 mmol) in toluene/ethanol/water (5/5/1 ml) to afford 250 mg (93.2% yield) of the titled compound after column purification using 1% methanol in DCM as eluent. MS: m/z=724.4 (M+1).

Step-ii: tert-butyl 4-(2-fluoro-4-(3-(1-(3-fluorobenzyl)-1H-pyrazol-4-yl)-1H-pyrrolo[2,3-b]pyridin-5-yl)phenyl)piperidine-1-carboxylate Using similar reaction conditions as described in step-iii of example-1, tert-butyl 4-(2-fluoro-4-(3-(1-(3-fluorobenzyl)-1H-pyrazol-4-yl)-1-tosyl-1H-pyrrolo[2,3-b]pyridin-5-yl)phenyl)piperidine-1-carboxylate (250 mg, 0.345 mmol) was hydrolyzed by lithium hydroxide (73 mg, 1.726 mmol) in THF/methanol/water (5/2/1 ml) to yield crude 150 mg (76.14% yield) of the titled compound. MS: m/z=570.2 (M+1).

Step-iii: 5-(3-fluoro-4-(piperidin-4-yl)phenyl)-3-(1-(3-fluorobenzyl)-1H-pyrazol-4-yl)-1H-pyrrolo[2,3-b]pyridine Using similar reaction conditions as described in step-ii of example-7, tert-butyl 4-(2-fluoro-4-(3-(1-(3-fluorobenzyl)-1H-pyrazol-4-yl)-1H-pyrrolo[2,3-b]pyridin-5-yl)phenyl)piperidine-1-carboxylate (150 mg, 0.263 mmol) was deprotected in TFA/DCM (2/5 ml). This afforded 30 mg (19.6% yield) of the titled. $^1$H NMR (CD$_3$OD, 400 MHz): δ 8.67-8.66 (d, 1H), 8.60 (s, 1H), 8.28 (s, 1H), 7.97 (s, 1H), 7.78 (s, 1H), 7.58-7.54 (m, 2H), 7.47-7.43 (t, 1H), 7.39-7.33 (q, 1H), 7.12-7.10 (d, 1H), 7.05-7.00 (m, 2H), 5.43 (s, 2H), 3.55-3.52 (d, 2H), 3.28-3.16 (m, 3H), 2.21-2.03 (m, 4H). MS: m/z=470.4 (M+1), HPLC: 98.34% in method A.

Example 85

3-(1-(3-methylbenzyl)-1H-pyrazol-4-yl)-5-(4-(piperidin-4-yl)phenyl)-1H-pyrrolo[2,3-b]pyridine

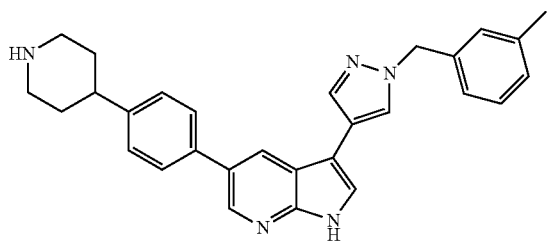 [SMILES: Cc1cccc(Cn2cc(-c3c[nH]c4ncc(-c5ccc(C6CCNCC6)cc5)cc34)cn2)c1]

Step-i: tert-butyl 4-(4-(3-(1-(3-methylbenzyl)-1H-pyrazol-4-yl)-1-tosyl-1H-pyrrolo[2,3-b]pyridin-5-yl)phenyl)piperidine-1-carboxylate Using similar reaction conditions as described in step-i of example-1, tert-butyl 4-(2-fluoro-4-(3-iodo-1-tosyl-1H-pyrrolo[2,3-b]pyridin-5-yl)phenyl)piperidine-1-carboxylate (intermediate 67B) (155 mg, 0.235 mmol) was coupled with 1-(3-methylbenzyl)-4-(4,4,5,5-tetramethyl-1,3,2-dioxaborolan-2-yl)-1H-pyrazole (intermediate 64D) (105 mg, 0.353 mmol) using Pd(dppf)Cl$_2$ (9 mg, 0.011 mol) and sodium carbonate (75 mg, 0.7070 mmol) in toluene/ethanol/water (20/10/5 ml) to afford 165 mg (crude) of the titled compound. MS: m/z=702.7 (M+1).

Step-ii: tert-butyl 4-(4-(3-(1-(3-methylbenzyl)-1H-pyrazol-4-yl)-1H-pyrrolo[2,3-b]pyridin-5-yl)phenyl)piperidine-1-carboxylate Using similar reaction conditions as described in step-iii of example-1, tert-butyl 4-(4-(3-(1-(3-methylbenzyl)-1H-pyrazol-4-yl)-1-tosyl-1H-pyrrolo[2,3-b]pyridin-5-yl)phenyl)piperidine-1-carboxylate (164 mg, 0.233 mmol) was hydrolyzed by lithium hydroxide (98 mg, 2.33 mmol) in THF/methanol/water (16/4/4 ml) to yield crude 109 mg (86% yield) of the titled compound after column purification using 1.5% methanol in DCM as eluent. MS: m/z=548.4 (M+1).

Step-iii: 3-(1-(3-methylbenzyl)-1H-pyrazol-4-yl)-5-(4-(piperidin-4-yl)phenyl)-1H-pyrrolo[2,3-b]pyridine Using similar reaction conditions as described in step-ii of example-7, tert-butyl 4-(4-(3-(1-(3-methylbenzyl)-1H-pyrazol-4-yl)-1H-pyrrolo[2,3-b]pyridin-5-yl)phenyl)piperidine-1-carboxylate (108 mg, 0.197 mmol) was deprotected in TFA/toluene (5/5 ml). This afforded 30 mg (27% yield) of the titled. $^1$H NMR (CD$_3$OD, 300 MHz): δ 8.627-8.622 (d, 1H), 8.56 (s, 1H), 8.20 (s, 1H), 7.94 (s, 1H), 7.75-7.71 (m, 3H), 7.44-7.42 (d, 2H), 7.25-7.20 (t, 1H), 7.13-7.07 (m, 3H), 5.37 (s, 2H), 3.55-3.51 (d, 2H), 3.21-3.13 (m, 2H), 3.03-2.94 (m, 1H), 2.31 (s, 3H), 2.14-2.10 (d, 2H), 2.03-1.89 (qd, 2H). MS: m/z=448.4 (M+1), HPLC: 98.27% in method A.

Example 86

Tert-butyl 4-(4-(3-(1-(3-fluorobenzyl)-1H-pyrazol-4-yl)-1H-pyrrolo[2,3-b]pyridin-5-yl)-2-methoxyphenyl) piperidine-1-carboxylate

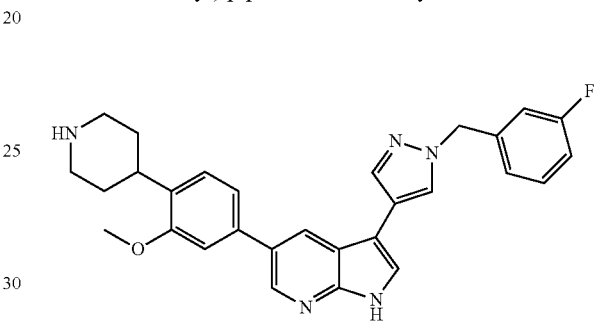

Step-i: tert-butyl 4-(4-(3-(1-(3-fluorobenzyl)-1H-pyrazol-4-yl)-1-tosyl-1H-pyrrolo[2,3-b]pyridin-5-yl)-2-methoxyphenyl)piperidine-1-carboxylate Using similar reaction conditions as described in step-i of example-1, tert-butyl 4-(4-(3-iodo-1-tosyl-1H-pyrrolo[2,3-b]pyridin-5-yl)-2-methoxyphenyl)piperidine-1-carboxylate (intermediate 67A) (260 mg, 0.378 mmol) was coupled with 1-(3-fluorobenzyl)-4-(4,4,5,5-tetramethyl-1,3,2-dioxaborolan-2-yl)-1H-pyrazole (intermediate 11) (172 mg, 0.567 mmol) using Pd(dppf)Cl$_2$ (14 mg, 0.018 mol) and sodium carbonate (121 mg, 1.134 mmol) in toluene/ethanol/water (6/2/1 ml) to afford 200 mg (71.9% yield) of the titled compound after column purification using 2% methanol in DCM as eluent. MS: m/z=736.4 (M+1).

Step-ii: tert-butyl 4-(4-(3-(1-(3-fluorobenzyl)-1H-pyrazol-4-yl)-1H-pyrrolo[2,3-b]pyridin-5-yl)-2-methoxyphenyl)piperidine-1-carboxylate Using similar reaction conditions as described in step-iii of example-1, tert-butyl 4-(4-(3-(1-(3-fluorobenzyl)-1H-pyrazol-4-yl)-1-tosyl-1H-pyrrolo[2,3-b]pyridin-5-yl)-2-methoxyphenyl)piperidine-1-carboxylate (200 mg, 0.271 mmol) was hydrolyzed by lithium hydroxide (57 mg, 1.358 mmol) in THF/methanol/water (5/2/2 ml) to yield crude 100 mg (63.2% yield) of the titled compound. MS: m/z=582.2 (M+1).

Step-iii: 3-(1-(3-fluorobenzyl)-1H-pyrazol-4-yl)-5-(3-methoxy-4-(piperidin-4-yl)phenyl)-1H-pyrrolo[2,3-b]pyridine Using similar reaction conditions as described in step-ii of example-7, tert-butyl 4-(4-(3-(1-(3-fluorobenzyl)-1H-pyrazol-4-yl)-1H-pyrrolo[2,3-b]pyridin-5-yl)-2-methoxyphenyl)piperidine-1-carboxylate (100 mg, 0.171 mmol) was deprotected in TFA/DCM (2/5 ml). This afforded 15 mg (14.7% yield) of the titled compound. $^1$H NMR (CD$_3$OD, 400 MHz): δ 8.06 (s, 2H), 8.24 (s, 1H), 7.96 (s, 1H), 7.75 (s, 1H), 7.38-7.29 (m, 4H), 7.12-7.10 (d, 1H), 7.04-7.00 (m, 2H), 5.42 (s, 2H), 3.95-3.93 (s, 3H), 3.53-3.50 (d, 2H), 3.34-3.30 (m, 1H), 3.19-3.13 (m, 2H), 2.09-1.97 (m, 4H). MS: m/z=482.2 (M+1), HPLC: 94.26% in method A.

Example 87

3-(1-(3-methoxybenzyl)-1H-pyrazol-4-yl)-5-(4-(piperidin-4-yl)phenyl)-1H-pyrrolo[2,3-b]pyridine

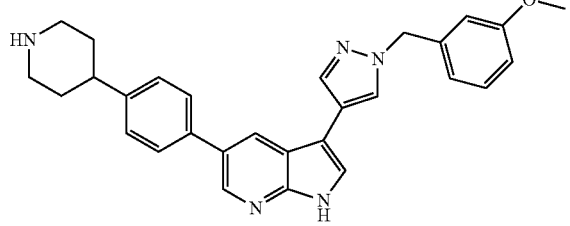

Step-i: tert-butyl 4-(4-(3-(1-(3-methoxybenzyl)-1H-pyrazol-4-yl)-1-tosyl-1H-pyrrolo[2,3-b]pyridin-5-yl)phenyl)piperidine-1-carboxylate Using similar reaction conditions as described in step-i of example-1, tert-butyl 4-(2-fluoro-4-(3-iodo-1-tosyl-1H-pyrrolo[2,3-b]pyridin-5-yl)phenyl)piperidine-1-carboxylate (intermediate 67B) (125 mg, 0.190 mmol) was coupled with 1-(3-methoxybenzyl)-4-(4,4,5,5-tetramethyl-1,3,2-dioxaborolan-2-yl)-1H-pyrazole (intermediate 64F) (90 mg, 0.285 mmol) using Pd(dppf)Cl$_2$ (7 mg, 0.009 mol) and sodium carbonate (181 mg, 0.578 mmol) in toluene/ethanol/water (20/10/5 ml) to afford 121 mg (crude) of the titled compound. MS: m/z=718.3 (M+1).

Step-ii: tert-butyl 4-(4-(3-(1-(3-methoxybenzyl)-1H-pyrazol-4-yl)-1H-pyrrolo[2,3-b]pyridin-5-yl)phenyl)piperidine-1-carboxylate Using similar reaction conditions as described in step-iii of example-1, tert-butyl 4-(4-(3-(1-(3-methoxybenzyl)-1H-pyrazol-4-yl)-1-tosyl-1H-pyrrolo[2,3-b]pyridin-5-yl)phenyl)piperidine-1-carboxylate (120 mg, 0.167 mmol) was hydrolyzed by lithium hydroxide (70 mg, 1.67 mmol) in THF/methanol/water (12/6/3 ml) to yield crude 86 mg (91% yield) of the titled compound. MS: m/z=564.3 (M+1).

Step-iii: 3-(1-(3-methoxybenzyl)-1H-pyrazol-4-yl)-5-(4-(piperidin-4-yl)phenyl)-1H-pyrrolo[2,3-b]pyridine Using similar reaction conditions as described in step-ii of example-7, tert-butyl 4-(4-(3-(1-(3-methoxybenzyl)-1H-pyrazol-4-yl)-1H-pyrrolo[2,3-b]pyridin-5-yl)phenyl)piperidine-1-carboxylate (85 mg, 0.150 mmol) was deprotected in TFA/toluene (2.5/5 ml). This afforded 11 mg (16.2% yield) of the titled compound. $^1$H NMR (CD$_3$OD, 300 MHz): δ 8.458-8.451 (d, 1H), 8.327-8.321 (d, 1H), 8.14 (s, 1H), 7.90 (s, 1H), 7.65-7.61 (m, 3H), 7.38-7.35 (d, 2H), 7.29-7.23 (m, 1H), 6.87-6.85 (m, 2H), 5.38 (s, 2H), 3.25-3.76 (s, 3H), 3.25-3.20 (d, 2H), 2.87-2.73 (m, 3H), 1.93-1.72 (m, 4H). MS: m/z=464.6 (M+1), HPLC: 90.63% in method A.

Example 88

3-(1-phenethyl-1H-pyrazol-4-yl)-5-(4-(piperidin-4-yl)phenyl)-1H-pyrrolo[2,3-b]pyridine

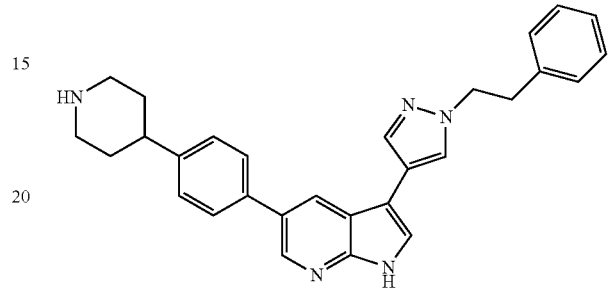

Step-i: tert-butyl 4-(4-(3-(1-phenethyl-1H-pyrazol-4-yl)-1-tosyl-1H-pyrrolo[2,3-b]pyridin-5-yl)phenyl)piperidine-1-carboxylate Using similar reaction conditions as described in step-i of example-1, tert-butyl 4-(2-fluoro-4-(3-iodo-1-tosyl-1H-pyrrolo[2,3-b]pyridin-5-yl)phenyl)piperidine-1-carboxylate (intermediate 67B) (125 mg, 0.190 mmol) was coupled with 1-phenethyl-4-(4,4,5,5-tetramethyl-1,3,2-dioxaborolan-2-yl)-1H-pyrazole (intermediate 59) (85 mg, 0.285 mmol) using Pd(dppf)Cl$_2$ (7 mg, 0.009 mol) and sodium carbonate (181 mg, 0.578 mmol) in toluene/ethanol/water (20/10/5 ml) to afford 129 mg (crude) of the titled compound. MS: m/z=702.3 (M+1).

Step-ii: tert-butyl 4-(4-(3-(1-phenethyl-1H-pyrazol-4-yl)-1H-pyrrolo[2,3-b]pyridin-5-yl)phenyl)piperidine-1-carboxylate Using similar reaction conditions as described in step-iii of example-1, tert-butyl 4-(4-(3-(1-phenethyl-1H-pyrazol-4-yl)-1-tosyl-1H-pyrrolo[2,3-b]pyridin-5-yl)phenyl)piperidine-1-carboxylate (125 mg, 0.178 mmol) was hydrolyzed by lithium hydroxide (75 mg, 1.78 mmol) in THF/methanol/water (12/6/3 ml) to yield crude 87 mg (89% yield) of the titled compound. MS: m/z=548.3 (M+1).

Step-iii: 3-(1-phenethyl-1H-pyrazol-4-yl)-5-(4-(piperidin-4-yl)phenyl)-1H-pyrrolo[2,3-b]pyridine Using similar reaction conditions as described in step-ii of example-7, tert-butyl 4-(4-(3-(1-phenethyl-1H-pyrazol-4-yl)-1H-pyrrolo[2,3-b]pyridin-5-yl)phenyl)piperidine-1-carboxylate (85 mg, 0.155 mmol) was deprotected in TFA/toluene (2.5/5 ml). This afforded 14 mg (20.2% yield) of the titled compound. $^1$H NMR (CD$_3$OD, 300 MHz): δ 8.576-8.571 (d, 1H), 8.46-8.45 (d, 1H), 7.90 (s, 1H), 7.81 (s, 1H), 7.73-7.71 (m, 3H), 7.48-7.46 (d, 2H), 7.25-7.20 (m, 2H), 7.14-7.07 (m, 3H), 7.48-7.43 (t, 2H), 3.56-3.52 (d, 2H), 3.22-3.15 (m, 4H), 3.07-2.98 (dt, 1H), 2.17-2.13 (d, 2H), 2.06-1.91 (m, 2H). MS: m/z=448.4 (M+1), HPLC: 91.78% in method B.

Example 89

5-(4-(piperidin-4-yl)phenyl)-3-(1-(pyridin-3-ylmethyl)-1H-pyrazol-4-yl)-1H-pyrrolo[2,3-b]pyridine

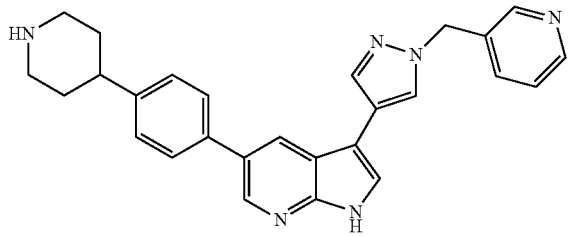 [SMILES: c1cncc(Cn2cc(-c3c[nH]c4ncc(-c5ccc(C6CCNCC6)cc5)cc34)cn2)c1]

Step-i: tert-butyl 4-(4-(3-(1-(pyridin-3-ylmethyl)-1H-pyrazol-4-yl)-1-tosyl-1H-pyrrolo[2,3-b]pyridin-5-yl)phenyl)piperidine-1-carboxylate Using similar reaction conditions as described in step-i of example-1, tert-butyl 4-(4-(3-iodo-1-tosyl-1H-pyrrolo[2,3-b]pyridin-5-yl)phenyl)piperidine-1-carboxylate (intermediate 67B) (200 mg, 0.304 mmol) was coupled with 3-((4-(4,4,5,5-tetramethyl-1,3,2-dioxaborolan-2-yl)-1H-pyrazol-1-yl)methyl)pyridine (intermediate 64) (104 mg, 0.364 mmol) using Pd(dppf)Cl$_2$ (11 mg, 0.015 mol) and sodium carbonate (97 mg, 0.912 mmol) in acetonitrile/water (3/1 ml) to afford 150 mg (72.0% yield) of the titled compound after column purification using 3% methanol in DCM as eluent.

Step-ii: tert-butyl 4-(4-(3-(1-(pyridin-3-ylmethyl)-1H-pyrazol-4-yl)-1H-pyrrolo[2,3-b]pyridin-5-yl)phenyl)piperidine-1-carboxylate Using similar reaction conditions as described in step-iii of example-1, tert-butyl 4-(4-(3-(1-(pyridin-3-ylmethyl)-1H-pyrazol-4-yl)-1-tosyl-1H-pyrrolo[2,3-b]pyridin-5-yl)phenyl)piperidine-1-carboxylate (150 mg, 0.217 mmol) was hydrolyzed by lithium hydroxide (27 mg, 0.653 mmol) in THF/methanol/water (3/3/3 ml) to yield crude 120 mg (crude) of the titled compound. MS: m/z=532.9 (M+1).

Step-iii: 5-(4-(piperidin-4-yl)phenyl)-3-(1-(pyridin-3-ylmethyl)-1H-pyrazol-4-yl)-1H-pyrrolo[2,3-b]pyridine Using similar reaction conditions as described in step-ii of example-7, tert-butyl 4-(4-(3-(1-(pyridin-3-ylmethyl)-1H-pyrazol-4-yl)-1H-pyrrolo[2,3-b]pyridin-5-yl)phenyl)piperidine-1-carboxylate (120 mg, 0.224 mmol) was deprotected in TFA/methanol (5/5 ml). This afforded 15 mg (12% yield) of the titled compound. $^1$H NMR (CD$_3$OD, 300 MHz): δ 8.76 (s, 2H), 8.56-8.55 (d, 2H), 8.36-8.34 (m, 2H), 8.02 (s, 1H), 7.95-7.91 (m, 1H), 7.75-7.72 (m, 3H), 7.45-7.42 (m, 2H), 5.66 (s, 2H), 3.56-3.51 (d, 2H), 3.22-3.14 (t, 2H), 3.10-2.99 (m, 1H), 2.16-2.11 (d, 2H), 2.03-1.93 (td, 2H). MS: m/z=435.2 (M+1), HPLC: 97.0% in method A.

Example 90

3-(1-(3-fluorobenzyl)-3-methyl-1H-pyrazol-4-yl)-5-(4-(piperidin-4-yl)phenyl)-1H-pyrrolo[2,3-b]pyridine

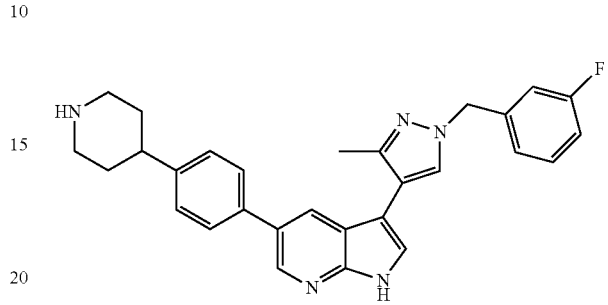

Step-i: tert-butyl 4-(4-(3-(1-(3-fluorobenzyl)-3-methyl-1H-pyrazol-4-yl)-1-tosyl-1H-pyrrolo[2,3-b]pyridin-5-yl)phenyl)piperidine-1-carboxylate Using similar reaction conditions as described in step-i of example-1, tert-butyl 4-(4-(3-iodo-1-tosyl-1H-pyrrolo[2,3-b]pyridin-5-yl)phenyl)piperidine-1-carboxylate (intermediate 67B) (120 mg, 0.182 mmol) was coupled with 1-(3-fluorobenzyl)-3-methyl-4-(4,4,5,5-tetramethyl-1,3,2-dioxaborolan-2-yl)-1H-pyrazole (intermediate 12) (64 mg, 0.200 mmol) using Pd(PPh$_3$)$_2$Cl$_2$ (6 mg, 0.009 mol) and sodium carbonate (58 mg, 0.547 mmol) in acetonitrile/water (3/2 ml) to afford 100 mg (76% yield) of the titled compound.

Step-ii: tert-butyl 4-(4-(3-(1-(3-fluorobenzyl)-3-methyl-1H-pyrazol-4-yl)-1H-pyrrolo[2,3-b]pyridin-5-yl)phenyl)piperidine-1-carboxylate Using similar reaction conditions as described in step-iii of example-1, tert-butyl 4-(4-(3-(1-(3-fluorobenzyl)-3-methyl-1H-pyrazol-4-yl)-1-tosyl-1H-pyrrolo[2,3-b]pyridin-5-yl)phenyl)piperidine-1-carboxylate (100 mg, 0.138 mmol) was hydrolyzed by lithium hydroxide (17 mg, 0.416 mmol) in THF/methanol/water (2/2/1 ml) to yield 100 mg (crude) of the titled compound.

Step-iii 3-(1-(3-fluorobenzyl)-3-methyl-1H-pyrazol-4-yl)-5-(4-(piperidin-4-yl)phenyl)-1H-pyrrolo[2,3-b]pyridine Using similar reaction conditions as described in step-ii of example-7, tert-butyl 4-(4-(3-(1-(3-fluorobenzyl)-3-methyl-1H-pyrazol-4-yl)-1H-pyrrolo[2,3-b]pyridin-5-yl)phenyl)piperidine-1-carboxylate (100 mg, 0.176 mmol) was deprotected in TFA/methanol (3/3 ml). This afforded 5 mg (152% yield) of the titled compound after purification by preparative HPLC along with one more isomer Example 91. $^1$H NMR (CD$_3$OD, 300 MHz): δ 8.51 (s, 1H), 8.24 (s, 1H), 7.80 (s, 1H), 7.72-7.67 (m, 2H), 7.51 (s, 1H), 7.42-7.34 (m, 3H), 7.06-6.87 (m, 3H), 5.46 (s, 2H), 3.61-3.51 (m, 2H), 3.21-3.13 (m, 2H), 3.02-2.94 (t, 1H), 2.37 (s, 3H), 2.15-2.11 (m, 2H), 2.02-1.89 (m, 2H). MS: m/z=466.2 (M+1), HPLC: 89.39% in method B.

Example 91

3-(1-(3-fluorobenzyl)-5-methyl-1H-pyrazol-4-yl)-5-(4-(piperidin-4-yl)phenyl)-1H-pyrrolo[2,3-b]pyridine

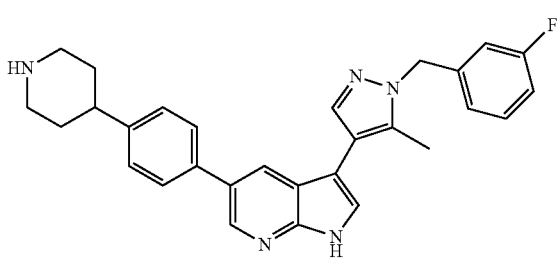 [SMILES: Cc1c(-c2c[nH]c3ncc(-c4ccc(C5CCNCC5)cc4)cc23)cnn1Cc1cccc(F)c1]

Yield 10 mg. ¹H NMR (CD₃OD, 300 MHz): δ 8.55 (s, 1H), 8.41-8.40 (m, 1H), 8.11 (s, 1H), 7.71-7.60 (m, 3H), 7.43-7.43 (m, 3H), 7.12-7.00 (m, 3H), 5.37 (s, 2H), 3.54-3.50 (d, 2H), 3.21-3.13 (t, 2H), 2.98-2.94 (m, 1H), 2.38 (s, 3H), 2.15-2.10 (d, 2H), 2.02-1.94 (m, 2H). MS: m/z=466.2 (M+1), HPLC: 92.74% in method A.

Example 92

3-(1-(3-fluorobenzyl)-3,5-dimethyl-1H-pyrazol-4-yl)-5-(4-(piperidin-4-yl)phenyl)-1H-pyrrolo[2,3-b]pyridine

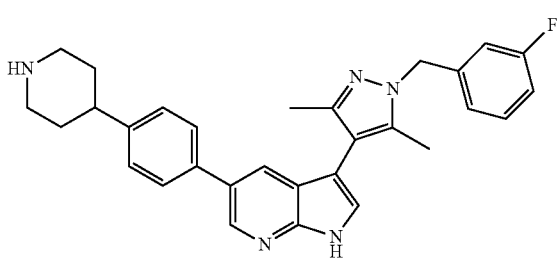 [SMILES: Cc1nn(Cc2cccc(F)c2)c(C)c1-c1c[nH]c2ncc(-c3ccc(C4CCNCC4)cc3)cc12]

Step-i: tert-butyl 4-(4-(3-(1-(3-fluorobenzyl)-3,5-dimethyl-1H-pyrazol-4-yl)-1-tosyl-1H-pyrrolo[2,3-b]pyridin-5-yl)phenyl)piperidine-1-carboxylate Using similar reaction conditions as described in step-i of example-1, tert-butyl 4-(4-(3-iodo-1-tosyl-1H-pyrrolo[2,3-b]pyridin-5-yl)phenyl)piperidine-1-carboxylate (intermediate 67B) (150 mg, 0.52 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (208 mg, 0.63 mmol) using Pd(PPh₃)₂Cl₂ (18 g, 1.56 mol) and sodium carbonate (165 mg, 1.56 mmol) in toluene/ethanol/water (10/10/2 ml) to afford 140 mg (83.6% yield) of the titled compound. MS: m/z=677.2 (M+1) (de t-butyl).

Step-ii: tert-butyl 4-(4-(3-(1-(3-fluorobenzyl)-3,5-dimethyl-1H-pyrazol-4-yl)-1H-pyrrolo[2,3-b]pyridin-5-yl)phenyl)piperidine-1-carboxylate Using similar reaction conditions as described in step-iii of example-1, tert-butyl 4-(4-(3-(1-(3-fluorobenzyl)-3,5-dim-ethyl-1H-pyrazol-4-yl)-1-tosyl-1H-pyrrolo[2,3-b]pyridin-5-yl)phenyl) piperidine-1-carboxylate (134 mg, 0.182 mmol) was hydrolyzed by lithium hydroxide (38 mg, 0.91 mmol) in THF/methanol/water (4/4/2 ml) to yield 103 mg (97.3% yield) of the titled compound. MS: m/z=580.3 (M+1).

Step-iii 3-(1-(3-fluorobenzyl)-3,5-dimethyl-1H-pyrazol-4-yl)-5-(4-(piperidin-4-yl)phenyl)-1H-pyrrolo[2,3-b]pyridine Using similar reaction conditions as described in step-ii of example-7, tert-butyl 4-(4-(3-(1-(3-fluorobenzyl)-3,5-dimethyl-1H-pyrazol-4-yl)-1H-pyrrolo[2,3-b]pyridin-5-yl)phenyl)piperidine-1-carboxylate (113 mg, 0.194 mmol) was deprotected in TFA/DCM (5/5 ml). This afforded 12 mg (12.9% yield) of the titled compound. ¹H NMR (CD₃OD, 300 MHz): δ 8.55 (s, 1H), 8.09-8.08 (d, 1H), 7.65-7.62 (m, 2H), 7.51 (s, 1H), 7.41-7.34 (m, 3H), 7.06-7.00 (m, 2H), 6.90-6.87 (s, 1H), 5.38 (s, 2H), 3.54-3.47 (m, 2H), 3.20-3.13 (m, 2H), 3.01-2.93 (m, 1H), 2.22 (s, 3H), 2.20 (s, 3H), 2.14-1.88 (m, 4H). MS: m/z=480.2 (M+1), HPLC: 98.73% in method B.

Example 93

5-(4-(piperidin-4-yl)phenyl)-3-(1-(pyridin-2-ylmethyl)-1H-pyrazol-4-yl)-1H-pyrrolo[2,3-b]pyridine

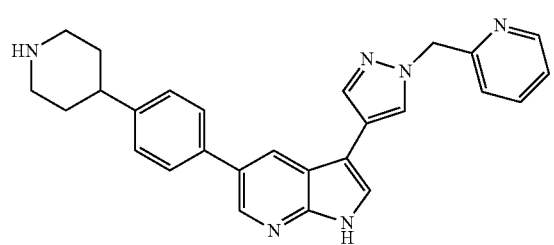 [SMILES: c1ccc(Cn2cc(-c3c[nH]c4ncc(-c5ccc(C6CCNCC6)cc5)cc34)cn2)nc1]

Step-i: tert-butyl 4-(4-(3-(1-(pyridin-2-ylmethyl)-1H-pyrazol-4-yl)-1-tosyl-1H-pyrrolo[2,3-b]pyridin-5-yl)phenyl)piperidine-1-carboxylate Using similar reaction conditions as described in step-i of example-1, tert-butyl 4-(4-(3-iodo-1-tosyl-1H-pyrrolo[2,3-b]pyridin-5-yl)phenyl)piperidine-1-carboxylate (intermediate 67B) (150 mg, 0.52 mmol) was coupled with 2-((4-(4,4,5,5-tetramethyl-1,3,2-dioxaborolan-2-yl)-1H-pyrazol-1-yl)methyl)pyridine (intermediate 64H) (180 mg, 0.63 mmol) using Pd(PPh₃)₂Cl₂ (18 mg, 0.026 mol) and sodium carbonate (165 mg, 1.56 mmol) in toluene/ethanol/water (10/10/2 ml) to afford 140 mg (97.2% yield) of the titled compound. MS: m/z=688.4 (M+1).

Step-ii: tert-butyl 4-(4-(3-(1-(pyridin-2-ylmethyl)-1H-pyrazol-4-yl)-1H-pyrrolo[2,3-b]pyridin-5-yl)phenyl)piperidine-1-carboxylate Using similar reaction conditions as described in step-iii of example-1, tert-butyl 4-(4-(3-(1-(pyridin-2-ylmethyl)-1H-pyrazol-4-yl)-1-tosyl-1H-pyrrolo[2,3-b]pyridin-5-yl)phenyl)piperidine-1-carboxylate (140 mg, 0.203 mmol) was hydrolyzed by lithium hydroxide (44 mg, 1.04 mmol) in THF/methanol/water (4/4/2 ml) to yield 110 mg (98.5% yield) of the titled compound. MS: m/z=535.3 (M+1).

Step-iii 5-(4-(piperidin-4-yl)phenyl)-3-(1-(pyridin-2-ylmethyl)-1H-pyrazol-4-yl)-1H-pyrrolo[2,3-b]pyridine Using similar reaction conditions as described in step-ii of example-7, tert-butyl 4-(4-(3-(1-(pyridin-2-ylmethyl)-1H-pyrazol-4-yl)-1H-pyrrolo[2,3-b]pyridin-5-yl)phenyl)piperidine-1-carboxylate (110 mg, 0.205 mmol) was deprotected in TFA/DCM (5/5 ml). This afforded 10 mg (11.1% yield) of the titled compound. ¹H NMR (CD₃OD, 300 MHz): δ 8.73 (s, 1H), 8.68-8.67 (d, 1H), 8.59 (s, 1H), 8.38 (s, 1H), 8.16-8.11 (t, 1H), 8.01 (s, 1H), 7.81 (s, 1H), 7.75-7.72 (d, 2H), 7.66-7.61 (t, 1H), 7.49-7.42 (m, 3H), 5.68 (s, 2H), 3.55-3.51 (d, 2H), 3.21-3.13 (m, 2H), 3.03-2.95 (m, 1H), 2.14-1.90 (m, 4H). MS: m/z=434.9 (M+1), HPLC: 92.12% in method A.

Example 94

N-(3-(3-(1-(3-fluorobenzyl)-3,5-dimethyl-1H-pyrazol-4-yl)-1H-pyrrolo[2,3-b]pyridin-5-yl)phenyl)piperidin-4-amine

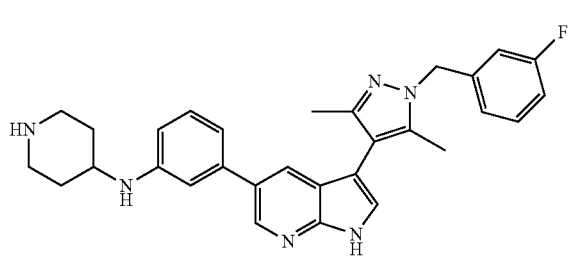 [SMILES: Cc1nn(Cc2cccc(F)c2)c(C)c1-c1c[nH]c2ncc(-c3cccc(NC4CCNCC4)c3)cc12]

Step-i: tert-butyl 4-((3-(3-(1-(3-fluorobenzyl)-3,5-dimethyl-1H-pyrazol-4-yl)-1-tosyl-1H-pyrrolo[2,3-b]pyridin-5-yl)phenyl)amino)piperidine-1-carboxylate Using similar reaction conditions as described in step-i of example-1, tert-butyl 4-((3-(3-iodo-1-tosyl-1H-pyrrolo[2,3-b]pyridin-5-yl)phenyl)amino)piperidine-1-carboxylate (intermediate 66E) (200 mg, 0.297 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (141 mg, 0.446 mmol) using Pd(PPh₃)₂Cl₂ (11 mg, 0.014 mmol) and sodium carbonate (79 mg, 0.744 mmol) in Toluene/ethanol/water (5/2/1 ml) to afford 150 mg (67.5% yield) of the titled compound after column purification using 1% methanol in DCM as eluent. MS: m/z=749.3 (M+1).

Step-ii: tert-butyl 4-((3-(3-(1-(3-fluorobenzyl)-3,5-dimethyl-1H-pyrazol-4-yl)-1H-pyrrolo[2,3-b]pyridin-5-yl)phenyl)amino)piperidine-1-carboxylate Using similar reaction conditions as described in step-iii of example-1, tert-butyl 4-((3-(3-(1-(3-fluorobenzyl)-3,5-dimethyl-1H-pyrazol-4-yl)-1-tosyl-1H-pyrrolo[2,3-b]pyridin-5-yl)phenyl)amino)piperidine-1-carboxylate (150 mg, 0.200 mmol) was hydrolyzed by lithium hydroxide (17 mg, 0.401 mmol) in THF/methanol/water (5/1/1 ml) to yield 80 mg (67.2% yield) of the titled compound after column purification using 2% methanol in DCM as eluent. MS: m/z=594.8 (M+1).

Step-iii: N-(3-(3-(1-(3-fluorobenzyl)-3,5-dimethyl-1H-pyrazol-4-yl)-1H-pyrrolo[2,3-b]pyridin-5-yl)phenyl)piperidin-4-amine Using similar reaction conditions as described in step-ii of example-7, tert-butyl 4-((3-(3-(1-(3-fluorobenzyl)-3,5-dimethyl-1H-pyrazol-4-yl)-1H-pyrrolo[2,3-b]pyridin-5-yl)phenyl)amino piperidine-1-carboxylate (80 mg, 0.134 mmol) was deprotected in HCl in methanol (5 ml). This afforded 16 mg (20.4% yield) of the titled compound. ¹H NMR (CD₃OD, 400 MHz): δ 8.8-8.6 (bs, 1H), 8.37 (s, 1H), 7.67 (s, 1H), 7.41-7.35 (m, 2H), 7.12-7.10 (m, 2H), 7.06-7.04 (m, 2H), 6.94-6.90 (m, 2H), 5.41 (s, 2H), 3.85-3.70 (m, 1H), 3.50-3.47 (m, 2H), 3.18-3.12 (t, 2H), 2.29-2.24 (m, 8H), 1.79-1.76 (m, 2H). MS: m/z=495.3 (M+1), HPLC: 85.03% in method A.

Example 95

N-(3-(3-(1-phenethyl-1H-pyrazol-4-yl)-1H-pyrrolo[2,3-b]pyridin-5-yl)phenyl)piperidin-4-amine

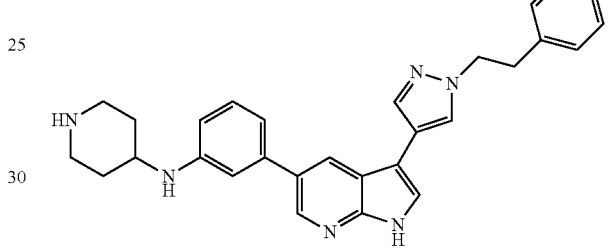

Step-i: tert-butyl 4-((3-(3-(1-phenethyl-1H-pyrazol-4-yl)-1-tosyl-1H-pyrrolo[2,3-b]pyridin-5-yl)phenyl)amino)piperidine-1-carboxylate Using similar reaction conditions as described in step-i of example-1, tert-butyl 4-((3-(3-iodo-1-tosyl-1H-pyrrolo[2,3-b]pyridin-5-yl)phenyl)amino)piperidine-1-carboxylate (intermediate 66E) (200 mg, 0.297 mmol) was coupled with 1-phenethyl-4-(4,4,5,5-tetramethyl-1,3,2-dioxaborolan-2-yl)-1H-pyrazole (intermediate 59) (133 mg, 0.446 mmol) using Pd(PPh₃)₂Cl₂ (11 mg, 0.014 mmol) and sodium carbonate (79 mg, 0.744 mmol) in toluene/ethanol/water (5/2/1 ml) to afford 150 mg (70.4% yield) of the titled compound after column purification using 1% methanol in DCM as eluent. MS: m/z=717.3 (M+1).

Step-ii: tert-butyl 4-((3-(3-(1-phenethyl-1H-pyrazol-4-yl)-1H-pyrrolo[2,3-b]pyridin-5-yl)phenyl)amino)piperidine-1-carboxylate Using similar reaction conditions as described in step-iii of example-1, tert-butyl 4-((3-(3-(1-phenethyl-1H-pyrazol-4-yl)-1-tosyl-1H-pyrrolo[2,3-b]pyridin-5-yl)phenyl)amino)piperidine-1-carboxylate (150 mg, 0.209 mmol) was hydrolyzed by lithium hydroxide (18 mg, 0.418 mmol) in THF/methanol/water (5/1/1 ml) to yield 80 mg (67.7% yield) of the titled compound after column purification using 2% methanol in DCM as eluent. MS: m/z=562.9 (M+1).

Step-iii: N-(3-(3-(1-phenethyl-1H-pyrazol-4-yl)-1H-pyrrolo[2,3-b]pyridin-5-yl)phenyl)piperidin-4-amine Using similar reaction conditions as described in step-ii of example-7, tert-butyl 4-((3-(3-(1-phenethyl-1H-pyrazol-4- yl)-1H-pyrrolo[2,3-b]pyridin-5-yl)phenyl)amino)piperidine-1-carboxylate (80 mg, 0.142 mmol) was deprotected in HCl in methanol (5 ml). This afforded 18 mg (21.9% yield) of the titled compound. ¹H NMR (CD₃OD, 400 MHz): δ 8.55 (s, 1H), 8.435-8.431 (d, 1H), 7.91 (s, 1H), 7.81 (s, 1H), 7.71 (s, 1H), 7.39-7.32 (t, 1H), 7.29-7.20 (t, 2H), 7.16-7.13 (m, 2H), 7.04-7.03 (m, 2H), 6.85-6.80 (d, 1H), 4.49-4.46 (t, 2H), 3.85-3.75 (m, 1H), 3.52-3.49 (m, 2H), 3.22-3.19 (m, 4H), 2.35-2.25 (dd, 2H), 1.80-1.65 (m, 2H). MS: m/z=463.3 (M+1), HPLC: 90.63% in method A.

Example 96

3-(1-(3-fluorobenzyl)-3,5-dimethyl-1H-pyrazol-4-yl)-5-(3-(piperidin-4-yloxy)phenyl)-1H-pyrrolo[2,3-b]pyridine

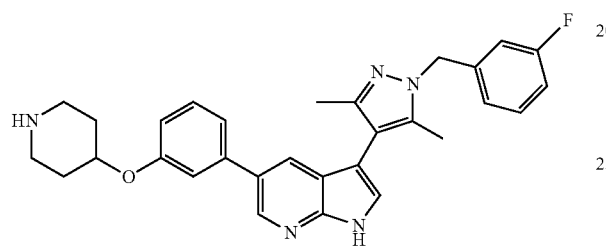

Step-i: tert-butyl 4-(3-(3-(1-(3-fluorobenzyl)-3,5-dimethyl-1H-pyrazol-4-yl)-1-tosyl-1H-pyrrolo[2,3-b]pyridin-5-yl)phenoxy)piperidine-1-carboxylate Using similar reaction conditions as described in step-i of example-1, tert-butyl 4-(3-(3-iodo-1-tosyl-1H-pyrrolo[2,3-b]pyridin-5-yl)phenoxy)piperidine-1-carboxylate (intermediate 13) (150 mg, 0.222 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (106 mg, 0.334 mmol) using Pd(PPh₃)₂Cl₂ (8 mg, 0.011 mmol) and sodium carbonate (59 mg, 0.557 mmol) in toluene/ethanol/water (4/1/1 ml) to afford 120 mg (71.8% yield) of the titled compound after column purification using 1% methanol in DCM as eluent. MS: m/z=750.4 (M+1).

Step-ii: tert-butyl 4-(3-(3-(1-(3-fluorobenzyl)-3,5-dimethyl-1H-pyrazol-4-yl)-1H-pyrrolo[2,3-b]pyridin-5-yl)phenoxy)piperidine-1-carboxylate Using similar reaction conditions as described in step-iii of example-1, tert-butyl 4-(3-(3-(1-(3-fluorobenzyl)-3,5-dimethyl-1H-pyrazol-4-yl)-1-tosyl-1H-pyrrolo[2,3-b]pyridin-5-yl)phenoxy) piperidine-1-carboxylate (120 mg, 0.160 mmol) was hydrolyzed by lithium hydroxide (14 mg, 0.320 mmol) in THF/methanol/water (5/1/1 ml) to yield 80 mg (84.2% yield) of the titled compound after column purification using 2% methanol in DCM as eluent. MS: m/z=595.8 (M+1).

Step-iii: 3-(1-(3-fluorobenzyl)-3,5-dimethyl-1H-pyrazol-4-yl)-5-(3-(piperidin-4-yloxy)phenyl)-1H-pyrrolo[2,3-b]pyridine Using similar reaction conditions as described in step-ii of example-7, tert-butyl 4-(3-(3-(1-(3-fluorobenzyl)-3,5-dimethyl-1H-pyrazol-4-yl)-1H-pyrrolo[2,3-b]pyridin-5-yl)phenoxy)piperidine-1-carboxylate (80 mg, 0.134 mmol) was deprotected in HCl in methanol (5 ml). This afforded 33 mg (40.2% yield) of the titled compound. ¹H NMR (CD₃OD, 400 MHz): δ 8.75-8.60 (bs, 1H), 8.37 (s, 1H), 7.66 (s, 1H), 7.48-7.44 (t, 1H), 7.42-7.37 (q, 1H), 7.33-7.29 (m, 2H), 7.11-7.04 (m, 3H), 6.93-6.91 (d, 1H), 5.41 (s, 2H), 4.85-4.82 (m, 1H), 3.48-3.41 (m, 2H), 3.28-3.23 (m, 2H), 2.25-2.28 (m, 8H), 2.12-2.06 (m, 2H). MS: m/z=496.3 (M+1), HPLC: 96.84% in method A.

Example 97

3-(1-phenethyl-1H-pyrazol-4-yl)-5-(3-(piperidin-4-yloxy)phenyl)-1H-pyrrolo[2,3-b]pyridine

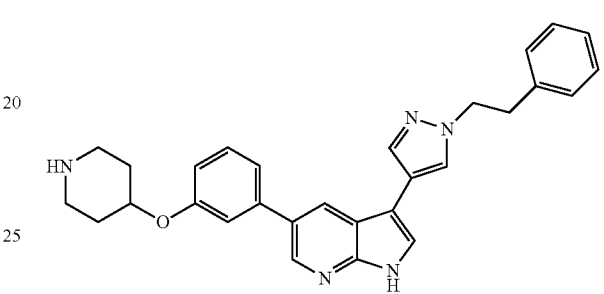

Step-i: tert-butyl 4-(3-(3-(1-phenethyl-1H-pyrazol-4-yl)-1-tosyl-1H-pyrrolo[2,3-b]pyridin-5-yl) phenoxy) piperidine-1-carboxylate Using similar reaction conditions as described in step-i of example-1, tert-butyl 4-(3-(3-iodo-1-tosyl-1H-pyrrolo[2,3-b]pyridin-5-yl)phenoxy)piperidine-1-carboxylate (intermediate 13) (150 mg, 0.222 mmol) was coupled with 1-phenethyl-4-(4,4,5,5-tetramethyl-1,3,2-dioxaborolan-2-yl)-1H-pyrazole (intermediate 59) (100 mg, 0.334 mmol) using Pd(PPh₃)₂Cl₂ (8 mg, 0.011 mmol) and sodium carbonate (59 mg, 0.557 mmol) in toluene/ethanol/water (4/1/1 ml) to afford 120 mg (75.0% yield) of the titled compound after column purification using 1% methanol in DCM as eluent. MS: m/z=718.4 (M+1).

Step-ii: tert-butyl 4-(3-(3-(1-phenethyl-1H-pyrazol-4-yl)-1H-pyrrolo[2,3-b]pyridin-5-yl)phenoxy) piperidine-1-carboxylate Using similar reaction conditions as described in step-iii of example-1, tert-butyl 4-(3-(3-(1-phenethyl-1H-pyrazol-4-yl)-1-tosyl-1H-pyrrolo[2,3-b]pyridin-5-yl)phenoxy)piperidine-1-carboxylate (120 mg, 0.167 mmol) was hydrolyzed by lithium hydroxide (14 mg, 0.334 mmol) in THF/methanol/water (5/1/1 ml) to yield 80 mg (85.1% yield) of the titled compound after column purification using 2% methanol in DCM as eluent. MS: m/z=563.8 (M+1).

Step-iii: 3-(1-phenethyl-1H-pyrazol-4-yl)-5-(3-(piperidin-4-yloxy)phenyl)-1H-pyrrolo[2,3-b]pyridine Using similar reaction conditions as described in step-ii of example-7, tert-butyl 4-(3-(3-(1-phenethyl-1H-pyrazol-4-yl)-1H-pyrrolo[2,3-b]pyridin-5-yl)phenoxy)piperidine-1-carboxylate (80 mg, 0.142 mmol) was deprotected in HCl in methanol (5 ml). This afforded 31 mg (37.7% yield) of the titled compound after purification by preparative HPLC. ¹H NMR (CD$_3$OD, 400 MHz): δ 8.70-8.50 (bs, 1H), 8.32 (s, 1H), 7.89 (s, 1H), 7.79 (s, 1H), 7.65 (s, 1H), 7.52-7.45 (t, 1H), 7.39-7.30 (m, 2H), 7.29-7.20 (t, 2H), 7.19-7.09 (m, 4H), 4.85-4.75 (m, 1H), 4.49-4.45 (t, 2H), 3.51-3.49 (m, 2H), 3.30-3.10 (m, 4H), 2.30-2.10 (m, 4H). MS: m/z=464.3 (M+1), HPLC: 95.43% in method A.

Example 98

3-(1-phenethyl-1H-pyrazol-4-yl)-5-(3-(piperidin-4-ylmethyl)phenyl)-1H-pyrrolo[2,3-b]pyridine

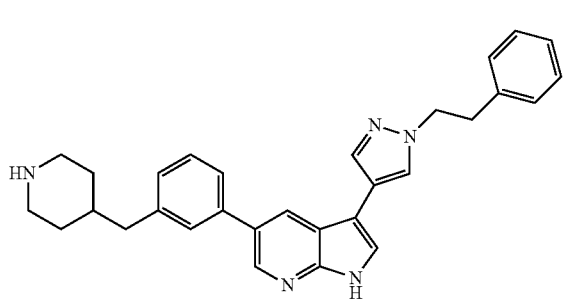 [SMILES: c1ccc(CCn2cc(-c3c[nH]c4ncc(-c5cccc(CC6CCNCC6)c5)cc34)cn2)cc1]

Step-i: tert-butyl 4-(3-(3-(1-phenethyl-1H-pyrazol-4-yl)-1-tosyl-1H-pyrrolo[2,3-b]pyridin-5-yl)benzyl)piperidine-1-carboxylate Using similar reaction conditions as described in step-i of example-1, tert-butyl 4-(3-(3-iodo-1-tosyl-1H-pyrrolo[2,3-b]pyridin-5-yl)benzyl)piperidine-1-carboxylate (intermediate 66G) (100 mg, 0.148 mmol) was coupled with 1-phenethyl-4-(4,4,5,5-tetramethyl-1,3,2-dioxaborolan-2-yl)-1H-pyrazole (intermediate 59) (67 mg, 0.223 mmol) using Pd(PPh$_3$)$_2$Cl$_2$ (6 mg, 0.007 mmol) and sodium carbonate (40 mg, 0.372 mmol) in toluene/ethanol/water (5/2/1 ml) to afford 90 mg (84.1% yield) of the titled compound after column purification using 50% ethyl acetate in hexane as eluent. MS: m/z=659.8 (M+1) (de t-butyl).

Step-ii: tert-butyl 4-(3-(3-(1-phenethyl-1H-pyrazol-4-yl)-1H-pyrrolo[2,3-b]pyridin-5-yl)benzyl) piperidine-1-carboxylate Using similar reaction conditions as described in step-iii of example-1, tert-butyl 4-(3-(3-(1-phenethyl-1H-pyrazol-4-yl)-1-tosyl-1H-pyrrolo[2,3-b]pyridin-5-yl)benzyl)piperidine-1-carboxylate (90 mg, 0.128 mmol) was hydrolyzed by lithium hydroxide (11 mg, 0.251 mmol) in THF/methanol/water (5/1/1 ml) to yield 60 mg (52.3% yield) of the titled compound after column purification using 2% methanol in DCM as eluent. MS: m/z=561.9 (M+1).

Step-iii: 3-(1-phenethyl-1H-pyrazol-4-yl)-5-(3-(piperidin-4-ylmethyl)phenyl)-1H-pyrrolo[2,3-b]pyridine Using similar reaction conditions as described in step-ii of example-7, tert-butyl 4-(3-(3-(1-phenethyl-1H-pyrazol-4-yl)-1H-pyrrolo[2,3-b]pyridin-5-yl)benzyl)piperidine-1-carboxylate (60 mg, 0.106 mmol) was deprotected in HCl in methanol (5 ml). This afforded 20 mg (32.4% yield) of the titled compound. $^1$H NMR (CD$_3$OD, 400 MHz): δ 8.65-8.60 (bs, 1H), 8.52 (s, 1H), 7.92 (s, 1H), 7.87 (s, 1H), 7.74 (s, 1H), 7.61-7.58 (d, 2H), 7.53-7.41 (t, 1H), 7.33-7.26 (d, 1H), 7.26- 7.22 (t, 2H), 7.15-7.09 (m, 3H), 4.49-4.45 (t, 2H), 3.41-3.38 (d, 2H), 3.22-3.18 (t, 2H), 2.99-2.93 (t, 2H), 2.77-2.76 (d, 2H), 2.01-1.90 (m, 3H), 1.56-1.46 (m, 2H). MS: m/z=462.7 (M+1), HPLC: 88.14% in method A.

Example 99

3-(1-(3-fluorobenzyl)-3,5-dimethyl-1H-pyrazol-4-yl)-5-(3-(piperidin-4-ylmethyl)phenyl)-1H-pyrrolo[2,3-b]pyridine

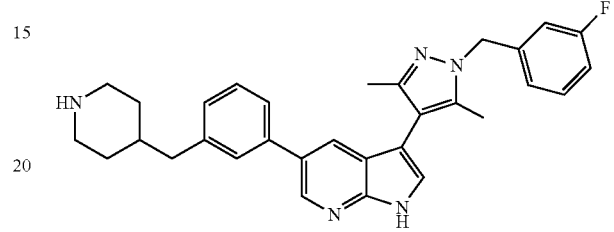

Step-i: tert-butyl 4-(3-(3-(1-(3-fluorobenzyl)-3,5-dimethyl-1H-pyrazol-4-yl)-1-tosyl-1H-pyrrolo[2,3-b]pyridin-5-yl)benzyl)piperidine-1-carboxylate Using similar reaction conditions as described in step-i of example-1, tert-butyl 4-(3-(3-iodo-1-tosyl-1H-pyrrolo[2,3-b]pyridin-5-yl)benzyl)piperidine-1-carboxylate (intermediate 66G) (100 mg, 0.148 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (74 mg, 0.223 mmol) using Pd(PPh$_3$)$_2$Cl$_2$ (6 mg, 0.007 mmol) and sodium carbonate (40 mg, 0.372 mmol) in toluene/ethanol/water (6/5/2 ml) to afford 100 mg (90.1% yield) of the titled compound after column purification using 50% ethyl acetate in hexane as eluent. MS: m/z=747.8 (M+1).

Step-ii: tert-butyl 4-(3-(3-(1-(3-fluorobenzyl)-3,5-dimethyl-1H-pyrazol-4-yl)-1H-pyrrolo[2,3-b]pyridin-5-yl)benzyl)piperidine-1-carboxylate Using similar reaction conditions as described in step-iii of example-1, tert-butyl 4-(3-(3-(1-(3-fluorobenzyl)-3,5-dimethyl-1H-pyrazol-4-yl)-1-tosyl-1H-pyrrolo[2,3-b]pyridin-5-yl)benzyl) piperidine-1-carboxylate (100 mg, 0.133 mmol) was hydrolyzed by lithium hydroxide (12 mg, 0.267 mmol) in THF/methanol/water (5/1/1 ml) to yield 60 mg (75.4% yield) of the titled compound after column purification using 2% methanol in DCM as eluent. MS: m/z=593.9 (M+1).

Step-iii: 3-(1-(3-fluorobenzyl)-3,5-dimethyl-1H-pyrazol-4-yl)-5-(3-(piperidin-4-ylmethyl)phenyl)-1H-pyrrolo[2,3-b]pyridine Using similar reaction conditions as described in step-ii of example-7, tert-butyl 4-(3-(3-(1-(3-fluorobenzyl)-3,5-dimethyl-1H-pyrazol-4-yl)-1H-pyrrolo[2,3-b]pyridin-5-yl)benzyl)piperidine-1-carboxylate (60 mg, 0.101 mmol) was deprotected in HCl in methanol (5 ml). This afforded 25 mg (40.6% yield) of the titled compound. $^1$H NMR (CD$_3$OD, 400 MHz): δ 8.67 (s, 1H), 8.34 (s, 1H), 7.66 (s, 1H), 7.56-7.54 (m, 2H), 7.48-7.38 (m, 2H), 7.30-7.28 (d, 1H), 7.08-7.04 (m, 2H), 6.93-6.91 (d, 1H), 5.42 (s, 2H), 3.40-3.37 (d, 2H), 2.98-2.92

(t, 2H), 2.74-2.72 (d, 2H), 2.25-2.23 (d, 6H), 2.10-1.90 (m, 3H), 1.53-1.47 (m, 2H). MS: m/z=494.3 (M+1), HPLC: 95.16% in method A.

Example 100

N-(4-(3-(1-(3-fluorobenzyl)-1H-pyrazol-4-yl)-1H-pyrrolo[2,3-b]pyridin-5-yl)phenyl)piperidin-4-amine

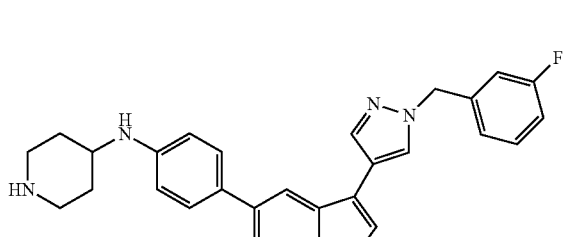

Step-i: tert-butyl 4-((4-(3-(1-(3-fluorobenzyl)-1H-pyrazol-4-yl)-1-tosyl-1H-pyrrolo[2,3-b]pyridin-5-yl)phenyl)amino)piperidine-1-carboxylate Using similar reaction conditions as described in step-ii of example-1, 5-bromo-3-(1-(3-fluorobenzyl)-1H-pyrazol-4-yl)-1-tosyl-1H-pyrrolo[2,3-b]pyridine (compound of Step-i of example 9) (150 mg, 0.280 mmol) was coupled with tert-butyl 4-((4-(4,4,5,5-tetramethyl-1,3,2-dioxaborolan-2-yl)phenyl)amino)piperidine-1-carboxylate (Intermediate 68)(137 mg, 0.34 mmol) using sodium carbonate (79 mg, 0.75 mmol) and Pd(PPh$_3$)$_2$Cl$_2$ (10 mg, 0.014 mmol) in DME/water (20/2 mL). This afforded 130 mg (63.4% yield) after purification by column (Silica gel 6/120) using 50% EtOAc/DCM as eluent. MS: m/z=720.8 (M+1).

Step-ii: tert-butyl 4-((4-(3-(1-(3-fluorobenzyl)-1H-pyrazol-4-yl)-1H-pyrrolo[2,3-b]pyridin-5-yl)phenyl)amino)piperidine-1-carboxylate Using similar reaction conditions as described in step-iii of example-1, tert-butyl 4-((4-(3-(1-(3-fluorobenzyl)-1H-pyrazol-4-yl)-1-tosyl-1H-pyrrolo[2,3-b]pyridin-5-yl)phenyl)amino)piperidine-1-carboxylate (130 mg, 0.18 mmol) was hydrolyzed with lithium hydroxide (37 mg, 0.9 mmol) in THF/methanol/water (2/2/1 mL) to yield 60 mg (58.8% yield) after purification by preparative TLC (Silicagel-1000 micron) using 3% methanol in chloroform as eluent. MS: m/z=566.8 (M+1).

Step-iii: N-(4-(3-(1-(3-fluorobenzyl)-1H-pyrazol-4-yl)-1H-pyrrolo[2,3-b]pyridin-5-yl)phenyl) piperidin-4-amine Using similar reaction conditions as described in step-ii of example-7, tert-butyl 4-((4-(3-(1-(3-fluorobenzyl)-1H-pyrazol-4-yl)-1H-pyrrolo[2,3-b]pyridin-5-yl)phenyl)amino)piperidine-1-carboxylate (60 mg, 0.10 mmol) was deprotected in methanol/ether HCl (3.0/0.3 ml). This afforded 40 mg (75.4% yield) of the titled. $^1$H NMR (CD$_3$OD, 400 MHz): δ 9.01-9.00 (d, 1H), 8.71-8.70 (d, 1H), 8.39 (s, 1H), 8.05 (s, 1H), 7.95 (s, 1H), 7.90-7.87 (m, 2H), 7.37-7.34 (m, 3H), 7.14-7.12 (s, 1H), 7.04-7.01 (m, 2H), 5.46 (s, 2H), 3.95-3.85 (m, 1H), 3.54-3.51 (d, 2H), 3.81-3.72 (t, 2H), 3.30-3.26 (d, 2H), 2.00-1.90 (m, 2H). MS: m/z=466.9 (M+1), HPLC: 96.60% in method A.

Example 101

N-(4-(3-(1-(3-fluorobenzyl)-3,5-dimethyl-1H-pyrazol-4-yl)-1H-pyrrolo[2,3-b]pyridin-5-yl)phenyl)piperidin-4-amine

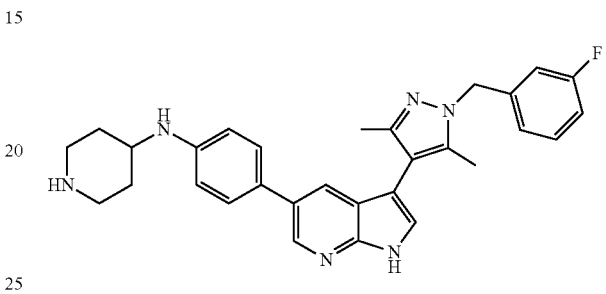

Step-i: tert-butyl 5-(4-((tert-butoxycarbonyl)(1-(tert-butoxycarbonyl)piperidin-4-yl)amino)phenyl)-3-(1-(3-fluorobenzyl)-3,5-dimethyl-1H-pyrazol-4-yl)-1H-pyrrolo[2,3-b]pyridine-1-carboxylate Using similar reaction conditions as described in step-i of example-1, tert-butyl 5-(4-((tert-butoxycarbonyl)(1-(tert-butoxycarbonyl)piperidin-4-yl)amino)phenyl)-3-iodo-1H-pyrrolo[2,3-b]pyridine-1-carboxylate (intermediate 66H) (150 mg, 0.20 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (89 mg, 0.27 mmol) using Pd(dppf)Cl$_2$ (8 mg, 0.01 mmol) and sodium carbonate (63 mg, 0.6 mmol) in toluene/ethanol/water (20/10/5 ml) to afford 40 mg (25.3% yield) of the titled compound after column purification using 35% ethyl acetate in hexane as eluent. MS: m/z=694.9 (M-Boc+1).

Step-ii: N-(4-(3-(1-(3-fluorobenzyl)-3,5-dimethyl-1H-pyrazol-4-yl)-1H-pyrrolo[2,3-b]pyridin-5-yl)phenyl)piperidin-4-amine Using similar reaction conditions as described in step-ii of example-7, tert-butyl 5-(4-((tert-butoxycarbonyl)(1-(tert-butoxycarbonyl)piperidin-4-yl)amino)phenyl)-3-(1-(3-fluorobenzyl)-3,5-dimethyl-1H-pyrazol-4-yl)-1H-pyrrolo[2,3-b]pyridine-1-carboxylate (25 mg, 0.050 mmol) was deprotected in methanol/ether HCl (3/2 ml). This afforded 5 mg (31.2% yield) of the titled compound. $^1$H NMR (CD$_3$OD, 400 MHz): δ 8.70 (s, 1H), 8.59 (s, 1H), 7.80 (s, 1H), 7.72-7.70 (d, 2H), 7.46-7.40 (m, 1H), 7.02-7.18 (d, 2H), 7.12-7.09 (m, 2H), 7.02-7.00 (d, 1H), 5.51 (s, 2H), 3.85-3.80 (m, 1H), 3.52-3.47 (d, 2H), 3.20-3.10 (t, 2H), 2.33-2.13 (m, 8H), 2.13-1.83 (m, 2H). MS: m/z=494.9 (M+1), HPLC: 95.22% in method B.

Example 102

3-(1-(3-fluorobenzyl)-1H-pyrazol-4-yl)-5-(3-(piperidin-4-ylmethyl)phenyl)-1H-pyrrolo[2,3-b]pyridine

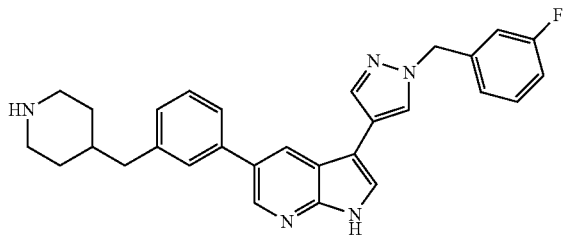 [SMILES: Fc1cccc(Cn2cc(-c3c[nH]c4ncc(-c5cccc(CC6CCNCC6)c5)cc34)cn2)c1]

Step-i: tert-butyl 4-(3-(3-(1-(3-fluorobenzyl)-1H-pyrazol-4-yl)-1-tosyl-1H-pyrrolo[2,3-b]pyridin-5-yl)benzyl)piperidine-1-carboxylate Using similar reaction conditions as described in step-i of example-1, tert-butyl 4-(3-(3-iodo-1-tosyl-1H-pyrrolo[2,3-b]pyridin-5-yl)benzyl)piperidine-1-carboxylate (intermediate 66G) (300 mg, 0.44 mmol) was coupled with 1-(3-fluorobenzyl)-4-(4,4,5,5-tetramethyl-1,3,2-dioxaborolan-2-yl)-1H-pyrazole (intermediate 11) (170 mg, 0.58 mmol) using Pd(DPPF)Cl$_2$ (15 mg, 0.02 mmol) and sodium carbonate (140 mg, 1.32 mmol) in toluene/ethanol/water (15/8/4 ml) to afford 200 mg (62.3% yield) of the titled compound after column purification using 30% ethyl acetate in hexane as eluent. MS: m/z=720.3 (M+1).

Step-ii: tert-butyl 4-(3-(3-(1-(3-fluorobenzyl)-1H-pyrazol-4-yl)-1H-pyrrolo[2,3-b]pyridin-5-yl)benzyl)piperidine-1-carboxylate Using similar reaction conditions as described in step-iii of example-1, tert-butyl 4-(3-(3-(1-(3-fluorobenzyl)-1H-pyrazol-4-yl)-1H-pyrrolo[2,3-b]pyridin-5-yl)benzyl)piperidine-1-carboxylate (200 mg, 0.277 mmol) was hydrolyzed by lithium hydroxide (116 mg, 2.77 mmol) in THF/methanol/water (10/10/5 ml) to yield 50 mg (31.8% yield) of the titled compound. MS: m/z=566.2 (M+1).

Step-iii: 3-(1-(3-fluorobenzyl)-1H-pyrazol-4-yl)-5-(3-(piperidin-4-ylmethyl)phenyl)-1H-pyrrolo[2,3-b]pyridine Using similar reaction conditions as described in step-ii of example-7, tert-butyl 4-(3-(3-(1-(3-fluorobenzyl)-1H-pyrazol-4-yl)-1H-pyrrolo[2,3-b]pyridin-5-yl)benzyl)piperidine-1-carboxylate (50 mg, 0.088 mmol) was deprotected in methanol/ether HCl (5/1 ml). This afforded 40 mg (90.9% yield) of the titled compound. $^1$H NMR (DMSO-d$_6$, 300 MHz): δ 11.9 (s, 1H), 8.75-8.65 (bs, 1H), 8.53-8.52 (d, 1H), 8.42-8.38 (m, 2H), 7.98 (s, 1H), 7.78-7.77 (d, 2H), 7.62-7.57 (m, 2H), 7.43-7.35 (m, 2H), 7.19-7.05 (m, 4H), 5.40 (s, 2H), 3.23-3.18 (d, 2H), 2.80-2.54 (m, 5H), 2.25-2.15 (bs, 1H), 1.76-1.71 (d, 2H), 1.45-1.30 (m, 2H). MS: m/z=466.2 (M+1), HPLC: 97.04% in method A.

Example 102A (S)-1-(4-(5-(3-(1-(3-fluorobenzyl)-1H-pyrazol-4-yl)-1H-pyrrolo[2,3-b]pyridin-5-yl)pyridin-2-yl)piperidin-1-yl)propan-2-ol

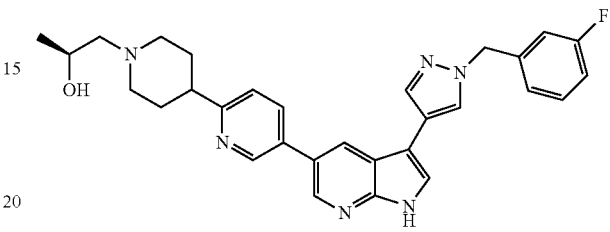

Step-i: tert-butyl 5-(3-(1-(3-fluorobenzyl)-1H-pyrazol-4-yl)-1-tosyl-1H-pyrrolo[2,3-b]pyridin-5-yl)-5',6'-dihydro-[2,4'-bipyridine]-1'(21H)-carboxylate Using similar reaction conditions as described in step-i of example-1, tert-butyl 5-(3-iodo-1-tosyl-1H-pyrrolo[2,3-b]pyridin-5-yl)-5',6'-dihydro-[2,4'-bipyridine]-1'(21H)-carboxylate (intermediate 66I) (225 mg, 0.342 mmol) was coupled with 1-(3-fluorobenzyl)-4-(4,4,5,5-tetramethyl-1,3,2-dioxaborolan-2-yl)-1H-pyrazole (intermediate 11) (155 mg, 0.513 mmol) using Pd(dppf) Cl$_2$ (13 mg, 0.017 mol) and sodium carbonate (109 mg, 0.017 mmol) in toluene/ethanol/water (20/10/4 ml) to afford 127 mg (47% yield) of the titled.

Step-ii: tert-butyl 4-(4-(3-(1-(3-fluorobenzyl)-1H-pyrazol-4-yl)-1-tosyl-1H-pyrrolo[2,3-b]pyridin-5-yl)phenyl)piperidine-1-carboxylate Using similar reaction conditions as described in step-ii of example-82, tert-butyl 5-(3-(1-(3-fluorobenzyl)-1H-pyrazol-4-yl)-1-tosyl-1H-pyrrolo[2,3-b]pyridin-5-yl)-5',6'-dihydro-[2,4'-bipyridine]-1'(21H)-carboxylate (100 mg, 0.141 mmol) was reduced with palladium hydroxide (25 mg) in ethyl acetate/ethanol 12/12 mL to get 96 mg (96.0% yield) of the titled compound. MS: m/z=706.3 (M+1).

Step-iii: 3-(1-(3-fluorobenzyl)-1H-pyrazol-4-yl)-5-(6-(piperidin-4-yl)pyridin-3-yl)-1-tosyl-1H-pyrrolo[2,3-b]pyridine hydrochloride Using similar reaction conditions as described in step-ii of example-7, tert-butyl 4-(4-(3-(1-(3-fluorobenzyl)-1H-pyrazol-4-yl)-1-tosyl-1H-pyrrolo[2,3-b]pyridin-5-yl)phenyl)piperidine-1-carboxylate (96 mg, 0.135 mmol) was deprotected in HCl in dioxane/MeOH (5/5 ml). This afforded 87 mg (99% yield) of the titled compound. MS: m/z=607.2 (M+1).

Step-iv: (S)-1-(4-(5-(3-(1-(3-fluorobenzyl)-1H-pyrazol-4-yl)-1-tosyl-1H-pyrrolo[2,3-b]pyridin-5-yl)pyridin-2-yl)piperidin-1-yl)propan-2-ol Using similar reaction conditions as described in step-i of example-82A, 3-(1-(3-fluorobenzyl)-1H-pyrazol-4-yl)-5-(6-(piperidin-4-yl)pyridin-3-yl)-1-tosyl-1H-pyrrolo[2,3-b]pyridine hydrochloride (85 mg. 0.132 mmol) was alkylated using (S)-2-methyloxirane (16 mg, 0.264 mmol), DIPEA (68 mg, 0.528 mmol) and ethanol (5 mL) to get 86 mg (97.8% yield) of the titled compound. MS: m/z=665.2 (M+1).

Step-v: (S)-1-(4-(5-(3-(1-(3-fluorobenzyl)-1H-pyrazol-4-yl)-1H-pyrrolo[2,3-b]pyridin-5-yl)pyridin-2-yl)piperidin-1-yl)propan-2-ol Using similar reaction conditions as described in step-iii of example-1, (S)-1-(4-(5-(3-(1-(3-fluorobenzyl)-1H-pyrazol-4-yl)-1-tosyl-1H-pyrrolo[2,3-b]pyridin-5-yl)pyridin-2-yl)piperidin-1-yl)propan-2-ol (86 mg, 0.129 mmol) was hydrolyzed by lithium hydroxide (54 mg, 1.293 mmol) in THF/methanol/water (15/7/4 ml) to yield 17 mg (25.7% yield) of the titled compound. $^1$H NMR (CD$_3$OD, 300 MHz): δ 9.01-9.00 (d, 1H), 8.56-8.55 (m, 2H), 8.45-8.42 (dd, 1H), 8.23 (s, 1H), 7.72 (s, 1H), 7.69-7.66 (d, 1H), 7.39-7.32 (m, 1H), 7.11-6.98 (m, 3H), 5.43 (s, 2H), 4.30-4.20 (m, 1H), 3.87-3.77 (t, 2H), 3.30-3.05 (m, 4H), 2.40-2.10 (m, 4H), 1.27-1.24 (d, 3H). MS: m/z=511.3 (M+1), HPLC: 96.17% in method A.

Example 103

2-(4-(4-(3-(1-(3-fluorobenzyl)-1H-pyrazol-4-yl)-1H-pyrrolo[2,3-b]pyridin-5-yl)phenyl)piperazin-1-yl)acetamide

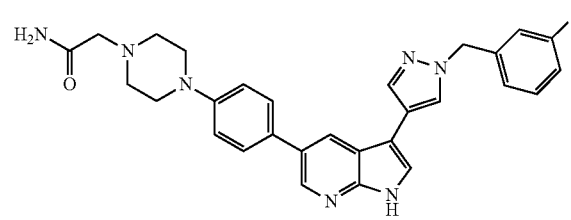

Step-i: 3-(1-(3-fluorobenzyl)-1H-pyrazol-4-yl)-5-(4-(piperazin-1-yl)phenyl)-1-tosyl-1H-pyrrolo[2,3-b]pyridine hydrochloride Using similar reaction conditions as described in step-ii of example-7, tert-butyl 4-(4-(3-(1-(3-fluorobenzyl)-1H-pyrazol-4-yl)-1-tosyl-1H-pyrrolo[2,3-b]pyridin-5-yl)phenyl)piperazine-1-carboxylate (step 1, example 39) (370 mg, 0.52 mmol) was deprotected in ether (5 ml) and HCl in ether (3 ml). This afforded 270 mg (80.35% yield) of the titled compound. MS: m/z=607.2 (M+1).

Step-ii 2-(4-(4-(3-(1-(3-fluorobenzyl)-1H-pyrazol-4-yl)-1-tosyl-1H-pyrrolo[2,3-b]pyridin-5-yl)phenyl)piperazin-1-yl)acetamide Using similar reaction conditions as described in step-i of example-82A, 3-(1-(3-fluorobenzyl)-1H-pyrazol-4-yl)-5-(4-(piperazin-1-yl)phenyl)-1-tosyl-1H-pyrrolo[2,3-b]pyridine hydrochloride (50 mg. 0.077 mmol) was alkylated using 2-chloroacetamide (10 mg, 0.116 mmol) and sodium bicarbonate (20 mg, 0.231 mmol) in acetone/ethanol (5/5 mL) to get 25 mg (49.01% yield) of the titled compound. MS: m/z=663.7 (M+1).

Step-iii: 2-(4-(4-(3-(1-(3-fluorobenzyl)-1H-pyrazol-4-yl)-1H-pyrrolo[2,3-b]pyridin-5-yl)phenyl)piperazin-1-yl)acetamide Using similar reaction conditions as described in step-iii of example-1, 2-(4-(4-(3-(1-(3-fluorobenzyl)-1H-pyrazol-4-yl)-1-tosyl-1H-pyrrolo[2,3-b]pyridin-5-yl)phenyl)piperazin-1-yl) acetamide (25 mg, 0.037 mmol) was hydrolyzed by lithium hydroxide (7 mg, 0.188 mmol) in THF/methanol/water (2/2/2 ml) to afford 10 mg (52.6% yield) of the titled compound after purification by preparative TLC (Silicagel-1000 micron) using 3% methanol in DCM as eluent. MS: m/z=553.2 (M+1). $^1$H NMR (CD$_3$OD, 400 MHz): δ 8.45-8.44 (d, 1H), 8.32-8.31 (d, 1H), 8.20 (s, 1H), 7.93 (s, 1H), 7.62-7.60 (m, 3H), 7.42-7.34 (q, 1H), 7.13-7.11 (m, 3H), 7.05-7.02 (m, 2H), 5.45 (s, 2H), 3.12 (s, 2H), 2.76 (s, 4H). MS: m/z=510.3 (M+1), HPLC: 92.51% in method A.

Example 104

(S)-1-(4-(4-(3-(1-(3-fluorobenzyl)-1H-pyrazol-4-yl)-1H-pyrrolo[2,3-b]pyridin-5-yl)phenyl) piperazin-1-yl)propan-2-ol

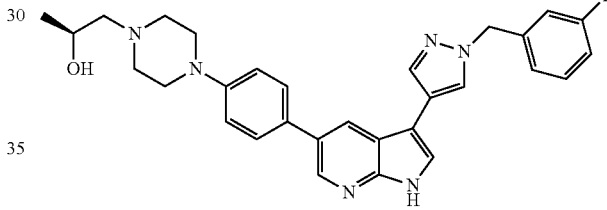

Step-i: (S)-1-(4-(4-(3-(1-(3-fluorobenzyl)-1H-pyrazol-4-yl)-1-tosyl-1H-pyrrolo[2,3-b]pyridin-5-yl)phenyl)piperazin-1-yl)propan-2-ol Using similar reaction conditions as described in step-i of example-82A, 3-(1-(3-fluorobenzyl)-1H-pyrazol-4-yl)-5-(4-(piperazin-1-yl)phenyl)-1-tosyl-1H-pyrrolo[2,3-b]pyridine-hydrochloride (step 1 example 103) (50 mg. 0.077 mmol) was alkylated using (S)-2-methyloxirane (9 mg, 0.155 mmol), DIPEA (29 mg, 0.231 mmol) and ethanol (2 mL) to get 25 mg (9.8% yield) of the titled compound. MS: m/z=664.8 (M+1).

Step-ii: (S)-1-(4-(4-(3-(1-(3-fluorobenzyl)-1H-pyrazol-4-yl)-1H-pyrrolo[2,3-b]pyridin-5-yl)phenyl) piperazin-1-yl)propan-2-ol Using similar reaction conditions as described in step-iii of example-1, (S)-1-(4-(4-(3-(1-(3-fluorobenzyl)-1H-pyrazol-4-yl)-1-tosyl-1H-pyrrolo[2,3-b]pyridin-5-yl)phenyl)piperazin-1-yl)propan-2-ol (25 mg, 0.037 mmol) was hydrolyzed by lithium hydroxide (7 mg, 0.188 mmol) in THF/methanol/water (2/2/1 ml) to afford 5 mg (26.31% yield) of the titled compound after purification by preparative TLC (Silicagel-1000 micron) using 3% methanol in DCM as eluent. $^1$H NMR (CD$_3$OD, 400 MHz): δ 8.45 (s, 1H), 8.30 (s, 1H), 8.20 (s, 1H), 7.95 (s, 1H), 7.65-7.55 (m, 3H), 7.45-7.35 (q, 1H), 7.15-7.00

(m, 4H), 5.45 (s, 2H), 4.05-3.95 (m, 1H), 3.70-3.45 (m, 2H), 2.85-2.35 (m, 6H), 1.22-1.98 (d, 3H). MS: m/z=511.6 (M+1), HPLC: 91.71% in method A.

Example 105

5-(3-(1-(3-fluorobenzyl)-1H-pyrazol-4-yl)-1H-pyrrolo[2,3-b]pyridin-5-yl)-2-(piperazin-1-yl) aniline

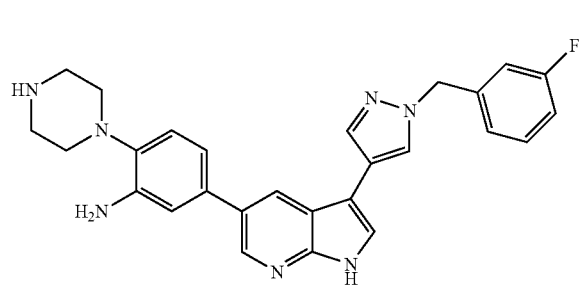 [SMILES: Nc1cc(-c2cnc3[nH]cc(-c4cnn(Cc5cccc(F)c5)c4)c3c2)ccc1N1CCNCC1]

Step-i: tert-butyl 4-(4-(3-(1-(3-fluorobenzyl)-1H-pyrazol-4-yl)-1-tosyl-1H-pyrrolo[2,3-b]pyridin-5-yl)-2-nitrophenyl)piperazine-1-carboxylate Using similar reaction conditions as described in step-i of example-1, tert-butyl 4-(4-(3-iodo-1-tosyl-1H-pyrrolo[2,3-b]pyridin-5-yl)-2-nitrophenyl)piperazine-1-carboxylate (intermediate 66J) (340 mg, 0.48 mmol) was coupled with 1-(3-fluorobenzyl)-4-(4,4,5,5-tetramethyl-1,3,2-dioxaborolan-2-yl)-1H-pyrazole (intermediate 11) (189 mg, 0.628 mmol) using Pd(dppf)Cl$_2$ (18 mg, 0.024 mol) and sodium carbonate (152 mg, 1.44 mmol) in toluene/ethanol/water (20/10/5 ml) to afford 120 mg (33.05% yield) of the titled. MS: m/z=752.2 (M+1).

Step-ii: tert-butyl 4-(4-(3-(1-(3-fluorobenzyl)-1H-pyrazol-4-yl)-1H-pyrrolo[2,3-b]pyridin-5-yl)-2-nitrophenyl)piperazine-1-carboxylate Using similar reaction conditions as described in step-iii of example-1, tert-butyl 4-(4-(3-(1-(3-fluorobenzyl)-1H-pyrazol-4-yl)-1-tosyl-1H-pyrrolo[2,3-b]pyridin-5-yl)-2-nitrophenyl)piperazine-1-carboxylate (120 mg, 0.15 mmol) was hydrolyzed by lithium hydroxide (20 mg, 0.47 mmol) in THF/methanol/water (5/5/2 ml) to yield crude 100 mg of the titled compound after purification by preparative TLC (Silicagel-1000 micron) using ethyl acetate as eluent.

Step-iii: tert-butyl 4-(2-amino-4-(3-(1-(3-fluorobenzyl)-1H-pyrazol-4-yl)-1H-pyrrolo[2,3-b]pyridin-5-yl)phenyl)piperazine-1-carboxylate Using similar reaction conditions as described in example-8, tert-butyl 4-(4-(3-(1-(3-fluorobenzyl)-1H-pyrazol-4-yl)-1H-pyrrolo[2,3-b]pyridin-5-yl)-2-nitrophenyl)piperazine-1-carboxylate (90 mg, 0.15 mmol) was reduced by 10% palladium on carbon (10 mg, 10% W/W) in methanol (10 mL) to yield crude 90 mg of the titled compound. MS: m/z=567.8 (M+1).

Step-iv: 5-(3-(1-(3-fluorobenzyl)-1H-pyrazol-4-yl)-1H-pyrrolo[2,3-b]pyridin-5-yl)-2-(piperazin-1-yl) aniline Using similar reaction conditions as described in step-ii of example-7, tert-butyl 4-(2-amino-4-(3-(1-(3-fluorobenzyl)-1H-pyrazol-4-yl)-1H-pyrrolo[2,3-b]pyridin-5-yl)phenyl)piperazine-1-carboxylate (90 mg, 0.15 mmol) was deprotected in HCl in ether/MeOH (0.2/5 ml). This afforded 5 mg (6.3% yield) of the titled compound. $^1$H NMR (CD$_3$OD, 400 MHz): δ 9.00 (s, 1H), 8.70 (s, 1H), 8.40 (s, 1H), 8.06 (s, 1H), 7.98 (s, 1H), 7.90-7.80 (m, 2H), 7.63-7.61 (d, 1H), 7.45-7.35 (q, 1H), 7.20-7.00 (m, 3H), 5.45 (s, 2H), 3.12 (s, 2H), 2.76 (s, 4H). MS: m/z=467.9 (M+1), HPLC: 95.53% in method A.

Example 106

N-(5-(3-(1-(3-fluorobenzyl)-1H-pyrazol-4-yl)-1H-pyrrolo[2,3-b]pyridin-5-yl)-2-(piperazin-1-yl)phenyl)methanesulfonamide hydrochloride

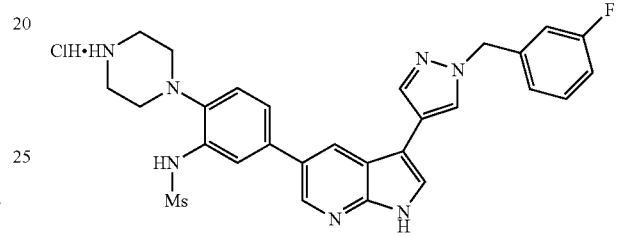

Step-i: tert-butyl 5-(4-(4-(tert-butoxycarbonyl)piperazin-1-yl)-3-(methylsulfonamido)phenyl)-3-(1-(3-fluorobenzyl)-1H-pyrazol-4-yl)-1H-pyrrolo[2,3-b]pyridine-1-carboxylate Using similar reaction conditions as described in step-ii of example-1, tert-butyl 5-(4-(4-(tert-butoxycarbonyl)piperazin-1-yl)-3-(methylsulfonamido)phenyl)-3-iodo-1H-pyrrolo[2,3-b]pyridine-1-carboxylate (intermediate 50) (150 mg, 0.215 mmol) was coupled with 1-(3-fluorobenzyl)-4-(4,4,5,5-tetramethyl-1,3,2-dioxaborolan-2-yl)-1H-pyrazole (intermediate 11) (78 mg, 0.258 mmol) using sodium carbonate (68 mg, 0.645 mmol) and Pd(PPh$_3$)$_2$Cl$_2$ (8 mg, 0.0107 mmol) in toluene/ethanol/water (5/2.5/1 ml) to afford 30 mg (18.7% yield) of titled compound after purification by preparative TLC (Silicagel-1000 micron) using 1% methanol in DCM as eluent.

Step-ii: N-(5-(3-(1-(3-fluorobenzyl)-1H-pyrazol-4-yl)-1H-pyrrolo[2,3-b]pyridin-5-yl)-2-(piperazin-1-yl)phenyl)methanesulfonamide hydrochloride Using similar reaction conditions as described in step-ii of example-7, tert-butyl 5-(4-(4-(tert-butoxycarbonyl)piperazin-1-yl)-3-(methylsulfonamido)phenyl)-3-(1-(3-fluorobenzyl)-1H-pyrazol-4-yl)-1H-pyrrolo[2,3-b]pyridine-1-carboxylate (27 mg, mmol) was deprotected in methanol/HCl in diethyl ether (3/1 ml) to afford 12 mg (57% yield) of the titled compound. $^1$H NMR (CD$_3$OD, 300 MHz): δ 9.01-9.00 (d, 1H), 8.71-8.70 (d, 1H), 8.41 (s, 1H), 8.09 (s, 1H), 7.98 (s, 1H), 7.87-7.86 (d, 1H), 7.66-7.63 (dd, 1H), 7.49-7.46 (d, 1H), 7.40-7.34 (m, 1H), 7.16-7.13 (m, 1H), 7.07-7.02 (m, 2H), 5.47 (s, 2H), 3.50-3.46 (m, 4H), 3.26-3.23 (m, 7H). MS: m/z=546.2 (M+1), HPLC: 98.49% in method B.

Example 107

N-(5-(3-(1-phenethyl-1H-pyrazol-4-yl)-1H-pyrrolo[2,3-b]pyridin-5-yl)-2-(piperazin-1-yl)phenyl) methanesulfonamide hydrochloride

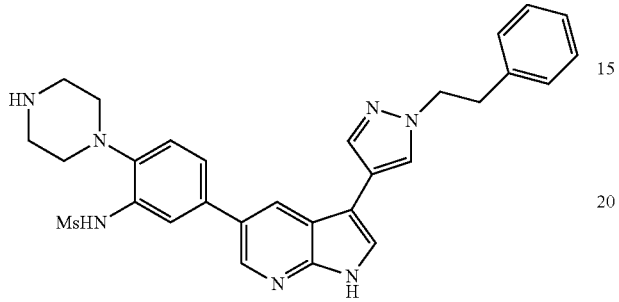

Step-i: tert-butyl 5-(4-(4-(tert-butoxycarbonyl)piperazin-1-yl)-3-(methylsulfonamido)phenyl)-3-(1-phenethyl-1H-pyrazol-4-yl)-1H-pyrrolo[2,3-b]pyridine-1-carboxylate Using similar reaction conditions as described in step-ii of example-1, tert-butyl 5-(4-(4-(tert-butoxycarbonyl)piperazin-1-yl)-3-(methylsulfonamido)phenyl)-3-iodo-1H-pyrrolo[2,3-b]pyridine-1-carboxylate (intermediate 50) (150 mg, 0.215 mmol) was coupled with 1-phenethyl-4-(4,4,5,5-tetramethyl-1,3,2-dioxaborolan-2-yl)-1H-pyrazole (intermediate 59) (76 mg, 0.258 mmol) using sodium carbonate (68 mg, 0.645 mmol) and Pd(PPh$_3$)$_2$Cl$_2$ (8 mg, 0.0107 mmol) in toluene/ethanol/water (5/5/2 ml) to afford 25 mg (15.7% yield) of titled compound after purification by preparative TLC (Silicagel-1000 micron) using 1% methanol in DCM as eluent. MS: m/z=742.4 (M+1).

Step-ii: N-(5-(3-(1-phenethyl-1H-pyrazol-4-yl)-1H-pyrrolo[2,3-b]pyridin-5-yl)-2-(piperazin-1-yl)phenyl)methanesulfonamide hydrochloride Using similar reaction conditions as described in step-ii of example-7, tert-butyl 5-(4-(4-(tert-butoxycarbonyl)piperazin-1-yl)-3-(methylsulfonamido)phenyl)-3-(1-phenethyl-1H-pyrazol-4-yl)-1H-pyrrolo[2,3-b]pyridine-1-carboxylate (21 mg, mmol) was deprotected in methanol/HCl in diethyl ether (2/1 ml) to afford 11 mg (68% yield) of the titled compound. $^1$H NMR (CD$_3$OD, 300 MHz): δ 8.859-8.853 (d, 1H), 8.736-8.73 (d, 1H), 8.37 (s, 1H), 8.33 (s, 1H), 8.00 (s, 1H), 7.867-7.861 (d, 1H), 7.66-7.63 (dd, 1H), 7.53-7.50 (d, 1H), 7.27-7.12 (m, 5H), 4.63-4.61 (t, 2H), 3.51-3.47 (t, 4H), 3.50-3.24 (m, 9H). MS: m/z=542.3 (M+1), HPLC: 98.49% in method B.

Example 108

4-(4-(3-(1-(3-fluorobenzyl)-1H-pyrazol-4-yl)-1H-pyrrolo[2,3-b]pyridin-5-yl)phenyl)piperazine-1-carboxamide

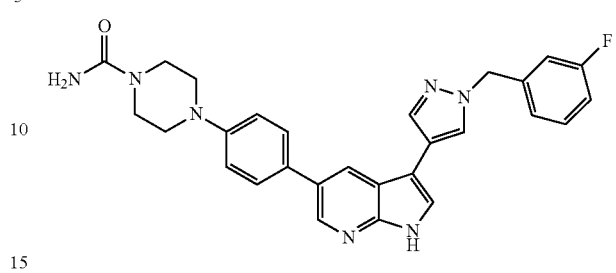

Step-i 4-(4-(3-(1-(3-fluorobenzyl)-1H-pyrazol-4-yl)-1-tosyl-1H-pyrrolo[2,3-b]pyridin-5-yl)phenyl) piperazine-1-carboxamide To a solution of 3-(1-(3-fluorobenzyl)-1H-pyrazol-4-yl)-5-(4-(piperazin-1-yl)phenyl)-1-tosyl-1H-pyrrolo[2,3-b]pyridine hydrochloride (step 1 example 103) (150 mg. 0.233 mmol) in chloroform (10 mL) triethyl amine (0.16 mL, 1.165 mmol) was added at 0° C. drop wise. This solution was added to a solution of triphosgene (59 mg, 0.233 mmol) in chloroform (10 mL) and stirred at RT for 30 minutes. Ammonia in THF was added to this solution drop wise and stirred at RT overnight. This was diluted with water and extracted in chloroform and distilled out the solvent to afford the 40 mg (26.4% yield) of the titled compound after purification with preparative TLC (silicagel-1000 micron) using 3% methanol in DCM as eluent. MS: m/z=649.7 (M+1).

Step-ii: 4-(4-(3-(1-(3-fluorobenzyl)-1H-pyrazol-4-yl)-1H-pyrrolo[2,3-b]pyridin-5-yl)phenyl) piperazine-1-carboxamide Using similar reaction conditions as described in step-iii of example-1, 4-(4-(3-(1-(3-fluorobenzyl)-1H-pyrazol-4-yl)-1-tosyl-1H-pyrrolo[2,3-b]pyridin-5-yl)phenyl)piperazine-1-carboxamide (40 mg, 0.075 mmol) was hydrolyzed by lithium hydroxide (15 mg, 0.377 mmol) in THF/methanol/water (2/2/1 ml) to afford 10 mg (33.33% yield) of the titled compound after purification by preparative TLC(Silicagel-1000 micron) using 3% methanol in DCM as eluent. $^1$H NMR (DMSO-d$_6$, 400 MHz): δ 11.7 (s, 1H), 8.46-8.41 (m, 2H), 8.27-8.26 (d, 1H), 7.99 (s, 1H), 7.72 (s, 1H), 7.63-7.61 (d, 2H), 7.42-7.35 (q, 1H), 7.15-7.05 (m, 5H), 6.04 (s, 2H), 5.39 (s, 2H), 3.45-3.43 (m, 4H), 3.13-3.11 (m, 4H). MS: m/z=496.4 (M+1), HPLC: 92.43% in method B.

Example 109

5-(4-(4-methylpiperazin-1-yl)phenyl)-3-(1-phenethyl-1H-pyrazol-4-yl)-1H-pyrrolo[2,3-b]pyridine

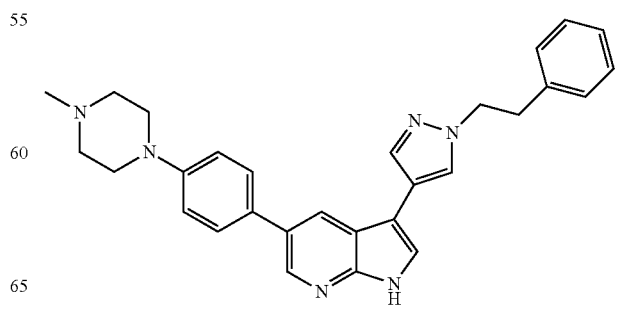

Step-i: 3,5-(4-(4-methylpiperazin-1-yl)phenyl)-3-(1-phenethyl-1H-pyrazol-4-yl)-1-tosyl-1H-pyrrolo[2,3-b]pyridine Using similar reaction conditions as described in step-ii of example-1, 3-iodo-5-(4-(4-methylpiperazin-1-yl)phenyl)-1-tosyl-1H-pyrrolo[2,3-b]pyridine (intermediate 48) (200 mg, 0.349 mmol) was coupled with 1-phenethyl-4-(4,4,5,5-tetramethyl-1,3,2-dioxaborolan-2-yl)-1H-pyrazole (intermediate 59) (104 mg, 0.349 mmol) using sodium carbonate (111 mg, 1.048 mmol) and Pd(dppf)Cl$_2$ (13 mg, 0.017 mmol) and toluene/ethanol/water (4/4/2 ml) to afford 110 mg of titled compound after purification by column (Silica gel 6/120) using 5% MeOH/DCM as eluent. MS: m/z=617.4 (M+1).

Step-ii: 5-(4-(4-methylpiperazin-1-yl)phenyl)-3-(1-phenethyl-1H-pyrazol-4-yl)-1H-pyrrolo[2,3-b]pyridine Using similar reaction conditions as described in step-iii of example-1, 5-(4-(4-methylpiperazin-1-yl)phenyl)-3-(1-phenethyl-1H-pyrazol-4-yl)-1-tosyl-1H-pyrrolo[2,3-b]pyridine (60 mg, 0.097 mmol) was hydrolyzed by lithium hydroxide (12 mg, 0.291 mmol) in THF/methanol/water (1/1/1 ml) to afford 20 mg (45.0% yield) of the titled compound. $^1$H NMR (CD$_3$OD, 400 MHz): δ 8.24 (s, 1H), 7.88 (s, 1H), 7.78 (s, 1H), 7.67-7.65 (d, 2H), 7.61 (s, 1H), 7.28-7.15 (m, 6H), 4.49-4.45 (t, 2H), 4.00-3.97 (d, 2H), 3.69-3.66 (d, 2H), 3.23-3.12 (m, 6H), 3.02 (s, 3H). MS: m/z=462.9 (M+1), HPLC: 96.28% in method B.

Example 110

2-(4-(4-(3-(1-(3-fluorobenzyl)-1H-pyrazol-4-yl)-1H-pyrrolo[2,3-b]pyridin-5-yl)-2-(methyl sulfonamido)phenyl)piperazin-1-yl)acetamide

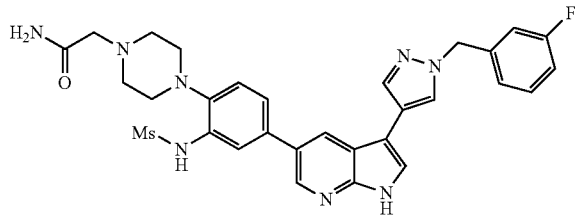 [SMILES: CS(=O)(=O)Nc1cc(-c2cnc3[nH]cc(-c4cnn(Cc5cccc(F)c5)c4)c3c2)ccc1N1CCN(CC(N)=O)CC1]

Step-i: 2-(4-(4-(3-(1-(3-fluorobenzyl)-1H-pyrazol-4-yl)-1-tosyl-1H-pyrrolo[2,3-b]pyridin-5-yl)-2-(methylsulfonamido)phenyl)piperazin-1-yl)acetamide Using similar reaction conditions as described in step-ii of example-1, 5-bromo-3-(1-(3-fluorobenzyl)-1H-pyrazol-4-yl)-1-tosyl-1H-pyrrolo[2,3-b]pyridine (compound of Step-i of example 9) (100 mg, 0.190 mmol) was coupled with 2-(4-(2-(methylsulfonamido)-4-(4,4,5,5-tetramethyl-1,3,2-dioxaborolan-2-yl)phenyl)piperazin-1-yl)acetamide (Intermediate 65A) 125 mg, 0.285 mmol) using sodium carbonate (60 mg, 0.567 mmol) and Pd(PPh$_3$)$_4$ (11 mg, 0.0095 mmol) in toluene/ethanol/water (2/2/1 mL). This afforded 82 mg (56.9% yield) after preparative TLC (Silicagel-1000 micron) using 5% ammoniated methanol in DCM as eluent. MS: m/z=757.2 (M+1).

Step-ii: 2-(4-(4-(3-(1-(3-fluorobenzyl)-1H-pyrazol-4-yl)-1H-pyrrolo[2,3-b]pyridin-5-yl)-2-(methyl sulfonamido)phenyl)piperazin-1-yl)acetamide Using similar reaction conditions as described in step-iii of example-1, 2-(4-(4-(3-(1-(3-fluorobenzyl)-1H-pyrazol-4-yl)-1-tosyl-1H-pyrrolo[2,3-b]pyridin-5-yl)-2-(methylsulfonamido)phenyl)piperazin-1-yl)acetamide (80 mg, 0.1 mmol) was hydrolyzed with lithium hydroxide (13 mg, 0.3 mmol) in THF/methanol/Water (2/2/1 mL) to yield 15 mg (23.6% yield). $^1$H NMR (DMSO-d$_6$, 400 MHz): δ 8.45-8.40 (m, 3H), 8.3 (s, 1H), 7.94 (s, 1H), 7.767-7.761 (d, 1H), 7.615-7.610 (d, 1H), 7.53-7.51 (d, 1H), 7.40-7.33 (m, 2H), 7.24-7.07 (m, 4H), 5.38 (s, 2H), 3.18 (s, 3H), 2.95-2.92 (m, 6H), 2.657 (s, 5H). MS: m/z=603.15 (M+1), HPLC: 93.36% in method A.

Example 111

3-(1-(3,5-difluorobenzyl)-1H-pyrazol-3-yl)-5-(4-(piperazin-1-yl)phenyl)-1H-pyrrolo[2,3-b]pyridine

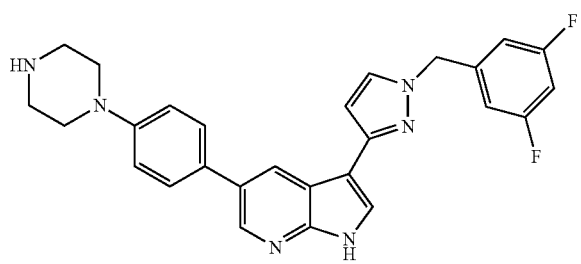 [SMILES: Fc1cc(F)cc(Cn2ccc(-c3c[nH]c4ncc(-c5ccc(N6CCNCC6)cc5)cc34)n2)c1]

Step-i: tert-butyl 4-(4-(3-(1-(3,5-difluorobenzyl)-1H-pyrazol-3-yl)-1-tosyl-1H-pyrrolo[2,3-b]pyridin-5-yl)phenyl)piperazine-1-carboxylate Using similar reaction conditions as described in step-ii of example-1, 5-bromo-3-(1-(3,5-difluorobenzyl)-1H-pyrazol-3-yl)-1-tosyl-1H-pyrrolo[2,3-b]pyridine (intermediate 63) (150 mg, 0.276 mmol) was coupled with 4-(4-(4,4,5,5-tetramethyl-1,3,2-dioxaborolan-2-yl)phenyl)piperazine-1-carboxylate (intermediate 40) (139 mg, 0.359 mmol) using sodium carbonate (82 mg, 0.78 mmol) and Pd(PPh$_3$)$_4$ (10 mg, 0.013 mmol) in DME/water (10/1 ml). This afforded 58 mg (28.7% yield) after purification by column (Silica gel 60/120) using 20% ethyl acetate in hexane as eluent. MS: m/z=725.4 (M+1).

Step-ii: tert-butyl 4-(4-(3-(1-(3,5-difluorobenzyl)-1H-pyrazol-3-yl)-1H-pyrrolo[2,3-b]pyridin-5-yl)phenyl)piperazine-1-carboxylate Using similar reaction conditions as described in step-iii of example-1, tert-butyl 4-(4-(3-(1-(3,5-difluorobenzyl)-1H-pyrazol-3-yl)-1-tosyl-1H-pyrrolo[2,3-b]pyridin-5-yl)phenyl)piperazine-1-carboxylate (55 mg, 0.0759 mmol) was hydrolyzed by lithium hydroxide (10 mg, 0.227 mmol) in THF/methanol/water (2/2/1 ml) to yield 15 mg (34.6% yield) of the titled compound.

Step-iii: 3-(1-(3,5-difluorobenzyl)-1H-pyrazol-3-yl)-5-(4-(piperazin-1-yl)phenyl)-1H-pyrrolo[2,3-b]pyridine hydrochloride Using similar reaction conditions as described in step-ii of example-7, tert-butyl 4-(4-(3-(1-(3,5-difluorobenzyl)-1H- pyrazol-3-yl)-1H-pyrrolo[2,3-b]pyridin-5-yl)phenyl)piperazine-1-carboxylate (27 mg, 0.047 mmol) was deprotected in methanol/HCl in diethyl ether (2/1 ml) to afford 15 mg (62.5% yield) of the titled compound. $^1$H NMR (DMSO-$d_6$, 300 MHz): δ 11.9 (s, 1H), 9.10-9.00 (bs, 2H), 8.598-8.52 (m, 2H), 7.91-7.89 (m, 2H), 7.60-7.57 (d, 2H), 7.17-7.00 (m, 4H), 6.71-6.70 (d, 1H), 5.41 (s, 2H), 3.23 (s, 5H). MS: m/z=471.3 (M+1), HPLC: 97.74% in method B.

Example 112

(S)-1-(4-(4-(3-(1-(3-fluorobenzyl)-1H-pyrazol-4-yl)-1H-pyrrolo[2,3-b]pyridin-5-yl)-2-methoxyphenyl)piperazin-1-yl)propan-2-ol

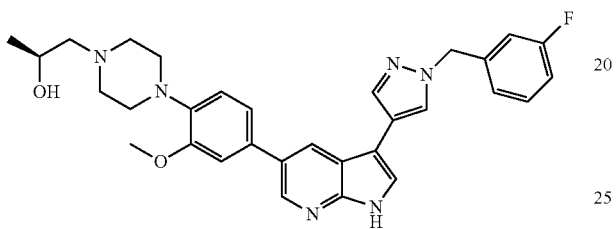

Step-i: tert-butyl 4-(4-(3-(1-(3-fluorobenzyl)-1H-pyrazol-4-yl)-1-tosyl-1H-pyrrolo[2,3-b]pyridin-5-yl)-2-methoxyphenyl)piperazine-1-carboxylate Using similar reaction conditions as described in step-ii of example-1, 5-bromo-3-(1-(3-fluorobenzyl)-1H-pyrazol-4-yl)-1-tosyl-1H-pyrrolo[2,3-b]pyridine (compound of Step-i of example 9) (200 mg, 0.380 mmol) was coupled with tert-butyl 4-(2-methoxy-4-(4,4,5,5-tetramethyl-1,3,2-dioxaborolan-2-yl)phenyl)piperazine-1-carboxylate (175 mg, 0.418 mmol) using sodium carbonate (121 mg, 1.1422 mmol) and Pd(dppf)Cl$_2$ (14 mg, 0.019 mmol) in toluene/ethanol/water (4/4/2 mL). This afforded 190 mg (68.0% yield) after purification by column (Silica gel 60/120) using 40% ethyl acetate in hexane as eluent. MS: m/z=737.1 (M+1).

Step-ii: 3-(1-(3-fluorobenzyl)-1H-pyrazol-4-yl)-5-(3-methoxy-4-(piperazin-1-yl)phenyl)-1-tosyl-1H-pyrrolo[2,3-b]pyridine hydrochloride Using similar reaction conditions as described in step-ii of example-7, tert-butyl 4-(4-(3-(1-(3-fluorobenzyl)-1H-pyrazol-4-yl)-1-tosyl-1H-pyrrolo[2,3-b]pyridin-5-yl)-2-methoxyphenyl)piperazine-1-carboxylate (190 mg, 0.257 mmol) was deprotected in methanol/HCl in diethyl ether (5/3 ml) to afford 120 mg (69.0% yield) of the titled compound. MS: m/z=637.3 (M+1).

Step-iii (S)-1-(4-(4-(3-(1-(3-fluorobenzyl)-1H-pyrazol-4-yl)-1-tosyl-1H-pyrrolo[2,3-b]pyridin-5-yl)-2-methoxyphenyl)piperazin-1-yl)propan-2-ol Using similar reaction conditions as described in step-i of example-82A, 3-(1-(3-fluorobenzyl)-1H-pyrazol-4-yl)-5-(3-methoxy-4-(piperazin-1-yl)phenyl)-1-tosyl-1H-pyrrolo[2,3-b]pyridine hydrochloride (100 mg. 0.148 mmol) was alkylated using (S)-2-methyloxirane (26 mg, 0.445 mmol), DIPEA (115 mg, 0.891 mmol) and ethanol (5 mL) to get crude 70 mg of the titled compound. MS: m/z=695.3 (M+1).

Step-iv: (S)-1-(4-(4-(3-(1-(3-fluorobenzyl)-1H-pyrazol-4-yl)-1H-pyrrolo[2,3-b]pyridin-5-yl)-2-methoxyphenyl)piperazin-1-yl)propan-2-ol Using similar reaction conditions as described in step-iii of example-1, (S)-1-(4-(4-(3-(1-(3-fluorobenzyl)-1H-pyrazol-4-yl)-1-tosyl-1H-pyrrolo[2,3-b]pyridin-5-yl)-2-methoxyphenyl)piperazin-1-yl)propan-2-ol (70 mg, 0.100 mmol) was hydrolyzed with lithium hydroxide (13 mg, 0.302 mmol) in THF/methanol/water (2/2/1 mL) to yield 35 mg (65% yield). $^1$H NMR (CD$_3$OD, 400 MHz): δ 8.48 (s, 1H), 8.34 (s, 1H), 8.20 (s, 1H), 7.95 (s, 1H), 7.39-7.36 (q, 1H), 7.30-7.28 (m, 2H), 7.13-7.11 (d, 2H), 7.07-7.02 (m, 2H), 5.45 (s, 2H), 4.20-4.30 (m, 1H), 3.99 (s, 3H), 3.60-3.80 (m, 4H), 3.1-3.3 (m, 3H), 1.29-1.28 (d, 3H). MS: m/z=541.6 (M+1), HPLC: 98.71% in method A.

Example 113

N-(5-(3-(1-(3,5-difluorobenzyl)-1H-pyrazol-3-yl)-1H-pyrrolo[2,3-b]pyridin-5-yl)-2-(piperazin-1-yl)phenyl)methanesulfonamide

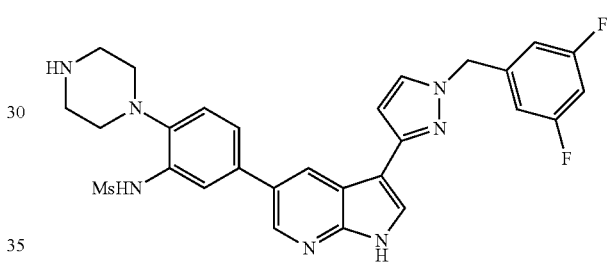

Step-i: tert-butyl 4-(4-(3-(1-(3,5-difluorobenzyl)-1H-pyrazol-3-yl)-1-tosyl-1H-pyrrolo[2,3-b]pyridin-5-yl)-2-(methylsulfonamido)phenyl)piperazine-1-carboxylate Using similar reaction conditions as described in step-ii of example-1, 5-bromo-3-(1-(3,5-difluorobenzyl)-1H-pyrazol-3-yl)-1-tosyl-1H-pyrrolo[2,3-b]pyridine (intermediate 63) (100 mg, 0.184 mmol) was coupled with tert-butyl 4-(2-(methylsulfonamido)-4-(4,4,5,5-tetramethyl-1,3,2-dioxaborolan-2-yl)phenyl)piperazine-1-carboxylate (intermediate 69G) (106 mg, 0.22 mmol) using sodium carbonate (58 mg, 0.552 mmol) and Pd(PPh$_3$)$_4$ (10 mg, 0.009 mmol) in toluene/ethanol/water (2/2/1 ml). This afforded 60 mg (39.9% yield) after preparative TLC (Silicagel-1000 micron) using 40% ethyl acetate in hexane as eluent. MS: m/z=818.6 (M+1).

Step-ii: tert-butyl 4-(4-(3-(1-(3,5-difluorobenzyl)-1H-pyrazol-3-yl)-1H-pyrrolo[2,3-b]pyridin-5-yl)-2-(methylsulfonamido)phenyl)piperazine-1-carboxylate Using similar reaction conditions as described in step-iii of example-1, tert-butyl 4-(4-(3-(1-(3,5-difluorobenzyl)-1H-pyrazol-3-yl)-1-tosyl-1H-pyrrolo[2,3-b]pyridin-5-yl)-2-(methylsulfonamido)phenyl)piperazine-1-carboxylate (55 mg, 0.067 mmol) was hydrolyzed by lithium hydroxide (9 mg, 0.201 mmol) in THF/methanol/water (2/2/1 ml) to yield 35 mg (79.0% yield) of the titled compound after preparative TLC (Silicagel-1000 micron) using 60% ethyl acetate in hexane as eluent.

Step-iii: N-(5-(3-(1-(3,5-difluorobenzyl)-1H-pyrazol-3-yl)-1H-pyrrolo[2,3-b]pyridin-5-yl)-2-(piperazin-1-yl)phenyl)methanesulfonamide Using similar reaction conditions as described in step-ii of example-7, tert-butyl 4-(4-(3-(1-(3,5-difluorobenzyl)-1H-pyrazol-3-yl)-1H-pyrrolo[2,3-b]pyridin-5-yl)-2-(methylsulfonamido)phenyl) piperazine-1-carboxylate (12 mg, 0.018 mmol) was deprotected in methanol/HCl in diethyl ether (1/2 ml) to afford 4 mg (26.8% yield) of the titled compound. $^1$H NMR (CD$_3$OD, 300 MHz): δ 9.32-9.31 (m, 1H), 8.69 (s, 1H), 8.08 (s, 1H), 7.899-7.892 (d, 1H), 7.858-7.850 (d, 1H), 7.58-7.55 (dd, 1H), 7.46-7.44 (d, 1H), 6.93-6.77 (m, 4H), 5.46 (s, 2H), 3.49-3.46 (t, 4H), 3.24-3.20 (m, 4H). MS: m/z=564.1 (M+1), HPLC: 96.35% in method B.

Example 114

(S)-1-(4-(2-fluoro-4-(3-(1-(3-fluorobenzyl)-1H-pyrazol-4-yl)-1H-pyrrolo[2,3-b]pyridin-5-yl)phenyl)piperazin-1-yl)propan-2-ol

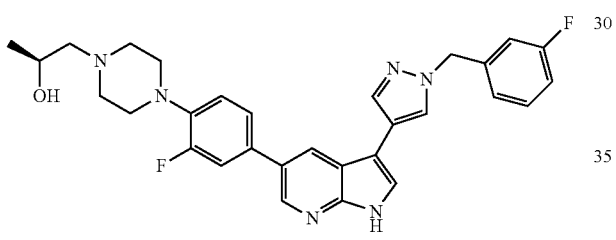

Step-i: tert-butyl 4-(2-fluoro-4-(3-(1-(3-fluorobenzyl)-1H-pyrazol-4-yl)-1-tosyl-1H-pyrrolo[2,3-b]pyridin-5-yl)phenyl)piperazine-1-carboxylate Using similar reaction conditions as described in step-ii of example-1, 5-bromo-3-(1-(3-fluorobenzyl)-1H-pyrazol-4-yl)-1-tosyl-1H-pyrrolo[2,3-b]pyridine (compound of Step-i of example 9) (160 g, 0.304 mmol) was coupled with tert-butyl 4-(2-fluoro-4-(4,4,5,5-tetramethyl-1,3,2-dioxaborolan-2-yl)phenyl)piperazine-1-carboxylate (intermediate 69) (216 mg, 0.530 mmol) using sodium carbonate (97 mg, 0.912 mmol) and Pd(PPh$_3$)$_2$Cl$_2$ (11 mg, 0.015 mmol) in DME/water (5/2 mL). This afforded 150 mg (68.10% yield) after purification by column (Silica gel 60/120) using 25% ethyl acetate in hexane as eluent. MS: m/z=725.3 (M+1).

Step-ii: 5-(3-fluoro-4-(piperazin-1-yl)phenyl)-3-(1-(3-fluorobenzyl)-1H-pyrazol-4-yl)-1-tosyl-1H-pyrrolo[2,3-b]pyridine Using similar reaction conditions as described in step-ii of example-7, tert-butyl 4-(2-fluoro-4-(3-(1-(3-fluorobenzyl)-1H-pyrazol-4-yl)-1-tosyl-1H-pyrrolo[2,3-b]pyridin-5-yl)phenyl)piperazine-1-carboxylate (150 mg, 0.206 mmol) was deprotected in TFA/DCM (1/1 ml) to afford 120 mg (93% yield) of the titled compound. MS: m/z=625.1 (M+1).

Step-iii: (S)-1-(4-(2-fluoro-4-(3-(1-(3-fluorobenzyl)-1H-pyrazol-4-yl)-1-tosyl-1H-pyrrolo[2,3-b]pyridin-5-yl)phenyl)piperazin-1-yl)propan-2-ol Using similar reaction conditions as described in step-i of example-82A, 5-(3-fluoro-4-(piperazin-1-yl)phenyl)-3-(1-(3-fluorobenzyl)-1H-pyrazol-4-yl)-1-tosyl-1H-pyrrolo[2,3-b]pyridine (120 mg. 0.192 mmol) was alkylated using (S)-2-methyloxirane (14 mg, 0.23 mmol), DIPEA (50 mg, 0.384 mmol) and ethanol (5 mL) to get 100 mg (76.9% yield) of the titled compound. MS: m/z=683.2 (M+1).

Step-iv: (S)-1-(4-(2-fluoro-4-(3-(1-(3-fluorobenzyl)-1H-pyrazol-4-yl)-1H-pyrrolo[2,3-b]pyridin-5-yl)phenyl)piperazin-1-yl)propan-2-ol Using similar reaction conditions as described in step-iii of example-1, (S)-1-(4-(2-fluoro-4-(3-(1-(3-fluorobenzyl)-1H-pyrazol-4-yl)-1-tosyl-1H-pyrrolo[2,3-b]pyridin-5-yl)phenyl)piperazin-1-yl) propan-2-ol (100 mg, 0.146 mmol) was hydrolyzed with lithium hydroxide (30 mg, 0.73 mmol) in THF/methanol/water (2/2/1 mL) to yield 45 mg (58.4% yield) of desired product. $^1$H NMR (CD$_3$OD, 400 MHz): δ 8.54 (s, 2H), 8.27 (s, 1H), 7.98 (s, 1H), 7.74 (s, 1H), 7.60-7.53 (m, 2H), 7.45-7.35 (q, 1H), 7.25-7.21 (t, 1H), 7.14-7.12 (d, 1H), 7.09-7.00 (m, 2H), 5.45 (s, 2H), 4.30-4.20 (m, 1H), 3.76-3.55 (m, 4H), 3.50-3.30 (m, 2H), 3.29-3.15 (m, 4H), 1.29-1.27 (d, 3H). MS: m/z=529.6 (M+1), HPLC: 98.28% in method A.

Example 115

(S)-1-(4-(4-(3-(1-(3-fluorobenzyl)-1H-pyrazol-4-yl)-1H-pyrrolo[2,3-b]pyridin-5-yl)-2-methyl phenyl)piperazin-1-yl)propan-2-ol

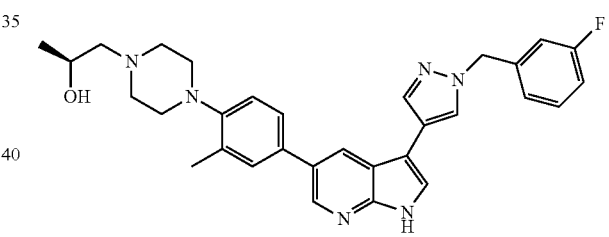

Step-i: tert-butyl 4-(4-(3-(1-(3-fluorobenzyl)-1H-pyrazol-4-yl)-1-tosyl-1H-pyrrolo[2,3-b]pyridin-5-yl)-2-methylphenyl)piperazine-1-carboxylate Using similar reaction conditions as described in step-ii of example-1, 5-bromo-3-(1-(3-fluorobenzyl)-1H-pyrazol-4-yl)-1-tosyl-1H-pyrrolo[2,3-b]pyridine (compound of Step-i of example 9) (200 g, 0.380 mmol) was coupled with tert-butyl 4-(2-methyl-4-(4,4,5,5-tetramethyl-1,3,2-dioxaborolan-2-yl)phenyl)piperazine-1-carboxylate (intermediate 69A) (280 mg, 0.694 mmol) using sodium carbonate (121 mg, 1.142 mmol) and Pd(PPh$_3$)$_2$Cl$_2$ (14 mg, 0.019 mmol) in DME/water (15/4 mL). This afforded 212 mg (77.3% yield) of the titled compound after purification by column (Silica gel 60/120) using 15% ethyl acetate in hexane as eluent. MS: m/z=721.3 (M+1).

Step-ii: 3-(1-(3-fluorobenzyl)-1H-pyrazol-4-yl)-5-(3-methyl-4-(piperazin-1-yl)phenyl)-1-tosyl-1H-pyrrolo[2,3-b]pyridine hydrochloride Using similar reaction conditions as described in step-ii of example-7, tert-butyl 4-(4-(3-(1-(3-fluorobenzyl)-1H-pyrazol-4-yl)-1-tosyl-1H-pyrrolo[2,3-b]pyridin-5-yl)-2-methylphenyl)piperazine-1-carboxylate (210 mg, 0.291 mmol) was deprotected in methanol/HCl in dioxane (5/10 ml) to afford 172 mg (95.5% yield) of the titled compound. MS: m/z=621.3 (M+1).

Step-iii: (S)-1-(4-(4-(3-(1-(3-fluorobenzyl)-1H-pyrazol-4-yl)-1-tosyl-1H-pyrrolo[2,3-b]pyridin-5-yl)-2-methylphenyl)piperazin-1-yl)propan-2-ol Using similar reaction conditions as described in step-i of example-82A, 3-(1-(3-fluorobenzyl)-1H-pyrazol-4-yl)-5-(3-methyl-4-(piperazin-1-yl)phenyl)-1-tosyl-1H-pyrrolo[2,3-b]pyridine hydrochloride (172 mg. 0.277 mmol) was alkylated using (S)-2-methyloxirane (24 mg, 0.416 mmol), DIPEA (54 mg, 0.416 mmol) and ethanol (4 mL) to get 183 mg (97.3% yield) of the titled compound. MS: m/z=679.3 (M+1).

Step-iv: (S)-1-(4-(4-(3-(1-(3-fluorobenzyl)-1H-pyrazol-4-yl)-1H-pyrrolo[2,3-b]pyridin-5-yl)-2-methylphenyl) piperazin-1-yl)propan-2-ol Using similar reaction conditions as described in step-iii of example-1, (S)-1-(4-(4-(3-(1-(3-fluorobenzyl)-1H-pyrazol-4-yl)-1-tosyl-1H-pyrrolo[2,3-b]pyridin-5-yl)-2-methylphenyl)piperazin-1-yl)propan-2-ol (183 mg, 0.269 mmol) was hydrolyzed with lithium hydroxide (57 mg, 1.347 mmol) in THF/methanol/water (20/10/5 mL) to yield 96 mg (55.8% yield) of desired product. $^1$H NMR (CD$_3$OD, 300 MHz): δ 8.63-8.62 (d, 1H), 8.54 (s, 1H), 8.26 (s, 1H), 7.97 (s, 1H), 7.77 (s, 1H), 7.65-7.63 (d, 1H), 7.60-7.56 (dd, 1H), 7.42-7.32 (q, 1H), 7.26-7.24 (d, 1H), 7.12-7.10 (d, 1H), 7.06-7.00 (m, 2H), 5.44 (s, 2H), 4.30-4.20 (m, 1H), 3.77-3.68 (t, 2H), 2.44 (s, 3H), 1.32-1.23 (m, 3H). MS: m/z=525.4 (M+1), HPLC: 90.77% in method B.

Example 116

(S)-1-(4-(4-(3-(1-(3-fluorobenzyl)-1H-pyrazol-4-yl)-1H-pyrrolo[2,3-b]pyridin-5-yl)-3-methoxy phenyl) piperazin-1-yl)propan-2-ol

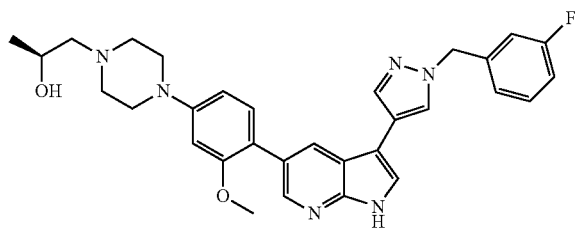 [SMILES: COc1cc(N2CCN(C[C@H](C)O)CC2)ccc1-c1cnc2[nH]cc(-c3cnn(Cc4cccc(F)c4)c3)c2c1]

Step-i: tert-butyl 4-(4-(3-(1-(3-fluorobenzyl)-1H-pyrazol-4-yl)-1-tosyl-1H-pyrrolo[2,3-b]pyridin-5-yl)-3-methoxyphenyl)piperazine-1-carboxylate Using similar reaction conditions as described in step-ii of example-1, tert-butyl 4-(4-(3-iodo-1-tosyl-1H-pyrrolo[2,3-b]pyridin-5-yl)-3-methoxyphenyl)piperazine-1-carboxylate (intermediate 52) (300 mg, 0.0435 mmol) was coupled with 1-(3-fluorobenzyl)-4-(4,4,5,5-tetramethyl-1,3,2-dioxaborolan-2-yl)-1H-pyrazole (intermediate 11) (145 mg, 0.479 mmol) using sodium carbonate (138 mg, 1.307 mmol) and Pd(dppf)Cl$_2$ (16 mg, 0.0217 mmol) in toluene/ethanol/water (6/6/3 ml) to afford 220 mg (62.0% yield) of titled compound after purification by column (Silica gel 60/120) using 10% ethyl acetate in DCM as eluent. MS: m/z=737.2 (M+1).

Step-ii: 3-(1-(3-fluorobenzyl)-1H-pyrazol-4-yl)-5-(2-methoxy-4-(piperazin-1-yl)phenyl)-1-tosyl-1H-pyrrolo[2,3-b]pyridine hydrochloride Using similar reaction conditions as described in step-ii of example-7, tert-butyl 4-(4-(3-(1-(3-fluorobenzyl)-1H-pyrazol-4-yl)-1-tosyl-1H-pyrrolo[2,3-b]pyridin-5-yl)-3-methoxyphenyl) piperazine-1-carboxylate (220 mg, 0.298 mmol) was deprotected in methanol/HCl in ether (3/2 ml) to afford 180 mg (90.0% yield) of the titled compound. MS: m/z=637.1 (M+1).

Step-iii: (S)-1-(4-(4-(3-(1-(3-fluorobenzyl)-1H-pyrazol-4-yl)-1-tosyl-1H-pyrrolo[2,3-b]pyridin-5-yl)-3-methoxyphenyl)piperazin-1-yl)propan-2-ol Using similar reaction conditions as described in step-i of example-82A, 3-(1-(3-fluorobenzyl)-1H-pyrazol-4-yl)-5-(2-methoxy-4-(piperazin-1-yl)phenyl)-1-tosyl-1H-pyrrolo[2,3-b]pyridine hydrochloride (180 mg. 0.267 mmol) was alkylated using (S)-2-methyloxirane (47 mg, 0.802 mmol), DIPEA (207 mg, 1.604 mmol) and ethanol (5 mL) to get 120 mg (crude) of the titled compound. MS: m/z=695.2 (M+1).

Step-iv: (S)-1-(4-(4-(3-(1-(3-fluorobenzyl)-1H-pyrazol-4-yl)-1H-pyrrolo[2,3-b]pyridin-5-yl)-3-methoxyphenyl)piperazin-1-yl)propan-2-ol Using similar reaction conditions as described in step-iii of example-1, (S)-1-(4-(4-(3-(1-(3-fluorobenzyl)-1H-pyrazol-4-yl)-1-tosyl-1H-pyrrolo[2,3-b]pyridin-5-yl)-3-methoxyphenyl)piperazin-1-yl)propan-2-ol (120 mg, 0.172 mmol) was hydrolyzed with lithium hydroxide (22 mg, 0.518 mmol) in THF/methanol/water (2/2/1 mL) to yield 27 mg (29.0% yield). $^1$H NMR (CD$_3$OD, 400 MHz): δ 8.55-8.54 (d, 1H), 8.438-8.434 (d, 1H), 8.19 (s, 1H), 7.94 (s, 1H), 7.76 (s, 1H), 7.42-7.38 (m, 2H), 7.14-7.12 (d, 1H), 7.05-7.03 (qd, 2H), 6.80-6.76 (m, 2H), 5.44 (s, 2H), 4.29-4.24 (m, 1H), 3.99-3.96 (m, 2H), 3.86 (s, 3H), 3.75-3.38 (m, 2H), 3.29-3.12 (m, 6H), 1.29-1.28 (d, 3H). MS: m/z=541.4 (M+1), HPLC: 92.28% in method A.

Example 117

(S)-1-(4-(4-(3-(1-phenethyl-1H-pyrazol-4-yl)-1H-pyrrolo[2,3-b]pyridin-5-yl)phenyl)piperazin-1-yl) propan-2-ol

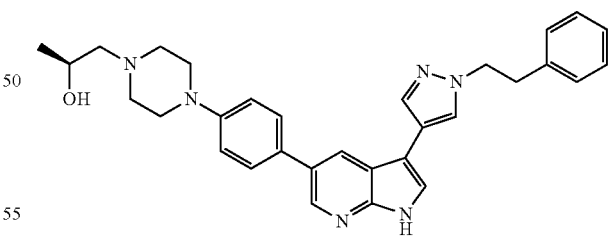

Step-i: tert-butyl 4-(4-(3-(1-phenethyl-1H-pyrazol-4-yl)-1-tosyl-1H-pyrrolo[2,3-b]pyridin-5-yl)phenyl) piperazine-1-carboxylate Using similar reaction conditions as described in step-ii of example-1, tert-butyl 4-(4-(3-iodo-1-tosyl-1H-pyrrolo[2,3-b]pyridin-5-yl)phenyl)piperazine-1-carboxylate (intermediate 41) (200 mg, 0.303 mmol) was coupled with 1-phenethyl-4-(4,4,5,5-tetramethyl-1,3,2-dioxaborolan-2-yl)-1H-pyrazole (intermediate 59) (136 mg, 0.455 mmol) using sodium carbonate (81 mg, 0.759 mmol) and Pd(PPh₃)₂Cl₂ (11 mg, 0.015 mmol) in Toluene/ethanol/water (10/2/1 ml) to afford 200 mg of titled compound after purification by column (Silica gel 6/120) using 50% EtOAc/hexane as eluent. MS: m/z=703.3 (M+1).

Step-ii: 3-(1-phenethyl-1H-pyrazol-4-yl)-5-(4-(piperazin-1-yl)phenyl)-1-tosyl-1H-pyrrolo[2,3-b]pyridine Using similar reaction conditions as described in step-ii of example-7, tert-butyl 4-(4-(3-(1-phenethyl-1H-pyrazol-4-yl)-1-tosyl-1H-pyrrolo[2,3-b]pyridin-5-yl)phenyl)piperazine-1-carboxylate (200 mg, 0.284 mmol) was deprotected in TFA/DCM (2/5 ml) to afford 175 mg (86.2% yield) of the titled compound. MS: m/z=603.2 (M+1).

Step-iii: (S)-1-(4-(4-(3-(1-phenethyl-1H-pyrazol-4-yl)-1-tosyl-1H-pyrrolo[2,3-b]pyridin-5-yl)phenyl) piperazin-1-yl)propan-2-ol Using similar reaction conditions as described in step-i of example-82A, 3-(1-phenethyl-1H-pyrazol-4-yl)-5-(4-(piperazin-1-yl)phenyl)-1-tosyl-1H-pyrrolo[2,3-b]pyridine (175 mg. 0.244 mmol) was alkylated using (S)-2-methyloxirane (26 mg, 0.488 mmol), DIPEA (171 μL, 0.977 mmol) and ethanol (5 mL) to get 100 mg (62.1% yield) of the titled compound. MS: m/z=661.7 (M+1).

Step-iv: (S)-1-(4-(4-(3-(1-phenethyl-1H-pyrazol-4-yl)-1H-pyrrolo[2,3-b]pyridin-5-yl)phenyl) piperazin-1-yl)propan-2-ol Using similar reaction conditions as described in step-iii of example-1, (S)-1-(4-(4-(3-(1-phenethyl-1H-pyrazol-4-yl)-1-tosyl-1H-pyrrolo[2,3-b]pyridin-5-yl)phenyl)piperazin-1-yl)propan-2-ol (100 mg, 0.151 mmol) was hydrolyzed with lithium hydroxide (13 mg, 0.302 mmol) in THF/methanol/water (5./1/1 mL) to yield 30 mg (31.9% yield) desired product. ¹H NMR (CD₃OD, 400 MHz): δ 8.56-8.55 (d, 1H), 8.49-8.48 (d, 1H), 7.90 (s, 1H), 7.84 (s, 1H), 7.73 (s, 1H), 7.68-7.66 (d, 2H), 7.26-7.19 (m, 4H), 7.14-7.10 (m, 3H), 4.47-4.44 (t, 2H), 4.30-4.25 (m, 1H), 3.99-3.94 (m, 2H), 3.78-3.74 (m, 2H), 3.31-3.21 (m, 2H), 3.19-3.12 (m, 4H), 1.29-1.28 (d, 3H). MS: m/z=507.60 (M+1), HPLC: 91.80% in method A.

Example 118

(S)-1-(4-(4-(3-(1-benzyl-1H-pyrazol-4-yl)-1H-pyrrolo[2,3-b]pyridin-5-yl)phenyl)piperazin-1-yl)propan-2-ol Step-i: tert-butyl 4-(4-(3-(1-benzyl-1H-pyrazol-4-yl)-1-tosyl-1H-pyrrolo[2,3-b]pyridin-5-yl)phenyl) piperazine-1-carboxylate Using similar reaction conditions as described in step-ii of example-1, tert-butyl 4-(4-(3-iodo-1-tosyl-1H-pyrrolo[2,3-b]pyridin-5-yl)phenyl)piperazine-1-carboxylate (intermediate 41) (200 mg, 0.303 mmol) was coupled with 1-benzyl-4-(4,4,5,5-tetramethyl-1,3,2-dioxaborolan-2-yl)-1H-pyrazole (intermediate 15) (130 mg, 0.455 mmol) using sodium carbonate (81 mg, 0.759 mmol) and Pd(PPh₃)₂Cl₂ (11 mg, 0.015 mmol) in toluene/ethanol/water (10/2/1 ml) to afford 200 mg (95.6% yield) of titled compound after purification by column (Silica gel 6/120) using 50% EtOAc/hexane as eluent. MS: m/z=689.3 (M+1).

Step-ii: 3-(1-benzyl-1H-pyrazol-4-yl)-5-(4-(piperazin-1-yl)phenyl)-1-tosyl-1H-pyrrolo[2,3-b]pyridine Using similar reaction conditions as described in step-ii of example-7, tert-butyl 4-(4-(3-(1-phenethyl-1H-pyrazol-4-yl)-1-tosyl-1H-pyrrolo[2,3-b]pyridin-5-yl)phenyl)piperazine-1-carboxylate (200 mg, 0.290 mmol) was deprotected in TFA/DCM (2/5 ml) to afford 175 mg (85.7% yield) of the titled compound. MS: m/z=589.2 (M+1).

Step-iii: (S)-1-(4-(4-(3-(1-benzyl-1H-pyrazol-4-yl)-1-tosyl-1H-pyrrolo[2,3-b]pyridin-5-yl)phenyl) piperazin-1-yl)propan-2-ol Using similar reaction conditions as described in step-i of example-82A, 3-(1-benzyl-1H-pyrazol-4-yl)-5-(4-(piperazin-1-yl)phenyl)-1-tosyl-1H-pyrrolo[2,3-b]pyridine (175 mg. 0.249 mmol) was alkylated using (S)-2-methyloxirane (27 mg, 0.498 mmol), DIPEA (129 mg, 0.996 mmol) and ethanol (5 mL) to get 100 mg (62.1% yield) of the titled compound. MS: m/z=647.2 (M+1).

Step-iv: (S)-1-(4-(4-(3-(1-benzyl-1H-pyrazol-4-yl)-1H-pyrrolo[2,3-b]pyridin-5-yl)phenyl)piperazin-1-yl)propan-2-ol Using similar reaction conditions as described in step-iii of example-1, (S)-1-(4-(4-(3-(1-benzyl-1H-pyrazol-4-yl)-1-tosyl-1H-pyrrolo[2,3-b]pyridin-5-yl)phenyl)piperazin-1-yl)propan-2-ol (100 mg, 0.154 mmol) was hydrolyzed with lithium hydroxide (13 mg, 0.309 mmol) in THF/methanol/water (5./1/1 mL) to yield 31 mg (32.9% yield) of desired product. ¹H NMR (CD₃OD, 400 MHz): δ 8.605-8.601 (d, 1H), 8.537-8.533 (d, 1H), 8.22 (s, 1H), 7.95 (s, 1H), 7.75 (s, 1H), 7.69-7.67 (d, 2H), 7.38-7.29 (m, 5H), 7.17-7.15 (d, 2H), 5.42 (s, 2H), 4.29-4.25 (m, 1H), 4.00-3.80 (m, 2H), 3.35-3.20 (m, 2H), 3.35 (s, 2H), 3.25-3.20 (m, 2H), 3.19-3.10 (m, 2H), 1.30-1.27 (m, 3H). MS: m/z=493.2 (M+1), HPLC: 90.54% in method A.

Example 119

(S)-1-(4-(4-(3-(1-(3-methylbenzyl)-1H-pyrazol-4-yl)-1H-pyrrolo[2,3-b]pyridin-5-yl)phenyl) piperazin-1-yl)propan-2-ol

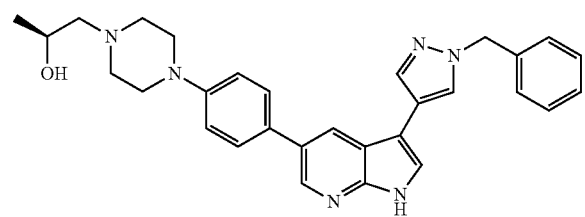 [SMILES: C[C@H](O)CN1CCN(c2ccc(-c3cnc4[nH]cc(-c5cnn(Cc6ccccc6)c5)c4c3)cc2)CC1]

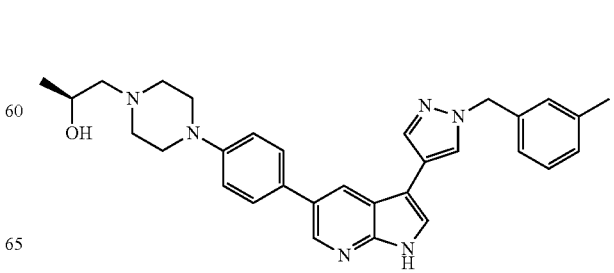

187

Step-i: tert-butyl 4-(4-(3-(1-(3-methylbenzyl)-1H-pyrazol-4-yl)-1-tosyl-1H-pyrrolo[2,3-b]pyridin-5-yl)phenyl)piperazine-1-carboxylate Using similar reaction conditions as described in step-ii of example-1, tert-butyl 4-(4-(3-iodo-1-tosyl-1H-pyrrolo[2,3-b]pyridin-5-yl)phenyl)piperazine-1-carboxylate (intermediate 41) (200 mg, 0.303 mmol) was coupled with 1-(3-methylbenzyl)-4-(4,4,5,5-tetramethyl-1,3,2-dioxaborolan-2-yl)-1H-pyrazole (intermediate 64D) (136 mg, 0.455 mmol) using sodium carbonate (81 mg, 0.759 mmol) and Pd(PPh$_3$)$_2$Cl$_2$ (11 mg, 0.015 mmol) in toluene/ethanol/water (10/2/1 ml) to afford 200 mg (93.8% yield) of titled compound after purification by column (Silica gel 6/120) using 50% EtOAc/hexane as eluent. MS: m/z=703.2 (M+1).

Step-ii: 3-(1-(3-methylbenzyl)-1H-pyrazol-4-yl)-5-(4-(piperazin-1-yl)phenyl)-1-tosyl-1H-pyrrolo[2,3-b]pyridine Using similar reaction conditions as described in step-ii of example-7, tert-butyl 4-(4-(3-(1-(3-methylbenzyl)-1H-pyrazol-4-yl)-1-tosyl-1H-pyrrolo[2,3-b]pyridin-5-yl)phenyl)piperazine-1-carboxylate (200 mg, 0.284 mmol) was deprotected in TFA/DCM (2/5 ml) to afford 175 mg (86.2% yield) of the titled compound. MS: m/z=603.2 (M+1).

Step-iii: (S)-1-(4-(4-(3-(1-(3-methylbenzyl)-1H-pyrazol-4-yl)-1-tosyl-1H-pyrrolo[2,3-b]pyridin-5-yl)phenyl)piperazin-1-yl)propan-2-ol Using similar reaction conditions as described in step-i of example-82A, 3-(1-(3-methylbenzyl)-1H-pyrazol-4-yl)-5-(4-(piperazin-1-yl)phenyl)-1-tosyl-1H-pyrrolo[2,3-b]pyridine (175 mg. 0.244 mmol) was alkylated using (S)-2-methyloxirane (26 mg, 0.488 mmol), DIPEA (171 µL, 0.977 mmol) and ethanol (5 mL) to get 100 mg (62.1% yield) of the titled compound. MS: m/z=661.2 (M+1).

Step-iv: (S)-1-(4-(4-(3-(1-(3-methylbenzyl)-1H-pyrazol-4-yl)-1H-pyrrolo[2,3-b]pyridin-5-yl)phenyl)piperazin-1-yl)propan-2-ol Using similar reaction conditions as described in step-iii of example-1, (S)-1-(4-(4-(3-(1-(3-methylbenzyl)-1H-pyrazol-4-yl)-1-tosyl-1H-pyrrolo[2,3-b]pyridin-5-yl)phenyl)piperazin-1-yl)propan-2-ol (100 mg, 0.151 mmol) was hydrolyzed with lithium hydroxide (13 mg, 0.302 mmol) in THF/methanol/water (5./1/1 mL) to yield 33 mg (35.1% yield) desired product. $^1$H NMR (CD$_3$OD, 400 MHz): δ 8.667-8.663 (d, 1H), 8.55-8.54 (d, 1H), 8.22 (s, 1H), 7.95 (s, 1H), 7.77 (s, 1H), 7.69-7.66 (d, 2H), 7.25-7.21 (t, 1H), 7.17-7.08 (m, 5H), 5.37 (s, 2H), 4.30-4.20 (m, 1H), 4.00-3.80 (m, 2H), 3.75-3.60 (m, 2H), 3.30-3.10 (m, 6H), 2.31 (s, 3H), 1.29-1.27 (d, 3H). MS: m/z=507.65 (M+1), HPLC: 91.66% in method A.

Example 120

(R)-1-(4-(4-(3-(1-(3-fluorobenzyl)-1H-pyrazol-4-yl)-1H-pyrrolo[2,3-b]pyridin-5-yl)phenyl) piperazin-1-yl)propan-2-ol

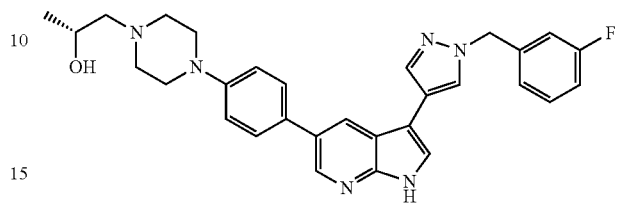

Step-i: (R)-1-(4-(4-(3-(1-(3-fluorobenzyl)-1H-pyrazol-4-yl)-1-tosyl-1H-pyrrolo[2,3-b]pyridin-5-yl)phenyl)piperazin-1-yl)propan-2-ol Using similar reaction conditions as described in step-i of example-82A, 3-(1-(3-fluorobenzyl)-1H-pyrazol-4-yl)-5-(4-(piperazin-1-yl)phenyl)-1-tosyl-1H-pyrrolo[2,3-b]pyridine hydrochloride (step 1 example 103) (150 mg. 0.606 mmol) was alkylated using (R)-2-methyloxirane (22 mg, 0.371 mmol), DIPEA (96 mg, 0.74 mmol) and ethanol (3 mL) to get 160 mg (97.5% yield) of the titled compound. MS: m/z=665.3 (M+1).

Step-ii: (R)-1-(4-(4-(3-(1-(3-fluorobenzyl)-1H-pyrazol-4-yl)-1H-pyrrolo[2,3-b]pyridin-5-yl)phenyl) piperazin-1-yl)propan-2-ol Using similar reaction conditions as described in step-iii of example-1, (R)-1-(4-(4-(3-(1-(3-fluorobenzyl)-1H-pyrazol-4-yl)-1-tosyl-1H-pyrrolo[2,3-b]pyridin-5-yl)phenyl)piperazin-1-yl)propan-2-ol (160 mg, 0.24 mmol) was hydrolyzed by lithium hydroxide (50 mg, 1.2 mmol) in THF/methanol/water (3/2/1 ml) to afford 35 mg (28.6% yield) of the titled compound. $^1$H NMR (CD$_3$OD, 300 MHz): δ 8.58-8.57 (d, 1H), 8.53 (s, 1H), 8.24 (s, 1H), 7.969-7.967 (d, 1H), 7.74 (s, 1H), 7.71-7.68 (d, 2H), 7.41-7.35 (m, 1H), 7.19-7.16 (d, 2H), 7.13-7.00 (m, 3H), 5.44 (s, 2H), 4.28-4.21 (m, 1H), 3.90-3.60 (m, 4H), 3.28-3.09 (m, 4H), 1.28-1.26 (d, 3H). MS: m/z=511.3 (M+1), HPLC: 95.39% in method B.

Example 121

(S)-1-(4-(3-fluoro-4-(3-(1-(3-fluorobenzyl)-1H-pyrazol-4-yl)-1H-pyrrolo[2,3-b]pyridin-5-yl)phenyl)piperazin-1-yl)propan-2-ol

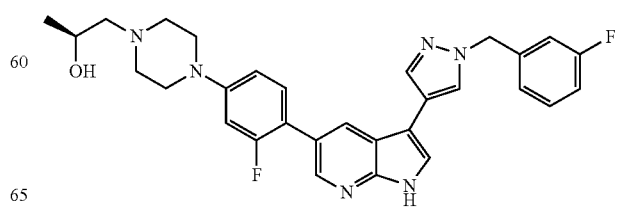

189

Step-i: tert-butyl 4-(3-fluoro-4-(3-(1-(3-fluorobenzyl)-1H-pyrazol-4-yl)-1-tosyl-1H-pyrrolo[2,3-b]pyridin-5-yl)phenyl)piperazine-1-carboxylate Using similar reaction conditions as described in step-ii of example-1, 5-bromo-3-(1-(3-fluorobenzyl)-1H-pyrazol-4-yl)-1-tosyl-1H-pyrrolo[2,3-b]pyridine (compound of Step-i of example 9) (130 g, 0.248 mmol) was coupled with tert-butyl 4-(3-fluoro-4-(4,4,5,5-tetramethyl-1,3,2-dioxaborolan-2-yl)phenyl)piperazine-1-carboxylate (intermediate 69B) (151 mg, 0.372 mmol) using sodium carbonate (79 mg, 0.714 mmol) and Pd(PPh$_3$)$_2$Cl$_2$ (9 mg, 0.124 mmol) in DME/water (5/2 mL). This afforded 150 mg (83.3% yield) after purification by column (Silica gel 60/120) using 50% ethyl acetate in hexane as eluent. MS: m/z=725.3 (M+1).

Step-ii: 5-(2-fluoro-4-(piperazin-1-yl)phenyl)-3-(1-(3-fluorobenzyl)-1H-pyrazol-4-yl)-1-tosyl-1H-pyrrolo[2,3-b]pyridine Using similar reaction conditions as described in step-ii of example-7, tert-butyl 4-(3-fluoro-4-(3-(1-(3-fluorobenzyl)-1H-pyrazol-4-yl)-1-tosyl-1H-pyrrolo[2,3-b]pyridin-5-yl)phenyl)piperazine-1-carboxylate (150 mg, 0.206 mmol) was deprotected in TFA/DCM (2/1 ml) to afford 120 mg (93% yield) of the titled compound. MS: m/z=625.1 (M+1).

Step-iii: (S)-1-(4-(3-fluoro-4-(3-(1-(3-fluorobenzyl)-1H-pyrazol-4-yl)-1-tosyl-1H-pyrrolo[2,3-b]pyridin-5-yl)phenyl)piperazin-1-yl)propan-2-ol Using similar reaction conditions as described in step-i of example-82A, 5-(2-fluoro-4-(piperazin-1-yl)phenyl)-3-(1-(3-fluorobenzyl)-1H-pyrazol-4-yl)-1-tosyl-1H-pyrrolo[2,3-b]pyridine (120 mg. 0.192 mmol) was alkylated using (S)-2-methyloxirane (17 mg, 0.288 mmol), DIPEA (75 mg, 0.576 mmol) and ethanol (3 mL) to get 100 mg (76.3%) of the titled compound. MS: m/z=683.2 (M+1).

Step-iv: (S)-1-(4-(3-fluoro-4-(3-(1-(3-fluorobenzyl)-1H-pyrazol-4-yl)-1H-pyrrolo[2,3-b]pyridin-5-yl)phenyl)piperazin-1-yl)propan-2-ol Using similar reaction conditions as described in step-iii of example-1, (S)-1-(4-(3-fluoro-4-(3-(1-(3-fluorobenzyl)-1H-pyrazol-4-yl)-1-tosyl-1H-pyrrolo[2,3-b]pyridin-5-yl)phenyl)piperazin-1-yl)propan-2-ol (100 mg, 0.146 mmol) was hydrolyzed with lithium hydroxide (30 mg, 0.73 mmol) in THF/methanol/water (3/2/1 mL) to yield 45 mg (58.4% yield) of desired product. $^1$H NMR (CD$_3$OD, 300 MHz): δ 8.39-8.36 (m, 2H), 8.15 (s, 1H), 7.914-7.912 (d, 1H), 7.67 (s, 1H), 7.59-7.50 (t, 1H), 7.42-4.30 (m, 1H), 7.11-6.92 (m, 5H), 5.42 (s, 2H), 4.30-4.20 (m, 1H), 4.00-3.60 (m, 4H), 3.27-3.13 (m, 4H), 1.27-1.25 (d, 3H). MS: m/z=529.3 (M+1), HPLC: 95.98% in method A.

190

Example 122

1-(4-(3-(1-(3-fluorobenzyl)-1H-pyrazol-4-yl)-1H-pyrrolo[2,3-b]pyridin-5-yl)phenyl)piperidin-4-ol

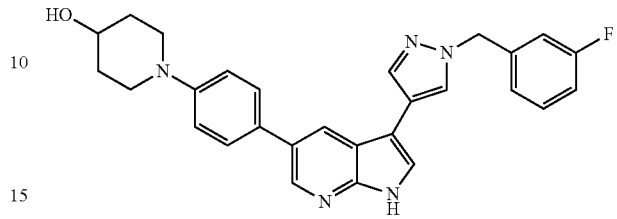

Step-i: 1-(4-(3-(1-(3-fluorobenzyl)-1H-pyrazol-4-yl)-1-tosyl-1H-pyrrolo[2,3-b]pyridin-5-yl)phenyl)piperidin-4-ol Using similar reaction conditions as described in step-ii of example-1, 5-bromo-3-(1-(3-fluorobenzyl)-1H-pyrazol-4-yl)-1-tosyl-1H-pyrrolo[2,3-b]pyridine (compound of Step-i of example 9) (150 mg, 0.28 mmol) was coupled with 1-(4-(4,4,5,5-tetramethyl-1,3,2-dioxaborolan-2-yl)phenyl)piperidin-4-ol (130 mg, 0.428 mmol) using sodium carbonate (89 mg, 0.84 mmol) and Pd(dppf)Cl$_2$ (10 mg, 0.14 mmol) in DME/water (10/1 mL). This afforded 130 mg (crude). MS: m/z=622.5 (M+1).

Step-ii: 1-(4-(3-(1-(3-fluorobenzyl)-1H-pyrazol-4-yl)-1H-pyrrolo[2,3-b]pyridin-5-yl)phenyl) piperidin-4-ol Using similar reaction conditions as described in step-iii of example-1, 1-(4-(3-(1-(3-fluorobenzyl)-1H-pyrazol-4-yl)-1-tosyl-1H-pyrrolo[2,3-b]pyridin-5-yl)phenyl)piperidin-4-ol (130 mg, 0.209 mmol) was hydrolyzed with lithium hydroxide (28 mg, 0.62 mmol) in THF/methanol/water (3/3/1 mL) to yield 35 mg (28.7% yield) of desired product. $^1$H NMR (CD$_3$OD, 300 MHz): δ 8.56 (s, 2H), 8.24 (s, 1H), 7.97-7.94 (m, 3H), 7.74-7.70 (m, 3H), 7.38-7.35 (m, 1H), 7.12-6.99 (m, 3H), 4.10-4.08 (m, 1H), 3.90-3.84 (m, 2H), 3.64-3.57 (m, 2H), 2.27-2.20 (m, 2H), 2.04-1.97 (m, 2H). MS: m/z=468.4 (M+1), HPLC: 91.74% in method B.

Example 123

(2S)-1-(4-(4-(3-(1-(3-fluorobenzyl)-3,5-dimethyl-1H-pyrazol-4-yl)-1H-pyrrolo[2,3-b]pyridin-5-yl)phenyl)piperazin-1-yl)propan-2-ol

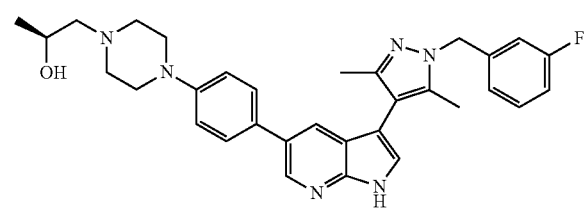 [SMILES: Cc1nn(Cc2cccc(F)c2)c(C)c1-c1c[nH]c2ncc(-c3ccc(N4CCN(C[C@H](C)O)CC4)cc3)cc12]

Step-i: 3-(1-(3-fluorobenzyl)-3,5-dimethyl-1H-pyrazol-4-yl)-5-(4-(piperazin-1-yl)phenyl)-1-tosyl-1H-pyrrolo[2,3-b]pyridine hydrochloride Using similar reaction conditions as described in step-ii of example-7, tert-butyl 4-(4-(3-(1-(3-fluorobenzyl)-3,5-dimethyl-1H-pyrazol-4-yl)-1-tosyl-1H-pyrrolo[2,3-b]pyridin-5-yl)phenyl)piperazine-1-carboxylate (example 40 step 1) (232 mg, 0.315 mmol) was deprotected in methanol (5 ml), HCl in dioxane (5 ml). This afforded 198 mg (93.8% yield) of the titled compound. MS: m/z=651.1 (M+1).

Step-ii (2S)-1-(4-(4-(3-(1-(3-fluorobenzyl)-3,5-dimethyl-1H-pyrazol-4-yl)-1-tosyl-1H-pyrrolo[2,3-b]pyridin-5-yl)phenyl)piperazin-1-yl)propan-2-ol Using similar reaction conditions as described in step-i of example-82A, 3-(1-(3-fluorobenzyl)-3,5-dimethyl-1H-pyrazol-4-yl)-5-(4-(piperazin-1-yl)phenyl)-1-tosyl-1H-pyrrolo[2,3-b]pyridine hydrochloride (197 mg, 0.294 mmol), DIPEA (76 mg, 0.588 mmol) and ethanol (4 mL) to get 167 mg (82.0%) of the titled compound. MS: m/z=693.7 (M+1).

Step-iii: (2S)-1-(4-(4-(3-(1-(3-fluorobenzyl)-3,5-dimethyl-1H-pyrazol-4-yl)-1H-pyrrolo[2,3-b]pyridin-5-yl)phenyl)piperazin-1-yl)propan-2-ol Using similar reaction conditions as described in step-iii of example-1, (2S)-1-(4-(4-(3-(1-(3-fluorobenzyl)-3,5-dimethyl-1H-pyrazol-4-yl)-1-tosyl-1H-pyrrolo[2,3-b]pyridin-5-yl)phenyl)piperazin-1-yl)propan-2-ol (165 mg, 0.238 mmol) was hydrolyzed with lithium hydroxide (100 mg, 2.38 mmol) in THF/methanol/water (20/10/5 mL) to yield 31 mg (13% yield) of desired product. $^1$H NMR (CD$_3$OD, 300 MHz): δ 8.43-8.42 (d, 1H), 7.838-7.831 (d, 1H), 7.50-7.57 (d, 2H), 7.40-7.30 (m, 2H), 7.05-6.95 (m, 4H), 6.95-6.84 (m, 1H), 5.35 (s, 2H), 4.05-3.95 (m, 1H), 3.25-3.22 (t, 4H), 2.80-2.62 (m, 4H), 2.50-2.30 (m, 2H), 2.20 (s, 3H), 2.16 (s, 3H), 1.17-1.15 (d, 3H). MS: m/z=538.9 (M+1), HPLC: 95.51% in method A.

Example 124

2-cyclopropyl-1-(4-(4-(3-(1-(3-fluorobenzyl)-1H-pyrazol-4-yl)-1H-pyrrolo[2,3-b]pyridin-5-yl)phenyl)piperazin-1-yl)ethanone

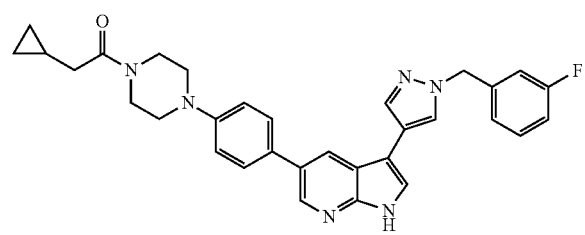 [SMILES: O=C(CC1CC1)N1CCN(c2ccc(-c3cnc4[nH]cc(-c5cnn(Cc6cccc(F)c6)c5)c4c3)cc2)CC1]

Step-i: 3-(1-(3-fluorobenzyl)-1H-pyrazol-4-yl)-5-(4-(piperazin-1-yl)phenyl)-1-tosyl-1H-pyrrolo[2,3-b]pyridine Using similar reaction conditions as described in step-ii of example-7, tert-butyl 4-(4-(3-(1-(3-fluorobenzyl)-1H-pyrazol-4-yl)-1-tosyl-1H-pyrrolo[2,3-b]pyridin-5-yl)phenyl)piperazine-1-carboxylate (example 39 step 1) (1.75 g, 2.475 mmol) was deprotected in TFA/DCM (2/20 mL). This afforded 950 mg (63.3% yield) of the titled compound after purification by column (Silica gel 60/120) using 4% methanol in DCM as eluent. MS: m/z=608.0 (M+1).

Step-ii: 2-cyclopropyl-1-(4-(4-(3-(1-(3-fluorobenzyl)-1H-pyrazol-4-yl)-1-tosyl-1H-pyrrolo[2,3-b]pyridin-5-yl)phenyl)piperazin-1-yl)ethanone To a solution of 3-(1-(3-fluorobenzyl)-1H-pyrazol-4-yl)-5-(4-(piperazin-1-yl)phenyl)-1-tosyl-1H-pyrrolo[2,3-b]pyridine (75 mg, 0.123 mmol) and 2-cyclopropylacetic acid hydrochloride (26 mg, 0.185 mmol) in DMF (2 mL) was added HATU (71 mg, 0.185 mmol), HOBt (25 mg, 0.185 mmol) and DIPEA (86 μL, 0.494 mmol) and stirred at RT overnight. Added ice water and extracted with 10% methanol in DCM. Organic layer was washed with brine solution, dried over sodium sulphate and distilled out the solvent to get 60 mg (70.58%) yield of the title compound. MS: m/z=689.2 (M+1).

Step-iii: 2-cyclopropyl-1-(4-(4-(3-(1-(3-fluorobenzyl)-1H-pyrazol-4-yl)-1H-pyrrolo[2,3-b]pyridin-5-yl)phenyl)piperazin-1-yl)ethanone Using similar reaction conditions as described in step-iii of example-1, 2-cyclopropyl-1-(4-(4-(3-(1-(3-fluorobenzyl)-1H-pyrazol-4-yl)-1-tosyl-1H-pyrrolo[2,3-b]pyridin-5-yl)phenyl)piperazin-1-yl)ethanone (60 mg, 0.087 mmol) was hydrolyzed with lithium hydroxide (19 mg, 0.435 mmol) in THF/methanol/water (5/1/1 mL) to yield 9 mg (16.0% yield) of the titled compound. $^1$H NMR (CD$_3$OD, 400 MHz): δ 8.58-8.57 (d, 1H), 8.51 (s, 1H), 8.26 (s, 1H), 7.97 (s, 1H), 7.75 (s, 1H), 7.65-7.63 (s, 2H), 7.40-7.35 (m, 1H), 7.13-7.11 (d, 3H), 7.07-7.02 (m, 2H), 6.93-6.86 (m, 1H), 6.51-6.46 (dt, 1H), 5.44 (s, 2H), 3.84-3.81 (t, 4H), 3.27 (s, 4H), 2.33-2.17 (m, 2H), 1.13-1.10 (t, 3H). MS: m/z=534.9 (M+1), HPLC: 95.19% in method B.

Example 125

3-(1-(3-fluorobenzyl)-1H-pyrazol-4-yl)-5-(4-(4-(methylsulfonyl)piperazin-1-yl)phenyl)-1H-pyrrolo[2,3-b]pyridine

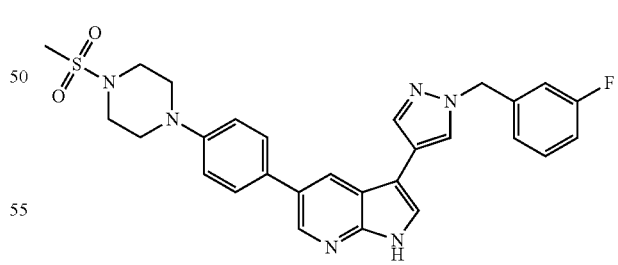

Step-i: 3-(1-(3-fluorobenzyl)-1H-pyrazol-4-yl)-5-(4-(4-(methylsulfonyl)piperazin-1-yl)phenyl)-1-tosyl-1H-pyrrolo[2,3-b]pyridine Using similar reaction conditions as described in step i of intermediate 17, 3-(1-(3-fluorobenzyl)-1H-pyrazol-4-yl)-5-(4-(piperazin-1-yl)phenyl)-1-tosyl-1H-pyrrolo[2,3-b]pyridine (product of step 1 of example 124) (75 mg, 0.123 mmol)

was mesylated with methane sulfonyl chloride (17 mg, 0.148 mol) using triethylamine (35 μL, 0.247 mmol) in DCM (5 mL) to afford 60 mg (71.42% yield) of the titled compound. MS: m/z=685.1 (M+1).

Step-ii: 3-(1-(3-fluorobenzyl)-1H-pyrazol-4-yl)-5-(4-(4-(methylsulfonyl)piperazin-1-yl)phenyl)-1H-pyrrolo[2,3-b]pyridine Using similar reaction conditions as described in step-iii of example-1, 3-(1-(3-fluorobenzyl)-1H-pyrazol-4-yl)-5-(4-(4-(methylsulfonyl)piperazin-1-yl)phenyl)-1-tosyl-1H-pyrrolo[2,3-b]pyridine (60 mg, 0.087 mmol) was hydrolyzed with lithium hydroxide (19 mg, 0.438 mmol) in THF/methanol/water (5/1/1 mL) to yield 40 mg (70.17% yield) of the titled compound. $^1$H NMR (CD$_3$OD, 400 MHz): δ 8.63-8.62 (d, 1H), 8.54 (s, 1H), 8.29 (s, 1H), 7.99 (s, 1H), 7.77 (s, 1H), 7.69-7.67 (d, 2H), 7.40-7.38 (q, 1H), 7.18-7.02 (m, 5H), 5.46 (s, 2H), 3.40-3.37 (m, 8H), 2.91 (s, 3H). MS: m/z=531.0 (M+1), HPLC: 99.35% in method B.

Example 126

2-(4-(4-(3-(1-(3-fluorobenzyl)-1H-pyrazol-4-yl)-1H-pyrrolo[2,3-b]pyridin-5-yl)phenyl)piperazin-1-yl)ethanol

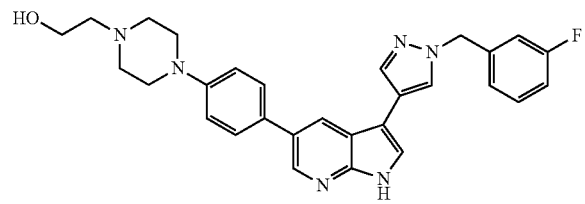 [SMILES: OCCN1CCN(c2ccc(-c3cnc4[nH]cc(-c5cnn(Cc6cccc(F)c6)c5)c4c3)cc2)CC1]

Step-i: 2-(4-(4-(3-(1-(3-fluorobenzyl)-1H-pyrazol-4-yl)-1-tosyl-1H-pyrrolo[2,3-b]pyridin-5-yl)phenyl)piperazin-1-yl)ethanol To a stirred solution of 3-(1-(3-fluorobenzyl)-1H-pyrazol-4-yl)-5-(4-(piperazin-1-yl)phenyl)-1-tosyl-1H-pyrrolo[2,3-b]pyridine (product of step 1 of example 124) (75 mg, 0.123 mmol), potassium carbonate (24 mg, 0.185 mmol) and DMF (5 ml) was added 2-bromoethanol (24 mg, 0.185 mmol) and the mixture stirred at RT for overnight. Then water was added, this was then extracted into 10% methanol in DCM, organic portion was dried over sodium sulfate and concentrated to give 60 mg (75% yield) of the titled compound. MS: m/z=651.2 (M+1).

Step-ii: 2-(4-(4-(3-(1-(3-fluorobenzyl)-1H-pyrazol-4-yl)-1H-pyrrolo[2,3-b]pyridin-5-yl)phenyl)piperazin-1-yl)ethanol Using similar reaction conditions as described in step-iii of example-1, 2-(4-(4-(3-(1-(3-fluorobenzyl)-1H-pyrazol-4-yl)-1-tosyl-1H-pyrrolo[2,3-b]pyridin-5-yl)phenyl)piperazin-1-yl)ethanol (60 mg, 0.092 mmol) was hydrolyzed by lithium hydroxide (20 mg, 0.461 mmol) in THF/methanol/water (5/1/1 ml) to yield 40 mg (13.3% yield) of the titled compound. $^1$H NMR (CD$_3$OD, 400 MHz): δ 8.747-8.742 (d, 2H), 8.586-8.583 (d, 1H), 8.30 (s, 1H), 7.99 (s, 1H), 7.82 (s, 1H), 7.72-7.69 (d, 2H), 7.38-7.35 (q, 1H), 7.19-7.17 (d, 2H), 7.13-7.11 (d, 1H), 7.08-7.01 (m, 2H), 5.44 (s, 2H), 3.99-3.90 (m, 5H), 3.85-3.75 (m, 2H), 3.39-3.33 (m, 3H), 3.30-3.20 (m, 2H). MS: m/z=496.9 (M+1), HPLC: 96.51% in method A.

Example 127

2-(dimethylamino)-1-(4-(4-(3-(1-(3-fluorobenzyl)-1H-pyrazol-4-yl)-1H-pyrrolo[2,3-b]pyridin-5-yl)phenyl)piperazin-1-yl)ethanone

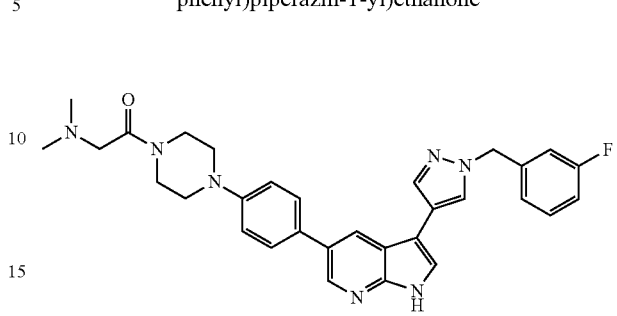

Step-i: 2-(dimethylamino)-1-(4-(4-(3-(1-(3-fluorobenzyl)-1H-pyrazol-4-yl)-1-tosyl-1H-pyrrolo[2,3-b]pyridin-5-yl)phenyl)piperazin-1-yl)ethanone Using similar reaction conditions as described in step-ii of example-124, 3-(1-(3-fluorobenzyl)-1H-pyrazol-4-yl)-5-(4-(piperazin-1-yl)phenyl)-1-tosyl-1H-pyrrolo[2,3-b]pyridine (product of step 1 of example 124) (75 mg, 0.123 mmol) was coupled with 2-(dimethylamino)acetic acid hydrochloride (26 mg, 0.185 mmol) using HATU (71 mg, 0.185 mmol), HOBt (25 mg, 0.185 mmol) and DIPEA (86 μL, 0.494 mmol) in DMF (2 mL) to get 80 mg (85.52%) yield of the title compound. MS: m/z=692.5 (M+1).

Step-ii: 2-(dimethylamino)-1-(4-(4-(3-(1-(3-fluorobenzyl)-1H-pyrazol-4-yl)-1H-pyrrolo[2,3-b]pyridin-5-yl)phenyl)piperazin-1-yl)ethanone Using similar reaction conditions as described in step-iii of example-1, 2-(dimethylamino)-1-(4-(4-(3-(1-(3-fluorobenzyl)-1H-pyrazol-4-yl)-1-tosyl-1H-pyrrolo[2,3-b]pyridin-5-yl)phenyl)piperazin-1-yl)ethanone (80 mg, 0.115 mmol) was hydrolyzed with lithium hydroxide (25 mg, 0.578 mmol) in THF/methanol/water (5/1/1 mL) to yield 60 mg (80.0% yield) of the titled compound. $^1$H NMR (CD$_3$OD, 400 MHz): δ 8.826-8.822 (d, 1H), 8.605-8.601 (d, 1H), 8.32 (s, 1H), 8.00 (s, 1H), 7.86 (s, 1H), 7.70-7.68 (d, 2H), 7.40-7.35 (q, 1H), 7.17-7.12 (m, 3H), 7.07-7.02 (m, 2H), 5.45 (s, 2H), 4.35 (s, 2H), 3.84-3.81 (t, 2H), 3.63-3.60 (t, 2H), 3.36-3.33 (t, 4H), 2.99 (s, 6H). MS: m/z=537.9 (M+1), HPLC: 91.53% in method A.

Example 128

1-(4-(4-(3-(1-(3-fluorobenzyl)-1H-pyrazol-4-yl)-1H-pyrrolo[2,3-b]pyridin-5-yl)phenyl)piperazin-1-yl)-2-hydroxyethanone

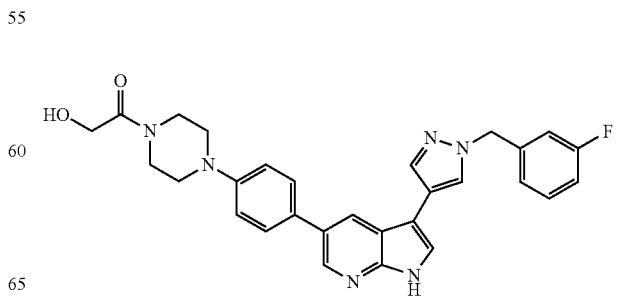

Step-i: 1-(4-(4-(3-(1-(3-fluorobenzyl)-1H-pyrazol-4-yl)-1-tosyl-1H-pyrrolo[2,3-b]pyridin-5-yl)phenyl)piperazin-1-yl)-2-hydroxyethanone Using similar reaction conditions as described in step-ii of example-124, 3-(1-(3-fluorobenzyl)-1H-pyrazol-4-yl)-5-(4-(piperazin-1-yl)phenyl)-1-tosyl-1H-pyrrolo[2,3-b]pyridine (product of step 1 of example 124) (75 mg, 0.123 mmol) was coupled with 2-hydroxyacetic acid (14 mg, 0.185 mmol) using HATU (71 mg, 0.185 mmol), HOBt (25 mg, 0.185 mmol) and DIPEA (86 μL, 0.494 mmol) in DMF (2 mL) to get 60 mg (73.1%) yield of the title compound. MS: m/z=665.3 (M+1).

Step-ii: 1-(4-(4-(3-(1-(3-fluorobenzyl)-1H-pyrazol-4-yl)-1H-pyrrolo[2,3-b]pyridin-5-yl)phenyl)piperazin-1-yl)-2-hydroxyethanone Using similar reaction conditions as described in step-iii of example-1, 1-(4-(4-(3-(1-(3-fluorobenzyl)-1H-pyrazol-4-yl)-1-tosyl-1H-pyrrolo[2,3-b]pyridin-5-yl)phenyl)piperazin-1-yl)-2-hydroxyethanone (60 mg, 0.090 mmol) was hydrolyzed with lithium hydroxide (19 mg, 0.451 mmol) in THF/methanol/water (5/1/1 mL) to yield 20 mg (35.7% yield) of the titled compound. $^1$H NMR (CD$_3$OD, 400 MHz): δ 8.822-8.820 (d, 1H), 8.59 (s, 1H), 8.33 (s, 1H), 8.01 (s, 1H), 7.86 (s, 1H), 7.70-7.68 (d, 2H), 7.41-7.35 (q, 1H), 7.17-7.02 (m, 5H), 5.45 (s, 2H), 4.33 (s, 2H), 3.82-3.79 (t, 2H), 3.62 (s, 2H). MS: m/z=510.8 (M+1), HPLC: 90.93% in method A.

Example 129

(S)-1-(4-(4-(3-(1-(3-fluorobenzyl)-5-methyl-1H-pyrazol-4-yl)-1H-pyrrolo[2,3-b]pyridin-5-yl)phenyl)piperazin-1-yl)propan-2-ol

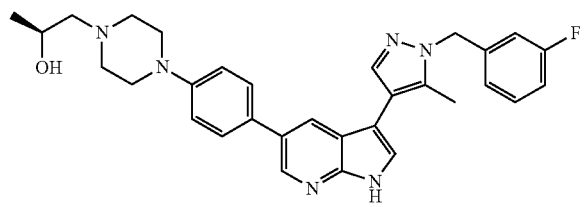 [SMILES: Cc1c(-c2c[nH]c3ncc(-c4ccc(N5CCN(C[C@H](C)O)CC5)cc4)cc23)cnn1Cc1cccc(F)c1]

Step-i: 3-(1-(3-fluorobenzyl)-5-methyl-1H-pyrazol-4-yl)-5-(4-(piperazin-1-yl)phenyl)-1-tosyl-1H-pyrrolo[2,3-b]pyridine hydrochloride Using similar reaction conditions as described in step-ii of example-7, tert-butyl 4-(4-(3-(1-(3-fluorobenzyl)-5-methyl-1H-pyrazol-4-yl)-1-tosyl-1H-pyrrolo[2,3-b]pyridin-5-yl)phenyl)piperazine-1-carboxylate (example 44, step 1) (290 mg, 0.40 mmol) was deprotected with HCl in ether (5 ml). This afforded 240 mg (96.1% yield) of the titled compound. MS: m/z=621.2 (M+1).

Step-ii: (S)-1-(4-(4-(3-(1-(3-fluorobenzyl)-5-methyl-1H-pyrazol-4-yl)-1-tosyl-1H-pyrrolo[2,3-b]pyridin-5-yl)phenyl)piperazin-1-yl)propan-2-ol Using similar reaction conditions as described in step-i of example-82A, 3-(1-(3-fluorobenzyl)-5-methyl-1H-pyrazol-4-yl)-5-(4-(piperazin-1-yl)phenyl)-1-tosyl-1H-pyrrolo[2,3-b]pyridine hydrochloride (230 mg, 0.349 mmol) was alkylated using (S)-2-methyloxirane (41 mg, 0.69 mmol) DIPEA (136 mg, 10 mmol) and ethanol (5 mL) to get 200 mg (crude) of the titled compound.

Step-iii: (S)-1-(4-(4-(3-(1-(3-fluorobenzyl)-5-methyl-1H-pyrazol-4-yl)-1H-pyrrolo[2,3-b]pyridin-5-yl)phenyl)piperazin-1-yl)propan-2-ol Using similar reaction conditions as described in step-iii of example-1, (S)-1-(4-(4-(3-(1-(3-fluorobenzyl)-5-methyl-1H-pyrazol-4-yl)-1-tosyl-1H-pyrrolo[2,3-b]pyridin-5-yl)phenyl)piperazin-1-yl)propan-2-ol (200 mg, 0.29 mmol) was hydrolyzed with lithium hydroxide (37 mg, 0.88 mmol) in THF/methanol/water (6/4/2 mL) to yield 10 mg (6.4% yield) after purification by preparative HPLC along with one more isomer example 130. $^1$H NMR (CDCl$_3$, 300 MHz): δ 9.12 (s, 1H), 8.548-8.542 (d, 1H), 8.02-8.01 (d, 1H), 7.59 (s, 1H), 7.54-7.51 (d, 2H), 7.36-7.29 (m, 2H), 7.26-6.91 (m, 5H), 5.32 (s, 2H), 3.95-3.90 (m, 1H), 3.30-3.23 (m, 4H), 2.90-2.86 (m, 2H), 2.62-2.60 (m, 2H), 2.43-2.31 (m, 5H), 1.19-1.17 (d, 3H). MS: m/z=524.9 (M+1), HPLC: 95.68% in method A.

Example 130

(S)-1-(4-(4-(3-(1-(3-fluorobenzyl)-3-methyl-1H-pyrazol-4-yl)-1H-pyrrolo[2,3-b]pyridin-5-yl)phenyl)piperazin-1-yl)propan-2-ol

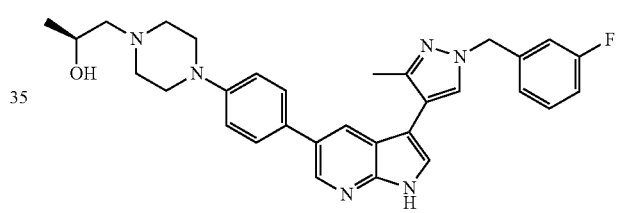

Yield 4 mg (2.5%). $^1$H NMR (CDCl$_3$, 300 MHz): δ 9.25 (s, 1H), 8.56-8.55 (d, 1H), 8.09-8.08 (d, 1H), 7.77 (s, 1H), 7.60-7.51 (m, 2H), 7.35-7.28 (m, 2H), 7.04-6.84 (m, 5H), 5.38 (s, 2H), 4.00-3.85 (m, 1H), 3.29-3.27 (m, 4H), 2.90-2.86 (m, 2H), 2.62-2.58 (m, 2H), 2.41-2.35 (m, 2H), 2.30 (s, 3H), 1.19-1.17 (d, 3H). MS: m/z=525.3 (M+1), HPLC: 95.37% in method A.

Example 131

5-(4-(piperazin-1-yl)phenyl)-3-(1-(pyridin-3-ylmethyl)-1H-pyrazol-4-yl)-1H-pyrrolo[2,3-b]pyridine

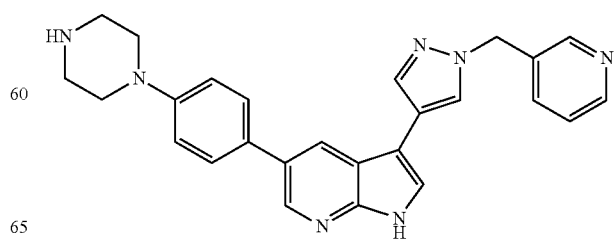

Step-i: tert-butyl 4-(4-(3-(1-(pyridin-3-ylmethyl)-1H-pyrazol-4-yl)-1-tosyl-1H-pyrrolo[2,3-b]pyridin-5-yl)phenyl)piperazine-1-carboxylate Using similar reaction conditions as described in step-ii of example-1, tert-butyl 4-(4-(3-iodo-1-tosyl-1H-pyrrolo[2,3-b]pyridin-5-yl)phenyl)piperazine-1-carboxylate (intermediate 41) (150 mg, 0.22 mmol) was coupled with 3-((4-(4,4,5,5-tetramethyl-1,3,2-dioxaborolan-2-yl)-1H-pyrazol-1-yl)methyl)pyridine (intermediate 64) (130 mg, 0.45 mmol) using sodium carbonate (70 mg, 0.66 mmol) and Pd(PPh$_3$)$_2$Cl$_2$ (7.7 mg, 0.011 mmol) in toluene/ethanol/water (10/10/2 ml) to give 110 mg (70% yield) of the titled compound after purification by column (Silica gel 60/120) using 35% ethyl acetate in hexane as eluent.

Step-ii: tert-butyl 4-(4-(3-(1-(pyridin-3-ylmethyl)-1H-pyrazol-4-yl)-1H-pyrrolo[2,3-b]pyridin-5-yl)phenyl)piperazine-1-carboxylate Using similar reaction conditions as described in step-iii of example-1, tert-butyl 4-(4-(3-(1-(pyridin-3-ylmethyl)-1H-pyrazol-4-yl)-1-tosyl-1H-pyrrolo[2,3-b]pyridin-5-yl)phenyl)piperazine-1-carboxylate (130 mg, 0.188 mmol) was hydrolyzed with lithium hydroxide (24 mg, 0.565 mmol) in THF/methanol/water (2/2/2 mL) to yield 100 mg (crude) of the titled compound. MS: m/z=536.7 (M+1).

Step-iii: 5-(4-(piperazin-1-yl)phenyl)-3-(1-(pyridin-3-ylmethyl)-1H-pyrazol-4-yl)-1H-pyrrolo[2,3-b]pyridine Using similar reaction conditions as described in step-ii of example-7, tert-butyl 4-(4-(3-(1-(pyridin-3-ylmethyl)-1H-pyrazol-4-yl)-1H-pyrrolo[2,3-b]pyridin-5-yl)phenyl)piperazine-1-carboxylate (100 mg, 0.186 mmol) was deprotected with HCl in ether/methanol (2/3 ml). This afforded 9 mg (11.0% yield) of the titled compound. $^1$H NMR (CD$_3$OD, 300 MHz): δ 8.54 (s, 1H), 8.34-8.28 (d, 1H), 8.50-8.49 (d, 1H), 8.43-8.42 (d, 1H), 8.307-8.300 (d, 1H), 8.23 (s, 1H), 7.93 (s, 1H), 7.79-7.77 (d, 1H), 7.64-7.61 (m, 3H), 7.45-7.41 (m, 1H), 7.14-7.11 (m, 2H), 5.49 (s, 2H), 3.38-3.31 (m, 4H), 3.30-3.23 (m, 4H). MS: m/z=436.2 (M+1), HPLC: 97.13% in method A.

Example 132

3-(1-(3-fluorobenzyl)-1H-pyrazol-4-yl)-5-(6-(piperazin-1-yl)pyridin-3-yl)-1H-pyrrolo[2,3-b]pyridine

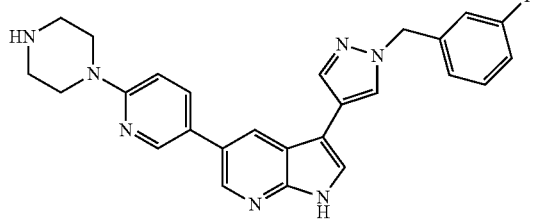

Step-i: tert-butyl 4-(5-(3-(1-(3-fluorobenzyl)-1H-pyrazol-4-yl)-1-tosyl-1H-pyrrolo[2,3-b]pyridin-5-yl)pyridin-2-yl)piperazine-1-carboxylate Using similar reaction conditions as described in step-ii of example-1, 5-bromo-3-(1-(3-fluorobenzyl)-1H-pyrazol-4-yl)-1-tosyl-1H-pyrrolo[2,3-b]pyridine (compound of Step-i of example 9) (150 mg, 0.286 mmol) was coupled with tert-butyl 4-(5-(4,4,5,5-tetramethyl-1,3,2-dioxaborolan-2-yl)pyridin-2-yl)piperazine-1-carboxylate (intermediate 69C) (167 mg, 0.429 mmol) in sodium carbonate (76 mg, 0.715 mmol), Pd(PPh$_3$)$_2$Cl$_2$ (10 mg, 0.014 mmol), DME/water (5/1 mL). This afforded 140 mg (69.0% yield) after purification by column chromatography (60-120 silica gel) using 2% methanol in DCM as eluent. MS: m/z=708.3 (M+1).

Step-ii: tert-butyl 4-(5-(3-(1-(3-fluorobenzyl)-1H-pyrazol-4-yl)-1-tosyl-1H-pyrrolo[2,3-b]pyridin-5-yl)pyridin-2-yl)piperazine-1-carboxylate Using similar reaction conditions as described in step-iii of example-1, tert-butyl 4-(5-(3-(1-(3-fluorobenzyl)-1H-pyrazol-4-yl)-1-tosyl-1H-pyrrolo[2,3-b]pyridin-5-yl)pyridin-2-yl)piperazine-1-carboxylate (140 mg, 0.197 mmol) was hydrolyzed with lithium hydroxide (17 mg, 0.395 mmol) in THF/methanol/water (5/2/1 mL) to yield 70 mg (63.9% yield) after purification by column chromatography (60-120 silica gel) using 2% methanol in DCM as eluent. MS: m/z=554.4 (M+1).

Step-iii: 3-(1-(3-fluorobenzyl)-1H-pyrazol-4-yl)-5-(6-(piperazin-1-yl)pyridin-3-yl)-1H-pyrrolo[2,3-b]pyridine Using similar reaction conditions as described in step-ii of example-7, tert-butyl 4-(5-(3-(1-(3-fluorobenzyl)-1H-pyrazol-4-yl)-1-tosyl-1H-pyrrolo[2,3-b]pyridin-5-yl)pyridin-2-yl)piperazine-1-carboxylate (70 mg, 0.126 mmol) was deprotected with TFA/DCM (1/5 ml). This afforded 17.5 mg (24.3% yield) of the titled compound. $^1$H NMR (CD$_3$OD, 300 MHz): δ 8.53 (s, 3H), 8.23 (s, 1H), 8.16-8.12 (dd, 1H), 7.97 (s, 1H), 7.73 (s, 1H), 7.40-7.30 (m, 1H), 7.20-7.10 (m, 2H), 7.09-6.95 (m, 1H), 5.43 (s, 2H), 3.92-2.89 (m, 4H), 3.40-3.36 (m, 4H). MS: m/z=464.2 (M+1), HPLC: 97.79% in method A.

Example 133

3-(1-(3,5-difluorobenzyl)-1H-pyrazol-4-yl)-5-(6-(4-methylpiperazin-1-yl)pyridin-3-yl)-1H-pyrrolo[2,3-b]pyridine

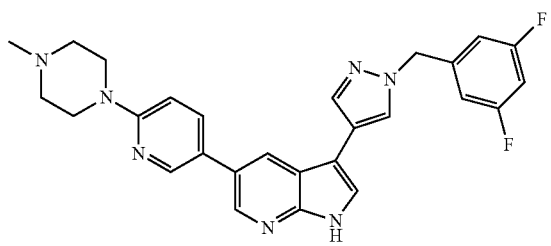 [SMILES: CN1CCN(c2ccc(-c3cnc4[nH]cc(-c5cnn(Cc6cc(F)cc(F)c6)c5)c4c3)cn2)CC1]

Step-i: tert-butyl 4-(5-(3-(1-(3,5-difluorobenzyl)-1H-pyrazol-4-yl)-1-tosyl-1H-pyrrolo[2,3-b]pyridin-5-yl)pyridin-2-yl)piperazine-1-carboxylate Using similar reaction conditions as described in step-ii of example-1, 5-bromo-3-(1-(3,5-difluorobenzyl)-1H-pyrazol-4-yl)-1-tosyl-1H-pyrrolo[2,3-b]pyridine (STEP 1 example 71) (1 g, 1.515 mmol) was coupled with tert-butyl 4-(5-(4,4,5,5-tetramethyl-1,3,2-dioxaborolan-2-yl)pyridin-2-yl)piperazine-1-carboxylate (intermediate 69C) (581 mg, 1.818 mmol) using sodium carbonate (481 mg, 4.545 mmol) and Pd(PPh$_3$)$_2$Cl$_2$ (53 mg, 0.075 mmol) in toluene/ethanol/water (10/15/2 ml). This afforded 1.12 g (100% yield) of the titled compound after purification by column (Silica gel 60/120) using 40% ethyl acetate in hexane as eluent. MS: m/z=726.3 (M+1).

Step-ii: 3-(1-(3,5-difluorobenzyl)-1H-pyrazol-4-yl)-5-(6-(piperazin-1-yl)pyridin-3-yl)-1-tosyl-1H-pyrrolo[2,3-b]pyridine Using similar reaction conditions as described in step-ii of example-7, tert-butyl 4-(5-(3-(1-(3,5-difluorobenzyl)-1H-pyrazol-4-yl)-1-tosyl-1H-pyrrolo[2,3-b]pyridin-5-yl)pyridin-2-yl)piperazine-1-carboxylate (1.12 g, 1.544 mmol) was deprotected in TFA/DCM (10/5 ml). This afforded 600 mg (64.8% yield) of the titled compound. MS: m/z=625.8 (M+1).

Step-iii: 3-(1-(3,5-difluorobenzyl)-1H-pyrazol-4-yl)-5-(6-(4-methylpiperazin-1-yl)pyridin-3-yl)-1-tosyl-1H-pyrrolo[2,3-b]pyridine To the solution of 3-(1-(3,5-difluorobenzyl)-1H-pyrazol-4-yl)-5-(6-(piperazin-1-yl)pyridin-3-yl)-1-tosyl-1H-pyrrolo[2,3-b]pyridine (100 mg, 0.16 mmol) and paraformaldehyde (10 mg, 0.32 mmol) in dichloroethane was added Na(OAc)$_3$BH (68 mg, 0.32 mmol) and stirred at RT overnight. Distilled off the solvent to get 95 mg (95.0% yield) of the titled compound after purification by column (Silica gel 60/120) using 5% methanol in dichloromethane as eluent. MS: m/z=640.2 (M+1).

Step-iv: 3-(1-(3,5-difluorobenzyl)-1H-pyrazol-4-yl)-5-(6-(4-methylpiperazin-1-yl)pyridin-3-yl)-1H-pyrrolo[2,3-b]pyridine Using similar reaction conditions as described in step-iii of example-1, 3-(1-(3,5-difluorobenzyl)-1H-pyrazol-4-yl)-5-(6-(4-methylpiperazin-1-yl)pyridin-3-yl)-1-tosyl-1H-pyrrolo[2,3-b]pyridine (95 mg, 0.148 mmol) was hydrolyzed with lithium hydroxide (17 mg, 0.399 mmol) in THF/methanol/water (2/2/1 mL) to yield 30 mg (81.0% yield) of the titled compound. $^1$H NMR (CDCl$_3$, 300 MHz): δ 9.14 (s, 1H), 8.49-8.46 (dd, 2H), 8.11 (s, 1H), 7.87 (s, 1H), 7.77-7.71 (m, 2H), 7.449-7.443 (d, 1H), 6.80-6.76 (m, 3H), 5.36 (s, 2H), 3.65-3.62 (m, 4H), 2.58-2.55 (m, 4H), 2.37 (s, 3H). MS: m/z=486.1 (M+1), HPLC: 93.44% in method B.

Example 134

3-(1-(3,5-difluorobenzyl)-1H-pyrazol-4-yl)-5-(6-(piperazin-1-yl)pyridin-3-yl)-1H-pyrrolo[2,3-b]pyridine

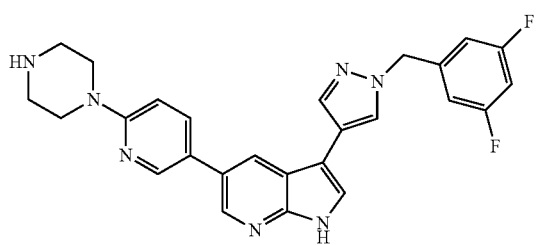 [SMILES: Fc1cc(F)cc(Cn2cc(-c3c[nH]c4ncc(-c5ccc(N6CCNCC6)nc5)cc34)cn2)c1]

Using similar reaction conditions as described in step-iii of example-1, 3-(1-(3,5-difluorobenzyl)-1H-pyrazol-4-yl)-5-(6-(piperazin-1-yl)pyridin-3-yl)-1-tosyl-1H-pyrrolo[2,3-b]pyridine (step 2 compound of example 133) (50 mg, 0.079 mmol) was hydrolyzed with lithium hydroxide (32 mg, 0.743 mmol) in THF/methanol/water (2/2/1 mL) to yield 46 mg (63.8% yield) of the titled compound. $^1$H NMR (CD$_3$OD, 300 MHz): δ 8.58 (s, 1H), 8.537-8.530 (d, 2H), 8.28 (s, 1H), 8.19-8.16 (dd, 1H), 8.00 (s, 1H), 7.77 (s, 1H), 7.22-7.19 (d, 1H), 6.88-6.85 (m, 3H), 5.43 (s, 2H), 3.94-3.90 (t, 4H), 3.41-3.37 (t, 4H). MS: m/z=472.3 (M+1), HPLC: 95.01% in method A.

Example 135

(S)-1-(4-(5-(3-(1-(3,5-difluorobenzyl)-1H-pyrazol-4-yl)-1H-pyrrolo[2,3-b]pyridin-5-yl)pyridin-2-yl)piperazin-1-yl)propan-2-ol

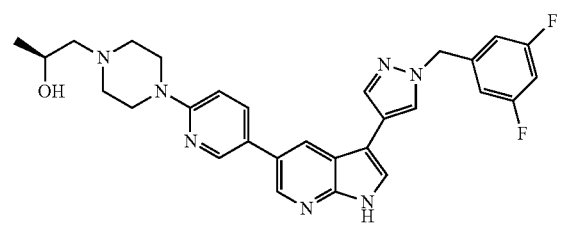 [SMILES: C[C@H](O)CN1CCN(c2ccc(-c3cnc4[nH]cc(-c5cnn(Cc6cc(F)cc(F)c6)c5)c4c3)cn2)CC1]

Step-i: (S)-1-(4-(5-(3-(1-(3,5-difluorobenzyl)-1H-pyrazol-4-yl)-1-tosyl-1H-pyrrolo[2,3-b]pyridin-5-yl)pyridin-2-yl)piperazin-1-yl)propan-2-ol Using similar reaction conditions as described in step-i of example-82A, 3-(1-(3,5-difluorobenzyl)-1H-pyrazol-4-yl)-5-(6-(piperazin-1-yl)pyridin-3-yl)-1-tosyl-1H-pyrrolo[2,3-b]pyridine (step 2 compound of example 133) (100 mg, 0.16 mmol) was alkylated using (S)-2-methyloxirane (14 mg, 0.24 mmol), DIPEA (31 mg, 0.24 mmol) and ethanol (2 mL) to get 90 mg (82.5%) of the titled compound after purification by column (Silica gel 60/120) using 5% methanol in dichloromethane as eluent. MS: m/z=684.2 (M+1).

Step-ii: (S)-1-(4-(5-(3-(1-(3,5-difluorobenzyl)-1H-pyrazol-4-yl)-1H-pyrrolo[2,3-b]pyridin-5-yl)pyridin-2-yl)piperazin-1-yl)propan-2-ol Using similar reaction conditions as described in step-iii of example-1, (S)-1-(4-(5-(3-(1-(3,5-difluorobenzyl)-1H-pyrazol-4-yl)-1-tosyl-1H-pyrrolo[2,3-b]pyridin-5-yl)pyridin-2-yl)piperazin-1-yl)propan-2-ol (90 mg, 0.131 mmol) was hydrolyzed with lithium hydroxide (28 mg, 0.658 mmol) in THF/methanol/water (2/2/1 mL) to yield 70 mg (100% yield) of desired product. $^1$H NMR (CD$_3$OD, 300 MHz): δ 8.74-8.73 (d, 1H), 8.61-8.56 (m, 2H), 8.31-8.25 (m, 2H), 8.02 (s, 1H), 7.83 (s, 1H), 7.30-7.27 (d, 1H), 7.10-6.85 (m, 2H), 5.44 (s, 2H), 4.30-4.20 (m, 1H), 3.60-3.50 (bs, 4H), 3.23-3.15 (m, 2H), 1.27-1.25 (d, 3H). MS: m/z=530.2 (M+1), HPLC: 97.51% in method A.

Example 136

2-(4-(5-(3-(1-(3,5-difluorobenzyl)-1H-pyrazol-4-yl)-1H-pyrrolo[2,3-b]pyridin-5-yl)pyridin-2-yl)piperazin-1-yl)acetamide

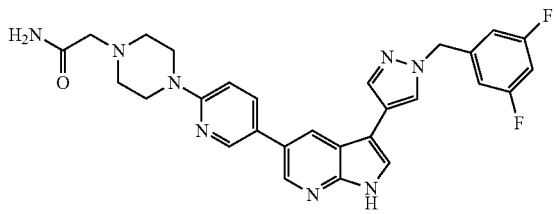 [SMILES: NC(=O)CN1CCN(c2ccc(-c3cnc4[nH]cc(-c5cnn(Cc6cc(F)cc(F)c6)c5)c4c3)cn2)CC1]

Step-i: 2-(4-(5-(3-(1-(3,5-difluorobenzyl)-1H-pyrazol-4-yl)-1-tosyl-1H-pyrrolo[2,3-b]pyridin-5-yl)pyridin-2-yl)piperazin-1-yl)acetamide Using similar reaction conditions as described in step-i of example-82A, 3-(1-(3,5-difluorobenzyl)-1H-pyrazol-4-yl)-5-(6-(piperazin-1-yl)pyridin-3-yl)-1-tosyl-1H-pyrrolo[2,3-b]pyridine (step 2 compound of example 133) (100 mg, 0.16 mmol) was alkylated using 2-chloroacetamide (30 mg, 0.32 mmol), sodium bicarbonate (40 mg, 0.48 mmol) and ethanol/acetone (3/3 mL) to get 100 mg (91.7%) of the titled compound after purification by column (Silica gel 60/120) using 5% methanol in dichloromethane as eluent. MS: m/z=683.3 (M+1).

Step-ii: 2-(4-(5-(3-(1-(3,5-difluorobenzyl)-1H-pyrazol-4-yl)-1H-pyrrolo[2,3-b]pyridin-5-yl)pyridin-2-yl)piperazin-1-yl)acetamide Using similar reaction conditions as described in step-iii of example-1, 2-(4-(5-(3-(1-(3,5-difluorobenzyl)-1H-pyrazol-4-yl)-1-tosyl-1H-pyrrolo[2,3-b]pyridin-5-yl)pyridin-2-yl)piperazin-1-yl) acetamide (100 mg, 0.146 mmol) was hydrolyzed with lithium hydroxide (31 mg, 0.733 mmol) in THF/methanol/water (2/2/1 mL) to yield 28 mg (36.3% yield) of desired product. $^1$H NMR (CD$_3$OD, 300 MHz): δ 8.53-8.48 (m, 3H), 8.259-8.257 (d, 1H), 8.15-8.05 (dd, 1H), 7.988-7.986 (d, 1H), 7.72 (s, 1H), 7.19-7.10 (d, 1H), 6.90-6.82 (m, 3H), 5.43 (s, 2H), 4.05-3.90 (m, 6H), 3.51-3.49 (t, 4H). MS: m/z=529.2 (M+1), HPLC: 98.61% in method A.

Example 137

3-(1-(3-fluorobenzyl)-1H-pyrazol-4-yl)-5-(6-(4-methylpiperazin-1-yl)pyridin-3-yl)-1H-pyrrolo[2,3-b]pyridine

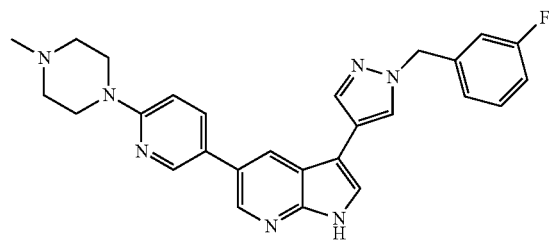 [SMILES: CN1CCN(c2ccc(-c3cnc4[nH]cc(-c5cnn(Cc6cccc(F)c6)c5)c4c3)cn2)CC1]

Step-i: 3-(1-(3-fluorobenzyl)-1H-pyrazol-4-yl)-5-(6-(piperazin-1-yl)pyridin-3-yl)-1-tosyl-1H-pyrrolo[2,3-b]pyridine Using similar reaction conditions as described in step-ii of example-7, tert-butyl 4-(5-(3-(1-(3-fluorobenzyl)-1H-pyrazol-4-yl)-1-tosyl-1H-pyrrolo[2,3-b]pyridin-5-yl)pyridin-2-yl)piperazine-1-carboxylate (step 1 of example 132) (700 mg, 0.9889 mmol) was deprotected with TFA/DCM (5/20 ml). This afforded 400 mg (66.6% yield) of the titled compound. MS: m/z=608.1 (M+1).

Step-ii: 3-(1-(3-fluorobenzyl)-1H-pyrazol-4-yl)-5-(6-(4-methylpiperazin-1-yl)pyridin-3-yl)-1-tosyl-1H-pyrrolo[2,3-b]pyridine Using similar reaction conditions as described in step-iii of example-133, 3-(1-(3-fluorobenzyl)-1H-pyrazol-4-yl)-5-(6-(piperazin-1-yl)pyridin-3-yl)-1-tosyl-1H-pyrrolo[2,3-b]pyridine (100 mg, 0.164 mmol) was methylated using paraformaldehyde (15 mg, 0.494 mmol) and Na(OAc)$_3$BH (105 mg, 0.494 mmol) in dichloroethane (5 mL) to afford 90 mg (88.2% yield) of the titled compound after purification by column (Silica gel 60/120) using 5% methanol in dichloromethane as eluent. MS: m/z=622.1 (M+1).

Step-iii: 3-(1-(3-fluorobenzyl)-1H-pyrazol-4-yl)-5-(6-(4-methylpiperazin-1-yl)pyridin-3-yl)-1H-pyrrolo[2,3-b]pyridine Using similar reaction conditions as described in step-iii of example-1, 3-(1-(3-fluorobenzyl)-1H-pyrazol-4-yl)-5-(6-(4-methylpiperazin-1-yl)pyridin-3-yl)-1-tosyl-1H-pyrrolo[2,3-b]pyridine (90 mg, 0.144 mmol) was hydrolyzed with lithium hydroxide (12 mg, 0.289 mmol) in THF/methanol/water (5/2/1 mL) to yield 40 mg (47.6% yield) of the titled compound. $^1$H NMR (CD$_3$OD, 400 MHz): δ 8.566-8.560 (d, 1H), 8.49-8.45 (m, 2H), 8.24 (s, 1H), 8.09-8.06 (dd, 1H), 7.97 (s, 1H), 7.71 (s, 1H), 7.40-7.38 (q, 1H), 7.14-7.12 (d, 2H), 7.10-7.00 (m, 2H), 5.45 (s, 2H), 3.00 (s, 3H). MS: m/z=468.2 (M+1), HPLC: 99.02% in method B.

Example 138

(S)-1-(4-(5-(3-(1-(3-fluorobenzyl)-1H-pyrazol-4-yl)-1H-pyrrolo[2,3-b]pyridin-5-yl)pyridin-2-yl)piperazin-1-yl)propan-2-ol

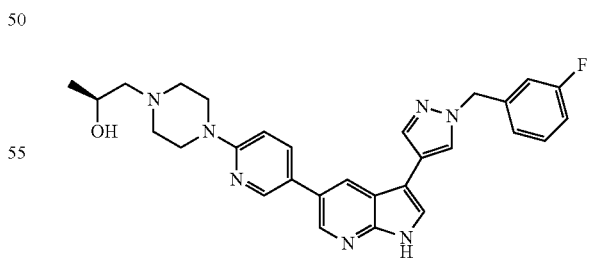

Step-i: (S)-1-(4-(5-(3-(1-(3-fluorobenzyl)-1H-pyrazol-4-yl)-1-tosyl-1H-pyrrolo[2,3-b]pyridin-5-yl)pyridin-2-yl)piperazin-1-yl)propan-2-ol Using similar reaction conditions as described in step-i of example-82A, 3-(1-(3-fluorobenzyl)-1H-pyrazol-4-yl)-5-(6-

(piperazin-1-yl)pyridin-3-yl)-1-tosyl-1H-pyrrolo[2,3-b]pyridine (step 1 compound of example 137) (100 mg, 0.164 mmol) was alkylated using (S)-2-methyloxirane (18 mg, 0.329 mmol) DIPEA (86 mg, 0.494 mmol) and ethanol (5 mL) to get 90 mg (81.8%) of the titled compound after purification by column (Silica gel 60/120) using 5% methanol in dichloromethane as eluent. MS: m/z=666.2 (M+1).

Step-ii: (S)-1-(4-(5-(3-(1-(3-fluorobenzyl)-1H-pyrazol-4-yl)-1H-pyrrolo[2,3-b]pyridin-5-yl)pyridin-2-yl) piperazin-1-yl)propan-2-ol Using similar reaction conditions as described in step-iii of example-1, (S)-1-(4-(5-(3-(1-(3-fluorobenzyl)-1H-pyrazol-4-yl)-1-tosyl-1H-pyrrolo[2,3-b]pyridin-5-yl)pyridin-2-yl)piperazin-1-yl) propan-2-ol (90 mg, 0.135 mmol) was hydrolyzed with lithium hydroxide (14 mg, 0.270 mmol) in THF/methanol/water (5/2/1 mL) to yield 52 mg (63.0% yield) of desired product. $^1$H NMR (CD$_3$OD, 400 MHz): δ 8.56-8.55 (d, 1H), 8.485-8.481 (d, 1H), 8.44-8.43 (d, 1H), 8.24 (s, 1H), 8.09-8.06 (dd, 1H), 7.98 (s, 1H), 7.71 (s, 1H), 7.40-7.38 (q, 1H), 7.13-7.11 (m, 2H), 7.10-7.00 (m, 2H), 5.45 (s, 2H), 4.70-4.40 (bs, 2H), 4.30-4.20 (m, 1H), 3.90-3.50 (bs, 4H), 3.17-3.11 (m, 2H), 1.30-1.27 (m, 3H). MS: m/z=512.3 (M+1), HPLC: 98.72% in method A.

Example 139

2-(4-(5-(3-(1-(3-fluorobenzyl)-1H-pyrazol-4-yl)-1H-pyrrolo[2,3-b]pyridin-5-yl)pyridin-2-yl) piperazin-1-yl)acetamide

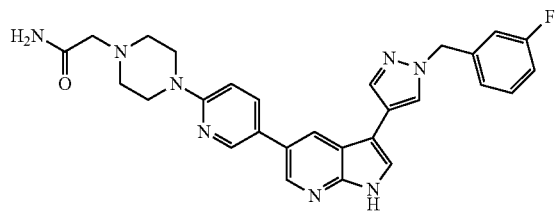

Step-i: 2-(4-(5-(3-(1-(3-fluorobenzyl)-1H-pyrazol-4-yl)-1-tosyl-1H-pyrrolo[2,3-b]pyridin-5-yl)pyridin-2-yl)piperazin-1-yl)acetamide Using similar reaction conditions as described in step-i of example-82A, 3-(1-(3-fluorobenzyl)-1H-pyrazol-4-yl)-5-(6-(piperazin-1-yl)pyridin-3-yl)-1-tosyl-1H-pyrrolo[2,3-b]pyridine (step 1 compound of example 137) (100 mg, 0.164 mmol) was alkylated using 2-chloroacetamide (23 mg, 0.247 mmol), sodium bicarbonate (42 mg, 0.494 mmol) and ethanol/acetone (3/3 mL) to get 80 mg (73.0%) of the titled compound after purification by column (Silica gel 60/120) chromatography using 5% methanol in dichloromethane as eluent. $^1$H NMR (CDCl$_3$, 300 MHz): δ 8.60-8.06 (d, 1H), 8.40-8.39 (d, 1H), 8.11-8.08 (d, 2H), 8.00-7.99 (d, 2H), 7.85 (s, 1H), 7.80 (s, 1H), 7.71-7.67 (m, 2H), 7.37-7.33 (m, 2H), 7.06-6.90 (m, 3H), 7.76-7.73 (d, 1H), 5.45 (s, 1H), 5.37 (s, 2H), 3.65-3.62 (t, 4H), 3.09 (s, 1H), 2.71-2.68 (t, 4H), 2.37 (s, 3H).

Step-ii: 2-(4-(5-(3-(1-(3-fluorobenzyl)-1H-pyrazol-4-yl)-1H-pyrrolo[2,3-b]pyridin-5-yl)pyridin-2-yl) piperazin-1-yl)acetamide Using similar reaction conditions as described in step-iii of example-1, 2-(4-(5-(3-(1-(3-fluorobenzyl)-1H-pyrazol-4-yl)-1-tosyl-1H-pyrrolo[2,3-b]pyridin-5-yl)pyridin-2-yl)piperazin-1-yl) acetamide (80 mg, 0.120 mmol) was hydrolyzed with lithium hydroxide (11 mg, 0.240 mmol) in THF/methanol/water (5/2/1 mL) to yield 17 mg (27.8% yield) of desired product. $^1$H NMR (DMSO-d$_6$, 400 MHz): δ 8.57-8.56 (d, 1H), 8.49-8.47 (m, 2H), 8.348-8.343 (d, 1H), 8.00-7.97 (m, 2H), 7.77-7.76 (d, 1H), 7.43-7.38 (m, 1H), 7.28 (s, 1H), 7.19-7.08 (m, 3H), 6.97-6.95 (d, 1H), 5.41 (s, 2H), 3.60-3.59 (t, 4H), 2.93 (s, 2H), 2.56-2.50 (t, 4H). MS: m/z=511.3 (M+1), HPLC: 90.86% in method A.

Example 140

3-(1-phenethyl-1H-pyrazol-4-yl)-5-(6-(piperazin-1-yl)pyridin-3-yl)-1H-pyrrolo[2,3-b]pyridine

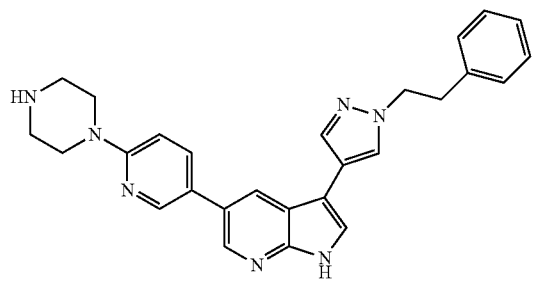 [SMILES: c1ccc(CCn2cc(-c3c[nH]c4ncc(-c5ccc(N6CCNCC6)nc5)cc34)cn2)cc1]

Step-i: tert-butyl 4-(5-(3-(1-phenethyl-1H-pyrazol-4-yl)-1-tosyl-1H-pyrrolo[2,3-b]pyridin-5-yl)pyridin-2-yl)piperazine-1-carboxylate Using similar reaction conditions as described in step-i of example-1, tert-butyl 4-(5-(3-iodo-1-tosyl-1H-pyrrolo[2,3-b]pyridin-5-yl)pyridin-2-yl)piperazine-1-carboxylate (Intermediate 66K) (150 mg, 0.227 mmol) was coupled with 1-phenethyl-4-(4,4,5,5-tetramethyl-1,3,2-dioxaborolan-2-yl)-1H-pyrazole (Intermediate 59) (101 mg, 0.34 mmol) using sodium carbonate (73 mg, 0.68 mmol) and Pd(PPh$_3$)$_2$Cl$_2$ (10 mg, 0.011 mmol) in toluene/ethanol/water (3/5/1 ml) to afford 140 mg (88.0% yield) of the pure product after column purification using 5% methanol in dichloromethane as eluent. MS: m/z=704.3 (M+1).

Step-ii: 3-(1-phenethyl-1H-pyrazol-4-yl)-5-(6-(piperazin-1-yl)pyridin-3-yl)-1-tosyl-1H-pyrrolo[2,3-b] pyridine Using similar reaction conditions as described in step-ii of example-7, tert-butyl 4-(5-(3-(1-phenethyl-1H-pyrazol-4-yl)-1-tosyl-1H-pyrrolo[2,3-b]pyridin-5-yl)pyridin-2-yl)piperazine-1-carboxylate (140 mg, 0.199 mmol) was deprotected with TFA/DCM (2/1 ml). This afforded 110 mg (91.6% yield) of the titled compound. MS: m/z=604.1 (M+1).

Step-iii: 3-(1-phenethyl-1H-pyrazol-4-yl)-5-(6-(piperazin-1-yl)pyridin-3-yl)-1H-pyrrolo[2,3-b]pyridine Using similar reaction conditions as described in step-iii of example-1, 3-(1-phenethyl-1H-pyrazol-4-yl)-5-(6-(piperazin-1-yl)pyridin-3-yl)-1-tosyl-1H-pyrrolo[2,3-b]pyridine (55 mg, 0.09 mmol) was hydrolyzed with lithium hydroxide (20 mg, 0.45 mmol) in THF/methanol/water (2/1/1 mL) to yield 40 mg (100% yield) of desired product. $^1$H NMR (CD$_3$OD, 300 MHz): δ 8.51-8.50 (d, 1H), 8.43 (s, 1H), 8.25-8.15 (dd, 1H), 7.91-7.86 (d, 2H), 7.68 (s, 1H), 7.27-7.21 (m, 3H), 7.14-7.12 (m, 3H), 4.50-4.40 (t, 2H), 3.97-3.94 (t, 4H), 3.43-3.34 (t, 4H), 3.20-3.18 (t, 2H). MS: m/z=450.4 (M+1), HPLC: 92.83% in method A.

Example 141

5-(6-(4-methylpiperazin-1-yl)pyridin-3-yl)-3-(1-phenethyl-1H-pyrazol-4-yl)-1H-pyrrolo[2,3-b]pyridine

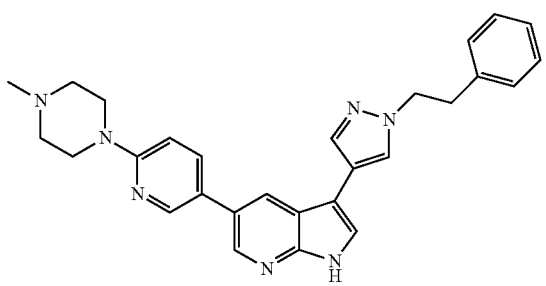 [SMILES: CN1CCN(c2ccc(-c3cnc4[nH]cc(-c5cnn(CCc6ccccc6)c5)c4c3)cn2)CC1]

Step-i: 5-(6-(4-methylpiperazin-1-yl)pyridin-3-yl)-3-(1-phenethyl-1H-pyrazol-4-yl)-1-tosyl-1H-pyrrolo[2,3-b]pyridine Using similar reaction conditions as described in step-iii of example-133, 3-(1-phenethyl-1H-pyrazol-4-yl)-5-(6-(piperazin-1-yl)pyridin-3-yl)-1-tosyl-1H-pyrrolo[2,3-b]pyridine (product of step 2 of example 140) (50 mg, 0.082 mmol) was methylated using paraformaldehyde (8 mg, 0.24 mmol) and Na(OAc)$_3$BH (35 mg, 0.164 mmol) in dichloroethane (10 mL) to afford 50 mg (99% yield) of the titled compound. MS: m/z=618.2 (M+1).

Step-ii: 5-(6-(4-methylpiperazin-1-yl)pyridin-3-yl)-3-(1-phenethyl-1H-pyrazol-4-yl)-1H-pyrrolo[2,3-b]pyridine Using similar reaction conditions as described in step-iii of example-1, 5-(6-(4-methylpiperazin-1-yl)pyridin-3-yl)-3-(1-phenethyl-1H-pyrazol-4-yl)-1-tosyl-1H-pyrrolo[2,3-b]pyridine (50 mg, 0.088 mmol) was hydrolyzed with lithium hydroxide (18 mg, 0.44 mmol) in THF/methanol/water (2/2/1 mL) to yield 40 mg (98.5% yield) of the titled compound. $^1$H NMR (CD$_3$OD, 300 MHz): δ 8.55-8.50 (d, 2H), 8.40 (s, 1H), 8.19-8.10 (dd, 1H), 7.89-7.84 (d, 2H), 7.68 (s, 1H), 7.24-7.21 (m, 3H), 7.15-7.11 (m, 3H), 4.50-4.50 (t, 2H), 3.20-3.10 (t, 2H), 2.98 (s, 3H). MS: m/z=464.2 (M+1), HPLC: 93.96% in method A.

Example 142

2-(4-(5-(3-(1-(3-fluorobenzyl)-1H-pyrazol-4-yl)-1H-pyrrolo[2,3-b]pyridin-5-yl)pyridin-2-yl) piperazin-1-yl)ethanol

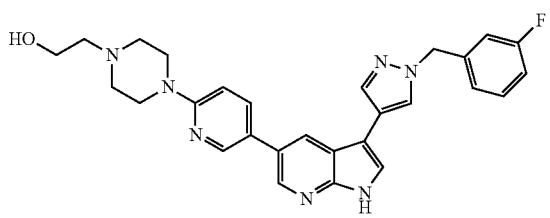 [SMILES: OCCN1CCN(c2ccc(-c3cnc4[nH]cc(-c5cnn(Cc6cccc(F)c6)c5)c4c3)cn2)CC1]

Step-i: 2-(4-(5-(3-(1-(3-fluorobenzyl)-1H-pyrazol-4-yl)-1-tosyl-1H-pyrrolo[2,3-b]pyridin-5-yl)pyridin-2-yl)piperazin-1-yl)ethanol Using similar reaction conditions as described in step-i of example-126, 3-(1-(3-fluorobenzyl)-1H-pyrazol-4-yl)-5-(6-(piperazin-1-yl)pyridin-3-yl)-1-tosyl-1H-pyrrolo[2,3-b]pyridine (step 1 compound of example 137) (150 mg, 0.297 mmol) was alkylated using 2-bromoethanol (62 mg, 0.494 mmol) and potassium carbonate (69 mg, 0.494 mmol) in DMF (1 ml) to afford 85 mg (52.7% yield) of the titled compound after purification by column (Silica gel 60/120) chromatography using 5% methanol in dichloromethane as eluent. MS: m/z=652.2 (M+1).

Step-ii: 2-(4-(5-(3-(1-(3-fluorobenzyl)-1H-pyrazol-4-yl)-1H-pyrrolo[2,3-b]pyridin-5-yl)pyridin-2-yl) piperazin-1-yl)ethanol Using similar reaction conditions as described in step-iii of example-1, 2-(4-(5-(3-(1-(3-fluorobenzyl)-1H-pyrazol-4-yl)-1-tosyl-1H-pyrrolo[2,3-b]pyridin-5-yl)pyridin-2-yl)piperazin-1-yl) ethanol (85 mg, 0.130 mmol) was hydrolyzed by lithium hydroxide (11 mg, 0.261 mmol) in THF/methanol/water (5/2/1 ml) to yield 15 mg (23.0% yield) of the titled compound. $^1$H NMR (CDCl$_3$, 400 MHz): δ 9.75 (s, 1H), 8.52-8.49 (dd, 2H), 8.149-8.144 (d, 1H), 7.88 (s, 1H), 7.80-7.77 (dd, 1H), 7.72 (s, 1H), 7.478-7.473 (d, 1H), 7.36-7.34 (q, 1H), 7.09-6.97 (m, 3H), 6.81-6.78 (d, 1H), 5.40 (s, 2H), 3.73-3.70 (t, 2H), 3.66-3.64 (t, 4H), 2.95-2.85 (bs, 1H), 2.70-2.64 (m, 6H). MS: m/z=498.3 (M+1), HPLC: 96.68% in method A.

Example 143

(S)-1-(4-(5-(3-(1-phenethyl-1H-pyrazol-4-yl)-1H-pyrrolo[2,3-b]pyridin-5-yl)pyridin-2-yl) piperazin-1-yl)propan-2-ol

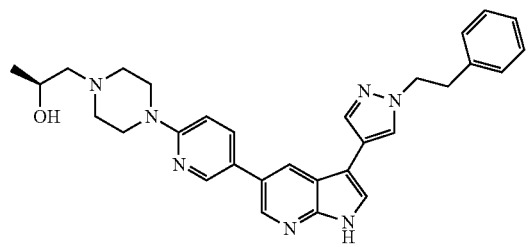 [SMILES: C[C@H](O)CN1CCN(c2ccc(-c3cnc4[nH]cc(-c5cnn(CCc6ccccc6)c5)c4c3)cn2)CC1]

Step-i: (S)-1-(4-(5-(3-(1-phenethyl-1H-pyrazol-4-yl)-1-tosyl-1H-pyrrolo[2,3-b]pyridin-5-yl)pyridin-2-yl) piperazin-1-yl)propan-2-ol Using similar reaction conditions as described in step-i of example-82A, 3-(1-phenethyl-1H-pyrazol-4-yl)-5-(6-(piperazin-1-yl)pyridin-3-yl)-1-tosyl-1H-pyrrolo[2,3-b]pyridine (product of step 2 of example 140) (85 mg, 0.14 mmol) was alkylated using (S)-2-methyloxirane (10 mg, 0.169 mmol), DIPEA (22 mg, 0.169 mmol) and ethanol (3 mL) to get 80 mg (86%) of the titled compound. MS: m/z=662.3 (M+1).

Step-ii: (S)-1-(4-(5-(3-(1-phenethyl-1H-pyrazol-4-yl)-1H-pyrrolo[2,3-b]pyridin-5-yl)pyridin-2-yl) piperazin-1-yl)propan-2-ol Using similar reaction conditions as described in step-iii of example-1, (S)-1-(4-(5-(3-(1-phenethyl-1H-pyrazol-4-yl)-1- tosyl-1H-pyrrolo[2,3-b]pyridin-5-yl)pyridin-2-yl)piperazin-1-yl)propan-2-ol (80 mg, 0.12 mmol) was hydrolyzed with lithium hydroxide (25 mg, 0.6 mmol) in THF/methanol/water (2/2/1 mL) to yield 50 mg (83.3% yield) of desired product. $^1$H NMR (CD$_3$OD, 300 MHz): δ 8.53-8.52 (d, 2H), 8.36-8.35 (d, 1H), 8.12-8.08 (dd, 1H), 7.896-7.893 (d, 1H), 7.818-7.816 (d, 1H), 7.67 (s, 1H), 7.26-7.20 (m, 3H), 7.17-7.12 (m, 3H), 4.47-4.43 (d, 2H), 4.30-4.20 (t, 1H), 3.60-3.40 (bs, 4H), 3.25-3.10 (m, 4H), 1.27-1.25 (d, 3H). MS: m/z=408.6 (M+1), HPLC: 93.50% in method A.

Example 144

(S)-1-(4-(5-(3-(1-(3-fluorobenzyl)-1H-pyrazol-4-yl)-1H-pyrrolo[2,3-b]pyridin-5-yl)-6-methoxy pyridin-2-yl)piperazin-1-yl)propan-2-ol

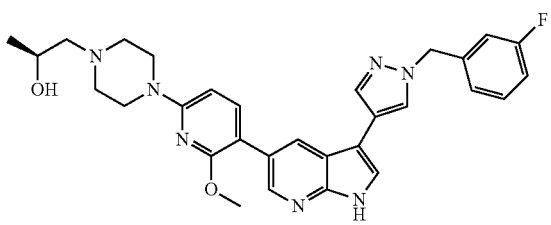 [SMILES: COc1nc(N2CCN(C[C@H](C)O)CC2)ccc1-c1cnc2[nH]cc(-c3cnn(Cc4cccc(F)c4)c3)c2c1]

Step-i: tert-butyl 4-(5-(3-(1-(3-fluorobenzyl)-1H-pyrazol-4-yl)-1-tosyl-1H-pyrrolo[2,3-b]pyridin-5-yl)-6-methoxypyridin-2-yl)piperazine-1-carboxylate Using similar reaction conditions as described in step-ii of example-1, tert-butyl 4-(5-(3-iodo-1-tosyl-1H-pyrrolo[2,3-b]pyridin-5-yl)-6-methoxypyridin-2-yl)piperazine-1-carboxylate (Intermediate 66L) (75 mg, 0.108 mmol) was coupled with 1-(3-fluorobenzyl)-4-(4,4,5,5-tetramethyl-1,3,2-dioxaborolan-2-yl)-1H-pyrazole (intermediate 11) (65 mg, 0.217 mmol) using sodium carbonate (35 mg, 0.326 mmol) and Pd(dppf)Cl$_2$ (4 mg, 0.005 mmol) in toluene/ethanol/water (20/10/5 mL). This afforded 68 mg (85% yield) of the titled compound.

Step-ii: 3-(1-(3-fluorobenzyl)-1H-pyrazol-4-yl)-5-(2-methoxy-6-(piperazin-1-yl)pyridin-3-yl)-1-tosyl-1H-pyrrolo[2,3-b]pyridine Using similar reaction conditions as described in step-ii of example-7, tert-butyl 4-(5-(3-(1-(3-fluorobenzyl)-1H-pyrazol-4-yl)-1-tosyl-1H-pyrrolo[2,3-b]pyridin-5-yl)-6-methoxypyridin-2-yl)piperazine-1-carboxylate (67 mg, 0.090 mmol) was deprotected in methanol/HCl in dioxane (2/5 ml) to afford 52 mg (89% yield) of the titled compound. MS: m/z=638.2 (M+1).

Step-iii: (S)-1-(4-(5-(3-(1-(3-fluorobenzyl)-1H-pyrazol-4-yl)-1-tosyl-1H-pyrrolo[2,3-b]pyridin-5-yl)-6-methoxypyridin-2-yl)piperazin-1-yl)propan-2-ol Using similar reaction conditions as described in step-i of example-82A, 3-(1-(3-fluorobenzyl)-1H-pyrazol-4-yl)-5-(2-methoxy-6-(piperazin-1-yl)pyridin-3-yl)-1-tosyl-1H-pyrrolo[2,3-b]pyridine (52 mg, 0.081 mmol) was alkylated using (S)-2-methyloxirane (8 mg, 0.137 mmol), DIPEA (18 mg, 0.137 mmol) and ethanol (5 mL) to get 61 mg (95.3%) of the titled compound.

Step-iv: (S)-1-(4-(5-(3-(1-(3-fluorobenzyl)-1H-pyrazol-4-yl)-1H-pyrrolo[2,3-b]pyridin-5-yl)-6-methoxy-pyridin-2-yl)piperazin-1-yl)propan-2-ol Using similar reaction conditions as described in step-iii of example-1, (S)-1-(4-(5-(3-(1-(3-fluorobenzyl)-1H-pyrazol-4-yl)-1-tosyl-1H-pyrrolo[2,3-b]pyridin-5-yl)-6-methoxypyridin-2-yl) piperazin-1-yl)propan-2-ol (60 mg, 0.086 mmol) was hydrolyzed with lithium hydroxide (36 mg, 0.862 mmol) in THF/methanol/water (10/5/2 mL) to yield 14 mg (25% yield) of desired product. $^1$H NMR (CD$_3$OD, 400 MHz): δ 8.615-8.612 (d, 1H), 8.51 (s, 1H), 8.20 (s, 1H), 7.95 (s, 1H), 7.82-7.80 (d, 1H), 7.76 (s, 1H), 7.41-7.36 (m, 1H), 7.14-7.12 (d, 1H), 7.08-7.01 (m, 2H), 6.61-6.59 (d, 1H), 5.44 (s, 2H), 4.52 (s, 2H), 4.29-4.24 (m, 1H), 3.96 (s, 3H), 3.74 (s, 2H), 3.36 (s, 2H), 3.26-3.11 (m, 4H), 1.28-1.27 (d, 2H). MS: m/z=542.2 (M+1), HPLC: 96.86% in method B.

Example 145

(S)-1-(4-(5-(3-(1-(3-methylbenzyl)-1H-pyrazol-4-yl)-1H-pyrrolo[2,3-b]pyridin-5-yl)pyridin-2-yl) piperazin-1-yl)propan-2-ol

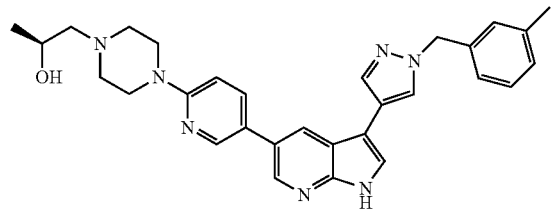 [SMILES: Cc1cccc(Cn2cc(-c3c[nH]c4ncc(-c5ccc(N6CCN(C[C@H](C)O)CC6)nc5)cc34)cn2)c1]

Step-i: tert-butyl 4-(5-(3-(1-(3-methylbenzyl)-1H-pyrazol-4-yl)-1-tosyl-1H-pyrrolo[2,3-b]pyridin-5-yl) pyridin-2-yl)piperazine-1-carboxylate Using similar reaction conditions as described in step-i of example-1, tert-butyl 4-(5-(3-iodo-1-tosyl-1H-pyrrolo[2,3-b]pyridin-5-yl)pyridin-2-yl)piperazine-1-carboxylate (Intermediate 66K) (200 mg, 0.303 mmol) was coupled with 1-(3-methylbenzyl)-4-(4,4,5,5-tetramethyl-1,3,2-dioxaborolan-2-yl)-1H-pyrazole (intermediate 64D) (99 mg, 0.333 mmol) using sodium carbonate (96 mg, 0.909 mmol) and Pd(PPh$_3$)$_2$Cl$_2$ (11 mg, 0.015 mmol) in toluene/ethanol/water (2/2/0.5 ml) to afford 200 mg (94% yield) of titled compound after purification by column (Silica gel 60/120) using 0.5% methanol in DCM as eluent. MS: m/z=704.3 (M+1).

Step-ii: 3-(1-(3-methylbenzyl)-1H-pyrazol-4-yl)-5-(6-(piperazin-1-yl)pyridin-3-yl)-1-tosyl-1H-pyrrolo [2,3-b]pyridine hydrochloride Using similar reaction conditions as described in step-ii of example-7, tert-butyl 4-(5-(3-(1-(3-methylbenzyl)-1H-pyrazol-4-yl)-1-tosyl-1H-pyrrolo[2,3-b]pyridin-5-yl)pyridin-2-yl)piperazine-1-carboxylate (200 mg, 0.284 mmol) was deprotected in HCl in ether/methanol (2/3 ml) to afford 120 mg (66% yield) of the titled compound. MS: m/z=605.2 (M+1).

Step-iii: (S)-1-(4-(5-(3-(1-(3-methylbenzyl)-1H-pyrazol-4-yl)-1-tosyl-1H-pyrrolo[2,3-b]pyridin-5-yl)pyridin-2-yl)piperazin-1-yl)propan-2-ol Using similar reaction conditions as described in step-i of example-82A, 3-(1-(3-methylbenzyl)-1H-pyrazol-4-yl)-5-(6-(piperazin-1-yl)pyridin-3-yl)-1-tosyl-1H-pyrrolo[2,3-b]pyridine hydrochloride (120 mg, 0.187 mmol) was alkylated using (S)-2-methyloxirane (33 mg, 0.562 mmol), DIPEA (145 mg, 1.124 mmol) and ethanol (5 mL) to get 100 mg (crude) of the titled compound. MS: m/z=662.3 (M+1).

Step-iv: (S)-1-(4-(5-(3-(1-(3-methylbenzyl)-1H-pyrazol-4-yl)-1H-pyrrolo[2,3-b]pyridin-5-yl)pyridin-2-yl)piperazin-1-yl)propan-2-ol Using similar reaction conditions as described in step-iii of example-1, (S)-1-(4-(5-(3-(1-(3-methylbenzyl)-1H-pyrazol-4-yl)-1-tosyl-1H-pyrrolo[2,3-b]pyridin-5-yl)pyridin-2-yl)piperazin-1-yl) propan-2-ol (100 mg, 0.151 mmol) was hydrolyzed with lithium hydroxide (19 mg, 0.453 mmol) in THF/methanol/water (2/2/0.5 mL) to yield 25 mg (21% yield) of desired product. $^1$H NMR (CD$_3$OD, 400 MHz): δ 8.559-8.553 (d, 1H), 8.479-8.474 (d, 1H), 8.425-8.420 (d, 1H), 8.17 (s, 1H), 8.08-8.06 (dd, 1H), 7.94 (s, 1H), 7.69 (s, 1H), 7.28-7.22 (t, 1H), 7.15-7.10 (m, 4H), 5.39 (s, 2H), 4.25-4.32 (m, 1H), 3.10-3.30 (m, 2H), 2.34 (s, 3H), 1.28-1.27 (d, 3H). MS: m/z=508.2 (M+1), HPLC: 98.90% in method A.

Example 146

(S)-1-(4-(6-(3-(1-(3-fluorobenzyl)-1H-pyrazol-4-yl)-1H-pyrrolo[2,3-b]pyridin-5-yl)pyridin-3-yl)piperazin-1-yl)propan-2-ol

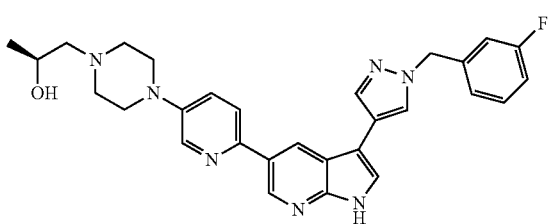 [SMILES: C[C@H](O)CN1CCN(c2ccc(-c3cnc4[nH]cc(-c5cnn(Cc6cccc(F)c6)c5)c4c3)nc2)CC1]

Step-i: tert-butyl 4-(6-(3-(1-(3-fluorobenzyl)-1H-pyrazol-4-yl)-1-tosyl-1H-pyrrolo[2,3-b]pyridin-5-yl)pyridin-3-yl)piperazine-1-carboxylate Using the same reaction conditions as described in step-ii of example-1, tert-butyl 4-(6-(3-iodo-1-tosyl-1H-pyrrolo[2,3-b]pyridin-5-yl)pyridin-3-yl)piperazine-1-carboxylate (Intermediate 66M) (1.0 g, 1.515 mmol) was coupled with 1-(3-fluorobenzyl)-4-(4,4,5,5-tetramethyl-1,3,2-dioxaborolan-2-yl)-1H-pyrazole (intermediate 11) (596 mg, 1.969 mmol) using sodium carbonate (402 mg, 3.787 mmol) and Pd(PPh$_3$)$_2$Cl$_2$ (54 mg, 0.075 mmol) in toluene/ethanol/water (10/3/3 mL) to afford 800 mg (74.6% yield) of the titled compound after purification by column (Silica gel 60/120) using 1.5% methanol in DCM as eluent. MS: m/z=708.3 (M+1).

Step-ii: 3-(1-(3-fluorobenzyl)-1H-pyrazol-4-yl)-5-(5-(piperazin-1-yl)pyridin-2-yl)-1-tosyl-1H-pyrrolo[2,3-b]pyridine Using similar reaction conditions as described in step-ii of example-7, tert-butyl 4-(6-(3-(1-(3-fluorobenzyl)-1H-pyrazol-4-yl)-1-tosyl-1H-pyrrolo[2,3-b]pyridin-5-yl)pyridin-3-yl)piperazine-1-carboxylate (800 mg, 1.130 mmol) was deprotected in TFA/DCM (3/10 ml) to afford 600 mg (87.4% yield) of the titled compound. MS: m/z=608.2 (M+1).

Step-iii: (S)-1-(4-(6-(3-(1-(3-fluorobenzyl)-1H-pyrazol-4-yl)-1-tosyl-1H-pyrrolo[2,3-b]pyridin-5-yl)pyridin-3-yl)piperazin-1-yl)propan-2-ol Using similar reaction conditions as described in step-i of example-82A, 3-(1-(3-fluorobenzyl)-1H-pyrazol-4-yl)-5-(5-(piperazin-1-yl)pyridin-2-yl)-1-tosyl-1H-pyrrolo[2,3-b]pyridine (100 mg, 0.164 mmol) was alkylated using (S)-2-methyloxirane (18 mg, 0.329 mmol), DIPEA (58 µL, 0.329 mmol) and ethanol (10 mL) to get 100 mg (91.7%) of the titled compound.

Step-iv: (S)-1-(4-(6-(3-(1-(3-fluorobenzyl)-1H-pyrazol-4-yl)-1H-pyrrolo[2,3-b]pyridin-5-yl)pyridin-3-yl)piperazin-1-yl)propan-2-ol Using similar reaction conditions as described in step-iii of example-1, (S)-1-(4-(6-(3-(1-(3-fluorobenzyl)-1H-pyrazol-4-yl)-1-tosyl-1H-pyrrolo[2,3-b]pyridin-5-yl)pyridin-3-yl)piperazin-1-yl) propan-2-ol (100 mg, 0.150 mmol) was hydrolyzed with lithium hydroxide (13 mg, 0.300 mmol) in THF/methanol/water (5/2/1 mL) to yield 17 mg (22.0% yield) of desired product. $^1$H NMR (CDCl$_3$, 400 MHz): δ 9.01 (s, 1H), 8.879-8.874 (d, 1H), 8.60-8.59 (d, 1H), 8.42-8.41 (d, 1H), 7.88 (s, 1H), 7.78 (s, 1H), 7.69-7.67 (d, 1H), 7.742-7.41 (d, 1H), 7.34-7.29 (m, 2H), 7.07-6.96 (m, 3H), 5.39 (s, 2H), 4.00 (3.90, m 1H), 3.60-3.50 (bs, 1H), 3.36-3.32 (m, 4H), 2.95-2.90 (m, 2H), 2.70-2.60 (m, 2H), 2.50-2.30 (m, 2H), 1.19-1.18 (d, 3H). MS: m/z=512.35 (M+1), HPLC: 91.12% in method A.

Example 147

2-(dimethylamino)-1-(4-(5-(3-(1-(3-fluorobenzyl)-1H-pyrazol-4-yl)-1H-pyrrolo[2,3-b]pyridin-5-yl)pyridin-2-yl)piperazin-1-yl)ethanone

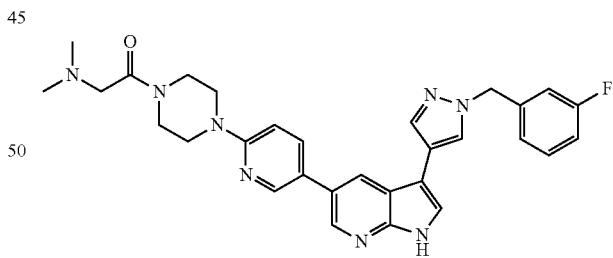

Step-i: 2-(dimethylamino)-1-(4-(5-(3-(1-(3-fluorobenzyl)-1H-pyrazol-4-yl)-1-tosyl-1H-pyrrolo[2,3-b]pyridin-5-yl)pyridin-2-yl)piperazin-1-yl)ethanone Using similar reaction conditions as described in step-ii of example-124, 3-(1-(3-fluorobenzyl)-1H-pyrazol-4-yl)-5-(6-(piperazin-1-yl)pyridin-3-yl)-1-tosyl-1H-pyrrolo[2,3-b]pyridine (step 1 compound of example 137) (75 mg, 0.124 mmol) was coupled with 2-(dimethylamino)acetic acid hydrochloride (26 mg, 0.186 mmol) using HATU (71 mg, 0.186 mmol), HOBt (26 mg, 0.186 mmol) and DIPEA (87 µL, 0.498 mmol) in DMF (2 mL) to get 80 mg (93.0%) yield of the title compound. MS: m/z=693.3 (M+1).

Step-ii: 2-(dimethylamino)-1-(4-(5-(3-(1-(3-fluorobenzyl)-1H-pyrazol-4-yl)-1H-pyrrolo[2,3-b]pyridin-5-yl)pyridin-2-yl)piperazin-1-yl)ethanone Using similar reaction conditions as described in step-iii of example-1, 22-(dimethylamino)-1-(4-(5-(3-(1-(3-fluorobenzyl)-1H-pyrazol-4-yl)-1-tosyl-1H-pyrrolo[2,3-b]pyridin-5-yl)pyridin-2-yl) piperazin-1-yl)ethanone (80 mg, 0.115 mmol) was hydrolyzed with lithium hydroxide (10 mg, 0.230 mmol) in THF/methanol/water (5/2/1 mL) to yield 32 mg (42.6% yield) of the titled compound. $^1$H NMR (CD$_3$OD, 400 MHz): δ 8.51-8.48 (m, 2H), 8.42-8.41 (d, 1H), 8.37-8.34 (dd, 1H), 8.25 (s, 1H), 7.98 (s, 1H), 7.73 (s, 1H), 7.40-7.35 (m, 2H), 7.13-7.11 (d, 1H), 7.06-7.00 (m, 2H), 5.44 (s, 2H), 4.36 (s, 1H), 3.88-3.82 (m, 6H), 3.72-3.679 (m, 2H), 3.00 (s, 6H). MS: m/z=539.4 (M+1), HPLC: 96.57% in method A.

Example 148

(S)-1-(4-(5-(3-(1-benzyl-1H-pyrazol-4-yl)-1H-pyrrolo[2,3-b]pyridin-5-yl)pyridin-2-yl)piperazin-1-yl)propan-2-ol

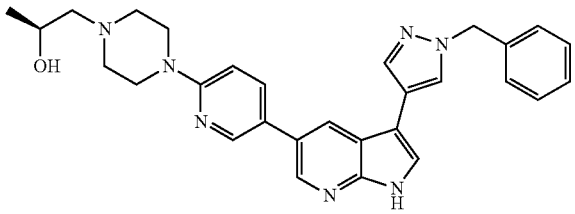 [SMILES: C[C@H](O)CN1CCN(c2ccc(-c3cnc4[nH]cc(-c5cnn(Cc6ccccc6)c5)c4c3)cn2)CC1]

Step-i: tert-butyl 4-(5-(3-(1-benzyl-1H-pyrazol-4-yl)-1-tosyl-1H-pyrrolo[2,3-b]pyridin-5-yl)pyridin-2-yl)piperazine-1-carboxylate Using similar reaction conditions as described in step-i of example-1, tert-butyl 4-(5-(3-iodo-1-tosyl-1H-pyrrolo[2,3-b]pyridin-5-yl)pyridin-2-yl)piperazine-1-carboxylate (Intermediate 66K) (200 mg, 0.3 mmol) was coupled with 1-benzyl-4-(4,4,5,5-tetramethyl-1,3,2-dioxaborolan-2-yl)-1H-pyrazole (intermediate 15) (103 mg, 0.36 mmol) using sodium carbonate (95 mg, 0.9 mmol) and Pd(dppf)Cl$_2$ (11 mg, 0.015 mmol) in toluene/ethanol/water (4/4/2 mL) to afford 100 mg (47.8% yield) of the titled compound after purification by column (Silica gel 60/120) using 30% ethyl acetate in hexane as eluent. MS: m/z=690.3 (M+1).

Step-ii: 3-(1-benzyl-1H-pyrazol-4-yl)-5-(6-(piperazin-1-yl)pyridin-3-yl)-1-tosyl-1H-pyrrolo[2,3-b]pyridine Using similar reaction conditions as described in step-ii of example-7, tert-butyl 4-(5-(3-(1-benzyl-1H-pyrazol-4-yl)-1-tosyl-1H-pyrrolo[2,3-b]pyridin-5-yl)pyridin-2-yl)piperazine-1-carboxylate (100 mg, 0.144 mmol) was deprotected in HCl in ether (8 ml) to afford 60 mg (66.1% yield) of the titled compound.

Step-iii: (S)-1-(4-(5-(3-(1-benzyl-1H-pyrazol-4-yl)-1-tosyl-1H-pyrrolo[2,3-b]pyridin-5-yl)pyridin-2-yl)piperazin-1-yl)propan-2-ol Using similar reaction conditions as described in step-i of example-82A, 33-(1-benzyl-1H-pyrazol-4-yl)-5-(6-(piperazin-1-yl)pyridin-3-yl)-1-tosyl-1H-pyrrolo[2,3-b]pyridine (60 mg. 0.095 mmol) was alkylated using (S)-2-methyloxirane (17 mg, 0.28 mmol), DIPEA (36 mg, 0.28 mmol) and ethanol (5 mL) to get 50 mg (crude) of the titled compound.

Step-iv: (S)-1-(4-(5-(3-(1-benzyl-1H-pyrazol-4-yl)-1H-pyrrolo[2,3-b]pyridin-5-yl)pyridin-2-yl) piperazin-1-yl)propan-2-ol Using similar reaction conditions as described in step-iii of example-1, (S)-1-(4-(5-(3-(1-benzyl-1H-pyrazol-4-yl)-1-tosyl-1H-pyrrolo[2,3-b]pyridin-5-yl)pyridin-2-yl)piperazin-1-yl)propan-2-ol (155 mg, 0.239 mmol) was hydrolyzed with lithium hydroxide (50 mg, 1.19 mmol) in THF/methanol/water (4/4/2 mL) to yield 40 mg (24.9% yield) of desired product. $^1$H NMR (DMSO-d$_6$, 300 MHz): δ 11.8 (s, 1H), 9.6 (s, 1H), 8.63-8.62 (d, 1H), 8.52-8.51 (d, 1H), 8.42 (s, 1H), 8.36-8.35 (d, 1H), 8.11-8.07 (dd, 1H), 7.97 (s, 1H), 7.769-7.761 (d, 1H), 7.38-7.27 (m, 4H), 7.10-7.07 (d, 1H), 5.38 (s, 2H), 4.47-4.35 (m, 2H), 4.20-4.10 (m, 1H), 3.50-3.00 (m, 6H), 1.15-1.13 (d, 3H). MS: m/z=494.6 (M+1), HPLC: 96.64% in method B.

Example 149

3-(1-(3-fluorobenzyl)-1H-pyrazol-4-yl)-5-(6-(4-(2-methoxyethyl)piperazin-1-yl)pyridin-3-yl)-1H-pyrrolo[2,3-b]pyridine

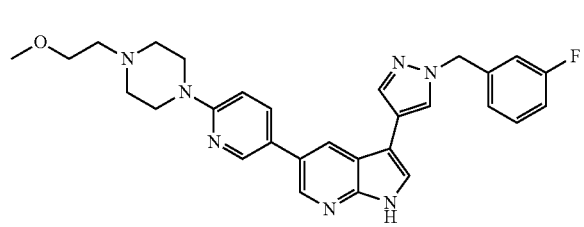 [SMILES: COCCN1CCN(c2ccc(-c3cnc4[nH]cc(-c5cnn(Cc6cccc(F)c6)c5)c4c3)cn2)CC1]

Step-i: 3-(1-(3-fluorobenzyl)-1H-pyrazol-4-yl)-5-(6-(4-(2-methoxyethyl)piperazin-1-yl)pyridin-3-yl)-1-tosyl-1H-pyrrolo[2,3-b]pyridine Using similar reaction conditions as described in step-i of example-126, 3-(1-(3-fluorobenzyl)-1H-pyrazol-4-yl)-5-(6-(piperazin-1-yl)pyridin-3-yl)-1-tosyl-1H-pyrrolo[2,3-b]pyridine (step 1 compound of example 137) (75 mg, 0.123 mmol) was alkylated using 2-1-bromo-2-methoxyethane (26 mg, 0.185 mmol) and potassium carbonate (43 mg, 0.308 mmol) in DMF (1 ml) to afford 70 mg (85.3% yield) of the titled compound. MS: m/z=666.1 (M+1).

Step-ii: 3-(1-(3-fluorobenzyl)-1H-pyrazol-4-yl)-5-(6-(4-(2-methoxyethyl)piperazin-1-yl)pyridin-3-yl)-1H-pyrrolo[2,3-b]pyridine Using similar reaction conditions as described in step-iii of example-1, 3-(1-(3-fluorobenzyl)-1H-pyrazol-4-yl)-5-(6-(4-(2-methoxyethyl)piperazin-1-yl)pyridin-3-yl)-1-tosyl-1H-pyrrolo[2,3-b]pyridine (70 mg, 0.105 mmol) was hydrolyzed by lithium hydroxide (25 mg, 0.63 mmol), THF/methanol/water (3/2/1 ml) to yield 20 mg (37.7% yield) of the titled compound. $^1$H NMR (CD$_3$OD, 300 MHz): δ 8.55-8.51 (m, 3H), 8.23 (s, 1H), 8.12-8.09 (dd, 1H), 7.97 (s, 1H), 7.73 (s, 1H), 7.40-7.30 (m, 1H), 7.15-7.10 (m, 2H), 7.06-7.00 (m, 2H), 5.45 (s, 2H), 3.79-3.76 (t, 2H), 3.60-2.90 (m, 8H). MS: m/z=512.15 (M+1), HPLC: 95.27% in method A.

Example 150

2-(4-(5-(3-(1-(3-fluorobenzyl)-1H-pyrazol-4-yl)-1H-pyrrolo[2,3-b]pyridin-5-yl)pyridin-2-yl) piperazin-1-yl)acetonitrile

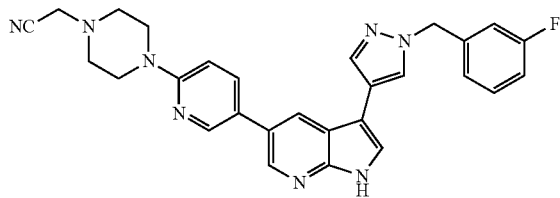 [SMILES: N#CCN1CCN(c2ccc(-c3cnc4[nH]cc(-c5cnn(Cc6cccc(F)c6)c5)c4c3)cn2)CC1]

Step-i: 2-(4-(5-(3-(1-(3-fluorobenzyl)-1H-pyrazol-4-yl)-1-tosyl-1H-pyrrolo[2,3-b]pyridin-5-yl)pyridin-2-yl)piperazin-1-yl)acetonitrile Using similar reaction conditions as described in step-i of example-126, 3-(1-(3-fluorobenzyl)-1H-pyrazol-4-yl)-5-(6-(piperazin-1-yl)pyridin-3-yl)-1-tosyl-1H-pyrrolo[2,3-b]pyridine (step 1 compound of example 137) (75 mg, 0.123 mmol) was alkylated using 2-bromoacetonitrile (23 mg, 0.185 mmol) and potassium carbonate (43 mg, 0.308 mmol) in DMF (1 ml) to afford 60 mg (75.0% yield) of the titled compound. MS: m/z=647.1 (M+1).

Step-ii: 2-(4-(5-(3-(1-(3-fluorobenzyl)-1H-pyrazol-4-yl)-1H-pyrrolo[2,3-b]pyridin-5-yl)pyridin-2-yl)piperazin-1-yl)acetonitrile Using similar reaction conditions as described in step-iii of example-1, 2-(4-(5-(3-(1-(3-fluorobenzyl)-1H-pyrazol-4-yl)-1-tosyl-1H-pyrrolo[2,3-b]pyridin-5-yl)pyridin-2-yl)piperazin-1-yl) acetonitrile (60 mg, 0.092 mmol) was hydrolyzed by lithium hydroxide (8 mg, 0.185 mmol) in THF/methanol/water (5/1/1 ml) to yield 15 mg (33.3% yield) of the titled compound. $^1$H NMR (CDCl$_3$, 400 MHz): δ 9.19 (s, 1H), 8.50-8.47 (dd, 2H), 8.128-8.123 (d, 1H), 7.86 (s, 1H), 7.79-7.76 (dd, 1H), 7.70 (s, 1H), 7.447-7.441 (d, 1H), 7.35-7.30 (m, 1H), 7.10-6.90 (m, 3H), 6.80-6.78 (d, 1H), 5.39 (s, 2H), 3.70-3.67 (t, 4H), 3.61 (s, 2H), 2.76-2.74 (t, 4H). MS: m/z=493.4 (M+1), HPLC: 97.07% in method A.

Example 151

(S)-3-((4-(5-(6-(4-(2-hydroxypropyl)piperazin-1-yl)pyridin-3-yl)-1H-pyrrolo[2,3-b]pyridin-3-yl)-1H-pyrazol-1-yl)methyl)phenol

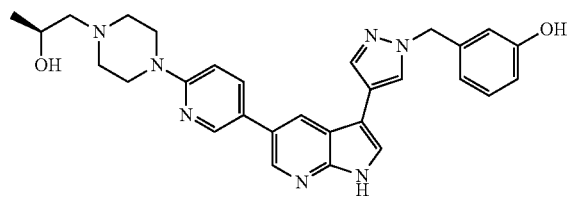 [SMILES: C[C@H](O)CN1CCN(c2ccc(-c3cnc4[nH]cc(-c5cnn(Cc6cccc(O)c6)c5)c4c3)cn2)CC1]

Step-i: tert-butyl 4-(5-(3-(1-(3-(benzyloxy)benzyl)-1H-pyrazol-4-yl)-1-tosyl-1H-pyrrolo[2,3-b]pyridin-5-yl)pyridin-2-yl)piperazine-1-carboxylate Using similar reaction conditions as described in step-i of example-1, tert-butyl 4-(5-(3-iodo-1-tosyl-1H-pyrrolo[2,3-b]pyridin-5-yl)pyridin-2-yl)piperazine-1-carboxylate (Intermediate 66K) (300 mg, 0.454 mmol) was coupled with 1-(3-(benzyloxy)benzyl)-4-(4,4,5,5-tetramethyl-1,3,2-dioxaborolan-2-yl)-1H-pyrazole (intermediate 64E) (195 mg, 0.500 mmol) using sodium carbonate (145 mg, 1.364 mmol) and Pd(dppf)Cl$_2$ (17 mg, 0.022 mmol) in toluene/ethanol/water (3/3/2 mL) to afford 250 mg (69% yield) of the titled compound after purification by column (Silica gel 60/120) using 0.5% methanol in DCM as eluent. MS: m/z=796.3 (M+1).

Step-ii: 3-(1-(3-(benzyloxy)benzyl)-1H-pyrazol-4-yl)-5-(6-(piperazin-1-yl)pyridin-3-yl)-1-tosyl-1H-pyrrolo[2,3-b]pyridine hydrochloride Using similar reaction conditions as described in step-ii of example-7, tert-butyl 4-(5-(3-(1-(3-(benzyloxy)benzyl)-1H-pyrazol-4-yl)-1-tosyl-1H-pyrrolo[2,3-b]pyridin-5-yl)pyridin-2-yl) piperazine-1-carboxylate (250 mg, 0.314 mmol) was deprotected in HCl in ether/methanol (2/3 ml) to afford 200 mg (87% yield) of the titled compound. MS: m/z=696.2 (M+1).

Step-iii: (S)-1-(4-(5-(3-(1-(3-(benzyloxy)benzyl)-1H-pyrazol-4-yl)-1-tosyl-1H-pyrrolo[2,3-b]pyridin-5-yl)pyridin-2-yl)piperazin-1-yl)propan-2-ol Using similar reaction conditions as described in step-i of example-82A, 3-(1-(3-(benzyloxy)benzyl)-1H-pyrazol-4-yl)-5-(6-(piperazin-1-yl)pyridin-3-yl)-1-tosyl-1H-pyrrolo[2,3-b]pyridine hydrochloride (200 mg. 0.273 mmol) was alkylated using (S)-2-methyloxirane (48 mg, 0.819 mmol), DIPEA (211 mg, 1.638 mmol) and ethanol (20 mL) to get 200 mg (crude) of the titled compound. MS: m/z=754.3 (M+1).

Step-iv: (S)-3-((4-(5-(6-(4-(2-hydroxypropyl)piperazin-1-yl)pyridin-3-yl)-1-tosyl-1H-pyrrolo[2,3-b]pyridin-3-yl)-1H-pyrazol-1-yl)methyl)phenol To the solution of (S)-1-(4-(5-(3-(1-(3-(benzyloxy)benzyl)-1H-pyrazol-4-yl)-1-tosyl-1H-pyrrolo[2,3-b]pyridin-5-yl)pyridin-2-yl)piperazin-1-yl)propan-2-ol (200 mg, 0265 mmol) in toluene/TFA (10/5 mL) was heated at 100° C. for 16 hours and distilled out the solvent. This was basified with triethylamine and distilled out the solvent to get 180 mg (crude) of the titled compound. MS: m/z=664.2 (M+1).

Step-v: (S)-3-((4-(5-(6-(4-(2-hydroxypropyl)piperazin-1-yl)pyridin-3-yl)-1H-pyrrolo[2,3-b]pyridin-3-yl)-1H-pyrazol-1-yl)methyl)phenol Using similar reaction conditions as described in step-iii of example-1, (S)-3-((4-(5-(6-(4-(2-hydroxypropyl)piperazin-1-yl)pyridin-3-yl)-1-tosyl-1H-pyrrolo[2,3-b]pyridin-3-yl)-1H-pyrazol-1-yl)methyl)phenol (180 mg, 0.271 mmol) was hydrolyzed with lithium hydroxide (34 mg, 0.813 mmol) in THF/methanol/water (2/2/0.5 mL) to yield 12 mg (9% yield) of desired product. ¹H NMR (CD₃OD, 400 MHz): δ 8.51-8.45 (m, 2H), 8.32-8.31 (m, 1H), 8.16 (s, 1H), 7.99-7.92 (m, 2H), 7.20-7.16 (t, 1H), 7.06-6.97 (m, 1H), 6.78-6.69 (m, 3H), 5.36 (s, 2H), 4.70-4.60 (m, 1H), 4.26-4.20 (t, 1H), 4.10-4.05 (q, 1H), 3.78-3.70 (m, 4H), 3.58-3.49 (m, 2H), 2.92-2.61 (m, 2H), 2.63-2.61 (m, 1H), 1.22-1.21 (m, 3H). MS: m/z=510.2 (M+1), HPLC: 98.41% in method A.

Example 152

3-(1-(3-fluorobenzyl)-1H-pyrazol-4-yl)-5-(6-(4-isobutylpiperazin-1-yl)pyridin-3-yl)-1H-pyrrolo[2,3-b]pyridine

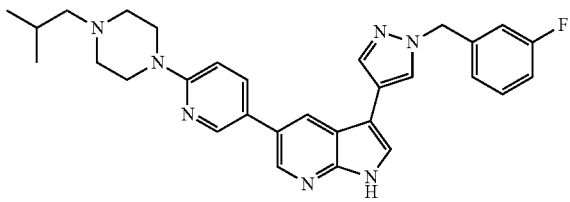 [SMILES: CC(C)CN1CCN(c2ccc(-c3cnc4[nH]cc(-c5cnn(Cc6cccc(F)c6)c5)c4c3)cn2)CC1]

Step-i: 3-(1-(3-fluorobenzyl)-1H-pyrazol-4-yl)-5-(6-(4-isobutylpiperazin-1-yl)pyridin-3-yl)-1-tosyl-1H-pyrrolo[2,3-b]pyridine Using similar reaction conditions as described in step-i of example-126, 3-(1-(3-fluorobenzyl)-1H-pyrazol-4-yl)-5-(6-(piperazin-1-yl)pyridin-3-yl)-1-tosyl-1H-pyrrolo[2,3-b]pyridine (step 1 compound of example 137) (75 mg, 0.123 mmol) was alkylated using 1-bromo-2-methylpropane (26 mg, 0.185 mmol) and potassium carbonate (43 mg, 0.308 mmol) in DMF (1 ml) to afford 70 mg (85.3% yield) of the titled compound. MS: m/z=664.6 (M+1).

Step-ii: 3-(1-(3-fluorobenzyl)-1H-pyrazol-4-yl)-5-(6-(4-isobutylpiperazin-1-yl)pyridin-3-yl)-1H-pyrrolo[2,3-b]pyridine Using similar reaction conditions as described in step-iii of example-1, 3-(1-(3-fluorobenzyl)-1H-pyrazol-4-yl)-5-(6-(4-isobutylpiperazin-1-yl)pyridin-3-yl)-1-tosyl-1H-pyrrolo[2,3-b]pyridine (70 mg, 0.105 mmol) was hydrolyzed by lithium hydroxide (27 mg, 0.632 mmol) in THF/methanol/water (3/2/1 ml) to yield 8 mg (15.0% yield) of the titled compound. ¹H NMR (CDCl₃, 300 MHz): δ 8.83 (s, 1H), 8.49-8.45 (dd, 2H), 8.11-8.10 (d, 1H), 7.85 (s, 1H), 7.76-7.69 (m, 2H), 7.42-7.41 (d, 1H), 7.39-7.30 (m, 1H), 7.10-6.90 (m, 3H), 6.77-6.74 (d, 1H), 5.38 (s, 2H), 3.60-3.59 (t, 4H), 2.60-2.50 (t, 4H), 2.16-2.14 (d, 2H), 1.90-1.80 (m, 1H), 0.95-0.93 (d, 6H). MS: m/z=510.3 (M+1), HPLC: 93.26% in method A.

Example 153

(S)-1-(4-(5-(3-(1-(3-chlorobenzyl)-1H-pyrazol-4-yl)-1H-pyrrolo[2,3-b]pyridin-5-yl)pyridin-2-yl)piperazin-1-yl)propan-2-ol

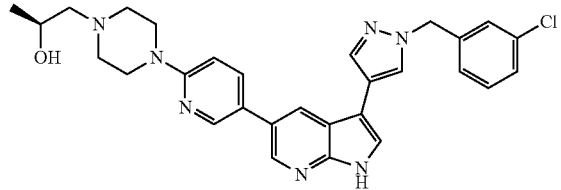 [SMILES: C[C@H](O)CN1CCN(c2ccc(-c3cnc4[nH]cc(-c5cnn(Cc6cccc(Cl)c6)c5)c4c3)cn2)CC1]

Step-i: tert-butyl 4-(5-(3-(1-(3-chlorobenzyl)-1H-pyrazol-4-yl)-1-tosyl-1H-pyrrolo[2,3-b]pyridin-5-yl)pyridin-2-yl)piperazine-1-carboxylate Using similar reaction conditions as described in step-i of example-1, tert-butyl 4-(5-(3-iodo-1-tosyl-1H-pyrrolo[2,3-b]pyridin-5-yl)pyridin-2-yl)piperazine-1-carboxylate (Intermediate 66K) (200 mg, 0.303 mmol) was coupled with 1-(3-chlorobenzyl)-4-(4,4,5,5-tetramethyl-1,3,2-dioxaborolan-2-yl)-1H-pyrazole (intermediate 64F) (116 mg, 0.36 mmol) using sodium carbonate (96 mg, 0.909 mmol) and Pd(dppf)Cl₂ (11 mg, 0.015 mmol) in toluene/ethanol/water (5/5/2 mL) to afford 188 mg (85.6% yield) of the titled compound after purification by column (Silica gel 60/120) using 50% ethyl acetate in hexane as eluent.

Step-ii: 3-(1-(3-chlorobenzyl)-1H-pyrazol-4-yl)-5-(6-(piperazin-1-yl)pyridin-3-yl)-1-tosyl-1H-pyrrolo[2,3-b]pyridine hydrochloride Using similar reaction conditions as described in step-ii of example-7, tert-butyl 4-(5-(3-(1-(3-chlorobenzyl)-1H-pyrazol-4-yl)-1-tosyl-1H-pyrrolo[2,3-b]pyridin-5-yl)pyridin-2-yl)piperazine-1-carboxylate (185 mg, 0.25 mmol) was deprotected in HCl in ether (10 ml) to afford 133 mg (78.8% yield) of the titled compound.

Step-iii (S)-1-(4-(5-(3-(1-(3-chlorobenzyl)-1H-pyrazol-4-yl)-1-tosyl-1H-pyrrolo[2,3-b]pyridin-5-yl)pyridin-2-yl)piperazin-1-yl)propan-2-ol Using similar reaction conditions as described in step-i of example-82A, 3-(1-(3-chlorobenzyl)-1H-pyrazol-4-yl)-5-(6-(piperazin-1-yl)pyridin-3-yl)-1-tosyl-1H-pyrrolo[2,3-b]pyridine hydrochloride (130 mg. 0.197 mmol) was alkylated using (S)-2-methyloxirane (34 mg, 0.59 mmol), DIPEA (73 mg, 0.59 mmol) and ethanol (5 mL) to get 124 mg (92.3% yield) of the titled compound.

Step-iv: (S)-1-(4-(5-(3-(1-(3-chlorobenzyl)-1H-pyrazol-4-yl)-1H-pyrrolo[2,3-b]pyridin-5-yl)pyridin-2-yl)piperazin-1-yl)propan-2-ol Using similar reaction conditions as described in step-iii of example-1, (S)-1-(4-(5-(3-(1-(3-chlorobenzyl)-1H-pyrazol- 4-yl)-1-tosyl-1H-pyrrolo[2,3-b]pyridin-5-yl)pyridin-2-yl) piperazin-1-yl) propan-2-ol (124 mg, 0.181 mmol) was hydrolyzed with lithium hydroxide (38 mg, 0.908 mmol) in THF/methanol/water (2/2/1 mL) to yield 30 mg (26.0% yield). $^1$H NMR (CD$_3$OD, 300 MHz): δ 8.54-8.53 (d, 1H), 8.45-8.41 (d, 1H), 8.41-8.40 (d, 1H), 8.21 (s, 1H), 8.07-8.03 (dd, 1H), 7.957-7.955 (d, 1H), 7.68 (s, 1H), 7.34-7.30 (m, 3H), 7.24-7.21 (dt, 1H), 7.11-7.08 (d, 1H), 5.42 (s, 2H), 4.30-4.20 (m, 1H), 3.26-3.08 (m, 2H), 1.27-1.25 (d, 3H). MS: m/z=528.4 (M+1), HPLC: 97.22% in method A.

Example 154

1-(4-(5-(3-(1-(3-fluorobenzyl)-1H-pyrazol-4-yl)-1H-pyrrolo[2,3-b]pyridin-5-yl)pyridin-2-yl) piperazin-1-yl)-2-hydroxyethanone

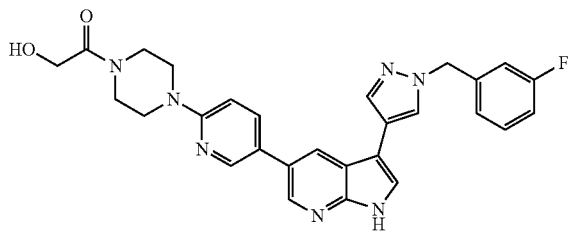 [SMILES: O=C(CO)N1CCN(c2ccc(-c3cnc4[nH]cc(-c5cnn(Cc6cccc(F)c6)c5)c4c3)cn2)CC1]

Step-i: 1-(4-(5-(3-(1-(3-fluorobenzyl)-1H-pyrazol-4-yl)-1-tosyl-1H-pyrrolo[2,3-b]pyridin-5-yl)pyridin-2-yl)piperazin-1-yl)-2-hydroxyethanone Using similar reaction conditions as described in step-ii of example-124, 3-(1-(3-fluorobenzyl)-1H-pyrazol-4-yl)-5-(6-(piperazin-1-yl)pyridin-3-yl)-1-tosyl-1H-pyrrolo[2,3-b]pyridine (step 1 compound of example 137) (75 mg, 0.123 mmol) was coupled with 2-hydroxyacetic acid (14 mg, 0.185 mmol) using HATU (71 mg, 0.185 mmol), HOBt (25 mg, 0.185 mmol) and DIPEA (86 µL, 0.493 mmol) in DMF (1 mL) to get 70 mg (85.3.0%) yield of the title compound after purification by column (Silica gel 60/120) chromatography using 5% methanol in dichloromethane as eluent. MS: m/z=666.5 (M+1).

Step-ii: 1-(4-(5-(3-(1-(3-fluorobenzyl)-1H-pyrazol-4-yl)-1H-pyrrolo[2,3-b]pyridin-5-yl)pyridin-2-yl) piperazin-1-yl)-2-hydroxyethanone Using similar reaction conditions as described in step-iii of example-1, 1-(4-(5-(3-(1-(3-fluorobenzyl)-1H-pyrazol-4-yl)-1-tosyl-1H-pyrrolo[2,3-b]pyridin-5-yl)pyridin-2-yl)piperazin-1-yl)-2-hydroxy ethanone (70 mg, 0.105 mmol) was hydrolyzed with lithium hydroxide (9 mg, 0.210 mmol) in THF/methanol/water (5/1/1 mL) to yield 7 mg (10.7% yield) of the titled compound. $^1$H NMR CD$_3$OD, 400 MHz): δ 8.497-8.493 (d, 1H), 8.44-8.43 (d, 1H), 8.39-8.38 (d, 1H), 8.32-8.29 (dd, 1H), 8.23 (s, 1H), 7.99 (s, 1H), 7.71 (s, 1H), 7.42-7.31 (m, 2H), 7.13-7.12 (d, 1H), 7.07-7.01 (m, 2H), 5.45 (s, 2H), 4.33 (s, 2H), 3.84-3.70 (m, 8H). MS: m/z=512.55 (M+1), HPLC: 96.01% in method A.

Example 155

1-(5-(3-(1-(3-fluorobenzyl)-1H-pyrazol-4-yl)-1H-pyrrolo[2,3-b]pyridin-5-yl)pyridin-2-yl)piperidin-4-ol

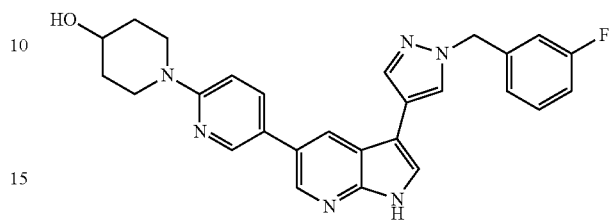

Step-i: 1-(5-(3-(1-(3-fluorobenzyl)-1H-pyrazol-4-yl)-1-tosyl-1H-pyrrolo[2,3-b]pyridin-5-yl)pyridin-2-yl)piperidin-4-ol Using similar reaction conditions as described in step-i of example-1, 5-bromo-3-(1-(3-fluorobenzyl)-1H-pyrazol-4-yl)-1-tosyl-1H-pyrrolo[2,3-b]pyridine (compound of Step-i of example 9) (150 mg, 0.28 mmol) was coupled with 1-(4-(4,4,5,5-tetramethyl-1,3,2-dioxaborolan-2-yl)phenyl)piperidin-4-ol (intermediate 69E) (173 mg, 0.56 mmol) using sodium carbonate (89 mg, 0.84 mmol) and Pd(dppf)Cl$_2$ (11 mg, 0.014 mmol) in DME/water (10/1 mL) to afford 160 mg (crude) of the titled compound. MS: m/z=623.6 (M+1).

Step-ii: 1-(5-(3-(1-(3-fluorobenzyl)-1H-pyrazol-4-yl)-1H-pyrrolo[2,3-b]pyridin-5-yl)pyridin-2-yl) piperidin-4-ol Using similar reaction conditions as described in step-iii of example-1, 1-(5-(3-(1-(3-fluorobenzyl)-1H-pyrazol-4-yl)-1-tosyl-1H-pyrrolo[2,3-b]pyridin-5-yl)pyridin-2-yl)piperidin-4-ol (160 mg, 0.25 mmol) was hydrolyzed with lithium hydroxide (33 mg, 0.77 mmol) in THF/methanol/water (3/3/1 mL) to yield 38 mg (25.4%) of desired product. $^1$H NMR (CD$_3$OD, 300 MHz): δ 8.49-8.41 (m, 3H), 8.21 (s, 2H), 7.98 (s, 1H), 7.70 (s, 1H), 7.55-7.51 (s, 1H), 7.42-7.33 (m, 1H), 7.11-6.97 (m, 3H), 5.43 (s, 2H), 4.06-3.98 (m, 3H), 3.65-3.57 (m, 2H), 2.09-2.03 (m, 2H), 1.80-1.65 (m, 2H). MS: m/z=469.2 (M+1), HPLC: 93.72% in method A.

Example 156

5-(6-(4-(ethylsulfonyl)piperazin-1-yl)pyridin-3-yl)-3-(1-(3-fluorobenzyl)-1H-pyrazol-4-yl)-1H-pyrrolo[2,3-b]pyridine

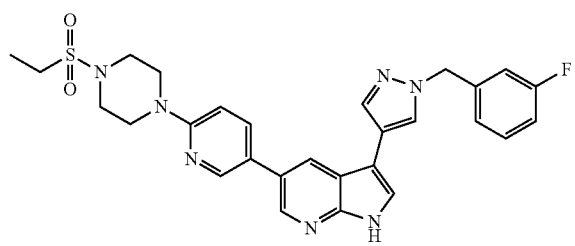 [SMILES: CCS(=O)(=O)N1CCN(c2ccc(-c3cnc4[nH]cc(-c5cnn(Cc6cccc(F)c6)c5)c4c3)cn2)CC1]

Step-i: 5-(6-(4-(ethylsulfonyl)piperazin-1-yl)pyridin-3-yl)-3-(1-(3-fluorobenzyl)-1H-pyrazol-4-yl)-1-tosyl-1H-pyrrolo[2,3-b]pyridine Using similar reaction conditions as described in step i of intermediate 17, 3-(1-(3-fluorobenzyl)-1H-pyrazol-4-yl)-5-(6-(piperazin-1-yl)pyridin-3-yl)-1-tosyl-1H-pyrrolo[2,3-b]pyridine (step 1 compound of example 137) (80 mg, 0.13 mmol) was alkylated with ethanesulfonyl chloride (25 mg, 0.196 mmol) using triethylamine (40 mg, 0.39 mmol) in DCM (3 mL) to afford 100 mg (100% yield) of the titled compound. MS: m/z=700.2 (M+1).

Step-ii: 5-(6-(4-(ethylsulfonyl)piperazin-1-yl)pyridin-3-yl)-3-(1-(3-fluorobenzyl)-1H-pyrazol-4-yl)-1H-pyrrolo[2,3-b]pyridine Using similar reaction conditions as described in step-iii of example-1, 5-(6-(4-(ethylsulfonyl)piperazin-1-yl)pyridin-3-yl)-3-(1-(3-fluorobenzyl)-1H-pyrazol-4-yl)-1-tosyl-1H-pyrrolo[2,3-b]pyridine (100 mg, 0.143 mmol) was hydrolyzed with lithium hydroxide (30 mg, 0.715 mmol) in THF/methanol/water (3/2/1 mL) to yield 45 mg (58.4% yield) of the titled compound. $^1$H NMR (CD$_3$OD, 300 MHz): δ 8.51-8.49 (m, 2H), 8.44-8.43 (d, 2H), 8.41-8.40 (d, 1H), 8.36-8.35 (d, 1H), 8.22 (s, 1H), 7.98 (s, 1H), 7.72 (s, 1H), 7.48-7.45 (d, 1H), 7.38-7.36 (m, 1H), 7.12-7.09 (d, 1H), 7.08-6.96 (m, 2H), 5.44 (s, 2H), 3.85-3.83 (t, 4H), 3.53-3.50 (t, 4H), 3.15-3.05 (q, 2H), 1.38-1.33 (t, 3H). MS: m/z=546.1 (M+1), HPLC: 94.35% in method A.

Example 157

Cyclopropyl(4-(5-(3-(1-(3-fluorobenzyl)-1H-pyrazol-4-yl)-1H-pyrrolo[2,3-b]pyridin-5-yl)pyridin-2-yl)piperazin-1-yl)methanone

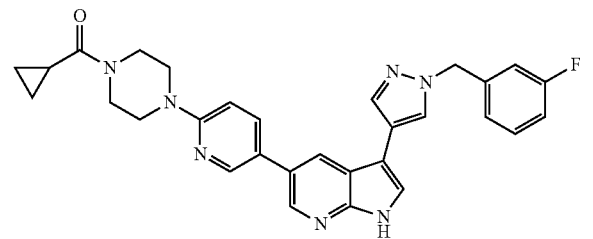 [SMILES: O=C(C1CC1)N1CCN(c2ccc(-c3cnc4[nH]cc(-c5cnn(Cc6cccc(F)c6)c5)c4c3)cn2)CC1]

Step-i: cyclopropyl(4-(5-(3-(1-(3-fluorobenzyl)-1H-pyrazol-4-yl)-1-tosyl-1H-pyrrolo[2,3-b]pyridin-5-yl)pyridin-2-yl)piperazin-1-yl)methanone Using similar reaction conditions as described in step i of intermediate 17, 3-(1-(3-fluorobenzyl)-1H-pyrazol-4-yl)-5-(6-(piperazin-1-yl)pyridin-3-yl)-1-tosyl-1H-pyrrolo[2,3-b]pyridine (step 1 compound of example 137) (80 mg, 0.13 mmol) was acylated with cyclopropane carbonyl chloride (22 mg, 0.196 mmol) using triethylamine (40 mg, 0.39 mmol) in DCM (3 mL) to afford 100 mg (100% yield) of the titled compound. MS: m/z=676.2 (M+1).

Step-ii: cyclopropyl(4-(5-(3-(1-(3-fluorobenzyl)-1H-pyrazol-4-yl)-1H-pyrrolo[2,3-b]pyridin-5-yl)pyridin-2-yl)piperazin-1-yl)methanone Using similar reaction conditions as described in step-iii of example-1, cyclopropyl(4-(5-(3-(1-(3-fluorobenzyl)-1H-pyrazol-4-yl)-1-tosyl-1H-pyrrolo[2,3-b]pyridin-5-yl)pyridin-2-yl)piperazin-1-yl)methanone (100 mg, 0.148 mmol) was hydrolyzed with lithium hydroxide (31 mg, 0.74 mmol) in THF/methanol/water (3/2/1 mL) to yield 42 mg (54.5% yield) of the titled compound. $^1$H NMR (CD$_3$OD, 300 MHz): δ 8.53 (s, 2H), 8.49-8.48 (d, 1H), 8.46-8.45 (d, 1H), 8.24 (s, 1H), 7.998-7.995 (d, 1H), 7.74 (s, 1H), 7.50-7.47 (d, 1H), 7.37-7.35 (m, 1H), 7.12-6.98 (m, 3H), 5.44 (s, 2H), 4.08-3.83 (m, 8H), 2.05-1.95 (m, 1H), 0.95-0.87 (m, 2H). MS: m/z=522.4 (M+1), HPLC: 96.90% in method A.

Example 158

3-(1-(3-fluorobenzyl)-1H-pyrazol-4-yl)-5-(6-(4-(methylsulfonyl)piperazin-1-yl)pyridin-3-yl)-1H-pyrrolo[2,3-b]pyridine

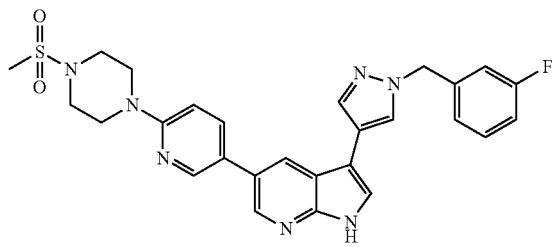 [SMILES: CS(=O)(=O)N1CCN(c2ccc(-c3cnc4[nH]cc(-c5cnn(Cc6cccc(F)c6)c5)c4c3)cn2)CC1]

Step-i: 3-(1-(3-fluorobenzyl)-1H-pyrazol-4-yl)-5-(6-(4-(methylsulfonyl)piperazin-1-yl)pyridin-3-yl)-1-tosyl-1H-pyrrolo[2,3-b]pyridine Using similar reaction conditions as described in step i of intermediate 17, 3-(1-(3-fluorobenzyl)-1H-pyrazol-4-yl)-5-(6-(piperazin-1-yl)pyridin-3-yl)-1-tosyl-1H-pyrrolo[2,3-b]pyridine (step 1 compound of example 137) (80 mg, 0.13 mmol) was mesylated with methanesulfonyl chloride (23 mg, 0.196 mmol) using triethylamine (40 mg, 0.39 mmol) in DCM (3 mL) to afford 100 mg (100% yield) of the titled compound. MS: m/z=686.2 (M+1).

Step-ii: 3-(1-(3-fluorobenzyl)-1H-pyrazol-4-yl)-5-(6-(4-(methylsulfonyl)piperazin-1-yl)pyridin-3-yl)-1H-pyrrolo[2,3-b]pyridine Using similar reaction conditions as described in step-iii of example-1, 3-(1-(3-fluorobenzyl)-1H-pyrazol-4-yl)-5-(6-(4-(methylsulfonyl)piperazin-1-yl)pyridin-3-yl)-1-tosyl-1H-pyrrolo[2,3-b]pyridine (100 mg, 0.145 mmol) was hydrolyzed with lithium hydroxide (30 mg, 0.729 mmol) in THF/methanol/water (3/2/1 mL) to yield 27 mg (35.0% yield) of the titled compound after purification by preparative HPLC. $^1$H NMR (CD$_3$OD, 300 MHz): δ 8.55 (s, 2H), 8.47-8.43 (dd, 1H), 8.386-8.380 (d, 1H), 8.247 (s, 1H), 7.997-7.995 (d, 1H), 7.75 (s, 1H), 7.50-7.47 (d, 1H), 7.37-7.35 (d, 1H), 7.42-7.32 (m, 1H), 7.12-6.97 (m, 3H), 5.43 (s, 2H), 3.88-3.85 (t, 4H), 3.47-3.44 (t, 4H), 2.92 (s, 3H). MS: m/z=532.05 (M+1), HPLC: 95.94% in method A.

Example 159

3-(1-(3-fluorobenzyl)-1H-pyrazol-4-yl)-5-(6-(piperidin-4-yl)pyridin-3-yl)-1H-pyrrolo[2,3-b]pyridine

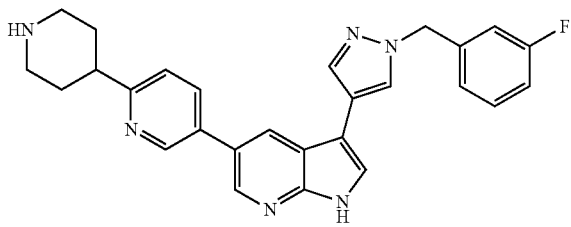 [SMILES: Fc1cccc(Cn2cc(-c3c[nH]c4ncc(-c5ccc(C6CCNCC6)nc5)cc34)cn2)c1]

Step-i: tert-butyl 4-(5-(3-(1-(3-fluorobenzyl)-1H-pyrazol-4-yl)-1H-pyrrolo[2,3-b]pyridin-5-yl)pyridin-2-yl)piperidine-1-carboxylate Using similar reaction conditions as described in step-iii of example-1, tert-butyl 4-(5-(3-(1-(3-fluorobenzyl)-1H-pyrazol-4-yl)-1-tosyl-1H-pyrrolo[2,3-b]pyridin-5-yl)pyridin-2-yl)piperidine-1-carboxylate (step ii of example 102A) (126 mg, 0.178 mmol) was hydrolyzed by lithium hydroxide (75 mg, 1.78 mmol) in THF/methanol/water (20/10/5 ml) to yield 96 mg (98% yield) of the titled compound. MS: m/z=553.2 (M+1).

Step-ii 3-(1-(3-fluorobenzyl)-1H-pyrazol-4-yl)-5-(6-(piperidin-4-yl)pyridin-3-yl)-1H-pyrrolo[2,3-b]pyridine Using similar reaction conditions as described in step-ii of example-7, tert-butyl 4-(5-(3-(1-(3-fluorobenzyl)-1H-pyrazol-4-yl)-1H-pyrrolo[2,3-b]pyridin-5-yl)pyridin-2-yl)piperidine-1-carboxylate (96 mg, 0.173 mmol) was deprotected in methanol/HCl in dioxane (5/5 ml) to afford 49 mg (63% yield) of the titled compound. $^1$H NMR (CD$_3$OD, 300 MHz): δ 9.178-9.170 (d, 1H), 8.78-8.74 (dd, 1H), 8.71-8.66 (dd, 2H), 8.26 (s, 1H), 7.99 (s, 1H), 7.95-7.92 (d, 1H), 7.77 (s, 1H), 7.40-7.31 (q, 1H), 7.10-7.08 (d, 1H), 7.03-6.96 (m, 2H), 5.42 (s, 2H), 3.63-3.59 (d, 2H), 3.55-3.40 (m, 1H), 3.30-3.19 (m, 2H), 2.32-2.08 (m, 4H). MS: m/z=453.5 (M+1), HPLC: 93.40% in method A.

Example 160

2-cyclopropyl-1-(4-(5-(3-(1-(3-fluorobenzyl)-1H-pyrazol-4-yl)-1H-pyrrolo[2,3-b]pyridin-5-yl)pyridin-2-yl)piperazin-1-yl)ethanone

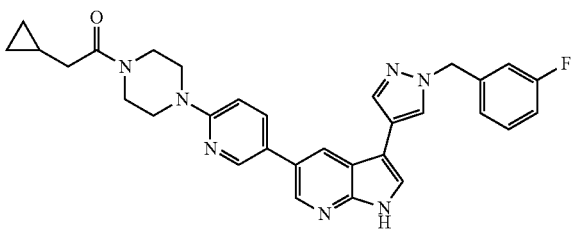 [SMILES: O=C(CC1CC1)N1CCN(c2ccc(-c3cnc4[nH]cc(-c5cnn(Cc6cccc(F)c6)c5)c4c3)cn2)CC1]

Step-i: 2-cyclopropyl-1-(4-(5-(3-(1-(3-fluorobenzyl)-1H-pyrazol-4-yl)-1-tosyl-1H-pyrrolo[2,3-b]pyridin-5-yl)pyridin-2-yl)piperazin-1-yl)ethanone Using similar reaction conditions as described in step-ii of example-124, 3-(1-(3-fluorobenzyl)-1H-pyrazol-4-yl)-5-(6-(piperazin-1-yl)pyridin-3-yl)-1-tosyl-1H-pyrrolo[2,3-b]pyridine (step 1 compound of example 137) (75 mg, 0.123 mmol) was coupled with 2-cyclopropylacetic acid (19 mg, 0.185 mmol) using HATU (70 mg, 0.185 mmol), HOBt (25 mg, 0.185 mmol) and DIPEA (48 mg, 0.37 mmol) in DMF (3 mL) to get 80 mg (95.2.0%) yield of the title compound. MS: m/z=690.6 (M+1).

Step-ii: 2-cyclopropyl-1-(4-(5-(3-(1-(3-fluorobenzyl)-1H-pyrazol-4-yl)-1H-pyrrolo[2,3-b]pyridin-5-yl)pyridin-2-yl)piperazin-1-yl)ethanone Using similar reaction conditions as described in step-iii of example-1, 2-cyclopropyl-1-(4-(5-(3-(1-(3-fluorobenzyl)-1H-pyrazol-4-yl)-1-tosyl-1H-pyrrolo[2,3-b]pyridin-5-yl)pyridin-2-yl)piperazin-1-yl)ethanone (80 mg, 0.116 mmol) was hydrolyzed with lithium hydroxide (25 mg, 0.58 mmol) in THF/methanol/water (3/2/1 mL) to yield 4 mg (6.4% yield) of the titled compound. $^1$H NMR (CD$_3$OD, 300 MHz): δ 8.52-8.45 (m, 3H), 8.33-8.32 (d, 1H), 8.225-8.222 (d, 1H), 7.993-7.990 (d, 1H), 7.73 (s, 1H), 7.50-7.46 (d, 1H), 7.38-7.33 (m, 1H), 7.12-7.09 (d, 1H), 7.04-6.89 (m, 3H), 6.50-6.43 (dt, 1H), 5.44 (s, 2H), 3.93-3.85 (m, 8H), 2.35-2.25 (m, 2H), 1.13-1.08 (t, 3H). MS: m/z=536.4 (M+1), HPLC: 97.55% in method B.

Example 161

(2S)-1-(4-(5-(3-(1-(3-fluorobenzyl)-3,5-dimethyl-1H-pyrazol-4-yl)-1H-pyrrolo[2,3-b]pyridin-5-yl)pyridin-2-yl)piperazin-1-yl)propan-2-ol

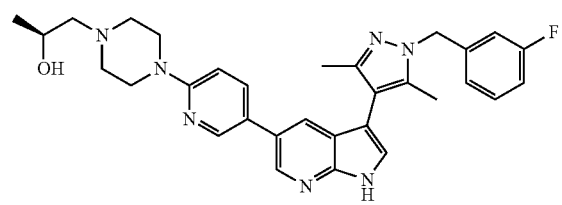 [SMILES: Cc1nn(Cc2cccc(F)c2)c(C)c1-c1c[nH]c2ncc(-c3ccc(N4CCN(C[C@H](C)O)CC4)nc3)cc12]

Step-i: tert-butyl 4-(5-(3-(1-(3-fluorobenzyl)-3,5-dimethyl-1H-pyrazol-4-yl)-1-tosyl-1H-pyrrolo[2,3-b]pyridin-5-yl)pyridin-2-yl)piperazine-1-carboxylate Using similar reaction conditions as described in step-ii of example-1, 5-bromo-3-(1-(3-fluorobenzyl)-3,5-dimethyl-1H-pyrazol-4-yl)-1-tosyl-1H-pyrrolo[2,3-b]pyridine (Step-i of example-14) (200 mg, 0.361 mmol) was coupled with tert-butyl 4-(5-(4,4,5,5-tetramethyl-1,3,2-dioxaborolan-2-yl)pyridin-2-yl)piperazine-1-carboxylate (intermediate 69C) (140 mg, 0.361 mmol) using Pd(dppf)Cl$_2$ (14 mg, 0.018 mmol) and sodium carbonate (114, 0.018 mmol) in DME/water (25/5 ml). This afforded 221 mg (83% yield) of the titled compound. MS: m/z=736.2 (M+1).

Step-ii: 3-(1-(3-fluorobenzyl)-3,5-dimethyl-1H-pyrazol-4-yl)-5-(6-(piperazin-1-yl)pyridin-3-yl)-1-tosyl-1H-pyrrolo[2,3-b]pyridine hydrochloride Using similar reaction conditions as described in step-ii of example-7, tert-butyl 4-(5-(3-(1-(3-fluorobenzyl)-3,5-dimethyl-1H-pyrazol-4-yl)-1-tosyl-1H-pyrrolo[2,3-b]pyridin-5-yl)pyridin-2-yl) piperazine-1-carboxylate (221 mg, 0.299 mmol) was deprotected in methanol/HCl in dioxane (5/5 ml) to afford 186 mg (93% yield) of the titled compound. MS: m/z=636.1 (M+1).

Step-iii (2S)-1-(4-(5-(3-(1-(3-fluorobenzyl)-3,5-dimethyl-1H-pyrazol-4-yl)-1-tosyl-1H-pyrrolo[2,3-b]pyridin-5-yl)pyridin-2-yl)piperazin-1-yl)propan-2-ol Using similar reaction conditions as described in step-i of example-82A, 3-(1-(3-fluorobenzyl)-3,5-dimethyl-1H-pyrazol-4-yl)-5-(6-(piperazin-1-yl)pyridin-3-yl)-1-tosyl-1H-pyrrolo[2,3-b]pyridine hydrochloride (186 mg, 0.277 mmol) was alkylated using (S)-2-methyloxirane (32 mg, 0.554 mmol), DIPEA (72 mg, 0.554 mmol) and ethanol (4 mL) to get 157 mg (82% yield) of the titled compound. MS: m/z=694.2 (M+1).

Step-iv: (2S)-1-(4-(5-(3-(1-(3-fluorobenzyl)-3,5-dimethyl-1H-pyrazol-4-yl)-1H-pyrrolo[2,3-b]pyridin-5-yl)pyridin-2-yl)piperazin-1-yl)propan-2-ol Using similar reaction conditions as described in step-iii of example-1, (2S)-1-(4-(5-(3-(1-(3-fluorobenzyl)-3,5-dimethyl-1H-pyrazol-4-yl)-1-tosyl-1H-pyrrolo[2,3-b]pyridin-5-yl)pyridin-2-yl)piperazin-1-yl)propan-2-ol (165 mg, 0.238 mmol) was hydrolyzed with lithium hydroxide (100 mg, 2.38 mmol) in THF/methanol/water (20/10/5 mL) to yield 31 mg (13% yield) of desired product. $^1$H NMR (CD$_3$OD, 300 MHz): δ 8.64-8.63 (d, 1H), 8.48-8.47 (d, 1H), 8.327-8.321 (d, 1H), 8.23-8.19 (dd, 1H), 7.64 (s, 1H), 7.42-7.35 (m, 1H), 7.31-7.28 (m, 2H), 7.07-7.02 (m, 2H), 6.95-6.91 (dt, 1H), 5.41 (s, 2H), 4.45-4.30 (m, 1H), 3.56 (s, 4H), 3.30-3.10 (m, 2H), 2.24 (s, 3H), 2.23 (s, 3H), 1.26-1.24 (d, 3H). MS: m/z=539.9 (M+1), HPLC: 95.5% in method A.

Example 162

(S)-1-(4-(5-(3-(1-(3-fluorobenzyl)-5-methyl-1H-pyrazol-4-yl)-1H-pyrrolo[2,3-b]pyridin-5-yl)pyridin-2-yl)piperazin-1-yl)propan-2-ol

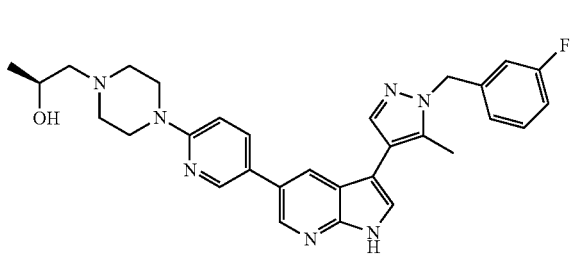 [SMILES: Cc1c(-c2c[nH]c3ncc(-c4ccc(N5CCN(C[C@H](C)O)CC5)nc4)cc23)cnn1Cc1cccc(F)c1]

Step-i: tert-butyl 4-(5-(3-(1-(3-fluorobenzyl)-5-methyl-1H-pyrazol-4-yl)-1-tosyl-1H-pyrrolo[2,3-b]pyridin-5-yl)pyridin-2-yl)piperazine-1-carboxylate Using similar reaction conditions as described in step-i of example-1, tert-butyl 4-(5-(3-iodo-1-tosyl-1H-pyrrolo[2,3-b]pyridin-5-yl)pyridin-2-yl)piperazine-1-carboxylate (Intermediate 66K) (200 mg, 0.303 mmol) was coupled with 1-(3-fluorobenzyl)-3-methyl-4-(4,4,5,5-tetramethyl-1,3,2-dioxaborolan-2-yl)-1H-pyrazole (intermediate 12) (116 mg, 0.363 mmol) using sodium carbonate (96 mg, 0.909 mmol) and Pd(dppf)Cl$_2$ (11 mg, 0.015 mmol) in toluene/ethanol/water (10/10/1 mL) to afford 250 mg (crude) of the titled compound after purification by column (Silica gel 60/120) using 50% ethyl acetate in hexane as eluent. MS: m/z=722.5 (M+1).

Step-ii: 3-(1-(3-fluorobenzyl)-5-methyl-1H-pyrazol-4-yl)-5-(6-(piperazin-1-yl)pyridin-3-yl)-1-tosyl-1H-pyrrolo[2,3-b]pyridine hydrochloride Using similar reaction conditions as described in step-ii of example-7, tert-butyl 4-(5-(3-(1-(3-fluorobenzyl)-5-methyl-1H-pyrazol-4-yl)-1-tosyl-1H-pyrrolo[2,3-b]pyridin-5-yl)pyridin-2-yl)piperazine-1-carboxylate (250 mg, 0.34 mmol) was deprotected in HCl in ether (5 ml) to afford 270 mg (crude) of the titled compound. MS: m/z=622.5 (M+1).

Step-iii: (S)-1-(4-(5-(3-(1-(3-fluorobenzyl)-5-methyl-1H-pyrazol-4-yl)-1-tosyl-1H-pyrrolo[2,3-b]pyridin-5-yl)pyridin-2-yl)piperazin-1-yl)propan-2-ol Using similar reaction conditions as described in step-i of example-82A, 3-(1-(3-fluorobenzyl)-5-methyl-1H-pyrazol-4-yl)-5-(6-(piperazin-1-yl)pyridin-3-yl)-1-tosyl-1H-pyrrolo[2,3-b]pyridine hydrochloride (270 mg, 0.41 mmol) was alkylated using (S)-2-methyloxirane (48 mg, 0.82 mmol), DIPEA (159 mg, 1.23 mmol) and ethanol (10 mL) to get 350 mg (crude) of the titled compound. MS: m/z=680.2 (M+1).

Step-iv: (S)-1-(4-(5-(3-(1-(3-fluorobenzyl)-5-methyl-1H-pyrazol-4-yl)-1H-pyrrolo[2,3-b]pyridin-5-yl)pyridin-2-yl)piperazin-1-yl)propan-2-ol Using similar reaction conditions as described in step-iii of example-1, (S)-1-(4-(5-(3-(1-(3-fluorobenzyl)-5-methyl-1H-pyrazol-4-yl)-1-tosyl-1H-pyrrolo[2,3-b]pyridin-5-yl)pyridin-2-yl) piperazin-1-yl)propan-2-ol (350 mg, 0.51 mmol) was hydrolyzed with lithium hydroxide (65 mg, 1.54 mmol) in THF/methanol/water (6/4/2 mL) to yield 40 mg (11% yield) after purification by preparative HPLC as a mixture of two isomers. MS: m/z=526.5 (M+1). HPLC: 89.1% in method B.

Example 163

(S)-1-(4-(5-(3-(1-(3-fluorobenzyl)-1H-pyrazol-4-yl)-1H-pyrrolo[2,3-b]pyridin-5-yl)pyrazin-2-yl) piperazin-1-yl)propan-2-ol

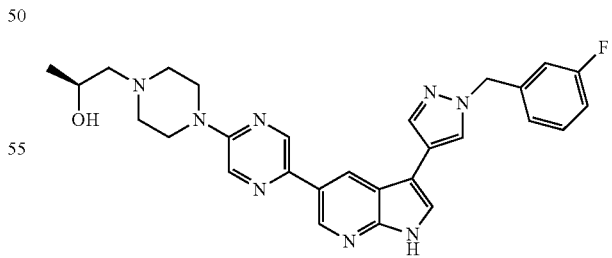

Step-i: tert-butyl 4-(5-(3-(1-(3-fluorobenzyl)-1H-pyrazol-4-yl)-1-tosyl-1H-pyrrolo[2,3-b]pyridin-5-yl) pyrazin-2-yl)piperazine-1-carboxylate Using similar reaction conditions as described in step-i of example-1, tert-butyl 4-(5-(3-iodo-1-tosyl-1H-pyrrolo[2,3- b]pyridin-5-yl)pyrazin-2-yl)piperazine-1-carboxylate (Intermediate 66N) (465 mg, 0.7 mmol) was coupled with 1-(3-fluorobenzyl)-4-(4,4,5,5-tetramethyl-1,3,2-dioxaborolan-2-yl)-1H-pyrazole (intermediate 11) (234 mg, 0.77 mmol) using sodium carbonate (223 mg, 21 mmol) and Pd(dppf)Cl$_2$ (26 mg, 0.035 mmol) in toluene/ethanol/water (6/6/2 mL) to afford 410 mg (82.1% yield) of the titled compound after purification by column (Silica gel 60/120) using 30% ethyl acetate in hexane as eluent. MS: m/z=709.3 (M+1).

Step-ii: 3-(1-(3-fluorobenzyl)-1H-pyrazol-4-yl)-5-(5-(piperazin-1-yl)pyrazin-2-yl)-1-tosyl-1H-pyrrolo[2,3-b]pyridine hydrochloride Using similar reaction conditions as described in step-ii of example-7, tert-butyl 4-(5-(3-(1-(3-fluorobenzyl)-1H-pyrazol-4-yl)-1-tosyl-1H-pyrrolo[2,3-b]pyridin-5-yl)pyrazin-2-yl)piperazine-1-carboxylate (400 mg, 0.56 mmol) was deprotected in HCl in ether (10 ml) to afford crude compound. Using similar reaction conditions as described in Step-i of example-82A, above crude was alkylated using (S)-2-methyloxirane (163 mg, 2.8 mmol), DIPEA (217 mg, 1.68 mmol) and ethanol (10 mL) to get 240 mg (63.7% yield) of the titled compound. MS: m/z=667.1 (M+1).

Step-iii: (S)-1-(4-(5-(3-(1-(3-fluorobenzyl)-1H-pyrazol-4-yl)-1H-pyrrolo[2,3-b]pyridin-5-yl)pyrazin-2-yl)piperazin-1-yl)propan-2-ol Using similar reaction conditions as described in step-iii of example-1, (S)-1-(4-(5-(3-(1-(3-fluorobenzyl)-1H-pyrazol-4-yl)-1-tosyl-1H-pyrrolo[2,3-b]pyridin-5-yl)pyrazin-2-yl)piperazin-1-yl) propan-2-ol (230 mg, 0.34 mmol) was hydrolyzed with lithium hydroxide (44 mg, 1.03 mmol) in THF/methanol/water (4/4/2 mL) to yield 40 mg (18.5% yield) of desired product. $^1$H NMR (CD$_3$OD, 300 MHz): δ 8.83-8.75 (m, 3H), 8.44-8.43 (d, 1H), 8.22 (s, 1H), 7.972-7.970 (d, 1H), 7.68 (s, 1H), 7.44-7.32 (m, 1H), 7.16-6.96 (m, 3H), 5.44 (s, 2H), 4.70-4.45 (m, 3H), 4.30-4.10 (m, 2H), 3.80-3.60 (m, 2H), 3.60-3.30 (m, 4H), 1.27-1.25 (d, 3H). MS: m/z=513.3 (M+1), HPLC: 97.55% in method B.

Example 164

(S)-1-(4-(4-(3-(1-(3-fluorobenzyl)-1H-pyrazol-4-yl)-1H-pyrrolo[2,3-b]pyridin-5-yl)phenyl)-1,4-diazepan-1-yl)propan-2-ol

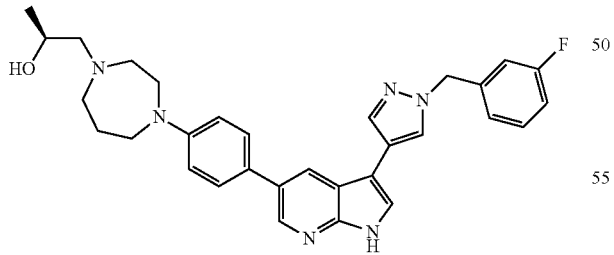

Step-i: tert-butyl 4-(4-(3-(1-(3-fluorobenzyl)-1H-pyrazol-4-yl)-1-tosyl-1H-pyrrolo[2,3-b]pyridin-5-yl)phenyl)-1,4-diazepane-1-carboxylate Using similar reaction conditions as described in step-i of example-1, -bromo-3-(1-(3-fluorobenzyl)-1H-pyrazol-4-yl)-1-tosyl-1H-pyrrolo[2,3-b]pyridine (compound of Step-i of example 9) (100 mg, 0.190 mmol) was coupled with tert-butyl 4-(4-(4,4,5,5-tetramethyl-1,3,2-dioxaborolan-2-yl)phenyl)-1,4-diazepane-1-carboxylate (intermediate 69F) (92 mg, 0.229 mmol) using sodium carbonate (60 mg, 0.57 mmol) and Pd(PPh$_3$)$_2$Cl$_2$ (7 mg, 0.095 mmol) in DME/water (3/1 mL) to afford 120 mg (86.9% yield) of the titled compound after purification by column (Silica gel 60/120) using 50% ethyl acetate in hexane as eluent. MS: m/z=722.3 (M+1).

Step-ii: 5-(4-(1,4-diazepan-1-yl)phenyl)-3-(1-(3-fluorobenzyl)-1H-pyrazol-4-yl)-1-tosyl-1H-pyrrolo[2,3-b]pyridine Using similar reaction conditions as described in step-ii of example-7, tert-butyl 4-(4-(3-(1-(3-fluorobenzyl)-1H-pyrazol-4-yl)-1-tosyl-1H-pyrrolo[2,3-b]pyridin-5-yl)phenyl)-1,4-diazepane-1-carboxylate (120 mg, 0.166 mmol) was deprotected in TFA/DCM (3/1 ml) to afford 100 mg (97.0% yield) of the titled compound. MS: m/z=621.2 (M+1).

Step-iii: (S)-1-(4-(4-(3-(1-(3-fluorobenzyl)-1H-pyrazol-4-yl)-1-tosyl-1H-pyrrolo[2,3-b]pyridin-5-yl)phenyl)-1,4-diazepan-1-yl)propan-2-ol Using similar reaction conditions as described in step-i of example-82A, 5-(4-(1,4-diazepan-1-yl)phenyl)-3-(1-(3-fluorobenzyl)-1H-pyrazol-4-yl)-1-tosyl-1H-pyrrolo[2,3-b]pyridine (100 mg, 0.161 mmol) was alkylated using (S)-2-methyloxirane (14 mg, 0.241 mmol), DIPEA (62 mg, 0.48 mmol) and ethanol (3 mL) to get 100 mg (91.7% yield) of the titled compound. MS: m/z=679.6 (M+1).

Step-iv: (S)-1-(4-(4-(3-(1-(3-fluorobenzyl)-1H-pyrazol-4-yl)-1H-pyrrolo[2,3-b]pyridin-5-yl)phenyl)-1,4-diazepan-1-yl)propan-2-ol Using similar reaction conditions as described in step-iii of example-1, (S)-1-(4-(4-(3-(1-(3-fluorobenzyl)-1H-pyrazol-4-yl)-1-tosyl-1H-pyrrolo[2,3-b]pyridin-5-yl)phenyl)-1,4-diazepan-1-yl) propan-2-ol (100 mg, 0.147 mmol) was hydrolyzed with lithium hydroxide (31 mg, 0.736 mmol) in THF/methanol/water (2/2/1 mL) to yield 33 mg (42.8% yield) of desired product. $^1$H NMR (CDCl$_3$, 300 MHz): δ 8.83 (s, 1H), 8.538-8.531 (d, 1H), 8.13-8.12 (d, 1H), 7.86 (s, 1H), 7.70 (s, 1H), 7.52-7.49 (d, 2H), 7.39-7.30 (m, 2H), 7.07-6.91 (m, 3H), 6.82-6.79 (d, 2H), 5.38 (s, 2H), 3.85-3.75 (m, 1H), 3.70-3.55 (m, 4H), 3.15-3.00 (m, 1H), 2.90-2.80 (m, 2H), 2.70-2.55 (m, 2H), 2.35-2.25 (m, 1H), 2.15-1.95 (m, 2H), 1.14-1.12 (d, 3H). MS: m/z=525.3 (M+1), HPLC: 92.75% in method A.

Example 165

5-(3-fluoro-4-(piperidin-4-yl)phenyl)-3-(1-(3-fluorobenzyl)-5-methyl-1H-pyrazol-4-yl)-1H-pyrrolo[2,3-b]pyridine

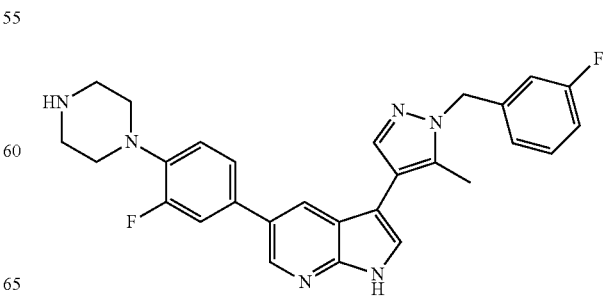

Step-i: 5-bromo-3-(1-(3-fluorobenzyl)-3-methyl-1H-pyrazol-4-yl)-1-tosyl-1H-pyrrolo[2,3-b]pyridine Using similar reaction conditions as described in step-i of example-1,5-bromo-3-iodo-1-tosyl-1H-pyrrolo[2,3-b]pyridine (Intermediate 1) (300 mg, 0.709 mmol) was coupled with 1-(3-fluorobenzyl)-3-methyl-4-(4,4,5,5-tetramethyl-1,3,2-dioxaborolan-2-yl)-1H-pyrazole (intermediate 12) (270 mg, 0.851 mmol) using sodium carbonate (220 mg, 2.12 mmol) and Pd(PPh$_3$)$_2$Cl$_2$ (25 mg, 0.035 mmol) in acetonitrile/water (10/2.5 ml) to afford 300 mg (78.5% yield) of the pure product after column purification using 40% ethyl acetate in hexane as eluent. MS: m/z=539.2 (M+1).

Step-ii: tert-butyl 4-(2-fluoro-4-(3-(1-(3-fluorobenzyl)-3-methyl-1H-pyrazol-4-yl)-1-tosyl-1H-pyrrolo[2,3-b]pyridin-5-yl)phenyl)-5,6-dihydropyridine-1(2H)-carboxylate Using similar reaction conditions as described in step-i of example-1, 5-bromo-3-(1-(3-fluorobenzyl)-3-methyl-1H-pyrazol-4-yl)-1-tosyl-1H-pyrrolo[2,3-b]pyridine (300 mg, 0.55 mmol) was coupled with tert-butyl 4-(2-fluoro-4-(4,4,5,5-tetramethyl-1,3,2-dioxaborolan-2-yl)phenyl)-5,6-dihydropyridine-1(2H)-carboxylate (intermediate 70) (270 mg, 0.66 mmol) using sodium carbonate (175 mg, 1.65 mmol) and Pd(PPh$_3$)$_2$Cl$_2$ (20 mg, 0.027 mmol) in DME/water (10/2.5 ml) to afford 250 mg (61.2% yield) of the pure product after column purification using 50% ethyl acetate in hexane as eluent. MS: m/z=736.4 (M+1).

Step-iii: tert-butyl 4-(2-fluoro-4-(3-(1-(3-fluorobenzyl)-3-methyl-1H-pyrazol-4-yl)-1-tosyl-1H-pyrrolo[2,3-b]pyridin-5-yl)phenyl)piperidine-1-carboxylate Using similar reaction conditions as described in step-ii of example-82, tert-butyl 4-(2-fluoro-4-(3-(1-(3-fluorobenzyl)-3-methyl-1H-pyrazol-4-yl)-1-tosyl-1H-pyrrolo[2,3-b]pyridin-5-yl)phenyl)-5,6-dihydropyridine-1(2H)-carboxylate (250 mg, 0.34 mmol) was reduced with palladium hydroxide (250 mg) in ethyl acetate/ethanol 10/10 mL to afford 200 mg (80.0% yield) of the titled compound. MS: m/z=738.6 (M+1).

Step-iv: tert-butyl 4-(2-fluoro-4-(3-(1-(3-fluorobenzyl)-3-methyl-1H-pyrazol-4-yl)-1H-pyrrolo[2,3-b]pyridin-5-yl)phenyl)piperidine-1-carboxylate Using similar reaction conditions as described in step-iii of example-1, tert-butyl 4-(2-fluoro-4-(3-(1-(3-fluorobenzyl)-3-methyl-1H-pyrazol-4-yl)-1-tosyl-1H-pyrrolo[2,3-b]pyridin-5-yl)phenyl)piperidine-1-carboxylate (200 mg, 0.271 mmol) was hydrolyzed by lithium hydroxide (57 mg, 1.356 mmol) in THF/methanol/water (5/4/1 ml) to yield 140 mg (88.6% yield) of the titled compound. MS: m/z=584.5 (M+1).

Step-v: 5-(3-fluoro-4-(piperidin-4-yl)phenyl)-3-(1-(3-fluorobenzyl)-3-methyl-1H-pyrazol-4-yl)-1H-pyrrolo[2,3-b]pyridine Using similar reaction conditions as described in step-ii of example-7, tert-butyl 4-(2-fluoro-4-(3-(1-(3-fluorobenzyl)-3-methyl-1H-pyrazol-4-yl)-1H-pyrrolo[2,3-b]pyridin-5-yl)phenyl)piperidine-1-carboxylate (140 mg, 0.239 mmol) was deprotected in TFA/DCM (5/1 mL) to afford 25 mg (17.48% yield) of the titled compound after purification by preparative HPLC along with one more isomer $^1$H NMR (CD$_3$OD, 300 MHz): δ 8.70-8.60 (bs, 1H), 8.59 (s, 1H), 8.20 (s, 1H), 7.70 (s, 1H), 7.60-7.30 (m, 4H), 7.20-6.95 (m, 3H), 5.37 (s, 2H), 3.60-3.50 (m, 2H), 3.30-3.10 (m, 3H), 2.40 (s, 3H), 2.15-2.00 (m, 4H). MS: m/z=484.4 (M+1), HPLC: 98.76% in method B.

Example 166

5-(3-fluoro-4-(piperidin-4-yl)phenyl)-3-(1-(3-fluorobenzyl)-3-methyl-1H-pyrazol-4-yl)-1H-pyrrolo[2,3-b]pyridine

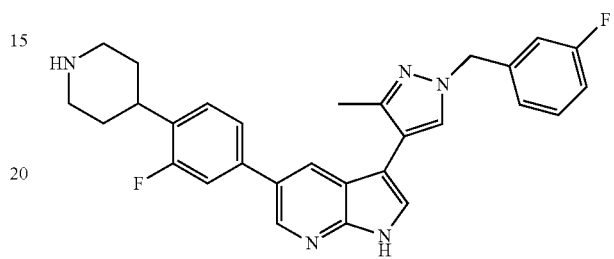

Yield 18 mg (12.58%). $^1$H NMR (CD$_3$OD, 300 MHz): δ 8.70-8.60 (bs, 1H), 8.60 (s, 1H), 7.85 (s, 1H), 7.60-7.30 (m, 4H), 7.05-7.00 (m, 2H), 6.95-6.90 (dd, 1H), 5.46 (s, 2H), 3.60-3.50 (m, 2H), 3.30-3.10 (m, 3H), 2.35 (s, 3H), 2.15-2.00 (m, 4H). MS: m/z=484.4 (M+1), HPLC: 94.72% in method B.

Example 167

5-(3-fluoro-4-(piperidin-4-yl)phenyl)-3-(1-phenethyl-1H-pyrazol-4-yl)-1H-pyrrolo[2,3-b]pyridine

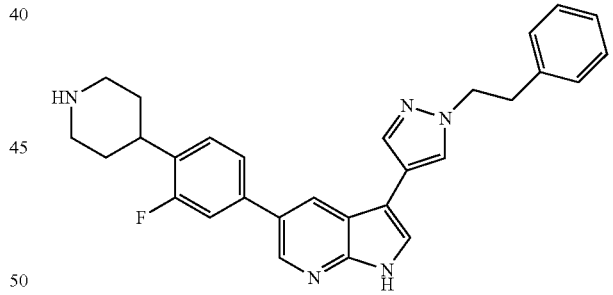

Step-i: tert-butyl 4-(2-fluoro-4-(3-(1-phenethyl-1H-pyrazol-4-yl)-1-tosyl-1H-pyrrolo[2,3-b]pyridin-5-yl)phenyl)-5,6-dihydropyridine-1(2H)-carboxylate Using similar reaction conditions as described in step-i of example-1, tert-butyl 4-(2-fluoro-4-(3-iodo-1-tosyl-1H-pyrrolo[2,3-b]pyridin-5-yl)phenyl)-5,6-dihydropyridine-1(2H)-carboxylate (intermediate 66Q) (170 mg, 0.253 mmol) was coupled with 1-phenethyl-4-(4,4,5,5-tetramethyl-1,3,2-dioxaborolan-2-yl)-1H-pyrazole (intermediate 59) (151 mg, 0.506 mmol) using Pd(dppf)Cl$_2$ (10 mg, 0.012 mol) and sodium carbonate (161 mg, 0.759 mmol) in toluene/ethanol/water (20/10/5 ml) to afford 171 mg (94% yield) of the titled. MS: m/z=718.3 (M+1).

Step-ii: tert-butyl 4-(2-fluoro-4-(3-(1-phenethyl-1H-pyrazol-4-yl)-1-tosyl-1H-pyrrolo[2,3-b]pyridin-5-yl)phenyl)piperidine-1-carboxylate Using similar reaction conditions as described in step-ii of example-82, tert-butyl 4-(2-fluoro-4-(3-(1-phenethyl-1H-pyrazol-4-yl)-1-tosyl-1H-pyrrolo[2,3-b]pyridin-5-yl)phenyl)-5,6-dihydropyridine-1(2H)-carboxylate (190 mg, 0.264 mmol) was reduced with palladium hydroxide (100 mg) in ethyl acetate/ethanol 10/20 mL to afford 141 mg (74% yield) of the titled compound. MS: m/z=720.7 (M+1).

Step-iii: tert-butyl 4-(2-fluoro-4-(3-(1-phenethyl-1H-pyrazol-4-yl)-1H-pyrrolo[2,3-b]pyridin-5-yl)phenyl)piperidine-1-carboxylate Using similar reaction conditions as described in step-iii of example-1, tert-butyl 4-(2-fluoro-4-(3-(1-phenethyl-1H-pyrazol-4-yl)-1-tosyl-1H-pyrrolo[2,3-b]pyridin-5-yl)phenyl)piperidine-1-carboxylate (140 mg, 0.194 mmol) was hydrolyzed by sodium hydroxide (78 mg, 1.947 mmol) in THF/methanol/water (12/4/3 mL) to yield 83 mg (75% yield) of the titled compound. MS: m/z=566.3 (M+1).

Step-iv: 5-(3-fluoro-4-(piperidin-4-yl)phenyl)-3-(1-phenethyl-1H-pyrazol-4-yl)-1H-pyrrolo[2,3-b]pyridine Using similar reaction conditions as described in step-ii of example-7, tert-butyl 4-(2-fluoro-4-(3-(1-phenethyl-1H-pyrazol-4-yl)-1H-pyrrolo[2,3-b]pyridin-5-yl)phenyl)piperidine-1-carboxylate (82 mg, 0.145 mmol) was deprotected in methanol/HCl in dioxane (5/5 mL) to afford 8.2 mg (12.2% yield) of the titled compound after purification by preparative TLC using 8% methanol in chloroform as eluent. $^1$H NMR (CD$_3$OD, 300 MHz): δ 8.448-8.442 (d, 1H), 8.098-8.091 (d, 1H), 7.839-7.837 (d, 1H), 7.73 (s, 1H), 7.54 (s, 1H), 7.48-7.38 (m, 3H), 7.26-7.12 (m, 5H), 7.44-7.41 (t, 2H), 3.37-3.31 (m, 1H), 3.19-3.15 (t, 3H), 3.03-2.93 (td, 2H), 1.97-1.88 (m, 5H). MS: m/z=466.5 (M+1), HPLC: 98.63% in method A.

Example 168

5-(3-fluoro-4-(piperidin-4-yl)phenyl)-3-(1-phenethyl-1H-pyrazol-3-yl)-1H-pyrrolo[2,3-b]pyridine

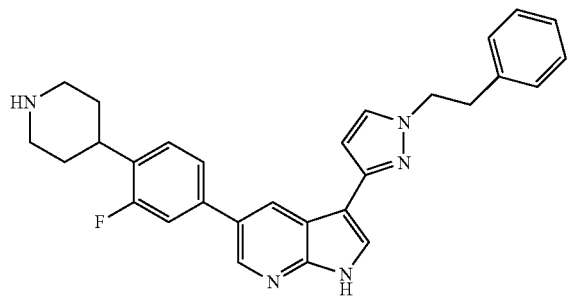 [SMILES: Fc1cc(-c2cnc3[nH]cc(-c4ccn(CCc5ccccc5)n4)c3c2)ccc1C1CCNCC1]

Step-i: tert-butyl 4-(2-fluoro-4-(3-(1-phenethyl-1H-pyrazol-3-yl)-1-tosyl-1H-pyrrolo[2,3-b]pyridin-5-yl)phenyl)-5,6-dihydropyridine-1(2H)-carboxylate Using similar reaction conditions as described in step-i of example-1, 5-bromo-3-(1-phenethyl-1H-pyrazol-3-yl)-1-tosyl-1H-pyrrolo[2,3-b]pyridine (intermediate 63A) (160 mg, 0.307 mmol) was coupled with tert-butyl 4-(2-fluoro-4-(4,4,5,5-tetramethyl-1,3,2-dioxaborolan-2-yl)phenyl)-5,6-dihydropyridine-1(2H)-carboxylate (intermediate 70) (307 mg, 0.769 mmol) using potassium phosphate (195 mg, 0.918 mmol), tricyclohexyl phosphine (13 mg, 0.046 mmol) and Pd$_2$(dba)$_3$ (28 mg, 0.030 mmol) in dioxane/water (15/3 ml) to afford 126 mg (57.2% yield) of the pure product after column purification using 35% ethyl acetate in hexane as eluent. MS: m/z=718.3 (M+1).

Step-ii: tert-butyl 4-(2-fluoro-4-(3-(1-phenethyl-1H-pyrazol-3-yl)-1-tosyl-1H-pyrrolo[2,3-b]pyridin-5-yl)phenyl)piperidine-1-carboxylate Using similar reaction conditions as described in step-ii of example-82, tert-butyl 4-(2-fluoro-4-(3-(1-phenethyl-1H-pyrazol-3-yl)-1-tosyl-1H-pyrrolo[2,3-b]pyridin-5-yl)phenyl)-5,6-dihydropyridine-1(2H)-carboxylate (125 mg, 0.174 mmol) was reduced with palladium hydroxide (90 mg) in ethyl acetate/ethanol 10/20 mL to afford 103 mg (81.6% yield) of the titled compound. MS: m/z=720.7 (M+1).

Step-iii: tert-butyl 4-(2-fluoro-4-(3-(1-phenethyl-1H-pyrazol-3-yl)-1H-pyrrolo[2,3-b]pyridin-5-yl)phenyl)piperidine-1-carboxylate Using similar reaction conditions as described in step-iii of example-1, tert-butyl 4-(2-fluoro-4-(3-(1-phenethyl-1H-pyrazol-3-yl)-1-tosyl-1H-pyrrolo[2,3-b]pyridin-5-yl)phenyl)piperidine-1-carboxylate (102 mg, 0.141 mmol) was hydrolyzed by sodium hydroxide (57 mg, 1.418 mmol) in THF/methanol/water (12/4/4 ml) to yield 67 mg (84% yield) of the titled compound. MS: m/z=566.5 (M+1).

Step-iv: 5-(3-fluoro-4-(piperidin-4-yl)phenyl)-3-(1-phenethyl-1H-pyrazol-3-yl)-1H-pyrrolo[2,3-b]pyridine Using similar reaction conditions as described in step-ii of example-7, tert-butyl 4-(2-fluoro-4-(3-(1-phenethyl-1H-pyrazol-3-yl)-1H-pyrrolo[2,3-b]pyridin-5-yl)phenyl)piperidine-1-carboxylate (66 mg, 0.116 mmol) was deprotected in TFA/toluene (5/5 mL) to afford 23 mg (34% yield) of the titled compound. $^1$H NMR (CD$_3$OD, 300 MHz): δ 8.82-8.81 (d, 1H), 8.58 (s, 1H), 7.87 (s, 1H), 7.58-7.45 (m, 4H), 7.23-7.11 (m, 5H), 6.577-6.570 (d, 1H), 4.48-4.44 (t, 2H), 3.56-3.52 (d, 2H), 3.24-3.15 (m, 5H), 2.15-2.03 (m, 4H). MS: m/z=466.5 (M+1), HPLC: 96.98% in method A.

Example 169

3-(1-(3,5-difluorobenzyl)-1H-pyrazol-4-yl)-5-(3-fluoro-4-(piperidin-4-yl)phenyl)-1H-pyrrolo[2,3-b]pyridine

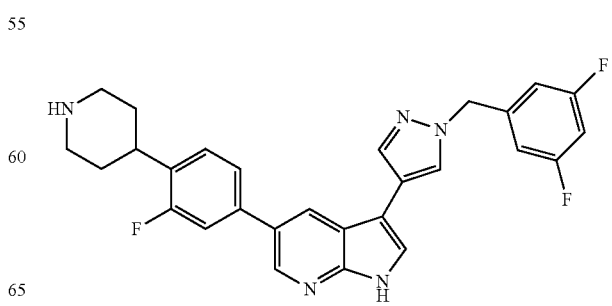

Step-i: tert-butyl 4-(4-(3-(1-(3,5-difluorobenzyl)-1H-pyrazol-4-yl)-1-tosyl-1H-pyrrolo[2,3-b]pyridin-5-yl)-2-fluorophenyl)-5,6-dihydropyridine-1(2H)-carboxylate Using similar reaction conditions as described in step-i of example-1, 5-bromo-3-(1-(3,5-difluorobenzyl)-1H-pyrazol-4-yl)-1-tosyl-1H-pyrrolo[2,3-b]pyridine (step 1 product of example 71) (200 mg, 0.368 mmol) was coupled with tert-butyl 4-(2-fluoro-4-(4,4,5,5-tetramethyl-1,3,2-dioxaborolan-2-yl)phenyl)-5,6-dihydropyridine-1(2H)-carboxylate (intermediate 70) (296 mg, 0.736 mmol) using potassium phosphate (234 mg, 1.104 mmol), tricyclohexyl phosphine (15 mg, 0.055 mmol) and $Pd_2(dba)_3$ (34 mg, 0.036 mmol) in dioxane/water (15/3 ml) to afford 104 mg (38.3% yield) of the pure product after column purification using 35% ethyl acetate in hexane as eluent. MS: m/z=740.7 (M+1).

Step-ii: tert-butyl 4-(4-(3-(1-(3,5-difluorobenzyl)-1H-pyrazol-4-yl)-1-tosyl-1H-pyrrolo[2,3-b]pyridin-5-yl)-2-fluorophenyl)piperidine-1-carboxylate Using similar reaction conditions as described in step-ii of example-82, tert-butyl 4-(4-(3-(1-(3,5-difluorobenzyl)-1H-pyrazol-4-yl)-1-tosyl-1H-pyrrolo[2,3-b]pyridin-5-yl)-2-fluorophenyl)-5,6-di hydropyridine-1(2H)-carboxylate (103 mg, 0.139 mmol) was reduced with palladium hydroxide (50 mg) in ethyl acetate/ethanol 5/15 mL to afford 102 mg (99% yield) of the titled compound. MS: m/z=742.6 (M+1).

Step-iii: tert-butyl 4-(4-(3-(1-(3,5-difluorobenzyl)-1H-pyrazol-4-yl)-1H-pyrrolo[2,3-b]pyridin-5-yl)-2-fluorophenyl)piperidine-1-carboxylate Using similar reaction conditions as described in step-iii of example-1, tert-butyl 4-(4-(3-(1-(3,5-difluorobenzyl)-1H-pyrazol-4-yl)-1-tosyl-1H-pyrrolo[2,3-b]pyridin-5-yl)-2-fluorophenyl)piperidine-1-carboxylate (101 mg, 0.136 mmol) was hydrolyzed by lithium hydroxide (57 mg, 1.363 mmol) in THF/methanol/water (12/4/4 ml) to yield 65 mg (81% yield) of the titled compound. MS: m/z=588.4 (M+1).

Step-iv: 3-(1-(3,5-difluorobenzyl)-1H-pyrazol-4-yl)-5-(3-fluoro-4-(piperidin-4-yl)phenyl)-1H-pyrrolo[2,3-b]pyridine Using similar reaction conditions as described in step-ii of example-7, tert-butyl 4-(4-(3-(1-(3,5-difluorobenzyl)-1H-pyrazol-4-yl)-1H-pyrrolo[2,3-b]pyridin-5-yl)-2-fluorophenyl)piperidine-1-carboxylate (64 mg, 0.109 mmol) was deprotected in TFA/toluene (5/5 mL) to afford 14.9 mg (28.3% yield) of the titled compound after purification by preparative TLC using 6% methanol in chloroform as eluent. $^1$H NMR (CD$_3$OD, 300 MHz): δ 8.48-8.47 (d, 1H), 8.38-8.37 (d, 1H), 8.25 (s, 1H), 7.96 (s, 1H), 7.66 (s, 1H), 7.53-7.39 (m, 3H), 6.92-6.86 (m, 3H), 5.44 (s, 2H), 3.24-3.20 (d, 2H), 3.09-3.07 (m, 1H), 2.87-2.80 (td, 2H), 1.89-1.77 (m, 4H). MS: m/z=488.3 (M+1), HPLC: 95.30% in method A.

Example 170

5-(3-fluoro-4-(1-methylpiperidin-4-yl)phenyl)-3-(1-(3-fluorobenzyl)-1H-pyrazol-4-yl)-1H-pyrrolo[2,3-b]pyridine

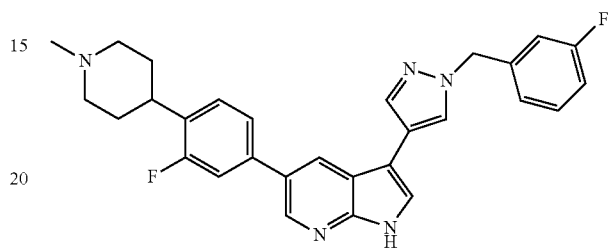

Step-i: 5-(3-fluoro-4-(piperidin-4-yl)phenyl)-3-(1-(3-fluorobenzyl)-1H-pyrazol-4-yl)-1-tosyl-1H-pyrrolo[2,3-b]pyridine Using similar reaction conditions as described in step-ii of example-7, tert-butyl 4-(2-fluoro-4-(3-(1-(3-fluorobenzyl)-1H-pyrazol-4-yl)-1-tosyl-1H-pyrrolo[2,3-b]pyridin-5-yl)phenyl)piperidine-1-carboxylate (product of step 1 of example 84) (130 mg, 0.179 mmol) was deprotected in methanol/HCl in dioxane (5/5 mL) to afford 110 mg (98.2% yield) of the titled compound. MS: m/z=624.4 (M+1).

Step-ii: 5-(3-fluoro-4-(piperidin-4-yl)phenyl)-3-(1-(3-fluorobenzyl)-1H-pyrazol-4-yl)-1-tosyl-1H-pyrrolo[2,3-b]pyridine Using similar reaction conditions as described in step-iii of example-133, tert-butyl 4-(2-fluoro-4-(3-(1-(3-fluorobenzyl)-1H-pyrazol-4-yl)-1-tosyl-1H-pyrrolo[2,3-b]pyridin-5-yl)phenyl) piperidine-1-carboxylate (109 mg, 0.175 mmol) was methylated using paraformaldehyde (16 mg, 0.524 mmol), Na(OAc)$_3$BH (111 mg, 0.524 mmol) and 3 drops of acetic acid in dichloroethane (10 mL) to afford 89 mg (80% yield) of the titled compound. MS: m/z=638.4 (M+1).

Step-iii: 5-(3-fluoro-4-(1-methylpiperidin-4-yl)phenyl)-3-(1-(3-fluorobenzyl)-1H-pyrazol-4-yl)-1-tosyl-1H-pyrrolo[2,3-b]pyridine Using similar reaction conditions as described in step-iii of example-1, 5-(3-fluoro-4-(piperidin-4-yl)phenyl)-3-(1-(3-fluorobenzyl)-1H-pyrazol-4-yl)-1-tosyl-1H-pyrrolo[2,3-b]pyridine (88 mg, 0.138 mmol) was hydrolyzed with lithium hydroxide (58 mg, 1.381 mmol) in THF/methanol/water (12/4/4 mL) to yield 17 mg (20.7% yield) of the titled compound. $^1$H NMR (CD$_3$OD, 300 MHz): δ 8.68-8.67 (d, 1H), 8.60 (s, 1H), 8.29 (s, 1H), 7.98 (s, 1H), 7.79 (s, 1H), 7.60-7.30 (m, 4H), 7.13-7.00 (m, 3H), 5.44 (s, 2H), 3.70-3.50 (m, 2H), 3.30-3.10 (m, 3H), 2.93 (s, 3H), 2.16-2.02 (m, 4H). MS: m/z=484.4 (M+1), HPLC: 97.49% in method A.

Example 171

5-(4-(piperidin-4-yl)phenyl)-3-(1-(pyridin-4-ylmethyl)-1H-pyrazol-4-yl)-1H-pyrrolo[2,3-b]pyridine

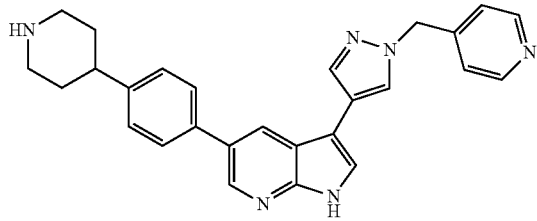 [SMILES: c1cc(Cn2cc(-c3c[nH]c4ncc(-c5ccc(C6CCNCC6)cc5)cc34)cn2)ccn1]

Step-i: tert-butyl 4-(4-(3-(1-(pyridin-4-ylmethyl)-1H-pyrazol-4-yl)-1-tosyl-1H-pyrrolo[2,3-b]pyridin-5-yl)phenyl)piperidine-1-carboxylate Using similar reaction conditions as described in step-ii of example-1, tert-butyl 4-(4-(3-iodo-1-tosyl-1H-pyrrolo[2,3-b]pyridin-5-yl)phenyl)piperidine-1-carboxylate (Intermediate 67B) (150 mg, 0.52 mmol) was coupled with 4-((4-(4,4,5,5-tetramethyl-1,3,2-dioxaborolan-2-yl)-1H-pyrazol-1-yl)methyl)pyridine (intermediate 64G) (180 mg, 0.63 mmol) using sodium carbonate (165 mg, 1.56 mmol) and Pd(dppf)Cl$_2$ (18 mg, 0.026 mmol) in toluene/ethanol/water (10/10/2 mL) to afford 142 mg (crude) of the titled compound. MS: m/z=589.4 (M-Boc+1).

Step-ii: tert-butyl 4-(4-(3-(1-(pyridin-4-ylmethyl)-1H-pyrazol-4-yl)-1H-pyrrolo[2,3-b]pyridin-5-yl)phenyl)piperidine-1-carboxylate Using similar reaction conditions as described in step-iii of example-1, tert-butyl 4-(4-(3-(1-(pyridin-4-ylmethyl)-1H-pyrazol-4-yl)-1-tosyl-1H-pyrrolo[2,3-b]pyridin-5-yl)phenyl)piperidine-1-carboxylate (142 mg, 0.206 mmol) was hydrolyzed with lithium hydroxide (43 mg, 1.030 mmol) in THF/methanol/water (4/4/2 mL) to yield 120 mg (99.6% yield). MS: m/z=535.3 (M+1).

Step-iii: 5-(4-(piperidin-4-yl)phenyl)-3-(1-(pyridin-4-ylmethyl)-1H-pyrazol-4-yl)-1H-pyrrolo[2,3-b]pyridine Using similar reaction conditions as described in step-ii of example-7, tert-butyl 4-(4-(3-(1-(pyridin-4-ylmethyl)-1H-pyrazol-4-yl)-1H-pyrrolo[2,3-b]pyridin-5-yl)phenyl)piperidine-1-carboxylate (120 mg, 0.224 mmol) was deprotected in TFA/DCM (5/5 ml) to afford 14 mg (14.3% yield) of the titled compound. $^1$H NMR (CD$_3$OD, 300 MHz): δ 8.78-8.76 (d, 2H), 8.53-8.51 (t, 2H), 8.35 (s, 1H), 8.07 (s, 1H), 7.75-7.70 (m, 5H), 7.43-7.41 (d, 2H), 5.78 (s, 2H), 3.55-3.51 (d, 2H), 3.21-3.13 (td, 2H), 3.03-2.95 (m, 1H), 2.03-1.90 (m, 2H). MS: m/z=435.6 (M+1), HPLC: 99.16% in method A.

Example 172

5-(3-fluoro-4-(piperazin-1-yl)phenyl)-3-(1-(3-fluorobenzyl)-1H-pyrazol-4-yl)-1H-pyrrolo[2,3-b]pyridine

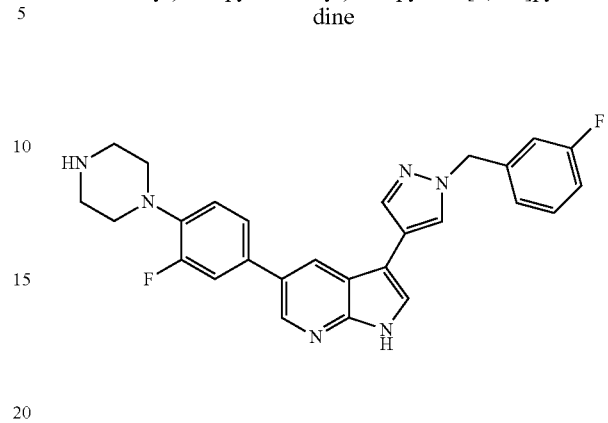

Step-i: tert-butyl 4-(2-fluoro-4-(3-(1-(3-fluorobenzyl)-1H-pyrazol-4-yl)-1H-pyrrolo[2,3-b]pyridin-5-yl)phenyl)piperazine-1-carboxylate Using similar reaction conditions as described in step-iii of example-1, tert-butyl 4-(2-fluoro-4-(3-(1-(3-fluorobenzyl)-1H-pyrazol-4-yl)-1-tosyl-1H-pyrrolo[2,3-b]pyridin-5-yl)phenyl)piperazine-1-carboxylate (product of step 1 of example 114) (120 mg, 0.165 mmol) was hydrolyzed with lithium hydroxide (35 mg, 0.827 mmol) in THF/methanol/water (5/5/2 mL) to afford 80 mg (85% yield) of the titled compound. MS: m/z=571.6 (M+1).

Step-ii: 5-(3-fluoro-4-(piperazin-1-yl)phenyl)-3-(1-(3-fluorobenzyl)-1H-pyrazol-4-yl)-1H-pyrrolo[2,3-b]pyridine Using similar reaction conditions as described in step-ii of example-7, tert-butyl 4-(2-fluoro-4-(3-(1-(3-fluorobenzyl)-1H-pyrazol-4-yl)-1H-pyrrolo[2,3-b]pyridin-5-yl)phenyl)piperazine-1-carboxylate (80 mg, 0.140 mmol) was deprotected in TFA/DCM (5/5 ml) to afford 12 mg (93% yield) of the titled compound. $^1$H NMR (CD$_3$OD, 300 MHz): δ 8.54 (s, 2H), 8.262-8.260 (d, 1H), 7.975-7.973 (d, 1H), 7.74 (s, 1H), 7.59-7.52 (m, 2H), 7.38-7.00 (m, 5H), 5.44 (s, 2H), 3.42-3.40 (m, 8H). MS: m/z=471.2 (M+1), HPLC: 97.06% in method B.

Example 173

5-(5-fluoro-6-(piperazin-1-yl)pyridin-3-yl)-3-(1-(3-fluorobenzyl)-1H-pyrazol-4-yl)-1H-pyrrolo[2,3-b]pyridine

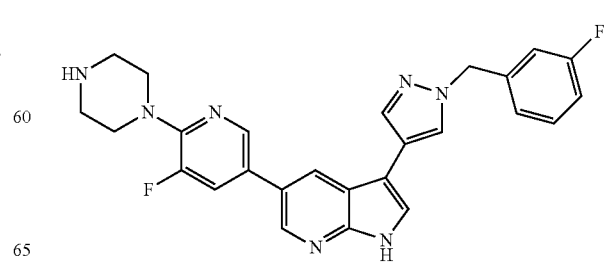

Step-i: tert-butyl 4-(3-fluoro-5-(3-(1-(3-fluorobenzyl)-1H-pyrazol-4-yl)-1-tosyl-1H-pyrrolo[2,3-b]pyridin-5-yl)pyridin-2-yl)piperazine-1-carboxylate Using similar reaction conditions as described in step-ii of example-1, tert-butyl 4-(3-fluoro-5-(3-iodo-1-tosyl-1H-pyrrolo[2,3-b]pyridin-5-yl)pyridin-2-yl)piperazine-1-carboxylate (Intermediate 66R) (170 mg, 0.251 mmol) was coupled with 1-(3-fluorobenzyl)-4-(4,4,5,5-tetramethyl-1,3,2-dioxaborolan-2-yl)-1H-pyrazole (intermediate 11) (113 mg, 0.376 mmol) using sodium carbonate (80 mg, 0.753 mmol) and Pd(dppf)Cl$_2$ (9.7 mg, 0.012 mmol) in toluene/ethanol/water (20/10/4 mL) to afford 160 mg (88% yield) of the titled compound after purification by column (Silica gel 60/120) using 37% ethyl acetate in hexane as eluent. MS: m/z=726.3 (M+1).

Step-ii: tert-butyl 4-(3-fluoro-5-(3-(1-(3-fluorobenzyl)-1H-pyrazol-4-yl)-1H-pyrrolo[2,3-b]pyridin-5-yl)pyridin-2-yl)piperazine-1-carboxylate Using similar reaction conditions as described in step-iii of example-1, tert-butyl 4-(3-fluoro-5-(3-(1-(3-fluorobenzyl)-1H-pyrazol-4-yl)-1-tosyl-1H-pyrrolo[2,3-b]pyridin-5-yl)pyridin-2-yl) piperazine-1-carboxylate (100 mg, 0.220 mmol) was hydrolyzed with lithium hydroxide (93 mg, 2.20 mmol) in THF/methanol/water (16/4/6 mL) to yield 125 mg (99% yield). MS: m/z=572.2 (M+1).

Step-iii: 5-(5-fluoro-6-(piperazin-1-yl)pyridin-3-yl)-3-(1-(3-fluorobenzyl)-1H-pyrazol-4-yl)-1H-pyrrolo[2,3-b]pyridine Using similar reaction conditions as described in step-ii of example-7, tert-butyl 4-(3-fluoro-5-(3-(1-(3-fluorobenzyl)-1H-pyrazol-4-yl)-1H-pyrrolo[2,3-b]pyridin-5-yl)pyridin-2-yl)piperazine-1-carboxylate (125 mg, 0.218 mmol) was deprotected in methanol/HCl in ether (5/2.5 ml) to afford 72 mg (56.2% yield) of the titled compound after purification by prep HPLC. $^1$H NMR (CD$_3$OD, 300 MHz): δ 8.646-8.640 (d, 1H), 8.56 (s, 1H), 8.419-8.415 (d, 1H), 8.28 (s, 1H), 7.97 (s, 1H), 7.94-7.93 (d, 1H), 7.77 (s, 1H), 7.36-7.33 (m, 1H), 7.11-6.98 (m, 3H), 5.42 (s, 2H), 3.80-3.77 (m, 4H), 3.40-3.31 (m, 4H). MS: m/z=472.3 (M+1), HPLC: 98.87% in method A.

Example 174

3-(1-(3-fluorobenzyl)-1H-pyrazol-4-yl)-5-(5-methoxy-6-(piperazin-1-yl)pyridin-3-yl)-1H-pyrrolo[2,3-b]pyridine

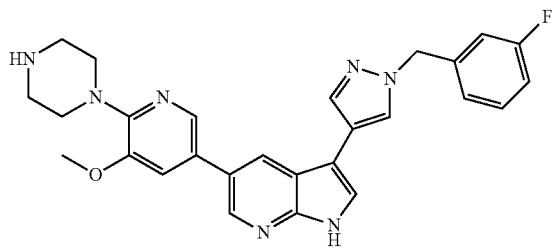 [SMILES: COc1cc(-c2cnc3[nH]cc(-c4cnn(Cc5cccc(F)c5)c4)c3c2)cnc1N1CCNCC1]

Step-i: tert-butyl 4-(5-(3-(1-(3-fluorobenzyl)-1H-pyrazol-4-yl)-1-tosyl-1H-pyrrolo[2,3-b]pyridin-5-yl)-3-methoxypyridin-2-yl)piperazine-1-carboxylate Using similar reaction conditions as described in step-ii of example-1, tert-butyl 4-(5-(3-iodo-1-tosyl-1H-pyrrolo[2,3-b]pyridin-5-yl)-3-methoxypyridin-2-yl)piperazine-1-carboxylate (Intermediate 66S) (175 mg, 0.254 mmol) was coupled with 1-(3-fluorobenzyl)-4-(4,4,5,5-tetramethyl-1,3,2-dioxaborolan-2-yl)-1H-pyrazole (intermediate 11) (115 mg, 0.380 mmol) using sodium carbonate (81 mg, 0.764 mmol) and Pd(dppf)Cl$_2$ (9.4 mg, 0.012 mmol) in toluene/ethanol/water (20/10/4 mL) to afford 131 mg (70% yield) of the titled compound after purification by column (Silica gel 60/120) using 37% ethyl acetate in hexane as eluent.

Step-ii: tert-butyl 4-(5-(3-(1-(3-fluorobenzyl)-1H-pyrazol-4-yl)-1H-pyrrolo[2,3-b]pyridin-5-yl)-3-methoxypyridin-2-yl)piperazine-1-carboxylate Using similar reaction conditions as described in step-iii of example-1, tert-butyl 4-(5-(3-(1-(3-fluorobenzyl)-1H-pyrazol-4-yl)-1-tosyl-1H-pyrrolo[2,3-b]pyridin-5-yl)-3-methoxypyridin-2-yl) piperazine-1-carboxylate (130 mg, 0.176 mmol) was hydrolyzed with lithium hydroxide (75 g, 1.763 mmol) in THF/methanol/water (16/4/6 mL) to yield 92 mg (90% yield). MS: m/z=584.00 (M+1).

Step-iii: 3-(1-(3-fluorobenzyl)-1H-pyrazol-4-yl)-5-(5-methoxy-6-(piperazin-1-yl)pyridin-3-yl)-1H-pyrrolo[2,3-b]pyridine Using similar reaction conditions as described in step-ii of example-7, tert-butyl 4-(5-(3-(1-(3-fluorobenzyl)-1H-pyrazol-4-yl)-1H-pyrrolo[2,3-b]pyridin-5-yl)-3-methoxypyridin-2-yl)piperazine-1-carboxylate (91 mg, 0.156 mmol) was deprotected in methanol/HCl in dioxane (5/5 ml) to afford 52 mg (56% yield) of the titled compound. $^1$H NMR (CD$_3$OD, 300 MHz): δ 8.727-8.722 (d, 1H), 8.626-8.622 (d, 1H), 8.29 (s, 1H), 8.19-8.18 (d, 1H), 8.00 (s, 1H), 7.81 (s, 1H), 7.75-7.74 (d, 1H), 7.37-7.35 (q, 1H), 7.12-7.10 (d, 1H), 7.02-6.99 (m, 2H), 5.44 (s, 2H), 4.03 (s, 3H), 3.78-3.74 (t, 4H), 3.39-3.32 (m, 4H). MS: m/z=484.3 (M+1), HPLC: 97.58% in method A.

Example 175

5-(3-fluoro-4-(piperidin-4-yl)phenyl)-3-(1-(3-fluorobenzyl)-3,5-dimethyl-1H-pyrazol-4-yl)-1H-pyrrolo[2,3-b]pyridine

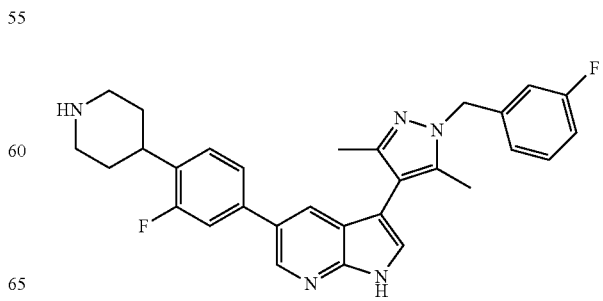

Step-i: tert-butyl 4-(2-fluoro-4-(3-(1-(3-fluorobenzyl)-3,5-dimethyl-1H-pyrazol-4-yl)-1-tosyl-1H-pyrrolo[2,3-b]pyridin-5-yl)phenyl)-5,6-dihydropyridine-1(2H)-carboxylate Using similar reaction conditions as described in step-i of example-1, tert-butyl 4-(2-fluoro-4-(3-iodo-1-tosyl-1H-pyrrolo[2,3-b]pyridin-5-yl)phenyl)-5,6-dihydropyridine-1(2H)-carboxylate (intermediate 66Q) (300 mg, 0.445 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (177 mg, 0.534 mmol) using Pd(dppf)Cl$_2$ (16 mg, 0.022 mol) and sodium carbonate (141 mg, 1.335 mmol) in toluene/ethanol/water (5/8/1 mL) to afford 250 mg (74.8% yield) of the titled compound. MS: m/z=750.4 (M+1).

Step-ii: tert-butyl 4-(2-fluoro-4-(3-(1-(3-fluorobenzyl)-3,5-dimethyl-1H-pyrazol-4-yl)-1-tosyl-1H-pyrrolo[2,3-b]pyridin-5-yl)phenyl)piperidine-1-carboxylate Using similar reaction conditions as described in step-ii of example-82, tert-butyl 4-(2-fluoro-4-(3-(1-(3-fluorobenzyl)-3,5-dimethyl-1H-pyrazol-4-yl)-1-tosyl-1H-pyrrolo[2,3-b]pyridin-5-yl)phenyl)-5,6-dihydropyridine-1(2H)-carboxylate (250 mg, 0.333 mmol) was reduced with palladium hydroxide (250 mg) in ethyl acetate/ethanol 10/10 mL to afford 200 mg (80% yield) of the titled compound. MS: m/z=752.9 (M+1).

Step-iii: tert-butyl 4-(2-fluoro-4-(3-(1-(3-fluorobenzyl)-3,5-dimethyl-1H-pyrazol-4-yl)-1H-pyrrolo[2,3-b]pyridin-5-yl)phenyl)piperidine-1-carboxylate Using similar reaction conditions as described in step-iii of example-1, tert-butyl 4-(2-fluoro-4-(3-(1-(3-fluorobenzyl)-3,5-dimethyl-1H-pyrazol-4-yl)-1-tosyl-1H-pyrrolo[2,3-b]pyridin-5-yl)phenyl)piperidine-1-carboxylate (200 mg, 0.265 mmol) was hydrolyzed by lithium hydroxide (56 mg, 1.329 mmol) in THF/methanol/water (5/3/1 mL) to yield 110 mg (69.6% yield) of the titled compound. MS: m/z=598.5 (M+1).

Step-iv: 5-(3-fluoro-4-(piperidin-4-yl)phenyl)-3-(1-(3-fluorobenzyl)-3,5-dimethyl-1H-pyrazol-4-yl)-1H-pyrrolo[2,3-b]pyridine Using similar reaction conditions as described in step-ii of example-7, tert-butyl 4-(2-fluoro-4-(3-(1-(3-fluorobenzyl)-3,5-dimethyl-1H-pyrazol-4-yl)-1H-pyrrolo[2,3-b]pyridin-5-yl)phenyl)piperidine-1-carboxylate (110 mg, 0.184 mmol) was deprotected in TFA/DCM (3/0.5 mL) to afford 9 mg (8.1% yield) of the titled compound. $^1$H NMR (CD$_3$OD, 400 MHz): δ 8.6 (s, 1H), 8.14-8.13 (d, 1H), 7.55 (s, 1H), 7.50-7.30 (m, 4H), 7.05-6.95 (td, 2H), 6.90-6.85 (d, 1H), 5.37 (s, 2H), 3.52-3.49 (d, 2H), 3.24-3.14 (m, 3H), 2.20 (s, 3H), 2.18 (s, 3H), 2.10-1.95 (m, 4H). MS: m/z=497.8 (M+1), HPLC: 96.3% in method A.

Example 176

N-(5-(3-(1-(3,5-difluorobenzyl)-1H-pyrazol-3-yl)-1H-pyrrolo[2,3-b]pyridin-5-yl)-2-(piperidin-4-yl)phenyl)methanesulfonamide

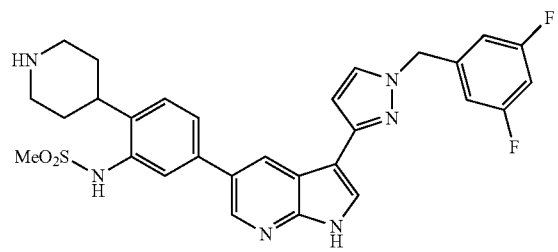 [SMILES: CS(=O)(=O)Nc1cc(-c2cnc3[nH]cc(-c4ccn(Cc5cc(F)cc(F)c5)n4)c3c2)ccc1C1CCNCC1]

Step-i: tert-butyl 4-(4-(3-(1-(3,5-difluorobenzyl)-1H-pyrazol-3-yl)-1-tosyl-1H-pyrrolo[2,3-b]pyridin-5-yl)-2-(methylsulfonamido)phenyl)-5,6-dihydropyridine-1(2H)-carboxylate Using similar reaction conditions as described in step-i of example-1, 5-bromo-3-(1-(3,5-difluorobenzyl)-1H-pyrazol-3-yl)-1-tosyl-1H-pyrrolo[2,3-b]pyridine (intermediate 63B) (200 mg, 0.368 mmol) was coupled with tert-butyl 4-(2-(methylsulfonamido)-4-(4,4,5,5-tetramethyl-1,3,2-dioxaborolan-2-yl)phenyl)-5,6-dihydropyridine-1(2H)-carboxylate (intermediate 65E) (210 mg, 0.44 mmol) using Pd(PPh$_3$)$_2$Cl$_2$ (13 mg, 0.018 mol) and sodium carbonate (117 mg, 11 mmol) in DME/water (10/1 mL) to afford 250 mg (83.3% yield) of the titled compound. MS: m/z=814.7 (M+1).

Step-ii: tert-butyl 4-(4-(3-(1-(3,5-difluorobenzyl)-1H-pyrazol-3-yl)-1-tosyl-1H-pyrrolo[2,3-b]pyridin-5-yl)-2-(methylsulfonamido)phenyl)piperidine-1-carboxylate Using similar reaction conditions as described in step-ii of example-82, tert-butyl 4-(4-(3-(1-(3,5-difluorobenzyl)-1H-pyrazol-3-yl)-1-tosyl-1H-pyrrolo[2,3-b]pyridin-5-yl)-2-(methylsulfonamido)phenyl)-5,6-dihydropyridine-1(2H)-carboxylate (250 mg, 0.307 mmol) was reduced with palladium hydroxide (250 mg) in ethyl acetate/ethanol 10/10 mL to afford 200 mg (80% yield) of the titled compound. MS: m/z=817.7 (M+1).

Step-iii: tert-butyl 4-(4-(3-(1-(3,5-difluorobenzyl)-1H-pyrazol-3-yl)-1H-pyrrolo[2,3-b]pyridin-5-yl)-2-(methylsulfonamido)phenyl)piperidine-1-carboxylate Using similar reaction conditions as described in step-iii of example-1, tert-butyl 4-(4-(3-(1-(3,5-difluorobenzyl)-1H-pyrazol-3-yl)-1-tosyl-1H-pyrrolo[2,3-b]pyridin-5-yl)-2-(methylsulfonamido)phenyl)piperidine-1-carboxylate (200 mg, 0.245 mmol) was hydrolyzed by lithium hydroxide (52 mg, 1.225 mmol) in THF/methanol/water (3/5/2 mL) to yield 110 mg (66.6% yield) of the titled compound. MS: m/z=662.8 (M+1)

Step-iv: N-(5-(3-(1-(3,5-difluorobenzyl)-1H-pyrazol-3-yl)-1H-pyrrolo[2,3-b]pyridin-5-yl)-2-(piperidin-4-yl)phenyl)methanesulfonamide Using similar reaction conditions as described in step-ii of example-7, tert-butyl 4-(4-(3-(1-(3,5-difluorobenzyl)-1H-pyrazol-3-yl)-1H-pyrrolo[2,3-b]pyridin-5-yl)-2-(methylsulfonamido)phenyl) piperidine-1-carboxylate (110 mg, 0.165 mmol) was deprotected in TFA/DCM (5/1 mL) to afford 3 mg (2.6% yield) of the titled compound. $^1$H NMR (CD$_3$OD, 400 MHz): δ 8.70-8.69 (d, 1H), 8.49-8.48 (d, 1H), 7.81 (s, 1H), 7.78-7.77 (d, 1H), 7.70-7.60 (m, 2H), 750-7.49 (d, 1H), 6.88-6.84 (m, 3H), 6.69-6.68 (d, 1H), 5.42 (s, 2H), 3.59-3.49 (m, 3H), 3.20-3.10 (t, 2H), 3.00 (s, 3H), 2.09-2.06 (d, 2H), 1.93-1.90 (m, 2H). MS: m/z=563.2 (M+1), HPLC: 95.6% in method A.

Example 177

5-(3-(1-(3,5-difluorobenzyl)-3,5-dimethyl-1H-pyrazol-4-yl)-1H-pyrrolo[2,3-b]pyridin-5-yl)-3-methoxypyridin-2-amine

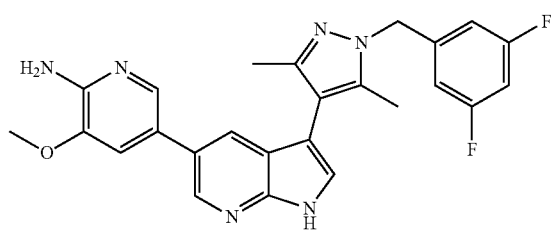 [SMILES: COc1cc(-c2cnc3[nH]cc(-c4c(C)nn(Cc5cc(F)cc(F)c5)c4C)c3c2)cnc1N]

Step-i: tert-butyl (5-(3-(1-(3,5-difluorobenzyl)-3,5-dimethyl-1H-pyrazol-4-yl)-1-tosyl-1H-pyrrolo[2,3-b]pyridin-5-yl)-3-methoxypyridin-2-yl)carbamate Using similar reaction conditions as described in step-i of example-1, tert-butyl (5-(3-iodo-1-tosyl-1H-pyrrolo[2,3-b]pyridin-5-yl)-3-methoxypyridin-2-yl)carbamate (intermediate 66B) (200 mg, 0.322 mmol) was coupled with 1-(3,5-difluorobenzyl)-3,5-dimethyl-4-(4,4,5,5-tetramethyl-1,3,2-dioxaborolan-2-yl)-1H-pyrazole (intermediate 24) (169 mg, 0.483 mmol) using Pd(dppf)Cl$_2$ (12 mg, 0.016 mol) and sodium carbonate (103 mg, 0.967 mmol) in toluene/ethanol/water (5/2/1 ml) to afford 200 mg (86.9% yield) of the titled compound after column purification using 2% methanol in DCM as eluent. MS: m/z=615.2 (M-Boc+1).

Step-ii: tert-butyl (5-(3-(1-(3,5-difluorobenzyl)-3,5-dimethyl-1H-pyrazol-4-yl)-1H-pyrrolo[2,3-b]pyridin-5-yl)-3-methoxypyridin-2-yl)carbamate Using similar reaction conditions as described in step-iii of example-1, tert-butyl (5-(3-(1-(3,5-difluorobenzyl)-3,5-dimethyl-1H-pyrazol-4-yl)-1-tosyl-1H-pyrrolo[2,3-b]pyridin-5-yl)-3-methoxypyridin-2-yl)carbamate (200 mg, 0.279 mmol) was hydrolyzed by lithium hydroxide (118 mg, 2.798 mmol) in THF/methanol/water (5/5/2 ml) to yield 100 mg (63.6% yield) of the titled compound. MS: m/z=560.9 (M+1).

Step-iii: 5-(3-(1-(3,5-difluorobenzyl)-3,5-dimethyl-1H-pyrazol-4-yl)-1H-pyrrolo[2,3-b]pyridin-5-yl)-3-methoxypyridin-2-amine Using similar reaction conditions as described in step-ii of example-7, tert-butyl (5-(3-(1-(3,5-difluorobenzyl)-3,5-dimethyl-1H-pyrazol-4-yl)-1H-pyrrolo[2,3-b]pyridin-5-yl)-3-methoxypyridin-2-yl)carbamate (100 mg, 0.178 mmol) was deprotected in TFA/DCM (2/5 ml) to afford 10 mg (9.8% yield) of the titled compound. $^1$H NMR (CD$_3$OD, 400 MHz): δ 8.56 (s, 1H), 8.14-8.13 (d, 1H), 7.70-7.69 (d, 2H), 7.53 (s, 1H), 6.91-6.86 (td, 1H), 6.79-6.76 (d, 2H), 5.36 (s, 2H), 4.07 (s, 3H), 2.20 (s, 3H), 2.18 (s, 3H). MS: m/z=461.3 (M+1), HPLC: 95.61% in method B.

Example 178

5-(3-(1-(3-fluorobenzyl)-3,5-dimethyl-1H-pyrazol-4-yl)-1H-pyrrolo[2,3-b]pyridin-5-yl)-3-methoxypyridin-2-amine

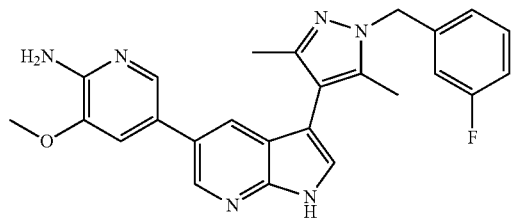 [SMILES: COc1cc(-c2cnc3[nH]cc(-c4c(C)nn(Cc5cccc(F)c5)c4C)c3c2)cnc1N]

Step-i: tert-butyl (5-(3-(1-(3-fluorobenzyl)-3,5-dimethyl-1H-pyrazol-4-yl)-1-tosyl-1H-pyrrolo[2,3-b]pyridin-5-yl)-3-methoxypyridin-2-yl)carbamate Using similar reaction conditions as described in step-i of example-1, tert-butyl (5-(3-iodo-1-tosyl-1H-pyrrolo[2,3-b]pyridin-5-yl)-3-methoxypyridin-2-yl)carbamate (intermediate 66B) (200 mg, 0.322 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (160 mg, 0.483 mmol) using Pd(dppf)Cl$_2$ (12 mg, 0.016 mol) and sodium carbonate (103 mg, 0.967 mmol) in toluene/ethanol/water (5/2/1 ml) to afford 200 mg (89.2% yield) of the titled compound after column purification using 2% methanol in DCM as eluent. MS: m/z=597.5 (M-Boc+1).

Step-ii: tert-butyl (5-(3-(1-(3-fluorobenzyl)-3,5-dimethyl-1H-pyrazol-4-yl)-1H-pyrrolo[2,3-b]pyridin-5-yl)-3-methoxypyridin-2-yl)carbamate Using similar reaction conditions as described in step-iii of example-1, tert-butyl (5-(3-(1-(3-fluorobenzyl)-3,5-dimethyl-1H-pyrazol-4-yl)-1-tosyl-1H-pyrrolo[2,3-b]pyridin-5-yl)-3-methoxypyridin-2-yl)carbamate (200 mg, 0.287 mmol) was hydrolyzed by lithium hydroxide (121 mg, 2.870 mmol) in THF/methanol/water (5/5/2 ml) to yield 100 mg (64.5% yield) of the titled compound.

Step-iii: 5-(3-(1-(3-fluorobenzyl)-3,5-dimethyl-1H-pyrazol-4-yl)-1H-pyrrolo[2,3-b]pyridin-5-yl)-3-methoxypyridin-2-amine Using similar reaction conditions as described in step-ii of example-7, tert-butyl (5-(3-(1-(3-fluorobenzyl)-3,5-dimethyl-1H-pyrazol-4-yl)-1H-pyrrolo[2,3-b]pyridin-5-yl)-3-methoxypyridin-2-yl) carbamate (100 mg, 0.184 mmol) was deprotected in TFA/DCM (2/5 ml). This afforded 5.2 mg (5.0% yield) of the titled compound. $^1$H NMR (CD$_3$OD, 400 MHz): δ 8.54 (s, 1H), 8.10-8.09 (d, 1H), 7.689-7.687 (d, 2H), 7.50 (s, 1H), 7.40-7.30 (m, 1H), 7.05-6.95 (m, 2H), 6.90-6.87 (t, 1H), 5.36 (s, 2H), 4.10 (s, 3H), 2.20 (s, 3H), 2.18 (s, 3H). MS: m/z=443.4 (M+1), HPLC: 93.64% in method A.

Example 179

5-(5-fluoro-6-(4-methylpiperazin-1-yl)pyridin-3-yl)-3-(1-(3-fluorobenzyl)-1H-pyrazol-4-yl)-1H-pyrrolo[2,3-b]pyridine

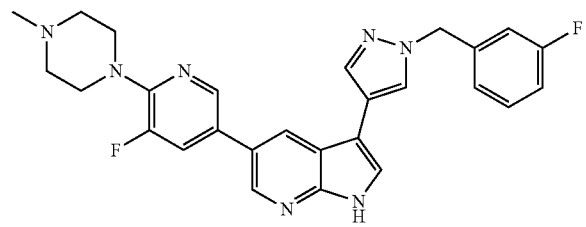 [SMILES: CN1CCN(c2ncc(-c3cnc4[nH]cc(-c5cnn(Cc6cccc(F)c6)c5)c4c3)cc2F)CC1]

Step-i: 5-(5-fluoro-6-(piperazin-1-yl)pyridin-3-yl)-3-(1-(3-fluorobenzyl)-1H-pyrazol-4-yl)-1-tosyl-1H-pyrrolo[2,3-b]pyridine Using similar reaction conditions as described in step-ii of example-7, tert-butyl 4-(3-fluoro-5-(3-(1-(3-fluorobenzyl)-1H-pyrazol-4-yl)-1-tosyl-1H-pyrrolo[2,3-b]pyridin-5-yl)pyridin-2-yl)piperazine-1-carboxylate (step 1 product of example 173) (550 mg, 0.758 mmol) was deprotected in methanol/HCl in dioxane (5/5 ml) to afford 342 mg (72% yield) of the titled compound. MS: m/z=626.5 (M+1).

Step-ii: 5-(5-fluoro-6-(4-methylpiperazin-1-yl)pyridin-3-yl)-3-(1-(3-fluorobenzyl)-1H-pyrazol-4-yl)-1-tosyl-1H-pyrrolo[2,3-b]pyridine Using similar reaction conditions as described in step-iii of example-133, 5-(5-fluoro-6-(piperazin-1-yl)pyridin-3-yl)-3-(1-(3-fluorobenzyl)-1H-pyrazol-4-yl)-1-tosyl-1H-pyrrolo[2,3-b]pyridine (170 mg, 0.272 mmol) was methylated using paraformaldehyde (24 mg, 0.816 mmol), Na(OAc)$_3$BH (172 mg, 0.816 mmol) and 3 drops of acetic acid in dichloroethane (10 mL) to afford 154 mg (89% yield) of the titled compound. MS: m/z=640.6 (M+1).

Step-iii: 5-(5-fluoro-6-(4-methylpiperazin-1-yl)pyridin-3-yl)-3-(1-(3-fluorobenzyl)-1H-pyrazol-4-yl)-1H-pyrrolo[2,3-b]pyridine Using similar reaction conditions as described in step-iii of example-1, 5-(5-fluoro-6-(4-methylpiperazin-1-yl)pyridin-3-yl)-3-(1-(3-fluorobenzyl)-1H-pyrazol-4-yl)-1-tosyl-1H-pyrrolo[2,3-b]pyridine (150 mg, 0.234 mmol) was hydrolyzed with lithium hydroxide (98 mg, 2.34 mmol) in THF/methanol/water (12/4/4 mL) to yield 34 mg (30% yield) after purification by prep TLC using 8% methanol in chloroform as eluent. $^1$H NMR (CD$_3$OD, 300 MHz): δ 8.459-8.452 (d, 1H), 8.36-8.34 (m, 2H), 8.24 (s, 1H), 7.94 (s, 1H), 7.85-7.79 (dd, 1H), 7.65 (s, 1H), 7.41-7.33 (q, 1H), 7.12-7.00 (m, 3H), 5.43 (s, 2H), 3.57-3.54 (t, 4H), 2.65-2.62 (m, 4H), 2.37 (s, 3H). MS: m/z=486.2 (M+1), HPLC: 98.03% in method A.

Example 180

(R)-1-(4-(3-fluoro-5-(3-(1-(3-fluorobenzyl)-1H-pyrazol-4-yl)-1H-pyrrolo[2,3-b]pyridin-5-yl)pyridin-2-yl)piperazin-1-yl)propan-2-ol

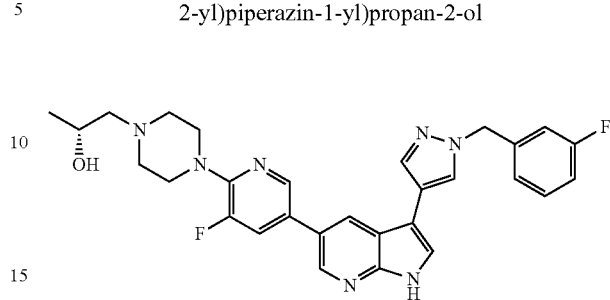

Step-i: (R)-1-(4-(3-fluoro-5-(3-(1-(3-fluorobenzyl)-1H-pyrazol-4-yl)-1-tosyl-1H-pyrrolo[2,3-b]pyridin-5-yl)pyridin-2-yl)piperazin-1-yl)propan-2-ol Using similar reaction conditions as described in step-i of example-82A, 5-(5-fluoro-6-(piperazin-1-yl)pyridin-3-yl)-3-(1-(3-fluorobenzyl)-1H-pyrazol-4-yl)-1-tosyl-1H-pyrrolo[2,3-b]pyridine (product of step 1 of example 179) (170 mg, 0.272 mmol) was alkylated using (S)-2-methyloxirane (32 mg, 0.544 mmol), DIPEA (105 mg, 0.812 mmol) and ethanol (5 mL) to get 147 mg (79% yield) of the titled compound. MS: m/z=684.2 (M+1).

Step-ii: (R)-1-(4-(3-fluoro-5-(3-(1-(3-fluorobenzyl)-1H-pyrazol-4-yl)-1H-pyrrolo[2,3-b]pyridin-5-yl)pyridin-2-yl)piperazin-1-yl)propan-2-ol Using similar reaction conditions as described in step-iii of example-1, (R)-1-(4-(3-fluoro-5-(3-(1-(3-fluorobenzyl)-1H-pyrazol-4-yl)-1-tosyl-1H-pyrrolo[2,3-b]pyridin-5-yl)pyridin-2-yl) piperazin-1-yl) propan-2-ol (146 mg, 0.213 mmol) was hydrolyzed with lithium hydroxide (89 mg, 2.137 mmol) in THF/methanol/water (12/4/4 mL) to yield 64 mg (57% yield) after purification by prep TLC using 8% methanol in chloroform as eluent. $^1$H NMR (CD$_3$OD, 300 MHz): δ 8.45-8.44 (d, 1H), 8.35-8.32 (m, 2H), 8.32 (s, 1H), 7.94 (s, 1H), 7.83-7.78 (dd, 1H), 7.65 (s, 1H), 7.40-7.33 (m, 1H), 7.12-7.00 (m, 3H), 5.43 (s, 2H), 4.02-3.95 (m, 1H), 3.56-3.53 (t, 4H), 2.77-2.63 (m, 4H), 2.47-2.33 (m, 2H), 1.18-1.16 (d, 3H). MS: m/z=530.2 (M+1), HPLC: 98.70% in method A.

Example 181

(S)-1-(4-(3-fluoro-5-(3-(1-(3-fluorobenzyl)-1H-pyrazol-4-yl)-1H-pyrrolo[2,3-b]pyridin-5-yl)pyridin-2-yl)piperazin-1-yl)propan-2-ol

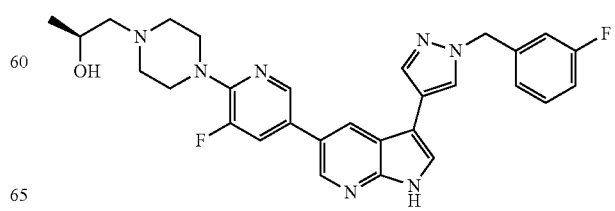

243

Step-i: (S)-1-(4-(3-fluoro-5-(3-(1-(3-fluorobenzyl)-1H-pyrazol-4-yl)-1-tosyl-1H-pyrrolo[2,3-b]pyridin-5-yl)pyridin-2-yl)piperazin-1-yl)propan-2-ol Using similar reaction conditions as described in step-i of example-82A, 5-(5-fluoro-6-(piperazin-1-yl)pyridin-3-yl)-3-(1-(3-fluorobenzyl)-1H-pyrazol-4-yl)-1-tosyl-1H-pyrrolo[2,3-b]pyridine (product of step 1 of example 179) (127 mg, 0.203 mmol) was alkylated using (S)-2-methyloxirane (23 mg, 0.406 mmol), DIPEA (105 mg, 0.812 mmol) and ethanol (5 mL) to get 135 mg (97.8% yield) of the titled compound. MS: m/z=684.7 (M+1).

Step-ii: (S)-1-(4-(3-fluoro-5-(3-(1-(3-fluorobenzyl)-1H-pyrazol-4-yl)-1H-pyrrolo[2,3-b]pyridin-5-yl)pyridin-2-yl)piperazin-1-yl)propan-2-ol Using similar reaction conditions as described in step-iii of example-1, (S)-1-(4-(3-fluoro-5-(3-(1-(3-fluorobenzyl)-1H-pyrazol-4-yl)-1-tosyl-1H-pyrrolo[2,3-b]pyridin-5-yl)pyridin-2-yl)piperazin-1-yl) propan-2-ol (134 mg, 0.196 mmol) was hydrolyzed with lithium hydroxide (82 mg, 1.964 mmol) in THF/methanol/water (12/4/4 mL) to yield 56 mg (54.6% yield) after purification by prep TLC using 8% methanol in chloroform as eluent. $^1$H NMR (CD$_3$OD, 300 MHz): δ 8.449-8.442 (d, 1H), 8.35-8.32 (m, 2H), 8.23 (s, 1H), 7.94 (s, 1H), 7.82-7.77 (dd, 1H), 7.64 (s, 1H), 7.40-7.33 (q, 1H), 7.12-7.00 (m, 3H), 5.43 (s, 2H), 4.05-3.95 (m, 1H), 3.56-3.32 (t, 4H), 2.77-2.62 (m, 4H), 2.47-2.33 (m, 2H), 1.18-1.16 (d, 3H). MS: m/z=530.3 (M+1), HPLC: 95.33% in method A.

Example 182

3-fluoro-5-(3-(1-(3-fluorobenzyl)-1H-pyrazol-4-yl)-1H-pyrrolo[2,3-b]pyridin-5-yl)pyridin-2-amine

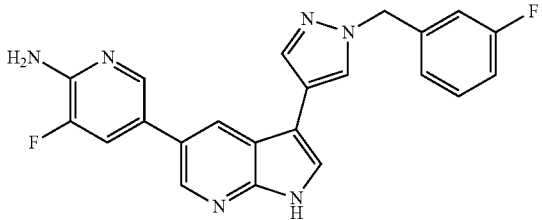 [SMILES: Nc1ncc(-c2cnc3[nH]cc(-c4cnn(Cc5cccc(F)c5)c4)c3c2)cc1F]

Step-i: tert-butyl (3-fluoro-5-(3-(1-(3-fluorobenzyl)-1H-pyrazol-4-yl)-1-tosyl-1H-pyrrolo[2,3-b]pyridin-5-yl)pyridin-2-yl)carbamate Using similar reaction conditions as described in step-i of example-1, tert-butyl (3-fluoro-5-(3-iodo-1-tosyl-1H-pyrrolo[2,3-b]pyridin-5-yl)pyridin-2-yl)carbamate (intermediate 66T) (150 mg, 0.24 mmol) was coupled with 1-(3-fluorobenzyl)-4-(4,4,5,5-tetramethyl-1,3,2-dioxaborolan-2-yl)-1H-pyrazole (intermediate 11) (82 mg, 0.27 mmol) using Pd(PPh$_3$)$_2$Cl$_2$ (8 mg, 0.012 mol) and sodium carbonate (76 mg, 0.72 mmol) in toluene/ethanol/water (10/10/2 mL) to afford 122 mg (crude) of the titled compound. MS: m/z=657.2 (M+1).

Step-ii: tert-butyl (3-fluoro-5-(3-(1-(3-fluorobenzyl)-1H-pyrazol-4-yl)-1H-pyrrolo[2,3-b]pyridin-5-yl)pyridin-2-yl)carbamate Using similar reaction conditions as described in step-iii of example-1, tert-butyl (3-fluoro-5-(3-(1-(3-fluorobenzyl)-1H-pyrazol-4-yl)-1-tosyl-1H-pyrrolo[2,3-b]pyridin-5-yl)pyridin-2-yl) carbamate (122 mg, 0.185 mmol) was hydrolyzed by lithium hydroxide (39 mg, 0.928 mmol) in THF/methanol/water (10/10/5 mL) to yield 90 mg (96.4% yield) of the titled compound. MS: m/z=447.1 (M+1) (de t-butyl).

Step-iii: 3-fluoro-5-(3-(1-(3-fluorobenzyl)-1H-pyrazol-4-yl)-1H-pyrrolo[2,3-b]pyridin-5-yl)pyridin-2-amine Using similar reaction conditions as described in step-ii of example-7, tert-butyl (3-fluoro-5-(3-(1-(3-fluorobenzyl)-1H-pyrazol-4-yl)-1H-pyrrolo[2,3-b]pyridin-5-yl)pyridin-2-yl)carbamate (90 mg, 0.179 mmol) was deprotected in TFA (10 mL) to afford 15 mg (16.3% yield) of the titled compound. $^1$H NMR (CD$_3$OD, 300 MHz): δ 8.47 (s, 1H), 8.42-8.41 (d, 1H), 8.26-8.21 (m, 2H), 8.11-0.810 (d, 1H), 7.98 (s, 1H), 7.69 (s, 1H), 7.41-7.33 (m, 1H), 7.12-6.99 (m, 3H), 5.44 (s, 2H). MS: m/z=403.4 (M+1), HPLC: 97.56% in method A.

Example 183

3-fluoro-5-(3-(1-(3-fluorobenzyl)-3,5-dimethyl-1H-pyrazol-4-yl)-1H-pyrrolo[2,3-b]pyridin-5-yl)pyridin-2-amine

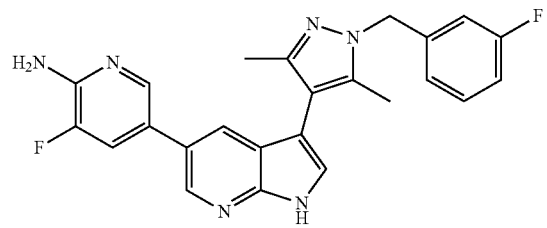 [SMILES: Cc1nn(Cc2cccc(F)c2)c(C)c1-c1c[nH]c2ncc(-c3cnc(N)c(F)c3)cc12]

Step-i: tert-butyl (3-fluoro-5-(3-(1-(3-fluorobenzyl)-3,5-dimethyl-1H-pyrazol-4-yl)-1-tosyl-1H-pyrrolo[2,3-b]pyridin-5-yl)pyridin-2-yl)carbamate Using similar reaction conditions as described in step-i of example-1, tert-butyl (3-fluoro-5-(3-iodo-1-tosyl-1H-pyrrolo[2,3-b]pyridin-5-yl)pyridin-2-yl)carbamate (intermediate 66T) (150 mg, 0.24 mmol) was coupled with 1-(3-fluorobenzyl)-3,5-dimethyl-4-(4,4,5,5-tetramethyl-1,3,2-dioxaborolan-2-yl)-1H-pyrazole (intermediate 16) (89 mg, 0.27 mmol) using Pd(PPh$_3$)$_2$Cl$_2$ (8.4 mg, 0.012 mol) and sodium carbonate (76 mg, 0.72 mmol) in toluene/ethanol/water (10/10/2 mL) to afford 110 mg (crude yield) of the titled compound. MS: m/z=685.2 (M+1).

Step-ii: tert-butyl (3-fluoro-5-(3-(1-(3-fluorobenzyl)-3,5-dimethyl-1H-pyrazol-4-yl)-1H-pyrrolo[2,3-b]pyridin-5-yl)pyridin-2-yl)carbamate Using similar reaction conditions as described in step-iii of example-1, tert-butyl (3-fluoro-5-(3-(1-(3-fluorobenzyl)-3,5-dimethyl-1H-pyrazol-4-yl)-1-tosyl-1H-pyrrolo[2,3-b]pyridin-5-yl)pyridin-2-yl)carbamate (110 mg, 0.16 mmol) was hydrolyzed by lithium hydroxide (33 mg, 0.8 mmol) in THF/methanol/water (5/5/2 mL) to yield 78 mg (91.5% yield) of the titled compound.

245

Step-iii: 3-fluoro-5-(3-(1-(3-fluorobenzyl)-3,5-dimethyl-1H-pyrazol-4-yl)-1H-pyrrolo[2,3-b]pyridin-5-yl)pyridin-2-amine Using similar reaction conditions as described in step-ii of example-7, tert-butyl (3-fluoro-5-(3-(1-(3-fluorobenzyl)-3,5-dimethyl-1H-pyrazol-4-yl)-1H-pyrrolo[2,3-b]pyridin-5-yl)pyridin-2-yl) carbamate (78 mg, 0.14 mmol) was deprotected in TFA (10 mL) to afford 10 mg (12.5% yield) of the titled compound. $^1$H NMR (DMSO-d$_6$, 300 MHz): δ 11.95 (s, 1H), 8.51 (s, 1H), 8.14 (s, 1H), 8.05-7.95 (m, 1H), 7.89 (s, 1H), 7.49 (s, 1H), 7.43-7.38 (m, 1H), 7.16-6.91 (m, 3H), 5.32 (s, 2H), 2.17 (s, 3H), 2.13 (s, 3H). MS: m/z=431.2 (M+1), HPLC: 98.88% in method B.

Example 184

2-(4-(3-(3-(1-(3-fluorobenzyl)-1H-pyrazol-4-yl)-1H-pyrrolo[2,3-b]pyridin-5-yl)benzyl)piperidin-1-yl)acetamide

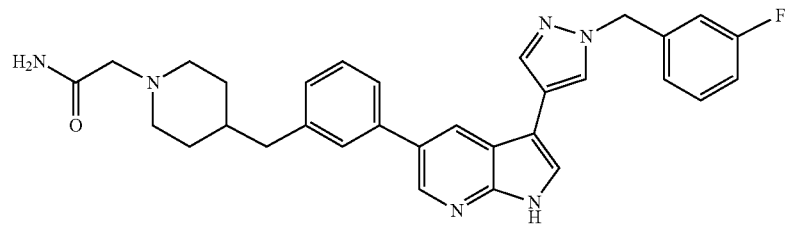 [SMILES: NC(=O)CN1CCC(Cc2cccc(-c3cnc4[nH]cc(-c5cnn(Cc6cccc(F)c6)c5)c4c3)c2)CC1]

Step-i: 3-(1-(3-fluorobenzyl)-1H-pyrazol-4-yl)-5-(3-(piperidin-4-ylmethyl)phenyl)-1-tosyl-1H-pyrrolo[2,3-b]pyridine hydrochloride Using similar reaction conditions as described in step-ii of example-7, tert-butyl 4-(3-(3-(1-(3-fluorobenzyl)-1H-pyrazol-4-yl)-1-tosyl-1H-pyrrolo[2,3-b]pyridin-5-yl)benzyl)piperidine-1-carboxylate (compound of step 1 of example 102) (32 mg, 0.44 mmol) was deprotected in methanol/ether HCl (5/0.3 ml). This afforded 210 mg (72.4% yield) of the titled compound.

Step-ii: 2-(4-(3-(3-(1-(3-fluorobenzyl)-1H-pyrazol-4-yl)-1-tosyl-1H-pyrrolo[2,3-b]pyridin-5-yl)benzyl)piperidin-1-yl)acetamide Using the same reaction conditions as described in step-i of example-82A 3-(1-(3-fluorobenzyl)-1H-pyrazol-4-yl)-5-(3-(piperidin-4-ylmethyl)phenyl)-1-tosyl-1H-pyrrolo[2,3-b]pyridine hydrochloride (75 mg, 0.114 mmol) was alkylated using 2-chloroacetamide (16 mg, 0.171 mmol) and sodium bicarbonate (29 mg, 0.342 mmol) in acetone/ethanol (5/5 mL) to get 30 mg (38.96% yield) of the titled compound. MS: m/z=676.8 (M+1).

Step-iii: 2-(4-(3-(3-(1-(3-fluorobenzyl)-1H-pyrazol-4-yl)-1H-pyrrolo[2,3-b]pyridin-5-yl)benzyl) piperidin-1-yl) acetamide Using similar reaction conditions as described in step-iii of example-1, 2-(4-(3-(3-(1-(3-fluorobenzyl)-1H-pyrazol-4-yl)-1-tosyl-1H-pyrrolo[2,3-b]pyridin-5-yl)benzyl)piperidin-1-yl) acetamide (30 mg, 0.044 mmol) was hydrolyzed by lithium hydroxide (18 mg, 0.44 mmol) in THF/methanol/water (2/2/1 ml) to yield 10 mg (43.4% yield) of the titled compound. $^1$H NMR (DMSO-d$_6$, 400 MHz): δ 8.516-8.512 (d, 1H), 8.43 (s, 1H), 8.347-8.343 (d, 1H), 7.98 (s, 1H), 7.77 (s, 1H), 7.59-7.54 (m, 2H), 7.42-7.38 (t, 2H), 7.17-7.09 (m, 5H), 5.41 (s, 2H), 2.78 (s, 4H), 2.65-2.55 (m, 2H), 1.99-1.93 (t, 2H), 1.59-1.56 (m, 3H), 1.31-1.23 (m, 3H). MS: m/z=523.4 (M+1), HPLC: 91.01% in method B.

Example 185

3-(1-phenethyl-1H-pyrazol-4-yl)-5-(4-(piperazin-1-yl)phenyl)-1H-pyrrolo[2,3-b]pyridine

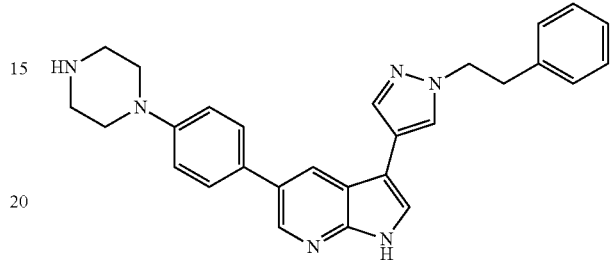

Step-i: tert-butyl 4-(4-(3-(1-phenethyl-1H-pyrazol-4-yl)-1-tosyl-1H-pyrrolo[2,3-b]pyridin-5-yl)phenyl)piperazine-1-carboxylate Using similar reaction conditions as described in step-ii of example-1, tert-butyl 4-(4-(3-iodo-1-tosyl-1H-pyrrolo[2,3-b]pyridin-5-yl)phenyl)piperazine-1-carboxylate (intermediate 41) (160 mg, 0.2277 mmol) was coupled with 1-phenethyl-4-(4,4,5,5-tetramethyl-1,3,2-dioxaborolan-2-yl)-1H-pyrazole (intermediate 59) (82 mg, 0.2733 mmol) in sodium carbonate (61 mg, 0.5694 mmol), Pd(PPh$_3$)$_2$Cl$_2$ (8 mg, 0.0113 mmol), toluene/ethanol/water (3/2/1 ml) to give 160 mg (100% yield) of the titled compound. MS: m/z=704.1 (M+1).

Step-ii: tert-butyl 4-(4-(3-(1-phenethyl-1H-pyrazol-4-yl)-1H-pyrrolo[2,3-b]pyridin-5-yl)phenyl)piperazine-1-carboxylate Using similar reaction conditions as described in step-iii of example-1, tert-butyl 4-(4-(3-(1-phenethyl-1H-pyrazol-4-yl)-1-tosyl-1H-pyrrolo[2,3-b]pyridin-5-yl)phenyl)piperazine-1-carboxylate (160 mg, 0.227 mmol) was hydrolyzed by lithium hydroxide (19 mg, 0.455 mmol), THF/Methanol/water (5/1/1 ml) to yield 130 mg (crude) of the titled compound. MS: m/z=549.4 (M+1).

Step-iii: 3-(1-phenethyl-1H-pyrazol-4-yl)-5-(4-(piperazin-1-yl)phenyl)-1H-pyrrolo[2,3-b]pyridine Using similar reaction conditions as described in step-ii of example-7, tert-butyl 4-(4-(3-(1-phenethyl-1H-pyrazol-4-yl)-1H-pyrrolo[2,3-b]pyridin-5-yl)phenyl)piperazine-1-carboxylate (130 mg, 0.238 mmol) was deprotected in methanolic HCl (5 ml). This afforded 78 mg (58.6% yield) of the titled compound. $^1$H NMR (CD$_3$OD, 400 MHz): δ 8.49 (s, 1H), 8.327-8.322 (d, 1H), 7.878-7.876 (d, 1H), 7.788-7.787 (d, 1H), 7.672-7.644 (m, 3H), 7.23-7.12 (m, 7H), 4.47-4.43 (t, 2H), 3.52-3.49 (m, 4H), 3.43-3.40 (m, 4H), 3.20-3.17 (t, 2H). MS: m/z=449.4 (M+1), HPLC: 95.50% in method A.

Example 186

2-(4-(3-(3-(1-(3-fluorobenzyl)-3,5-dimethyl-1H-pyrazol-4-yl)-1H-pyrrolo[2,3-b]pyridin-5-yl)phenyl)piperazin-1-yl)ethanol

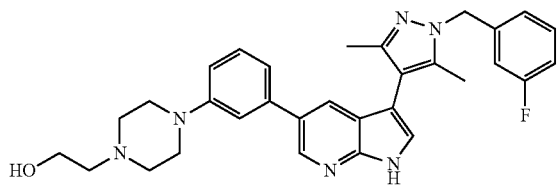 [SMILES: Cc1nn(Cc2cccc(F)c2)c(C)c1-c1c[nH]c2ncc(-c3cccc(N4CCN(CCO)CC4)c3)cc12]

Step-i: 3-(1-(3-fluorobenzyl)-3,5-dimethyl-1H-pyrazol-4-yl)-5-(3-(piperazin-1-yl)phenyl)-1-tosyl-1H-pyrrolo[2,3-b]pyridine Using similar reaction conditions as described in step-ii of example-7, tert-butyl 4-(3-(3-(1-(3-fluorobenzyl)-3,5-dimethyl-1H-pyrazol-4-yl)-1-tosyl-1H-pyrrolo[2,3-b]pyridin-5-yl)phenyl) piperazine-1-carboxylate (compound of Step-iii in example-38) (107 mg, 0.145 mmol) was deprotected in methanol (5 ml), HCl in dioaxane (5 ml). This afforded 94 mg (95.9% yield) of the titled compound. MS: m/z=635.2 (M+1).

Step-ii: 2-(4-(3-(3-(1-(3-fluorobenzyl)-3,5-dimethyl-1H-pyrazol-4-yl)-1-tosyl-1H-pyrrolo[2,3-b]pyridin-5-yl)phenyl)piperazin-1-yl)ethanol Using the same reaction conditions as described in step-ii of example-35, 3-(1-(3-fluorobenzyl)-3,5-dimethyl-1H-pyrazol-4-yl)-5-(3-(piperazin-1-yl)phenyl)-1-tosyl-1H-pyrrolo[2,3-b]pyridine (70 mg, 0.104 mmol) was alkylated with 2-bromoethanol (13 mg, 0.104 mmol) using potassium carbonate (73 mg, 0.522 mmol), DMF (2 ml) to yield 60 mg (84.5%) of the titled compound. MS: m/z=679.3 (M+1).

Step-iii: 2-(4-(3-(3-(1-(3-fluorobenzyl)-3,5-dimethyl-1H-pyrazol-4-yl)-1H-pyrrolo[2,3-b]pyridin-5-yl)phenyl)piperazin-1-yl)ethanol Using the same reaction conditions as described in step-iii of example-1, 2-(4-(3-(3-(1-(3-fluorobenzyl)-3,5-dimethyl-1H-pyrazol-4-yl)-1-tosyl-1H-pyrrolo[2,3-b]pyridin-5-yl) phenyl) piperazin-1-yl)ethanol (58 mg, 0.085 mmol) was hydrolyzed by lithium hydroxide (36 mg, 0.85 mmol), THF/Methanol/water (12/6/3 ml) to yield 7 mg (16%) of the titled compound. $^1$H NMR (CD$_3$OD, 400 MHz): δ 8.46-8.45 (d, 1H), 7.87-7.86 (d, 1H), 7.39-7.31 (m, 3H), 7.16 (s, 1H), 7.10-7.08 (m, 1H), 7.04-6.97 (m, 3H), 6.87-6.84 (m, 1H), 3.75-3.74 (t, 2H), 2.82 (b, 4H), 2.53 (m, 2H), 2.21 (s, 3H), 2.17 (s, 3H). MS: m/z=525.0 (M+1), HPLC: 91.007% in method A.

Pharmacological Activity

ALK Wild Type (WT)

The ALK WT cell free assay was set up to evaluate the effects of these compounds as inhibitors of ALK enzyme. The enzymatic assay was standardized using recombinant human ALK enzyme (Cat#08-518) from Carna Biosciences using Ultra Light Poly GT (Cat# TRF 0100D) from Perkin Elmer as a substrate. TR-FRET (Time resolved fluorescence resonance energy transfer) detection technology was used for the read out. The final assay conditions were 50 mM HEPES pH 7.1, 10 mM MgCl$_2$, 2 mM MnCl$_2$, 0.01% BSA, 2.5 mM DTT, 0.1 mM Na$_3$ VO$_4$, 40 nM Ultra Light Poly GT, 2.5 ng ALK WT enzyme, 1 μM ATP and 125 nM Lance Eu-W1024 labeled anti phospho tyrosine antibody (Cat# AD0203, Perkin Elmer) in 384 well format. The assay reaction time with the substrate was 30 minutes after which the antibody detection mix is added. The TR-FRET signal (Excitation at 340 nm, Emission at 615 nm and 665 nm) was read with 50 μs delay time on Victor$^3$ V fluorimeter. The data is calculated using the ratio of reading at 665 nM to 615 nM. The final concentration of DMSO was 1% in the assay. Compounds were screened at 100 nM and 1 μM concentrations with pre-incubation of the enzymes with compound for 30 minutes. Each individual IC$_{50}$ was determined using 10 point dose response curve generated by GraphPad Prism software Version 4 (San Diego, Calif., USA) using non linear regression curve fit for sigmoidal dose response (variable slope).

The compounds prepared were tested using the above assay procedure and the results obtained are given in Table-8. Percentage inhibition at concentrations of 100 nM and 1.0 μM are given in table along with the IC$_{50}$ (nM) details for selected examples. The IC$_{50}$ values of the compounds are set forth in Table-8 wherein "A" refers to an IC$_{50}$ value of less than 50 nM, "B" refers to IC$_{50}$ value in range of 50.01 to 250 nM and "C" refers to IC$_{50}$ value of greater than 250 nM.

TABLE 8

| | In-vitro screening result of compounds of invention | | |
|---|---|---|---|
| Example No | ALK-100 nM % inhibition | ALK-1 μM % inhibition | IC$_{50}$ (nM) ALK WT |
| 1 | — | 92 | B |
| 2 | — | 33 | C |
| 3 | — | 65 | C |
| 4 | — | 95 | B |
| 5 | — | 69 | B |
| 6 | — | 99 | A |
| 7 | 20 | 53 | — |
| 8 | 81 | 97 | A |
| 9 | — | 98 | A |
| 10 | — | 81 | B |
| 11 | 64 | 90 | A |
| 12 | — | 87 | C |
| 13 | — | 96 | A |
| 14 | — | 95 | A |
| 15 | 33 | 75 | — |
| 16 | 33 | 66 | — |
| 17 | 13 | 53 | — |
| 18 | 62 | 94 | B |
| 19 | 63 | 96 | B |
| 20 | 17 | 75 | C |
| 21 | 82 | 96 | A |
| 22 | 62 | 87 | A |
| 23 | 73 | 99 | B |
| 24 | 53 | 96 | A |
| 25 | 86 | 93 | A |
| 26 | 96 | 100 | A |
| 27 | 9 | 8 | — |
| 28 | 14 | 49 | — |
| 29 | 28 | 48 | — |

TABLE 8-continued

In-vitro screening result of compounds of invention

| Example No | ALK-100 nM % inhibition | ALK-1 μM % inhibition | IC$_{50}$ (nM) ALK WT |
|---|---|---|---|
| 30 | 21 | 21 | — |
| 31 | — | 55 | C |
| 32 | — | 99 | A |
| 33 | 97 | 100 | A |
| 34 | 91 | 99 | A |
| 35 | 98 | 99 | A |
| 36 | 96 | 99 | A |
| 37 | 93 | 98 | A |
| 38 | 87 | 99 | A |
| 39 | 92 | 99 | A |
| 40 | 94 | 100 | A |
| 41 | 90 | 100 | A |
| 42 | 92 | 100 | A |
| 43 | 92 | 99 | A |
| 44 | 95 | 100 | A |
| 45 | 51 | 80 | B |
| 46 | 80 | 98 | A |
| 47 | 90 | 100 | A |
| 48 | 52 | 83 | B |
| 49 | 70 | 91 | A |
| 50 | 60 | 89 | A |
| 51 | 84 | 100 | A |
| 52 | 12 | 80 | C |
| 53 | — | — | — |
| 54 | 0 | 25 | — |
| 55 | 2 | 43 | — |
| 56 | 91 | 100 | A |
| 57 | 93 | 100 | A |
| 58 | 92 | 100 | A |
| 59 | 49 | 77 | B |
| 60 | 9 | 10 | — |
| 61 | 73 | 96 | A |
| 62 | 87 | 100 | A |
| 63 | 15 | 48 | — |
| 64 | 59 | 82 | A |
| 65 | 97 | 100 | A |
| 66 | 38 | 95 | — |
| 67 | 98 | 100 | A |
| 68 | 70 | 93 | — |
| 69 | 15 | 76 | — |
| 70 | 91 | 99 | A |
| 71 | 94 | 100 | A |
| 72 | 76 | 100 | B |
| 73 | 92 | 97 | A |
| 74 | 51 | 92 | B |
| 75 | 61 | 100 | A |
| 76 | 32 | 94 | B |
| 77 | 85 | 100 | A |
| 78 | 100 | 101 | A |
| 79 | 101 | 102 | A |
| 80 | 65 | 93 | B |
| 81 | 94 | 96 | A |
| 82 | 99 | 100 | A |
| 82A | 96 | 98 | A |
| 83 | 96 | 100 | A |
| 84 | 98 | 100 | A |
| 85 | 95 | 100 | A |
| 86 | 96 | 98 | A |
| 87 | 84 | 99 | A |
| 88 | 89 | 99 | A |
| 89 | 84 | 98 | A |
| 90 | 97 | 100 | A |
| 91 | 99 | 100 | A |
| 92 | 98 | 100 | A |
| 93 | 79 | 97 | A |
| 94 | 98 | 100 | A |
| 95 | 83 | 99 | B |
| 96 | 70 | 100 | A |
| 97 | 76 | 98 | A |
| 98 | 24 | 95 | B |
| 99 | 89 | 99 | A |
| 100 | 100 | 100 | A |
| 101 | 99 | 100 | A |
| 102 | 91 | 100 | A |
| 102A | 91 | 94 | A |
| 103 | 95 | 100 | A |
| 104 | 98 | 100 | A |
| 105 | 98 | 100 | A |
| 106 | 97 | 100 | A |
| 107 | 99 | 100 | A |
| 108 | 97 | 100 | A |
| 109 | 76 | 100 | — |
| 110 | 94 | 98 | A |
| 111 | 82 | 100 | A |
| 112 | 90 | 100 | — |
| 113 | 90 | 97 | A |
| 114 | 92 | 99 | — |
| 115 | 94 | 100 | — |
| 116 | 68 | 97 | B |
| 117 | 91 | 95 | A |
| 118 | 94 | 98 | A |
| 119 | 86 | 93 | A |
| 120 | 95 | 99 | A |
| 121 | 91 | 95 | A |
| 122 | 90 | 96 | A |
| 123 | 92 | 96 | A |
| 124 | 17 | 86 | C |
| 125 | 86 | 97 | A |
| 126 | 95 | 97 | A |
| 127 | 96 | 97 | A |
| 128 | 92 | 94 | A |
| 129 | 96 | 99 | A |
| 130 | 88 | 99 | A |
| 131 | 83 | 99 | A |
| 132 | 100 | 100 | A |
| 133 | 97 | 100 | A |
| 134 | 97 | 100 | A |
| 135 | 95 | 100 | A |
| 136 | 97 | 99 | A |
| 137 | 99 | 100 | A |
| 138 | 100 | 100 | A |
| 139 | 99 | 100 | A |
| 140 | 80 | 95 | A |
| 141 | 58 | 96 | A |
| 142 | 94 | 100 | — |
| 143 | 60 | 98 | — |
| 144 | 76 | 94 | A |
| 145 | 83 | 99 | A |
| 146 | 60 | 97 | B |
| 147 | 99 | 100 | A |
| 148 | 94 | 100 | A |
| 149 | 95 | 100 | A |
| 150 | 92 | 100 | A |
| 151 | 92 | 97 | A |
| 152 | 80 | 100 | A |
| 153 | 93 | 100 | A |
| 154 | 99 | 100 | A |
| 155 | 86 | 97 | A |
| 156 | 69 | 91 | A |
| 157 | 77 | 93 | A |
| 158 | 85 | 94 | A |
| 159 | 91 | 100 | A |
| 160 | 20 | 84 | B |
| 161 | 86 | 97 | A |
| 162 | 75 | 96 | A |
| 163 | 88 | 98 | A |
| 164 | 96 | 99 | A |
| 165 | 99 | 100 | A |
| 166 | 90 | 98 | A |
| 167 | 69 | 97 | B |
| 168 | 23 | 71 | C |
| 169 | 99 | 100 | A |
| 170 | 98 | 100 | A |
| 171 | 41 | 88 | B |
| 172 | 99 | 100 | A |
| 173 | 92 | 98 | A |
| 174 | 96 | 100 | A |
| 175 | 96 | 100 | A |
| 176 | 86 | 99 | A |
| 177 | 96 | 100 | A |

TABLE 8-continued

In-vitro screening result of compounds of invention

| Example No | ALK-100 nM % inhibition | ALK-1 µM % inhibition | IC$_{50}$ (nM) ALK WT |
|---|---|---|---|
| 178 | 94 | 100 | A |
| 179 | 92 | 99 | A |
| 180 | 93 | 100 | A |
| 184 | 92 | 100 | A |
| 185 | 80 | 86 | — |
| 186 | 83 | 96 | A |

We claim:

1. A compound of formula (I);

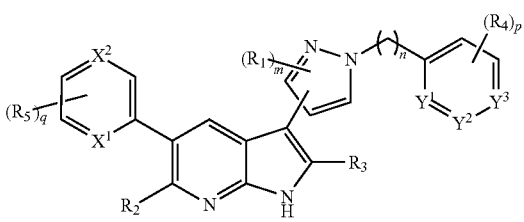

(I)

or pharmaceutically acceptable salts or stereoisomers thereof;
wherein,
$X^1$ and $X^2$ are independently CH or N;
—$Y^1$—$Y^2$—$Y^3$— is:
 —N=CH—CH=;
 —CH=N—CH=;
 —CH=CH—N=; or
 —CH=CH—CH=;
each $R_1$ represents alkyl;
$R_2$ and $R_3$ are independently hydrogen, alkyl or cycloalkyl;
each $R_4$ is independently alkyl, halo, haloalkyl, hydroxyl, alkoxy, haloalkoxy, —N($R_a$)$R_b$, nitro, cyano or —NHC(O)alkyl;
each $R_5$ is independently alkyl, —O$R_a$, —O(CH$_2$)$_q$N($R_a$)$R_b$, —O(CH$_2$)$_q$O$R_a$, —N(H)SO$_2$$R_a$, —SO$_2$NHR$_a$, —N($R_a$)$R_b$, halo, optionally substituted piperidinylalkyl, optionally substituted piperazinyl, optionally substituted piperidinyl, optionally substituted pyridinyl, optionally substituted pyrazinyl, or optionally substituted 1,4-diazepanyl; wherein the optional substituent at each occurrence is independently selected from alkyl, cyanoalkyl, hydroxyl, hydroxyalkyl, —C(O)O$R_a$, —C(O)$R_a$, —(CH$_2$)$_n$N($R_a$)$R_b$, —(CH$_2$)$_n$C(O)N($R_a$)$R_b$, —C(O)N($R_a$)$R_b$, —C(O)(CH$_2$)$_n$$R_a$, —SO$_2$$R_a$, —C(O)(CH$_2$)$_n$N($R_a$)$R_b$, —C(O)(CH$_2$)$_n$O$R_a$, or —(CH$_2$)$_n$O$R_a$;
$R_a$ and $R_b$ are independently hydrogen, alkyl, cycloalkyl or heterocyclyl;
'm' and 'p' are integers 0 to 2 inclusive;
'n' is an integer selected from 1 to 2 inclusive; and
'q' is an integer selected from 1 to 3 inclusive;
wherein
i) when q is 1, then $R_5$ is not —N($R_a$)$R_b$ where $R_a$ and $R_b$ are hydrogen or alkyl, and
ii) when q is 2 or 3 then each $R_5$ is different.

2. The compound of claim 1, wherein $R_1$ is methyl.
3. The compound of claim 1, wherein $X^1$ and $X^2$ are CH.
4. The compound of claim 1, wherein $X^1$ is CH and $X^2$ is N.
5. The compound of claim 1, wherein $X^1$ is N and $X^2$ is CH.
6. The compound of claim 1, wherein —$Y^1$—$Y^2$—$Y^3$— is —CH=CH—CH=.
7. The compound of claim 1, wherein $R_2$ and $R_3$ are hydrogen.

8. The compound of claim 1, wherein the compound of formula (I) is a compound of formula (IA):

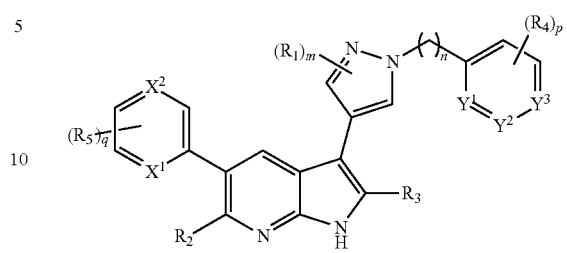

(IA)

wherein, $R_1$, $R_2$, $R_3$, $R_4$, $R_5$, $X^1$, $X^2$, $Y^1$, $Y^2$, $Y^3$, m, n, p and q are same as defined in claim 1; or a pharmaceutically acceptable salts or a stereoisomers thereof.

9. The compound of claim 1, wherein the compound of formula (I) is a compound of formula (IB):

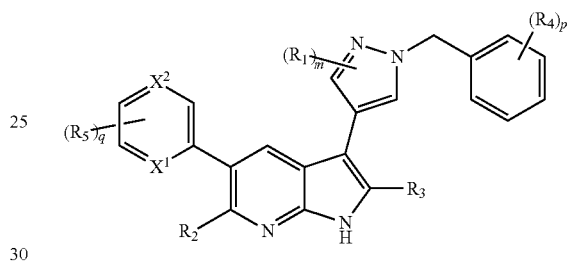

(IB)

wherein, $R_1$, $R_2$, $R_3$, $R_4$, $R_5$, $X^1$, $X^2$, m, p and q are same as defined in claim 1; or a pharmaceutically acceptable salts or a stereoisomers thereof.

10. The compound of claim 1, wherein the compound of formula (I) is a compound of formula (IC):

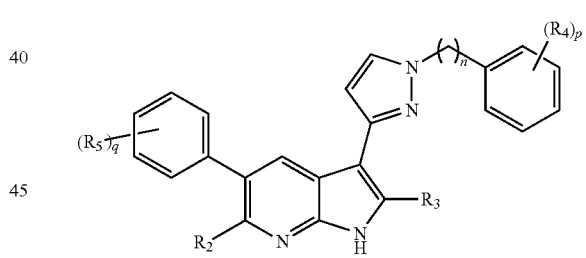

(IC)

wherein, $R_2$, $R_3$, $R_4$, $R_5$, n, p and q are same as defined in claim 1; or a pharmaceutically acceptable salts or a stereoisomers thereof.

11. The compound of claim 1, wherein the compound of formula (I) is a compound of formula (ID):

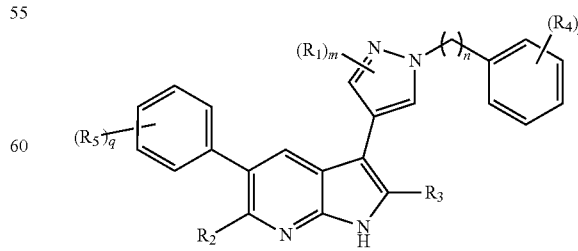

(ID)

wherein, $R_1$, $R_2$, $R_3$, $R_4$, $R_5$, m, n, p and q are same as defined in claim 1; or a pharmaceutically acceptable salts or a stereoisomers thereof.

12. The compound of claim 1 that is:

| Ex. No | IUPAC NAME |
|---|---|
| 1 | N-(3-(3-(1-(2-fluorobenzyl)-1H-pyrazol-4-yl)-1H-pyrrolo[2,3-b]pyridin-5-yl)phenyl)methanesulfonamide; |
| 2 | N-(3-(3-(1-(3-(trifluoromethyl)benzyl)-1H-pyrazol-4-yl)-1H-pyrrolo[2,3-b]pyridin-5-yl)phenyl)methanesulfonamide; |
| 3 | N-(3-(3-(1-(4-methoxybenzyl)-1H-pyrazol-4-yl)-1H-pyrrolo[2,3-b]pyridin-5-yl)phenyl)methanesulfonamide; |
| 4 | N-(3-(3-(1-(2,5-difluorobenzyl)-1H-pyrazol-4-yl)-1H-pyrrolo[2,3-b]pyridin-5-yl)phenyl)methanesulfonamide; |
| 5 | N-(3-(3-(1-(4-fluorobenzyl)-1H-pyrazol-4-yl)-1H-pyrrolo[2,3-b]pyridin-5-yl)phenyl)methanesulfonamide; |
| 6 | N-(3-(3-(1-(3,5-difluorobenzyl)-1H-pyrazol-4-yl)-1H-pyrrolo[2,3-b]pyridin-5-yl)phenyl)methanesulfonamide; |
| 7 | N-(3-(3-(1-(3-nitrobenzyl)-1H-pyrazol-4-yl)-1H-pyrrolo[2,3-b]pyridin-5-yl)phenyl)methanesulfonamide; |
| 8 | N-(3-(3-(1-(3-aminobenzyl)-1H-pyrazol-4-yl)-1H-pyrrolo[2,3-b]pyridin-5-yl)phenyl)methanesulfonamide; |
| 9 | N-(3-(3-(1-(3-fluorobenzyl)-1H-pyrazol-4-yl)-1H-pyrrolo[2,3-b]pyridin-5-yl)phenyl)methanesulfonamide; |
| 10 | N-(3-(3-(1-(3-chlorobenzyl)-1H-pyrazol-4-yl)-1H-pyrrolo[2,3-b]pyridin-5-yl)phenyl)methanesulfonamide; |
| 11 | N-(3-(3-(1-(3-cyanobenzyl)-1H-pyrazol-4-yl)-1H-pyrrolo[2,3-b]pyridin-5-yl)phenyl)methanesulfonamide; |
| 12 | N-(3-(3-(1-benzyl-1H-pyrazol-4-yl)-1H-pyrrolo[2,3-b]pyridin-5-yl)phenyl)methanesulfonamide; |
| 13 | N-(5-(3-(1-(3-fluorobenzyl)-1H-pyrazol-4-yl)-1H-pyrrolo[2,3-b]pyridin-5-yl)-2-methoxyphenyl)methanesulfonamide; |
| 14 | N-(5-(3-(1-(3-fluorobenzyl)-3,5-dimethyl-1H-pyrazol-4-yl)-1H-pyrrolo[2,3-b]pyridin-5-yl)-2-methoxyphenyl)methanesulfonamide; |
| 15 | N-(5-(3-(1-(3-fluorobenzyl)-3,5-dimethyl-1H-pyrazol-4-yl)-1H-pyrrolo[2,3-b]pyridin-5-yl)-2-methoxyphenyl)ethanesulfonamide; |
| 16 | N-(5-(3-(1-(3-fluorobenzyl)-1H-pyrazol-4-yl)-1H-pyrrolo[2,3-b]pyridin-5-yl)-2-methoxyphenyl)cyclopropanesulfonamide; |
| 18 | 5-(3-(1-(3-fluorobenzyl)-3,5-dimethyl-1H-pyrazol-4-yl)-1H-pyrrolo[2,3-b]pyridin-5-yl)-2-methoxy-N-methylbenzenesulfonamide; |
| 19 | N-(5-(3-(1-(3,5-difluorobenzyl)-3,5-dimethyl-1H-pyrazol-4-yl)-1H-pyrrolo[2,3-b]pyridin-5-yl)-2-methoxyphenyl)methanesulfonamide; |
| 20 | 5-(3-(1-(2,5-difluorobenzyl)-3,5-dimethyl-1H-pyrazol-4-yl)-1H-pyrrolo[2,3-b]pyridin-5-yl)-2-methoxy-N-methylbenzenesulfonamide; |
| 21 | 5-(3-(1-(3,5-difluorobenzyl)-3,5-dimethyl-1H-pyrazol-4-yl)-1H-pyrrolo[2,3-b]pyridin-5-yl)-2-methoxy-N-methylbenzenesulfonamide; |
| 22 | N-(5-(3-(1-(2,5-difluorobenzyl)-3,5-dimethyl-1H-pyrazol-4-yl)-1H-pyrrolo[2,3-b]pyridin-5-yl)-2-methoxyphenyl)methanesulfonamide; |
| 23 | N-(2-(2-(dimethylamino)ethoxy)-5-(3-(1-(3-fluorobenzyl)-3,5-dimethyl-1H-pyrazol-4-yl)-1H-pyrrolo[2,3-b]pyridin-5-yl)phenyl)methanesulfonamide;; |
| 24 | N-(5-(3-(1-(3-fluorobenzyl)-3,5-dimethyl-1H-pyrazol-4-yl)-1H-pyrrolo[2,3-b]pyridin-5-yl)-2-(2-hydroxyethoxy)phenyl)methanesulfonamide; |
| 25 | N-(5-(3-(1-(3-fluorobenzyl)-3,5-dimethyl-1H-pyrazol-4-yl)-1H-pyrrolo[2,3-b]pyridin-5-yl)-2-(3-hydroxypropoxy)phenyl)methanesulfonamide; |
| 26 | N-(2-(3-(dimethylamino)propoxy)-5-(3-(1-(3-fluorobenzyl)-3,5-dimethyl-1H-pyrazol-4-yl)-1H-pyrrolo[2,3-b]pyridin-5-yl)phenyl)methanesulfonamide; |
| 27 | N-(5-(6-cyclopropyl-3-(1-(3,5-difluorobenzyl)-3,5-dimethyl-1H-pyrazol-4-yl)-1H-pyrrolo[2,3-b]pyridin-5-yl)-2-methoxyphenyl)methanesulfonamide; |
| 28 | N-(5-(6-cyclopropyl-3-(1-(3-fluorobenzyl)-3,5-dimethyl-1H-pyrazol-4-yl)-1H-pyrrolo[2,3-b]pyridin-5-yl)-2-methoxyphenyl)methanesulfonamide; |
| 30 | N-(5-(2-cyclopropyl-3-(1-(3-fluorobenzyl)-3,5-dimethyl-1H-pyrazol-4-yl)-1H-pyrrolo[2,3-b]pyridin-5-yl)-2-methoxyphenyl)methanesulfonamide; |
| 31 | N-(5-(2-cyclopropyl-3-(1-(3-fluorobenzyl)-3,5-dimethyl-1H-pyrazol-4-yl)-1H-pyrrolo[2,3-b]pyridin-5-yl)-2-methoxyphenyl)methanesulfonamide; |
| 32 | 3-(1-(2,5-difluorobenzyl)-1H-pyrazol-4-yl)-5-(3-(piperazin-1-yl)phenyl)-1H-pyrrolo[2,3-b]pyridine; |
| 33 | 3-(1-(3-fluorobenzyl)-1H-pyrazol-4-yl)-5-(3-(piperazin-1-yl)phenyl)-1H-pyrrolo[2,3-b]pyridine; |
| 34 | 3-(4-(3-(3-(1-(3-fluorobenzyl)-1H-pyrazol-4-yl)-1H-pyrrolo[2,3-b]pyridin-5-yl)phenyl)piperazin-1-yl)propanenitrile; |
| 35 | 3-(1-(3-fluorobenzyl)-1H-pyrazol-4-yl)-5-(3-(4-isopropylpiperazin-1-yl)phenyl)-1H-pyrrolo[2,3-b]pyridine; |
| 36 | 3-(1-(3-fluorobenzyl)-1H-pyrazol-4-yl)-5-(3-(4-methylpiperazin-1-yl)phenyl)-1H-pyrrolo[2,3-b]pyridine; |
| 37 | 3-(1-(3-fluorobenzyl)-3-methyl-1H-pyrazol-4-yl)-5-(3-(piperazin-1-yl)phenyl)-1H-pyrrolo[2,3-b]pyridine; |
| 38 | 3-(1-(3-fluorobenzyl)-3,5-dimethyl-1H-pyrazol-4-yl)-5-(3-(piperazin-1-yl)phenyl)-1H-pyrrolo[2,3-b]pyridine; |
| 39 | 3-(1-(3-fluorobenzyl)-1H-pyrazol-4-yl)-5-(4-(piperazin-1-yl)phenyl)-1H-pyrrolo[2,3-b]pyridine; |

-continued

| Ex. No | IUPAC NAME |
|---|---|
| 40 | 3-(1-(3-fluorobenzyl)-3,5-dimethyl-1H-pyrazol-4-yl)-5-(4-(piperazin-1-yl)phenyl)-1H-pyrrolo[2,3-b]pyridine; |
| 41 | 2-(4-(4-(3-(1-(3-fluorobenzyl)-3,5-dimethyl-1H-pyrazol-4-yl)-1H-pyrrolo[2,3-b]pyridin-5-yl)phenyl)piperazin-1-yl)ethanol; |
| 42 | 3-(1-(2,5-difluorobenzyl)-3,5-dimethyl-1H-pyrazol-4-yl)-5-(4-(piperazin-1-yl)phenyl)-1H-pyrrolo[2,3-b]pyridine hydrochloride; |
| 43 | 3-(1-(3,5-difluorobenzyl)-3,5-dimethyl-1H-pyrazol-4-yl)-5-(4-(piperazin-1-yl)phenyl)-1H-pyrrolo[2,3-b]pyridine; |
| 44 | 3-(1-(3-fluorobenzyl)-5-methyl-1H-pyrazol-4-yl)-5-(4-(piperazin-1-yl)phenyl)-1H-pyrrolo[2,3-b]pyridine; |
| 46 | 3-(1-(3-methoxybenzyl)-3,5-dimethyl-1H-pyrazol-4-yl)-5-(4-(piperazin-1-yl)phenyl)-1H-pyrrolo[2,3-b]pyridine; |
| 47 | 3-(1-(3-chlorobenzyl)-3,5-dimethyl-1H-pyrazol-4-yl)-5-(4-(piperazin-1-yl)phenyl)-1H-pyrrolo[2,3-b]pyridine; |
| 48 | 3-((3,5-dimethyl-4-(5-(4-(piperazin-1-yl)phenyl)-1H-pyrrolo[2,3-b]pyridin-3-yl)-1H-pyrazol-1-yl)methyl)benzonitrile; |
| 49 | 1-(4-(4-(3-(1-(3-fluorobenzyl)-3,5-dimethyl-1H-pyrazol-4-yl)-1H-pyrrolo[2,3-b]pyridin-5-yl)phenyl)piperazin-1-yl)ethanone; |
| 50 | N-(3-((3,5-dimethyl-4-(5-(4-(piperazin-1-yl)phenyl)-1H-pyrrolo[2,3-b]pyridin-3-yl)-1H-pyrazol-1-yl)methyl)phenyl)acetamide; |
| 51 | 3-(3,5-dimethyl-1-(3-methylbenzyl)-1H-pyrazol-4-yl)-5-(4-(piperazin-1-yl)phenyl)-1H-pyrrolo[2,3-b]pyridine; |
| 52 | 3-(3,5-dimethyl-1-(3-(trifluoromethoxy)benzyl)-1H-pyrazol-4-yl)-5-(4-(piperazin-1-yl)phenyl)-1H-pyrrolo[2,3-b]pyridine; |
| 53 | 3-(1-(3-fluorobenzyl)-3,5-dimethyl-1H-pyrazol-4-yl)-5-(4-(pyridin-4-yl)phenyl)-1H-pyrrolo[2,3-b]pyridine; |
| 54 | 3-(1-(3-ethoxybenzyl)-3,5-dimethyl-1H-pyrazol-4-yl)-5-(4-(piperazin-1-yl)phenyl)-1H-pyrrolo[2,3-b]pyridine; |
| 55 | 6-cyclopropyl-3-(1-(3-fluorobenzyl)-3,5-dimethyl-1H-pyrazol-4-yl)-5-(4-(piperazin-1-yl)phenyl)-1H-pyrrolo[2,3-b]pyridine; |
| 56 | 3-(1-(3-fluorobenzyl)-3,5-dimethyl-1H-pyrazol-4-yl)-5-(4-(4-methylpiperazin-1-yl)phenyl)-1H-pyrrolo[2,3-b]pyridine; |
| 57 | 2-(4-(4-(3-(1-(3-fluorobenzyl)-3,5-dimethyl-1H-pyrazol-4-yl)-1H-pyrrolo[2,3-b]pyridin-5-yl)phenyl)piperazin-1-yl)-N,N-dimethylethanamine; |
| 58 | N-(5-(3-(1-(3-fluorobenzyl)-3,5-dimethyl-1H-pyrazol-4-yl)-1H-pyrrolo[2,3-b]pyridin-5-yl)-2-(piperazin-1-yl)phenyl)methanesulfonamide; |
| 59 | N-(5-(3-(1-(3-fluorobenzyl)-3,5-dimethyl-1H-pyrazol-4-yl)-1H-pyrrolo[2,3-b]pyridin-5-yl)-2-morpholinophenyl)methanesulfonamide; |
| 60 | 2-cyclopropyl-3-(1-(3-fluorobenzyl)-3,5-dimethyl-1H-pyrazol-4-yl)-5-(4-(piperazin-1-yl)phenyl)-1H-pyrrolo[2,3-b]pyridine; |
| 61 | 3-(1-(3-fluorobenzyl)-3,5-dimethyl-1H-pyrazol-4-yl)-5-(2-methoxy-4-(piperazin-1-yl)phenyl)-1H-pyrrolo[2,3-b]pyridine; |
| 62 | 3-(1-(3-fluorobenzyl)-3,5-dimethyl-1H-pyrazol-4-yl)-5-(3-methoxy-4-(piperazin-1-yl)phenyl)-1H-pyrrolo[2,3-b]pyridine; |
| 63 | 2-cyclopropyl-3-(1-(3-fluorobenzyl)-3,5-dimethyl-1H-pyrazol-4-yl)-5-(4-(piperazin-1-yl)phenyl)-1H-pyrrolo[2,3-b]pyridine; |
| 64 | N-(2-methoxy-5-(3-(1-phenethyl-1H-pyrazol-4-yl)-1H-pyrrolo[2,3-b]pyridin-5-yl)phenyl)methanesulfonamide; |
| 65 | 5-(3-(1-(3-fluorobenzyl)-1H-pyrazol-4-yl)-1H-pyrrolo[2,3-b]pyridin-5-yl)-2-methoxypyridin-3-amine; |
| 66 | N-(5-(3-(1-(3-fluorobenzyl)-3,5-dimethyl-1H-pyrazol-4-yl)-1H-pyrrolo[2,3-b]pyridin-5-yl)-2-hydroxypyridin-3-yl)methanesulfonamide; |
| 67 | N-(5-(3-(1-(3-fluorobenzyl)-1H-pyrazol-4-yl)-1H-pyrrolo[2,3-b]pyridin-5-yl)-2-methoxypyridin-3-yl)methanesulfonamide; |
| 68 | N-(4-(3-(1-(3-fluorobenzyl)-1H-pyrazol-4-yl)-1H-pyrrolo[2,3-b]pyridin-5-yl)-2-methoxyphenyl)methanesulfonamide; |
| 69 | N-(5-(3-(1-(3,5-difluorobenzyl)-1H-pyrazol-3-yl)-1H-pyrrolo[2,3-b]pyridin-5-yl)-2-methoxyphenyl)methanesulfonamide; |
| 70 | N-(5-(3-(1-(2,5-difluorobenzyl)-1H-pyrazol-4-yl)-1H-pyrrolo[2,3-b]pyridin-5-yl)-2-methoxyphenyl)methanesulfonamide; |
| 71 | N-(5-(3-(1-(3,5-difluorobenzyl)-1H-pyrazol-4-yl)-1H-pyrrolo[2,3-b]pyridin-5-yl)-2-methoxyphenyl)methanesulfonamide; |
| 72 | N-(2-methoxy-5-(3-(1-(pyridin-3-ylmethyl)-1H-pyrazol-4-yl)-1H-pyrrolo[2,3-b]pyridin-5-yl)phenyl)methanesulfonamide; |
| 73 | N-(4-(3-(1-(3,5-difluorobenzyl)-1H-pyrazol-4-yl)-1H-pyrrolo[2,3-b]pyridin-5-yl)-2-methoxyphenyl)methanesulfonamide; |
| 74 | N-(5-(3-(1-(2-fluorophenethyl)-1H-pyrazol-4-yl)-1H-pyrrolo[2,3-b]pyridin-5-yl)-2-methoxyphenyl)methanesulfonamide; |
| 75 | N-(5-(3-(1-(3-fluorophenethyl)-1H-pyrazol-4-yl)-1H-pyrrolo[2,3-b]pyridin-5-yl)-2-methoxyphenyl)methanesulfonamide; |
| 76 | N-(5-(3-(1-(4-fluorophenethyl)-1H-pyrazol-4-yl)-1H-pyrrolo[2,3-b]pyridin-5-yl)-2-methoxyphenyl)methanesulfonamide; |
| 77 | N-(2-fluoro-5-(3-(1-phenethyl-1H-pyrazol-4-yl)-1H-pyrrolo[2,3-b]pyridin-5-yl)phenyl)methanesulfonamide; |

-continued

| Ex. No | IUPAC NAME |
|---|---|
| 78 | N-(2-fluoro-5-(3-(1-(3-fluorobenzyl)-1H-pyrazol-4-yl)-1H-pyrrolo[2,3-b]pyridin-5-yl)phenyl)methanesulfonamide; |
| 79 | N-(5-(3-(1-(3,5-difluorobenzyl)-1H-pyrazol-4-yl)-1H-pyrrolo[2,3-b]pyridin-5-yl)-2-fluorophenyl)methanesulfonamide; |
| 80 | N-(5-(3-(1-(3,5-difluorobenzyl)-3,5-dimethyl-1H-pyrazol-4-yl)-1H-pyrrolo[2,3-b]pyridin-5-yl)-2-fluorophenyl)methanesulfonamide; |
| 81 | 5-(3-(1-(3-fluorobenzyl)-1H-pyrazol-4-yl)-1H-pyrrolo[2,3-b]pyridin-5-yl)-3-methoxypyridin-2-amine; |
| 82 | 3-(1-(3-fluorobenzyl)-1H-pyrazol-4-yl)-5-(4-(piperidin-4-yl)phenyl)-1H-pyrrolo[2,3-b]pyridine; |
| 82A | (S)-1-(4-(4-(3-(1-(3-fluorobenzyl)-1H-pyrazol-4-yl)-1H-pyrrolo[2,3-b]pyridin-5-yl)phenyl)piperidin-1-yl)propan-2-ol; |
| 83 | 3-(1-(3-fluorobenzyl)-1H-pyrazol-4-yl)-5-(4-(1-methylpiperidin-4-yl)phenyl)-1H-pyrrolo[2,3-b]pyridine; |
| 84 | 5-(3-fluoro-4-(piperidin-4-yl) phenyl)-3-(1-(3-fluorobenzyl)-1H-pyrazol-4-yl)-1H-pyrrolo[2,3-b]pyridine; |
| 85 | 3-(1-(3-methylbenzyl)-1H-pyrazol-4-yl)-5-(4-(piperidin-4-yl) phenyl)-1H-pyrrolo[2,3-b]pyridine; |
| 86 | Tert-butyl 4-(4-(3-(1-(3-fluorobenzyl)-1H-pyrazol-4-yl)-1H-pyrrolo [2,3-b] pyridin-5-yl)-2-methoxyphenyl) piperidine-1-carboxylate; |
| 87 | 3-(1-(3-methoxybenzyl)-1H-pyrazol-4-yl)-5-(4-(piperidin-4-yl)phenyl)-1H-pyrrolo[2,3-b]pyridine; |
| 88 | 3-(1-phenethyl-1H-pyrazol-4-yl)-5-(4-(piperidin-4-yl)phenyl)-1H-pyrrolo[2,3-b]pyridine; |
| 89 | 5-(4-(piperidin-4-yl)phenyl)-3-(1-(pyridin-3-ylmethyl)-1H-pyrazol-4-yl)-1H-pyrrolo[2,3-b]pyridine; |
| 90 | 3-(1-(3-fluorobenzyl)-3-methyl-1H-pyrazol-4-yl)-5-(4-(piperidin-4-yl)phenyl)-1H-pyrrolo[2,3-b]pyridine; |
| 91 | 3-(1-(3-fluorobenzyl)-5-methyl-1H-pyrazol-4-yl)-5-(4-(piperidin-4-yl)phenyl)-1H-pyrrolo[2,3-b]pyridine; |
| 92 | 3-(1-(3-fluorobenzyl)-3,5-dimethyl-1H-pyrazol-4-yl)-5-(4-(piperidin-4-yl)phenyl)-1H-pyrrolo[2,3-b]pyridine; |
| 93 | 5-(4-(piperidin-4-yl)phenyl)-3-(1-(pyridin-2-ylmethyl)-1H-pyrazol-4-yl)-1H-pyrrolo[2,3-b]pyridine; |
| 94 | N-(3-(3-(1-(3-fluorobenzyl)-3,5-dimethyl-1H-pyrazol-4-yl)-1H-pyrrolo[2,3-b]pyridin-5-yl)phenyl)piperidin-4-amine; |
| 95 | N-(3-(3-(1-phenethyl-1H-pyrazol-4-yl)-1H-pyrrolo[2,3-b]pyridin-5-yl)phenyl)piperidin-4-amine; |
| 96 | 3-(1-(3-fluorobenzyl)-3,5-dimethyl-1H-pyrazol-4-yl)-5-(3-(piperidin-4-yloxy)phenyl)-1H-pyrrolo[2,3-b]pyridine; |
| 97 | 3-(1-phenethyl-1H-pyrazol-4-yl)-5-(3-(piperidin-4-yloxy)phenyl)-1H-pyrrolo[2,3-b]pyridine; |
| 98 | 3-(1-phenethyl-1H-pyrazol-4-yl)-5-(3-(piperidin-4-ylmethyl) phenyl)-1H-pyrrolo[2,3-b] pyridine; |
| 99 | 3-(1-(3-fluorobenzyl)-3,5-dimethyl-1H-pyrazol-4-yl)-5-(3-(piperidin-4-ylmethyl)phenyl)-1H-pyrrolo[2,3-b]pyridine; |
| 100 | N-(4-(3-(1-(3-fluorobenzyl)-1H-pyrazol-4-yl)-1H-pyrrolo[2,3-b]pyridin-5-yl)phenyl)piperidin-4-amine; |
| 101 | N-(4-(3-(1-(3-fluorobenzyl)-3,5-dimethyl-1H-pyrazol-4-yl)-1H-pyrrolo [2,3-b] pyridin-5-yl)phenyl) piperidin-4-amine; |
| 102 | 3-(1-(3-fluorobenzyl)-1H-pyrazol-4-yl)-5-(3-(piperidin-4-ylmethyl)phenyl)-1H-pyrrolo[2,3-b]pyridine; |
| 102A | (S)-1-(4-(5-(3-(1-(3-fluorobenzyl)-1H-pyrazol-4-yl)-1H-pyrrolo[2,3-b]pyridin-5-yl)pyridin-2-yl)piperidin-1-yl)propan-2-ol; |
| 103 | 2-(4-(4-(3-(1-(3-fluorobenzyl)-1H-pyrazol-4-yl)-1H-pyrrolo[2,3-b]pyridin-5-yl)phenyl)piperazin-1-yl)acetamide; |
| 104 | (S)-1-(4-(4-(3-(1-(3-fluorobenzyl)-1H-pyrazol-4-yl)-1H-pyrrolo[2,3-b]pyridin-5-yl)phenyl)piperazin-1-yl)propan-2-ol; |
| 105 | 5-(3-(1-(3-fluorobenzyl)-1H-pyrazol-4-yl)-1H-pyrrolo[2,3-b]pyridin-5-yl)-2-(piperazin-1-yl)aniline; |
| 106 | N-(5-(3-(1-(3-fluorobenzyl)-1H-pyrazol-4-yl)-1H-pyrrolo[2,3-b]pyridin-5-yl)-2-(piperazin-1-yl)phenyl)methanesulfonamide hydrochloride; |
| 107 | N-(5-(3-(1-phenethyl-1H-pyrazol-4-yl)-1H-pyrrolo[2,3-b]pyridin-5-yl)-2-(piperazin-1-yl)phenyl)methanesulfonamide hydrochloride; |
| 108 | 4-(4-(3-(1-(3-fluorobenzyl)-1H-pyrazol-4-yl)-1H-pyrrolo[2,3-b]pyridin-5-yl)phenyl)piperazine-1-carboxamide; |
| 109 | 5-(4-(4-methylpiperazin-1-yl)phenyl)-3-(1-phenethyl-1H-pyrazol-4-yl)-1H-pyrrolo[2,3-b]pyridine; |
| 110 | 2-(4-(4-(3-(1-(3-fluorobenzyl)-1H-pyrazol-4-yl)-1H-pyrrolo[2,3-b]pyridin-5-yl)-2-(methylsulfonamido)phenyl)piperazin-1-yl)acetamide; |
| 111 | 3-(1-(3,5-difluorobenzyl)-1H-pyrazol-3-yl)-5-(4-(piperazin-1-yl)phenyl)-1H-pyrrolo[2,3-b]pyridine; |
| 112 | (S)-1-(4-(4-(3-(1-(3-fluorobenzyl)-1H-pyrazol-4-yl)-1H-pyrrolo[2,3-b]pyridin-5-yl)-2-methoxyphenyl)piperazin-1-yl)propan-2-ol; |

| Ex. No | IUPAC NAME |
|---|---|
| 113 | N-(5-(3-(1-(3,5-difluorobenzyl)-1H-pyrazol-3-yl)-1H-pyrrolo[2,3-b]pyridin-5-yl)-2-(piperazin-1-yl)phenyl)methanesulfonamide; |
| 114 | (S)-1-(4-(2-fluoro-4-(3-(1-(3-fluorobenzyl)-1H-pyrazol-4-yl)-1H-pyrrolo[2,3-b]pyridin-5-yl)phenyl)piperazin-1-yl)propan-2-ol; |
| 115 | (S)-1-(4-(4-(3-(1-(3-fluorobenzyl)-1H-pyrazol-4-yl)-1H-pyrrolo[2,3-b]pyridin-5-yl)-2-methylphenyl)piperazin-1-yl)propan-2-ol; |
| 116 | (S)-1-(4-(4-(3-(1-(3-fluorobenzyl)-1H-pyrazol-4-yl)-1H-pyrrolo[2,3-b]pyridin-5-yl)-3-methoxyphenyl)piperazin-1-yl)propan-2-ol; |
| 117 | (S)-1-(4-(4-(3-(1-phenethyl-1H-pyrazol-4-yl)-1H-pyrrolo[2,3-b]pyridin-5-yl)phenyl)piperazin-1-yl)propan-2-ol; |
| 118 | (S)-1-(4-(4-(3-(1-benzyl-1H-pyrazol-4-yl)-1H-pyrrolo[2,3-b]pyridin-5-yl)phenyl)piperazin-1-yl)propan-2-ol; |
| 119 | (S)-1-(4-(4-(3-(1-(3-methylbenzyl)-1H-pyrazol-4-yl)-1H-pyrrolo[2,3-b]pyridin-5-yl)phenyl)piperazin-1-yl)propan-2-ol; |
| 120 | (R)-1-(4-(4-(3-(1-(3-fluorobenzyl)-1H-pyrazol-4-yl)-1H-pyrrolo[2,3-b]pyridin-5-yl)phenyl)piperazin-1-yl)propan-2-ol; |
| 121 | (S)-1-(4-(3-fluoro-4-(3-(1-(3-fluorobenzyl)-1H-pyrazol-4-yl)-1H-pyrrolo[2,3-b]pyridin-5-yl)phenyl)piperazin-1-yl)propan-2-ol; |
| 122 | 1-(4-(3-(1-(3-fluorobenzyl)-1H-pyrazol-4-yl)-1H-pyrrolo[2,3-b]pyridin-5-yl)phenyl)piperidin-4-ol; |
| 123 | (2S)-1-(4-(4-(3-(1-(3-fluorobenzyl)-3,5-dimethyl-1H-pyrazol-4-yl)-1H-pyrrolo[2,3-b]pyridin-5-yl)phenyl)piperazin-1-yl)propan-2-ol; |
| 124 | 2-cyclopropyl-1-(4-(4-(3-(1-(3-fluorobenzyl)-1H-pyrazol-4-yl)-1H-pyrrolo[2,3-b]pyridin-5-yl)phenyl)piperazin-1-yl)ethanone; |
| 125 | 3-(1-(3-fluorobenzyl)-1H-pyrazol-4-yl)-5-(4-(4-(methylsulfonyl)piperazin-1-yl)phenyl)-1H-pyrrolo[2,3-b]pyridine; |
| 126 | 2-(4-(4-(3-(1-(3-fluorobenzyl)-1H-pyrazol-4-yl)-1H-pyrrolo[2,3-b]pyridin-5-yl)phenyl)piperazin-1-yl)ethanol; |
| 127 | 2-(dimethylamino)-1-(4-(4-(3-(1-(3-fluorobenzyl)-1H-pyrazol-4-yl)-1H-pyrrolo[2,3-b]pyridin-5-yl)phenyl)piperazin-1-yl)ethanone; |
| 128 | 1-(4-(4-(3-(1-(3-fluorobenzyl)-1H-pyrazol-4-yl)-1H-pyrrolo[2,3-b]pyridin-5-yl)phenyl)piperazin-1-yl)-2-hydroxyethanone; |
| 129 | (S)-1-(4-(4-(3-(1-(3-fluorobenzyl)-5-methyl-1H-pyrazol-4-yl)-1H-pyrrolo[2,3-b]pyridin-5-yl)phenyl)piperazin-1-yl)propan-2-ol; |
| 130 | (S)-1-(4-(4-(3-(1-(3-fluorobenzyl)-3-methyl-1H-pyrazol-4-yl)-1H-pyrrolo[2,3-b]pyridin-5-yl)phenyl)piperazin-1-yl)propan-2-ol; |
| 131 | 5-(4-(piperazin-1-yl)phenyl)-3-(1-(pyridin-3-ylmethyl)-1H-pyrazol-4-yl)-1H-pyrrolo[2,3-b]pyridine; |
| 132 | 3-(1-(3-fluorobenzyl)-1H-pyrazol-4-yl)-5-(6-(piperazin-1-yl)pyridin-3-yl)-1H-pyrrolo[2,3-b]pyridine; |
| 133 | 3-(1-(3,5-difluorobenzyl)-1H-pyrazol-4-yl)-5-(6-(4-methylpiperazin-1-yl)pyridin-3-yl)-1H-pyrrolo[2,3-b]pyridine; |
| 134 | 3-(1-(3,5-difluorobenzyl)-1H-pyrazol-4-yl)-5-(6-(piperazin-1-yl)pyridin-3-yl)-1H-pyrrolo[2,3-b]pyridine; |
| 135 | (S)-1-(4-(5-(3-(1-(3,5-difluorobenzyl)-1H-pyrazol-4-yl)-1H-pyrrolo[2,3-b]pyridin-5-yl)pyridin-2-yl)piperazin-1-yl)propan-2-ol; |
| 136 | 2-(4-(5-(3-(1-(3,5-difluorobenzyl)-1H-pyrazol-4-yl)-1H-pyrrolo[2,3-b]pyridin-5-yl)pyridin-2-yl)piperazin-1-yl)acetamide; |
| 137 | 3-(1-(3-fluorobenzyl)-1H-pyrazol-4-yl)-5-(6-(4-methylpiperazin-1-yl)pyridin-3-yl)-1H-pyrrolo[2,3-b]pyridine; |
| 138 | (S)-1-(4-(5-(3-(1-(3-fluorobenzyl)-1H-pyrazol-4-yl)-1H-pyrrolo[2,3-b]pyridin-5-yl)pyridin-2-yl)piperazin-1-yl)propan-2-ol; |
| 139 | 2-(4-(5-(3-(1-(3-fluorobenzyl)-1H-pyrazol-4-yl)-1H-pyrrolo[2,3-b]pyridin-5-yl)pyridin-2-yl)piperazin-1-yl)acetamide; |
| 140 | 3-(1-phenethyl-1H-pyrazol-4-yl)-5-(6-(piperazin-1-yl)pyridin-3-yl)-1H-pyrrolo[2,3-b]pyridine; |
| 141 | 5-(6-(4-methylpiperazin-1-yl)pyridin-3-yl)-3-(1-phenethyl-1H-pyrazol-4-yl)-1H-pyrrolo[2,3-b]pyridine; |
| 142 | 2-(4-(5-(3-(1-(3-fluorobenzyl)-1H-pyrazol-4-yl)-1H-pyrrolo[2,3-b]pyridin-5-yl)pyridin-2-yl)piperazin-1-yl)ethanol; |
| 143 | (S)-1-(4-(5-(3-(1-phenethyl-1H-pyrazol-4-yl)-1H-pyrrolo[2,3-b]pyridin-5-yl)pyridin-2-yl)piperazin-1-yl)propan-2-ol; |
| 144 | (S)-1-(4-(5-(3-(1-(3-fluorobenzyl)-1H-pyrazol-4-yl)-1H-pyrrolo[2,3-b]pyridin-5-yl)-6-methoxypyridin-2-yl)piperazin-1-yl)propan-2-ol; |
| 145 | (S)-1-(4-(5-(3-(1-(3-methylbenzyl)-1H-pyrazol-4-yl)-1H-pyrrolo[2,3-b]pyridin-5-yl)pyridin-2-yl)piperazin-1-yl)propan-2-ol; |
| 146 | (S)-1-(4-(6-(3-(1-(3-fluorobenzyl)-1H-pyrazol-4-yl)-1H-pyrrolo[2,3-b]pyridin-5-yl)pyridin-3-yl)piperazin-1-yl)propan-2-ol; |
| 147 | 2-(dimethylamino)-1-(4-(5-(3-(1-(3-fluorobenzyl)-1H-pyrazol-4-yl)-1H-pyrrolo[2,3-b]pyridin-5-yl)pyridin-2-yl)piperazin-1-yl)ethanone; |
| 148 | (S)-1-(4-(5-(3-(1-benzyl-1H-pyrazol-4-yl)-1H-pyrrolo[2,3-b]pyridin-5-yl)pyridin-2-yl)piperazin-1-yl)propan-2-ol; |
| 149 | 3-(1-(3-fluorobenzyl)-1H-pyrazol-4-yl)-5-(6-(4-(2-methoxyethyl)piperazin-1-yl)pyridin-3-yl)-1H-pyrrolo[2,3-b]pyridine; |
| 150 | 2-(4-(5-(3-(1-(3-fluorobenzyl)-1H-pyrazol-4-yl)-1H-pyrrolo[2,3-b]pyridin-5-yl)pyridin-2-yl)piperazin-1-yl)acetonitrile; |

| Ex. No | IUPAC NAME |
|---|---|
| 151 | (S)-3-((4-(5-(6-(4-(2-hydroxypropyl)piperazin-1-yl)pyridin-3-yl)-1H-pyrrolo[2,3-b]pyridin-3-yl)-1H-pyrazol-1-yl)methyl)phenol; |
| 152 | 3-(1-(3-fluorobenzyl)-1H-pyrazol-4-yl)-5-(6-(4-isobutylpiperazin-1-yl)pyridin-3-yl)-1H-pyrrolo[2,3-b]pyridine; |
| 153 | (S)-1-(4-(5-(3-(1-(3-chlorobenzyl)-1H-pyrazol-4-yl)-1H-pyrrolo[2,3-b]pyridin-5-yl)pyridin-2-yl)piperazin-1-yl)propan-2-ol; |
| 154 | 1-(4-(5-(3-(1-(3-fluorobenzyl)-1H-pyrazol-4-yl)-1H-pyrrolo[2,3-b]pyridin-5-yl)pyridin-2-yl)piperazin-1-yl)-2-hydroxyethanone; |
| 155 | 1-(5-(3-(1-(3-fluorobenzyl)-1H-pyrazol-4-yl)-1H-pyrrolo[2,3-b]pyridin-5-yl)pyridin-2-yl)piperidin-4-ol; |
| 156 | 5-(6-(4-(ethylsulfonyl)piperazin-1-yl)pyridin-3-yl)-3-(1-(3-fluorobenzyl)-1H-pyrazol-4-yl)-1H-pyrrolo[2,3-b]pyridine; |
| 157 | cyclopropyl(4-(5-(3-(1-(3-fluorobenzyl)-1H-pyrazol-4-yl)-1H-pyrrolo[2,3-b]pyridin-5-yl)pyridin-2-yl)piperazin-1-yl)methanone; |
| 158 | 3-(1-(3-fluorobenzyl)-1H-pyrazol-4-yl)-5-(6-(4-(methylsulfonyl)piperazin-1-yl)pyridin-3-yl)-1H-pyrrolo[2,3-b]pyridine; |
| 159 | 3-(1-(3-fluorobenzyl)-1H-pyrazol-4-yl)-5-(6-(piperidin-4-yl)pyridin-3-yl)-1H-pyrrolo[2,3-b]pyridine; |
| 160 | 2-cyclopropyl-1-(4-(5-(3-(1-(3-fluorobenzyl)-1H-pyrazol-4-yl)-1H-pyrrolo[2,3-b]pyridin-5-yl)pyridin-2-yl)piperazin-1-yl)ethanone; |
| 161 | (2S)-1-(4-(5-(3-(1-(3-fluorobenzyl)-3,5-dimethyl-1H-pyrazol-4-yl)-1H-pyrrolo[2,3-b]pyridin-5-yl)pyridin-2-yl)piperazin-1-yl)propan-2-ol; |
| 162 | (S)-1-(4-(5-(3-(1-(3-fluorobenzyl)-5-methyl-1H-pyrazol-4-yl)-1H-pyrrolo[2,3-b]pyridin-5-yl)pyridin-2-yl)piperazin-1-yl)propan-2-ol; |
| 163 | (S)-1-(4-(5-(3-(1-(3-fluorobenzyl)-1H-pyrazol-4-yl)-1H-pyrrolo[2,3-b]pyridin-5-yl)pyrazin-2-yl)piperazin-1-yl)propan-2-ol; |
| 164 | (S)-1-(4-(4-(3-(1-(3-fluorobenzyl)-1H-pyrazol-4-yl)-1H-pyrrolo[2,3-b]pyridin-5-yl)phenyl)-1,4-diazepan-1-yl)propan-2-ol; |
| 165 | 5-(3-fluoro-4-(piperidin-4-yl)phenyl)-3-(1-(3-fluorobenzyl)-5-methyl-1H-pyrazol-4-yl)-1H-pyrrolo[2,3-b]pyridine; |
| 166 | 5-(3-fluoro-4-(piperidin-4-yl)phenyl)-3-(1-(3-fluorobenzyl)-3-methyl-1H-pyrazol-4-yl)-1H-pyrrolo[2,3-b]pyridine; |
| 167 | 5-(3-fluoro-4-(piperidin-4-yl)phenyl)-3-(1-phenethyl-1H-pyrazol-4-yl)-1H-pyrrolo[2,3-b]pyridine; |
| 168 | 5-(3-fluoro-4-(piperidin-4-yl)phenyl)-3-(1-phenethyl-1H-pyrazol-3-yl)-1H-pyrrolo[2,3-b]pyridine; |
| 169 | 3-(1-(3,5-difluorobenzyl)-1H-pyrazol-4-yl)-5-(3-fluoro-4-(piperidin-4-yl)phenyl)-1H-pyrrolo[2,3-b]pyridine; |
| 170 | 5-(3-fluoro-4-(1-methylpiperidin-4-yl)phenyl)-3-(1-(3-fluorobenzyl)-1H-pyrazol-4-yl)-1H-pyrrolo[2,3-b]pyridine; |
| 171 | 5-(4-(piperidin-4-yl)phenyl)-3-(1-(pyridin-4-ylmethyl)-1H-pyrazol-4-yl)-1H-pyrrolo[2,3-b]pyridine; |
| 172 | 5-(3-fluoro-4-(piperazin-1-yl)phenyl)-3-(1-(3-fluorobenzyl)-1H-pyrazol-4-yl)-1H-pyrrolo[2,3-b]pyridine; |
| 173 | 5-(5-fluoro-6-(piperazin-1-yl)pyridin-3-yl)-3-(1-(3-fluorobenzyl)-1H-pyrazol-4-yl)-1H-pyrrolo[2,3-b]pyridine; |
| 174 | 3-(1-(3-fluorobenzyl)-1H-pyrazol-4-yl)-5-(5-methoxy-6-(piperazin-1-yl)pyridin-3-yl)-1H-pyrrolo[2,3-b]pyridine; |
| 175 | 5-(3-fluoro-4-(piperidin-4-yl)phenyl)-3-(1-(3-fluorobenzyl)-3,5-dimethyl-1H-pyrazol-4-yl)-1H-pyrrolo[2,3-b]pyridine; |
| 176 | N-(5-(3-(1-(3,5-difluorobenzyl)-1H-pyrazol-3-yl)-1H-pyrrolo[2,3-b]pyridin-5-yl)-2-(piperidin-4-yl)phenyl)methanesulfonamide; |
| 177 | 5-(3-(1-(3,5-difluorobenzyl)-3,5-dimethyl-1H-pyrazol-4-yl)-1H-pyrrolo[2,3-b]pyridin-5-yl)-3-methoxypyridin-2-amine; |
| 178 | 5-(3-(1-(3-fluorobenzyl)-3,5-dimethyl-1H-pyrazol-4-yl)-1H-pyrrolo[2,3-b]pyridin-5-yl)-3-methoxypyridin-2-amine; |
| 179 | 5-(5-fluoro-6-(4-methylpiperazin-1-yl)pyridin-3-yl)-3-(1-(3-fluorobenzyl)-1H-pyrazol-4-yl)-1H-pyrrolo[2,3-b]pyridine; |
| 180 | (R)-1-(4-(3-fluoro-5-(3-(1-(3-fluorobenzyl)-1H-pyrazol-4-yl)-1H-pyrrolo[2,3-b]pyridin-5-yl)pyridin-2-yl)piperazin-1-yl)propan-2-ol; |
| 181 | (S)-1-(4-(3-fluoro-5-(3-(1-(3-fluorobenzyl)-1H-pyrazol-4-yl)-1H-pyrrolo[2,3-b]pyridin-5-yl)pyridin-2-yl)piperazin-1-yl)propan-2-ol; |
| 182 | 3-fluoro-5-(3-(1-(3-fluorobenzyl)-1H-pyrazol-4-yl)-1H-pyrrolo[2,3-b]pyridin-5-yl)pyridin-2-amine; |
| 183 | 3-fluoro-5-(3-(1-(3-fluorobenzyl)-3,5-dimethyl-1H-pyrazol-4-yl)-1H-pyrrolo[2,3-b]pyridin-5-yl)pyridin-2-amine; |
| 184 | 2-(4-(3-(1-(3-fluorobenzyl)-1H-pyrazol-4-yl)-1H-pyrrolo[2,3-b]pyridin-5-yl)benzyl)piperidin-1-yl)acetamide; |

| Ex. No | IUPAC NAME |
|---|---|
| 185 | 3-(1-phenethyl-1H-pyrazol-4-yl)-5-(4-(piperazin-1-yl)phenyl)-1H-pyrrolo[2,3-b]pyridine; or |
| 186 | 2-(4-(3-(3-(1-(3-fluorobenzyl)-3,5-dimethyl-1H-pyrazol-4-yl)-1H-pyrrolo[2,3-b]pyridin-5-yl)phenyl)piperazin-1-yl)ethanol; | or a pharmaceutically acceptable salt or a stereoisomer thereof.

13. A pharmaceutical composition, comprising at least one compound of claim 1 and/or pharmaceutically acceptable salts or stereoisomers thereof, and a pharmaceutically acceptable carrier or excipient.

14. A method of inhibiting an activity of anaplastic lymphoma kinase (ALK) to treat a condition in a subject, comprising administering to the subject an effective amount of the pharmaceutical composition of claim 13.

15. The method of claim 14, wherein the condition in the subject is a cancer that expresses an oncogenic ALK fusion protein.

16. The method of claim 15, wherein the oncogenic ALK fusion protein is EML4-ALK fusion protein or NPM-ALK fusion protein.

17. The method of claim 15, wherein the cancer is adenocarcinoma, lung cancer, non-small cell lung carcinoma, breast cancer, colorectal cancer, lymphoma, neuroblastoma, ovarian cancer, mesothelioma, melanoma, glioblastoma, diffuse large B-cell lymphomas, systemic histiocytosis, or inflammatory myofibroblastic tumors.

* * * * *